(12) United States Patent
Mitsudera et al.

(10) Patent No.: US 9,814,235 B2
(45) Date of Patent: Nov. 14, 2017

(54) METHOD FOR CONTROLLING ARTHROPOD PEST

(71) Applicant: SUMITOMO CHEMICAL COMPANY, LIMITED, Tokyo (JP)

(72) Inventors: Hiromasa Mitsudera, Tokyo (JP); Kenichiro Awasaguchi, Takarazuka (JP); Tomotsugu Awano, Takarazuka (JP); Kazuya Ujihara, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/655,967

(22) PCT Filed: Jan. 24, 2014

(86) PCT No.: PCT/JP2014/052175
§ 371 (c)(1),
(2) Date: Jun. 26, 2015

(87) PCT Pub. No.: WO2014/119696
PCT Pub. Date: Aug. 7, 2014

(65) Prior Publication Data
US 2015/0344466 A1    Dec. 3, 2015

(30) Foreign Application Priority Data

Jan. 30, 2013 (JP) .................... 2013-015196
Feb. 25, 2013 (JP) .................... 2013-034250

(51) Int. Cl.
| | | |
|---|---|---|
| C07D 261/06 | (2006.01) |
| A61K 31/42 | (2006.01) |
| A01N 43/56 | (2006.01) |
| A01N 47/02 | (2006.01) |
| C07D 413/14 | (2006.01) |
| A01N 43/647 | (2006.01) |
| A01N 43/713 | (2006.01) |
| A01N 43/76 | (2006.01) |
| A01N 43/78 | (2006.01) |
| A01N 43/80 | (2006.01) |
| A01N 47/06 | (2006.01) |
| C07D 405/12 | (2006.01) |

(Continued)

(52) U.S. Cl.
CPC ........... *A01N 43/56* (2013.01); *A01N 43/647* (2013.01); *A01N 43/713* (2013.01); *A01N 43/76* (2013.01); *A01N 43/78* (2013.01); *A01N 43/80* (2013.01); *A01N 43/82* (2013.01); *A01N 47/02* (2013.01); *A01N 47/06* (2013.01); *A01N 55/00* (2013.01); *C07D 405/12* (2013.01); *C07D 413/12* (2013.01); *C07D 413/14* (2013.01); *C07D 417/12* (2013.01)

(58) Field of Classification Search
CPC .............................. A61K 31/42; C07D 261/08
USPC ........................................... 514/378; 548/247
See application file for complete search history.

(56) References Cited

U.S. PATENT DOCUMENTS 5,693,594 A   12/1997   Niedermann et al.
6,069,160 A    5/2000   Stolle et al.

FOREIGN PATENT DOCUMENTS

JP      8-301869 A    11/1996
JP      8-510461 A    11/1996
(Continued)

OTHER PUBLICATIONS

International Preliminary Report on Patentability and Written Opinion of the International Searching Authority (Forma PCT/IB/338, PCT/IB/373 and PCT/ISA/237)dated Aug. 13, 2015, for International Application No. PCT/JP2014/052175.

(Continued)

*Primary Examiner* — Raymond Henley, III
(74) *Attorney, Agent, or Firm* — Birch, Stewart, Kolasch & Birch, LLP

(57) ABSTRACT

An amide compound represented by formula (I):

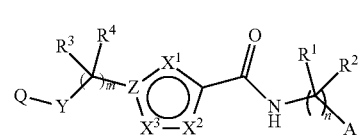

[wherein A represents a 3- to 7-membered saturated heterocyclic ring which contains, as ring-forming component(s), one or more atoms or groups selected from the group consisting of an oxygen atom and —S(O)$_t$—, t represents 0, etc., $R^1$ and $R^2$ are the same or different and represent a hydrogen atom, etc., n represents 0, etc., the following formula (II):

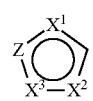

represents a 5-membered aromatic ring, in which Z represents a nitrogen atom or a carbon atom and $X^1$, $X^2$ and $X^3$ are the same or different and represent a nitrogen atom, etc., $R^3$ and $R^4$ are the same or different and represent a hydrogen atom, etc., m represents 0 to 2, Q represents one group selected from group A or a C1 to C8 chain hydrocarbon group optionally having one group selected from group A, Y (Continued)

represents an oxygen atom, etc., u represents 0, etc., and v represents 0, etc.] has excellent arthropod pest controlling effects.

8 Claims, No Drawings

(51) Int. Cl.
    *C07D 413/12*     (2006.01)
    *C07D 417/12*     (2006.01)
    *A01N 43/82*     (2006.01)
    *A01N 55/00*     (2006.01)

(56) References Cited

FOREIGN PATENT DOCUMENTS

| | | |
|---|---|---|
| JP | 2006-56788 A | 3/2006 |
| WO | WO 2009/028280 A1 | 3/2009 |

OTHER PUBLICATIONS

International Search Report, issued in PCT/JP2014/052175, dated Apr. 1, 2014.
Rüger et al., "Synthesis of tetra-substituted pyrazoles", Tetrahedron, 2012, vol. 68, pp. 8823-8829.

METHOD FOR CONTROLLING ARTHROPOD PEST

TECHNICAL FIELD

The present invention relates to a method for controlling an arthropod pest using an amide compound.

BACKGROUND ART

Conventionally, many arthropod pest control agents have been developed for controlling arthropod pests, and put to practical use.

SUMMARY OF THE INVENTION

The present invention provides a method for controlling arthropod pests using an amino compound represented by the following formula (I).

The present invention is as described below.

[1]

A method for controlling arthropod pests comprising applying an effective amount of an amide compound represented by formula (I):

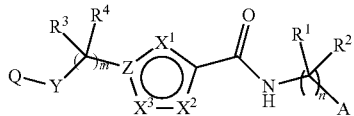

wherein,

A represents a 3 to 7-membered saturated heterocyclic ring which contains, as ring-forming component(s), one or more atoms or groups selected from the group consisting of an oxygen atom and —S(O)$_t$—, and the saturated heterocyclic ring may have one to three atoms or groups selected from group D, t represents 0, 1 or 2, $R^1$ and $R^2$ are the same or different and represent a C1 to C4 alkyl group optionally having one or more halogen atoms or a hydrogen atom, n represents 0, 1 or 2, and the formula (II):

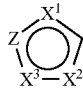

represents a 5-membered aromatic ring,

Z represents a nitrogen atom or a carbon atom, when Z represents a nitrogen atom, $X^1$, $X^2$ and $X^3$ are the same or different and represent a nitrogen atom, $CR^5$, an oxygen atom, a sulfur atom or $NR^6$, and at least one of the $X^1$, $X^2$ and $X^3$ is a nitrogen atom, an oxygen atom, a sulfur atom or $NR^6$, when Z represents a carbon atom, $X^1$, $X^2$ and $X^3$ are the same or different and represent a nitrogen atom, $CR^5$, an oxygen atom, a sulfur atom or $NR^6$, at least two of the $X^1$, $X^2$ and $X^3$ are a nitrogen atom, an oxygen atom, a sulfur atom or $NR^6$, and at least one of the $X^1$, $X^2$ and $X^3$ is a nitrogen atom or $NR^6$, $R^5$s are the same or different and each represent a halogen atom, a cyano group, a formyl group, a carboxyl group, a C1 to C4 alkoxycarbonyl group optionally having one or more halogen atoms, a carbamoyl group, a C1 to C3 hydrocarbon group optionally having one or more atoms or groups selected from the group consisting of —$OR^7$ and halogen atoms, or a hydrogen atom, $R^6$ represents a methyl group or a hydrogen atom, $R^7$ represents —C(=S)$SR^8$ or a hydrogen atom, $R^8$ represents a C1 to C3 hydrocarbon group optionally having one or more halogen atoms, $R^3$ and $R^4$ are the same or different and represent a C1 to C4 alkyl group optionally having one or more halogen atoms, a halogen atom, a phenyl group optionally having one or more atoms or groups selected from group B, or a hydrogen atom, Y represents a single bond, an oxygen atom or —S(O)$_u$—, when Y is a single bond, m represents 0, when Y is an oxygen atom or —S(O)$_u$—, m represents 0, 1, 2, 3, 4, 5, 6 or 7, when Y is a single bond, Q represents a C1 to C8 chain hydrocarbon group optionally having one or more atoms or groups selected from group F, or a C3 to C8 chain hydrocarbon group, when Y is an oxygen atom or —S(O)$_u$—, Q represents a C1 to C8 chain hydrocarbon group optionally having one or more atoms or groups selected from group G, or a group selected from group A, and u represents 0, 1 or 2, Group A: A group consisting of C3 to C8 cycloalkyl groups optionally having one or more atoms or groups selected from group B, indanyl groups optionally having one or more atoms or groups selected from group B, 1,2,3,4-tetrahydronaphthyl groups optionally having one or more atoms or groups selected from group B, phenyl groups optionally having one or more atoms or groups selected from group B, naphthyl groups optionally having one or more atoms or groups selected from group B, pyridyl groups optionally having one or more atoms or groups selected from group B, quinolyl groups optionally having one or more atoms or groups selected from group B, furyl groups optionally having one or more atoms or groups selected from group B, thienyl groups optionally having one or more atoms or groups selected from group B, benzofuranyl groups optionally having one or more atoms or groups selected from group B, and benzothienyl groups optionally having one or more atoms or groups selected from group B, Group B: A group consisting of C1 to C4 alkyl groups optionally having one or more halogen atoms, C1 to C4 alkyl groups optionally having one or more benzyloxy groups, C1 to C4 alkoxy groups optionally having one or more halogen atoms, C1 to C4 alkylthio groups optionally having one or more halogen atoms, C1 to C4 alkylsulfinyl groups optionally having one or more halogen atoms, C1 to C4 alkylsulfonyl groups optionally having one or more halogen atoms, C1 to C4 alkoxycarbonyl groups optionally having one or more halogen atoms, vinyl groups optionally having one or more atoms or groups selected from group E, ethynyl groups optionally having an atom or group selected from group E, a phenyl group, a phenoxy group, a cyano group, a nitro group, a carboxyl group, a hydroxyl group, —CONR$^{12}$R$^{13}$ group, a methoxymethyl group, and halogen atoms, R$^{12}$ and R$^{13}$ are the same or different and represent a C1 to C4 alkyl group optionally having one or more halogen atoms or a hydrogen atom, Group D: A group consisting of C1 to C4 alkyl groups optionally having one or more halogen atoms, C1 to C4 alkoxy groups optionally having one or more halogen atoms, and halogen atoms, Group E: A group consisting of C1 to C4 alkyl groups optionally having one or more halogen atoms and halogen atoms, Group F: A group consisting of C3 to C8 cycloalkyl groups optionally having one or more atoms or groups selected from group B, indanyl groups optionally having one or more atoms or groups selected from group B, 1,2,3,4-tetrahydronaphthyl groups optionally having one or more atoms or groups selected from group B, phenyl groups optionally having one or more atoms or groups selected from group B, naphthyl groups optionally having one or more atoms or groups selected from group B, pyridyl groups optionally having one or more atoms or groups selected from group B, quinolyl groups optionally having one or more atoms or groups selected from group B, furyl groups optionally having one or more atoms or groups selected from group B, thienyl groups optionally having one or more atoms or groups selected from group B, benzofuranyl groups optionally having one or more atoms or groups selected from group B, benzothienyl groups optionally having one or more atoms or groups selected from group B, 1,3-benzodioxolanyl groups optionally having one or more atoms or groups selected from group B, 1,4-benzodioxanyl groups optionally having one or more atoms or groups selected from group B, halogen atoms, C1 to C4 alkoxycarbonyl group optionally having one or more halogen atoms, a cyano group, a nitro group, a carboxyl group, a hydroxyl group, and —CONR$^{12}$R$^{13}$ group, Group G: A group consisting of C3 to C8 cycloalkyl groups optionally having one or more atoms or groups selected from group B, indanyl groups optionally having one or more atoms or groups selected from group B, 1,2,3,4-tetrahydronaphthyl groups optionally having one or more atoms or groups selected from group B, phenyl groups optionally having one or more atoms or groups selected from group B, phenoxy groups optionally having one or more atoms or groups selected from group B, naphthyl groups optionally having one or more atoms or groups selected from group B, pyridyl groups optionally having one or more atoms or groups selected from group B, quinolyl groups optionally having one or more atoms or groups selected from group B, furyl groups optionally having one or more atoms or groups selected from group B, thienyl groups optionally having one or more atoms or groups selected from group B, benzofuranyl groups optionally having one or more atoms or groups selected from group B, benzothienyl groups optionally having one or more atoms or groups selected from group B, 1,3-benzodioxolanyl groups optionally having one or more atoms or groups selected from group B, 1,4-benzodioxanyl groups optionally having one or more atoms or groups selected from group B, halogen atoms, C1 to C4 alkoxycarbonyl group optionally having one or more halogen atoms, a cyano group, a nitro group, a carboxyl group, a hydroxyl group, and —CONR$^{12}$R$^{13}$ group, to an arthropod pest or an arthropod pest-infested area.

[2]

The method for controlling arthropod pests according to [1], wherein R$^5$s are the same or different and are a halogen atom, a cyano group, a methyl group or a hydrogen atom, R$^3$ and R$^4$ are the same or different, and are a C1 to C4 alkyl group optionally having one or more halogen atoms, a halogen atom or a hydrogen atom, Y is a single bond, an oxygen atom or —S(O)$_u$—, when Y is an oxygen atom or —S(O)$_u$—, m is 0, 1, 2, 3 or 4, and when Y is an oxygen atom or —S(O)$_u$—, Q is a C1 to C8 chain hydrocarbon group having one or more atoms or groups selected from group F or a group selected from group A, and group B is a group consisting of C1 to C4 alkyl groups optionally having one or more halogen atoms, C1 to C4 alkoxy groups optionally having one or more halogen atoms, C1 to C4 alkylthio groups optionally having one or more halogen atoms, C1 to C4 alkylsulfinyl groups optionally having one or more halogen atoms, C1 to C4 alkylsulfonyl groups optionally having one or more halogen atoms, C1 to C4 alkoxycarbonyl groups optionally having one or more halogen atoms, vinyl groups optionally having one or more atoms or groups selected from group E, ethynyl groups optionally having an atom or group selected from group E, a cyano group, a nitro group, a carboxyl group, a hydroxyl group, —CONR$^{12}$R$^{13}$ group, a methoxymethyl group, and halogen atoms.

[3]

The method for controlling arthropod pests according to [1], wherein R$^5$s are the same or different and are a halogen atom, a cyano group, a methyl group optionally having a halogen atom or a hydrogen atom, m is 0 to 2, Q is a group selected from group A or a C1 to C8 chain hydrocarbon group optionally having a group selected from group A, Y is —CR$^8$R$^9$—, —CR$^9$=CR$^9$—, an oxygen atom, or —S(O)$_u$—, R$^8$ represents a C1 to C4 alkyl group optionally having one or more halogen atoms, a halogen atom or a hydrogen atom, or R$^3$ and R$^8$ form —(CR$^{10}$R$^{11}$)$_v$—, an oxygen atom, or a sulfur atom together, R$^9$ is a C1 to C4 alkyl group optionally having one or more halogen atoms, a halogen atom, or a hydrogen atom, R$^{10}$ and R$^{11}$ are the same or different and are a C1 to C4 alkyl group optionally having one or more halogen atoms, a halogen atom, or a hydrogen atom, v is 1, 2, 3 or 4, and group B is a group consisting of C1 to C4 alkyl groups optionally having one or more halogen atoms, C1 to C4 alkoxy groups optionally having one or more halogen atoms, C1 to C4 alkylthio groups optionally having one or more halogen atoms, C1 to C4 alkylsulfinyl groups optionally having one or more halogen atoms, C1 to C4 alkylsulfonyl groups optionally having one or more halogen atoms, C1 to C4 alkoxycarbonyl groups optionally having one or more halogen atoms, vinyl groups optionally having one or more atoms or groups selected from group E, ethynyl groups optionally having an atom or group selected from group E, a cyano group, a nitro group, a carboxyl group, a hydroxyl group, —CONR$^{12}$R$^{13}$ group, and halogen atoms.

[4]

The method for controlling arthropod pests according to [1] to [3], wherein A is a group represented by the following formula (III-a) or (III-b):

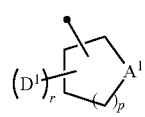

(III-a)

-continued

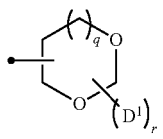
(III-b)

wherein $A^1$ represents an oxygen atom or a sulfur atom, $D^1$ represents an atom or group selected from group D, r represents 0 or 1, p represents 0, 1 or 2, and q represents 0 or 1.

[5]

The method for controlling arthropod pests according to [1] to [3], wherein in the formula (I), A is a group represented by the following formula (III-d):

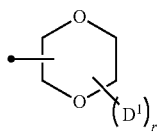
(III-d)

wherein $D^1$ represents an atom or group selected from group D, and r represents 0 or 1.

[6]

The method for controlling arthropod pests according to [1] to [3], wherein A is a group represented by the following formula (III-c):

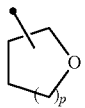
(III-c)

wherein p represents 0, 1 or 2.

[7]

The method for controlling arthropod pests according to [1] to [6], represented by formula (I-a):

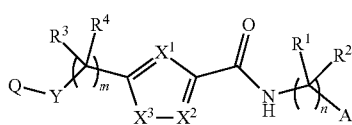
(I-a)

wherein $R^1$, $R^2$, $R^3$, $R^4$, A, Q, Y, m and n have the same meaning as defined in [1], $X^1$ and $X^2$ are the same or different and represent a nitrogen atom or $CR^5$, one to two of $X^1$ and $X^2$ represent a nitrogen atom, $X^3$ represents an oxygen atom, a sulfur atom or $NR^6$, and $R^5$ and $R^6$ have the same meaning as defined in [1].

[8]

The method for controlling arthropod pests according to [1] to [6], represented by formula (I-b):

(I-b)

wherein $R^1$, $R^2$, $R^3$, $R^4$, A, Q, Y, m and n have the same meaning as defined in [1], $X^1$ and $X^3$ are the same or different and represent a nitrogen atom or $CR^5$, one to two of $X^1$ and $X^3$ represent a nitrogen atom, $X^2$ represents an oxygen atom, a sulfur atom or $NR^6$, and $R^5$ and $R^4$ have the same meaning as defined in [1].

[9]

The method for controlling arthropod pests according to [1] to [6], represented by formula (I-c):

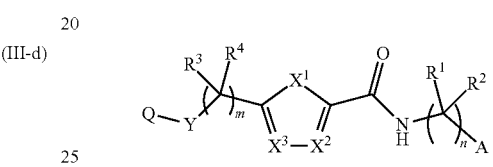
(I-c)

wherein $R^1$, $R^2$, $R^3$, $R^4$, A, Q, Y, m and n have the same meaning as defined in [1], $X^2$ and $X^3$ are the same or different and represent a nitrogen atom or $CR^5$, one to two of $X^2$ and $X^3$ represent a nitrogen atom, $X^1$ represents an oxygen atom, a sulfur atom or $NR^6$, and $R^5$ and $R^6$ have the same meaning as defined in [1].

[10]

The method for controlling arthropod pests according to [1] to [6], represented by formula (I-d):

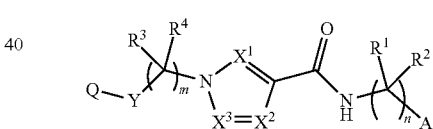
(I-d)

wherein $R^1$, $R^2$, $R^3$, $R^4$, A, Q, Y, m and n have the same meaning as defined in [1], $X^1$, $X^2$ and $X^3$ are the same or different and represent a nitrogen atom or $CR^5$, one to three of $X^1$, $X^2$ and $X^3$ represent a nitrogen atom, and $R^5$ has the same meaning as defined in [1].

[11]

The method for controlling arthropod pests according to [1] to [6], represented by formula (I-e):

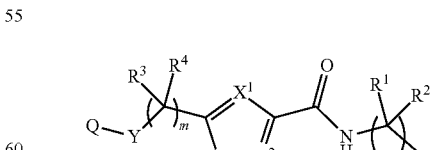
(I-e)

wherein $R^1$, $R^2$, $R^3$, $R^4$, A, Q, Y, m and n have the same meaning as defined in [1], $X^1$ and $X^2$ are the same or different and represent a nitrogen atom or $CR^5$, one to two of $X^1$ and $X^2$ represent a nitrogen atom, and $R^5$ has the same meaning as defined in [1].

[12]
The method for controlling arthropod pests according to [1] to [6], represented by formula (I-f):

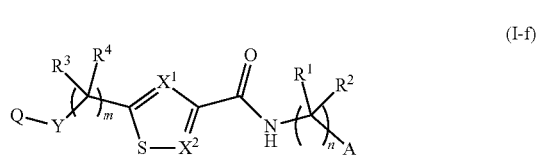

(I-f)

wherein $R^1$, $R^2$, $R^3$, $R^4$, A, Q, Y, m and n have the same meaning as defined in [1], $X^1$ and $X^2$ are the same or different and represent a nitrogen atom or $CR^5$, one to two of $X^1$ and $X^2$ represent a nitrogen atom, and $R^5$ has the same meaning as defined in [1].

[13]
The method for controlling arthropod pests according to [1] to [6], represented by formula (I-g):

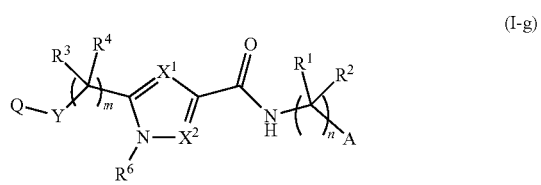

(I-g)

wherein $R^1$, $R^2$, $R^3$, $R^4$, A, Q, Y, m and n have the same meaning as defined in [1], $X^1$ and $X^2$ are the same or different and represent a nitrogen atom or $CR^5$, one to two of $X^1$ and $X^2$ represent a nitrogen atom, and $R^5$ and $R^6$ have the same meaning as defined in [1].

[14]
The method for controlling arthropod pests according to [1] to [6], represented by formula (I-h):

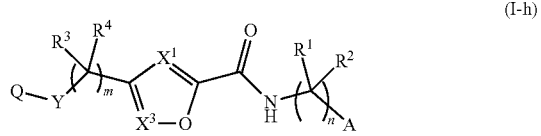

(I-h)

wherein $R^1$, $R^2$, $R^3$, $R^4$, A, Q, Y, m and n have the same meaning as defined in [1], $X^1$ and $X^3$ are the same or different and represent a nitrogen atom or $CR^5$, one to two of $X^1$ and $X^3$ represent a nitrogen atom, and $R^5$ has the same meaning as defined in [1].

[15]
The method for controlling arthropod pests according to [1] to [6], represented by formula (I-i):

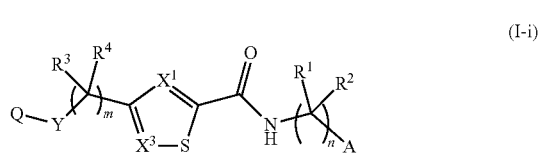

(I-i)

wherein $R^1$, $R^2$, $R^3$, $R^4$, A, Q, Y, m and n have the same meaning as defined in [1], $X^1$ and $X^3$ are the same or different and represent a nitrogen atom or $CR^5$, one to two of $X^1$ and $X^3$ represent a nitrogen atom, and $R^5$ has the same meaning as defined in [1].

[16]
The method for controlling arthropod pests according to [1] to [6], represented by formula (I-j):

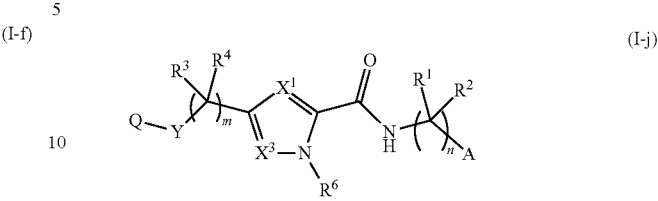

(I-j)

wherein $R^1$, $R^2$, $R^3$, $R^4$, A, Q, Y, m and n have the same meaning as defined in [1], $X^1$ and $X^3$ are the same or different and represent a nitrogen atom or $CR^5$, one to two of $X^1$ and $X^3$ represent a nitrogen atom, and $R^5$ and $R^6$ have the same meaning as defined in [1].

[17]
The method for controlling arthropod pests according to [1] to [6], represented by formula (I-k):

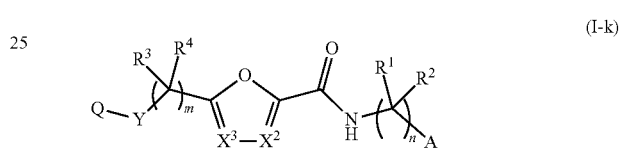

(I-k)

wherein $R^1$, $R^2$, $R^3$, $R^4$, A, Q, Y, m and n have the same meaning as defined in [1], $X^2$ and $X^3$ are the same or different and represent a nitrogen atom or $CR^5$, one to two of $X^2$ and $X^3$ represent a nitrogen atom, and $R^5$ has the same meaning as defined in [1].

[18]
The method for controlling arthropod pests according to [1] to [6], represented by formula (I-l):

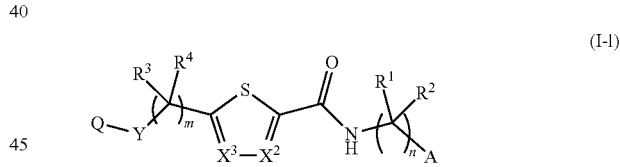

(I-l)

wherein $R^1$, $R^2$, $R^3$, $R^4$, A, Q, Y, m and n have the same meaning as defined in [1], $X^2$ and $X^3$ are the same or different and represent a nitrogen atom or $CR^5$, one to two of $X^2$ and $X^3$ represent a nitrogen atom, and $R^5$ has the same meaning as defined in [1].

[19]
The method for controlling arthropod pests according to [1] to [6], represented by formula (I-k):

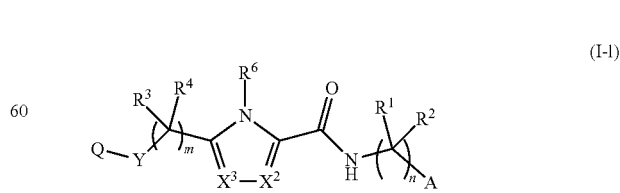

(I-l)

wherein $R^1$, $R^2$, $R^3$, $R^4$, A, Q, Y, m and n have the same meaning as defined in [1], $X^2$ and $X^3$ are the same or different and represent a nitrogen atom or $CR^5$, one to two of $X^2$ and $X^3$ represent a nitrogen atom, and $R^5$ and $R^6$ have the same meaning as defined in [1].

[20]

The method for controlling arthropod pests according to [1] to [6], represented by formula (I-m):

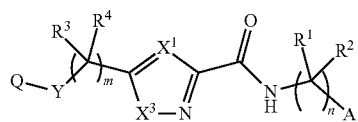

(I-m)

wherein $R^1$, $R^2$, $R^3$, $R^4$, A, Q, Y, m and n have the same meaning as defined in [1], $X^1$ represents a nitrogen atom or $CR^5$, $X^3$ represents an oxygen atom, a sulfur atom or $NR^6$, and $R^5$ and $R^6$ have the same meaning as defined in [1].

[21]

The method for controlling arthropod pests according to [1] to [6], represented by formula (I-n):

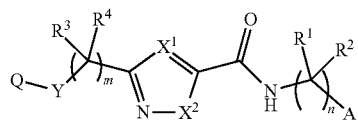

(I-n)

wherein $R^1$, $R^2$, $R^3$, $R^4$, A, Q, Y, m and n have the same meaning as defined in [1], $X^1$ represents a nitrogen atom or $CR^5$, $X^2$ represents an oxygen atom, a sulfur atom or $NR^6$, and $R^5$ and $R^6$ have the same meaning as defined in [1].

[22]

The method for controlling arthropod pests according to [1] to [6], represented by formula (I-o):

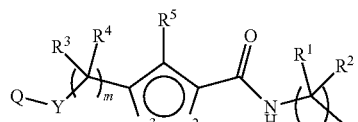

(I-o)

wherein $R^1$, $R^2$, $R^3$, $R^4$, $R^5$, A, Q, Y, m and n have the same meaning as defined in [1], one of $X^2$ and $X^3$ is a nitrogen atom, the other one represents an oxygen atom, a sulfur atom or $NR^6$, and $R^6$ has the same meaning as defined in [1].

[23]

The method for controlling arthropod pests according to [1] to [6], represented by formula (I-p):

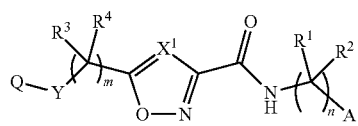

(I-p)

wherein $R^1$, $R^2$, $R^3$, $R^4$, A, Q, Y, m and n have the same meaning as defined in [1], $X^1$ represents a nitrogen atom or $CR^5$, and $R^5$ has the same meaning as defined in [1].

[24]

The method for controlling arthropod pests according to [1] to [6], represented by formula (I-q):

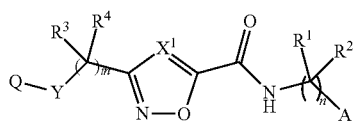

(I-q)

wherein $R^1$, $R^2$, $R^3$, $R^4$, A, Q, Y, m and n have the same meaning as defined in [1], $X^1$ represents a nitrogen atom or $CR^5$, and $R^5$ has the same meaning as defined in [1].

[25]

The method for controlling arthropod pests according to [24], wherein $X^1$ is $CR^5$.

[26]

The method for controlling arthropod pests according to [1] to [6], represented by formula (I-r):

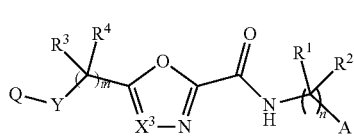

(I-r)

wherein $R^1$, $R^2$, $R^3$, $R^4$, A, Q, Y, m and n have the same meaning as defined in [1], $X^3$ represents a nitrogen atom or $CR^5$, and $R^5$ has the same meaning as defined in [1].

[27]

The method for controlling arthropod pests according to [1] to [6], represented by formula (I-s):

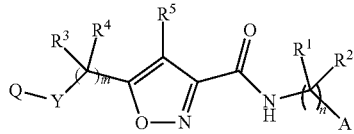

(I-s)

wherein $R^1$, $R^2$, $R^3$, $R^4$, $R^5$, A, Q, Y, m and n have the same meaning as defined in [1].

[28]

The method for controlling arthropod pests according to [1] to [6], represented by formula (I-t):

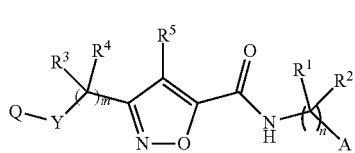

(I-t)

wherein $R^1$, $R^2$, $R^3$, $R^4$, $R^5$, A, Q, Y, m and n have the same meaning as defined in [1].

[29]

The method for controlling arthropod pests according to [1] to [6], represented by formula (I-u):

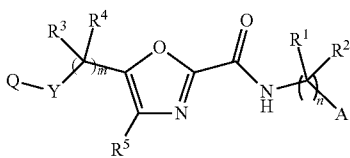

wherein $R^1$, $R^2$, $R^3$, $R^4$, $R^5$, A, Q, Y, m and n have the same meaning as defined in [1].

[30]
The method for controlling arthropod pests according to [1] to [6], represented by formula (I-v):

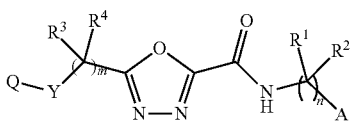

wherein $R^1$, $R^2$, $R^3$, $R^4$, A, Q, Y, m and n have the same meaning as defined in [1].

[31]
The method for controlling arthropod pests according to [1] to [30], wherein n is 1.

[32]
The method for controlling arthropod pests according to [1] to [31], wherein m is 1.

[33]
The method for controlling arthropod pests according to [1] to [32], wherein Y is an oxygen atom.

[34]
The method for controlling arthropod pests according to [3] to [32], wherein Y is —$CR^8R^9$—.

[35]
The method for controlling arthropod pests according to [3] to [32], wherein Y is —$CR^8R^9$—, and $R^8$ and $R^9$ are a hydrogen atom.

[36]
The method for controlling arthropod pests according to [1] to [35], wherein Q is a group selected from group A.

[37]
The method for controlling arthropod pests according to [2] to [35], wherein Q is a C1 to C8 chain hydrocarbon group.

[38]
The method for controlling arthropod pests according to [1], [2] and [4] to [30], wherein Y is a single bond.

[39]
The method for controlling arthropod pests according to [3] to [35], wherein Q is a C1 to C8 chain hydrocarbon group having a group selected from group A.

[40]
The method for controlling arthropod pests according to [3] to [35], wherein Q is a methyl group having a group selected from group A.

[41]
The method for controlling arthropod pests according to [1], [2] and [4] to [35], wherein Q is a C3 to C8 chain hydrocarbon group.

[42]
The method for controlling arthropod pests according to [2] to [35], wherein Q is a C1 to C8 chain hydrocarbon group optionally having one or more atoms or groups selected from group F.

[43]
The method for controlling arthropod pests according to [1] and [4] to [35], wherein Q is a C1 to C8 chain hydrocarbon group having one or more atoms or groups selected from group G.

[44]
The method for controlling arthropod pests according to [1], [2] and [4] to [35], wherein Q is a C1 to C8 chain hydrocarbon group having one or more atoms or groups selected from group F.

[45]
The method for controlling arthropod pests according to [1], [2] and [4] to [35], wherein Q is a C1 to C8 chain hydrocarbon group having a group selected from group F.

[46]
The method for controlling arthropod pests according to [2] to [35], wherein Q is a methyl group having a group selected from group F.

[47]
An arthropod pest control agent comprising an amide compound represented by formula (I) used in any one of [1] to [46], and an inert carrier.

[48]
An amide compound represented by formula (I-s):

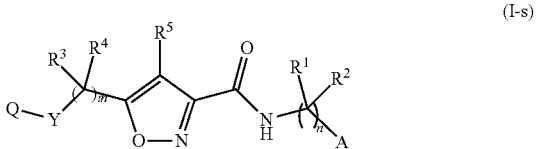

wherein A, $R^1$, $R^2$, $R^3$, $R^4$, $R^5$, $R^6$, $R^7$, $R^{12}$, $R^{13}$, Y, m, n, t, u, group A, group B, group D, group E, group F and group G have the same meaning as defined in [1], when Y is a single bond, Q represents a C1 to C8 chain hydrocarbon group having one or more atoms or groups selected from group F, when Y is an oxygen atom, and m is 0, 2, 3, 4, 5, 6 or 7, or when Y is —$S(O)_u$—, Q represents a C1 to C8 chain hydrocarbon group optionally having one or more atoms or groups selected from group G, or a group selected from group A, and when Y is an oxygen atom, and m is 1, Q represents a C1 to C8 chain hydrocarbon group optionally having one or more atoms or groups selected from group G, or a group selected from group H, Group H: A group consisting of C3 to C8 cycloalkyl groups optionally having one or more atoms or groups selected from group B, indanyl groups optionally having one or more atoms or groups selected from group B, furyl groups optionally having one or more atoms or groups selected from group B, thienyl groups optionally having one or more atoms or groups selected from group B, benzofuranyl groups optionally having one or more atoms or groups selected from group B, and benzothienyl groups optionally having one or more atoms or groups selected from group B.

[49]
The amide compound according to [48], wherein $R^5$ is a halogen atom, a cyano group, a methyl group or a hydrogen atom, $R^3$ and $R^4$ are the same or different, and are a C1 to C4 alkyl group optionally having one or more halogen atoms, a halogen atom or a hydrogen atom, when Y is an oxygen atom or —$S(O)_u$—, m is 0, 1, 2, 3 or 4, and when Y is an oxygen atom or —S(O)$_u$—, Q is a C1 to C8 chain hydrocarbon group having one or more atoms or groups selected from group F, and group B is a group consisting of C1 to C4 alkyl groups optionally having one or more halogen atoms, C1 to C4 alkoxy groups optionally having one or more halogen atoms, C1 to C4 alkylthio groups optionally having one or more halogen atoms, C1 to C4 alkylsulfinyl groups optionally having one or more halogen atoms, C1 to C4 alkylsulfonyl groups optionally having one or more halogen atoms, C1 to C4 alkoxycarbonyl groups optionally having one or more halogen atoms, vinyl groups optionally having one or more atoms or groups selected from group E, ethynyl groups optionally having an atom or group selected from group E, a cyano group, a nitro group, a carboxyl group, a hydroxyl group, —CONR$^{12}$R$^{13}$ group, a methoxymethyl group, and halogen atoms.

[50]
The amide compound according to [48] or [49], wherein A is a group represented by the following formula (III-a) or (III-b):

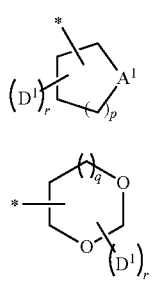

(III-a)

(III-b)

wherein A$^1$ represents an oxygen atom or a sulfur atom, D$^1$ represents an atom or group selected from group D, r represents 0 or 1, p represents 0, 1 or 2, and q represents 0 or 1.

[51]
The amide compound according to [48] or [49], wherein A is a group represented by the following formula (III-d):

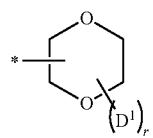

(III-d)

wherein D$^1$ represents an atom or group selected from group D, and r represents 0 or 1.

[52]
The amide compound according to [48] or [49], wherein A is a group represented by the following formula (III-c):

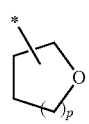

(III-c)

wherein p represents 0, 1 or 2.

[53]
The amide compound according to [48] to [52], wherein n is 1.

[54]
The amide compound according to [48] to [53], wherein m is 1.

[55]
The amide compound according to [48] to [54], wherein Y is an oxygen atom.

[56]
The amide compound according to [48] to [54], wherein Y is a single bond.

[57]
The amide compound according to [48] to [56], wherein Q is a group selected from group A.

[58]
The amide compound according to [48] to [58], wherein Q is a group selected from group H.

[59]
The amide compound according to [48] to [55], wherein Q is a C1 to C8 chain hydrocarbon group optionally having one or more atoms or groups selected from group G.

[60]
The amide compound according to [48] to [54] and [56], wherein Q is a C1 to C8 chain hydrocarbon group having one or more atoms or groups selected from group F.

[61]
The amide compound according to [48] to [56], wherein Q is a C1 to C8 chain hydrocarbon group having a group selected from group F.

[62]
The amide compound according to [48] to [56], wherein Q is a methyl group having a group selected from group F.

MODE FOR CARRYING OUT THE INVENTION

In the present invention, examples of the "a 3 to 7-membered saturated heterocyclic ring which contains, as ring-forming component (s), one or more atoms or groups that are selected from the group consisting of an oxygen atom and —S(O)$_t$— (herein, the saturated heterocyclic ring may have one to three atoms or groups selected from group D.)" include 3 to 7-membered saturated heterocyclic rings which contain, as ring-forming component(s), one or more oxygen atoms and optionally having one to three atoms or groups selected from group D, such as an oxetan-2-yl group, an oxetan-3-yl group, a tetrahydrofuran-2-yl group, a tetrahydrofuran-3-yl group, a 1,3-dioxolan-2-yl group, a 1,3-dioxolan-4-yl group, a tetrahydropyran-2-yl group, a tetrahydropyran-3-yl group, a tetrahydropyran-4-yl group, a 1,3-dioxan-4-yl group, a 1,3-dioxan-5-yl group, a 1,4-dioxan-2-yl group, an oxepan-2-yl group, an oxepan-3-yl group, an oxepan-4-yl group, a 1,3-dioxepan-4-yl group, a 1,3-dioxepan-5-yl group, a 1,4-dioxepan-2-yl group, a 1,4-dioxepan-5-yl group and a 1,4-dioxepan-6-yl group; 3 to 7-membered saturated heterocyclic rings which contain, as ring-forming component(s), one or more sulfur atoms and optionally having one to three atoms or groups selected from group D, such as a thietan-2-yl group, a thietan-3-yl group, a tetrahydrothiophen-2-yl group, a tetrahydrothiophen-3-yl group, a 1,3-dithiolan-4-yl group, a tetrahydrothiopyran-2-yl group, a tetrahydrothiopyran-3-yl group, a tetrahydrothiopyran-4-yl group, a 1,3-dithian-4-yl group, a 1,3-dithian-5-yl group, a 1,4-dithian-2-yl group, a thiepan-2-yl group, a thiepan-3-yl group, a thiepan-4-yl group, a 1,3-dithiepan-4-yl group, a 1,3-dithiepan-5-yl group, a 1,4-dithiepan-2-yl group, a 1,4-dithiepan-5-yl group and a 1,4-dithiepan-6-yl group; 3 to 7-membered saturated heterocyclic rings which contain, as ring-forming component(s), one or more —SO— and optionally having one to three atoms or groups selected from group D, such as an 1-oxo-thietan-2-yl group, an 1-oxo-thietan-3-yl group, an 1-oxo-tetrahydrothiophen-2-yl group, an 1-oxo-tetrahydrothiophen-3-yl group, an 1-oxo-tetrahydrothiopyran-2-yl group, an 1-oxo-tetrahydrothiopyran-3-yl group, an 1-oxo-tetrahydrothiopyran-4-yl group, an 1-oxo-thiepan-2-yl group, an 1-oxo-thiepan-3-yl group and an 1-oxo-thiepan-4-yl group; 3 to 7-membered saturated heterocyclic rings which contain, as ring-forming component(s), one or more —SO$_2$— and optionally having one to three atoms or groups that are selected from group D, such as a 1,1-dioxothietan-2-yl group, a 1,1-dioxothietan-3-yl group, a 1,1-dioxotetrahydrothiophen-2-yl group, a 1,1-dioxotetrahydrothiophen-3-yl group, a 1,1-dioxotetrahydrothiopyran-2-yl group, a 1,1-dioxotetrahydrothiopyran-3-yl group, a 1,1-dioxotetrahydrothiopyran-4-yl group, a 1,1-dioxothiepan-2-yl group, a 1,1-dioxothiepan-3-yl group and a 1,1-dioxothiepan-4-yl group; and 3 to 7-membered saturated heterocyclic rings which contain, as ring-forming component(s), one or more oxygen atoms and one or more —S(O)$_t$— and optionally having one to three atoms or groups selected from group D, such as an 1,3-oxathietan-2-yl group, an 1,3-oxathiolan-2-yl group, an 1,3-oxathiolan-4-yl group, an 1,3-oxathiolan-5-yl group, an 1,3-oxathian-2-yl group, an 1,3-oxathiolan-4-yl group, an 1,3-oxathiolan-5-yl group, an 1,4-oxathian-2-yl group and an 1,4-oxathian-3-yl group.

The halogen atom in the present invention includes a fluorine atom, a chlorine atom, a bromine atom, and an iodine atom.

The C1 to C4 alkyl group optionally having one or more halogen atoms in the present invention includes a methyl group, an ethyl group, a propyl group, an isopropyl group, a butyl group, an isobutyl group, a sec-butyl group, a tert-butyl group, an iodomethyl group, a bromomethyl group, a chloromethyl group, a fluoromethyl group, a difluoromethyl group, a chlorodifluoromethyl group, a bromodifluoromethyl group, a dichlorofluoromethyl group, a trichloromethyl group, a trifluoromethyl group, a 2,2,2-trifluoroethyl group, a 1,1,2,2-tetrafluoroethyl group and a 1,1,2,2,2-pentafluoroethyl group.

In the present invention, the circle in the following formula (II):

(II)

means that a cyclic structure has aromaticity.

Examples of the 5-membered aromatic ring represented by the following formula (II) include imidazole, oxazole, thiazole, pyrazole, isoxazole, isothiazole, 1,2,3-triazole, 1,2,4-triazole, 1,2,4-oxadiazole, 1,3,4-oxadiazole, 1,2,4-thiadiazole, 1,3,4-thiadiazole, 1,2,4-triazole, 1,3,4-triazole, and tetrazole. Examples of the compound of the present invention having the 5-membered aromatic ring include compounds represented by the following formulae (I-s), (I-t), (I-v) and (I-1) to (I-31) (wherein, Y, A, Q, R$^1$, R$^2$, R$^3$, R$^4$, R$^5$, R$^6$, n and n have the same meaning as in [1].).

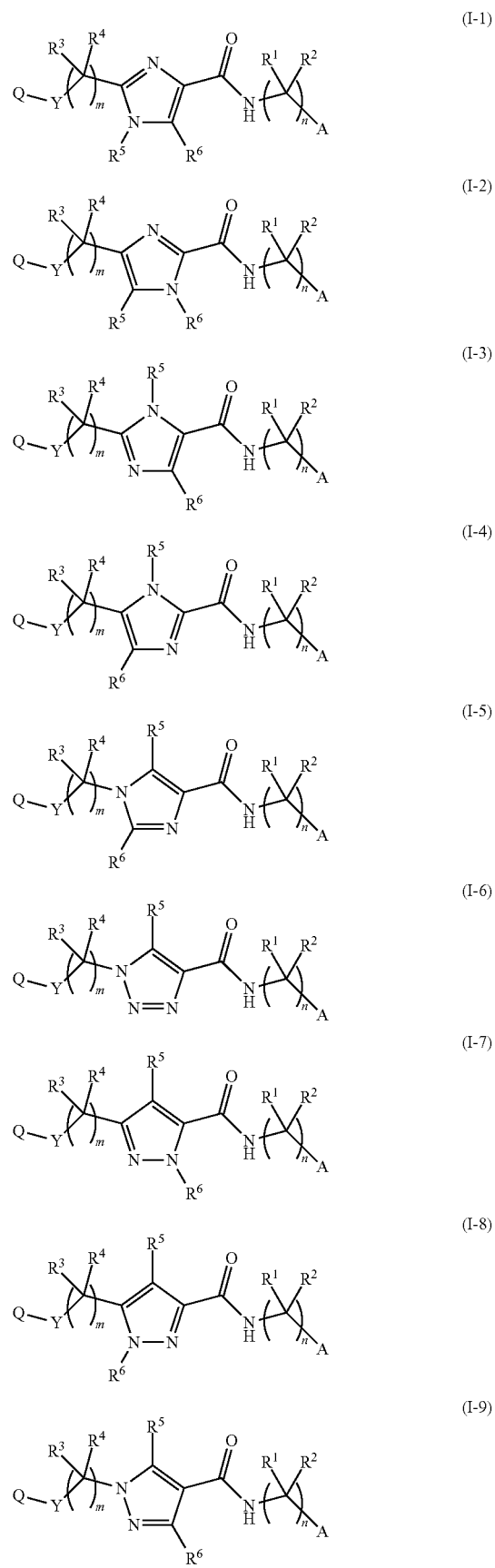

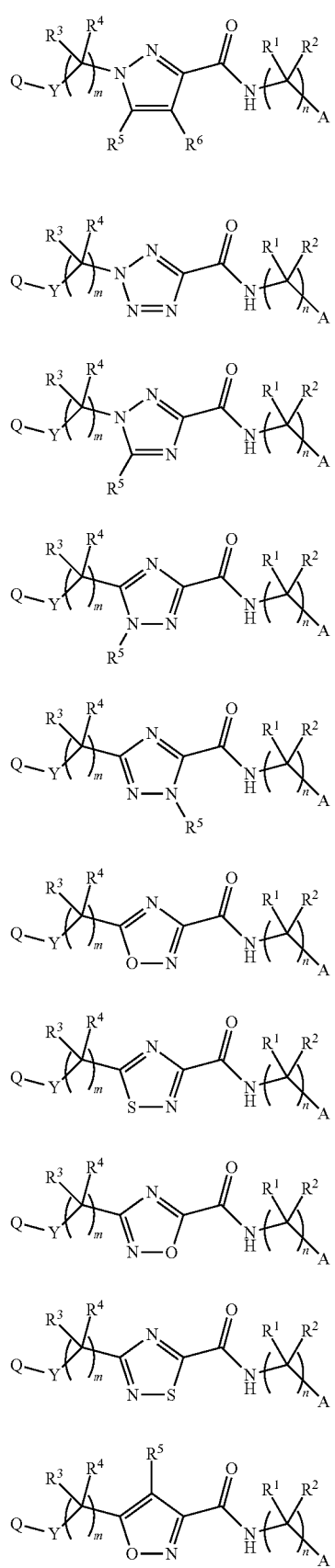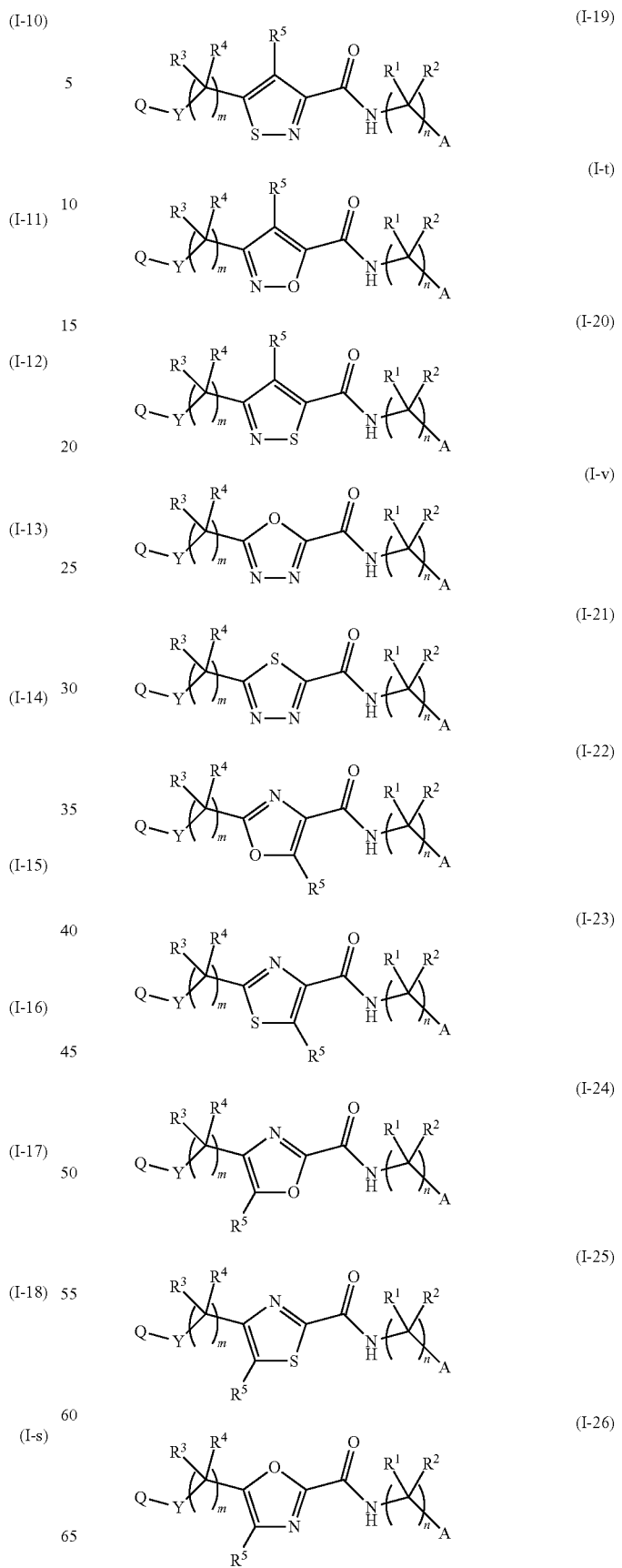

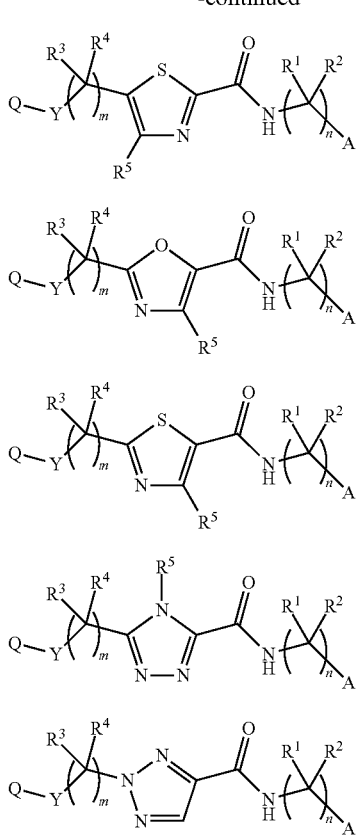

(I-27)
(I-28)
(I-29)
(I-30)
(I-31)

Examples of the methyl group optionally having a halogen atom in the present invention include a methyl group, an iodomethyl group, a bromomethyl group, a chloromethyl group, a fluoromethyl group, a difluoromethyl group, a chlorodifluoromethyl group, a bromodifluoromethyl group, a dichlorofluoromethyl group, a trichloromethyl group, and a trifluoromethyl group.

Examples of the C1 to C3 hydrocarbon group optionally having one or more atoms or groups selected from a group consisting of —$OR^7$ and halogen atoms in the present invention include a methyl group, an ethyl group, a propyl group, an isopropyl group, an iodomethyl group, a bromomethyl group, a chloromethyl group, a fluoromethyl group, a difluoromethyl group, a chlorodifluoromethyl group, a bromodifluoromethyl group, a dichlorofluoromethyl group, a trichloromethyl group, a trifluoromethyl group, a 1-fluoroethyl group, a 2-fluoroethyl group, a 1-fluoropropyl group, a 2-fluoropropyl group, a 3-fluoropropyl group, a 1-fluoro-1-methylethyl group, a 1-chloroethyl group, a 2-chloroethyl group, a 1-chloropropyl group, a 2-chloropropyl group, a 3-chloropropyl group, a 1-chloro-1-methylethyl group, a 1-bromoethyl group, a 2-bromoethyl group, a 1-bromopropyl group, a 2-bromopropyl group, a 3-bromopropyl group, a 1-bromo-1-methylethyl group, a 2,2,2-trifluoroethyl group, a 1,1,2,2-tetrafluoroethyl group, a 1,1,2,2,2-pentafluoroethyl group, a hydroxymethyl group, a 1-hydroxyethyl group, a 2-hydroxyethyl group, a 1-hydroxypropyl group, a 2-hydroxypropyl group, a 3-hydroxypropyl group, a 1-hydroxy-1-methylethyl group, a 1-(S-methyldithiocarbonyloxy)methyl group, a 1-(S-methyldithiocarbonyloxy)ethyl group, a 2-(S-methyldithiocarbonyloxy)ethyl group, a 1-(S-methyldithiocarbonyloxy)propyl group, a 2-(S-methyldithiocarbonyloxy)propyl group, a 3-(S-methyldithiocarbonyloxy)propyl group, a 1-(S-methyldithiocarbonyloxy)-1-methylethyl group, a 1-(S-ethyldithiocarbonyloxy)methyl group, a 1-(S-ethyldithiocarbonyloxy)ethyl group, a 2-(S-ethyldithiocarbonyloxy)ethyl group, a 1-(S-ethyldithiocarbonyloxy)propyl group, a 2-(S-ethyldithiocarbonyloxy)propyl group, a 3-(S-ethyldithiocarbonyloxy)propyl group, a 1-(S-ethyldithiocarbonyloxy)-1-methylethyl group, a 1-(S-propyldithiocarbonyloxy)methyl group, a 1-(S-propyldithiocarbonyloxy)ethyl group, a 2-(S-propyldithiocarbonyloxy)ethyl group, a 1-(S-propyldithiocarbonyloxy)propyl group, a 2-(S-propyldithiocarbonyloxy)propyl group, a 3-(S-propyldithiocarbonyloxy)propyl group, a 1-(S-propyldithiocarbonyloxy)-1-methylethyl group, a 1-(S-isopropyldithiocarbonyloxy)methyl group, a 1-(S-isopropyldithiocarbonyloxy)ethyl group, a 2-(S-isopropyldithiocarbonyloxy)ethyl group, a 1-(S-isopropyldithiocarbonyloxy)propyl group, a 2-(S-isopropyldithiocarbonyloxy)propyl group, a 3-(S-isopropyldithiocarbonyloxy)propyl group, and a 1-(S-isopropyldithiocarbonyloxy)-1-methylethyl group.

Examples of the C1 to C3 hydrocarbon group optionally having one or more halogen atoms in the present invention include a methyl group, an ethyl group, a propyl group, an isopropyl group, an iodomethyl group, a bromomethyl group, a chloromethyl group, a fluoromethyl group, a difluoromethyl group, a chlorodifluoromethyl group, a bromodifluoromethyl group, a dichlorofluoromethyl group, a trichloromethyl group, a trifluoromethyl group, a 1-fluoroethyl group, a 2-fluoroethyl group, a 1-fluoropropyl group, a 2-fluoropropyl group, a 3-fluoropropyl group, a 1-fluoro-1-methylethyl group, a 1-chloroethyl group, a 2-chloroethyl group, a 1-chloropropyl group, a 2-chloropropyl group, a 3-chloropropyl group, a 1-chloro-1-methylethyl group, a 1-bromoethyl group, a 2-bromoethyl group, a 1-bromopropyl group, a 2-bromopropyl group, a 3-bromopropyl group, a 1-bromo-1-methylethyl group, a 2,2,2-trifluoroethyl group, a 1,1,2,2-tetrafluoroethyl group, and a 1,1,2,2,2-pentafluoroethyl group.

Examples of the C3 to C8 cycloalkyl group optionally having one or more atoms or groups selected from group B in the present invention include a cyclopropyl group, a 1-methylcyclopropyl group, a 2,2-dichlorocyclopropyl group, a 2,2-difluorocyclopropyl group, a cyclopentyl group, a 1-methylcyclopentyl group, a 2-methylcyclopentyl group, a 3-methylcyclopentyl group, a 2-chlorocyclopentyl group, a 3-chlorocyclopentyl group, a 2-fluorocyclopentyl group, a 3-fluorocyclopentyl group, a 2,2-difluorocyclopentyl group, a 3,3-difluorocyclopentyl group, a 2-cyanocyclopentyl group, a 3-cyanocyclopentyl group, a cyclohexyl group, a 1-methylcyclohexyl group, a 2-methylcyclohexyl group, a 3-methylcyclohexyl group, a 4-methylcyclohexyl group, a 2-chlorocyclohexyl group, a 3-chlorocyclohexyl group, a 4-chlorocyclohexyl group, a 4,4-dichlorocyclohexyl group, a 4,4-difluorocyclohexyl group, a 4-cyanocyclohexyl group, a cycloheptyl group, and a cyclooctyl group.

Examples of the indanyl group optionally having one or more atoms or groups selected from group B in the present invention include 1-indanyl groups optionally having one or more atoms or groups selected from group B such as an 1-indanyl group, a 4-methyl-1-indanyl group, a 5-methyl-1-indanyl group, a 4-cyano-1-indanyl group, a 5-cyano-1-indanyl group, a 4-carboxyl-1-indanyl group, a 5-carboxyl-1-indanyl group, a 4-hydroxyl-1-indanyl group, a 5-hydroxyl-1-indanyl group, a 4-trifluoromethyl-1-indanyl group, a 5-trifluoromethyl-1-indanyl group, a 4-trifluoromethoxy-1-indanyl group, a 5-trifluoromethoxy-1-indanyl group, a 4-trifluoromethylthio-1-indanyl group, a 5-trifluoromethylthio-1-indanyl group, a 4-trifluoromethanesulfinyl- 1-indanyl group, a 5-trifluoromethanesulfinyl-1-indanyl group, a 4-trifluoromethanesulfonyl-1-indanyl group, a 5-trifluoromethanesulfonyl-1-indanyl group, a 4-fluoro-1-indanyl group, a 5-fluoro-1-indanyl group, a 4-chloro-1-indanyl group, a 5-chloro-1-indanyl group, a 4-bromo-1-indanyl group, and a 5-bromo-1-indanyl group; and 2-indanyl groups optionally having one or more atoms or groups selected from group B such as a 2-indanyl group, a 4-methyl-2-indanyl group, a 5-methyl-2-indanyl group, a 6-methyl-2-indanyl group, a 7-methyl-2-indanyl group, a 4-cyano-2-indanyl group, a 5-cyano-2-indanyl group, a 6-cyano-2-indanyl group, a 7-cyano-2-indanyl group, a 4-carboxyl-2-indanyl group, a 5-carboxyl-2-indanyl group, a 6-carboxyl-2-indanyl group, a 7-carboxyl-2-indanyl group, a 4-hydroxyl-2-indanyl group, a 5-hydroxyl-2-indanyl group, a 6-hydroxyl-2-indanyl group, a 7-hydroxyl-2-indanyl group, a 4-trifluoromethyl-2-indanyl group, a 5-trifluoromethyl-2-indanyl group, a 6-trifluoromethyl-2-indanyl group, a 7-trifluoromethyl-2-indanyl group, a 4-trifluoromethoxy-2-indanyl group, a 5-trifluoromethoxy-2-indanyl group, a 6-trifluoromethoxy-2-indanyl group, a 7-trifluoromethoxy-2-indanyl group, a 4-trifluoromethylthio-2-indanyl group, a 5-trifluoromethylthio-2-indanyl group, a 6-trifluoromethylthio-2-indanyl group, a 7-trifluoromethylthio-2-indanyl group, a 4-trifluoromethanesulfinyl-2-indanyl group, a 5-trifluoromethanesulfinyl-2-indanyl group, a 6-trifluoromethanesulfinyl-2-indanyl group, a 7-trifluoromethanesulfinyl-2-indanyl group, a 4-trifluoromethanesulfonyl-2-indanyl group, a 5-trifluoromethanesulfonyl-2-indanyl group, a 6-trifluoromethanesulfonyl-2-indanyl group, a 7-trifluoromethanesulfonyl-2-indanyl group, a 4-fluoro-2-indanyl group, a 5-fluoro-2-indanyl group, a 6-fluoro-2-indanyl group, a 7-fluoro-2-indanyl group, a 4-chloro-2-indanyl group, a 5-chloro-2-indanyl group, a 6-chloro-2-indanyl group, a 7-chloro-2-indanyl group, a 4-bromo-2-indanyl group, a 5-bromo-2-indanyl group, a 6-bromo-2-indanyl group, and a 7-bromo-2-indanyl group.

Examples of the 1,2,3,4-tetrahydronaphthyl group optionally having one or more atoms or groups selected from group B in the present invention include "1-(1,2,3,4-tetrahydronaphthyl) groups optionally having one or more atoms or groups selected from group B" such as a 1-(5-methyl-1,2,3,4-tetrahydronaphthyl) group, a 1-(6-methyl-1,2,3,4-tetrahydronaphthyl) group, a 1-(7-methyl-1,2,3,4-tetrahydronaphthyl) group, a 1-(8-methyl-1,2,3,4-tetrahydronaphthyl) group, a 1-(5-cyano-1,2,3,4-tetrahydronaphthyl) group, a 1-(6-cyano-1,2,3,4 tetrahydronaphthyl) group, a 1-(7-cyano-1,2,3,4-tetrahydronaphthyl) group, a 1-(8-cyano-1,2,3,4-tetrahydronaphthyl) group, a 1-(5-carboxyl-1,2,3,4-tetrahydronaphthyl) group, a 1-(6-carboxyl-1,2,3,4-tetrahydronaphthyl) group, a 1-(7-carboxyl-1,2,3,4 tetrahydronaphthyl) group, a 1-(8-carboxyl-1,2,3,4-tetrahydronaphthyl) group, a 1-(5-hydroxyl-1,2,3,4-tetrahydronaphthyl) group, a 1-(6-hydroxyl-1,2,3,4-tetrahydronaphthyl) group, a 1-(7-hydroxyl-1,2,3,4-tetrahydronaphthyl) group, a 1-(8-hydroxyl-1,2,3,4 tetrahydronaphthyl) group, a 1-(5-trifluoromethyl-1,2,3,4-tetrahydronaphthyl) group, a 1-(6-trifluoromethyl-1,2,3,4-tetrahydronaphthyl) group, a 1-(7-trifluoromethyl-1,2,3,4-tetrahydronaphthyl) group, a 1-(8-trifluoromethyl-1,2,3,4-tetrahydronaphthyl) group, a 1-(5-trifluoromethylthio-1,2,3,4-tetrahydronaphthyl) group, a 1-(6-trifluoromethylthio-1,2,3,4-tetrahydronaphthyl) group, a 1-(7-trifluoromethylthio-1,2,3,4-tetrahydronaphthyl) group, a 1-(8-trifluoromethylthio-1,2,3,4-tetrahydronaphthyl) group, a 1-(5-trifluoromethoxy-1,2,3,4-tetrahydronaphthyl) group, a 1-(6-trifluoromethoxy-1,2,3,4-tetrahydronaphthyl) group, a 1-(7-trifluoromethoxy-1,2,3,4-tetrahydronaphthyl) group, a 1-(8-trifluoromethoxy-1,2,3,4-tetrahydronaphthyl) group, a 1-(5-trifluoromethanesulfinyl-1,2,3,4-tetrahydronaphthyl) group, a 1-(6-trifluoromethanesulfinyl-1,2,3,4-tetrahydronaphthyl) group, a 1-(7-trifluoromethanesulfinyl-1,2,3,4-tetrahydronaphthyl) group, a 1-(8-trifluoromethanesulfinyl-1,2,3,4-tetrahydronaphthyl) group, a 1-(5-trifluoromethanesulfonyl-1,2,3,4-tetrahydronaphthyl) group, a 1-(6-trifluoromethanesulfonyl-1,2,3,4-tetrahydronaphthyl) group, a 1-(7-trifluoromethanesulfonyl-1,2,3,4-tetrahydronaphthyl) group, and a 1-(8-trifluoromethanesulfonyl-1,2,3,4-tetrahydronaphthyl) group; and 2-(1,2,3,4-tetrahydronaphthyl) groups optionally having one or more atoms or groups selected from group B such as a 2-(5-methyl-1,2,3,4-tetrahydronaphthyl) group, a 2-(6-methyl-1,2,3,4-tetrahydronaphthyl) group, a 2-(7-methyl-1,2,3,4-tetrahydronaphthyl) group, a 2-(8-methyl-1,2,3,4-tetrahydronaphthyl) group, a 2-(5-cyano-1,2,3,4-tetrahydronaphthyl) group, a 2-(6-cyano-1,2,3,4-tetrahydronaphthyl) group, a 2-(7-cyano-1,2,3,4-tetrahydronaphthyl) group, a 2-(8-cyano-1,2,3,4-tetrahydronaphthyl) group, a 2-(5-carboxyl-1,2,3,4-tetrahydronaphthyl) group, a 2-(6-carboxyl-1,2,3,4-tetrahydronaphthyl) group, a 2-(7-carboxyl-1,2,3,4-tetrahydronaphthyl) group, a 2-(8-carboxyl-1,2,3,4-tetrahydronaphthyl) group, a 2-(5-hydroxyl-1,2,3,4-tetrahydronaphthyl) group, a 2-(6-hydroxyl-1,2,3,4-tetrahydronaphthyl) group, a 2-(7-hydroxyl-1,2,3,4-tetrahydronaphthyl) group, a 2-(8-hydroxyl-1,2,3,4-tetrahydronaphthyl) group, a 2-(5-trifluoromethyl-1,2,3,4-tetrahydronaphthyl) group, a 2-(6-trifluoromethyl-1,2,3,4-tetrahydronaphthyl) group, a 2-(7-trifluoromethyl-1,2,3,4-tetrahydronaphthyl) group, a 2-(8-trifluoromethyl-1,2,3,4-tetrahydronaphthyl) group, a 2-(5-trifluoromethylthio-1,2,3,4-tetrahydronaphthyl) group, a 2-(6-trifluoromethylthio-1,2,3,4-tetrahydronaphthyl) group, a 2-(7-trifluoromethylthio-1,2,3,4-tetrahydronaphthyl) group, a 2-(8-trifluoromethylthio-1,2,3,4-tetrahydronaphthyl) group, a 2-(5-trifluoromethoxy-1,2,3,4-tetrahydronaphthyl) group, a 2-(6-trifluoromethoxy-1,2,3,4-tetrahydronaphthyl) group, a 2-(7-trifluoromethoxy-1,2,3,4-tetrahydronaphthyl) group, a 2-(8-trifluoromethoxy-1,2,3,4-tetrahydronaphthyl) group, a 2-(5-trifluoromethanesulfinyl 1,2,3,4-tetrahydronaphthyl) group, a 2-(6-trifluoromethanesulfinyl-1,2,3,4-tetrahydronaphthyl) group, a 2-(7-trifluoromethanesulfinyl-1,2,3,4-tetrahydronaphthyl) group, a 2-(8 trifluoromethanesulfinyl-1,2,3,4-tetrahydronaphthyl) group, a 2-(5-trifluoromethanesulfonyl-1,2,3,4-tetrahydronaphthyl) group, a 2-(6-trifluoromethanesulfonyl-1,2,3,4-tetrahydronaphthyl) group, a 2-(7-trifluoromethanesulfonyl-1,2,3,4-tetrahydronaphthyl) group, and a 2-(8-trifluoromethanesulfonyl-1,2,3,4-tetrahydronaphthyl) group.

Examples of the phenyl group optionally having one or more atoms or groups selected from group B in the present invention include a phenyl group, a 2-cyanophenyl group, a 3-cyanophenyl group, a 4-cyanophenyl group, a 2-nitrophenyl group, a 3-nitrophenyl group, a 4-nitrophenyl group, a 2-carboxylphenyl group, a 3-carboxylphenyl group, a 4-carboxylphenyl group, a 2-hydroxylphenyl group, a 3-hydroxylphenyl group, a 4-hydroxylphenyl group, a 2-(N-methylcarboamide)phenyl group, a 3-(N-methylcarboamide)phenyl group, a 4-(N-methylcarboamide)phenyl group, a 2-(N,N-dimethylcarboamide)phenyl group, a 3-(N,N-dimethylcarboamide)phenyl group, a 4-(N,N-dimethylcarboamide)phenyl group, a 2-methylphenyl group, a 3-methylphenyl group, a 4-methylphenyl group, a 3,4-dimethylphenyl group, a 2-ethylphenyl group, a 3-ethylphenyl group, a 4-ethylphenyl group, a 2-trifluoromethylphenyl group, a 3-trifluoromethylphenyl group, a 4-trifluoromethylphenyl group, a 3,4-ditrifluoromethylphenyl group, a 2-methoxyphenyl group, a 3-methoxyphenyl group, a 4-methoxyphenyl group, a 2-trifluoromethoxyphenyl group, a 3-trifluoromethoxyphenyl group, a 4-trifluoromethoxy phenyl group, a 2-methylthiophenyl group, a 3-methylthiophenyl group, a 4-methylthiophenyl group, a 2-methylsulfinylphenyl group, a 3-methylsulfinylphenyl group, a 4-methylsulfinylphenyl group, a 2-methylsulfonylphenyl group, a 3-methylsulfonylphenyl group, a 4-methylsulfonylphenyl group, a 2-trifluoromethylthiophenyl group, a 3-trifluoromethylthiophenyl group, a 4-trifluoromethylthiophenyl group, a 2-trifluoromethylsulfinylphenyl group, a 3-trifluoromethylsulfinylphenyl group, a 4-trifluoromethylsulfinylphenyl group, a 2-trifluoromethylsulfonylphenyl group, a 3-trifluoromethylsulfonylphenyl group, a 4-trifluoromethylsulfonylphenyl group, a 2-methoxycarbonylphenyl group, a 3-methoxycarbonylphenyl group, a 4-methoxycarbonylphenyl group, a 2-vinylphenyl group, a 3-vinylphenyl group, a 4-vinylphenyl group, a 2-(2',2'-difluorovinyl)phenyl group, a 3-(2',2'-difluorovinyl)phenyl group, a 4-(2',2'-difluorovinyl)phenyl group, an 2-ethynylphenyl group, an 3-ethynylphenyl group, an 4-ethynylphenyl group, a 2-(2'-fluoroethynyl)phenyl group, a 3-(2'-fluoroethynyl)phenyl group, a 4-(2'-fluoroethynyl) phenyl group, a 2-fluorophenyl group, a 3-fluorophenyl group, a 4-fluorophenyl group, a 3,4-difluorophenyl group, a pentafluorophenyl group, a 2-chlorophenyl group, a 3-chlorophenyl group, a 4-chlorophenyl group, and a 3,4-dichlorophenyl group.

Examples of the phenoxy group optionally having one or more atoms or groups selected from group B in the present invention include a phenoxy group, a 2-cyanophenoxy group, a 3-cyanophenoxy group, a 4-cyanophenoxy group, a 2-nitrophenoxy group, a 3-nitrophenoxy group, a 4-nitrophenoxy group, a 2-carboxylphenoxy group, a 3-carboxylphenoxy group, a 4-carboxylphenoxy group, a 2-hydroxylphenoxy group, a 3-hydroxylphenoxy group, a 4-hydroxylphenoxy group, a 2-(N-methylcarboamide)phenoxy group, a 3-(N-methylcarboamide)phenoxy group, a 4-(N-methylcarboamide)phenoxy group, a 2-(N,N-dimethylcarboamide)phenoxy group, a 3-(N,N-dimethylcarboamide)phenoxy group, a 4-(N,N-dimethylcarboamide)phenoxy group, a 2-methylphenoxy group, a 3-methylphenoxy group, a 4-methylphenoxy group, a 3,4-dimethylphenoxy group, a 2-ethylphenoxy group, a 3-ethylphenoxy group, a 4-ethylphenoxy group, a 2-trifluoromethylphenoxy group, a 3-trifluoromethylphenoxy group, a 4-trifluoromethylphenoxy group, a 3,4-ditrifluoromethylphenoxy group, a 2-methoxyphenoxy group, a 3-methoxyphenoxy group, a 4-methoxyphenoxy group, a 2-trifluoromethoxyphenoxy group, a 3-trifluoromethoxyphenoxy group, a 4-trifluoromethoxyphenoxy group, a 2-methylthiophenoxy group, a 3-methylthiophenoxy group, a 4-methylthiophenoxy group, a 2-methylsulfinylphenoxy group, a 3-methylsulfinylphenoxy group, a 4-methylsulfinylphenoxy group, a 2-methylsulfonylphenoxy group, a 3-methylsulfonylphenoxy group, a 4-methylsulfonylphenoxy group, a 2-trifluoromethylthiophenoxy group, a 3-trifluorormethylthiophenoxy group, a 4-trifluoromethylthiophenoxy group, a 2-trifluoromethylsulfinylphenoxy group, a 3-trifluoromethyl sulfinylphenoxy group, a 4-trifluoromethylsulfinylphenoxy group, a 2-trifluoromethylsulfonylphenoxy group, a 3-trifluoromethylsulfonylphenoxy group, a 4-trifluoromethylsulfonylphenoxy group, a 2-methoxycarbonylphenoxy group, a 3-methoxycarbonylphenoxy group, a 4-methoxycarbonylphenoxy group, a 2-vinylphenoxy group, a 3-vinylphenoxy group, a 4-vinylphenoxy group, a 2-(2',2'-difluorovinyl) phenoxy group, a 3-(2',2'-difluorovinyl)phenoxy group, a 4-(2',2'-difluorovinyl)phenoxy group, an 2-ethynylphenoxy group, an 3-ethynylphenoxy group, an 4-ethynylphenoxy group, a 2-(2'-fluoroethynyl)phenoxy group, a 3-(2'-fluoroethynyl)phenoxy group, a 4-(2'-fluoroethynyl) phenoxy group, a 2-fluorophenoxy group, a 3-fluorophenoxy group, a 4-fluorophenoxy group, a 3,4-difluorophenoxy group, a pentafluorophenoxy group, a 2-chlorophenoxy group, a 3-chlorophenoxy group, a 4-chlorophenoxy group, and a 3,4-dichlorophenoxy group.

Examples of the naphthyl group optionally having one or more atoms or groups selected from group B in the present invention include 1-naphthyl groups optionally having one or more atoms or groups selected from group B such as a 1-naphthyl group, a 2-cyano-1-naphthyl group, a 3-cyano-1-naphthyl group, a 4-cyano-1-naphthyl group, a 2-nitro-1-naphthyl group, a 3-nitro-1-naphthyl group, a 4-nitro-1-naphthyl group, a 2-carboxyl-1-naphthyl group, a 3-carboxyl-1-naphthyl group, a 4-carboxyl-1-naphthyl group, a 2-hydroxyl-1-naphthyl group, a 3-hydroxyl-1-naphthyl group, a 4-hydroxyl-1-naphthyl group, a 2-methyl-1-naphthyl group, a 3-methyl-1-naphthyl group, a 4-methyl-1-naphthyl group, a 2-trifluoromethyl-1-naphthyl group, a 3-trifluoromethyl-1-naphthyl group, a 4-trifluoromethyl-1-naphthyl group, a 2-methoxy-1-naphthyl group, a 3-methoxy-1-naphthyl group, a 4-methoxy-1-naphthyl group, a 2-trifluoromethoxy-1-naphthyl group, a 3-trifluoromethoxy-1-naphthyl group, a 4-trifluoromethoxy-1-naphthyl group, a 2-trifluoromethylthio-1-naphthyl group, a 3-trifluoromethylthio-1-naphthyl group, a 4-trifluoromethylthio-1-naphthyl group, a 2-trifluoromethylsulfinyl-1-naphthyl group, a 3-trifluoromethylsulfinyl-1-naphthyl group, a 4-trifluoromethylsulfinyl-1-naphthyl group, a 2-trifluoromethylsulfonyl-1-naphthyl group, a 3-trifluoromethylsulfonyl-1-naphthyl group, a 4-trifluoromethylsulfonyl-1-naphthyl group, a 2-methoxycarbonyl-1-naphthyl group, a 3-methoxycarbonyl-1-naphthyl group, a 4-methoxycarbonyl-1-naphthyl group, a 2-vinyl-1-naphthyl group, a 3-vinyl-1-naphthyl group, a 4-vinyl-1-naphthyl group, a 2-(2',2'-difluorovinyl)-1-naphthyl group, a 3-(2',2'-difluorovinyl)-1-naphthyl group, a 4-(2',2'-difluorovinyl)-1-naphthyl group, an 2-ethynyl-1-naphthyl group, an 3-ethynyl-1-naphthyl group, an 4-ethynyl-1-naphthyl group, a 2-(2'-fluoroethynyl)-1-naphthyl group, a 3-(2'-fluoroethynyl)-1-naphthyl group, a 4-(2'-fluoroethynyl)-1-naphthyl group, a 2-fluoro-1-naphthyl group, a 3-fluoro-1-naphthyl group, a 4-fluoro-1-naphthyl group, a 2-chloro-1-naphthyl group, a 3-chloro-1-naphthyl group, and a 4-chloro-1-naphthyl group; and 2-naphthyl groups optionally having one or more atoms or groups selected from group B such as a 2-naphthyl group, a 1-cyano-2-naphthyl group, a 3-cyano-2-naphthyl group, a 4-cyano-2-naphthyl group, a 1-nitro-2-naphthyl group, a 3-nitro-2-naphthyl group, a 4-nitro-2-naphthyl group, a 1-carboxyl-2-naphthyl group, a 3-carboxyl-2-naphthyl group, a 4-carboxyl-2-naphthyl group, a 1-hydroxyl-2-naphthyl group, a 3-hydroxyl-2-naphthyl group, a 4-hydroxyl-2-naphthyl group, a 1-methyl-2-naphthyl group, a 3-methyl-2-naphthyl group, a 4-methyl-2-naphthyl group, a 1-trifluoromethyl-2-naphthyl group, a 3-trifluoromethyl-2-naphthyl group, a 4-trifluoromethyl-2-naphthyl group, a 1-methoxy-2-naphthyl group, a 3-methoxy-2-naphthyl group, a 4-methoxy-2-naphthyl group, a 1-trifluoromethoxy-2-naphthyl group, a 3-trifluoromethoxy-2-naphthyl group, a 4-trifluoromethoxy-2-naphthyl group, a 1-trifluoromethylthio-2-naphthyl group, a 3-trifluoromethylthio-2-naphthyl group, a 4-trifluoromethylthio-2-naphthyl group, a 1-trifluoromethylsulfinyl-2-naphthyl group, a 3-trifluororomethylsulfinyl-2-naphthyl group, a 4-trifluoromethylsulfinyl-2-naphthyl group, a 1-trifluoromethylsulfonyl-2-naphthyl group, a 3-trifluoromethylsulfonyl-2-naphthyl group, a 4-trifluoromethylsulfonyl-2-naphthyl group, a 1-methoxycarbonyl-2-naphthyl group, a 3-methoxycarbonyl-2-naphthyl group, a 4-methoxycarbonyl-2-naphthyl group, a 1-vinyl-2-naphthyl group, a 3-vinyl-2-naphthyl group, a 4-vinyl-2-naphthyl group, a 1-(2',2'-difluorovinyl)-2-naphthyl group, a 3-(2',2'-difluorovinyl)-2-naphthyl group, a 4-(2',2'-difluorovinyl)-2-naphthyl group, an 1-ethynyl-2-naphthyl group, an 3-ethynyl-2-naphthyl group, an 4-ethynyl-2-naphthyl group, a 1-(2'-fluoroethynyl)-2-naphthyl group, a 3-(2'-fluoroethynyl)-2-naphthyl group, a 4-(2'-fluoroethynyl)-2-naphthyl group, a 1-fluoro-2-naphthyl group, a 3-fluoro-2-naphthyl group, a 4-fluoro-2-naphthyl group, a 1-chloro-2-naphthyl group, a 3-chloro-2-naphthyl group, and a 4-chloro-2-naphthyl group.

Examples of the pyridyl group optionally having one or more atoms or groups selected from group B in the present invention include 2-pyridyl groups optionally having one or more atoms or groups selected from group B such as a 2-pyridyl group, a 3-cyano-2-pyridyl group, a 4-cyano-2-pyridyl group, a 5-cyano-2-pyridyl group, a 6-cyano-2-pyridyl group, a 3-nitro-2-pyridyl group, a 4-nitro-2-pyridyl group, a 5-nitro-2-pyridyl group, a 6-nitro-2-pyridyl group, a 3-carboxyl-2-pyridyl group, a 4-carboxyl-2-pyridyl group, a 5-carboxyl-2-pyridyl group, a 6-carboxyl-2-pyridyl group, a 3-hydroxyl-2-pyridyl group, a 4-hydroxyl-2-pyridyl group, a 5-hydroxyl-2-pyridyl group, a 6-hydroxyl-2-pyridyl group, a 3-methyl-2-pyridyl group, a 4-methyl-2-pyridyl group, a 5-methyl-2-pyridyl group, a 6-methyl-2-pyridyl group, a 3-trifluoromethyl-2-pyridyl group, a 4-trifluoromethyl-2-pyridyl group, a 5-trifluoromethyl-2-pyridyl group, a 6-trifluoromethyl-2-pyridyl group, a 3-methoxy-2-pyridyl group, a 4-methoxy-2-pyridyl group, a 5-methoxy-2-pyridyl group, a 6-methoxy-2-pyridyl group, a 3-trifluoromethoxy-2-pyridyl group, a 4-trifluoromethoxy-2-pyridyl group, a 5-trifluoromethoxy-2-pyridyl group, a 6-trifluoromethoxy-2-pyridyl group, a 3-methoxycarbonyl-2-pyridyl group, a 4-methoxycarbonyl-2-pyridyl group, a 5-methoxycarbonyl-2-pyridyl group, a 6-methoxycarbonyl-2-pyridyl group, a 3-vinyl-2-pyridyl group, a 4-vinyl-2-pyridyl group, a 5-vinyl-2-pyridyl group, a 6-vinyl-2-pyridyl group, a 3-(2',2'-difluorovinyl)-2-pyridyl group, a 4-(2',2'-difluorovinyl)-2-pyridyl group, a 5-(2',2'-difluorovinyl)-2-pyridyl group, a 6-(2',2'-difluorovinyl)-2-pyridyl group, an 3-ethynyl-2-pyridyl group, an 4-ethynyl-2-pyridyl group, an 5-ethynyl-2-pyridyl group, an 6-ethynyl-2-pyridyl group, a 3-(2'-fluoroethynyl)-2-pyridyl group, a 4-(2'-fluoroethynyl)-2-pyridyl group, a 5-(2'-fluoroethynyl)-2-pyridyl group, a 6-(2'-fluoroethynyl)-2-pyridyl group, a 3-fluoro-2-pyridyl group, a 4-fluoro-2-pyridyl group, a 5-fluoro-2-pyridyl group, a 6-fluoro-2-pyridyl group, a 3-chloro-2-pyridyl group, a 4-chloro-2-pyridyl group, a 5-chloro-2-pyridyl group, and a 6-chloro-2-pyridyl group; 3-pyridyl groups optionally having one or more atoms or groups selected from group B such as a 3-pyridyl group, a 2-cyano-3-pyridyl group, a 4-cyano-3-pyridyl group, a 5-cyano-3-pyridyl group, a 6-cyano-3-pyridyl group, a 2-nitro-3-pyridyl group, a 4-nitro-3-pyridyl group, a 5-nitro-3-pyridyl group, a 6-nitro-3-pyridyl group, a 2-carboxyl-3-pyridyl group, a 4-carboxyl-3-pyridyl group, a 5-carboxyl-3-pyridyl group, a 6-carboxyl-3-pyridyl group, a 2-hydroxyl-3-pyridyl group, a 4-hydroxyl-3-pyridyl group, a 5-hydroxyl-3-pyridyl group, a 6-hydroxyl-3-pyridyl group, a 2-methyl-3-pyridyl group, a 4-methyl-3-pyridyl group, a 5-methyl-3-pyridyl group, a 6-methyl-3-pyridyl group, a 2-trifluoromethyl-3-pyridyl group, a 4-trifluoromethyl-3-pyridyl group, a 5-trifluoromethyl-3-pyridyl group, a 6-trifluoromethyl-3-pyridyl group, a 2-methoxy-3-pyridyl group, a 4-methoxy-3-pyridyl group, a 5-methoxy-3-pyridyl group, a 6-methoxy-3-pyridyl group, a 2-trifluoromethoxy-3-pyridyl group, a 4-trifluoromethoxy-3-pyridyl group, a 5-trifluoromethoxy-3-pyridyl group, a 6-trifluoromethoxy-3-pyridyl group, a 2-methoxycarbonyl-3-pyridyl group, a 4-methoxycarbonyl-3-pyridyl group, a 5-methoxycarbonyl-3-pyridyl group, a 6-methoxycarbonyl-3-pyridyl group, a 2-vinyl-3-pyridyl group, a 4-vinyl-3-pyridyl group, a 5-vinyl-3-pyridyl group, a 6-vinyl-3-pyridyl group, a 2-(2',2'-difluorovinyl)-3-pyridyl group, a 4-(2',2'-difluorovinyl)-3-pyridyl group, a 5-(2',2'-difluorovinyl)-3-pyridyl group, a 6-(2',2'-difluorovinyl)-3-pyridyl group, an 2-ethynyl-3-pyridyl group, an 4-ethynyl-3-pyridyl group, an 5-ethynyl-3-pyridyl group, an 6-ethynyl-3-pyridyl group, a 2-(2'-fluoroethynyl)-3-pyridyl group, a 4-(2'-fluoroethynyl)-3-pyridyl group, a 5-(2'-fluoroethynyl)-3-pyridyl group, a 6-(2'-fluoroethynyl)-3-pyridyl group, a 2-fluoro-3-pyridyl group, a 4-fluoro-3-pyridyl group, a 5-fluoro-3-pyridyl group, a 6-fluoro-3-pyridyl group, a 2-chloro-3-pyridyl group, a 4-chloro-3-pyridyl group, a 5-chloro-3-pyridyl group, and a 6-chloro-3-pyridyl group; and 4-pyridyl groups optionally having one or more atoms or groups selected from group B such as a 4-pyridyl group, a 2-cyano-4-pyridyl group, a 3-cyano-4-pyridyl group, a 2-nitro-4-pyridyl group, a 3-nitro-4-pyridyl group, a 2-carboxyl-4-pyridyl group, a 3-carboxyl-4-pyridyl group, a 2-hydroxyl-4-pyridyl group, a 3-hydroxyl-4-pyridyl group, a 2-methyl-4-pyridyl group, a 3-methyl-4-pyridyl group, a 2-trifluoromethyl-4-pyridyl group, a 3-trifluoromethyl-4-pyridyl group, a 2-methoxy-4-pyridyl group, a 3-methoxy-4-pyridyl group, a 2-trifluoromethoxy-4-pyridyl group, a 3-trifluoromethoxy-4-pyridyl group, a 2-methoxycarbonyl-4-pyridyl group, a 3-methoxycarbonyl-4-pyridyl group, a 2-vinyl-4-pyridyl group, a 3-vinyl-4-pyridyl group, a 2-(2',2'-difluorovinyl)-4-pyridyl group, a 3-(2',2'-difluorovinyl)-4-pyridyl group, an 2-ethynyl-4-pyridyl group, an 3-ethynyl-4-pyridyl group, a 2-(2'-fluoroethynyl)-4-pyridyl group, a 3-(2'-fluoroethynyl)-4-pyridyl group, a 2-fluoro-4-pyridyl group, a 3-fluoro-4-pyridyl group, a 2-chloro-4-pyridyl group, and a 3-chloro-4-pyridyl group.

Examples of the quinolyl group optionally having one or more atoms or groups selected from group B in the present invention include 2-quinolyl groups optionally having one or more atoms or groups selected from group B such as a 2-quinolyl group, a 5-cyano-2-quinolyl group, a 6-cyano-2-quinolyl group, a 7-cyano-2-quinolyl group, a 8-cyano-2-quinolyl group, a 5-nitro-2-quinolyl group, a 6-nitro-2-quinolyl group, a 7-nitro-2-quinolyl group, a 7-nitro-2-quinolyl group, a 5-carboxyl-2-quinolyl group, a 6-carboxyl-2-quinolyl group, a 7-carboxyl-2-quinolyl group, a 8-carboxyl-2-quinolyl group, a 5-hydroxyl-2-quinolyl group, a 6-hydroxyl-2-quinolyl group, a 7-hydroxyl-2-quinolyl group, a 8-hydroxyl-2-quinolyl group, a 5-methyl-2-quinolyl group, a 6-methyl-2-quinolyl group, a 7-methyl-2-quinolyl group, a 8-methyl-2-quinolyl group, a 5-trifluoromethyl-2-quinolyl group, a 6-trifluoromethyl-2-quinolyl group, a 7-trifluoromethyl-2-quinolyl group, a 8-trifluoromethyl-2-quinolyl group, a 5-methoxy-2-quinolyl group, a 6-methoxy-2-quinolyl group, a 7-methoxy-2-quinolyl group, a 8-methoxy-2-quinolyl group, a 5-trifluoromethoxy-2-quinolyl group, a 6-trifluoromethoxy-2-quinolyl group, a 7-trifluoromethoxy-2-quinolyl group, a 8-trifluoromethoxy-2-quinolyl group, a 5-methoxycarbonyl-2-quinolyl group, a 6-methoxycarbonyl-2-quinolyl group, a 7-methoxycarbonyl-2-quinolyl group, a 8-methoxycarbonyl-2-quinolyl group, a 5-vinyl-2-quinolyl group, a 6-vinyl-2-quinolyl group, a 7-vinyl-2-quinolyl group, a 8-vinyl-2-quinolyl group, a 5-(2',2'-difluorovinyl)-2-quinolyl group, a 6-(2',2'-difluorovinyl)-2-quinolyl group, a 7-(2',2'-difluorovinyl)-2-quinolyl group, a 8-(2',2'-difluorovinyl)-2-quinolyl group, an 5-ethynyl-2-quinolyl group, an 6-ethynyl-2-quinolyl group, an 7-ethynyl-2-quinolyl group, an 8-ethynyl-2-quinolyl group, a 5-(2'-fluoroethynyl)-2-quinolyl group, a 6-(2'-fluoroethynyl)-2-quinolyl group, a 7-(2'-fluoroethynyl)-2-quinolyl group, a 8-(2'-fluoroethynyl)-2-quinolyl group, a 5-fluoro-2-quinolyl group, a 6-fluoro-2-quinolyl group, a 7-fluoro-2-quinolyl group, a 8-fluoro-2-quinolyl group, a 5,6,7,8-tetrafluoro-2-quinolyl group, a 5-chloro-2-quinolyl group, a 6-chloro-2-quinolyl group, a 7-chloro-2-quinolyl group, and a 8-chloro-2-quinolyl group; 3-quinolyl groups optionally having one or more atoms or groups selected from group B such as a 3-quinolyl group, a 5-cyano-3-quinolyl group, a 6-cyano-3-quinolyl group, a 7-cyano-3-quinolyl group, a 8-cyano-3-quinolyl group, a 5-nitro-3-quinolyl group, a 6-nitro-3-quinolyl group, a 7-nitro-3-quinolyl group, a 7-nitro-3-quinolyl group, a 5-carboxyl-3-quinolyl group, a 6-carboxyl-3-quinolyl group, a 7-carboxyl-3-quinolyl group, a 8-carboxyl-3-quinolyl group, a 5-hydroxyl-3-quinolyl group, a 6-hydroxyl-3-quinolyl group, a 7-hydroxyl-3-quinolyl group, a 8-hydroxyl-3-quinolyl group, a 5-methyl-3-quinolyl group, a 6-methyl-3-quinolyl group, a 7-methyl-3-quinolyl group, a 8-methyl-3-quinolyl group, a 5-trifluoromethyl-3-quinolyl group, a 6-trifluoromethyl-3-quinolyl group, a 7-trifluoromethyl-3-quinolyl group, a 8-trifluoromethyl-3-quinolyl group, a 5-methoxy-3-quinolyl group, a 6-methoxy-3-quinolyl group, a 7-methoxy-3-quinolyl group, a 8-methoxy-3-quinolyl group, a 5-trifluoromethoxy-3-quinolyl group, a 6-trifluoromethoxy-3-quinolyl group, a 7-trifluoromethoxy-3-quinolyl group, a 8-trifluoromethoxy-3-quinolyl group, a 5-methoxycarbonyl-3-quinolyl group, a 6-methoxycarbonyl-3-quinolyl group, a 7-methoxycarbonyl-3-quinolyl group, a 8-methoxycarbonyl-3-quinolyl group, a 5-vinyl-3-quinolyl group, a 6-vinyl-3-quinolyl group, a 7-vinyl-3-quinolyl group, a 8-vinyl-3-quinolyl group, a 5-(2',2'-difluorovinyl)-3-quinolyl group, a 6-(2',2'-difluorovinyl)-3-quinolyl group, a 7-(2',2'-difluorovinyl)-3-quinolyl group, a 8-(2',2'-difluorovinyl)-3-quinolyl group, an 5-ethynyl-3-quinolyl group, an 6-ethynyl-3-quinolyl group, an 7-ethynyl-3-quinolyl group, an 8-ethynyl-3-quinolyl group, a 5-(2'-fluoroethynyl)-3-quinolyl group, a 6-(2'-fluoroethynyl)-3-quinolyl group, a 7-(2'-fluoroethynyl)-3-quinolyl group, a 8-(2'-fluoroethynyl)-3-quinolyl group, a 5-fluoro-3-quinolyl group, a 6-fluoro-3-quinolyl group, a 7-fluoro-3-quinolyl group, a 8-fluoro-3-quinolyl group, a 5,6,7,8-tetrafluoro-3-quinolyl group, a 5-chloro-3-quinolyl group, a 6-chloro-3-quinolyl group, a 7-chloro-3-quinolyl group, and a 8-chloro-3-quinolyl group; and 4-quinolyl groups optionally having one or more atoms or groups selected from group B such as a 4-quinolyl group, a 2-cyano-4-quinolyl group, a 3-cyano-4-quinolyl group, a 2-nitro-4-quinolyl group, a 3-nitro-4-quinolyl group, a 2-carboxyl-4-quinolyl group, a 3-carboxyl-4-quinolyl group, a 2-hydroxyl-4-quinolyl group, a 3-hydroxyl-4-quinolyl group, a 2-methyl-4-quinolyl group, a 3-methyl-4-quinolyl group, a 2-trifluoromethyl-4-quinolyl group, a 3-trifluoromethyl-4-quinolyl group, a 2-methoxy-4-quinolyl group, a 3-methoxy-4-quinolyl group, a 2-trifluoromethoxy-4-quinolyl group, a 3-trifluoromethoxy-4-quinolyl group, a 2-methoxycarbonyl-4-quinolyl group, a 3-methoxycarbonyl-4-quinolyl group, a 2-vinyl-4-quinolyl group, a 3-vinyl-4-quinolyl group, a 2-(2',2'-difluorovinyl)-4-quinolyl group, a 3-(2',2'-difluorovinyl)-4-quinolyl group, an 2-ethynyl-4-quinolyl group, an 3-ethynyl-4-quinolyl group, a 2-(2'-fluoroethynyl)-4-quinolyl group, a 3-(2'-fluoroethynyl)-4-quinolyl group, a 2-fluoro-4-quinolyl group, a 3-fluoro-4-quinolyl group, a 2-chloro-4-quinolyl group, and a 3-chloro-4-quinolyl group.

Examples of the furyl group optionally having one or more atoms or groups selected from group B in the present invention include 2-furyl groups optionally having one or more atoms or groups selected from group B such as a 2-furyl group, a 3-cyano-2-furyl group, a 4-cyano-2-furyl group, a 5-cyano-2-furyl group, a 3-nitro-2-furyl group, a 4-nitro-2-furyl group, a 5-nitro-2-furyl group, a 3-carboxyl-2-furyl group, a 4-carboxyl-2-furyl group, a 5-carboxyl-2-furyl group, a 3-hydroxyl-2-furyl group, a 4-hydroxyl-2-furyl group, a 5-hydroxyl-2-furyl group, a 3-methyl-2-furyl group, a 4-methyl-2-furyl group, a 5-methyl-2-furyl group, a 3-trifluoromethyl-2-furyl group, a 4-trifluoromethyl-2-furyl group, a 5-trifluoromethyl-2-furyl group, a 3-methoxy-2-furyl group, a 4-methoxy-2-furyl group, a 5-methoxy-2-furyl group, a 3-trifluoromethoxy-2-furyl group, a 4-trifluoromethoxy-2-furyl group, a 5-trifluoromethoxy-2-furyl group, a 3-methoxycarbonyl-2-furyl group, a 4-methoxycarbonyl-2-furyl group, a 5-methoxycarbonyl-2-furyl group, a 3-vinyl-2-furyl group, a 4-vinyl-2-furyl group, a 5-vinyl-2-furyl group, a 3-(2',2'-difluorovinyl)-2-furyl group, a 4-(2',2'-difluorovinyl)-2-furyl group, a 5-(2',2'-difluorovinyl)-2-furyl group, an 3-ethynyl-2-furyl group, an 4-ethynyl-2-furyl group, an 5-ethynyl-2-furyl group, a 3-(2'-fluoroethynyl)-2-furyl group, a 4-(2'-fluoroethynyl)-2-furyl group, a 5-(2'-fluoroethynyl)-2-furyl group, a 3-fluoro-2-furyl group, a 4-fluoro-2-furyl group, a 5-fluoro-2-furyl group, a 3-chloro-2-furyl group, a 4-chloro-2-furyl group, and a 5-chloro-2-furyl group; and 3-furyl groups optionally having one or more atoms or groups selected from group B such as a 3-furyl group, a 2-cyano-3-furyl group, a 4-cyano-3-furyl group, a 5-cyano-3-furyl group, a 2-nitro-3-furyl group, a 4-nitro-3-furyl group, a 5-nitro-3-furyl group, a 2-carboxyl-3-furyl group, a 4-carboxyl-3-furyl group, a 5-carboxyl-3-furyl group, a 2-hydroxyl-3-furyl group, a 4-hydroxyl-3-furyl group, a 5-hydroxyl-3-furyl group, a 2-methyl-3-furyl group, a 4-methyl-3-furyl group, a 5-methyl-3-furyl group, a 2-trifluoromethyl-3-furyl group, a 4-trifluoromethyl-3-furyl group, a 5-trifluoromethyl-3-furyl group, a 2-methoxy-3-furyl group, a 4-methoxy-3-furyl group, a 5-methoxy-3-furyl group, a 2-trifluoromethoxy-3-furyl group, a 4-trifluoromethoxy-3-furyl group, a 5-trifluoromethoxy-3-furyl group, a 2-methoxycarbonyl-3-furyl group, a 4-methoxycarbonyl-3-furyl group, a 5-methoxycarbonyl-3-furyl group, a 2-vinyl-3-furyl group, a 4-vinyl-3-furyl group, a 5-vinyl-3-furyl group, a 2-(2',2'-difluorovinyl)-3-furyl group, a 4-(2',2'-difluorovinyl)-3-furyl group, a 5-(2',2'-difluorovinyl)-3-furyl group, an 2-ethynyl-3-furyl group, an 4-ethynyl-3-furyl group, an 5-ethynyl-3-furyl group, a 2-(2'-fluoroethynyl)-3-furyl group, a 4-(2'-fluoroethynyl)-3-furyl group, a 5-(2'-fluoroethynyl)-3-furyl group, a 2-fluoro-3-furyl group, a 4-fluoro-3-furyl group, a 5-fluoro-3-furyl group, a 2-chloro-3-furyl group, a 4-chloro-3-furyl group, and a 5-chloro-3-furyl group.

Examples of the thienyl group optionally having one or more atoms or groups selected from group B in the present invention include 2-thienyl groups optionally having one or more atoms or groups selected from group B such as a 2-thienyl group, a 3-cyano-2-thienyl group, a 4-cyano-2-thienyl group, a 5-cyano-2-thienyl group, a 3-nitro-2-thienyl group, a 4-nitro-2-thienyl group, a 5-nitro-2-thienyl group, a 3-carboxyl-2-thienyl group, a 4-carboxyl-2-thienyl group, a 5-carboxyl-2-thienyl group, a 3-hydroxyl-2-thienyl group, a 4-hydroxyl-2-thienyl group, a 5-hydroxyl-2-thienyl group, a 3-methyl-2-thienyl group, a 4-methyl-2-thienyl group, a 5-methyl-2-thienyl group, a 3-trifluoromethyl-2-thienyl group, a 4-trifluoromethyl-2-thienyl group, a 5-trifluoromethyl-2-thienyl group, a 3-methoxy-2-thienyl group, a 4-methoxy-2-thienyl group, a 5-methoxy-2-thienyl group, a 3-trifluoromethoxy-2-thienyl group, a 4-trifluoromethoxy-2-thienyl group, a 5-trifluoromethoxy-2-thienyl group, a 3-methoxycarbonyl-2-thienyl group, a 4-methoxycarbonyl-2-thienyl group, a 5-methoxycarbonyl-2-thienyl group, a 3-vinyl-2-thienyl group, a 4-vinyl-2-thienyl group, a 5-vinyl-2-thienyl group, a 3-(2',2'-difluorovinyl)-2-thienyl group, a 4-(2',2'-difluorovinyl)-2-thienyl group, a 5-(2',2'-difluorovinyl)-2-thienyl group, an 3-ethynyl-2-thienyl group, an 4-ethynyl-2-thienyl group, an 5-ethynyl-2-thienyl group, a 3-(2'-fluoroethynyl)-2-thienyl group, a 4-(2'-fluoroethynyl)-2-thienyl group, a 5-(2'-fluoroethynyl)-2-thienyl group, a 3-fluoro-2-thienyl group, a 4-fluoro-2-thienyl group, a 5-fluoro-2-thienyl group, a 3-chloro-2-thienyl group, a 4-chloro-2-thienyl group, and a 5-chloro-2-thienyl group; and 3-thienyl groups optionally having one or more atoms or groups selected from group B such as a 3-thienyl group, a 2-cyano-3-thienyl group, a 4-cyano-3-thienyl group, a 5-cyano-3-thienyl group, a 2-nitro-3-thienyl group, a 4-nitro-3-thienyl group, a 5-nitro-3-thienyl group, a 2-carboxyl-3-thienyl group, a 4-carboxyl-3-thienyl group, a 5-carboxyl-3-thienyl group, a 2-hydroxyl-3-thienyl group, a 4-hydroxyl-3-thienyl group, a 5-hydroxyl-3-thienyl group, a 2-methyl-3-thienyl group, a 4-methyl-3-thienyl group, a 5-methyl-3-thienyl group, a 2-trifluoromethyl-3-thienyl group, a 4-trifluoromethyl-3-thienyl group, a 5-trifluoromethyl-3-thienyl group, a 2-methoxy-3-thienyl group, a 4-methoxy-3-thienyl group, a 5-methoxy-3-thienyl group, a 2-trifluoromethoxy-3-thienyl group, a 4-trifluoromethoxy-3-thienyl group, a 5-trifluoromethoxy-3-thienyl group, a 2-methoxycarbonyl-3-thienyl group, a 4-methoxycarbonyl-3-thienyl group, a 5-methoxycarbonyl-3-thienyl group, a 2-vinyl-3-thienyl group, a 4-vinyl-3-thienyl group, a 5-vinyl-3-thienyl group, a 2-(2',2'-difluorovinyl)-3-thienyl group, a 4-(2',2'-difluorovinyl)-3-thienyl group, a 5-(2',2'-difluorovinyl)-3-thienyl group, an 2-ethynyl-3-thienyl group, an 4-ethynyl-3-thienyl group, an 5-ethynyl-3-thienyl group, a 2-(2'-fluoroethynyl)-3-thienyl group, a 4-(2'-fluoroethynyl)-3-thienyl group, a 5-(2'-fluoroethynyl)-3-thienyl group, a 2-fluoro-3-thienyl group, a 4-fluoro-3-thienyl group, a 5-fluoro-3-thienyl group, a 2-chloro-3-thienyl group, a 4-chloro-3-thienyl group, and a 5-chloro-3-thienyl group.

Examples of the benzofuranyl group optionally having one or more atoms or groups selected from group B in the present invention include 2-(1-benzofuranyl) groups optionally having one or more atoms or groups selected from group B such as a 2-(1-benzofuranyl) group, a 4-cyano-2-(1-benzofuranyl) group, a 5-cyano-2-(1-benzofuranyl) group, a 6-cyano-2-(1-benzofuranyl) group, a 7-cyano-2-(1-benzofuranyl) group, a 4-nitro-2-(1-benzofuranyl) group, a 5-nitro-2-(1-benzofuranyl) group, a 6-nitro-2-(1-benzofuranyl) group, a 7-nitro-2-(1-benzofuranyl) group, a 4-carboxyl-2-(1-benzofuranyl) group, a 5-carboxyl-2-(1-benzofuranyl) group, a 6-carboxyl-2-(1-benzofuranyl) group, a 7-carboxyl-2-(1-benzofuranyl) group, a 4-hydroxyl-2-(1-benzofuranyl) group, a 5-hydroxyl-2-(1-benzofuranyl) group, a 6-hydroxyl-2-(1-benzofuranyl) group, a 7-hydroxyl-2-(1-benzofuranyl) group, a 4-methyl-2-(1-benzofuranyl) group, a 5-methyl-2-(1-benzofuranyl) group, a 6-methyl-2-(1-benzofuranyl) group, a 7-methyl-2-(1-benzofuranyl) group, a 4-trifluoromethyl-2-(1-benzofuranyl) group, a 5-trifluoromethyl-2-(1-benzofuranyl) group, a 6-trifluoromethyl-2-(1-benzofuranyl) group, a 7-trifluoromethyl-2-(1-benzofuranyl) group, a 4-methoxy-2-(1-benzofuranyl) group, a 5-methoxy-2-(1-benzofuranyl) group, a 6-methoxy-2-(1-benzofuranyl) group, a 7-methoxy-2-(1-benzofuranyl) group, a 4-trifluoromethoxy-2-(1-benzofuranyl) group, a 5-trifluoromethoxy-2-(1-benzofuranyl) group, a 6-trifluoromethoxy-2-(1-benzofuranyl) group, a 7-trifluoromethoxy-2-(1-benzofuranyl) group, a 4-methoxycarbonyl-2-(1-benzofuranyl) group, a 5-methoxycarbonyl-2-(1-benzofuranyl) group, a 6-methoxycarbonyl-2-(1-benzofuranyl) group, a 7-methoxycarbonyl-2-(1-benzofuranyl) group, a 4-vinyl-2-(1-benzofuranyl) group, a 5-vinyl-2-(1-benzofuranyl) group, a 6-vinyl-2-(1-benzofuranyl) group, a 7-vinyl-2-(1-benzofuranyl) group, a 4-(2',2'-difluorovinyl)-2-(1-benzofuranyl) group, a 5-(2',2'-difluorovinyl)-2-(1-benzofuranyl) group, a 6-(2',2'-difluorovinyl)-2-(1-benzofuranyl) group, a 7-(2',2'-difluorovinyl)-2-(1-benzofuranyl) group, an 4-ethynyl-2-(1-benzofuranyl) group, an 5-ethynyl-2-(1-benzofuranyl) group, an 6-ethynyl-2-(1-benzofuranyl) group, an 7-ethynyl-2-(1-benzofuranyl) group, a 4-(2'-fluoroethynyl)-2-(1-benzofuranyl) group, a 5-(2'-fluoroethynyl)-2-(1-benzofuranyl) group, a 6-(2'-fluoroethynyl)-2-(1-benzofuranyl) group, a 7-(2'-fluoroethynyl)-2-(1-benzofuranyl) group, a 4-fluoro-2-(1-benzofuranyl) group, a 5-fluoro-2-(1-benzofuranyl) group, a 6-fluoro-2-(1-benzofuranyl) group, a 7-fluoro-2-(1-benzofuranyl) group, a 4,5,6,7-tetrafluoro-2-(1-benzofuranyl) group, a 4-chloro-2-(1-benzofuranyl) group, a 5-chloro-2-(1-benzofuranyl) group, a 6-chloro-2-(1-benzofuranyl) group, and a 7-chloro-2-(1-benzofuranyl) group; and 3-(1-benzofuranyl) groups optionally having one or more atoms or groups selected from group B such as a 3-(1-benzofuranyl) group, a 4-cyano-3-(1-benzofuranyl) group, a 5-cyano-3-(1-benzofuranyl) group, a 6-cyano-3-(1-benzofuranyl) group, a 7-cyano-3-(1-benzofuranyl) group, a 4-nitro-3-(1-benzofuranyl) group, a 5-nitro-3-(1-benzofuranyl) group, a 6-nitro-3-(1-benzofuranyl) group, a 7-nitro-3-(1-benzofuranyl) group, a 4-carboxyl-3-(1-benzofuranyl) group, a 5-carboxyl-3-(1-benzofuranyl) group, a 6-carboxyl-3-(1-benzofuranyl) group, a 7-carboxyl-3-(1-benzofuranyl) group, a 4-hydroxyl-3-(1-benzofuranyl) group, a 5-hydroxyl-3-(1-benzofuranyl) group, a 6-hydroxyl-3-(1-benzofuranyl) group, a 7-hydroxyl-3-(1-benzofuranyl) group, a 4-methyl-3-(1-benzofuranyl) group, a 5-methyl-3-(1-benzofuranyl) group, a 6-methyl-3-(1-benzofuranyl) group, a 7-methyl-3-(1-benzofuranyl) group, a 4-trifluoromethyl-3-(1-benzofuranyl) group, a 5-trifluoromethyl-3-(1-benzofuranyl) group, a 6-trifluoromethyl-3-(1-benzofuranyl) group, a 7-trifluoromethyl-3-(1-benzofuranyl) group, a 4-methoxy-3-(1-benzofuranyl) group, a 5-methoxy-3-(1-benzofuranyl) group, a 6-methoxy-3-(1-benzofuranyl) group, a 7-methoxy-3-(1-benzofuranyl) group, a 4-trifluoromethoxy-3-(1-benzofuranyl) group, a 5-trifluoromethoxy-3-(1-benzofuranyl) group, a 6-trifluoromethoxy-3-(1-benzofuranyl) group, a 7-trifluoromethoxy-3-(1-benzofuranyl) group, a 4-methoxycarbonyl-3-(1-benzofuranyl) group, a 5-methoxycarbonyl-3-(1-benzofuranyl) group, a 6-methoxycarbonyl-3-(1-benzofuranyl) group, a 7-methoxycarbonyl-3-(1-benzofuranyl) group, a 4-vinyl-3-(1-benzofuranyl) group, a 5-vinyl-3-(1-benzofuranyl) group, a 6-vinyl-3-(1-benzofuranyl) group, a 7-vinyl-3-(1-benzofuranyl) group, a 4-(2',2'-difluorovinyl)-3-(1-benzofuranyl) group, a 5-(2',2'-difluorovinyl)-3-(1-benzofuranyl)

group, a 6-(2',2'-difluorovinyl)-3-(1-benzofuranyl) group, a 7-(2',2'-difluorovinyl)-3-(1-benzofuranyl) group, an 4-ethynyl-3-(1-benzofuranyl) group, an 5-ethynyl-3-(1-benzofuranyl) group, an 6-ethynyl-3-(1-benzofuranyl) group, an 7-ethynyl-3-(1-benzofuranyl) group, a 4-(2'-fluoroethynyl)-3-(1-benzofuranyl) group, a 5-(2'-fluoroethynyl)-3-(1-benzofuranyl) group, a 6-(2'-fluoroethynyl)-3-(1-benzofuranyl) group, a 7-(2'-fluoroethynyl)-3-(1-benzofuranyl) group, a 4-fluoro-3-(1-benzofuranyl) group, a 5-fluoro-3-(1-benzofuranyl) group, a 6-fluoro-3-(1-benzofuranyl) group, a 7-fluoro-3-(1-benzofuranyl) group, a 4,5,6,7-tetrafluoro-3-(1-benzofuranyl) group, a 4-chloro-3-(1-benzofuranyl) group, a 5-chloro-3-(1-benzofuranyl) group, a 6-chloro-3-(1-benzofuranyl) group, and a 7-chloro-3-(1-benzofuranyl) group.

Examples of the benzothienyl group optionally having one or more atoms or groups selected from group B in the present invention include 2-(1-benzothienyl) groups optionally having one or more atoms or groups selected from group B such as a 2-(1-benzothienyl) group, a 4-cyano-2-(1-benzothienyl) group, a 5-cyano-2-(1-benzothienyl) group, a 6-cyano-2-(1-benzothienyl) group, a 7-cyano-2-(1-benzothienyl) group, a 4-nitro-2-(1-benzothienyl) group, a 5-nitro-2-(1-benzothienyl) group, a 6-nitro-2-(1-benzothienyl) group, a 7-nitro-2-(1-benzothienyl) group, a 4-carboxyl-2-(1-benzothienyl) group, a 5-carboxyl-2-(1-benzothienyl) group, a 6-carboxyl-2-(1-benzothienyl) group, a 7-carboxyl-2-(1-benzothienyl) group, a 4-hydroxyl-2-(1-benzothienyl) group, a 5-hydroxyl-2-(1-benzothienyl) group, a 6-hydroxyl-2-(1-benzothienyl) group, a 7-hydroxyl-2-(1-benzothienyl) group, a 4-methyl-2-(1-benzothienyl) group, a 5-methyl-2-(1-benzothienyl) group, a 6-methyl-2-(1-benzothienyl) group, a 7-methyl-2-(1-benzothienyl) group, a 4-trifluoromethyl-2-(1-benzothienyl) group, a 5-trifluoromethyl-2-(1-benzothienyl) group, a 6-trifluoromethyl-2-(1-benzothienyl) group, a 7-trifluoromethyl-2-(1-benzothienyl) group, a 4-methoxy-2-(1-benzothienyl) group, a 5-methoxy-2-(1-benzothienyl) group, a 6-methoxy-2-(1-benzothienyl) group, a 7-methoxy-2-(1-benzothienyl) group, a 4-trifluoromethoxy-2-(1-benzothienyl) group, a 5-trifluoromethoxy-2-(1-benzothienyl) group, a 6-trifluoromethoxy-2-(1-benzothienyl) group, a 7-trifluoromethoxy-2-(1-benzothienyl) group, a 4-methoxycarbonyl-2-(1-benzothienyl) group, a 5-methoxycarbonyl-2-(1-benzothienyl) group, a 6-methoxycarbonyl-2-(1-benzothienyl) group, a 7-methoxycarbonyl-2-(1-benzothienyl) group, a 4-vinyl-2-(1-benzothienyl) group, a 5-vinyl-2-(1-benzothienyl) group, a 6-vinyl-2-(1-benzothienyl) group, a 7-vinyl-2-(1-benzothienyl) group, a 4-(2',2'-difluorovinyl)-2-(1-benzothienyl) group, a 5-(2',2'-difluorovinyl)-2-(1-benzothienyl) group, a 6-(2',2'-difluorovinyl)-2-(1-benzothienyl) group, a 7-(2',2'-difluorovinyl)-2-(1-benzothienyl) group, an 4-ethynyl-2-(1-benzothienyl) group, an 5-ethynyl-2-(1-benzothienyl) group, an 6-ethynyl-2-(1-benzothienyl) group, an 7-ethynyl-2-(1-benzothienyl) group, a 4-(2'-fluoroethynyl)-2-(1-benzothienyl) group, a 5-(2'-fluoroethynyl)-2-(1-benzothienyl) group, a 6-(2'-fluoroethynyl)-2-(1-benzothienyl) group, a 7-(2'-fluoroethynyl)-2-(1-benzothienyl) group, a 4-fluoro-2-(1-benzothienyl) group, a 5-fluoro-2-(1-benzothienyl) group, a 6-fluoro-2-(1-benzothienyl) group, a 7-fluoro-2-(1-benzothienyl) group, a 4,5,6,7-tetrafluoro-2-(1-benzothienyl) group, a 4-chloro-2-(1-benzothienyl) group, a 5-chloro-2-(1-benzothienyl) group, a 6-chloro-2-(1-benzothienyl) group, and a 7-chloro-2-(1-benzothienyl) group; and 3-(1-benzothienyl) groups optionally having one or more atoms or groups selected from group B such as a 3-(1-benzothienyl) group, a 4-cyano-3-(1-benzothienyl) group, a 5-cyano-3-(1-benzothienyl) group, a 6-cyano-3-(1-benzothienyl) group, a 7-cyano-3-(1-benzothienyl) group, a 4-nitro-3-(1-benzothienyl) group, a 5-nitro-3-(1-benzothienyl) group, a 6-nitro-3-(1-benzothienyl) group, a 7-nitro-3-(1-benzothienyl) group, a 4-carboxyl-3-(1-benzothienyl) group, a 5-carboxyl-3-(1-benzothienyl) group, a 6-carboxyl-3-(1-benzothienyl) group, a 7-carboxyl-3-(1-benzothienyl) group, a 4-hydroxyl-3-(1-benzothienyl) group, a 5-hydroxyl-3-(1-benzothienyl) group, a 6-hydroxyl-3-(1-benzothienyl) group, a 7-hydroxyl-3-(1-benzothienyl) group, a 4-methyl-3-(1-benzothienyl) group, a 5-methyl-3-(1-benzothienyl) group, a 6-methyl-3-(1-benzothienyl) group, a 7-methyl-3-(1-benzothienyl) group, a 4-trifluoromethyl-3-(1-benzothienyl) group, a 5-trifluoromethyl-3-(1-benzothienyl) group, a 6-trifluoromethyl-3-(1-benzothienyl) group, a 7-trifluoromethyl-3-(1-benzothienyl) group, a 4-methoxy-3-(1-benzothienyl) group, a 5-methoxy-3-(1-benzothienyl) group, a 6-methoxy-3-(1-benzothienyl) group, a 7-methoxy-3-(1-benzothienyl) group, a 4-trifluoromethoxy-3-(1-benzothienyl) group, a 5-trifluoromethoxy-3-(1-benzothienyl) group, a 6-trifluoromethoxy-3-(1-benzothienyl) group, a 7-trifluoromethoxy-3-(1-benzothienyl) group, a 4-methoxycarbonyl-3-(1-benzothienyl) group, a 5-methoxycarbonyl-3-(1-benzothienyl) group, a 6-methoxycarbonyl-3-(1-benzothienyl) group, a 7-methoxycarbonyl-3-(1-benzothienyl) group, a 4-vinyl-3-(1-benzothienyl) group, a 5-vinyl-3-(1-benzothienyl) group, a 6-vinyl-3-(1-benzothienyl) group, a 7-vinyl-3-(1-benzothienyl) group, a 4-(2',2'-difluorovinyl)-3-(1-benzothienyl) group, a 5-(2',2'-difluorovinyl)-3-(1-benzothienyl) group, a 6-(2',2'-difluorovinyl)-3-(1-benzothienyl) group, a 7-(2',2'-difluorovinyl)-3-(1-benzothienyl) group, an 4-ethynyl-3-(1-benzothienyl) group, an 5-ethynyl-3-(1-benzothienyl) group, an 6-ethynyl-3-(1-benzothienyl) group, an 7-ethynyl-3-(1-benzothienyl) group, a 4-(2'-fluoroethynyl)-3-(1-benzothienyl) group, a 5-(2'-fluoroethynyl)-3-(1-benzothienyl) group, a 6-(2'-fluoroethynyl)-3-(1-benzothienyl) group, a 7-(2'-fluoroethynyl)-3-(1-benzothienyl) group, a 4-fluoro-3-(1-benzothienyl) group, a 5-fluoro-3-(1-benzothienyl) group, a 6-fluoro-3-(1-benzothienyl) group, a 7-fluoro-3-(1-benzothienyl) group, a 4,5,6,7-tetrafluoro-3-(1-benzothienyl) group, a 4-chloro-3-(1-benzothienyl) group, a 5-chloro-3-(1-benzothienyl) group, a 6-chloro-3-(1-benzothienyl) group, and a 7-chloro-3-(1-benzothienyl) group.

Examples of the 1,3-benzodioxolanyl groups optionally having one or more atoms or groups selected from group B in the present invention include 2-(1,3-benzodioxolanyl) groups optionally having one or more atoms or groups selected from group B such as a 2-(1,3-benzodioxolanyl) group, a 4-cyano-2-(1,3-benzodioxolanyl) group, a 5-cyano-2-(1,3-benzodioxolanyl) group, a 4-nitro-2-(1,3-benzodioxolanyl) group, a 5-nitro-2-(1,3-benzodioxolanyl) group, a 4-carboxyl-2-(1,3-benzodioxolanyl) group, a 5-carboxyl-2-(1,3-benzodioxolanyl) group, a 4-hydroxyl-2-(1,3-benzodioxolanyl) group, a 5-hydroxyl-2-(1,3-benzodioxolanyl) group, a 4-methyl-2-(1,3-benzodioxolanyl) group, a 5-methyl-2-(1,3-benzodioxolanyl) group, a 4-trifluoromethyl-2-(1,3-benzodioxolanyl) group, a 5-trifluoromethyl-2-(1,3-benzodioxolanyl) group, a 4-methoxy-2-(1,3-benzodioxolanyl) group, a 5-methoxy-2-(1,3-benzodioxolanyl) group, a 4-trifluoromethoxy-2-(1,3-benzodioxolanyl) group, a 5-trifluoromethoxy-2-(1,3-benzodioxolanyl) group, a 4-methoxycarbonyl-2-(1,3-benzodioxolanyl) group, a 5-methoxycarbonyl-2-(1,3-benzodioxolanyl) group, a 4-vinyl-2-(1,3-benzodioxolanyl) group, a 5-vinyl-2-(1,3-benzodioxolanyl) group, an 4-ethynyl-2-(1,3-benzodioxolanyl) group, an 5-ethynyl-2-(1,3- benzodioxolanyl) group, a 4-fluoro-2-(1,3-benzodioxolanyl) group, a 5-fluoro-2-(1,3-benzodioxolanyl) group, a 4,5,6,7-tetrafluoro-2-(1,3-benzodioxolanyl) group, a 4-chloro-2-(1,3-benzodioxolanyl) group, and a 5-chloro-2-(1,3-benzodioxolanyl) group; 4-(1,3-benzodioxolanyl) groups optionally having one or more atoms or groups selected from group B such as a 4-(1,3-benzodioxolanyl) group, a 4-(1,3-benzodioxolanyl) group, a 5-cyano-4-(1,3-benzodioxolanyl) group, a 6-cyano-4-(1,3-benzodioxolanyl) group, a 7-cyano-4-(1,3-benzodioxolanyl) group, a 5-nitro-4-(1,3-benzodioxolanyl) group, a 6-nitro-4-(1,3-benzodioxolanyl) group, a 7-nitro-4-(1,3-benzodioxolanyl) group, a 5-carboxyl-4-(1,3-benzodioxolanyl) group, a 6-carboxyl-4-(1,3-benzodioxolanyl) group, a 7-carboxyl-4-(1,3-benzodioxolanyl) group, a 5-hydroxyl-4-(1,3-benzodioxolanyl) group, a 6-hydroxyl-4-(1,3-benzodioxolanyl) group, a 7-hydroxyl-4-(1,3-benzodioxolanyl) group, a 5-methyl-4-(1,3-benzodioxolanyl) group, a 6-methyl-4-(1,3-benzodioxolanyl) group, a 7-methyl-4-(1,3-benzodioxolanyl) group, a 5-trifluoromethyl-4-(1,3-benzodioxolanyl) group, a 6-trifluoromethyl-4-(1,3-benzodioxolanyl) group, a 7-trifluoromethyl-4-(1,3-benzodioxolanyl) group, a 5-methoxy-4-(1,3-benzodioxolanyl) group, a 6-methoxy-4-(1,3-benzodioxolanyl) group, a 7-methoxy-4-(1,3-benzodioxolanyl) group, a 5-trifluoromethoxy-4-(1,3-benzodioxolanyl) group, a 6-trifluoromethoxy-4-(1,3-benzodioxolanyl) group, a 7-trifluoromethoxy-4-(1,3-benzodioxolanyl) group, a 5-methoxycarbonyl-4-(1,3-benzodioxolanyl) group, a 6-methoxycarbonyl-4-(1,3-benzodioxolanyl) group, a 7-methoxycarbonyl-4-(1,3-benzodioxolanyl) group, a 5-vinyl-4-(1,3-benzodioxolanyl) group, a 6-vinyl-4-(1,3-benzodioxolanyl) group, a 7-vinyl-4-(1,3-benzodioxolanyl) group, an 5-ethynyl-4-(1,3-benzodioxolanyl) group, an 6-ethynyl-4-(1,3-benzodioxolanyl) group, an 7-ethynyl-4-(1,3-benzodioxolanyl) group, a 5-fluoro-4-(1,3-benzodioxolanyl) group, a 6-fluoro-4-(1,3-benzodioxolanyl) group, a 7-fluoro-4-(1,3-benzodioxolanyl) group, a 4,5,6,7-tetrafluoro-4-(1,3-benzodioxolanyl) group, a 4-chloro-4-(1,3-benzodioxolanyl) group, a 5-chloro-4-(1,3-benzodioxolanyl) group, a 6-chloro-4-(1,3-benzodioxolanyl) group, a 7-chloro-4-(1,3-benzodioxolanyl) group, and a 4-(2,2-difluoro-1,3-benzodioxolanyl) group; and 5-(1,3-benzodioxolanyl) groups optionally having one or more atoms or groups selected from group B such as a 5-(1,3-benzodioxolanyl) group, a 5-(1,3-benzodioxolanyl) group, a 4-cyano-5-(1,3-benzodioxolanyl) group, a 6-cyano-5-(1,3-benzodioxolanyl) group, a 7-cyano-5-(1,3-benzodioxolanyl) group, a 4-nitro-5-(1,3-benzodioxolanyl) group, a 6-nitro-5-(1,3-benzodioxolanyl) group, a 7-nitro-5-(1,3-benzodioxolanyl) group, a 4-carboxyl-5-(1,3-benzodioxolanyl) group, a 6-carboxyl-5-(1,3-benzodioxolanyl) group, a 7-carboxyl-5-(1,3-benzodioxolanyl) group, a 4-hydroxyl-5-(1,3-benzodioxolanyl) group, a 6-hydroxyl-5-(1,3-benzodioxolanyl) group, a 7-hydroxyl-5-(1,3-benzodioxolanyl) group, a 4-methyl-5-(1,3-benzodioxolanyl) group, a 6-methyl-5-(1,3-benzodioxolanyl) group, a 7-methyl-5-(1,3-benzodioxolanyl) group, a 4-trifluoromethyl-5-(1,3-benzodioxolanyl) group, a 6-trifluoromethyl-5-(1,3-benzodioxolanyl) group, a 7-trifluoromethyl-5-(1,3-benzodioxolanyl) group, a 4-methoxy-5-(1,3-benzodioxolanyl) group, a 6-methoxy-5-(1,3-benzodioxolanyl) group, a 7-methoxy-5-(1,3-benzodioxolanyl) group, a 4-trifluoromethoxy-5-(1,3-benzodioxolanyl) group, a 6-trifluoromethoxy-5-(1,3-benzodioxolanyl) group, a 7-trifluoromethoxy-5-(1,3-benzodioxolanyl) group, a 4-methoxycarbonyl-5-(1,3-benzodioxolanyl) group, a 6-methoxycarbonyl-5-(1,3-benzodioxolanyl) group, a 7-methoxycarbonyl-4-(1,3-benzodioxolanyl) group, a 4-vinyl-5-(1,3-benzodioxolanyl) group, a 6-vinyl-5-(1,3-benzodioxolanyl) group, a 7-vinyl-5-(1,3-benzodioxolanyl) group, an 4-ethynyl-5-(1,3-benzodioxolanyl) group, an 6-ethynyl-5-(1,3-benzodioxolanyl) group, an 7-ethynyl-5-(1,3-benzodioxolanyl) group, a 4-fluoro-5-(1,3-benzodioxolanyl) group, a 6-fluoro-5-(1,3-benzodioxolanyl) group, a 7-fluoro-5-(1,3-benzodioxolanyl) group, a 4,5,6,7-tetrafluoro-5-(1,3-benzodioxolanyl) group, a 4-chloro-5-(1,3-benzodioxolanyl) group, a 6-chloro-5-(1,3-benzodioxolanyl) group, a 7-chloro-5-(1,3-benzodioxolanyl) group, and a 5-(2,2-difluoro-1,3-benzodioxolanyl) group.

Examples of the 1,4-benzodioxanyl groups optionally having one or more atoms or groups selected from group B in the present invention include 2-(1,4-benzodioxanyl) groups optionally having one or more atoms or groups selected from group B such as a 2-(1,4-benzodioxanyl) group, a 5-cyano-2-(1,4-benzodioxanyl) group, a 6-cyano-2-(1,4-benzodioxanyl) group, a 5-nitro-2-(1,4-benzodioxanyl) group, a 6-nitro-2-(1,4-benzodioxanyl) group, a 5-carboxyl-2-(1,4-benzodioxanyl) group, a 6-carboxyl-2-(1,4-benzodioxanyl) group, a 5-hydroxyl-2-(1,4-benzodioxanyl) group, a 6-hydroxyl-2-(1,4-benzodioxanyl) group, a 5-methyl-2-(1,4-benzodioxanyl) group, a 6-methyl-2-(1,4-benzodioxanyl) group, a 5-trifluoromethyl-2-(1,4-benzodioxanyl) group, a 6-trifluoromethyl-2-(1,4-benzodioxanyl) group, a 5-methoxy-2-(1,4-benzodioxanyl) group, a 6-methoxy-2-(1,4-benzodioxanyl) group, a 5-trifluoromethoxy-2-(1,4-benzodioxanyl) group, a 6-trifluoromethoxy-2-(1,4-benzodioxanyl) group, a 5-methoxycarbonyl-2-(1,4-benzodioxanyl) group, a 6-methoxycarbonyl-2-(1,4-benzodioxanyl) group, a 5-vinyl-2-(1,4-benzodioxanyl) group, a 6-vinyl-2-(1,4-benzodioxanyl) group, an 5-ethynyl-2-(1,4-benzodioxanyl) group, an 6-ethynyl-2-(1,4-benzodioxanyl) group, a 5-fluoro-2-(1,4-benzodioxanyl) group, a 6-fluoro-2-(1,4-benzodioxanyl) group, a 4,5,6,7-tetrafluoro-2-(1,4-benzodioxanyl) group, a 5-chloro-2-(1,4-benzodioxanyl) group, and a 6-chloro-2-(1,4-benzodioxanyl) group; and 5-(1,4-benzodioxanyl) groups optionally having one or more atoms or groups selected from group B such as a 5-(1,4-benzodioxanyl) group, a 4-cyano-5-(1,4-benzodioxanyl) group, a 6-cyano-5-(1,4-benzodioxanyl) group, a 7-cyano-5-(1,4-benzodioxanyl) group, a 4-nitro-5-(1,4-benzodioxanyl) group, a 6-nitro-5-(1,4-benzodioxanyl) group, a 7-nitro-5-(1,4-benzodioxanyl) group, a 4-carboxyl-5-(1,4-benzodioxanyl) group, a 6-carboxyl-5-(1,4-benzodioxanyl) group, a 7-carboxyl-5-(1,4-benzodioxanyl) group, a 4-hydroxyl-5-(1,4-benzodioxanyl) group, a 6-hydroxyl-5-(1,4-benzodioxanyl) group, a 7-hydroxyl-5-(1,4-benzodioxanyl) group, a 4-methyl-5-(1,4-benzodioxanyl) group, a 6-methyl-5-(1,4-benzodioxanyl) group, a 7-methyl-5-(1,4-benzodioxanyl) group, a 4-trifluoromethyl-5-(1,4-benzodioxanyl) group, a 6-trifluoromethyl-5-(1,4-benzodioxanyl) group, a 7-trifluoromethyl-5-(1,4-benzodioxanyl) group, a 4-methoxy-5-(1,4-benzodioxanyl) group, a 6-methoxy-5-(1,4-benzodioxanyl) group, a 7-methoxy-5-(1,4-benzodioxanyl) group, a 4-trifluoromethoxy-5-(1,4-benzodioxanyl) group, a 6-trifluoromethoxy-5-(1,4-benzodioxanyl) group, a 7-trifluoromethoxy-5-(1,4-benzodioxanyl) group, a 4-methoxycarbonyl-5-(1,4-benzodioxanyl) group, a 6-methoxycarbonyl-5-(1,4-benzodioxanyl) group, a 7-methoxycarbonyl-4-(1,4-benzodioxanyl) group, a 4-vinyl-5-(1,4-benzodioxanyl) group, a 6-vinyl-5-(1,4-benzodioxanyl) group, a 7-vinyl-5-(1,4-benzodioxanyl) group, an 4-ethynyl-5-(1,4-benzodioxanyl) group, an 6-ethynyl-5-(1,4-benzodioxanyl) group, an 7-ethynyl-5-(1,4-benzodioxanyl) group, a 4-fluoro-5-(1,4-benzodioxanyl) group, a 6-fluoro-5-(1,4-benzodioxanyl) group, a 7-fluoro-5-(1,4-benzodioxanyl) group, a 4,5,6,7-tetrafluoro-5-(1,4-benzodioxanyl) group, a 4-chloro-5-(1,4-benzodioxanyl) group, a 6-chloro-5-(1,4-benzodioxanyl) group, and a 7-chloro-5-(1,4-benzodioxanyl) group.

Examples of C1 to C8 chain hydrocarbon group in the C1 to C8 chain hydrocarbon group optionally having one or more atoms or groups selected from group F and the C1 to C8 chain hydrocarbon group optionally having one or more atoms or groups selected from group G include C1 to C8 alkyl groups such as a methyl group, an ethyl group, an isopropyl group, a tert-butyl group, a propyl group, a sec-butyl group, an isobutyl group, a 1,1-dimethylpropyl group, a 2,2-dimethylpropyl group, a 1,2-dimethylpropyl group, an 1-ethylpropyl group, a butyl group, a 1-methylbutyl group, a 2-methylbutyl group, a 3-methylbutyl group, a 1,1-dimethylbutyl group, a 2,2-dimethylbutyl group, a 3,3-dimethylbutyl group, a 1,2,3-trimethylbutyl group, an 1-ethylbutyl group, an 2-ethylbutyl group, a pentyl group, a 1-methylpentyl group, a 2-methylpentyl group, a 3-methylpentyl group, a 4-methylpentyl group, a 1,1-dimethylpentyl group, a 2,2-dimethylpentyl group, a 3,3-dimethylpentyl group, a 4,4-dimethylpentyl group, an 1-ethylpentyl group, an 2-ethylpentyl group, an 3-ethylpentyl group, a 1-propylpentyl group, a 2-propylpentyl group, a hexyl group, a 1-methylhexyl group, a 2-methylhexyl group, a 3-methylhexyl group, a 4-methylhexyl group, a 5-methylhexyl group, a 1,1-dimethylhexyl group, a 2,2-dimethylhexyl group, a 3,3-dimethylhexyl group, a 4,4-dimethylhexyl group, a 5,5-dimethylhexyl group, an 1-ethylhexyl group, an 2-ethylhexyl group, an 3-ethylhexyl group, an 4-ethylhexyl group, a heptyl group, a 1-methylheptyl group, a 2-methylheptyl group, a 3-methylheptyl group, a 4-methylheptyl group, a 5-methylheptyl group, a 6-methylheptyl group, and an octyl group;

C2 to C8 alkenyl groups such as a vinyl group, a 1-propenyl group, a 2-propenyl group, a 1-methyl-1-propenyl group, a 1-methyl-2-propenyl group, a 1,2-dimethyl-1-propenyl group, a 1,1-dimethyl-2-propenyl group, an 1-ethyl-1-propenyl group, an 1-ethyl-2-propenyl group, a 1-butenyl group, a 2-butenyl group, a 3-butenyl group, a 1-methyl-1-butenyl group, a 2-methyl-1-butenyl group, a 2-methyl-2-butenyl group, a 2-methyl-3-butenyl group, a 3-methyl-3-butenyl group, a 1,1-dimethyl-3-butenyl group, a 1,1-dimethyl-2-butenyl group, an 1-ethyl-1-butenyl group, an 1-ethyl-2-butenyl group, an 1-ethyl-3-butenyl group, a 1-pentenyl group, a 2-pentenyl group, a 3-pentenyl group, a 4-pentenyl group, a 1-methyl-1-pentenyl group, a 1-methyl-2-pentenyl group, a 1-methyl-3-pentenyl group, a 1-methyl-4-pentenyl group, a 2-methyl-1-pentenyl group, a 2-methyl-2-pentenyl group, a 2-methyl-3-pentenyl group, a 3-methyl-3-pentenyl group, a 4-methyl-3-pentenyl group, a 4-methyl-4-pentenyl group, a 1,1-dimethyl-2-pentenyl group, a 1,1-dimethyl-3-pentenyl group, a 1,1-dimethyl-4-pentenyl group, an 1-ethyl-1-pentenyl group, an 1-ethyl-2-pentenyl group, an 1-ethyl-3-pentenyl group, an 1-ethyl-4-pentenyl group, a 1-hexenyl group, a 2-hexenyl group, a 3-hexenyl group, a 4-hexenyl group, a 5-hexenyl group, a 1-methyl-1-hexenyl group, a 1-methyl-2-hexenyl group, a 1-methyl-3-hexenyl group, a 1-methyl-4-hexenyl group, a 1-methyl-5-hexenyl group, a 2-methyl-1-hexenyl group, a 2-methyl-2-hexenyl group, a 3-methyl-2-hexenyl group, a 3-methyl-3-hexenyl group, a 4-methyl-3-hexenyl group, a 4-methyl-4-hexenyl group, a 5-methyl-4-hexenyl group, a 5-methyl-5-hexenyl group, a 1,1-dimethyl-2-hexenyl group, a 1,1-dimethyl-3-hexenyl group, a 1,1-dimethyl-4-hexenyl group, a 1,1-dimethyl-5-hexenyl group, an 1-ethyl-1-hexenyl group, an 1-ethyl-2-hexenyl group, an 1-ethyl-3-hexenyl group, an 1-ethyl-4-hexenyl group, an 1-ethyl-5-hexenyl group, a 1-heptenyl group, a 2-heptenyl group, a 3-heptenyl group, a 4-heptenyl group, a 5-heptenyl group, a 6-heptenyl group, a 1-methyl-1-heptenyl group, a 1-methyl-2-heptenyl group, a 1-methyl-3-heptenyl group, a 1-methyl-4-heptenyl group, a 1-methyl-5-heptenyl group, a 1-methyl-6-heptenyl group, a 2-methyl-1-heptenyl group, a 2-methyl-2-heptenyl group, a 3-methyl-2-heptenyl group, a 3-methyl-3-heptenyl group, a 4-methyl-3-heptenyl group, a 4-methyl-4-heptenyl group, a 5-methyl-4-heptenyl group, a 5-methyl-5-heptenyl group, a 6-methyl-5-heptenyl group, a 6-methyl-6-heptenyl group, an 1-octenyl group, an 2-octenyl group, an 3-octenyl group, an 4-octenyl group, an 5-octenyl group, an 6-octenyl group, and an 7-octenyl group; and C2 to C8 alkynyl groups such as an ethynyl group, a 1-propynyl group, a 2-propynyl group, a 1-methyl-2-propynyl group, a 1,1-dimethyl-2-propynyl group, an 1-ethyl-2-propynyl group, a 1-butynyl group, a 2-butynyl group, a 3-butynyl group, a 1-methyl-2-butynyl group, a 1-methyl-3-butynyl group, a 1,1-dimethyl-2-butynyl group, a 1,1-dimethyl-3-butynyl group, an 1-ethyl-2-butynyl group, an 1-ethyl-3-butynyl group, a 1-pentynyl group, a 2-pentynyl group, a 3-pentynyl group, a 4-pentynyl group, a 1-methyl-2-pentynyl group, a 1-methyl-3-pentynyl group, a 1-methyl-4-pentynyl group, a 1,1-dimethyl-2-pentynyl group, a 1,1-dimethyl-3-pentynyl group, a 1,1-dimethyl-4-pentynyl group, an 1-ethyl-2-pentynyl group, an 1-ethyl-3-pentynyl group, an 1-ethyl-4-pentynyl group, a 1-hexynyl group, a 2-hexynyl group, a 3-hexynyl group, a 4-hexynyl group, a 5-hexynyl group, a 1-methyl-2-hexynyl group, a 1-methyl-3-hexynyl group, a 1-methyl-4-hexynyl group, a 1-methyl-5-hexynyl group, a 1,1-dimethyl-2-hexynyl group, a 1,1-dimethyl-3-hexynyl group, a 1,1-dimethyl-4-hexynyl group, a 1,1-dimethyl-5-hexynyl group, an 1-ethyl-2-hexynyl group, an 1-ethyl-3-hexynyl group, an 1-ethyl-4-hexynyl group, an 1-ethyl-5-hexynyl group, a 1-heptynyl group, a 2-heptynyl group, a 3-heptynyl group, a 4-heptynyl group, a 5-heptynyl group, a 6-heptynyl group, a 1-methyl-2-heptynyl group, a 1-methyl-3-heptynyl group, a 1-methyl-4-heptynyl group, a 1-methyl-5-heptynyl group, a 1-methyl-6-heptynyl group, an 1-octynyl group, an 2-octynyl group, an 3-octynyl group, an 4-octynyl group, an 5-octynyl group, an 6-octynyl group, and an 7-octynyl group.

Examples of the C3 to C8 chain hydrocarbon group include

C3 to C8 alkyl groups such as an isopropyl group, a tert-butyl group, a propyl group, a sec-butyl group, an isobutyl group, a 1,1-dimethylpropyl group, a 2,2-dimethylpropyl group, a 1,2-dimethylpropyl group, an 1-ethylpropyl group, a butyl group, a 1-methylbutyl group, a 2-methylbutyl group, a 3-methylbutyl group, a 1,1-dimethylbutyl group, a 2,2-dimethylbutyl group, a 3,3-dimethylbutyl group, a 1,2,3-trimethylbutyl group, an 1-ethylbutyl group, an 2-ethylbutyl group, a pentyl group, a 1-methylpentyl group, a 2-methylpentyl group, a 3-methylpentyl group, a 4-methylpentyl group, a 1,1-dimethylpentyl group, a 2,2-dimethylpentyl group, a 3,3-dimethylpentyl group, a 4,4-dimethylpentyl group, an 1-ethylpentyl group, an 2-ethylpentyl group, an 3-ethylpentyl group, a 1-propylpentyl group, a 2-propylpentyl group, a hexyl group, a 1-methylhexyl group, a 2-methylhexyl group, a 3-methylhexyl group, a 4-methylhexyl group, a 5-methylhexyl group, a 1,1-dimethylhexyl group, a 2,2-dimethylhexyl group, a 3,3-dimethylhexyl group, a 4,4-dimethylhexyl group, a 5,5-dimethylhexyl group, an 1-ethylhexyl group, an 2-ethylhexyl group, an 3-ethylhexyl group, an 4-ethylhexyl group, a heptyl group, a 1-methylheptyl group, a 2-methylheptyl group, a 3-methylheptyl group, a 4-methylheptyl group, a 5-methylheptyl group, a 6-methylheptyl group, and an octyl group; C3 to C8 alkenyl groups such as a 1-propenyl group, a 2-propenyl group, a 1-methyl-1-propenyl group, a 1-methyl-2-propenyl group, a 1,2-dimethyl-1-propenyl group, a 1,1-dimethyl-2-propenyl group, an 1-ethyl-1-propenyl group, an 1-ethyl-2-propenyl group, a 1-butenyl group, a 2-butenyl group, a 3-butenyl group, a 1-methyl-1-butenyl group, a 2-methyl-1-butenyl group, a 2-methyl-2-butenyl group, a 2-methyl-3-butenyl group, a 3-methyl-3-butenyl group, a 1,1-dimethyl-3-butenyl group, a 1,1-dimethyl-2-butenyl group, an 1-ethyl-1-butenyl group, an 1-ethyl-2-butenyl group, an 1-ethyl-3-butenyl group, a 1-pentenyl group, a 2-pentenyl group, a 3-pentenyl group, a 4-pentenyl group, a 1-methyl-1-pentenyl group, a 1-methyl-2-pentenyl group, a 1-methyl-3-pentenyl group, a 1-methyl-4-pentenyl group, a 2-methyl-1-pentenyl group, a 2-methyl-2-pentenyl group, a 3-methyl-2-pentenyl group, a 3-methyl-3-pentenyl group, a 4-methyl-3-pentenyl group, a 4-methyl-4-pentenyl group, a 1,1-dimethyl-2-pentenyl group, a 1,1-dimethyl-3-pentenyl group, a 1,1-dimethyl-4-pentenyl group, an 1-ethyl-1-pentenyl group, an 1-ethyl-2-pentenyl group, an 1-ethyl-3-pentenyl group, an 1-ethyl-4-pentenyl group, a 1-hexenyl group, a 2-hexenyl group, a 3-hexenyl group, a 4-hexenyl group, a 5-hexenyl group, a 1-methyl-1-hexenyl group, a 1-methyl-2-hexenyl group, a 1-methyl-3-hexenyl group, a 1-methyl-4-hexenyl group, a 1-methyl-5-hexenyl group, a 2-methyl-1-hexenyl group, a 2-methyl-2-hexenyl group, a 3-methyl-2-hexenyl group, a 3-methyl-3-hexenyl group, a 4-methyl-3-hexenyl group, a 4-methyl-4-hexenyl group, a 5-methyl-4-hexenyl group, a 5-methyl-5-hexenyl group, a 1,1-dimethyl-2-hexenyl group, a 1,1-dimethyl-3-hexenyl group, a 1,1-dimethyl-4-hexenyl group, a 1,1-dimethyl-5-hexenyl group, an 1-ethyl-1-hexenyl group, an 1-ethyl-2-hexenyl group, an 1-ethyl-3-hexenyl group, an 1-ethyl-4-hexenyl group, an 1-ethyl-5-hexenyl group, a 1-heptenyl group, a 2-heptenyl group, a 3-heptenyl group, a 4-heptenyl group, a 5-heptenyl group, a 6-heptenyl group, a 1-methyl-1-heptenyl group, a 1-methyl-2-heptenyl group, a 1-methyl-3-heptenyl group, a 1-methyl-4-heptenyl group, a 1-methyl-5-heptenyl group, a 1-methyl-6-heptenyl group, a 2-methyl-1-heptenyl group, a 2-methyl-2-heptenyl group, a 3-methyl-2-heptenyl group, a 3-methyl-3-heptenyl group, a 4-methyl-3-heptenyl group, a 4-methyl-4-heptenyl group, a 5-methyl-4-heptenyl group, a 5-methyl-5-heptenyl group, a 6-methyl-5-heptenyl group, a 6-methyl-6-heptenyl group, an 1-octenyl group, an 2-octenyl group, an 3-octenyl group, an 4-octenyl group, an 5-octenyl group, an 6-octenyl group, and an 7-octenyl group; and C3 to C8 alkynyl groups such as a 1-propynyl group, a 2-propynyl group, a 1-methyl-2-propynyl group, a 1,1-dimethyl-2-propynyl group, an 1-ethyl-2-propynyl group, a 1-butynyl group, a 2-butynyl group, a 3-butynyl group, a 1-methyl-2-butynyl group, a 1-methyl-3-butynyl group, a 1,1-dimethyl-2-butynyl group, a 1,1-dimethyl-3-butynyl group, an 1-ethyl-2-butynyl group, an 1-ethyl-3-butynyl group, a 1-pentynyl group, a 2-pentynyl group, a 3-pentynyl group, a 4-pentynyl group, a 1-methyl-2-pentynyl group, a 1-methyl-3-pentynyl group, a 1-methyl-4-pentynyl group, a 1,1-dimethyl-2-pentynyl group, a 1,1-dimethyl-3-pentynyl group, a 1,1-dimethyl-4-pentynyl group, an 1-ethyl-2-pentynyl group, an 1-ethyl-3-pentynyl group, an 1-ethyl-4-pentynyl group, a 1-hexynyl group, a 2-hexynyl group, a 3-hexynyl group, a 4-hexynyl group, a 5-hexynyl group, a 1-methyl-2-hexynyl group, a 1-methyl-3-hexynyl group, a 1-methyl-4-hexynyl group, a 1-methyl-5-hexynyl group, a 1,1-dimethyl-2-hexynyl group, a 1,1-dimethyl-3-hexynyl group, a 1,1-dimethyl-4-hexynyl group, a 1,1-dimethyl-5-hexynyl group, an 1-ethyl-2-hexynyl group, an 1-ethyl-3-hexynyl group, an 1-ethyl-4-hexynyl group, an 1-ethyl-5-hexynyl group, a 1-heptynyl group, a 2-heptynyl group, a 3-heptynyl group, a 4-heptynyl group, a 5-heptynyl group, a 6-heptynyl group, a 1-methyl-2-heptynyl group, a 1-methyl-3-heptynyl group, a 1-methyl-4-heptynyl group, a 1-methyl-5-heptynyl group, a 1-methyl-6-heptynyl group, an 1-octynyl group, an 2-octynyl group, an 3-octynyl group, an 4-octynyl group, an 5-octynyl group, an 6-octynyl group, and an 7-octynyl group.

Examples of the C1 to C8 chain hydrocarbon group optionally having a group selected from group A in the present invention include a benzyl group, a 1-phenylethyl group, a 2-phenylethyl group, a 3-phenylpropyl group, a 4-phenylbutyl group, a 5-phenylpentyl group, a 6-phenylhexyl group, a 7-phenylheptyl group, a 8-phenyloctyl group, a 4-cyanobenzyl group, a 4-nitrobenzyl group, a 4-carboxylbenzyl group, a 4-hydroxylbenzyl group, a 4-(N-methylcarboamide)benzyl group, a 4-(N,N-dimethylcarboamide)benzyl group, a 4-methylbenzyl group, a 4-trifluoromethylbenzyl group, a 4-methoxybenzyl group, a 4-trifluoromethoxybenzyl group, a 4-methylthiobenzyl group, a 4-methylsulfinylbenzyl group, a 4-methylsulfonylbenzyl group, a 4-methoxycarbonylbenzyl group, a 4-vinylbenzyl group, a 4-(2',2'-difluorovinyl)benzyl group, an 4-ethynylbenzyl group, a 4-(2'-fluoroethynyl)benzyl group, a 4-fluorobenzyl group, a 4-chlorobenzyl group, a 3,4-dichlorobenzyl group, a 1-naphthylmethyl group, a 1-(1'-naphthyl)ethyl group, a 2-(1'-naphthyl)ethyl group, a 3-(1'-naphthyl)propyl group, a 4-(1'-naphthyl)butyl group, a 5-(1'-naphthyl)pentyl group, a 6-(1'-naphthyl)hexyl group, a 7-(1'-naphthyl)heptyl group, a 8-(1'-naphthyl)octyl group, a 6-cyano-1-naphthylmethyl group, a 6-nitro-1-naphthylmethyl group, a 6-carboxyl-1-naphthylmethyl group, a 6-hydroxyl-1-naphthylmethyl group, a 6-(N-methylcarboamide)-1-naphthylmethyl group, a 6-(N,N-dimethylcarboamide)-1-naphthylmethyl group, a 6-methyl-1-naphthylmethyl group, a 6-trifluoromethyl-1-naphthylmethyl group, a 6-methoxy-1-naphthylmethyl group, a 6-trifluoromethoxy-1-naphthylmethyl group, a 6-methylthio-1-naphthylmethyl group, a 6-methylsulfinyl-1-naphthylmethyl group, a 6-methylsulfonyl-1-naphthylmethyl group, a 6-methoxycarbonyl-1-naphthylmethyl group, a 6-vinyl-1-naphthylmethyl group, a 6-(2',2'-difluorovinyl)-1-naphthylmethyl group, an 6-ethynyl-1-naphthylmethyl group, a 6-(2'-fluoroethynyl)-1-naphthylmethyl group, a 6-fluoro-1-naphthylmethyl group, a 6-chloro-1-naphthylmethyl group, a 2-naphthylmethyl group, a 1-(2'-naphthyl)ethyl group, a 2-(2'-naphthyl)ethyl group, a 3-(2'-naphthyl)propyl group, a 4-(2'-naphthyl)butyl group, a 5-(2'-naphthyl)pentyl group, a 6-(2'-naphthyl)hexyl group, a 7-(2'-naphthyl)heptyl group, a 8-(2'-naphthyl)octyl group, a 6-cyano-2-naphthylmethyl group, a 6-nitro-2-naphthylmethyl group, a 6-carboxyl-2-naphthylmethyl group, a 6-hydroxyl-2-naphthylmethyl group, a 6-(N-methylcarboamide)-2-naphthylmethyl group, a 6-(N,N-dimethylcarboamide)-2-naphthylmethyl group, a 6-methyl-2-naphthylmethyl group, a 6-trifluoromethyl-2-naphthylmethyl group, a 6-methoxy-2-naphthylmethyl group, a 6-trifluoromethoxy-2-naphthylmethyl group, a 6-methylthio-2-naphthylmethyl group, a 6-methylsulfinyl-2-naphthylmethyl group, a 6-methylsulfonyl-2-naphthylmethyl group, a 6-methoxycarbonyl-2-naphthylmethyl group, a 6-vinyl-2-naphthylmethyl group, a 6-(2',2'-difluorovinyl)-2-naphthylmethyl group, an 6-ethynyl-2-naphthylmethyl group, a 6-(2'-fluoroethynyl)-2-naphthylmethyl group, a 6-fluoro-2-naphthylmethyl group, a 6-chloro-2-naphthylmethyl group, a 2-pyridylmethyl group, a 1-(2'-pyridyl)ethyl group, a 2-(2'-pyridyl)ethyl group, a 3-(2'-pyridyl)propyl group, a 4-(2'-pyridyl)butyl group, a 5-(2'-pyridyl)pentyl group, a 6-(2'-pyridyl)hexyl group, a 7-(2'-pyridyl)heptyl group, a 8-(2'-pyridyl)octyl group, a 4-cyano-2-pyridylmethyl group, a 4-nitro-2-pyridylmethyl group, a 4-carboxyl-2-pyridylmethyl group, a 4-hydroxyl-2-pyridylmethyl group, a 4-(N-methylcarboamide)-2-pyridylmethyl group, a 4-(N,N-dimethylcarboamide)-2-pyridylmethyl group, a 4-methyl-2-pyridylmethyl group, a 4-trifluoromethyl-2-pyridylmethyl group, a 4-methoxy-2-pyridylmethyl group, a 4-trifluoromethoxy-2-pyridylmethyl group, a 4-methylthio-2-pyridylmethyl group, a 4-methylsulfinyl-2-pyridylmethyl group, a 4-methylsulfonyl-2-pyridylmethyl group, a 4-methoxycarbonyl-2-pyridylmethyl group, a 4-vinyl-2-pyridylmethyl group, a 4-(2',2'-difluorovinyl)-2-pyridylmethyl group, an 4-ethynyl-2-pyridylmethyl group, a 4-(2'-fluoroethynyl)-2-pyridylmethyl group, a 4-fluoro-2-pyridylmethyl group, a 4-chloro-2-pyridylmethyl group, a 5-cyano-2-pyridylmethyl group, a 5-nitro-2-pyridylmethyl group, a 5-carboxyl-2-pyridylmethyl group, a 5-hydroxyl-2-pyridylmethyl group, a 5-(N-methylcarboamide)-2-pyridylmethyl group, a 5-(N,N-dimethylcarboamide)-2-pyridylmethyl group, a 5-methyl-2-pyridylmethyl group, a 5-trifluoromethyl-2-pyridylmethyl group, a 5-methoxy-2-pyridylmethyl group, a 5-trifluoromethoxy-2-pyridylmethyl group, a 5-methylthio-2-pyridylmethyl group, a 5-methylsulfinyl-2-pyridylmethyl group, a 5-methylsulfonyl-2-pyridylmethyl group, a 5-methoxycarbonyl-2-pyridylmethyl group, a 5-vinyl-2-pyridylmethyl group, a 5-(2',2'-difluorovinyl)-2-pyridylmethyl group, an 5-ethynyl-2-pyridylmethyl group, a 5-(2'-fluoroethynyl)-2-pyridylmethyl group, a 5-fluoro-2-pyridylmethyl group, a 5-chloro-2-pyridylmethyl group, a 5,5-dichloro-2-pyridylmethyl group, a 6-cyano-2-pyridylmethyl group, a 6-nitro-2-pyridylmethyl group, a 6-carboxyl-2-pyridylmethyl group, a 6-hydroxyl-2-pyridylmethyl group, a 6-(N-methylcarboamide)-2-pyridylmethyl group, a 6-(N,N-dimethylcarboamide)-2-pyridylmethyl group, a 6-methyl-2-pyridylmethyl group, a 6-trifluoromethyl-2-pyridylmethyl group, a 6-methoxy-2-pyridylmethyl group, a 6-trifluoromethoxy-2-pyridylmethyl group, a 6-methylthio-2-pyridylmethyl group, a 6-methylsulfinyl-2-pyridylmethyl group, a 6-methylsulfonyl-2-pyridylmethyl group, a 6-methoxycarbonyl-2-pyridylmethyl group, a 6-vinyl-2-pyridylmethyl group, a 6-(2',2'-difluorovinyl)-2-pyridylmethyl group, an 6-ethynyl-2-pyridylmethyl group, a 6-(2'-fluoroethynyl)-2-pyridylmethyl group, a 6-fluoro-2-pyridylmethyl group, a 6-chloro-2-pyridylmethyl group, a 6,6-dichloro-2-pyridylmethyl group, a 3-pyridylmethyl group, a 1-(3'-pyridyl)ethyl group, a 2-(3'-pyridyl)ethyl group, a 3-(3'-pyridyl)propyl group, a 4-(3'-pyridyl)butyl group, a 5-(3'-pyridyl)pentyl group, a 6-(3'-pyridyl)hexyl group, a 7-(3'-pyridyl)heptyl group, a 8-(3'-pyridyl)octyl group, a 5-cyano-3-pyridylmethyl group, a 5-nitro-3-pyridylmethyl group, a 5-carboxyl-3-pyridylmethyl group, a 5-hydroxyl-3-pyridylmethyl group, a 5-(N-methylcarboamide)-3-pyridylmethyl group, a 5-(N, N-dimethylcarboamide)-3-pyridylmethyl group, a 5-methyl-3-pyridylmethyl group, a 5-trifluoromethyl-3-pyridylmethyl group, a 5-methoxy-3-pyridylmethyl group, a 5-trifluoromethoxy-3-pyridylmethyl group, a 5-methylthio-3-pyridylmethyl group, a 5-methylsulfinyl-3-pyridylmethyl group, a 5-methylsulfonyl-3-pyridylmethyl group, a 5-methoxycarbonyl-3-pyridylmethyl group, a 5-vinyl-3-pyridylmethyl group, a 5-(2',2'-difluorovinyl)-3-pyridylmethyl group, an 5-ethynyl-3-pyridylmethyl group, a 5-(2'-fluoroethynyl)-3-pyridylmethyl group, a 5-fluoro-3-pyridylmethyl group, a 5-chloro-3-pyridylmethyl group, a 6-cyano-3-pyridylmethyl group, a 6-nitro-3-pyridylmethyl group, a 6-carboxyl-3-pyridylmethyl group, a 6-hydroxyl-3-pyridylmethyl group, a 6-(N-methylcarboamide)-3-pyridylmethyl group, a 6-(N,N-dimethylcarboamide)-3-pyridylmethyl group, a 6-methyl-3-pyridylmethyl group, a 6-trifluoromethyl-3-pyridylmethyl group, a 6-methoxy-3-pyridylmethyl group, a 6-trifluoromethoxy-3-pyridylmethyl group, a 6-methylthio-3-pyridylmethyl group, a 6-methylsulfinyl-3-pyridylmethyl group, a 6-methylsulfonyl-3-pyridylmethyl group, a 6-methoxycarbonyl-3-pyridylmethyl group, a 6-vinyl-3-pyridylmethyl group, a 6-(2',2'-difluorovinyl)-3-pyridylmethyl group, an 6-ethynyl-3-pyridylmethyl group, a 6-(2'-fluoroethynyl)-3-pyridylmethyl group, a 6-fluoro-3-pyridylmethyl group, a 6-chloro-3-pyridylmethyl group, a 4-pyridylmethyl group, a 1-(4'-pyridyl)ethyl group, a 2-(4'-pyridyl)ethyl group, a 3-(4'-pyridyl)propyl group, a 4-(4'-pyridyl)butyl group, a 5-(4'-pyridyl)pentyl group, a 6-(4'-pyridyl)hexyl group, a 7-(4'-pyridyl)heptyl group, a 8-(4'-pyridyl)octyl group, a 2-cyano-4-pyridylmethyl group, a 2-nitro-4-pyridylmethyl group, a 2-carboxyl-4-pyridylmethyl group, a 2-hydroxyl-4-pyridylmethyl group, a 2-(N-methylcarboamide)-4-pyridylmethyl group, a 2-(N,N-dimethylcarboamide)-4-pyridylmethyl group, a 2-methyl-4-pyridylmethyl group, a 2-trifluoromethyl-4-pyridylmethyl group, a 2-methoxy-4-pyridylmethyl group, a 2-trifluoromethoxy-4-pyridylmethyl group, a 2-methylthio-4-pyridylmethyl group, a 2-methylsulfinyl-4-pyridylmethyl group, a 2-methylsulfonyl-4-pyridylmethyl group, a 2-methoxycarbonyl-4-pyridylmethyl group, a 2-vinyl-4-pyridylmethyl group, a 2-(2',2'-difluorovinyl)-4-pyridylmethyl group, an 2-ethynyl-4-pyridylmethyl group, a 2-(2'-fluoroethynyl)-4-pyridylmethyl group, a 2-fluoro-4-pyridylmethyl group, a 2-chloro-4-pyridylmethyl group, a 6-cyano-4-pyridylmethyl group, a 6-nitro-4-pyridylmethyl group, a 6-carboxyl-4-pyridylmethyl group, a 6-hydroxyl-4-pyridylmethyl group, a 6-(N-methylcarboamide)-4-pyridylmethyl group, a 6-(N,N-dimethylcarboamide)-4-pyridylmethyl group, a 6-methyl-4-pyridylmethyl group, a 6-trifluoromethyl-4-pyridylmethyl group, a 6-methoxy-4-pyridylmethyl group, a 6-trifluoromethoxy-4-pyridylmethyl group, a 6-methylthio-4-pyridylmethyl group, a 6-methylsulfinyl-4-pyridylmethyl group, a 6-methylsulfonyl-4-pyridylmethyl group, a 6-methoxycarbonyl-4-pyridylmethyl group, a 6-vinyl-4-pyridylmethyl group, a 6-(2',2'-difluorovinyl)-4-pyridylmethyl group, an 6-ethynyl-4-pyridylmethyl group, a 6-(2'-fluoroethynyl)-4-pyridylmethyl group, a 6-fluoro-4-pyridylmethyl group, a 6-chloro-4-pyridylmethyl group, a 2-quinolylmethyl group, a 1-(2'-quinolyl)ethyl group, a 2-(2'-quinolyl)ethyl group, a 3-(2'-quinolyl)propyl group, a 4-(2'-quinolyl)butyl group, a 5-(2'-quinolyl)pentyl group, a 6-(2'-quinolyl)hexyl group, a 7-(2'-quinolyl)heptyl group, a 8-(2'-quinolyl)octyl group, a 6-cyano-2-quinolylmethyl group, a 6-nitro-2-quinolylmethyl group, a 6-carboxyl-2-quinolylmethyl group, a 6-hydroxyl-2-quinolylmethyl group, a 6-(N-methylcarboamide)-2-quinolylmethyl group, a 6-(N,N-dimethylcarboamide)-2-quinolylmethyl group, a 6-methyl-2-quinolylmethyl group, a 6-trifluoromethyl-2-quinolylmethyl group, a 6-methoxy-2-quinolylmethyl group, a 6-trifluoromethoxy-2-quinolylmethyl group, a 6-methylthio-2-quinolylmethyl group, a 6-methylsulfinyl-2-quinolylmethyl group, a 6-methylsulfonyl-2-quinolylmethyl group, a 6-methoxycarbonyl-2-quinolylmethyl group, a 6-vinyl-2-quinolylmethyl group, a 6-(2',2'-difluorovinyl)-2-quinolylmethyl group, an 6-ethynyl-2-quinolylmethyl group, a 6-(2'-fluoroethynyl)-2-quinolylmethyl group, a 6-fluoro-2-quinolylmethyl group, a 6-chloro-2-quinolylmethyl group, a 3-quinolylmethyl group, a 1-(3'-quinolyl)ethyl group, a 2-(3'-quinolyl)ethyl group, a 3-(3'-quinolyl)propyl group, a 4-(3'-quinolyl)butyl group, a 5-(3'-quinolyl)pentyl group, a 6-(3'-quinolyl)hexyl group, a 7-(3'-quinolyl)heptyl group, a 8-(3'-quinolyl)octyl group, a 6-cyano-3-quinolylmethyl group, a 6-nitro-3-quinolylmethyl group, 6-carboxyl-3-quinolylmethyl group, a 6-hydroxyl-3-quinolylmethyl group, a 6-(N-methylcarboamide)-3-quinolylmethyl group, a 6-(N,N-dimethylcarboamide)-3-quinolylmethyl group, a 6-methyl-3-quinolylmethyl group, a 6-trifluoromethyl-3-quinolylmethyl group, a 6-methoxy-3-quinolylmethyl group, a 6-trifluoromethoxy-3-quinolylmethyl group, a 6-methylthio-3-quinolylmethyl group, a 6-methylsulfinyl-3-quinolylmethyl group, a 6-methylsulfonyl-3-quinolylmethyl group, a 6-methoxycarbonyl-3-quinolylmethyl group, a 6-vinyl-3-quinolylmethyl group, a 6-(2',2'-difluorovinyl)-3-quinolylmethyl group, an 6-ethynyl-3-quinolylmethyl group, a 6-(2'-fluoroethynyl)-3-quinolylmethyl group, a 6-fluoro-3-quinolylmethyl group, a 6-chloro-3-quinolylmethyl group, a 4-quinolylmethyl group, a 1-(4'-quinolyl)ethyl group, a 2-(4'-quinolyl)ethyl group, a 3-(4'-quinolyl)propyl group, a 4-(4'-quinolyl)butyl group, a 5-(3'-quinolyl)pentyl group, a 6-(4'-quinolyl)hexyl group, a 7-(4'-quinolyl)heptyl group, a 8-(4'-quinolyl)octyl group, a 6-cyano-4-quinolylmethyl group, a 6-nitro-4-quinolylmethyl group, a 6-carboxyl-4-quinolylmethyl group, a 6-hydroxyl-4-quinolylmethyl group, a 6-(N-methylcarboamide)-4-quinolylmethyl group, a 6-(N,N-dimethylcarboamide)-4-quinolylmethyl group, a 6-methyl-4-quinolylmethyl group, a 6-trifluoromethyl-4-quinolylmethyl group, a 6-methoxy-4-quinolylmethyl group, a 6-trifluoromethoxy-4-quinolylmethyl group, a 6-methylthio-4-quinolylmethyl group, a 6-methylsulfinyl-4-quinolylmethyl group, a 6-methylsulfonyl-4-quinolylmethyl group, a 6-methoxycarbonyl-4-quinolylmethyl group, a 6-vinyl-4-quinolylmethyl group, a 6-(2',2'-difluorovinyl)-4-quinolylmethyl group, an 6-ethynyl-4-quinolylmethyl group, a 6-(2'-fluoroethynyl)-4-quinolylmethyl group, a 6-fluoro-4-quinolylmethyl group, a 6-chloro-4-quinolylmethyl group, a 2-furylmethyl group, a 1-(2'-furyl)ethyl group, a 2-(2'-furyl)ethyl group, a 3-(2'-furyl)propyl group, a 4-(2'-furyl)butyl group, a 5-(2'-furyl)pentyl group, a 6-(2'-furyl)hexyl group, a 7-(2'-furyl)heptyl group, a 8-(2'-furyl)octyl group, a 4-cyano-2-furylmethyl group, a 4-nitro-2-furylmethyl group, a 4-carboxyl-2-furylmethyl group, a 4-hydroxyl-2-furylmethyl group, a 4-(N-methylcarboamide)-2-furylmethyl group, a 4-(N,N-dimethylcarboamide)-2-furylmethyl group, a 4-methyl-2-furylmethyl group, a 4-trifluoromethyl-2-furylmethyl group, a 4-methoxy-2-furylmethyl group, a 4-trifluoromethoxy-2-furylmethyl group, a 4-methylthio-2-furylmethyl group, a 4-methylsulfinyl-2-furylmethyl group, a 4-methylsulfonyl-2-furylmethyl group, a 4-methoxycarbonyl-2-furylmethyl group, a 4-vinyl-2-furylmethyl group, a 4-(2',2'-difluorovinyl)-2-furylmethyl group, an 4-ethynyl-2-furylmethyl group, a 4-(2'-fluoroethynyl)-2-furylmethyl group, a 4-fluoro-2-furylmethyl group, a 4-chloro-2-furylmethyl group, a 3-furylmethyl group, a 1-(3'-furyl)ethyl group, a 2-(3'-furyl)ethyl group, a 3-(3'-furyl)propyl group, a 4-(3'-furyl)butyl group, a 5-(3'-furyl)pentyl group, a 6-(3'-furyl)hexyl group, a 7-(3'-furyl)heptyl group, a 8-(3'-furyl)octyl group, a 4-cyano-3-furylmethyl group, a 4-nitro-3-furylmethyl group, a 4-carboxyl-3-furylmethyl group, a 4-hydroxyl-3-furylmethyl group, a 4-(N-methylcarboamide)-3-furylmethyl group, a 4-(N,N-dimethylcarboamide)-3-furylmethyl group, a 4-methyl-3-furylmethyl group, a 4-trifluoromethyl-3-furylmethyl group, a 4-methoxy-3-furylmethyl group, a 4-trifluoromethoxy-3-furylmethyl group, a 4-methylthio-3-furylmethyl group, a 4-methylsulfinyl-3-furylmethyl group, a 4-methylsulfonyl-3-furylmethyl group, a 4-methoxycarbonyl-3-furylmethyl group, a 4-vinyl-3-furylmethyl group, a 4-(2',2'-difluorovinyl)-3-furylmethyl group, an 4-ethynyl-3-furylmethyl group, a 4-(2'-fluoroethynyl)-3-furylmethyl group, a 4-fluoro-3-furylmethyl group, a 4-chloro-3-furylmethyl group, a 2-thienylmethyl group, a 1-(2'-thienyl)ethyl group, a 2-(2'-thienyl)ethyl group, a 3-(2'-thienyl)propyl group, a 4-(2'-thienyl)butyl group, a 5-(2'-thienyl)pentyl group, a 6-(2'-thienyl)hexyl group, a 7-(2'-thienyl)heptyl group, a 8-(2'-thienyl)octyl group, a 4-cyano-2-thienylmethyl group, a 4-nitro-2-thienylmethyl group, a 4-carboxyl-2-thienylmethyl group, a 4-hydroxyl-2-thienylmethyl group, a 4-(N-methylcarboamide)-2-thienylmethyl group, a 4-(N,N-dimethylcarboamide)-2-thienylmethyl group, a 4-methyl-2-thienylmethyl group, a 4-trifluoromethyl-2-thienylmethyl group, a 4-methoxy-2-thienylmethyl group, a 4-trifluoromethoxy-2-thienylmethyl group, a 4-methylthio-2-thienylmethyl group, a 4-methylsulfinyl-2-thienylmethyl group, a 4-methylsulfonyl-2-thienylmethyl group, a 4-methoxycarbonyl-2-thienylmethyl group, a 4-vinyl-2-thienylmethyl group, a 4-(2',2'-difluorovinyl)-2-thienylmethyl group, an 4-ethynyl-2-thienylmethyl group, a 4-(2'-fluoroethynyl)-2-thienylmethyl group, a 4-fluoro-2-thienylmethyl group, a 4-chloro-2-thienylmethyl group, a 3-thienylmethyl group, a 1-(3'-thienyl)ethyl group, a 2-(3'-thienyl)ethyl group, a 3-(3'-thienyl)propyl group, a 4-(3'-thienyl)butyl group, a 5-(3'-thienyl)pentyl group, a 6-(3'-thienyl)hexyl group, a 7-(3'-thienyl)heptyl group, a 8-(3'-thienyl)octyl group, a 4-cyano-3-thienylmethyl group, a 4-nitro-3-thienylmethyl group, a 4-carboxyl-3-thienylmethyl group, a 4-hydroxyl-3-thienylmethyl group, a 4-(N-methylcarboamide)-3-thienylmethyl group, a 4-(N,N-dimethylcarboamide)-3-thienylmethyl group, a 4-methyl-3-thienylmethyl group, a 4-trifluoromethyl-3-thienylmethyl group, a 4-methoxy-3-thienylmethyl group, a 4-trifluoromethoxy-3-thienylmethyl group, a 4-methylthio-3-thienylmethyl group, a 4-methylsulfinyl-3-thienylmethyl group, a 4-methylsulfonyl-3-thienylmethyl group, a 4-methoxycarbonyl-3-thienylmethyl group, a 4-vinyl-3-thienylmethyl group, a 4-(2',2'-difluorovinyl)-3-thienylmethyl group, an 4-ethynyl-3-thienylmethyl group, a 4-(2'-fluoroethynyl)-3-thienylmethyl group, a 4-fluoro-3-thienylmethyl group, a 4-chloro-3-thienylmethyl group, a 2-(1-benzofuranyl)methyl group, a 1-(2'-(1'-benzofuranyl))ethyl group, a 2-(2'-(1'-benzofuranyl))ethyl group, a 3-(2'-(1'-benzofuranyl))propyl group, a 4-(2'-(1'-benzofuranyl))butyl group, a 5-(2'-(1'-benzofuranyl))pentyl group, a 6-(2'-(1'-benzofuranyl))hexyl group, a 7-(2'-(1'-benzofuranyl))heptyl group, a 8-(2'-(1'-benzofuranyl))octyl group, a 5-cyano-2-(1-benzofuranyl)methyl group, a 5-nitro-2-(1-benzofuranyl)methyl group, a 5-carboxyl-2-(1-benzofuranyl)methyl group, a 5-hydroxyl-2-(1-benzofuranyl)methyl group, a 5-(N-methylcarboamide)-2-(1-benzofuranyl)methyl group, a 5-(N,N-dimethylcarboamide)-2-(1-benzofuranyl)methyl group, a 5-methyl-2-(1-benzofuranyl)methyl group, a 5-trifluoromethyl-2-(1-benzofuranyl)methyl group, a 5-methoxy-2-(1-benzofuranyl)methyl group, a 5-trifluoromethoxy-2-(1-benzofuranyl)methyl group, a 5-methylthio-2-(1-benzofuranyl)methyl group, a 5-methylsulfinyl-2-(1-benzofuranyl)methyl group, a 5-methylsulfonyl-2-(1-benzofuranyl)methyl group, a 5-methoxycarbonyl-2-(1-benzofuranyl)methyl group, a 5-vinyl-2-(1-benzofuranyl)methyl group, a 5-(2',2'-difluorovinyl)-2-(1-benzofuranyl)methyl group, an 5-ethynyl-2-(1-benzofuranyl)methyl group, a 5-(2'-fluoroethynyl)-2-(1-benzofuranyl)methyl group, a 5-fluoro-2-(1-benzofuranyl)methyl group, a 5-chloro-2-(1-benzofuranyl)methyl group, a 3-(1-benzofuranyl)methyl group, a 1-(3'-(1'-benzofuranyl))ethyl group, a 2-(3'-(1'-benzofuranyl))ethyl group, a 3-(3'-(1'-benzofuranyl))propyl group, a 4-(3'-(1'-benzofuranyl))butyl group, a 5-(3'-(1'-benzofuranyl))pentyl group, a 6-(3'-(1'-benzofuranyl))hexyl group, a 7-(3'-(1'-benzofuranyl))heptyl group, a 8-(3'-(1'-benzofuranyl))octyl group, a 5-cyano-3-(1-benzofuranyl)methyl group, a 5-nitro-3-(1-benzofuranyl)methyl group, a 5-carboxyl-3-(1-benzofuranyl)methyl group, a 5-hydroxyl-3-(1-benzofuranyl)methyl group, a 5-(N-methylcarboamide)-3-(1-benzofuranyl)methyl group, a 5-(N,N-dimethylcarboamide)-3-(1-benzofuranyl)methyl group, a 5-methyl-3-(1-benzofuranyl)methyl group, a 5-trifluoromethyl-3-(1-benzofuranyl)methyl group, a 5-methoxy-3-(1-benzofuranyl)methyl group, a 5-trifluoromethoxy-3-(1-benzofuranyl)methyl group, a 5-methylthio-3-(1-benzofuranyl)methyl group, a 5-methylsulfinyl-3-(1-benzofuranyl)methyl group, a 5-methylsulfonyl-3-(1-benzofuranyl)methyl group, a 5-methoxycarbonyl-3-(1-benzofuranyl)methyl group, a 5-vinyl-3-(1-benzofuranyl)methyl group, a 5-(2',2'-difluorovinyl)-3-(1-benzofuranyl)methyl group, an 5-ethynyl-3-(1-benzofuranyl)methyl group, a 5-(2'-fluoroethynyl)-3-(1-benzofuranyl)methyl group, a 5-fluoro-3-(1-benzofuranyl)methyl group, a 5-chloro-3-(1-benzofuranyl)methyl group, a 2-(1-benzothienyl)methyl group, a 1-(2'-(1'-benzothienyl))ethyl group, a 2-(2'-(1'-benzothienyl))ethyl group, a 3-(2'-(1'-benzothienyl))propyl group, a 4-(2'-(1'-benzothienyl))butyl group, a 5-(2'-(1'-benzothienyl))pentyl group, a 6-(2'-(1'-benzothienyl))hexyl group, a 7-(2'-(1'-benzothienyl))heptyl group, a 8-(2'-(1'-benzothienyl))octyl group, a 5-cyano-2-(1-benzothienyl)methyl group, a 5-nitro-2-(1-benzothienyl)methyl group, a 5-carboxyl-2-(1-benzothienyl)methyl group, a 5-hydroxyl-2-(1-benzothienylmethyl group, a 5-(N-methylcarboamide)-2-(1-benzothienyl)methyl group, a 5-(N,N-dimethylcarboamide)-2-(1-benzothienyl)methyl group, a 5-methyl-2-(1-benzothienyl)methyl group, a 5-trifluoromethyl-2-(1-benzothienyl)methyl group, 5-methoxy-2-(1-benzothienyl)methyl group, a 5-trifluoromethoxy-2-(1-benzothienyl)methyl group, a 5-methylthio-2-(1-benzothienyl)methyl group, a 5-methylsulfinyl-2-(1-benzothienyl)methyl group, a 5-methylsulfonyl-2-(1-benzothienyl)methyl group, a 5-methoxycarbonyl-2-(1-benzothienyl)methyl group, a 5-vinyl-2-(1-benzothienyl)methyl group, a 5-(2',2'-difluorovinyl)-2-(1-benzothienyl)methyl group, an 5-ethynyl-2-(1-benzothienyl)methyl group, a 5-(2'-fluoroethynyl)-2-(1-benzothienyl)methyl group, a 5-fluoro-2-(1-benzothienyl)methyl group, a 5-chloro-2-(1-benzothienyl)methyl group, a 3-(1-benzothienyl)methyl group, a 1-(3'-(1'-benzothienyl))ethyl group, a 2-(3'-(1'-benzothienyl))ethyl group, a 3-(3'-(1'-benzothienyl))propyl group, a 4-(3'-(1'-benzothienyl))butyl group, a 5-(3'-(1'-benzothienyl))pentyl group, a 6-(3'-(1'-benzothienyl))hexyl group, a 7-(3'-(1'-benzothienyl))heptyl group, a 8-(3'-(1'-benzothienyl))octyl group, a 5-cyano-3-(1-benzothienyl)methyl group, a 5-nitro-3-(1-benzothienyl)methyl group, a 5-carboxyl-3-(1-benzothienyl)methyl group, a 5-hydroxyl-3-(1-benzothienyl)methyl group, a 5-(N-methylcarboamide)-3-(1-benzothienyl)methyl group, a 5-(N,N-dimethylcarboamide)-3-(1-benzothienyl)methyl group, a 5-methyl-3-(1-benzothienyl)methyl group, a 5-trifluoromethyl-3-(1-benzothienyl)methyl group, a 5-methoxy-3-(1-benzothienyl)methyl group, a 5-trifluoromethoxy-3-(1-benzothienyl)methyl group, a 5-methylthio-3-(1-benzothienyl)methyl group, a 5-methylsulfinyl-3-(1-benzothienyl)methyl group, a 5-methylsulfonyl-3-(1-benzothienyl)methyl group, a 5-methoxycarbonyl-3-(1-benzothienyl)methyl group, a 5-vinyl-3-(1-benzothienyl)methyl group, a 5-(2',2'-difluorovinyl)-3-(1-benzothienyl)methyl group, an 5-ethynyl-3-(1-benzothienyl)methyl group, a 5-(2'-fluoroethynyl)-3-(1-benzothienyl)methyl group, a 5-fluoro-3-(1-benzothienyl)methyl group, a 5-chloro-3-(1-benzothienyl)methyl group, and the like.

Examples of the C1 to C8 chain hydrocarbon group optionally having one or more atoms or groups selected from group F in the present invention include a benzyl group, a phenyldifluoromethyl group, a 1-phenylethyl group, a 1,1-difluoro-1-phenylethyl group, a 2,2,2-trifluoro-1-phenylethyl group, a 1,1,2,2,2-pentafluoro-1-phenylethyl group, a 2-phenylethyl group, a 1,1-difluoro-2-phenylethyl group, a 2,2-difluoro-2-phenylethyl group, a 1,1,2,2-tetrafluoro-2-phenylethyl group, a 3-phenylpropyl group, a 1,1-difluoro-3-phenylpropyl group, a 2,2-difluoro-3-phenylpropyl group, a 3,3-difluoro-3-phenylpropyl group, a 1,1,2,2,3,3-hexafluoro-3-phenylpropyl group, a 4-phenylbutyl group, a 1,1-difluoro-4-phenylbutyl group, a 2,2-difluoro-4-phenylbutyl group, a 3,3-difluoro-4-phenylbutyl group, a 4,4-difluoro-4-phenylbutyl group, a 1,1,2,2,3,3,4,4-octafluoro-3-4-phenylbutyl group, a 5-phenylpentyl group, a 1,1-difluoro-5-phenylpentyl group, a 2,2-difluoro-5-phenylpentyl group, a 3,3-difluoro-5-phenylpentyl group, a 4,4-difluoro-5-phenylpentyl group, a 5,5-difluoro-5-phenylpentyl group, a 6-phenylhexyl group, a 1,1-difluoro-6-phenylhexyl group, a 2,2-difluoro-6-phenylhexyl group, a 3,3-difluoro-6-phenylhexyl group, a 4,4-difluoro-6-phenylhexyl group, a 5,5-difluoro-6-phenylhexyl group, a 6,6-difluoro-6-phenylhexyl group, a 7-phenylheptyl group, a 1,1-difluoro-7-phenylheptyl group, a 2,2-difluoro-7-phenylheptyl group, a 3,3-difluoro-7-phenylheptyl group, a 4,4-difluoro-7-phenylheptyl group, a 5,5-difluoro-7-phenylheptyl group, a 6,6-difluoro-7-phenylheptyl group, a 7,7-difluoro-7-phenylheptyl group, a 8-phenyloctyl group, a 1,1-difluoro-8-phenyloctyl group, a 2,2-difluoro-8-phenyloctyl group, a 3,3-difluoro-8-phenyloctyl group, a 4,4-difluoro-8-phenyloctyl group, a 5,5-difluoro-8-phenyloctyl group, a 6,6-difluoro-8-phenyloctyl group, a 7,7-difluoro-8-phenyloctyl group, a 8,8-difluoro-8-phenyloctyl group, a 4-cyanobenzyl group, a 4-nitrobenzyl group, a 4-carboxylbenzyl group, a 4-hydroxylbenzyl group, a 4-(N-methylcarboamide)benzyl group, a 4-(N,N-dimethylcarboamide)benzyl group, a 4-methylbenzyl group, a 4-trifluoromethylbenzyl group, a 4-methoxybenzyl group, a 4-trifluoromethoxybenzyl group, a 4-methylthiobenzyl group, a 4-methylsulfinylbenzyl group, a 4-methylsulfonylbenzyl group, a 4-methoxycarbonylbenzyl group, a 4-vinylbenzyl group, a 4-(2',2'-difluorovinyl)benzyl group, an 4-ethynylbenzyl group, a 4-(2'-fluoroethynyl)benzyl group, a 4-fluorobenzyl group, a 4-chlorobenzyl group, a 3,4-dichlorobenzyl group, a (4'-cyanophenyl)difluoromethyl group, a (4'-nitrophenyl)difluoromethyl group, a (4'-carboxylphenyl)difluoromethyl group, a (4'-hydroxylphenyl)difluoromethyl group, a (4'-(N-methylcarboamide)phenyl)difluoromethyl group, a (4'-(N,N-dimethylcarboamide)phenyl)difluoromethyl group, a (4'-methylphenyl)difluoromethyl group, a (4'-trifluoromethylphenyl)difluoromethyl group, a (4'-methoxyphenyl)difluoromethyl group, a (4'-trifluoromethoxyphenyl)difluoromethyl group, a (4'-methylthiophenyl)difluoromethyl group, a (4'-methylsulfinylphenyl)difluoromethyl group, a (4'-methylsulfonylphenyl)difluoromethyl group, a (4'-methoxycarbonylphenyl)difluoromethyl group, a (4'-vinylphenyl)difluoromethyl group, a (4'-(2',2'-difluorovinyl)phenyl)difluoromethyl group, a (4'-ethynylphenyl)difluoromethyl group, a (4'-(2'-fluoroethynyl)phenyl)difluoromethyl group, a (4'-fluorophenyl)difluoromethyl group, a (4'-chlorophenyl)difluoromethyl group, a 3,(4'-dichlorophenyl)difluoromethyl group, a 1-naphthylmethyl group, a (1'-naphthyl)difluoromethyl group, a 1-(1'-naphthyl)ethyl group, a 1,1-difluoro-1-(1'-naphthyl)ethyl group, a 2,2,2-trifluoro-1-(1'-naphthyl)ethyl group, a 1,1,2,2,2-pentafluoro-1-(1'-naphthyl)ethyl group, a 2-(1'-naphthyl)ethyl group, a 1,1-difluoro-2-(1'-naphthyl)ethyl group, a 2,2-difluoro-2-(1'-naphthyl)ethyl group, a 1,1,2,2-tetrafluoro-2-(1'-naphthyl)ethyl group, a 3-(1'-naphthyl)propyl group, a 1,1-difluoro-3-(1'-naphthyl)propyl group, a 2,2-difluoro-3-(1'-naphthyl)propyl group, a 3,3-difluoro-3-(1'-naphthyl)propyl group, a 1,1,2,2,3,3-hexafluoro-3-(1'-naphthyl)propyl group, a 4-(1'-naphthyl)butyl group, a 1,1-difluoro-4-(1'-naphthyl)butyl group, a 2,2-difluoro-4-(1'-naphthyl)butyl group, a 3,3-difluoro-4-(1'-naphthyl)butyl group, a 4,4-difluoro-4-(1'-naphthyl)butyl group, a 1,1,2,2,3,3,4,4-octafluoro-3-4-(1'-naphthyl)butyl group, a 5-(1'-naphthyl)pentyl group, a 1,1-difluoro-5-(1'-naphthyl)pentyl group, a 2,2-difluoro-5-(1'-naphthyl)pentyl group, a 3,3-difluoro-5-(1'-naphthyl)pentyl group, a 4,4-difluoro-5-(1'-naphthyl)pentyl group, a 5,5-difluoro-5-(1'-naphthyl)pentyl group, a 6-(1'-naphthyl)hexyl group, a 1,1-difluoro-6-(1'-naphthyl)hexyl group, a 2,2-difluoro-6-(1'-naphthyl)hexyl group, a 3,3-difluoro-6-(1'-naphthyl)hexyl group, a 4,4-difluoro-6-(1'-naphthyl)hexyl group, a 5,5-difluoro-6-(1'-naphthyl)hexyl group, a 6,6-difluoro-6-(1'-naphthyl)hexyl group, a 7-(1'-naphthyl)heptyl group, a 1,1-difluoro-7-(1'-naphthyl)heptyl group, a 2,2-difluoro-7-(1'-naphthyl)heptyl group, a 3,3-difluoro-7-(1'-naphthyl)heptyl group, a 4,4-difluoro-7-(1'-naphthyl)heptyl group, a 5,5-difluoro-7-(1'-naphthyl)heptyl group, a 6,6-difluoro-7-(1'-naphthyl)heptyl group, a 7,7-difluoro-7-(1'-naphthyl)heptyl group, a 8-(1'-naphthyl)octyl group, a 1,1-difluoro-8-(1'-naphthyl)octyl group, a 2,2-difluoro-8-(1'-naphthyl)octyl group, a 3,3-difluoro-8-(1'-naphthyl)octyl group, a 4,4-difluoro-8-(1'-naphthyl)octyl group, a 5,5-difluoro-8-(1'-naphthyl)octyl group, a 6,6-difluoro-8-(1'-naphthyl)octyl group, a 7,7-difluoro-8-(1'-naphthyl)octyl group, a 8,8-difluoro-8-(1'-naphthyl)octyl group, a 6-cyano-1-naphthylmethyl group, a 6-nitro-1-naphthylmethyl group, a 6-carboxyl-1-naphthylmethyl group, a 6-hydroxyl-1-naphthylmethyl group, a 6-(N-methylcarboamide)-1-naphthylmethyl group, a 6-(N,N-dimethylcarboamide)-1-naphthylmethyl group, a 6-methyl-1-naphthylmethyl group, a 6-trifluoromethyl-1-naphthylmethyl group, a 6-methoxy-1-naphthylmethyl group, a 6-trifluoromethoxy-1-naphthylmethyl group, a 6-methylthio-1-naphthylmethyl group, a 6-methylsulfinyl-1-naphthylmethyl group, a 6-methylsulfonyl-1-naphthylmethyl group, a 6-methoxycarbonyl-1-naphthylmethyl group, a 6-vinyl-1-naphthylmethyl group, a 6-(2',2'-difluorovinyl)-1-naphthylmethyl group, an 6-ethynyl-1-naphthylmethyl group, a 6-(2'-fluoroethynyl)-1-naphthylmethyl group, a 6-fluoro-1-naphthylmethyl group, a 6-chloro-1-naphthylmethyl group, a (6'-cyano-1-naphthyl)difluoromethyl group, a (6'-nitro-1-naphthyl)difluoromethyl group, a (6'-carboxyl-1-naphthyl)difluoromethyl group, a (6'-hydroxyl-1-naphthyl)difluoromethyl group, a (6'-(N-methylcarboamide)-1-naphthyl)difluoromethyl group, a (6'-(N,N-dimethylcarboamide)-1-naphthyl)difluoromethyl group, a (6'-methyl-1-naphthyl)difluoromethyl group, a (6'-trifluoromethyl-1-naphthyl)difluoromethyl group, a (6'-methoxy-1-naphthyl)difluoromethyl group, a (6'-trifluoromethoxy-1-naphthyl)difluoromethyl group, a (6'-methylthio-1-naphthyl)difluoromethyl group, a (6'-methylsulfinyl-1-naphthyl)difluoromethyl group, a (6'-methylsulfonyl-1-naphthyl)difluoromethyl group, a (6'-methoxycarbonyl-1-naphthyl)difluoromethyl group, a (6'-vinyl-1-naphthyl)difluoromethyl group, a (6'-(2',2'-difluorovinyl)-1-naphthyl)difluoromethyl group, an (6'-ethynyl-1-naphthyl)difluoromethyl group, a (6'-(2'-fluoroethynyl)-1-naphthyl)difluoromethyl group, a (6'-fluoro-1-naphthyl)difluoromethyl group, a (6'-chloro-1-naphthyl)difluoromethyl group, a 2-naphthylmethyl group, a (2'-naphthyl)difluoromethyl group, a 1-(2'-naphthyl)ethyl group, a 1,1-difluro-1-(2'-naphthyl)ethyl group, a 2,2,2-trifluoro-1-(2'-naphthyl)ethyl group, a 1,1,2,2,2-pentafluoro-1-(2'-naphthyl)ethyl group, a 2-(2'-naphthyl)ethyl group, a 1,1-difluro-2-(2'-naphthyl)ethyl group, a 2,2-difluoro-2-(2'-naphthyl)ethyl group, a 1,1,2,2-tetrafluoro-2-(2'-naphthyl)ethyl group, a 3-(2'-naphthyl)propyl group, a 1,1-difluoro-3-(2'-naphthyl)propyl group, a 2,2-difluoro-3-(2'-naphthyl)propyl group, a 3,3-difluoro-3-(2'-naphthyl)propyl group, a 1,1,2,2,3,3-hexafluoro-3-(2'-naphthyl)propyl group, a 4-(2'-naphthyl)butyl group, a 1,1-difluoro-4-(2'-naphthyl)butyl group, a 2,2-difluoro-4-(2'-naphthyl)butyl group, a 3,3-difluoro-4-(2'-naphthyl)butyl group, a 4,4-difluoro-4-(2'-naphthyl)butyl group, a 1,1,2,2,3,3,4,4-octafluoro-3-4-(2'-naphthyl)butyl group, a 5-(2'-naphthyl)pentyl group, a 1,1-difluoro-5-(2'-naphthyl)pentyl group, a 2,2-difluoro-5-(2'-naphthyl)pentyl group, a 3,3-difluoro-5-(2'-naphthyl)pentyl group, a 4,4-difluoro-5-(2'-naphthyl)pentyl group, a 5,5-difluoro-5-(2'-naphthyl)pentyl group, a 6-(2'-naphthyl)hexyl group, a 1,1-difluoro-6-(2'-naphthyl)hexyl group, a 2,2-difluoro-6-(2'-naphthyl)hexyl group, a 3,3-difluoro-6-(2'-naphthyl)hexyl group, a 4,4-difluoro-6-(2'-naphthyl)hexyl group, a 5,5-difluoro-6-(2'-naphthyl)hexyl group, a 6,6-difluoro-6-(2'-naphthyl)hexyl group, a 7-(2'-naphthyl)heptyl group, a 1,1-difluoro-7-(2'-naphthyl)heptyl group, a 2,2-difluoro-7-(2'-naphthyl)heptyl group, a 3,3-difluoro-7-(2'-naphthyl)heptyl group, a 4,4-difluoro-7-(2'-naphthyl)heptyl group, a 5,5-difluoro-7-(2'-naphthyl)heptyl group, a 6,6-difluoro-7-(2'-naphthyl)heptyl group, a 7,7-difluoro-7-(2'-naphthyl)heptyl group, a 8-(2'-naphthyl)octyl group, a 1,1-difluoro-8-(2'-naphthyl)octyl group, a 2,2-difluoro-8-(2'-naphthyl)octyl group, a 3,3-difluoro-8-(2'-naphthyl)octyl group, a 4,4-difluoro-8-(2'-naphthyl)octyl group, a 5,5-difluoro-8-(2'-naphthyl)octyl group, a 6,6-difluoro-8-(2'-naphthyl)octyl group, a 7,7-difluoro-8-(2'-naphthyl)octyl group, a 8,8-difluoro-8-(2'-naphthyl)octyl group, a 6-cyano-2-naphthylmethyl group, a 6-nitro-2-naphthylmethyl group, a 6-carboxyl-2-naphthylmethyl group, a 6-hydroxyl-2-naphthylmethyl group, a 6-(N-methylcarboamide)-2-naphthylmethyl group, a 6-(N,N-dimethylcarboamide)-2-naphthylmethyl group, a 6-methyl-2-naphthylmethyl group, a 6-trifluoromethyl-2-naphthylmethyl group, a 6-methoxy-2-naphthylmethyl group, a 6-trifluoromethoxy-2-naphthylmethyl group, a 6-methylthio-2-naphthylmethyl group, a 6-methylsulfinyl-2-naphthylmethyl group, a 6-methylsulfonyl-2-naphthylmethyl group, a 6-methoxycarbonyl-2-naphthylmethyl group, a 6-vinyl-2-naphthylmethyl group, a 6-(2',2'-difluorovinyl)-2-naphthylmethyl group, an 6-ethynyl-2-naphthylmethyl group, a 6-(2'-fluoroethynyl)-2-naphthylmethyl group, a 6-fluoro-2-naphthylmethyl group, a 6-chloro-2-naphthylmethyl group, a (6'-cyano-1-naphthyl)difluoromethyl group, a (6'-nitro-2-naphthyl)difluoromethyl group, a (6'-carboxyl-2-naphthyl)difluoromethyl group, a (6'-hydroxyl-2-naphthyl)difluoromethyl group, a (6'-(N-methylcarboamide)-2-naphthyl)difluoromethyl group, a (6'-(N,N-dimethylcarboamide)-2-naphthyl)difluoromethyl group, a (6'-methyl-2-naphthyl)difluoromethyl group, a (6'-trifluoromethyl-2-naphthyl)difluoromethyl group, a (6'-methoxy-2-naphthyl)difluoromethyl group, a (6'-trifluoromethoxy-2-naphthyl)difluoromethyl group, a (6'-methylthio-2-naphthyl)difluoromethyl group, a (6'-methylsulfinyl-2-naphthyl)difluoromethyl group, a (6'- methylsulfonyl-2-naphthyl)difluoromethyl group, a (6'-methoxycarbonyl-2-naphthyl)difluoromethyl group, a (6'-vinyl-2-naphthyl)difluoromethyl group, a (6'-(2',2'-difluorovinyl)-2-naphthyl)difluoromethyl group, an (6'-ethynyl-2-naphthyl)difluoromethyl group, a (6'-(2'-fluoroethynyl)-2-naphthyl)difluoromethyl group, a (6'-fluoro-1-naphthyl)difluoromethyl group, a (6'-chloro-2-naphthyl)difluoromethyl group, a 2-pyridylmethyl group, a 1-(2'-pyridyl)ethyl group, a 2-(2'-pyridyl)ethyl group, a 3-(2'-pyridyl)propyl group, a 4-(2'-pyridyl)butyl group, a 5-(2'-pyridyl)pentyl group, a 6-(2'-pyridyl)hexyl group, a 7-(2'-pyridyl)heptyl group, a 8-(2'-pyridyl)octyl group, a 4-cyano-2-pyridylmethyl group, a 4-nitro-2-pyridylmethyl group, a 4-carboxyl-2-pyridylmethyl group, a 4-hydroxyl-2-pyridylmethyl group, a 4-(N-methylcarboamide)-2-pyridylmethyl group, a 4-(N,N-dimethylcarboamide)-2-pyridylmethyl group, a 4-methyl-2-pyridylmethyl group, a 4-trifluoromethyl-2-pyridylmethyl group, a 4-methoxy-2-pyridylmethyl group, a 4-trifluoromethoxy-2-pyridylmethyl group, a 4-methylthio-2-pyridylmethyl group, a 4-methylsulfinyl-2-pyridylmethyl group, a 4-methylsulfonyl-2-pyridylmethyl group, a 4-methoxycarbonyl-2-pyridylmethyl group, a 4-vinyl-2-pyridylmethyl group, a 4-(2',2'-difluorovinyl)-2-pyridylmethyl group, an 4-ethynyl-2-pyridylmethyl group, a 4-(2'-fluoroethynyl)-2-pyridylmethyl group, a 4-fluoro-2-pyridylmethyl group, a 4-chloro-2-pyridylmethyl group, a 5-cyano-2-pyridylmethyl group, a 5-nitro-2-pyridylmethyl group, a 5-carboxyl-2-pyridylmethyl group, a 5-hydroxyl-2-pyridylmethyl group, a 5-(N-methylcarboamide)-2-pyridylmethyl group, a 5-(N, N-dimethylcarboamide)-2-pyridylmethyl group, a 5-methyl-2-pyridylmethyl group, a 5-trifluoromethyl-2-pyridylmethyl group, a 5-methoxy-2-pyridylmethyl group, a 5-trifluoromethoxy-2-pyridylmethyl group, a 5-methylthio-2-pyridylmethyl group, a 5-methylsulfinyl-2-pyridylmethyl group, a 5-methylsulfonyl-2-pyridylmethyl group, a 5-methoxycarbonyl-2-pyridylmethyl group, a 5-vinyl-2-pyridylmethyl group, a 5-(2',2'-difluorovinyl)-2-pyridylmethyl group, an 5-ethynyl-2-pyridylmethyl group, a 5-(2'-fluoroethynyl)-2-pyridylmethyl group, a 5-fluoro-2-pyridylmethyl group, a 5-chloro-2-pyridylmethyl group, a 5,5-dichloro-2-pyridylmethyl group, a 6-cyano-2-pyridylmethyl group, a 6-nitro-2-pyridylmethyl group, a 6-carboxyl-2-pyridylmethyl group, a 6-hydroxyl-2-pyridylmethyl group, a 6-(N-methylcarboamide)-2-pyridylmethyl group, a 6-(N, N-dimethylcarboamide)-2-pyridylmethyl group, a 6-methyl-2-pyridylmethyl group, a 6-trifluormethyl-2-pyridylmethyl group, a 6-methoxy-2-pyridylmethyl group, a 6-trifluoromethoxy-2-pyridylmethyl group, a 6-methylthio-2-pyridylmethyl group, a 6-methylsulfinyl-2-pyridylmethyl group, a 6-methylsulfonyl-2-pyridylmethyl group, a 6-methoxycarbonyl-2-pyridylmethyl group, a 6-vinyl-2-pyridylmethyl group, a 6-(2',2'-difluorovinyl)-2-pyridylmethyl group, an 6-ethynyl-2-pyridylmethyl group, a 6-(2'-fluoroethynyl)-2-pyridylmethyl group, a 6-fluoro-2-pyridylmethyl group, a 6-chloro-2-pyridylmethyl group, a 6,6-dichloro-2-pyridylmethyl group, a 3-pyridylmethyl group, a 1-(3'-pyridyl)ethyl group, a 2-(3'-pyridyl)ethyl group, a 3-(3'-pyridyl)propyl group, a 4-(3'-pyridyl)butyl group, a 5-(3'-pyridyl)pentyl group, a 6-(3'-pyridyl)hexyl group, a 7-(3'-pyridyl)heptyl group, a 8-(3'-pyridyl)octyl group, a 5-cyano-3-pyridylmethyl group, a 5-nitro-3-pyridylmethyl group, a 5-carboxyl-3-pyridylmethyl group, a 5-hydroxyl-3-pyridylmethyl group, a 5-(N-methylcarboamide)-3-pyridylmethyl group, a 5-(N,N-dimethylcarboamide)-3-pyridylmethyl group, a 5-methyl-3-pyridylmethyl group, a 5-trifluoromethyl-3-pyridylmethyl group, a 5-methoxy-3-pyridylmethyl group, a 5-trifluoromethoxy-3-pyridylmethyl group, a 5-methylthio-3-pyridylmethyl group, a 5-methylsulfinyl-3-pyridylmethyl group, a 5-methylsulfonyl-3-pyridylmethyl group, a 5-methoxycarbonyl-3-pyridylmethyl group, a 5-vinyl-3-pyridylmethyl group, a 5-(2',2'-difluorovinyl)-3-pyridylmethyl group, an 5-ethynyl-3-pyridylmethyl group, a 5-(2'-fluoroethynyl)-3-pyridylmethyl group, a 5-fluoro-3-pyridylmethyl group, a 5-chloro-3-pyridylmethyl group, a 6-cyano-3-pyridylmethyl group, a 6-nitro-3-pyridylmethyl group, a 6-carboxyl-3-pyridylmethyl group, a 6-hydroxyl-3-pyridylmethyl group, a 6-(N-methylcarboamide)-3-pyridylmethyl group, a 6-(N,N-dimethylcarboamide)-3-pyridylmethyl group, a 6-methyl-3-pyridylmethyl group, a 6-trifluoromethyl-3-pyridylmethyl group, a 6-methoxy-3-pyridylmethyl group, a 6-trifluoromethoxy-3-pyridylmethyl group, a 6-methylthio-3-pyridylmethyl group, a 6-methylsulfinyl-3-pyridylmethyl group, a 6-methylsulfonyl-3-pyridylmethyl group, a 6-methoxycarbonyl-3-pyridylmethyl group, a 6-vinyl-3-pyridylmethyl group, a 6-(2',2'-difluorovinyl)-3-pyridylmethyl group, an 6-ethynyl-3-pyridylmethyl group, a 6-(2'-fluoroethynyl)-3-pyridylmethyl group, a 6-fluoro-3-pyridylmethyl group, a 6-chloro-3-pyridylmethyl group, a 4-pyridylmethyl group, a 1-(4'-pyridyl)ethyl group, a 2-(4'-pyridyl)ethyl group, a 3-(4'-pyridyl)propyl group, a 4-(4'-pyridyl)butyl group, a 5-(4'-pyridyl)pentyl group, a 6-(4'-pyridyl)hexyl group, a 7-(4'-pyridyl)heptyl group, a 8-(4'-pyridyl)octyl group, a 2-cyano-4-pyridylmethyl group, a 2-nitro-4-pyridylmethyl group, a 2-carboxyl-4-pyridylmethyl group, a 2-hydroxyl-4-pyridylmethyl group, a 2-(N-methylcarboamide)-4-pyridylmethyl group, a 2-(N,N-dimethylcarboamide)-4-pyridylmethyl group, a 2-methyl-4-pyridylmethyl group, a 2-trifluoromethyl-4-pyridylmethyl group, a 2-methoxy-4-pyridylmethyl group, a 2-trifluoromethoxy-4-pyridylmethyl group, a 2-methylthio-4-pyridylmethyl group, a 2-methylsulfinyl-4-pyridylmethyl group, a 2-methylsulfonyl-4-pyridylmethyl group, a 2-methoxycarbonyl-4-pyridylmethyl group, a 2-vinyl-4-pyridylmethyl group, a 2-(2',2'-difluorovinyl)-4-pyridylmethyl group, an 2-ethynyl-4-pyridylmethyl group, a 2-(2'-fluoroethynyl)-4-pyridylmethyl group, a 2-fluoro-4-pyridylmethyl group, a 2-chloro-4-pyridylmethyl group, a 6-cyano-4-pyridylmethyl group, a 6-nitro-4-pyridylmethyl group, a 6-carboxyl-4-pyridylmethyl group, a 6-hydroxyl-4-pyridylmethyl group, a 6-(N-methylcarboamide)-4-pyridylmethyl group, a 6-(N, N-dimethylcarboamide)-4-pyridylmethyl group, a 6-methyl-4-pyridylmethyl group, a 6-trifluoromethyl-4-pyridylmethyl group, a 6-methoxy-4-pyridylmethyl group, a 6-trifluoromethoxy-4-pyridylmethyl group, a 6-methylthio-4-pyridylmethyl group, a 6-methylsulfinyl-4-pyridylmethyl group, a 6-methylsulfonyl-4-pyridylmethyl group, a 6-methoxycarbonyl-4-pyridylmethyl group, a 6-vinyl-4-pyridylmethyl group, a 6-(2',2'-difluorovinyl)-4-pyridylmethyl group, an 6-ethynyl-4-pyridylmethyl group, a 6-(2'-fluoroethynyl)-4-pyridylmethyl group, a 6-fluoro-4-pyridylmethyl group, a 6-chloro-4-pyridylmethyl group, a 2-quinolylmethyl group, a 1-(2'-quinolyl)ethyl group, a 2-(2'-quinolyl)ethyl group, a 3-(2'-quinolyl)propyl group, a 4-(2'-quinolyl)butyl group, a 5-(2'-quinolyl)pentyl group, a 6-(2'-quinolyl)hexyl group, a 7-(2'-quinolyl)heptyl group, a 8-(2'-quinolyl)octyl group, a 6-cyano-2-quinolylmethyl group, a 6-nitro-2-quinolylmethyl group, a 6-carboxyl-2-quinolylmethyl group, a 6-hydroxyl-2-quinolylmethyl group, a 6-(N-methylcarboamide)-2-quinolylmethyl group, a 6-(N,N-dimethylcarboamide)-2-quinolylmethyl group, a 6-methyl-2-quinolylmethyl group, 6-trifluoromethyl-2-quinolylmethyl group, a 6-methoxy-2-quinolylmethyl group, a 6-trifluoromethoxy-2-quinolylmethyl group, a 6-methylthio-2-quinolylmethyl group, a 6-methylsulfinyl-2-quinolylmethyl group, a 6-methylsulfonyl-2-quinolylmethyl group, a 6-methoxycarbonyl-2-quinolylmethyl group, a 6-vinyl-2-quinolylmethyl group, a 6-(2',2'-difluorovinyl)-2-quinolylmethyl group, an 6-ethynyl-2-quinolylmethyl group, a 6-(2'-fluoroethynyl)-2-quinolylmethyl group, a 6-fluoro-2-quinolylmethyl group, a 6-chloro-2-quinolylmethyl group, a 3-quinolylmethyl group, a 1-(3'-quinolyl)ethyl group, a 2-(3'-quinolyl)ethyl group, a 3-(3'-quinolyl)propyl group, a 4-(3'-quinolyl)butyl group, a 5-(3'-quinolyl)pentyl group, a 6-(3'-quinolyl)hexyl group, a 7-(3'-quinolyl)heptyl group, a 8-(3'-quinolyl)octyl group, a 6-cyano-3-quinolylmethyl group, a 6-nitro-3-quinolylmethyl group, a 6-carboxyl-3-quinolylmethyl group, a 6-hydroxyl-3-quinolylmethyl group, a 6-(N-methylcarboamide)-3-quinolylmethyl group, a 6-(N,N-dimethylcarboamide)-3-quinolylmethyl group, a 6-methyl-3-quinolylmethyl group, a 6-trifluoromethyl-3-quinolylmethyl group, a 6-methoxy-3-quinolylmethyl group, a 6-trifluoromethoxy-3-quinolylmethyl group, a 6-methylthio-3-quinolylmethyl group, a 6-methylsulfinyl-3-quinolylmethyl group, a 6-methylsulfonyl-3-quinolylmethyl group, a 6-methoxycarbonyl-3-quinolylmethyl group, a 6-vinyl-3-quinolylmethyl group, a 6-(2',2'-difluorovinyl)-3-quinolylmethyl group, an 6-ethynyl-3-quinolylmethyl group, a 6-(2'-fluoroethynyl)-3-quinolylmethyl group, a 6-fluoro-3-quinolylmethyl group, a 6-chloro-3-quinolylmethyl group, a 4-quinolylmethyl group, a 1-(4'-quinolyl)ethyl group, a 2-(4'-quinolyl)ethyl group, a 3-(4'-quinolyl)propyl group, a 4-(4'-quinolyl)butyl group, a 5-(3'-quinolyl)pentyl group, a 6-(4'-quinolyl)hexyl group, a 7-(4'-quinolyl)heptyl group, a 8-(4'-quinolyl)octyl group, a 6-cyano-4-quinolylmethyl group, a 6-nitro-4-quinolylmethyl group, a 6-carboxyl-4-quinolylmethyl group, a 6-hydroxyl-4-quinolylmethyl group, a 6-(N-methylcarboamide)-4-quinolylmethyl group, a 6-(N,N-dimethylcarboamide)-4-quinolylmethyl group, a 6-methyl-4-quinolylmethyl group, a 6-trifluoromethyl-4-quinolylmethyl group, a 6-methoxy-4-quinolylmethyl group, a 6-trifluoromethoxy-4-quinolylmethyl group, a 6-methylthio-4-quinolylmethyl group, a 6-methylsulfinyl-4-quinolylmethyl group, a 6-methylsulfonyl-4-quinolylmethyl group, a 6-methoxycarbonyl-4-quinolylmethyl group, a 6-vinyl-4-quinolylmethyl group, a 6-(2',2'-difluorovinyl)-4-quinolylmethyl group, an 6-ethynyl-4-quinolylmethyl group, a 6-(2'-fluoroethynyl)-4-quinolylmethyl group, a 6-fluoro-4-quinolylmethyl group, a 6-chloro-4-quinolylmethyl group, a 2-furylmethyl group, a 1-(2'-furyl)ethyl group, a 2-(2'-furyl)ethyl group, a 3-(2'-furyl)propyl group, a 4-(2'-furyl)butyl group, a 5-(2'-furyl)pentyl group, a 6-(2'-furyl)hexyl group, a 7-(2'-furyl)heptyl group, a 8-(2'-furyl)octyl group, a 4-cyano-2-furylmethyl group, a 4-nitro-2-furylmethyl group, a 4-carboxyl-2-furylmethyl group, a 4-hydroxyl-2-furylmethyl group, a 4-(N-methylcarboamide)-2-furylmethyl group, a 4-(N,N-dimethylcarboamide)-2-furylmethyl group, a 4-methyl-2-furylmethyl group, a 4-trifluoromethyl-2-furylmethyl group, a 4-methoxy-2-furylmethyl group, a 4-trifluoromethoxy-2-furylmethyl group, a 4-methylthio-2-furylmethyl group, a 4-methylsulfinyl-2-furylmethyl group, a 4-methylsulfonyl-2-furylmethyl group, a 4-methoxycarbonyl-2-furylmethyl group, a 4-vinyl-2-furylmethyl group, a 4-(2',2'-difluorovinyl)-2-furylmethyl group, an 4-ethynyl-2-furylmethyl group, a 4-(2'-fluoroethynyl)-2-furylmethyl group, a 4-fluoro-2-furylmethyl group, a 4-chloro-2-furylmethyl group, a 3-furylmethyl group, a 1-(3'-furyl)ethyl group, a 2-(3'-furyl)ethyl group, a 3-(3'-furyl)propyl group, a 4-(3'-furyl)butyl group, a 5-(3'-furyl)pentyl group, a 6-(3'-furyl)hexyl group, a 7-(3'-furyl)heptyl group, a 8-(3'-furyl)octyl group, a 4-cyano-3-furylmethyl group, a 4-nitro-3-furylmethyl group, a 4-carboxyl-3-furylmethyl group, a 4-hydroxyl-3-furylmethyl group, a 4-(N-methylcarboamide)-3-furylmethyl group, a 4-(N,N-dimethylcarboamide)-3-furylmethyl group, a 4-methyl-3-furylmethyl group, a 4-trifluoromethyl-3-furylmethyl group, a 4-methoxy-3-furylmethyl group, a 4-trifluoromethoxy-3-furylmethyl group, a 4-methylthio-3-furylmethyl group, a 4-methylsulfinyl-3-furylmethyl group, a 4-methylsulfonyl-3-furylmethyl group, a 4-methoxycarbonyl-3-furylmethyl group, a 4-vinyl-3-furylmethyl group, a 4-(2',2'-difluorovinyl)-3-furylmethyl group, an 4-ethynyl-3-furylmethyl group, a 4-(2'-fluoroethynyl)-3-furylmethyl group, a 4-fluoro-3-furylmethyl group, a 4-chloro-3-furylmethyl group, a 2-thienylmethyl group, a 1-(2'-thienyl)ethyl group, a 2-(2'-thienyl)ethyl group, a 3-(2'-thienyl)propyl group, a 4-(2'-thienyl)butyl group, a 5-(2'-thienyl)pentyl group, a 6-(2'-thienyl)hexyl group, a 7-(2'-thienyl)heptyl group, a 8-(2'-thienyl)octyl group, a 4-cyano-2-thienylmethyl group, a 4-nitro-2-thienylmethyl group, a 4-carboxyl-2-thienylmethyl group, a 4-hydroxyl-2-thienylmethyl group, a 4-(N-methylcarboamide)-2-thienylmethyl group, a 4-(N,N-dimethylcarboamide)-2-thienylmethyl group, a 4-methyl-2-thienylmethyl group, a 4-trifluoromethyl-2-thienylmethyl group, a 4-methoxy-2-thienylmethyl group, a 4-trifluoromethoxy-2-thienylmethyl group, a 4-methylthio-2-thienylmethyl group, a 4-methylsulfinyl-2-thienylmethyl group, a 4-methylsulfonyl-2-thienylmethyl group, a 4-methoxycarbonyl-2-thienylmethyl group, a 4-vinyl-2-thienylmethyl group, a 4-(2',2'-difluorovinyl)-2-thienylmethyl group, an 4-ethynyl-2-thienylmethyl group, a 4-(2'-fluoroethynyl)-2-thienylmethyl group, a 4-fluoro-2-thienylmethyl group, a 4-chloro-2-thienylmethyl group, a 3-thienylmethyl group, a 1-(3'-thienyl)ethyl group, a 2-(3'-thienyl)ethyl group, a 3-(3'-thienyl)propyl group, a 4-(3'-thienyl)butyl group, a 5-(3'-thienyl)pentyl group, a 6-(3'-thienyl)hexyl group, a 7-(3'-thienyl)heptyl group, a 8-(3'-thienyl)octyl group, a 4-cyano-3-thienylmethyl group, a 4-nitro-3-thienylmethyl group, a 4-carboxyl-3-thienylmethyl group, a 4-hydroxyl-3-thienylmethyl group, a 4-(N-methylcarboamide)-3-thienylmethyl group, a 4-(N,N-dimethylcarboamide)-3-thienylmethyl group, a 4-methyl-3-thienylmethyl group, a 4-trifluoromethyl-3-thienylmethyl group, a 4-methoxy-3-thienylmethyl group, a 4-trifluoromethoxy-3-thienylmethyl group, a 4-methylthio-3-thienylmethyl group, a 4-methylsulfinyl-3-thienylmethyl group, a 4-methylsulfonyl-3-thienylmethyl group, a 4-methoxycarbonyl-3-thienylmethyl group, a 4-vinyl-3-thienylmethyl group, a 4-(2',2'-difluorovinyl)-3-thienylmethyl group, an 4-ethynyl-3-thienylmethyl group, a 4-(2'-fluoroethynyl)-3-thienylmethyl group, a 4-fluoro-3-thienylmethyl group, a 4-chloro-3-thienylmethyl group, a 2-(1-benzofuranyl)methyl group, a 1-(2'-(1'-benzofuranyl))ethyl group, a 2-(2'-(1'-benzofuranyl))ethyl group, a 3-(2'-(1'-benzofuranyl))propyl group, a 4-(2'-(1'-benzofuranyl))butyl group, a 5-(2'-(1'-benzofuranyl))pentyl group, a 6-(2'-(1'-benzofuranyl))hexyl group, a 7-(2'-(1'-benzofuranyl))heptyl group, a 8-(2'-(1'-benzofuranyl))octyl group, a 5-cyano-2-(1-benzofuranyl)methyl group, a 5-nitro-2-(1-benzofuranyl)methyl group, a 5-carboxyl-2-(1-benzofuranyl)methyl group, a 5-hydroxyl-2-(1-benzofuranyl)methyl group, a 5-(N-methylcarboamide)-2-(1-benzofuranyl)methyl group, a 5-(N,N-dimethylcarboamide)-2-(1-benzofuranyl)methyl group, a 5-methyl-2-(1-benzofuranyl)methyl group, a 5-trifluoromethyl-2-(1-benzofuranyl)methyl group, a 5-methoxy-2-(1-benzofuranyl)methyl group, a 5-trifluoromethoxy-2-(1-benzofuranyl)methyl group, a 5-methylthio-2-(1-benzofuranyl)methyl group, a 5-methylsulfinyl-2-

(1-benzofuranyl)methyl group, a 5-methylsulfonyl-2-(1-benzofuranyl)methyl group, a 5-methoxycarbonyl-2-(1-benzofuranyl)methyl group, a 5-vinyl-2-(1-benzofuranyl)methyl group, a 5-(2',2'-difluorovinyl)-2-(1-benzofuranyl)methyl group, an 5-ethynyl-2-(1-benzofuranyl)methyl group, a 5-(2'-fluoroethynyl)-2-(1-benzofuranyl)methyl group, a 5-fluoro-2-(1-benzofuranyl)methyl group, a 5-chloro-2-(1-benzofuranyl)methyl group, a 3-(1-benzofuranyl)methyl group, a 1-(3'-(1'-benzofuranyl))ethyl group, a 2-(3'-(1'-benzofuranyl))ethyl group, a 3-(3'-(1'-benzofuranyl))propyl group, a 4-(3'-(1'-benzofuranyl))butyl group, a 5-(3'-(1'-benzofuranyl))pentyl group, a 6-(3'-(1'-benzofuranyl))hexyl group, a 7-(3'-(1'-benzofuranyl))heptyl group, a 8-(3'-(1'-benzofuranyl))octyl group, a 5-cyano-3-(1-benzofuranyl)methyl group, a 5-nitro-3-(1-benzofuranyl)methyl group, a 5-carboxyl-3-(1-benzofuranyl)methyl group, a 5-hydroxyl-3-(1-benzofuranyl)methyl group, a 5-(N-methylcarboamide)-3-(1-benzofuranyl)methyl group, a 5-(N,N-dimethylcarboamide)-3-(1-benzofuranyl)methyl group, a 5-methyl-3-(1-benzofuranyl)methyl group, a 5-trifluoromethyl-3-(1-benzofuranyl)methyl group, a 5-methoxy-3-(1-benzofuranyl)methyl group, a 5-trifluoromethoxy-3-(1-benzofuranyl)methyl group, a 5-methylthio-3-(1-benzofuranyl)methyl group, a 5-methylsulfinyl-3-(1-benzofuranyl)methyl group, a 5-methylsulfonyl-3-(1-benzofuranyl)methyl group, a 5-methoxycarbonyl-3-(1-benzofuranyl)methyl group, a 5-vinyl-3-(1-benzofuranyl)methyl group, a 5-(2',2'-difluorovinyl)-3-(1-benzofuranyl)methyl group, an 5-ethynyl-3-(1-benzofuranyl)methyl group, a 5-(2'-fluoroethynyl)-3-(1-benzofuranyl)methyl group, a 5-fluoro-3-(1-benzofuranyl)methyl group, a 5-chloro-3-(1-benzofuranyl)methyl group, a 2-(1-benzothienyl)methyl group, a 1-(2'-(1'-benzothienyl))ethyl group, a 2-(2'-(1'-benzothienyl))ethyl group, a 3-(2'-(1'-benzothienyl))propyl group, a 4-(2'-(1'-benzothienyl))butyl group, a 5-(2'-(1'-benzothienyl))pentyl group, a 6-(2'-(1'-benzothienyl))hexyl group, a 7-(2'-(1'-benzothienyl))heptyl group, a 8-(2'-(1'-benzothienyl))octyl group, a 5-cyano-2-(1-benzothienyl)methyl group, a 5-nitro-2-(1-benzothienyl)methyl group, a 5-carboxyl-2-(1-benzothienyl)methyl group, a 5-hydroxyl-2-(1-benzothienyl)methyl group, a 5-(N-methylcarboamide)-2-(1-benzothienyl)methyl group, a 5-(N,N-dimethylcarboamide)-2-(1-benzothienyl)methyl group, a 5-methyl-2-(1-benzothienyl)methyl group, a 5-trifluoromethyl-2-(1-benzothienyl)methyl group, 5-methoxy-2-(1-benzothienyl)methyl group, a 5-trifluoromethoxy-2-(1-benzothienyl)methyl group, a 5-methylthio-2-(1-benzothienyl)methyl group, a 5-methylsulfinyl-2-(1-benzothienyl)methyl group, a 5-methylsulfonyl-2-(1-benzothienyl)methyl group, a 5-methoxycarbonyl-2-(1-benzothienyl)methyl group, a 5-vinyl-2-(1-benzothienyl)methyl group, a 5-(2',2'-difluorovinyl)-2-(1-benzothienyl)methyl group, an 5-ethynyl-2-(1-benzothienyl)methyl group, a 5-(2'-fluoroethynyl)-2-(1-benzothienyl)methyl group, a 5-fluoro-2-(1-benzothienyl)methyl group, a 5-chloro-2-(1-benzothienyl)methyl group, a 3-(1-benzothienyl)methyl group, a 1-(3'-(1'-benzothienyl))ethyl group, a 2-(3'-(1'-benzothienyl))ethyl group, a 3-(3'-(1'-benzothienyl))propyl group, a 4-(3'-(1'-benzothienyl))butyl group, a 5-(3'-(1'-benzothienyl))pentyl group, a 6-(3'-(1'-benzothienyl))hexyl group, a 7-(3'-(1'-benzothienyl))heptyl group, a 8-(3'-(1'-benzothienyl))octyl group, a 5-cyano-3-(1-benzothienyl)methyl group, a 5-nitro-3-(1-benzothienyl)methyl group, a 5-carboxyl-3-(1-benzothienyl)methyl group, a 5-hydroxyl-3-(1-benzothienyl)methyl group, a 5-(N-methylcarboamide)-3-(1-benzothienyl)methyl group, a 5-(N,N-dimethylcarboamide)-3-(1-benzothienyl)mrnethyl group, a 5-methyl-3-(1-benzothienyl)methyl group, a 5-trifluoromethyl-3-(1-benzothienyl)methyl group, a 5-methoxy-3-(1-benzothienyl)methyl group, a 5-trifluoromethoxy-3-(1-benzothienyl)methyl group, a 5-methylthio-3-(1-benzothienyl)methyl group, a 5-methylsulfinyl-3-(1-benzothienyl)methyl group, a 5-methylsulfonyl-3-(1-benzothienyl)methyl group, a 5-methoxycarbonyl-3-(1-benzothienyl)methyl group, a 5-vinyl-3-(1-benzothienyl)methyl group, a 5-(2',2'-difluorovinyl)-3-(1-benzothienyl)methyl group, an 5-ethynyl-3-(1-benzothienyl)methyl group, a 5-(2'-fluoroethynyl)-3-(1-benzothienyl)methyl group, a 5-fluoro-3-(1-benzothienyl)methyl group, a 5-chloro-3-(1-benzothienyl)methyl group, a fluoromethyl group, a 1-fluoroethyl group, a 1,1-difluoroethyl group, a 2-fluoroethyl group, a 2,2-difluoroethyl group, a 2,2,2-trifluoroethyl group, a 3-fluoropropyl group, a 3,3,3-trifluoropropyl group, a 4-fluorobutyl group, a 4,4,4-trifluorobutyl group, a 3,3,4,4,4-pentafluorobutyl group, a 5-fluoropentyl group, a 6-fluorohexyl group, a 7-fluoroheptyl group, a 8-fluorooctyl group, a chloromethyl group, a 1-chloroethyl group, a 2-chloroethyl group, a 3-chloropropyl group, a 4-chlorobutyl group, a 5-chloropentyl group, a 6-chlorohexyl group, a 7-chloroheptyl group, a 8-chlorooctyl group, a bromomethyl group, a 1-bromoethyl group, a 2-bromoethyl group, a 3-bromopropyl group, a 4-bromobutyl group, a 5-bromopentyl group, a 6-bromohexyl group, a 7-bromoheptyl group, a 8-bromooctyl group, a (methoxycarbonyl)methyl group, a 1-(methoxycarbonyl)ethyl group, a 2-(methoxycarbonyl)ethyl group, a 3-(methoxycarbonyl)propyl group, a 4-(methoxycarbonyl)butyl group, a 5-(methoxycarbonyl)pentyl group, a 6-(methoxycarbonyl)hexyl group, a 7-(methoxycarbonyl) heptyl group, a 8-(methoxycarbonyl)octyl group, a cyanomethyl group, a 1-cyanoethyl group, a 2-cyanoethyl group, a 3-cyanopropyl group, a 4-cyanobutyl group, a 5-cyanopentyl group, a 6-cyanohexyl group, a 7-cyanoheptyl group, a 8-cyanooctyl group, a nitromethyl group, a 1-nitroethyl group, a 2-nitroethyl group, a 3-nitropropyl group, a 4-nitrobutyl group, a 5-nitropentyl group, a 6-nitrohexyl group, a 7-nitroheptyl group, a 8-nitrooctyl group, a (carboxy)methyl group, a 1-(carboxy)ethyl group, a 2-(carboxy)ethyl group, a 3-(carboxy)propyl group, a 4-(carboxy)butyl group, a 5-(carboxy)pentyl group, a 6-(carboxy)hexyl group, a 7-(carboxy)heptyl group, a 8-(carboxy)octyl group, a hydroxymethyl group, a 1-hydrozyethyl group, a 2-hydroxyethyl group, a 3-hydroxypropyl group, a 4-hydroxybutyl group, a 5-hydroxypentyl group, a 6-hydroxyhexyl group, a 7-hydroxyheptyl group, and a 8-hydroxyoctyl group.

Examples of the C1 to C8 chain hydrocarbon group optionally having one or more atoms or groups selected from group F include a benzyl group, a phenyldifluoromethyl group, a 1-phenylethyl group, a 1,1-difluoro-1-phenylethyl group, a 2,2,2-trifluoro-1-phenylethyl group, a 1,1,2,2,2-pentafluoro-1-phenylethyl group, a 2-phenylethyl group, a 1,1-difluoro-2-phenylethyl group, a 2,2-difluoro-2-phenylethyl group, a 1,1,2,2-tetrafluoro-2-phenylethyl group, a 3-phenylpropyl group, a 1,1-difluoro-3-phenylpropyl group, a 2,2-difluoro-3-phenylpropyl group, a 3,3-difluoro-3-phenylpropyl group, a 1,1,2,2,3,3-hexafluoro-3-phenylpropyl group, a 4-phenylbutyl group, a 1,1-difluoro-4-phenylbutyl group, a 2,2-difluoro-4-phenylbutyl group, a 3,3-difluoro-4-phenylbutyl group, a 4,4-difluoro-4-phenylbutyl group, a 1,1,2,2,3,3,4,4-octafluoro-3-4-phenylbutyl group, a 5-phenylpentyl group, a 1,1-difluoro-5-phenylpentyl group, a 2,2-difluoro-5-phenylpentyl group, a 3,3-difluoro-5-phenylpentyl group, a 4,4-difluoro-5-phenylpentyl group, a 5,5-difluoro-5-phenylpentyl group, a 6-phenylhexyl group, a 1,1-difluoro-6-phenylhexyl group, a 2,2-difluoro-6-phenylhexyl group, a 3,3-difluoro-6-phenylhexyl group, a 4,4-difluoro-6-phenylhexyl group, a 5,5-difluoro-6-phenylhexyl group, a 6,6-difluoro-6-phenylhexyl group, a 7-phenylheptyl group, a 1,1-difluoro-7-phenylheptyl group, a 2,2-difluoro-7-phenylheptyl group, a 3,3-difluoro-7-phenylheptyl group, a 4,4-difluoro-7-phenylheptyl group, a 5,5-difluoro-7-phenylheptyl group, a 6,6-difluoro-7-phenylheptyl group, a 7,7-difluoro-7-phenylheptyl group, a 8-phenyloctyl group, a 1,1-difluoro-8-phenyloctyl group, a 2,2-difluoro-8-phenyloctyl group, a 3,3-difluoro-8-phenyloctyl group, a 4,4-difluoro-8-phenyloctyl group, a 5,5-difluoro-8-phenyloctyl group, a 6,6-difluoro-8-phenyloctyl group, a 7,7-difluoro-8-phenyloctyl group, a 8,8-difluoro-8-phenyloctyl group, a 4-cyanobenzyl group, a 4-nitrobenzyl group, a 4-carboxylbenzyl group, a 4-hydroxylbenzyl group, a 4-(N-methylcarboamide)benzyl group, a 4-(N,N-dimethylcarboamide)benzyl group, a 4-methylbenzyl group, a 4-trifluoromethylbenzyl group, a 4-methoxybenzyl group, a 4-trifluoromethoxybenzyl group, a 4-methylthiobenzyl group, a 4-methylsulfinylbenzyl group, a 4-methylsulfonylbenzyl group, a 4-methoxycarbonylbenzyl group, a 4-vinylbenzyl group, a 4-(2',2'-difluorovinyl)benzyl group, an 4-ethynylbenzyl group, a 4-(2'-fluoroethynyl)benzyl group, a 4-fluorobenzyl group, a 4-chlorobenzyl group, a 3,4-dichlorobenzyl group, a (4'-cyanophenyl)difluoromethyl group, a (4'-nitrophenyl)difluoromethyl group, a (4'-carboxylphenyl)difluoromethyl group, a (4'-hydroxylphenyl)difluoromethyl group, a (4'-(N-methylcarboamide)phenyl)difluoromethyl group, a (4'-(N,N-dimethylcarboamide)phenyl)difluoromethyl group, a (4'-methylphenyl)difluoromethyl group, a (4'-trifluoromethylphenyl)difluoromethyl group, a (4'-methoxyphenyl)difluoromethyl group, a (4'-trifluoromethoxyphenyl)difluoromethyl group, a (4'-methylthiophenyl)difluoromethyl group, a (4'-methylsulfinylphenyl)difluoromethyl group, a (4'-methylsulfonylphenyl)difluoromethyl group, a (4'-methoxycarbonylphenyl)difluoromethyl group, a (4'-vinylphenyl)difluoromethyl group, a (4'-(2',2'-difluorovinyl)phenyl)difluoromethyl group, a (4'-ethynylphenyl)difluoromethyl group, a (4'-(2'-fluoroethynyl)phenyl)difluoromethyl group, a (4'-fluorophenyl)difluoromethyl group, a (4'-chlorophenyl)difluoromethyl group, a 3,(4'-dichlorophenyl)difluoromethyl group, a 1-naphthylmethyl group, a (1'-naphthyl)difluoromethyl group, a 1-(1'-naphthyl)ethyl group, a 1,1-difluoro-1-(1'-naphthyl)ethyl group, a 2,2,2-trifluoro-1-(1'-naphthyl)ethyl group, a 1,1,2,2,2-pentafluoro-1-(1'-naphthyl)ethyl group, a 2-(1'-naphthyl)ethyl group, a 1,1-difluoro-2-(1'-naphthyl)ethyl group, a 2,2-difluoro-2-(1'-naphthyl)ethyl group, a 1,1,2,2-tetrafluoro-2-(1'-naphthyl)ethyl group, a 3-(1'-naphthyl)propyl group, a 1,1-difluoro-3-(1'-naphthyl)propyl group, a 2,2-difluoro-3-(1'-naphthyl)propyl group, a 3,3-difluoro-3-(1'-naphthyl)propyl group, a 1,1,2,2,3,3-hexafluoro-3-(1'-naphthyl)propyl group, a 4-(1'-naphthyl)butyl group, a 1,1-difluoro-4-(1'-naphthyl)butyl group, a 2,2-difluoro-4-(1'-naphthyl)butyl group, a 3,3-difluoro-4-(1'-naphthyl)butyl group, a 4,4-difluoro-4-(1'-naphthyl)butyl group, a 1,1,2,2,3,3,4,4-octafluoro-3-4-(1'-naphthyl)butyl group, a 5-(1'-naphthyl)pentyl group, a 1,1-difluoro-5-(1'-naphthyl)pentyl group, a 2,2-difluoro-5-(1'-naphthyl)pentyl group, a 3,3-difluoro-5-(1'-naphthyl)pentyl group, a 4,4-difluoro-5-(1'-naphthyl)pentyl group, a 5,5-difluoro-5-(1'-naphthyl)pentyl group, a 6-(1'-naphthyl)hexyl group, a 1,1-difluoro-6-(1'-naphthyl)hexyl group, a 2,2-difluoro-6-(1'-naphthyl)hexyl group, a 3,3-difluoro-6-(1'-naphthyl)hexyl group, a 4,4-difluoro-6-(1'-naphthyl)hexyl group, a 5,5-difluoro-6-(1'-naphthyl)hexyl group, a 6,6-difluoro-6-(1'-naphthyl)hexyl group, a 7-(1'-naphthyl)heptyl group, a 1,1-difluoro-7-(1'-naphthyl)heptyl group, a 2,2-difluoro-7-(1'-naphthyl)heptyl group, a 3,3-difluoro-7-(1'-naphthyl)heptyl group, a 4,4-difluoro-7-(1'-naphthyl)heptyl group, a 5,5-difluoro-7-(1'-naphthyl)heptyl group, a 6,6-difluoro-7-(1'-naphthyl)heptyl group, a 7,7-difluoro-7-(1'-naphthyl)heptyl group, a 8-(1'-naphthyl)octyl group, a 1,1-difluoro-8-(1'-naphthyl)octyl group, a 2,2-difluoro-8-(1'-naphthyl)octyl group, a 3,3-difluoro-8-(1'-naphthyl)octyl group, a 4,4-difluoro-8-(1'-naphthyl)octyl group, a 5,5-difluoro-8-(1'-naphthyl)octyl group, a 6,6-difluoro-8-(1'-naphthyl)octyl group, a 7,7-difluoro-8-(1'-naphthyl)octyl group, a 8,8-difluoro-8-(1'-naphthyl)octyl group, a 6-cyano-1-naphthylmethyl group, a 6-nitro-1-naphthylmethyl group, a 6-carboxyl-1-naphthylmethyl group, a 6-hydroxyl-1-naphthylmethyl group, a 6-(N-methylcarboamide)-1-naphthylmethyl group, a 6-(N,N-dimethylcarboamide)-1-naphthylmethyl group, a 6-methyl-1-naphthylmethyl group, a 6-trifluoromethyl-1-naphthylmethyl group, a 6-methoxy-1-naphthylmethyl group, a 6-trifluoromethoxy-1-naphthylmethyl group, a 6-methylthio-1-naphthylmethyl group, a 6-methylsulfinyl-1-naphthylmethyl group, a 6-methylsulfonyl-1-naphthylmethyl group, a 6-methoxycarbonyl-1-naphthylmethyl group, a 6-vinyl-1-naphthylmethyl group, a 6-(2',2'-difluorovinyl)-1-naphthylmethyl group, an 6-ethynyl-1-naphthylmethyl group, a 6-(2'-fluoroethynyl)-1-naphthylmethyl group, a 6-fluoro-1-naphthylmethyl group, a 6-chloro-1-naphthylmethyl group, a (6'-cyano-1-naphthyl)difluoromethyl group, a (6'-nitro-1-naphthyl)difluoromethyl group, a (6'-carboxyl-1-naphthyl)difluoromethyl group, a (6'-hydroxyl-1-naphthyl)difluoromethyl group, a (6'-(N-methylcarboamide)-1-naphthyl)difluoromethyl group, a (6'-(N,N-dimethylcarboamide)-1-naphthyl)difluoromethyl group, a (6'-methyl-1-naphthyl)difluoromethyl group, a (6'-trifluoromethyl-1-naphthyl)difluoromethyl group, a (6'-methoxy-1-naphthyl)difluoromethyl group, a (6'-trifluoromethoxy-1-naphthyl)difluoromethyl group, a (6'-methylthio-1-naphthyl)difluoromethyl group, a (6'-methylsulfinyl-1-naphthyl)difluoromethyl group, a (6'-methylsulfonyl-1-naphthyl)difluoromethyl group, a (6'-methoxycarbonyl-1-naphthyl)difluoromethyl group, a (6'-vinyl-1-naphthyl)difluoromethyl group, a (6'-(2',2'-difluorovinyl)-1-naphthyl)difluoromethyl group, an (6'-ethynyl-1-naphthyl)difluoromethyl group, a (6'-(2'-fluoroethynyl)-1-naphthyl)difluoromethyl group, a (6'-fluoro-1-naphthyl)difluoromethyl group, a (6'-chloro-1-naphthyl)difluoromethyl group, a 2-naphthylmethyl group, a (2'-naphthyl)difluoromethyl group, a 1-(2'-naphthyl)ethyl group, a 1,1-difluro-1-(2'-naphthyl)ethyl group, a 2,2,2-trifluoro-1-(2'-naphthyl)ethyl group, a 1,1,2,2,2-pentafluoro-1-(2'-naphthyl)ethyl group, a 2-(2'-naphthyl)ethyl group, a 1,1-difluro-2-(2'-naphthyl)ethyl group, a 2,2-difluoro-2-(2'-naphthyl)ethyl group, a 1,1,2,2-tetrafluoro-2-(2'-naphthyl)ethyl group, a 3-(2'-naphthyl)propyl group, a 1,1-difluoro-3-(2'-naphthyl)propyl group, a 2,2-difluoro-3-(2'-naphthyl)propyl group, a 3,3-difluoro-3-(2'-naphthyl)propyl group, a 1,1,2,2,3,3-hexafluoro-3-(2'-naphthyl)propyl group, a 4-(2'-naphthyl)butyl group, a 1,1-difluoro-4-(2'-naphthyl)butyl group, a 2,2-difluoro-4-(2'-naphthyl)butyl group, a 3,3-difluoro-4-(2'-naphthyl)butyl group, a 4,4-difluoro-4-(2'-naphthyl)butyl group, a 1,1,2,2,3,3,4,4-octafluoro-3-4-(2'-naphthyl)butyl group, a 5-(2'-naphthyl)pentyl group, a 1,1-difluoro-5-(2'-naphthyl)pentyl group, a 2,2-difluoro-5-(2'-naphthyl)pentyl group, a 3,3-difluoro-5-(2'-naphthyl)pentyl group, a 4,4-difluoro-5-(2'-naphthyl)pentyl group, a 5,5-difluoro-5-(2'-naphthyl)pentyl group, a 6-(2'-naphthyl)hexyl group, a 1,1-difluoro-6-(2'-naphthyl)hexyl group, a 2,2-difluoro-6-(2'-naphthyl)hexyl group, a 3,3-difluoro-6-(2'-naphthyl)hexyl group, a 4,4-difluoro-6-(2'-naphthyl)hexyl group, a 5,5-difluoro-6-(2'-naphthyl)hexyl group, a 6,6-difluoro-6-(2'-naphthyl)hexyl group, a 7-(2'-naphthyl)heptyl group, a 1,1-difluoro-7-(2'-naphthyl)heptyl group, a 2,2-difluoro-7-(2'-naphthyl)heptyl group, a 3,3-difluoro-7-(2'-naphthyl) heptyl group, a 4,4-difluoro-7-(2'-naphthyl)heptyl group, a 5,5-difluoro-7-(2'-naphthyl)heptyl group, a 6,6-difluoro-7-(2'-naphthyl)heptyl group, a 7,7-difluoro-7-(2'-naphthyl) heptyl group, a 8-(2'-naphthyl)octyl group, a 1,1-difluoro-8-(2'-naphthyl)octyl group, a 2,2-difluoro-8-(2'-naphthyl) octyl group, a 3,3-difluoro-8-(2'-naphthyl)octyl group, a 4,4-difluoro-8-(2'-naphthyl)octyl group, a 5,5-difluoro-8-(2'-naphthyl)octyl group, a 6,6-difluoro-8-(2'-naphthyl) octyl group, a 7,7-difluoro-8-(2'-naphthyl)octyl group, a 8,8-difluoro-8-(2'-naphthyl)octyl group, a 6-cyano-2-naphthylmethyl group, a 6-nitro-2-naphthylmethyl group, a 6-carboxyl-2-naphthylmethyl group, a 6-hydroxyl-2-naphthylmethyl group, a 6-(N-methylcarboamide)-2-naphthylmethyl group, a 6-(N,N-dimethylcarboamide)-2-naphthylmethyl group, a 6-methyl-2-naphthylmethyl group, a 6-trifluoromethyl-2-naphthylmethyl group, a 6-methoxy-2-naphthylmethyl group, a 6-trifluoromethoxy-2-naphthylmethyl group, a 6-methylthio-2-naphthylmethyl group, a 6-methylsulfinyl-2-naphthylmethyl group, a 6-methylsulfonyl-2-naphthylmethyl group, a 6-methoxycarbonyl-2-naphthylmethyl group, a 6-vinyl-2-naphthylmethyl group, a 6-(2',2'-difluorovinyl)-2-naphthylmethyl group, an 6-ethynyl-2-naphthylmethyl group, a 6-(2'-fluoroethynyl)-2-naphthylmethyl group, a 6-fluoro-2-naphthylmethyl group, a 6-chloro-2-naphthylmethyl group, a (6'-cyano-1-naphthyl) difluoromethyl group, a (6'-nitro-2-naphthyl)difluoromethyl group, a (6'-carboxyl-2-naphthyl)difluoromethyl group, a (6'-hydroxyl-2-naphthyl)difluoromethyl group, a (6'-(N-methylcarboamide)-2-naphthyl)difluoromethyl group, a (6'-(N,N-dimethylcarboamide)-2-naphthyl)difluoromethyl group, a (6'-methyl-2-naphthyl)difluoromethyl group, a (6'-trifluoromethyl-2-naphthyl)difluoromethyl group, a (6'-methoxy-2-naphthyl)difluoromethyl group, a (6'-trifluoromethoxy-2-naphthyl)difluoromethyl group, a (6'-methylthio-2-naphthyl)difluoromethyl group, a (6'-methylsulfinyl-2-naphthyl)difluoromethyl group, a (6'-methylsulfonyl-2-naphthyl)difluoromethyl group, a (6'-methoxycarbonyl-2-naphthyl)difluoromethyl group, a (6'-vinyl-2-naphthyl)difluoromethyl group, a (6'-(2',2'-difluorovinyl)-2-naphthyl)difluoromethyl group, an (6'-ethynyl-2-naphthyl)difluoromethyl group, a (6'-(2'-fluoroethynyl)-2-naphthyl)difluoromethyl group, a (6'-fluoro-1-naphthyl)difluoromethyl group, a (6'-chloro-2-naphthyl)difluoromethyl group, a 2-pyridylmethyl group, a 1-(2'-pyridyl)ethyl group, a 2-(2'-pyridyl)ethyl group, a 3-(2'-pyridyl)propyl group, a 4-(2'-pyridyl)butyl group, a 5-(2'-pyridyl)pentyl group, a 6-(2'-pyridyl)hexyl group, a 7-(2'-pyridyl)heptyl group, a 8-(2'-pyridyl)octyl group, a 4-cyano-2-pyridylmethyl group, a 4-nitro-2-pyridylmethyl group, a 4-carboxyl-2-pyridylmethyl group, a 4-hydroxyl-2-pyridylmethyl group, a 4-(N-methylcarboamide)-2-pyridylmethyl group, a 4-(N,N-dimethylcarboamide)-2-pyridylmethyl group, a 4-methyl-2-pyridylmethyl group, a 4-trifluoromethyl-2-pyridylmethyl group, a 4-methoxy-2-pyridylmethyl group, a 4-trifluoromethoxy-2-pyridylmethyl group, a 4-methylthio-2-pyridylmethyl group, a 4-methylsulfinyl-2-pyridylmethyl group, a 4-methylsulfonyl-2-pyridylmethyl group, a 4-methoxycarbonyl-2-pyridylmethyl group, a 4-vinyl-2-pyridylmethyl group, a 4-(2',2'-difluorovinyl)-2-pyridylmethyl group, an 4-ethynyl-2-pyridylmethyl group, a 4-(2'-fluoroethynyl)-2-pyridylmethyl group, a 4-fluoro-2-pyridylmethyl group, a 4-chloro-2-pyridylmethyl group, a 5-cyano-2-pyridylmethyl group, a 5-nitro-2-pyridylmethyl group, a 5-carboxyl-2-pyridylmethyl group, a 5-hydroxyl-2-pyridylmethyl group, a 5-(N-methylcarboamide)-2-pyridylmethyl group, a 5-(N, N-dimethylcarboamide)-2-pyridylmethyl group, a 5-methyl-2-pyridylmethyl group, a 5-trifluoromethyl-2-pyridylmethyl group, a 5-methoxy-2-pyridylmethyl group, a 5-trifluoromethoxy-2-pyridylmethyl group, a 5-methylthio-2-pyridylmethyl group, a 5-methylsulfinyl-2-pyridylmethyl group, a 5-methylsulfonyl-2-pyridylmethyl group, a 5-methoxycarbonyl-2-pyridylmethyl group, a 5-vinyl-2-pyridylmethyl group, a 5-(2',2'-difluorovinyl)-2-pyridylmethyl group, an 5-ethynyl-2-pyridylmethyl group, a 5-(2'-fluoroethynyl)-2-pyridylmethyl group, a 5-fluoro-2-pyridylmethyl group, a 5-chloro-2-pyridylmethyl group, a 5,5-dichloro-2-pyridylmethyl group, a 6-cyano-2-pyridylmethyl group, a 6-nitro-2-pyridylmethyl group, a 6-carboxyl-2-pyridylmethyl group, a 6-hydroxyl-2-pyridylmethyl group, a 6-(N-methylcarboamide)-2-pyridylmethyl group, a 6-(N, N-dimethylcarboamide)-2-pyridylmethyl group, a 6-methyl-2-pyridylmethyl group, a 6-trifluoromethyl-2-pyridylmethyl group, a 6-methoxy-2-pyridylmethyl group, a 6-trifluoromethoxy-2-pyridylmethyl group, a 6-methylthio-2-pyridylmethyl group, a 6-methylsulfinyl-2-pyridylmethyl group, a 6-methylsulfonyl-2-pyridylmethyl group, a 6-methoxycarbonyl-2-pyridylmethyl group, a 6-vinyl-2-pyridylmethyl group, a 6-(2',2'-difluorovinyl)-2-pyridylmethyl group, an 6-ethynyl-2-pyridylmethyl group, a 6-(2'-fluoroethynyl)-2-pyridylmethyl group, a 6-fluoro-2-pyridylmethyl group, a 6-chloro-2-pyridylmethyl group, a 6,6-dichloro-2-pyridylmethyl group, a 3-pyridylmethyl group, a 1-(3'-pyridyl)ethyl group, a 2-(3'-pyridyl)ethyl group, a 3-(3'-pyridyl)propyl group, a 4-(3'-pyridyl)butyl group, a 5-(3'-pyridyl)pentyl group, a 6-(3'-pyridyl)hexyl group, a 7-(3'-pyridyl)heptyl group, a 8-(3'-pyridyl)octyl group, a 5-cyano-3-pyridylmethyl group, a 5-nitro-3-pyridylmethyl group, a 5-carboxyl-3-pyridylmethyl group, a 5-hydroxyl-3-pyridylmethyl group, a 5-(N-methylcarboamide)-3-pyridylmethyl group, a 5-(N,N-dimethylcarboamide)-3-pyridylmethyl group, a 5-methyl-3-pyridylmethyl group, a 5-trifluoromethyl-3-pyridylmethyl group, a 5-methoxy-3-pyridylmethyl group, a 5-trifluoromethoxy-3-pyridylmethyl group, a 5-methylthio-3-pyridylmethyl group, a 5-methylsulfinyl-3-pyridylmethyl group, a 5-methylsulfonyl-3-pyridylmethyl group, a 5-methoxycarbonyl-3-pyridylmethyl group, a 5-vinyl-3-pyridylmethyl group, a 5-(2',2'-difluorovinyl)-3-pyridylmethyl group, an 5-ethynyl-3-pyridylmethyl group, a 5-(2'-fluoroethynyl)-3-pyridylmethyl group, a 5-fluoro-3-pyridylmethyl group, a 5-chloro-3-pyridylmethyl group, a 6-cyano-3-pyridylmethyl group, a 6-nitro-3-pyridylmethyl group, a 6-carboxyl-3-pyridylmethyl group, a 6-hydroxyl-3-pyridylmethyl group, a 6-(N-methylcarboamide)-3-pyridylmethyl group, a 6-(N,N-dimethylcarboamide)-3-pyridylmethyl group, a 6-methyl-3-pyridylmethyl group, a 6-trifluoromethyl-3-pyridylmethyl group, a 6-methoxy-3-pyridylmethyl group, a 6-trifluoromethoxy-3-pyridylmethyl group, a 6-methylthio-3-pyridylmethyl group, a 6-methylsulfinyl-3-pyridylmethyl group, a 6-methylsulfonyl-3-pyridylmethyl group, a 6-methoxycarbonyl-3-pyridylmethyl group, a 6-vinyl-3-pyridylmethyl group, a 6-(2',2'-difluorovinyl)-3-pyridylmethyl group, an 6-ethynyl-3-pyridylmethyl group, a 6-(2'-fluoroethynyl)-3-pyridylmethyl group, a 6-fluoro-3-pyridylmethyl group, a 6-chloro-3-pyridylmethyl group, a 4-pyridylmethyl group, a 1-(4'-pyridyl)ethyl group, a 2-(4'-pyridyl)ethyl group, a 3-(4'-pyridyl)propyl group, a 4-(4'-pyridyl)butyl group, a 5-(4'-pyridyl)pentyl group, a 6-(4'-pyridyl)hexyl group, a 7-(4'-pyridyl)heptyl group, a 8-(4'-pyridyl)octyl group, a 2-cyano-4-pyridylmethyl group, a 2-nitro-4-pyridylmethyl group, a 2-carboxyl-4-pyridylmethyl group, a 2-hydroxyl-4-pyridylmethyl group, a 2-(N-methylcarboamide)-4-pyridylmethyl group, a 2-(N,N-dimethylcarboamide)-4-pyridylmethyl group, a 2-methyl-4-pyridylmethyl group, a 2-trifluoromethyl-4-pyridylmethyl group, a 2-methoxy-4-pyridylmethyl group, a 2-trifluoromethoxy-4-pyridylmethyl group, a 2-methylthio-4-pyridylmethyl group, a 2-methylsulfinyl-4-pyridylmethyl group, a 2-methylsulfonyl-4-pyridylmethyl group, a 2-methoxycarbonyl-4-pyridylmethyl group, a 2-vinyl-4-pyridylmethyl group, a 2-(2',2'-difluorovinyl)-4-pyridylmethyl group, an 2-ethynyl-4-pyridylmethyl group, a 2-(2'-fluoroethynyl)-4-pyridylmethyl group, a 2-fluoro-4-pyridylmethyl group, a 2-chloro-4-pyridylmethyl group, a 6-cyano-4-pyridylmethyl group, a 6-nitro-4-pyridylmethyl group, a 6-carboxyl-4-pyridylmethyl group, a 6-hydroxyl-4-pyridylmethyl group, a 6-(N-methylcarboamide)-4-pyridylmethyl group, a 6-(N, N-dimethylcarboamide)-4-pyridylmethyl group, a 6-methyl-4-pyridylmethyl group, a 6-trifluoromethyl-4-pyridylmethyl group, a 6-methoxy-4-pyridylmethyl group, a 6-trifluoromethoxy-4-pyridylmethyl group, a 6-methylthio-4-pyridylmethyl group, a 6-methylsulfinyl-4-pyridylmethyl group, a 6-methylsulfonyl-4-pyridylmethyl group, a 6-methoxycarbonyl-4-pyridylmethyl group, a 6-vinyl-4-pyridylmethyl group, a 6-(2',2'-difluorovinyl)-4-pyridylmethyl group, an 6-ethynyl-4-pyridylmethyl group, a 6-(2'-fluoroethynyl)-4-pyridylmethyl group, a 6-fluoro-4-pyridylmethyl group, a 6-chloro-4-pyridylmethyl group, a 2-quinolylmethyl group, a 1-(2'-quinolyl)ethyl group, a 2-(2'-quinolyl)ethyl group, a 3-(2'-quinolyl)propyl group, a 4-(2'-quinolyl)butyl group, a 5-(2'-quinolyl)pentyl group, a 6-(2'-quinolyl)hexyl group, a 7-(2'-quinolyl)heptyl group, a 8-(2'-quinolyl)octyl group, a 6-cyano-2-quinolylmethyl group, a 6-nitro-2-quinolylmethyl group, a 6-carboxyl-2-quinolylmethyl group, a 6-hydroxyl-2-quinolylmethyl group, a 6-(N-methylcarboamide)-2-quinolylmethyl group, a 6-(N,N-dimethylcarboamide)-2-quinolylmethyl group, a 6-methyl-2-quinolylmethyl group, 6-trifluoromethyl-2-quinolylmethyl group, a 6-methoxy-2-quinolylmethyl group, a 6-trifluoromethoxy-2-quinolylmethyl group, a 6-methylthio-2-quinolylmethyl group, a 6-methylsulfinyl-2-quinolylmethyl group, a 6-methylsulfonyl-2-quinolylmethyl group, a 6-methoxycarbonyl-2-quinolylmethyl group, a 6-vinyl-2-quinolylmethyl group, a 6-(2',2'-difluorovinyl)-2-quinolylmethyl group, an 6-ethynyl-2-quinolylmethyl group, a 6-(2'-fluoroethynyl)-2-quinolylmethyl group, a 6-fluoro-2-quinolylmethyl group, a 6-chloro-2-quinolylmethyl group, a 3-quinolylmethyl group, a 1-(3'-quinolyl)ethyl group, a 2-(3'-quinolyl)ethyl group, a 3-(3'-quinolyl)propyl group, a 4-(3'-quinolyl)butyl group, a 5-(3'-quinolyl)pentyl group, a 6-(3'-quinolyl)hexyl group, a 7-(3'-quinolyl)heptyl group, a 8-(3'-quinolyl)octyl group, a 6-cyano-3-quinolylmethyl group, a 6-nitro-3-quinolylmethyl group, a 6-carboxyl-3-quinolylmethyl group, a 6-hydroxyl-3-quinolylmethyl group, a 6-(N-methylcarboamide)-3-quinolylmethyl group, a 6-(N,N-dimethylcarboamide)-3-quinolylmethyl group, a 6-methyl-3-quinolylmethyl group, a 6-trifluoromethyl-3-quinolylmethyl group, a 6-methoxy-3-quinolylmethyl group, a 6-trifluoromethoxy-3-quinolylmethyl group, a 6-methylthio-3-quinolylmethyl group, a 6-methylsulfinyl-3-quinolylmethyl group, a 6-methylsulfonyl-3-quinolylmethyl group, a 6-methoxycarbonyl-3-quinolylmethyl group, a 6-vinyl-3-quinolylmethyl group, a 6-(2',2'-difluorovinyl)-3-quinolylmethyl group, an 6-ethynyl-3-quinolylmethyl group, a 6-(2'-fluoroethynyl)-3-quinolylmethyl group, a 6-fluoro-3-quinolylmethyl group, a 6-chloro-3-quinolylmethyl group, a 4-quinolylmethyl group, a 1-(4'-quinolyl)ethyl group, a 2-(4'-quinolyl)ethyl group, a 3-(4'-quinolyl)propyl group, a 4-(4'-quinolyl)butyl group, a 5-(3'-quinolyl)pentyl group, a 6-(4'-quinolyl)hexyl group, a 7-(4'-quinolyl)heptyl group, a 8-(4'-quinolyl)octyl group, a 6-cyano-4-quinolylmethyl group, a 6-nitro-4-quinolylmethyl group, a 6-carboxyl-4-quinolylmethyl group, a 6-hydroxyl-4-quinolylmethyl group, a 6-(N-methylcarboamide)-4-quinolylmethyl group, a 6-(N,N-dimethylcarboamide)-4-quinolylmethyl group, a 6-methyl-4-quinolylmethyl group, a 6-trifluormethyl-4-quinolylmethyl group, a 6-methoxy-4-quinolylmethyl group, a 6-trifluoromethoxy-4-quinolylmethyl group, a 6-methylthio-4-quinolylmethyl group, a 6-methylsulfinyl-4-quinolylmethyl group, a 6-methylsulfonyl-4-quinolylmethyl group, a 6-methoxycarbonyl-4-quinolylmethyl group, a 6-vinyl-4-quinolylmethyl group, a 6-(2',2'-difluorovinyl)-4-quinolylmethyl group, an 6-ethynyl-4-quinolylmethyl group, a 6-(2'-fluoroethynyl)-4-quinolylmethyl group, a 6-fluoro-4-quinolylmethyl group, a 6-chloro-4-quinolylmethyl group, a 2-furylmethyl group, a 1-(2'-furyl)ethyl group, a 2-(2'-furyl)ethyl group, a 3-(2'-furyl)propyl group, a 4-(2'-furyl)butyl group, a 5-(2'-furyl)pentyl group, a 6-(2'-furyl)hexyl group, a 7-(2'-furyl)heptyl group, a 8-(2'-furyl)octyl group, a 4-cyano-2-furylmethyl group, a 4-nitro-2-furylmethyl group, a 4-carboxyl-2-furylmethyl group, a 4-hydroxyl-2-furylmethyl group, a 4-(N-methylcarboamide)-2-furylmethyl group, a 4-(N,N-dimethylcarboamide)-2-furylmethyl group, a 4-methyl-2-furylmethyl group, a 4-trifluoromethyl-2-furylmethyl group, a 4-methoxy-2-furylmethyl group, a 4-trifluoromethoxy-2-furylmethyl group, a 4-methylthio-2-furylmethyl group, a 4-methylsulfinyl-2-furylmethyl group, a 4-methylsulfonyl-2-furylmethyl group, a 4-methoxycarbonyl-2-furylmethyl group, a 4-vinyl-2-furylmethyl group, a 4-(2',2'-difluorovinyl)-2-furylmethyl group, an 4-ethynyl-2-furylmethyl group, a 4-(2'-fluoroethynyl)-2-furylmethyl group, a 4-fluoro-2-furylmethyl group, a 4-chloro-2-furylmethyl group, a 3-furylmethyl group, a 1-(3'-furyl)ethyl group, a 2-(3'-furyl)ethyl group, a 3-(3'-furyl)propyl group, a 4-(3'-furyl)butyl group, a 5-(3'-furyl)pentyl group, a 6-(3'-furyl) hexyl group, a 7-(3'-furyl)heptyl group, a 8-(3'-furyl)octyl group, a 4-cyano-3-furylmethyl group, a 4-nitro-3-furylmethyl group, a 4-carboxyl-3-furylmethyl group, a 4-hydroxyl-3-furylmethyl group, a 4-(N-methylcarboamide)-3-furylmethyl group, a 4-(N,N-dimethylcarboamide)-3-furylmethyl group, a 4-methyl-3-furylmethyl group, a 4-trifluoromethyl-3-furylmethyl group, a 4-methoxy-3-furylmethyl group, a 4-trifluoromethoxy-3-furylmethyl group, a 4-methylthio-3-furylmethyl group, a 4-methylsulfinyl-3-furylmethyl group, a 4-methylsulfonyl-3-furylmethyl group, a 4-methoxycarbonyl-3-furylmethyl group, a 4-vinyl-3-furylmethyl group, a 4-(2',2'-difluorovinyl)-3-furylmethyl group, an 4-ethynyl-3-furylmethyl group, a 4-(2'-fluoroethynyl)-3-furylmethyl group, a 4-fluoro-3-furylmethyl group, a 4-chloro-3-furylmethyl group, a 2-thienylmethyl group, a 1-(2'-thienyl)ethyl group, a 2-(2'-thienyl)ethyl group, a 3-(2'-thienyl)propyl group, a 4-(2'-thienyl)butyl group, a 5-(2'-thienyl)pentyl group, a 6-(2'-thienyl)hexyl group, a 7-(2'-thienyl)heptyl group, a 8-(2'-thienyl)octyl group, a 4-cyano-2-thienylmethyl group, a 4-nitro-2-thienylmethyl group, a 4-carboxyl-2-thienylmethyl group, a 4-hydroxyl-2-thienylmethyl group, a 4-(N-methylcarboamide)-2-thienylmethyl group, a 4-(N,N-dimethylcarboamide)-2-thienylmethyl group, a 4-methyl-2-thienylmethyl group, a 4-trifluoromethyl-2-thienylmethyl group, a 4-methoxy-2-thienylmethyl group, a 4-trifluoromethoxy-2-thienylmethyl group, a 4-methylthio-2-thienylmethyl group, a 4-methylsulfinyl-2-thienylmethyl group, a 4-methylsulfonyl-2-thienylmethyl group, a 4-methoxycarbonyl-2-thienylmethyl group, a 4-vinyl-2-thienylmethyl group, a 4-(2',2'-difluorovinyl)-2-thienylmethyl group, an 4-ethynyl-2-thienylmethyl group, a 4-(2'-fluoroethynyl)-2-thienylmethyl group, a 4-fluoro-2-thienylmethyl group, a 4-chloro-2-thienylmethyl group, a 3-thienylmethyl group, a 1-(3'-thienyl)ethyl group, a 2-(3'-thienyl)ethyl group, a 3-(3'-thienyl)propyl group, a 4-(3'-thienyl)butyl group, a 5-(3'-thienyl)pentyl group, a 6-(3'-thienyl)hexyl group, a 7-(3'-thienyl)heptyl group, a 8-(3'-thienyl)octyl group, a 4-cyano-3-thienylmethyl group, a 4-nitro-3-thienylmethyl group, a 4-carboxyl-3-thienylmethyl group, a 4-hydroxyl-3-thienylmethyl group, a 4-(N-methylcarboamide)-3-thienylmethyl group, a 4-(N,N-dimethylcarboamide)-3-thienylmethyl group, a 4-methyl-3-thienylmethyl group, a 4-trifluoromethyl-3-thienylmethyl group, a 4-methoxy-3-thienylmethyl group, a 4-trifluoromethoxy-3-thienylmethyl group, a 4-methylthio-3-thienylmethyl group, a 4-methylsulfinyl-3-thienylmethyl group, a 4-methylsulfonyl-3-thienylmethyl group, a 4-methoxycarbonyl-3-thienylmethyl group, a 4-vinyl-3-thienylmethyl group, a 4-(2',2'-difluorovinyl)-3-thienylmethyl group, an 4-ethynyl-3-thienylmethyl group, a 4-(2'-fluoroethynyl)-3-thienylmethyl group, a 4-fluoro-3-thienylmethyl group, a 4-chloro-3-thienylmethyl group, a 2-(1-benzofuranyl)methyl group, a 1-(2'-(1'-benzofuranyl))ethyl group, a 2-(2'-(1'-benzofuranyl))ethyl group, a 3-(2'-(1'-benzofuranyl))propyl group, a 4-(2'-(1'-benzofuranyl))butyl group, a 5-(2'-(1'-benzofuranyl))pentyl group, a 6-(2'-(1'-benzofuranyl))hexyl group, a 7-(2'-(1'-benzofuranyl))heptyl group, a 8-(2'-(1'-benzofuranyl))octyl group, a 5-cyano-2-(1-benzofuranyl)methyl group, a 5-nitro-2-(1-benzofuranyl)methyl group, a 5-carboxyl-2-(1-benzofuranyl)methyl group, a 5-hydroxyl-2-(1-benzofuranyl)methyl group, a 5-(N-methylcarboamide)-2-(1-benzofuranyl)methyl group, a 5-(N,N-dimethylcarboamide)-2-(1-benzofuranyl)methyl group, a 5-methyl-2-(1-benzofuranyl)methyl group, a 5-trifluoromethyl-2-(1-benzofuranyl)methyl group, a 5-methoxy-2-(1-benzofuranyl)methyl group, a 5-trifluoromethoxy-2-(1-benzofuranyl)methyl group, a 5-methylthio-2-(1-benzofuranyl)methyl group, a 5-methylsulfinyl-2-(1-benzofuranyl)methyl group, a 5-methylsulfonyl-2-(1-benzofuranyl)methyl group, a 5-methoxycarbonyl-2-(1-benzofuranyl)methyl group, a 5-vinyl-2-(1-benzofuranyl)methyl group, a 5-(2',2'-difluorovinyl)-2-(1-benzofuranyl)methyl group, an 5-ethynyl-2-(1-benzofuranyl)methyl group, a 5-(2'-fluoroethynyl)-2-(1-benzofuranyl)methyl group, a 5-fluoro-2-(1-benzofuranyl)methyl group, a 5-chloro-2-(1-benzofuranyl)methyl group, a 3-(1-benzofuranyl)methyl group, a 1-(3'-(1'-benzofuranyl))ethyl group, a 2-(3'-(1'-benzofuranyl))ethyl group, a 3-(3'-(1'-benzofuranyl))propyl group, a 4-(3'-(1'-benzofuranyl))butyl group, a 5-(3'-(1'-benzofuranyl))pentyl group, a 6-(3'-(1'-benzofuranyl))hexyl group, a 7-(3'-(1'-benzofuranyl))heptyl group, a 8-(3'-(1'-benzofuranyl))octyl group, a 5-cyano-3-(1-benzofuranyl)methyl group, a 5-nitro-3-(1-benzofuranyl)methyl group, a 5-carboxyl-3-(1-benzofuranyl)methyl group, a 5-hydroxyl-3-(1-benzofuranyl)methyl group, a 5-(N-methylcarboamide)-3-(1-benzofuranyl)methyl group, a 5-(N,N-dimethylcarboamide)-3-(1-benzofuranyl)methyl group, a 5-methyl-3-(1-benzofuranyl)methyl group, a 5-trifluoromethyl-3-(1-benzofuranyl)methyl group, a 5-methoxy-3-(1-benzofuranyl)methyl group, a 5-trifluoromethoxy-3-(1-benzofuranyl)methyl group, a 5-methylthio-3-(1-benzofuranyl)methyl group, a 5-methylsulfinyl-3-(1-benzofuranyl)methyl group, a 5-methylsulfonyl-3-(1-benzofuranyl)methyl group, a 5-methoxycarbonyl-3-(1-benzofuranyl)methyl group, a 5-vinyl-3-(1-benzofuranyl)methyl group, a 5-(2',2'-difluorovinyl)-3-(1-benzofuranyl)methyl group, an 5-ethynyl-3-(1-benzofuranyl)methyl group, a 5-(2'-fluoroethynyl)-3-(1-benzofuranyl)methyl group, a 5-fluoro-3-(1-benzofuranyl)methyl group, a 5-chloro-3-(1-benzofuranyl)methyl group, a 2-(1-benzothienyl)methyl group, a 1-(2'-(1'-benzothienyl))ethyl group, a 2-(2'-(1'-benzothienyl))ethyl group, a 3-(2'-(1'-benzothienyl))propyl group, a 4-(2'-(1'-benzothienyl))butyl group, a 5-(2'-(1'-benzothienyl))pentyl group, a 6-(2'-(1'-benzothienyl))hexyl group, a 7-(2'-(1'-benzothienyl))heptyl group, a 8-(2'-(1'-benzothienyl))octyl group, a 5-cyano-2-(1-benzothienyl)methyl group, a 5-nitro-2-(1-benzothienyl)methyl group, a 5-carboxyl-2-(1-benzothienyl)methyl group, a 5-hydroxyl-2-(1-benzothienyl)methyl group, a 5-(N-methylcarboamide)-2-(1-benzothienyl)methyl group, a 5-(N,N-dimethylcarboamide)-2-(1-benzothienyl)methyl group, a 5-methyl-2-(1-benzothienyl)methyl group, a 5-trifluoromethyl-2-(1-benzothienyl)methyl group, 5-methoxy-2-(1-benzothienyl)methyl group, a 5-trifluoromethoxy-2-(1-benzothienyl)methyl group, a 5-methylthio-2-(1-benzothienyl)methyl group, a 5-methylsulfinyl-2-(1-benzothienyl)methyl group, a 5-methylsulfonyl-2-(1-benzothienyl)methyl group, a 5-methoxycarbonyl-2-(1-benzothienyl)methyl group, a 5-vinyl-2-(1-benzothienyl)methyl group, a 5-(2',2'-difluorovinyl)-2-(1-benzothienyl)methyl group, an 5-ethynyl-2-(1-benzothienyl)methyl group, a 5-(2'-fluoroethynyl)-2-(1-benzothienyl)methyl group, a 5-fluoro-2-(1-benzothienyl)methyl group, a 5-chloro-2-(1-benzothienyl)methyl group, a 3-(1-benzothienyl)methyl group, a 1-(3'-(1'-benzothienyl))ethyl group, a 2-(3'-(1'-benzothienyl))ethyl group, a 3-(3'-(1'-benzothienyl))propyl group, a 4-(3'-(1'-benzothienyl))butyl group, a 5-(3'-(1'-benzothienyl))pentyl group, a 6-(3'-(1'-benzothienyl))hexyl group, a 7-(3'-(1'-benzothienyl))heptyl group, a 8-(3'-(1'-benzothienyl))octyl group, a 5-cyano-3-(1-benzothienyl)methyl group, a 5-nitro-3-(1-benzothienyl)methyl group, a 5-carboxyl-3-(1-benzothienyl)methyl group, a 5-hydroxyl-3-(1-benzothienyl)methyl group, a 5-(N-methylcarboamide)-3-(1-benzothienyl)methyl group, a 5-(N,N-dimethylcarboamide)-3-(1-benzothienyl)methyl group, a 5-methyl-3-(1-benzothienyl)methyl group, a 5-trifluoromethyl-3-(1-benzothienyl)methyl group, a 5-methoxy-3-(1-benzothienyl)methyl group, a 5-trifluoromethoxy-3-(1-benzothienyl)methyl group, a 5-methylthio-3-(1-benzothienyl)methyl group, a 5-methylsulfinyl-3-(1-benzothienyl)methyl group, a 5-methylsulfonyl-3-(1-benzothienyl)methyl group, a 5-methoxycarbonyl-3-(1-benzothienyl)methyl group, a 5-vinyl-3-(1-benzothienyl)methyl group, a 5-(2',2'-difluorovinyl)-3-(1-benzothienyl)methyl group, an 5-ethynyl-3-(1-benzothienyl)methyl group, a 5-(2'-fluoroethynyl)-3-(1-benzothienyl)methyl group, a 5-fluoro-3-(1-benzothienyl)methyl group, a 5-chloro-3-(1-benzothienyl)methyl group, a fluoromethyl group, a 1-fluoroethyl group, a 1,1-difluoroethyl group, a 2-fluoroethyl group, a 2,2-difluoroethyl group, a 2,2,2-trifluoroethyl group, a 3-fluoropropyl group, a 3,3,3-trifluoropropyl group, a 4-fluorobutyl group, a 4,4,4-trifluorobutyl group, a 3,3,4,4,4-pentafluorobutyl group, a 5-fluoropentyl group, a 6-fluorohexyl group, a 7-fluoroheptyl group, a 8-fluorooctyl group, a chloromethyl group, a 1-chloroethyl group, a 2-chloroethyl group, a 3-chloropropyl group, a 4-chlorobutyl group, a 5-chloropentyl group, a 6-chlorohexyl group, a 7-chloroheptyl group, a 8-chlorooctyl group, a bromomethyl group, a 1-bromoethyl group, a 2-bromoethyl group, a 3-bromopropyl group, a 4-bromobutyl group, a 5-bromopentyl group, a 6-bromohexyl group, a 7-bromoheptyl group, a 8-bromooctyl group, a (methoxycarbonyl)methyl group, a 1-(methoxycarbonyl)ethyl group, a 2-(methoxycarbonyl)ethyl group, a 3-(methoxycarbonyl)propyl group, a 4-(methoxycarbonyl)butyl group, a 5-(methoxycarbonyl)pentyl group, a 6-(methoxycarbonyl)hexyl group, a 7-(methoxycarbonyl) heptyl group, a 8-(methoxycarbonyl)octyl group, a cyanomethyl group, a 1-cyanoethyl group, a 2-cyanoethyl group, a 3-cyanopropyl group, a 4-cyanobutyl group, a 5-cyanopentyl group, a 6-cyanohexyl group, a 7-cyanoheptyl group, a 8-cyanooctyl group, a nitromethyl group, a 1-nitroethyl group, a 2-nitroethyl group, a 3-nitropropyl group, a 4-nitrobutyl group, a 5-nitropentyl group, a 6-nitrohexyl group, a 7-nitroheptyl group, a 8-nitrooctyl group, a (carboxy)methyl group, a 1-(carboxy)ethyl group, a 2-(carboxy)ethyl group, a 3-(carboxy)propyl group, a 4-(carboxy)butyl group, a 5-(carboxy)pentyl group, a 6-(carboxy)hexyl group, a 7-(carboxy)heptyl group, a 8-(carboxy)octyl group, a hydroxymethyl group, a 1-hydroxyethyl group, a 2-hydroxyethyl group, a 3-hydroxypropyl group, a 4-hydroxybutyl group, a 5-hydroxypentyl group, a 6-hydroxyhexyl group, a 7-hydroxyheptyl group, and a 8-hydroxyoctyl group.

Examples of the C1 to C8 chain hydrocarbon group optionally having one or more atoms or groups selected from group G in the present invention include a benzyl group, a phenyldifluoromethyl group, a 1-phenylethyl group, a 1,1-difluoro-1-phenylethyl group, a 2,2,2-trifluoro-1-phenylethyl group, a 1,1,2,2,2-pentafluoro-1-phenylethyl group, a 2-phenylethyl group, a 1,1-difluoro-2-phenylethyl group, a 2,2-difluoro-2-phenylethyl group, a 1,1,2,2-tetrafluoro-2-phenylethyl group, a 3-phenylpropyl group, a 1,1-difluoro-3-phenylpropyl group, a 2,2-difluoro-3-phenylpropyl group, a 3,3-difluoro-3-phenylpropyl group, a 1,1,2,2,3,3-hexafluoro-3-phenylpropyl group, a 4-phenylbutyl group, a 1,1-difluoro-4-phenylbutyl group, a 2,2-difluoro-4-phenylbutyl group, a 3,3-difluoro-4-phenylbutyl group, a 4,4-difluoro-4-phenylbutyl group, a 1,1,2,2,3,3,4,4-octafluoro-3-4-phenylbutyl group, a 5-phenylpentyl group, a 1,1-difluoro-5-phenylpentyl group, a 2,2-difluoro-5-phenylpentyl group, a 3,3-difluoro-5-phenylpentyl group, a 4,4-difluoro-5-phenylpentyl group, a 5,5-difluoro-5-phenylpentyl group, a 6-phenylhexyl group, a 1,1-difluoro-6-phenylhexyl group, a 2,2-difluoro-6-phenylhexyl group, a 3,3-difluoro-6-phenylhexyl group, a 4,4-difluoro-6-phenylhexyl group, a 5,5-difluoro-6-phenylhexyl group, a 6,6-difluoro-6-phenylhexyl group, a 7-phenylheptyl group, a 1,1-difluoro-7-phenylheptyl group, a 2,2-difluoro-7-phenylheptyl group, a 3,3-difluoro-7-phenylheptyl group, a 4,4-difluoro-7-phenylheptyl group, a 5,5-difluoro-7-phenylheptyl group, a 6,6-difluoro-7-phenylheptyl group, a 7,7-difluoro-7-phenylheptyl group, a 8-phenyloctyl group, a 1,1-difluoro-8-phenyloctyl group, a 2,2-difluoro-8-phenyloctyl group, a 3,3-difluoro-8-phenyloctyl group, a 4,4-difluoro-8-phenyloctyl group, a 5,5-difluoro-8-phenyloctyl group, a 6,6-difluoro-8-phenyloctyl group, a 7,7-difluoro-8-phenyloctyl group, a 8,8-difluoro-8-phenyloctyl group, a 4-cyanobenzyl group, a 4-nitrobenzyl group, a 4-carboxylbenzyl group, a 4-hydroxylbenzyl group, a 4-(N-methylcarboamide)benzyl group, a 4-(N,N-dimethylcarboamide)benzyl group, a 4-methylbenzyl group, a 4-trifluoromethylbenzyl group, a 4-methoxybenzyl group, a 4-trifluoromethoxybenzyl group, a 4-methylthiobenzyl group, a 4-methylsulfinylbenzyl group, a 4-methylsulfonylbenzyl group, a 4-methoxycarbonylbenzyl group, a 4-vinylbenzyl group, a 4-(2',2'-difluorovinyl)benzyl group, an 4-ethynylbenzyl group, a 4-(2'-fluoroethynyl)benzyl group, a 4-fluorobenzyl group, a 4-chlorobenzyl group, a 3,4-dichlorobenzyl group, a (4'-cyanophenyl)difluoromethyl group, a (4'-nitrophenyl)difluoromethyl group, a (4'-carboxylphenyl)difluoromethyl group, a (4'-hydroxylphenyl)difluoromethyl group, a (4'-(N-methylcarboamide)phenyl)difluoromethyl group, a (4'-(N,N-dimethylcarboamide)phenyl)difluoromethyl group, a (4'-methylphenyl)difluoromethyl group, a (4'-trifluoromethylphenyl)difluoromethyl group, a (4'-methoxyphenyl)difluoromethyl group, a (4'-trifluoromethoxyphenyl)difluoromethyl group, a (4'-methylthiophenyl)difluoromethyl group, a (4'-methylsulfinylphenyl)difluoromethyl group, a (4'-methylsulfonylphenyl)difluoromethyl group, a (4'-methoxycarbonylphenyl)difluoromethyl group, a (4'-vinylphenyl)difluoromethyl group, a (4'-(2',2'-difluorovinyl)phenyl)difluoromethyl group, a (4'-ethynylphenyl)difluoromethyl group, a (4'-(2'-fluoroethynyl)phenyl)difluoromethyl group, a (4'-fluorophenyl)difluoromethyl group, a (4'-chlorophenyl)difluoromethyl group, a 3,(4'-dichlorophenyl)difluoromethyl group, a 1-naphthylmethyl group, a (1'-naphthyl)difluoromethyl group, a 1-(1'-naphthyl)ethyl group, a 1,1-difluoro-1-(1'-naphthyl)ethyl group, a 2,2,2-trifluoro-1-(1'-naphthyl)ethyl group, a 1,1,2,2,2-pentafluoro-1-(1'-naphthyl)ethyl group, a 2-(1'-naphthyl)ethyl group, a 1,1-difluoro-2-(1'-naphthyl)ethyl group, a 2,2-difluoro-2-(1'-naphthyl)ethyl group, a 1,1,2,2-tetrafluoro-2-(1'-naphthyl)ethyl group, a 3-(1'-naphthyl)propyl group, a 1,1-difluoro-3-(1'-naphthyl)propyl group, a 2,2-difluoro-3-(1'-naphthyl)propyl group, a 3,3-difluoro-3-(1'-naphthyl)propyl group, a 1,1,2,2,3,3-hexafluoro-3-(1'-naphthyl)propyl group, a 4-(1'-naphthyl)butyl group, a 1,1-difluoro-4-(1'-naphthyl)butyl group, a 2,2-difluoro-4-(1'-naphthyl)butyl group, a 3,3-difluoro-4-(1'-naphthyl)butyl group, a 4,4-difluoro-4-(1'-naphthyl)butyl group, a 1,1,2,2,3,3,4,4-octafluoro-3-4-(1'-naphthyl)butyl group, a 5-(1'-naphthyl)pentyl group, a 1,1-difluoro-5-(1'-naphthyl)pentyl group, a 2,2-difluoro-5-(1'-naphthyl)pentyl group, a 3,3-difluoro-5-(1'-naphthyl)pentyl group, a 4,4-difluoro-5-(1'-naphthyl)pentyl group, a 5,5-difluoro-5-(1'-naphthyl)pentyl group, a 6-(1'-naphthyl)hexyl group, a 1,1-difluoro-6-(1'-naphthyl)hexyl group, a 2,2-difluoro-6-(1'-naphthyl)hexyl group, a 3,3-difluoro-6-(1'-naphthyl)hexyl group, a 4,4-difluoro-6-(1'-naphthyl)hexyl group, a 5,5-difluoro-6-(1'-naphthyl)hexyl group, a 6,6-difluoro-6-(1'-naphthyl)hexyl group, a 7-(1'-naphthyl)heptyl group, a 1,1-difluoro-7-(1'-naphthyl)heptyl group, a 2,2-difluoro-7-(1'-naphthyl)heptyl group, a 3,3-difluoro-7-(1'-naphthyl)heptyl group, a 4,4-difluoro-7-(1'-naphthyl)heptyl group, a 5,5-difluoro-7-(1'-naphthyl)heptyl group, a 6,6-difluoro-7-(1'-naphthyl)heptyl group, a 7,7-difluoro-7-(1'-naphthyl)heptyl group, a 8-(1'-naphthyl)octyl group, a 1,1-difluoro-8-(1'-naphthyl)octyl group, a 2,2-difluoro-8-(1'-naphthyl)octyl group, a 3,3-difluoro-8-(1'-naphthyl)octyl group, a 4,4-difluoro-8-(1'-naphthyl)octyl group, a 5,5-difluoro-8-(1'-naphthyl)octyl group, a 6,6-difluoro-8-(1'-naphthyl)octyl group, a 7,7-difluoro-8-(1'-naphthyl)octyl group, a 8,8-difluoro-8-(1'-naphthyl)octyl group, a 6-cyano-1-naphthylmethyl group, a 6-nitro-1-naphthylmethyl group, a 6-carboxyl-1-naphthylmethyl group, a 6-hydroxyl-1-naphthylmethyl group, a 6-(N-methylcarboamide)-1-naphthylmethyl group, a 6-(N,N-dimethylcarboamide)-1-naphthylmethyl group, a 6-methyl-1-naphthylmethyl group, a 6-trifluoromethyl-1-naphthylmethyl group, a 6-methoxy-1-naphthylmethyl group, a 6-trifluoromethoxy-1-naphthylmethyl group, a 6-methylthio-1-naphthylmethyl group, a 6-methylsulfinyl-1-naphthylmethyl group, a 6-methylsulfonyl-1-naphthylmethyl group, a 6-methoxycarbonyl-1-naphthylmethyl group, a 6-vinyl-1-naphthylmethyl group, a 6-(2',2'-difluorovinyl)-1-naphthylmethyl group, an 6-ethynyl-1-naphthylmethyl group, a 6-(2'-fluoroethynyl)-1-naphthylmethyl group, a 6-fluoro-1-naphthylmethyl group, a 6-chloro-1-naphthylmethyl group, a (6'-cyano-1-naphthyl)

difluoromethyl group, a (6'-nitro-1-naphthyl)difluoromethyl group, a (6'-carboxyl-1-naphthyl)difluoromethyl group, a (6'-hydroxyl-1-naphthyl)difluoromethyl group, a (6'-(N-methylcarboamide)-1-naphthyl)difluoromethyl group, a (6'-(N,N-dimethylcarboamide)-1-naphthyl)difluoromethyl group, a (6'-methyl-1-naphthyl)difluoromethyl group, a (6'-trifluoromethyl-1-naphthyl)difluoromethyl group, a (6'-methoxy-1-naphthyl)difluoromethyl group, a (6'-trifluoromethoxy-1-naphthyl)difluoromethyl group, a (6'-methylthio-1-naphthyl)difluoromethyl group, a (6'-methylsulfinyl-1-naphthyl)difluoromethyl group, a (6'-methylsulfonyl-1-naphthyl)difluoromethyl group, a (6'-methoxycarbonyl-1-naphthyl)difluoromethyl group, a (6'-vinyl-1-naphthyl)difluoromethyl group, a (6'-(2',2'-difluorovinyl)-1-naphthyl)difluoromethyl group, an (6'-ethynyl-1-naphthyl)difluoromethyl group, a (6'-(2'-fluoroethynyl)-1-naphthyl)difluoromethyl group, a (6'-fluoro-1-naphthyl)difluoromethyl group, a (6'-chloro-1-naphthyl)difluoromethyl group, a 2-naphthylmethyl group, a (2'-naphthyl)difluoromethyl group, a 1-(2'-naphthyl)ethyl group, a 1,1-difluro-1-(2'-naphthyl)ethyl group, a 2,2,2-trifluoro-1-(2'-naphthyl)ethyl group, a 1,1,2,2,2-pentafluoro-1-(2'-naphthyl)ethyl group, a 2-(2'-naphthyl)ethyl group, a 1,1-difluro-2-(2'-naphthyl)ethyl group, a 2,2-difluoro-2-(2'-naphthyl)ethyl group, a 1,1,2,2-tetrafluoro-2-(2'-naphthyl)ethyl group, a 3-(2'-naphthyl)propyl group, a 1,1-difluoro-3-(2'-naphthyl)propyl group, a 2,2-difluoro-3-(2'-naphthyl)propyl group, a 3,3-difluoro-3-(2'-naphthyl)propyl group, a 1,1,2,2,3,3-hexafluoro-3-(2'-naphthyl)propyl group, a 4-(2'-naphthyl)butyl group, a 1,1-difluoro-4-(2'-naphthyl)butyl group, a 2,2-difluoro-4-(2'-naphthyl)butyl group, a 3,3-difluoro-4-(2'-naphthyl)butyl group, a 4,4-difluoro-4-(2'-naphthyl)butyl group, a 1,1,2,2,3,3,4,4-octafluoro-3-4-(2'-naphthyl)butyl group, a 5-(2'-naphthyl)pentyl group, a 1,1-difluoro-5-(2'-naphthyl)pentyl group, a 2,2-difluoro-5-(2'-naphthyl)pentyl group, a 3,3-difluoro-5-(2'-naphthyl)pentyl group, a 4,4-difluoro-5-(2'-naphthyl)pentyl group, a 5,5-difluoro-5-(2'-naphthyl)pentyl group, a 6-(2'-naphthyl)hexyl group, a 1,1-difluoro-6-(2'-naphthyl)hexyl group, a 2,2-difluoro-6-(2'-naphthyl)hexyl group, a 3,3-difluoro-6-(2'-naphthyl)hexyl group, a 4,4-difluoro-6-(2'-naphthyl)hexyl group, a 5,5-difluoro-6-(2'-naphthyl)hexyl group, a 6,6-difluoro-6-(2'-naphthyl)hexyl group, a 7-(2'-naphthyl)heptyl group, a 1,1-difluoro-7-(2'-naphthyl)heptyl group, a 2,2-difluoro-7-(2'-naphthyl)heptyl group, a 3,3-difluoro-7-(2'-naphthyl)heptyl group, a 4,4-difluoro-7-(2'-naphthyl)heptyl group, a 5,5-difluoro-7-(2'-naphthyl)heptyl group, a 6,6-difluoro-7-(2'-naphthyl)heptyl group, a 7,7-difluoro-7-(2'-naphthyl)heptyl group, a 8-(2'-naphthyl)octyl group, a 1,1-difluoro-8-(2'-naphthyl)octyl group, a 2,2-difluoro-8-(2'-naphthyl)octyl group, a 3,3-difluoro-8-(2'-naphthyl)octyl group, a 4,4-difluoro-8-(2'-naphthyl)octyl group, a 5,5-difluoro-8-(2'-naphthyl)octyl group, a 6,6-difluoro-8-(2'-naphthyl)octyl group, a 7,7-difluoro-8-(2'-naphthyl)octyl group, a 8,8-difluoro-8-(2'-naphthyl)octyl group, a 6-cyano-2-naphthylmethyl group, a 6-nitro-2-naphthylmethyl group, a 6-carboxyl-2-naphthylmethyl group, a 6-hydroxyl-2-naphthylmethyl group, a 6-(N-methylcarboamide)-2-naphthylmethyl group, a 6-(N,N-dimethylcarboamide)-2-naphthylmethyl group, a 6-methyl-2-naphthylmethyl group, a 6-trifluoromethyl-2-naphthylmethyl group, a 6-methoxy-2-naphthylmethyl group, a 6-trifluoromethoxy-2-naphthylmethyl group, a 6-methylthio-2-naphthylmethyl group, a 6-methylsulfinyl-2-naphthylmethyl group, a 6-methylsulfonyl-2-naphthylmethyl group, a 6-methoxycarbonyl-2-naphthylmethyl group, a 6-vinyl-2-naphthylmethyl group, a 6-(2',2'-difluorovinyl)-2-naphthylmethyl group, an 6-ethynyl-2-naphthylmethyl group, a 6-(2'-fluoroethynyl)-2-naphthylmethyl group, a 6-fluoro-2-naphthylmethyl group, a 6-chloro-2-naphthylmethyl group, a (6'-cyano-1-naphthyl)difluoromethyl group, a (6'-nitro-2-naphthyl)difluoromethyl group, a (6'-carboxyl-2-naphthyl)difluoromethyl group, a (6'-hydroxyl-2-naphthyl)difluoromethyl group, a (6'-(N-methylcarboamide)-2-naphthyl)difluoromethyl group, a (6'-(N,N-dimethylcarboamide)-2-naphthyl)difluoromethyl group, a (6'-methyl-2-naphthyl)difluoromethyl group, a (6'-trifluoromethyl-2-naphthyl)difluoromethyl group, a (6'-methoxy-2-naphthyl)difluoromethyl group, a (6'-trifluoromethoxy-2-naphthyl)difluoromethyl group, a (6'-methylthio-2-naphthyl)difluoromethyl group, a (6'-methylsulfinyl-2-naphthyl)difluoromethyl group, a (6'-methylsulfonyl-2-naphthyl)difluoromethyl group, a (6'-methoxycarbonyl-2-naphthyl)difluoromethyl group, a (6'-vinyl-2-naphthyl)difluoromethyl group, a (6'-(2',2'-difluorovinyl)-2-naphthyl)difluoromethyl group, an (6'-ethynyl-2-naphthyl)difluoromethyl group, a (6'-(2'-fluoroethynyl)-2-naphthyl)difluoromethyl group, a (6'-fluoro-1-naphthyl)difluoromethyl group, a (6'-chloro-2-naphthyl)difluoromethyl group, a 2-pyridylmethyl group, a 1-(2'-pyridyl)ethyl group, a 2-(2'-pyridyl)ethyl group, a 3-(2'-pyridyl)propyl group, a 4-(2'-pyridyl)butyl group, a 5-(2'-pyridyl)pentyl group, a 6-(2'-pyridyl)hexyl group, a 7-(2'-pyridyl)heptyl group, a 8-(2'-pyridyl)octyl group, a 4-cyano-2-pyridylmethyl group, a 4-nitro-2-pyridylmethyl group, a 4-carboxyl-2-pyridylmethyl group, a 4-hydroxyl-2-pyridylmethyl group, a 4-(N-methylcarboamide)-2-pyridylmethyl group, a 4-(N,N-dimethylcarboamide)-2-pyridylmethyl group, a 4-methyl-2-pyridylmethyl group, a 4-trifluoromethyl-2-pyridylmethyl group, a 4-methoxy-2-pyridylmethyl group, a 4-trifluoromethoxy-2-pyridylmethyl group, a 4-methylthio-2-pyridylmethyl group, a 4-methylsulfinyl-2-pyridylmethyl group, a 4-methylsulfonyl-2-pyridylmethyl group, a 4-methoxycarbonyl-2-pyridylmethyl group, a 4-vinyl-2-pyridylmethyl group, a 4-(2',2'-difluorovinyl)-2-pyridylmethyl group, an 4-ethynyl-2-pyridylmethyl group, a 4-(2'-fluoroethynyl)-2-pyridylmethyl group, a 4-fluoro-2-pyridylmethyl group, a 4-chloro-2-pyridylmethyl group, a 5-cyano-2-pyridylmethyl group, a 5-nitro-2-pyridylmethyl group, a 5-carboxyl-2-pyridylmethyl group, a 5-hydroxyl-2-pyridylmethyl group, a 5-(N-methylcarboamide)-2-pyridylmethyl group, a 5-(N, N-dimethylcarboamide)-2-pyridylmethyl group, a 5-methyl-2-pyridylmethyl group, a 5-trifluoromethyl-2-pyridylmethyl group, a 5-methoxy-2-pyridylmethyl group, a 5-trifluoromethoxy-2-pyridylmethyl group, a 5-methylthio-2-pyridylmethyl group, a 5-methylsulfinyl-2-pyridylmethyl group, a 5-methylsulfonyl-2-pyridylmethyl group, a 5-methoxycarbonyl-2-pyridylmethyl group, a 5-vinyl-2-pyridylmethyl group, a 5-(2',2'-difluorovinyl)-2-pyridylmethyl group, an 5-ethynyl-2-pyridylmethyl group, a 5-(2'-fluoroethynyl)-2-pyridylmethyl group, a 5-fluoro-2-pyridylmethyl group, a 5-chloro-2-pyridylmethyl group, a 5,5-dichloro-2-pyridylmethyl group, a 6-cyano-2-pyridylmethyl group, a 6-nitro-2-pyridylmethyl group, a 6-carboxyl-2-pyridylmethyl group, a 6-hydroxyl-2-pyridylmethyl group, a 6-(N-methylcarboamide)-2-pyridylmethyl group, a 6-(N, N-dimethylcarboamide)-2-pyridylmethyl group, a 6-methyl-2-pyridylmethyl group, a 6-trifluoromethyl-2-pyridylmethyl group, a 6-methoxy-2-pyridylmethyl group, a 6-trifluoromethoxy-2-pyridylmethyl group, a 6-methylthio-2-pyridylmethyl group, a 6-methylsulfinyl-2-pyridylmethyl group, a 6-methylsulfonyl-2-pyridylmethyl group, a 6-methoxycarbonyl-2-pyridylmethyl group, a 6-vinyl-2-pyridylmethyl group, a 6-(2',2'-difluorovinyl)-2-pyridylmethyl group, an 6-ethynyl- 2-pyridylmethyl group, a 6-(2'-fluoroethynyl)-2-pyridylmethyl group, a 6-fluoro-2-pyridylmethyl group, a 6-chloro-2-pyridylmethyl group, a 6,6-dichloro-2-pyridylmethyl group, a 3-pyridylmethyl group, a 1-(3'-pyridyl)ethyl group, a 2-(3'-pyridyl)ethyl group, a 3-(3'-pyridyl)propyl group, a 4-(3'-pyridyl)butyl group, a 5-(3'-pyridyl)pentyl group, a 6-(3'-pyridyl)hexyl group, a 7-(3'-pyridyl)heptyl group, a 8-(3'-pyridyl)octyl group, a 5-cyano-3-pyridylmethyl group, a 5-nitro-3-pyridylmethyl group, a 5-carboxyl-3-pyridylmethyl group, a 5-hydroxyl-3-pyridylmethyl group, a 5-(N-methylcarboamide)-3-pyridylmethyl group, a 5-(N,N-dimethylcarboamide)-3-pyridylmethyl group, a 5-methyl-3-pyridylmethyl group, a 5-trifluoromethyl-3-pyridylmethyl group, a 5-methoxy-3-pyridylmethyl group, a 5-trifluoromethoxy-3-pyridylmethyl group, a 5-methylthio-3-pyridylmethyl group, a 5-methylsulfinyl-3-pyridylmethyl group, a 5-methylsulfonyl-3-pyridylmethyl group, a 5-methoxycarbonyl-3-pyridylmethyl group, a 5-vinyl-3-pyridylmethyl group, a 5-(2',2'-difluorovinyl)-3-pyridylmethyl group, an 5-ethynyl-3-pyridylmethyl group, a 5-(2'-fluoroethynyl)-3-pyridylmethyl group, a 5-fluoro-3-pyridylmethyl group, a 5-chloro-3-pyridylmethyl group, a 6-cyano-3-pyridylmethyl group, a 6-nitro-3-pyridylmethyl group, a 6-carboxyl-3-pyridylmethyl group, a 6-hydroxyl-3-pyridylmethyl group, a 6-(N-methylcarboamide)-3-pyridylmethyl group, a 6-(N,N-dimethylcarboamide)-3-pyridylmethyl group, a 6-methyl-3-pyridylmethyl group, a 6-trifluoromethyl-3-pyridylmethyl group, a 6-methoxy-3-pyridylmethyl group, a 6-trifluoromethoxy-3-pyridylmethyl group, a 6-methylthio-3-pyridylmethyl group, a 6-methylsulfinyl-3-pyridylmethyl group, a 6-methylsulfonyl-3-pyridylmethyl group, a 6-methoxycarbonyl-3-pyridylmethyl group, a 6-vinyl-3-pyridylmethyl group, a 6-(2',2'-difluorovinyl)-3-pyridylmethyl group, an 6-ethynyl-3-pyridylmethyl group, a 6-(2'-fluoroethynyl)-3-pyridylmethyl group, a 6-fluoro-3-pyridylmethyl group, a 6-chloro-3-pyridylmethyl group, a 4-pyridylmethyl group, a 1-(4'-pyridyl)ethyl group, a 2-(4'-pyridyl)ethyl group, a 3-(4'-pyridyl)propyl group, a 4-(4'-pyridyl)butyl group, a 5-(4'-pyridyl)pentyl group, a 6-(4'-pyridyl)hexyl group, a 7-(4'-pyridyl)heptyl group, a 8-(4'-pyridyl)octyl group, a 2-cyano-4-pyridylmethyl group, a 2-nitro-4-pyridylmethyl group, a 2-carboxyl-4-pyridylmethyl group, a 2-hydroxyl-4-pyridylmethyl group, a 2-(N-methylcarboamide)-4-pyridylmethyl group, a 2-(N,N-dimethylcarboamide)-4-pyridylmethyl group, a 2-methyl-4-pyridylmethyl group, a 2-trifluoromethyl-4-pyridylmethyl group, a 2-methoxy-4-pyridylmethyl group, a 2-trifluoromethoxy-4-pyridylmethyl group, a 2-methylthio-4-pyridylmethyl group, a 2-methylsulfinyl-4-pyridylmethyl group, a 2-methylsulfonyl-4-pyridylmethyl group, a 2-methoxycarbonyl-4-pyridylmethyl group, a 2-vinyl-4-pyridylmethyl group, a 2-(2',2'-difluorovinyl)-4-pyridylmethyl group, an 2-ethynyl-4-pyridylmethyl group, a 2-(2'-fluoroethynyl)-4-pyridylmethyl group, a 2-fluoro-4-pyridylmethyl group, a 2-chloro-4-pyridylmethyl group, a 6-cyano-4-pyridylmethyl group, a 6-nitro-4-pyridylmethyl group, a 6-carboxyl-4-pyridylmethyl group, a 6-hydroxyl-4-pyridylmethyl group, a 6-(N-methylcarboamide)-4-pyridylmethyl group, a 6-(N, N-dimethylcarboamide)-4-pyridylmethyl group, a 6-methyl-4-pyridylmethyl group, a 6-trifluoromethyl-4-pyridylmethyl group, a 6-methoxy-4-pyridylmethyl group, a 6-trifluoromethoxy-4-pyridylmethyl group, a 6-methylthio-4-pyridylmethyl group, a 6-methylsulfinyl-4-pyridylmethyl group, a 6-methylsulfonyl-4-pyridylmethyl group, a 6-methoxycarbonyl-4-pyridylmethyl group, a 6-vinyl-4-pyridylmethyl group, a 6-(2',2'-difluorovinyl)-4-pyridylmethyl group, an 6-ethynyl-4-pyridylmethyl group, a 6-(2'-fluoroethynyl)-4-pyridylmethyl group, a 6-fluoro-4-pyridylmethyl group, a 6-chloro-4-pyridylmethyl group, a 2-quinolylmethyl group, a 1-(2'-quinolyl)ethyl group, a 2-(2'-quinolyl)ethyl group, a 3-(2'-quinolyl)propyl group, a 4-(2'-quinolyl)butyl group, a 5-(2'-quinolyl)pentyl group, a 6-(2'-quinolyl)hexyl group, a 7-(2'-quinolyl)heptyl group, a 8-(2'-quinolyl)octyl group, a 6-cyano-2-quinolylmethyl group, a 6-nitro-2-quinolylmethyl group, a 6-carboxyl-2-quinolylmethyl group, a 6-hydroxyl-2-quinolylmethyl group, a 6-(N-methylcarboamide)-2-quinolylmethyl group, a 6-(N,N-dimethylcarboamide)-2-quinolylmethyl group, a 6-methyl-2-quinolylmethyl group, 6-trifluoromethyl-2-quinolylmethyl group, a 6-methoxy-2-quinolylmethyl group, a 6-trifluoromethoxy-2-quinolylmethyl group, a 6-methylthio-2-quinolylmethyl group, a 6-methylsulfinyl-2-quinolylmethyl group, a 6-methylsulfonyl-2-quinolylmethyl group, a 6-methoxycarbonyl-2-quinolylmethyl group, a 6-vinyl-2-quinolylmethyl group, a 6-(2',2'-difluorovinyl)-2-quinolylmethyl group, an 6-ethynyl-2-quinolylmethyl group, a 6-(2'-fluoroethynyl)-2-quinolylmethyl group, a 6-fluoro-2-quinolylmethyl group, a 6-chloro-2-quinolylmethyl group, a 3-quinolylmethyl group, a 1-(3'-quinolyl)ethyl group, a 2-(3'-quinolyl)ethyl group, a 3-(3'-quinolyl)propyl group, a 4-(3'-quinolyl)butyl group, a 5-(3'-quinolyl)pentyl group, a 6-(3'-quinolyl)hexyl group, a 7-(3'-quinolyl)heptyl group, a 8-(3'-quinolyl)octyl group, a 6-cyano-3-quinolylmethyl group, a 6-nitro-3-quinolylmethyl group, a 6-carboxyl-3-quinolylmethyl group, a 6-hydroxyl-3-quinolylmethyl group, a 6-(N-methylcarboamide)-3-quinolylmethyl group, a 6-(N,N-dimethylcarboamide)-3-quinolylmethyl group, a 6-methyl-3-quinolylmethyl group, a 6-trifluoromethyl-3-quinolylmethyl group, a 6-methoxy-3-quinolylmethyl group, a 6-trifluoromethoxy-3-quinolylmethyl group, a 6-methylthio-3-quinolylmethyl group, a 6-methylsulfinyl-3-quinolylmethyl group, a 6-methylsulfonyl-3-quinolylmethyl group, a 6-methoxycarbonyl-3-quinolylmethyl group, a 6-vinyl-3-quinolylmethyl group, a 6-(2',2'-difluorovinyl)-3-quinolylmethyl group, an 6-ethynyl-3-quinolylmethyl group, a 6-(2'-fluoroethynyl)-3-quinolylmethyl group, a 6-fluoro-3-quinolylmethyl group, a 6-chloro-3-quinolylmethyl group, a 4-quinolylmethyl group, a 1-(4'-quinolyl)ethyl group, a 2-(4'-quinolyl)ethyl group, a 3-(4'-quinolyl)propyl group, a 4-(4'-quinolyl)butyl group, a 5-(3'-quinolyl)pentyl group, a 6-(4'-quinolyl)hexyl group, a 7-(4'-quinolyl)heptyl group, a 8-(4'-quinolyl)octyl group, a 6-cyano-4-quinolylmethyl group, a 6-nitro-4-quinolylmethyl group, a 6-carboxyl-4-quinolylmethyl group, a 6-hydroxyl-4-quinolylmethyl group, a 6-(N-methylcarboamide)-4-quinolylmethyl group, a 6-(N,N-dimethylcarboamide)-4-quinolylmethyl group, a 6-methyl-4-quinolylmethyl group, a 6-trifluormethyl-4-quinolylmethyl group, a 6-methoxy-4-quinolylmethyl group, a 6-trifluoromethoxy-4-quinolylmethyl group, a 6-methylthio-4-quinolylmethyl group, a 6-methylsulfinyl-4-quinolylmethyl group, a 6-methylsulfonyl-4-quinolylmethyl group, a 6-methoxycarbonyl-4-quinolylmethyl group, a 6-vinyl-4-quinolylmethyl group, a 6-(2',2'-difluorovinyl)-4-quinolylmethyl group, an 6-ethynyl-4-quinolylmethyl group, a 6-(2'-fluoroethynyl)-4-quinolylmethyl group, a 6-fluoro-4-quinolylmethyl group, a 6-chloro-4-quinolylmethyl group, a 2-furylmethyl group, a 1-(2'-furyl)ethyl group, a 2-(2'-furyl)ethyl group, a 3-(2'-furyl)propyl group, a 4-(2'-furyl)butyl group, a 5-(2'-furyl)pentyl group, a 6-(2'-furyl)hexyl group, a 7-(2'-furyl)heptyl group, a 8-(2'-furyl)octyl group, a 4-cyano-2-furylmethyl group, a 4-nitro-2-furylmethyl group, a 4-carboxyl-2-furylmethyl group, a 4-hydroxyl-2-furylmethyl group, a 4-(N-methylcarboamide)-2-furylmethyl group, a 4-(N,N-dimethylcarboamide)-2-furylmethyl group, a 4-methyl-2-furylmethyl group, a 4-trifluoromethyl-2-furylmethyl group, a 4-methoxy-2-furylmethyl group, a 4-trifluoromethoxy-2-furylmethyl group, a 4-methylthio-2-furylmethyl group, a 4-methylsulfinyl-2-furylmethyl group, a 4-methylsulfonyl-2-furylmethyl group, a 4-methoxycarbonyl-2-furylmethyl group, a 4-vinyl-2-furylmethyl group, a 4-(2',2'-difluorovinyl)-2-furylmethyl group, an 4-ethynyl-2-furylmethyl group, a 4-(2'-fluoroethynyl)-2-furylmethyl group, a 4-fluoro-2-furylmethyl group, a 4-chloro-2-furylmethyl group, a 3-furylmethyl group, a 1-(3'-furyl)ethyl group, a 2-(3'-furyl)ethyl group, a 3-(3'-furyl)propyl group, a 4-(3'-furyl)butyl group, a 5-(3'-furyl)pentyl group, a 6-(3'-furyl)hexyl group, a 7-(3'-furyl)heptyl group, a 8-(3'-furyl)octyl group, a 4-cyano-3-furylmethyl group, a 4-nitro-3-furylmethyl group, a 4-carboxyl-3-furylmethyl group, a 4-hydroxyl-3-furylmethyl group, a 4-(N-methylcarboamide)-3-furylmethyl group, a 4-(N,N-dimethylcarboamide)-3-furylmethyl group, a 4-methyl-3-furylmethyl group, a 4-trifluoromethyl-3-furylmethyl group, a 4-methoxy-3-furylmethyl group, a 4-trifluoromethoxy-3-furylmethyl group, a 4-methylthio-3-furylmethyl group, a 4-methylsulfinyl-3-furylmethyl group, a 4-methylsulfonyl-3-furylmethyl group, a 4-methoxycarbonyl-3-furylmethyl group, a 4-vinyl-3-furylmethyl group, a 4-(2',2'-difluorovinyl)-3-furylmethyl group, an 4-ethynyl-3-furylmethyl group, a 4-(2'-fluoroethynyl)-3-furylmethyl group, a 4-fluoro-3-furylmethyl group, a 4-chloro-3-furylmethyl group, a 2-thienylmethyl group, a 1-(2'-thienyl)ethyl group, a 2-(2'-thienyl)ethyl group, a 3-(2'-thienyl)propyl group, a 4-(2'-thienyl)butyl group, a 5-(2'-thienyl)pentyl group, a 6-(2'-thienyl)hexyl group, a 7-(2'-thienyl)heptyl group, a 8-(2'-thienyl)octyl group, a 4-cyano-2-thienylmethyl group, a 4-nitro-2-thienylmethyl group, a 4-carboxyl-2-thienylmethyl group, a 4-hydroxyl-2-thienylmethyl group, a 4-(N-methylcarboamide)-2-thienylmethyl group, a 4-(N,N-dimethylcarboamide)-2-thienylmethyl group, a 4-methyl-2-thienylmethyl group, a 4-trifluoromethyl-2-thienylmethyl group, a 4-methoxy-2-thienylmethyl group, a 4-trifluoromethoxy-2-thienylmethyl group, a 4-methylthio-2-thienylmethyl group, a 4-methylsulfinyl-2-thienylmethyl group, a 4-methylsulfonyl-2-thienylmethyl group, a 4-methoxycarbonyl-2-thienylmethyl group, a 4-vinyl-2-thienylmethyl group, a 4-(2',2'-difluorovinyl)-2-thienylmethyl group, an 4-ethynyl-2-thienylmethyl group, a 4-(2'-fluoroethynyl)-2-thienylmethyl group, a 4-fluoro-2-thienylmethyl group, a 4-chloro-2-thienylmethyl group, a 3-thienylmethyl group, a 1-(3'-thienyl)ethyl group, a 2-(3'-thienyl)ethyl group, a 3-(3'-thienyl)propyl group, a 4-(3'-thienyl)butyl group, a 5-(3'-thienyl)pentyl group, a 6-(3'-thienyl)hexyl group, a 7-(3'-thienyl)heptyl group, a 8-(3'-thienyl)octyl group, a 4-cyano-3-thienylmethyl group, a 4-nitro-3-thienylmethyl group, a 4-carboxyl-3-thienylmethyl group, a 4-hydroxyl-3-thienylmethyl group, a 4-(N-methylcarboamide)-3-thienylmethyl group, a 4-(N,N-dimethylcarboamide)-3-thienylmethyl group, a 4-methyl-3-thienylmethyl group, a 4-trifluoromethyl-3-thienylmethyl group, a 4-methoxy-3-thienylmethyl group, a 4-trifluoromethoxy-3-thienylmethyl group, a 4-methylthio-3-thienylmethyl group, a 4-methylsulfinyl-3-thienylmethyl group, a 4-methylsulfonyl-3-thienylmethyl group, a 4-methoxycarbonyl-3-thienylmethyl group, a 4-vinyl-3-thienylmethyl group, a 4-(2',2'-difluorovinyl)-3-thienylmethyl group, an 4-ethynyl-3-thienylmethyl group, a 4-(2'-fluoroethynyl)-3-thienylmethyl group, a 4-fluoro-3-thienylmethyl group, a 4-chloro-3-thienylmethyl group, a 2-(1-benzofuranyl)methyl group, a 1-(2'-(1'-benzofuranyl))ethyl group, a 2-(2'-(1'-benzofuranyl))ethyl group, a 3-(2'-(1'-benzofuranyl))propyl group, a 4-(2'-(1'-benzofuranyl))butyl group, a 5-(2'-(1'-benzofuranyl))pentyl group, a 6-(2'-(1'-benzofuranyl))hexyl group, a 7-(2'-(1'-benzofuranyl))heptyl group, a 8-(2'-(1'-benzofuranyl))octyl group, a 5-cyano-2-(1-benzofuranyl)methyl group, a 5-nitro-2-(1-benzofuranyl)methyl group, a 5-carboxyl-2-(1-benzofuranyl)methyl group, a 5-hydroxyl-2-(1-benzofuranyl)methyl group, a 5-(N-methylcarboamide)-2-(1-benzofuranyl)methyl group, a 5-(N,N-dimethylcarboamide)-2-(1-benzofuranyl)methyl group, a 5-methyl-2-(1-benzofuranyl)methyl group, a 5-trifluoromethyl-2-(1-benzofuranyl)methyl group, a 5-methoxy-2-(1-benzofuranyl)methyl group, a 5-trifluoromethoxy-2-(1-benzofuranyl)methyl group, a 5-methylthio-2-(1-benzofuranyl)methyl group, a 5-methylsulfinyl-2-(1-benzofuranyl)methyl group, a 5-methylsulfonyl-2-(1-benzofuranyl)methyl group, a 5-methoxycarbonyl-2-(1-benzofuranyl)methyl group, a 5-vinyl-2-(1-benzofuranyl)methyl group, a 5-(2',2'-difluorovinyl)-2-(1-benzofuranyl)methyl group, an 5-ethynyl-2-(1-benzofuranyl)methyl group, a 5-(2'-fluoroethynyl)-2-(1-benzofuranyl)methyl group, a 5-fluoro-2-(1-benzofuranyl)methyl group, a 5-chloro-2-(1-benzofuranyl)methyl group, a 3-(1-benzofuranyl)methyl group, a 1-(3'-(1'-benzofuranyl))ethyl group, a 2-(3'-(1'-benzofuranyl))ethyl group, a 3-(3'-(1'-benzofuranyl))propyl group, a 4-(3'-(1'-benzofuranyl))butyl group, a 5-(3'-(1'-benzofuranyl))pentyl group, a 6-(3'-(1'-benzofuranyl))hexyl group, a 7-(3'-(1'-benzofuranyl))heptyl group, a 8-(3'-(1'-benzofuranyl))octyl group, a 5-cyano-3-(1-benzofuranyl)methyl group, a 5-nitro-3-(1-benzofuranyl)methyl group, a 5-carboxyl-3-(1-benzofuranyl)methyl group, a 5-hydroxyl-3-(1-benzofuranyl)methyl group, a 5-(N-methylcarboamide)-3-(1-benzofuranyl)methyl group, a 5-(N,N-dimethylcarboamide)-3-(1-benzofuranyl)methyl group, a 5-methyl-3-(1-benzofuranyl)methyl group, a 5-trifluoromethyl-3-(1-benzofuranyl)methyl group, a 5-methoxy-3-(1-benzofuranyl)methyl group, a 5-trifluoromethoxy-3-(1-benzofuranyl)methyl group, a 5-methylthio-3-(1-benzofuranyl)methyl group, a 5-methylsulfinyl-3-(1-benzofuranyl)methyl group, a 5-methylsulfonyl-3-(1-benzofuranyl)methyl group, a 5-methoxycarbonyl-3-(1-benzofuranyl)methyl group, a 5-vinyl-3-(1-benzofuranyl)methyl group, a 5-(2',2'-difluorovinyl)-3-(1-benzofuranyl)methyl group, an 5-ethynyl-3-(1-benzofuranyl)methyl group, a 5-(2'-fluoroethynyl)-3-(1-benzofuranyl)methyl group, a 5-fluoro-3-(1-benzofuranyl)methyl group, a 5-chloro-3-(1-benzofuranyl)methyl group, a 2-(1-benzothienyl)methyl group, a 1-(2'-(1'-benzothienyl))ethyl group, a 2-(2'-(1'-benzothienyl))ethyl group, a 3-(2'-(1'-benzothienyl))propyl group, a 4-(2'-(1'-benzothienyl))butyl group, a 5-(2'-(1'-benzothienyl))pentyl group, a 6-(2'-(1'-benzothienyl))hexyl group, a 7-(2'-(1'-benzothienyl))heptyl group, a 8-(2'-(1'-benzothienyl))octyl group, a 5-cyano-2-(1-benzothienyl)methyl group, a 5-nitro-2-(1-benzothienyl)methyl group, a 5-carboxyl-2-(1-benzothienyl)methyl group, a 5-hydroxyl-2-(1-benzothienyl)methyl group, a 5-(N-methylcarboamide)-2-(1-benzothienyl)methyl group, a 5-(N,N-dimethylcarboamide)-2-(1-benzothienyl)methyl group, a 5-methyl-2-(1-benzothienyl)methyl group, a 5-trifluoromethyl-2-(1-benzothienyl)methyl group, 5-methoxy-2-(1-benzothienyl)methyl group, a 5-trifluoromethoxy-2-(1-benzothienyl)methyl group, a 5-methylthio-2-(1-benzothienyl)methyl group, a 5-methylsulfinyl-2-(1-benzothienyl)methyl group, a 5-methylsulfonyl-2-(1-benzothienyl)methyl group, a 5-methoxycarbonyl-2-(1-benzothienyl)methyl group, a 5-vinyl-2-(1-benzothienyl)methyl group, a 5-(2',2'-difluorovinyl)-2-(1-benzothienyl)methyl group, an 5-ethynyl-2-(1-benzothienyl)methyl group, a 5-(2'-fluoroethynyl)-2-(1-benzothienyl)methyl group, a 5-fluoro-2-(1-benzothienyl)methyl group, a 5-chloro-2-(1-benzothienyl)methyl group, a 3-(1-benzothienyl)methyl group, a 1-(3'-(1'-benzothienyl))ethyl group, a 2-(3'-(1'-benzothienyl))ethyl group, a 3-(3'-(1'-benzothienyl))propyl group, a 4-(3'-(1'-benzothienyl))butyl group, a 5-(3'-(1'-benzothienyl))pentyl group, a 6-(3'-(1'-benzothienyl))hexyl group, a 7-(3'-(1'-benzothienyl))heptyl group, a 8-(3'-(1'-benzothienyl))octyl group, a 5-cyano-3-(1-benzothienyl)methyl group, a 5-nitro-3-(1-benzothienyl)methyl group, a 5-carboxyl-3-(1-benzothienyl)methyl group, a 5-hydroxyl-3-(1-benzothienyl)methyl group, a 5-(N-methylcarboamide)-3-(1-benzothienyl)methyl group, a 5-(N,N-dimethylcarboamide)-3-(1-benzothienyl)methyl group, a 5-methyl-3-(1-benzothienyl)methyl group, a 5-trifluoromethyl-3-(1-benzothienyl)methyl group, a 5-methoxy-3-(1-benzothienyl)methyl group, a 5-trifluoromethoxy-3-(1-benzothienyl)methyl group, a 5-methylthio-3-(1-benzothienyl)methyl group, a 5-methylsulfinyl-3-(1-benzothienyl)methyl group, a 5-methylsulfonyl-3-(1-benzothienyl)methyl group, a 5-methoxycarbonyl-3-(1-benzothienyl)methyl group, a 5-vinyl-3-(1-benzothienyl)methyl group, a 5-(2',2'-difluorovinyl)-3-(1-benzothienyl)methyl group, an 5-ethynyl-3-(1-benzothienyl)methyl group, a 5-(2'-fluoroethynyl)-3-(1-benzothienyl)methyl group, a 5-fluoro-3-(1-benzothienyl)methyl group, a 5-chloro-3-(1-benzothienyl)methyl group, a fluoromethyl group, a 1-fluoroethyl group, a 1,1-difluoroethyl group, a 2-fluoroethyl group, a 2,2-difluoroethyl group, a 2,2,2-trifluoroethyl group, a 3-fluoropropyl group, a 3,3,3-trifluoropropyl group, a 4-fluorobutyl group, a 4,4,4-trifluorobutyl group, a 3,3,4,4,4-pentafluorobutyl group, a 5-fluoropentyl group, a 6-fluorohexyl group, a 7-fluoroheptyl group, a 8-fluorooctyl group, a chloromethyl group, a 1-chloroethyl group, a 2-chloroethyl group, a 3-chloropropyl group, a 4-chlorobutyl group, a 5-chloropentyl group, a 6-chlorohexyl group, a 7-chloroheptyl group, a 8-chlorooctyl group, a bromomethyl group, a 1-bromoethyl group, a 2-bromoethyl group, a 3-bromopropyl group, a 4-bromobutyl group, a 5-bromopentyl group, a 6-bromohexyl group, a 7-bromoheptyl group, a 8-bromooctyl group, a (methoxycarbonyl)methyl group, a 1-(methoxycarbonyl)ethyl group, a 2-(methoxycarbonyl)ethyl group, a 3-(methoxycarbonyl)propyl group, a 4-(methoxycarbonyl)butyl group, a 5-(methoxycarbonyl)pentyl group, a 6-(methoxycarbonyl)hexyl group, a 7-(methoxycarbonyl) heptyl group, a 8-(methoxycarbonyl)octyl group, a cyanomethyl group, a 1-cyanoethyl group, a 2-cyanoethyl group, a 3-cyanopropyl group, a 4-cyanobutyl group, a 5-cyanopentyl group, a 6-cyanohexyl group, a 7-cyanoheptyl group, a 8-cyanooctyl group, a nitromethyl group, a 1-nitroethyl group, a 2-nitroethyl group, a 3-nitropropyl group, a 4-nitrobutyl group, a 5-nitropentyl group, a 6-nitrohexyl group, a 7-nitroheptyl group, a 8-nitrooctyl group, a (carboxy)methyl group, a 1-(carboxy)ethyl group, a 2-(carboxy)ethyl group, a 3-(carboxy)propyl group, a 4-(carboxy)butyl group, a 5-(carboxy)pentyl group, a 6-(carboxy)hexyl group, a 7-(carboxy)heptyl group, a 8-(carboxy)octyl group, a hydroxymethyl group, a 1-hydroxyethyl group, a 2-hydroxyethyl group, a 3-hydroxypropyl group, a 4-hydroxybutyl group, a 5-hydroxypentyl group, a 6-hydroxyhexyl group, a 7-hydroxyheptyl group, and a 8-hydroxyoctyl group.

Examples of the C1 to C4 alkyl group optionally having one or more benzyloxy groups in the present invention include a benzyloxymethyl group, a 1-benzyloxyethyl group, a 2-benzyloxyethyl group, a 1-benzyloxypropyl group, a 2-benzyloxypropyl group, a 3-benzyloxypropyl group, a 1-benzyloxy-1-methylethyl group, a 1-benzyloxybutyl group, a 2-benzyloxybutyl group, a 3-benzyloxybutyl group, a 4-benzyloxybutyl group, a 1-benzyloxy-1-methylpropyl group, a 2-benzyloxy-1-methylpropyl group, a 1-benzyloxy-2-methylpropyl group, and a 2-benzyloxy-2-methylpropyl group.

Examples of the C1 to C4 alkoxy group optionally having one or more halogen atoms in the present invention include a methoxy group, an ethoxy group, a propoxy group, an isopropoxy group, an isobutoxy group, a difluoromethoxy group, a trifluoromethoxy group, a trichloromethoxy group, a 2,2,2-trifluoroethoxy group, a 1,1,2,2-tetrafluoroethoxy group, and a 1,1,2,2,2-pentafluoroethoxy group.

Examples of the C1 to C4 alkylthio group optionally having one or more halogen atoms in the present invention include a methylthio group, an ethylthio group, a 1-propylthio group, a 2-propylthio group, an isobutylthio group, a difluoromethylthio group, a trifluoromethylthio group, a trichloromethylthio group, a 2,2,2-trifluoroethylthio group, a 1,1,2,2-tetrafluoroethylthio group, and a 1,1,2,2,2-pentafluoroethylthio group.

Examples of the C1 to C4 alkylsulfinyl group optionally having one or more halogen atoms in the present invention include a methanesulfinyl group, an ethanesulfinyl group, a 1-propanesulfinyl group, a 2-propanesulfinyl group, an isobutanesulfinyl group, a difluoromethanesulfinyl group, a trifluoromethanesulfinyl group, a trichloromethanesulfinyl group, a 2,2,2-trifluoroethanesulfinyl group, a 1,1,2,2-tetrafluoroethanesulfinyl group, and a 1,1,2,2,2-pentafluoroethanesulfinyl group.

Examples of the C1 to C4 alkylsulfonyl group optionally having one or more halogen atoms in the present invention include a methanesulfonyl group, an ethanesulfonyl group, a 1-propanesulfonyl group, a 2-propanesulfonyl group, an isobutanesulfonyl group, a difluoromethanesulfonyl group, a trifluoromethanesulfonyl group, a trichloromethanesulfonyl group, a 2,2,2-trifluoroethanesulfonyl group, a 1,1,2,2-tetrafluoroethanesulfonyl group, and a 1,1,2,2,2-pentafluoroethanesulfonyl group.

Examples of the C1 to C4 alkoxycarbonyl group optionally having one or more halogen atoms in the present invention include a methoxycarbonyl group, an ethoxycarbonyl group, a propoxycarbonyl group, an isopropoxycarbonyl group, a butoxycarbonyl group, a tert-butoxycarbonyl group, a difluoromethoxycarbonyl group, a trifluoromethoxycarbonyl group, a trichloromethoxycarbonyl group, a 2,2,2-trifluoroethoxycarbonyl group, a 1,1,2,2-tetrafluoroethoxycarbonyl group, and a 1,1,2,2,2-pentafluoroethoxycarbonyl group.

Examples of the vinyl group optionally having one or more atoms or groups selected from group E in the present invention include a vinyl group, a 2-fluorovinyl group, a 2,2-difluorovinyl group, and a 2,2-dichlorovinyl group.

Examples of the ethynyl group optionally having an atom or group selected from group E in the present invention include an ethynyl group and a 2-fluoroethynyl group.

Examples of the C1 to C3 hydrocarbon groups having one or more atoms or groups selected from the group consisting of hydroxyl groups and halogen atoms in the present invention include a hydroxymethyl group, a 1-hydroxy-1-ethyl group, a 1-hydroxy-1-propyl group, a difluoromethyl group, a 1-hydroxy-2,2,2-trifluoro-1-ethyl group, a 1-hydroxy-2,2,3,3-pentafluoro-1-propyl group, and a 1-hydroxy-3,3,3-trifluoro-1-propyl group.

Examples of the C1 to C3 hydrocarbon groups optionally having one or more atoms or groups selected from the group consisting of hydroxyl groups and halogen atoms in the present invention include a methyl group, an ethyl group, a propyl group, a hydroxymethyl group, a 1-hydroxy-1-ethyl group, a 1-hydroxy-1-propyl group, a difluoromethyl group, a 1-hydroxy-2,2,2-trifluoro-1-ethyl group, a 1-hydroxy-2,2,3,3-pentafluoro-1-propyl group, and a 1-hydroxy-3,3,3-trifluoro-1-propyl group.

Examples of the C1 to C2 hydrocarbon group optionally having one or more halogen atoms in the present invention include a methyl group, an ethyl group, an iodomethyl group, a bromomethyl group, a chloromethyl group, a fluoromethyl group, a difluoromethyl group, a chlorodifluoromethyl group, a bromodifluoromethyl group, a dichlorofluoromethyl group, a trichloromethyl group, a trifluoromethyl group, a 1-fluoroethyl group, a 2-fluoroethyl group, a 1-fluoro-1-methylethyl group, a 1-chloroethyl group, a 2-chloroethyl group, a 1-chloro-1-methylethyl group, a 1-bromoethyl group, a 2-bromoethyl group, a 1-bromo-1-methylethyl group, a 2,2,2-trifluoroethyl group, a 1,1,2,2-tetrafluoroethyl group, and a 1,1,2,2,2-pentafluoroethyl group.

Examples of the C1 to C8 chain hydrocarbon group having one group selected from the group F in the present invention include a benzyl group, a 1-phenylethyl group, a 3-phenylpropyl group, a 4-phenylbutyl group, a 5-phenylpentyl group, a 6-phenylhexyl group, a 7-phenylheptyl group, a 8-phenyloctyl group, a 4-cyanobenzyl group, a 4-nitrobenzyl group, a 4-carboxylbenzyl group, a 4-hydroxylbenzyl group, a 4-(N-methylcarboamide)benzyl group, a 4-(N,N-dimethylcarboamide)benzyl group, a 4-methylbenzyl group, a 4-trifluoromethylbenzyl group, a 4-methoxybenzyl group, a 4-trifluoromethoxybenzyl group, a 4-methylthiobenzyl group, a 4-methylsulfinylbenzyl group, a 4-methylsulfonylbenzyl group, a 4-methoxycarbonylbenzyl group, a 4-vinylbenzyl group, a 4-(2',2'-difluorovinyl)benzyl group, a 4-ethynylbenzyl group, a 4-(2'-fluoroethynyl)benzyl group, a 4-fluorobenzyl group, a 4-chlorobenzyl group, a 3,4-dichlorobenzyl group, a 1-naphthylmethyl group, a 2-naphthylmethyl group, a 1-(1'-naphthyl)ethyl group, a 2-(1'-naphthyl)ethyl group, a 3-(1'-naphthyl)propyl group, a 4-(1'-naphthyl)butyl group, a 5-(1'-naphthyl)pentyl group, a 6-(1'-naphthyl)hexyl group, a 7-(1'-naphthyl)heptyl group, a 8-(1'-naphthyl)octyl group, a 6-cyano-1-naphthylmethyl group, a 6-nitro-1-naphthylmethyl group, a 6-carboxyl-1-naphthylmethyl group, a 6-hydroxyl-1-naphthylmethyl group, a 6-(N-methylcarboamide)-1-naphthylmethyl group, a 6-(N,N-dimethylcarboamide)-1-naphthylmethyl group, a 6-methyl-1-naphthylmethyl group, a 6-trifluoromethyl-1-naphthylmethyl group, a 6-methoxy-1-naphthylmethyl group, a 6-trifluoromethoxy-1-naphthylmethyl group, a 6-methylthio-1-naphthylmethyl group, a 6-methylsulfinyl-1-naphthylmethyl group, a 6-methylsulfonyl-1-naphthylmethyl group, a 6-methoxycarbonyl-1-naphthylmethyl group, a 6-vinyl-1-naphthylmethyl group, a 6-(2',2'-difluorovinyl)-1-naphthylmethyl group, an 6-ethynyl-1-naphthylmethyl group, a 6-(2'-fluoroethynyl)-1-naphthylmethyl group, a 6-fluoro-1-naphthylmethyl group, a 6-chloro-1-naphthylmethyl group, a 1-(2'-naphthyl)ethyl group, a 3-(2'-naphthyl)propyl group, a 4-(2'-naphthyl)butyl group, a 5-(2'-naphthyl)pentyl group, a 6-(2'-naphthyl)hexyl group, a 7-(2'-naphthyl)heptyl group, a 8-(2'-naphthyl)octyl group, a 6-cyano-2-naphthylmethyl group, a 6-nitro-2-naphthylmethyl group, a 6-carboxyl-2-naphthylmethyl group, a 6-hydroxyl-2-naphthylmethyl group, a 6-(N-methylcarboamide)-2-naphthylmethyl group, a 6-(N,N-dimethylcarboamide)-2-naphthylmethyl group, a 6-methyl-2-naphthylmethyl group, a 6-trifluoromethyl-2-naphthylmethyl group, a 6-methoxy-2-naphthylmethyl group, a 6-trifluoromethoxy-2-naphthylmethyl group, a 6-methylthio-2-naphthylmethyl group, a 6-methylsulfinyl-2-naphthylmethyl group, a 6-methylsulfonyl-2-naphthylmethyl group, a 6-methoxycarbonyl-2-naphthylmethyl group, a 6-vinyl-2-naphthylmethyl group, a 6-(2',2'-difluorovinyl)-2-naphthylmethyl group, an 6-ethynyl-2-naphthylmethyl group, a 6-(2'-fluoroethynyl)-2-naphthylmethyl group, a 6-fluoro-2-naphthylmethyl group, a 6-chloro-2-naphthylmethyl group, a 2-pyridylmethyl group, a 1-(2'-pyridyl)ethyl group, a 2-(2'-pyridyl)ethyl group, a 3-(2'-pyridyl)propyl group, a 4-(2'-pyridyl)butyl group, a 5-(2'-pyridyl)pentyl group, a 6-(2'-pyridyl)hexyl group, a 7-(2'-pyridyl)heptyl group, a 8-(2'-pyridyl)octyl group, a 4-cyano-2-pyridylmethyl group, a 4-nitro-2-pyridylmethyl group, a 4-carboxyl-2-pyridylmethyl group, a 4-hydroxyl-2-pyridylmethyl group, a 4-(N-methylcarboamide)-2-pyridylmethyl group, a 4-(N, N-dimethylcarboamide)-2-pyridylmethyl group, a 4-methyl-2-pyridylmethyl group, a 4-trifluoromethyl-2-pyridylmethyl group, a 4-methoxy-2-pyridylmethyl group, a 4-trifluoromethoxy-2-pyridylmethyl group, a 4-methylthio-2-pyridylmethyl group, a 4-methylsulfinyl-2-pyridylmethyl group, a 4-methylsulfonyl-2-pyridylmethyl group, a 4-methoxycarbonyl-2-pyridylmethyl group, a 4-vinyl-2-pyridylmethyl group, a 4-(2',2'-difluorovinyl)-2-pyridylmethyl group, an 4-ethynyl-2-pyridylmethyl group, a 4-(2'-fluoroethynyl)-2-pyridylmethyl group, a 4-fluoro-2-pyridylmethyl group, a 4-chloro-2-pyridylmethyl group, a 5-cyano-2-pyridylmethyl group, a 5-nitro-2-pyridylmethyl group, a 5-carboxyl-2-pyridylmethyl group, a 5-hydroxyl-2-pyridylmethyl group, a 5-(N-methylcarboamide)-2-pyridylmethyl group, a 5-(N,N-dimethyl carbonate amide)-2-pyridylmethyl group, a 5-methyl-2-pyridylmethyl group, a 5-trifluoromethyl-2-pyridylmethyl group, a 5-methoxy-2-pyridylmethyl group, a 5-trifluoromethoxy-2-pyridylmethyl group, a 5-methylthio-2-pyridylmethyl group, a 5-methylsulfinyl-2-pyridylmethyl group, a 5-methylsulfonyl-2-pyridylmethyl group, a 5-methoxycarbonyl-2-pyridylmethyl group, a 5-vinyl-2-pyridylmethyl group, a 5-(2',2'-difluorovinyl)-2-pyridylmethyl group, an 5-ethynyl-2-pyridylmethyl group, a 5-(2'-fluoroethynyl)-2-pyridylmethyl group, a 5-fluoro-2-pyridylmethyl group, a 5-chloro-2-pyridylmethyl group, a 5,5-dichloro-2-pyridylmethyl group, a 6-cyano-2-pyridylmethyl group, a 6-nitro-2-pyridylmethyl group, a 6-carboxyl-2-pyridylmethyl group, a 6-hydroxyl-2-pyridylmethyl group, a 6-(N-methylcarboamide)-2-pyridylethyl group, a 6-(N,N-dimethylcarboamide)-2-pyridylmethyl group, a 6-methyl-2-pyridylmethyl group, a 6-trifluoromethyl-2-pyridylmethyl group, a 6-methoxy-2-pyridylmethyl group, a 6-trifluoromethoxy-2-pyridylmethyl group, a 6-methylthio-2-pyridylmethyl group, a 6-methylsulfinyl-2-pyridylmethyl group, a 6-methylsulfonyl-2-pyridylmethyl group, a 6-methoxycarbonyl-2-pyridylmethyl group, a 6-vinyl-2-pyridylmethyl group, a 6-(2',2'-difluorovinyl)-2-pyridylmethyl group, an 6-ethynyl-2-pyridylmethyl group, a 6-(2'-fluoroethynyl)-2-pyridylmethyl group, a 6-fluoro-2-pyridylmethyl group, a 6-chloro-2-pyridylmethyl group, a 6,6-dichloro-2-pyridylmethyl group, a 3-pyridylmethyl group, a 1-(3'-pyridyl)ethyl group, a 2-(3'-pyridyl)ethyl group, a 3-(3'-pyridyl)propyl group, a 4-(3'-pyridyl)butyl group, a 5-(3'-pyridyl)pentyl group, a 6-(3'-pyridyl)hexyl group, a 7-(3'-pyridyl)heptyl group, a 8-(3'-pyridyl)octyl group, a 5-cyano-3-pyridylmethyl group, a 5-nitro-3-pyridylmethyl group, a 5-carboxyl-3-pyridylmethyl group, a 5-hydroxyl-3-pyridylmethyl group, a 5-(N-methylcarboamide)-3-pyridylmethyl, a 5-(N,N-dimethylcarboamide)-3-pyridylmethyl group, a 5-methyl-3-pyridylmethyl group, a 5-trifluoromethyl-3-pyridylmethyl group, a 5-methoxy-3-pyridylmethyl group, a 5-trifluoromethoxy-3-pyridylmethyl group, a 5-methylthio-3-pyridylmethyl group, a 5-methylsulfinyl-3-pyridylmethyl group, a 5-methylsulfonyl-3- pyridylmethyl group, a 5-methoxycarbonyl-3-pyridylmethyl group, a 5-vinyl-3-pyridylmethyl group, a 5-(2',2'-difluorovinyl)-3-pyridylmethyl group, an 5-ethynyl-3-pyridylmethyl group, a 5-(2'-fluoroethynyl)-3-pyridylmethyl group, a 5-fluoro-3-pyridylmethyl group, a 5-chloro-3-pyridylmethyl group, a 6-cyano-3-pyridylmethyl group, a 6-nitro-3-pyridylmethyl group, a 6-carboxyl-3-pyridylmethyl group, a 6-hydroxyl-3-pyridylmethyl group, a 6-(N-methylcarboamide)-3-pyridylmethyl group, a 6-(N,N-dimethylcarboamide)-3-pyridylmethyl group, a 6-methyl-3-pyridylmethyl group, a 6-trifluoromethyl-3-pyridylmethyl group, a 6-methoxy-3-pyridylmethyl group, a 6-trifluoromethoxy-3-pyridylmethyl group, a 6-methylthio-3-pyridylmethyl group, a 6-methylsulfinyl-3-pyridylmethyl group, a 6-methylsulfonyl-3-pyridylmethyl group, a 6-methoxycarbonyl-3-pyridyl methyl group, a 6-vinyl-3-pyridylmethyl group, a 6-(2',2'-difluorovinyl)-3-pyridylmethyl group, an 6-ethynyl-3-pyridylmethyl group, a 6-(2'-fluoroethynyl)-3-pyridylmethyl group, a 6-fluoro-3-pyridylmethyl group, a 6-chloro-3-pyridylmethyl group, a 4-pyridylmethyl group, a 1-(4'-pyridyl)ethyl group, a 2-(4'-pyridyl)ethyl group, a 3-(4'-pyridyl)propyl group, a 4-(4'-pyridyl)butyl group, a 5-(4'-pyridyl)pentyl group, a 6-(4'-pyridyl)hexyl group, a 7-(4'-pyridyl)heptyl group, a 8-(4'-pyridyl)octyl group, a 2-cyano-4-pyridylmethyl group, a 2-nitro-4-pyridylmethyl group, a 2-carboxyl-4-pyridylmethyl group, a 2-hydroxyl-4-pyridylmethyl group, a 2-(N-methylcarboamide)-4-pyridylmethyl group, a 2-(N, N-dimethylcarboamide)-4-pyridylmethyl group, a 2-methyl-4-pyridylmethyl group, a 2-trifluoromethyl-4-pyridylmethyl group, a 2-methoxy-4-pyridylmethyl group, a 2-trifluoromethoxy-4-pyridylmethyl group, a 2-methylthio-4-pyridylmethyl group, a 2-methylsulfinyl-4-pyridylmethyl group, a 2-methylsulfonyl-4-pyridylmethyl group, a 2-methoxycarbonyl-4-pyridylmethyl group, a 2-vinyl-4-pyridylmethyl group, a 2-(2',2'-difluorovinyl)-4-pyridylmethyl group, an 2-ethynyl-4-pyridylmethyl group, a 2-(2'-fluoroethynyl)-4-pyridylmethyl group, a 2-fluoro-4-pyridylmethyl group, a 2-chloro-4-pyridylmethyl group, a 6-cyano-4-pyridylmethyl group, a 6-nitro-4-pyridylmethyl group, a 6-carboxyl-4-pyridylmethyl group, a 6-hydroxyl-4-pyridylmethyl group, a 6-(N-methylcarboamide)-4-pyridylmethyl group, a 6-(N,N-dimethylcarboamide)-4-pyridylmethyl group, a 6-methyl-4-pyridylmethyl group, a 6-trifluoromethyl-4-pyridylmethyl group, a 6-methoxy-4-pyridylmethyl group, a 6-trifluoromethoxy-4-pyridylmethyl group, a 6-methylthio-4-pyridylmethyl group, a 6-methylsulfinyl-4-pyridylmethyl group, a 6-methylsulfonyl-4-pyridylmethyl group, a 6-methoxycarbonyl-4-pyridylmethyl group, a 6-vinyl-4-pyridylmethyl group, a 6-(2',2'-difluorovinyl)-4-pyridylmethyl group, an 6-ethynyl-4-pyridylmethyl group, a 6-(2'-fluoroethynyl)-4-pyridylmethyl group, a 6-fluoro-4-pyridylmethyl group, a 6-chloro-4-pyridylmethyl group, a 2-quinolylmethyl group, a 1-(2'-quinolyl)ethyl group, a 2-(2'-quinolyl)ethyl group, a 3-(2'-quinolyl)propyl group, a 4-(2'-quinolyl)butyl group, a 5-(2'-quinolyl)pentyl group, a 6-(2'-quinolyl)hexyl group, a 7-(2'-quinolyl)heptyl group, a 8-(2'-quinolyl)octyl group, a 6-cyano-2-quinolylmethyl group, a 6-nitro-2-quinolylmethyl group, a 6-carboxyl-2-quinolylmethyl group, a 6-hydroxyl-2-quinolylmethyl group, a 6-(N-methylcarboamide)-2-quinolylmethyl group, a 6-(N,N-dimethylcarboamide)-2-quinolylmethyl group, a 6-methyl-2-quinolylmethyl group, a 6-trifluoromethyl-2-quinolylmethyl group, a 6-methoxy-2-quinolylmethyl group, a 6-trifluoromethoxy-2-quinolylmethyl group, a 6-methylthio-2-quinolylmethyl group, a 6-methylsulfinyl-2-quinolylmethyl group, a 6-methylsulfonyl-2-quinolylmethyl group, a 6-methoxycarbonyl-2-quinolylmethyl group, a 6-vinyl-2-quinolylmethyl group, a 6-(2',2'-difluorovinyl)-2-quinolylmethyl group, an 6-ethynyl-2-quinolylmethyl group, a 6-(2'-fluoroethynyl)-2-quinolylmethyl group, a 6-fluoro-2-quinolylmethyl group, a 6-chloro-2-quinolylmethyl group, a 3-quinolylmethyl group, a 1-(3'-quinolyl)ethyl group, a 2-(3'-quinolyl)ethyl group, a 3-(3'-quinolyl)propyl group, a 4-(3'-quinolyl)butyl group, a 5-(3'-quinolyl)pentyl group, a 6-(3'-quinolyl)hexyl group, a 7-(3'-quinolyl)heptyl group, a 8-(3'-quinolyl)octyl group, a 6-cyano-3-quinolylmethyl group, a 6-nitro-3-quinolylmethyl group, a 6-carboxyl-3-quinolylmethyl group, a 6-hydroxyl-3-quinolylmethyl group, a 6-(N-methylcarboamide)-3-quinolylmethyl group, a 6-(N,N-dimethylcarboamide)-3-quinolylmethyl group, a 6-methyl-3-quinolylmethyl group, a 6-trifluoromethyl-3-quinolylmethyl group, a 6-methoxy-3-quinolylmethyl group, a 6-trifluoromethoxy-3-quinolylmethyl group, a 6-methylthio-3-quinolylmethyl group, a 6-methylsulfinyl-3-quinolylmethyl group, a 6-methylsulfonyl-3-quinolylmethyl group, a 6-methoxycarbonyl-3-quinolylmethyl group, a 6-vinyl-3-quinolylmethyl group, a 6-(2',2'-difluorovinyl)-3-quinolylmethyl group, an 6-ethynyl-3-quinolylmethyl group, a 6-(2'-fluoroethynyl)-3-quinolylmethyl group, a 6-fluoro-3-quinolylmethyl group, a 6-chloro-3-quinolylmethyl group, a 4-quinolylmethyl group, a 1-(4'-quinolyl)ethyl group, a 2-(4'-quinolyl)ethyl group, a 3-(4'-quinolyl)propyl group, a 4-(4'-quinolyl)butyl group, a 5-(3'-quinolyl)pentyl group, a 6-(4'-quinolyl)hexyl group, a 7-(4'-quinolyl)heptyl group, a 8-(4'-quinolyl)octyl group, a 6-cyano-4-quinolylmethyl group, a 6-nitro-4-quinolylmethyl group, a 6-carboxyl-4-quinolylmethyl group, a 6-hydroxyl-4-quinolylmethyl group, a 6-(N-methylcarboamide)-4-quinolylmethyl group, a 6-(N,N-dimethylcarboamide)-4-quinolylmethyl group, a 6-methyl-4-quinolylmethyl group, a 6-trifluoromethyl-4-quinolylmethyl group, a 6-methoxy-4-quinolylmethyl group, a 6-trifluoromethoxy-4-quinolylmethyl group, a 6-methylthio-4-quinolylmethyl group, a 6-methylsulfinyl-4-quinolylmethyl group, a 6-methylsulfonyl-4-quinolylmethyl group, a 6-methoxy-carbonyl 4-quinolylmethyl group, a 6-vinyl-4-quinolylmethyl group, a 6-(2',2'-difluorovinyl)-4-quinolylmethyl group, an 6-ethynyl-4-quinolylmethyl group, a 6-(2'-fluoroethynyl)-4-quinolylmethyl group, a 6-fluoro-4-quinolylmethyl group, a 6-chloro-4-quinolylmethyl group, a 2-furylmethyl group, a 1-(2'-furyl)ethyl group, a 2-(2'-furyl)ethyl group, a 3-(2'-furyl)propyl group, a 4-(2'-furyl)butyl group, a 5-(2'-furyl)pentyl group, a 6-(2'-furyl)hexyl group, a 7-(2'-furyl)heptyl group, a 8-(2'-furyl)octyl group, a 4-cyano-2-furylmethyl group, a 4-nitro-2-furylmethyl group, a 4-carboxyl-2-furylmethyl group, a 4-hydroxyl-2-furylmethyl group, a 4-(N-methylcarboamide)-2-furylmethyl group, a 4-(N, N-dimethylcarboamide)-2-furylmethyl group, a 4-methyl-2-furylmethyl group, a 4-trifluoromethyl-2-furylmethyl group, a 4-methoxy-2-furylmethyl group, a 4-trifluoromethoxy-2-furylmethyl group, a 4-methylthio-2-furylmethyl group, a 4-methylsulfinyl-2-furylmethyl group, a 4-methylsulfonyl-2-furylmethyl group, a 4-methoxycarbonyl-2-furylmethyl group, a 4-vinyl-2-furylmethyl group, a 4-(2',2'-difluorovinyl)-2-furylmethyl group, an 4-ethynyl-2-furylmethyl group, a 4-(2'-fluoroethynyl)-2-furylmethyl group, a 4-fluoro-2-furylmethyl group, a 4-chloro-2-furylmethyl group, a 3-furylmethyl group, a 1-(3'-furyl)ethyl group, a 2-(3'-furyl)ethyl group, a 3-(3'-furyl)propyl group, a 4-(3'-furyl)butyl group, a 5-(3'-furyl)pentyl group, a 6-(3'-furyl)hexyl group, a 7-(3'-furyl)heptyl group, a 8-(3'-furyl)octyl group, a 4-cyano-3-furylmethyl group, a 4-nitro-3-furylmethyl group, a 4-carboxyl-3-furylmethyl group, a 4-hydroxyl-3-furylmethyl group, a 4-(N-methylcarboamide)-3- furylmethyl group, a 4-(N,N-dimethylcarboamide)-3-furylmethyl group, a 4-methyl-3-furylmethyl group, a 4-trifluoromethyl-3-furylmethyl group, a 4-methoxy-3-furylmethyl group, a 4-trifluoromethoxy-3-furylmethyl group, a 4-methylthio-3-furylmethyl group, a 4-methylsulfinyl-3-furylmethyl group, a 4-methylsulfonyl-3-furylmethyl group, a 4-methoxycarbonyl-3-furylmethyl group, a 4-vinyl-3-furylmethyl group, a 4-(2',2'-difluorovinyl)-3-furylmethyl group, an 4-ethynyl-3-furylmethyl group, a 4-(2'-fluoroethynyl)-3-furylmethyl group, a 4-fluoro-3-furylmethyl group, a 4-chloro-3-furylmethyl group, a 2-thienylmethyl group, a 1-(2'-thienyl)ethyl group, a 2-(2'-thienyl)ethyl group, a 3-(2'-thienyl)propyl group, a 4-(2'-thienyl)butyl group, a 5-(2'-thienyl)pentyl group, a 6-(2'-thienyl)hexyl group, a 7-(2'-thienyl)heptyl group, a 8-(2'-thienyl)octyl group, a 4-cyano-2-thienylmethyl group, a 4-nitro-2-thienylmethyl group, a 4-carboxyl-2-thienylmethyl group, a 4-hydroxyl-2-thienylmethyl group, a 4-(N-methylcarboamide)-2-thienylmethyl group, a 4-(N,N-dimethylcarboamide)-2-thienylmethyl group, a 4-methyl-2-thienylmethyl group, a 4-trifluoromethyl-2-thienylmethyl group, a 4-methoxy-2-thienylmethyl group, a 4-trifluoromethoxy-2-thienylmethyl group, a 4-methylthio-2-thienylmethyl group, a 4-methylsulfinyl-2-thienylmethyl group, a 4-methylsulfonyl-2-thienylmethyl group, a 4-methoxycarbonyl-2-thienylmethyl group, a 4-vinyl-2-thienylmethyl group, a 4-(2',2'-difluorovinyl)-2-thienylmethyl group, an 4-ethynyl-2-thienylmethyl group, a 4-(2'-fluoroethynyl)-2-thienylmethyl group, a 4-fluoro-2-thienylmethyl group, a 4-chloro-2-thienylmethyl group, a 3-thienylmethyl group, a 1-(3'-thienyl)ethyl group, a 2-(3'-thienyl)ethyl group, a 3-(3'-thienyl)propyl group, a 4-(3'-thienyl)butyl group, a 5-(3'-thienyl)pentyl group, a 6-(3'-thienyl) hexyl group, a 7-(3'-thienyl)heptyl group, a 8-(3'-thienyl)octyl group, a 4-cyano-3-thienylmethyl group, a 4-nitro-3-thienylmethyl group, a 4-carboxyl-3-thienylmethyl group, a 4-hydroxyl-3-thienylmethyl group, a 4-(N-methylcarboamide)-3-thienylmethyl group, a 4-(N,N-dimethylcarboamide)-3-thienylmethyl group, a 4-methyl-3-thienylmethyl group, a 4-trifluoromethyl-3-thienylmethyl group, a 4-methoxy-3-thienylmethyl group, a 4-trifluoromethoxy-3-thienylmethyl group, a 4-methylthio-3-thienylmethyl group, a 4-methylsulfinyl-3-thienylmethyl group, a 4-methylsulfonyl-3-thienylmethyl group, a 4-methoxycarbonyl-3-thienylmethyl group, a 4-vinyl-3-thienylmethyl group, a 4-(2',2'-difluorovinyl)-3-thienylmethyl, an 4-ethynyl-3-thienylmethyl group, a 4-(2'-fluoroethynyl)-3-thienylmethyl group, a 4-fluoro-3-thienylmethyl group, a 4-chloro-3-thienylmethyl group, a 2-(1-benzofuranyl)methyl group, a 1-(2'-(1'-benzofuranyl))ethyl group, a 2-(2'-(1'-benzofuranyl))ethyl group, a 3-(2'-(1'-benzofuranyl))propyl group, a 4-(2'-(1'-benzofuranyl))butyl group, a 5-(2'-(1'-benzofuranyl))pentyl group, a 6-(2'-(1'-benzofuranyl))hexyl group, a 7-(2'-(1'-benzofuranyl))heptyl group, a 8-(2'-(1'-benzofuranyl))octyl group, a 5-cyano-2-(1-benzofuranyl)methyl group, a 5-nitro-2-(1-benzofuranyl)methyl group, a 5-carboxyl-2-(1-benzofuranyl)methyl group, a 5-hydroxyl-2-(1-benzofuranyl)methyl group, a 5-(N-methylcarboamide)-2-(1-benzofuranyl)methyl group, a 5-(N,N-dimethylcarboamide)-2-(1-benzofuranyl)methyl group, a 5-methyl-2-(1-benzofuranyl)methyl group, a 5-trifluoromethyl-2-(1-benzofuranyl)methyl group, a 5-methoxy-2-(1-benzofuranyl)methyl group, a 5-trifluoromethoxy-2-(1-benzofuranyl)methyl group, a 5-methylthio-2-(1-benzofuranyl)methyl group, a 5-methylsulfinyl-2-(1-benzofuranyl)methyl group, a 5-methylsulfonyl-2-(1-benzofuranyl)methyl group, a 5-methoxycarbonyl-2-(1-benzofuranyl)methyl group, a 5-vinyl-2-(1-benzofuranyl)methyl group, a 5-(2',2'-difluorovinyl)-2-(1-benzofuranyl)methyl, an 5-ethynyl-2-(1-benzofuranyl)methyl group, a 5-(2'-fluoroethynyl)-2-(1-benzofuranyl)methyl group, a 5-fluoro-2-(1-benzofuranyl)methyl group, a 5-chloro-2-(1-benzofuranyl)methyl group, a 3-(1-benzofuranyl)methyl group, a 1-(3'-(1'-benzofuranyl))ethyl group, a 2-(3'-(1'-benzofuranyl))ethyl group, a 3-(3'-(1'-benzofuranyl))propyl group, a 4-(3'-(1'-benzofuranyl))butyl group, a 5-(3'-(1'-benzofuranyl))pentyl group, a 6-(3'-(1'-benzofuranyl))hexyl group, a 7-(3'-(1'-benzofuranyl))heptyl group, a 8-(3'-(1'-benzofuranyl))octyl group, a 5-cyano-3-(1-benzofuranyl)methyl group, a 5-nitro-3-(1-benzofuranyl)methyl group, a 5-carboxyl-3-(1-benzofuranyl)methyl group, a 5-hydroxyl-3-(1-benzofuranyl)methyl group, a 5-(N-methylcarboamide)-3-(1-benzofuranyl)methyl group, a 5-(N,N-dimethylcarboamide)-3-(1-benzofuranyl)methyl group, a 5-methyl-3-(1-benzofuranyl)methyl group, a 5-trifluoromethyl-3-(1-benzofuranyl)methyl group, a 5-methoxy-3-(1-benzofuranyl)methyl group, a 5-trifluoromethoxy-3-(1-benzofuranyl)methyl group, a 5-methylthio-3-(1-benzofuranyl)methyl group, a 5-methylsulfinyl-3-(1-benzofuranyl)methyl group, a 5-methylsulfonyl-3-(1-benzofuranyl)methyl group, a 5-methoxycarbonyl-3-(1-benzofuranyl)methyl group, a 5-vinyl-3-(1-benzofuranyl)methyl group, a 5-(2',2'-difluorovinyl)-3-(1-benzofuranyl)methyl group, an 5-ethynyl-3-(1-benzofuranyl)methyl group, a 5-(2'-fluoroethynyl)-3-(1-benzofuranyl)methyl group, a 5-fluoro-3-(1-benzofuranyl)methyl group, a 5-chloro-3-(1-benzofuranyl)methyl group, a 2-(1-benzothienyl)methyl group, a 1-(2'-(1'-benzothienyl))ethyl group, a 2-(2'-(1'-benzothienyl))ethyl group, a 3-(2'-(1'-benzothienyl))propyl group, a 4-(2'-(1'-benzothienyl))butyl group, a 5-(2'-(1'-benzothienyl))pentyl group, a 6-(2'-(1'-benzothienyl))hexyl group, a 7-(2'-(1'-benzothienyl))heptyl group, a 8-(2'-(1'-benzothienyl))octyl group, a 5-cyano-2-(1-benzothienyl)methyl group, a 5-nitro-2-(1-benzothienyl)methyl group, a 5-carboxyl-2-(1-benzothienyl)methyl group, a 5-hydroxyl-2-(1-benzothienyl)methyl group, a 5-(N-methylcarboamide)-2-(1-benzothienyl)methyl group, a 5-(N,N-dimethylcarboamide)-2-(1-benzothienyl)methyl group, a 5-methyl-2-(1-benzothienyl)methyl group, a 5-trifluoromethyl-2-(1-benzothienyl)methyl group, a 5-methoxy-2-(1-benzothienyl)methyl group, a 5-trifluoromethoxy-2-(1-benzothienyl)methyl group, a 5-methylthio-2-(1-benzothienyl)methyl group, a 5-methylsulfinyl-2-(1-benzothienyl)methyl group, a 5-methylsulfonyl-2-(1-benzothienyl)methyl group, a 5-methoxycarbonyl-2-(1-benzothienyl)methyl group, a 5-vinyl-2-(1-benzothienyl)methyl group, a 5-(2',2'-difluorovinyl)-2-(1-benzothienyl)methyl group, an 5-ethynyl-2-(1-benzothienyl)methyl group, a 5-(2'-fluoroethynyl)-2-(1-benzothienyl)methyl group, a 5-fluoro-2-(1-benzothienyl)methyl group, a 5-chloro-2-(1-benzothienyl)methyl group, a 3-(1-benzothienyl)methyl group, a 1-(3'-(1'-benzothienyl))ethyl group, a 2-(3'-(1'-benzothienyl))ethyl group, a 3-(3'-(1'-benzothienyl))propyl group, a 4-(3'-(1'-benzothienyl))butyl group, a 5-(3'-(1'-benzothienyl))pentyl group, a 6-(3'-(1'-benzothienyl))hexyl group, a 7-(3'-(1'-benzothienyl))heptyl group, a 8-(3'-(1'-benzothienyl))octyl group, a 5-cyano-3-(1-benzothienyl)methyl group, a 5-nitro-3-(1-benzothienyl)methyl group, a 5-carboxyl-3-(1-benzothienyl)methyl group, a 5-hydroxyl-3-(1-benzothienyl)methyl group, a 5-(N-methylcarboamide)-3-(1-benzothienyl)methyl group, a 5-(N,N-dimethylcarboamide)-3-(1-benzothienyl)methyl group, a 5-methyl-3-(1-benzothienyl)methyl group, a 5-trifluoromethyl-3-(1-benzothienyl)methyl group, a 5-methoxy-3-(1-benzothienyl)methyl group, a 5-trifluoromethoxy-3-(1-benzothienyl)methyl group, a 5-methylthio-3-(1-benzothienyl)methyl group, a 5-methylsulfinyl-3-

(1-benzothienyl)methyl group, a 5-methylsulfonyl-3-(1-benzothienyl)methyl group, a 5-methoxycarbonyl-3-(1-benzothienyl)methyl group, a 5-vinyl-3-(1-benzothienyl)methyl group, a 5-(2',2'-difluorovinyl)-3-(1-benzothienyl)methyl group, an 5-ethynyl-3-(1-benzothienyl)methyl group, a 5-(2'-fluoroethynyl)-3-(1-benzothienyl)methyl group, a 5-fluoro-3-(1-benzothienyl)methyl group, a 5-chloro-3-(1-benzothienyl)methyl group, a (methoxycarbonyl)methyl group, a 1-(methoxycarbonyl)ethyl group, a 2-(methoxycarbonyl)ethyl group, a 3-(methoxycarbonyl)propyl group, a 4-(methoxycarbonyl)butyl group, a 5-(methoxycarbonyl)pentyl group, a 6-(methoxycarbonyl)hexyl group, a 7-(methoxycarbonyl)heptyl group, a 8-(methoxycarbonyl)octyl group, a cyanomethyl group, a 1-cyanoethyl group, a 2-cyanoethyl group, a 3-cyanopropyl group, a 4-cyanobutyl group, a 5-cyanopentyl group, a 6-cyanohexyl group, a 7-cyanoheptyl group, a 8-cyanooctyl group, a nitromethyl group, a 1-nitroethyl group, a 2-nitroethyl group, a 3-nitropropyl group, a 4-nitrobutyl group, a 5-nitropentyl group, a 6-nitrohexyl group, a 7-nitroheptyl group, a 8-nitrooctyl group, a (carboxy)methyl group, a 1-(carboxy)ethyl group, a 2-(carboxy)ethyl group, a 3-(carboxy)propyl group, a 4-(carboxy)butyl group, a 5-(carboxy)pentyl group, a 6-(carboxy)hexyl group, a 7-(carboxy)heptyl group, a 8-(carboxy)octyl group, a hydroxymethyl group, a 1-hydroxyethyl group, a 2-hydroxyethyl group, a 3-hydroxypropyl group, a 4-hydroxybutyl group, a 5-hydroxypentyl group, a 6-hydroxyhexyl group, a 7-hydroxyheptyl group, and a 8-hydroxyoctyl group.

Examples of the methyl group having one group selected from the group F in the present invention include a benzyl group, a 4-cyanobenzyl group, a 4-nitrobenzyl group, a 4-carboxybenzyl group, a 4-hydroxybenzyl group, a 4-(N-methylcarboamide)benzyl group, a 4-(N,N-dimethylcarboamide)benzyl group, a 4-methylbenzyl group, a 4-trifluoromethylbenzyl group, a 4-methoxybenzyl group, a 4-trifluoromethoxybenzyl group, a 4-methylthiobenzyl group, a 4-methylsulfinylbenzyl group, a 4-methylsulfonylbenzyl group, a 4-methoxycarbonylbenzyl group, a 4-vinylbenzyl group, a 4-(2',2'-difluorovinyl)benzyl group, a 4-ethynylbenzyl group, a 4-(2'-fluoroethynyl)benzyl group, a 4-fluorobenzyl group, a 4-chlorobenzyl group, a 3,4-dichlorobenzyl group, a 1-naphthylmethyl group, a 2-naphthylmethyl group, a 6-cyano-1-naphthylmethyl group, a 6-nitro-1-naphthylmethyl group, a 6-carboxyl-1-naphthylmethyl group, a 6-hydroxyl-1-naphthylmethyl group, a 6-(N-methylcarboamide)-1-naphthylmethyl group, a 6-(N,N-dimethylcarboamide)-1-naphthylmethyl group, a 6-methyl-1-naphthylmethyl group, a 6-trifluoromethyl-1-naphthylmethyl group, a 6-methoxy-1-naphthylmethyl group, a 6-trifluoromethoxy-1-naphthylmethyl group, a 6-methylthio-1-naphthylmethyl group, a 6-methylsulfinyl-1-naphthylmethyl group, a 6-methylsulfonyl-1-naphthylmethyl group, a 6-methoxycarbonyl-1-naphthylmethyl group, a 6-vinyl-1-naphthylmethyl group, a 6-(2',2'-difluorovinyl)-1-naphthylmethyl group, an 6-ethynyl-1-naphthylmethyl group, 6-(2'-fluoroethynyl)-1-naphthylmethyl group, a 6-fluoro-1-naphthylmethyl group, a 6-chloro-1-naphthylmethyl group, a 6-cyano-2-naphthylmethyl group, a 6-nitro-2-naphthylmethyl group, a 6-carboxyl-2-naphthylmethyl group, a 6-hydroxyl-2-naphthylmethyl group, a 6-(N-methylcarboamide)-2-naphthylmethyl group, a 6-(N,N-dimethylcarboamide)-2-naphthylmethyl group, a 6-methyl-2-naphthylmethyl group, a 6-trifluoromethyl-2-naphthylmethyl group, a 6-methoxy-2-naphthylmethyl group, a 6-trifluoromethoxy-2-naphthylmethyl group, a 6-methylthio-2-naphthylmethyl group, a 6-methylsulfinyl-2-naphthylmethyl group, a 6-methylsulfonyl-2-naphthylmethyl group, a 6-methoxycarbonyl-2-naphthylmethyl group, a 6-vinyl-2-naphthylmethyl group, a 6-(2',2'-difluorovinyl)-2-naphthylmethyl group, an 6-ethynyl-2-naphthylmethyl group, 6-(2'-fluoroethynyl)-2-naphthylmethyl group, a 6-fluoro-2-naphthylmethyl group, a 6-chloro-2-naphthylmethyl group, a 2-pyridylmethyl group, a 4-cyano-2-pyridylmethyl group, a 4-nitro-2-pyridylmethyl group, a 4-carboxyl-2-pyridylmethyl group, a 4-hydroxyl-2-pyridylmethyl group, a 4-(N-methylcarboamide)-2-pyridylmethyl group, a 4-(N,N-dimethylcarboamide)-2-pyridylmethyl group, a 4-methyl-2-pyridylmethyl group, a 4-trifluoromethyl-2-pyridyl methyl group, a 4-methoxy-2-pyridylmethyl group, a 4-trifluoromethoxy-2-pyridylmethyl group, a 4-methylthio-2-pyridylmethyl group, a 4-methylsulfinyl-2-pyridylmethyl group, a 4-methylsulfonyl-2-pyridylmethyl group, a 4-methoxycarbonyl-2-pyridylmethyl group, a 4-vinyl-2-pyridylmethyl group, a 4-(2',2'-difluorovinyl)-2-pyridylmethyl group, an 4-ethynyl-2-pyridylmethyl group, a 4-(2'-fluoroethynyl)-2-pyridylmethyl group, a 4-fluoro-2-pyridylmethyl group, a 4-chloro-2-pyridylmethyl group, a 5-cyano-2-pyridylmethyl group, a 5-nitro-2-pyridylmethyl group, a 5-carboxyl-2-pyridylmethyl group, a 5-hydroxyl-2-pyridylmethyl group, a 5-(N-methylcarboamide)-2-pyridylmethyl group, a 5-(N,N-dimethylcarboamide)-2-pyridylmethyl group, a 5-methyl-2-pyridylmethyl group, a 5-trifluoromethyl-2-pyridylmethyl group, a 5-methoxy-2-pyridylmethyl group, a 5-trifluoromethoxy-2-pyridylmethyl group, a 5-methylthio-2-pyridylmethyl group, a 5-methylsulfinyl-2-pyridylmethyl group, a 5-methylsulfonyl-2-pyridylmethyl group, a 5-methoxycarbonyl-2-pyridylmethyl group, a 5-vinyl-2-pyridylmethyl group, a 5-(2',2'-difluorovinyl)-2-pyridylmethyl group, an 5-ethynyl-2-pyridylmethyl group, a 5-(2'-fluoroethynyl)-2-pyridylmethyl group, a 5-fluoro-2-pyridylmethyl group, a 5-chloro-2-pyridylmethyl group, a 5,5-dichloro-2-pyridylmethyl group, a 6-cyano-2-pyridylmethyl group, a 6-nitro-2-pyridylmethyl group, a 6-carboxyl-2-pyridylmethyl group, a 6-hydroxyl-2-pyridylmethyl group, a 6-(N-methylcarboamide)-2-pyridylmethyl group, a 6-(N,N-dimethylcarboamide)-2-pyridylmethyl group, a 6-methyl-2-pyridylmethyl group, a 6-trifluoromethyl-2-pyridylmethyl group, a 6-methoxy-2-pyridylmethyl group, a 6-trifluoromethoxy-2-pyridylmethyl group, a 6-methylthio-2-pyridylmethyl group, a 6-methylsulfinyl-2-pyridylmethyl group, a 6-methylsulfonyl-2-pyridylmethyl group, a 6-methoxycarbonyl-2-pyridylmethyl group, a 6-vinyl-2-pyridylmethyl group, a 6-(2',2'-difluorovinyl)-2-pyridylmethyl group, an 6-ethynyl-2-pyridylmethyl group, a 6-(2'-fluoroethynyl)-2-pyridylmethyl group, a 6-fluoro-2-pyridylmethyl group, a 6-chloro-2-pyridylmethyl group, a 6,6-dichloro-2-pyridylmethyl group, a 3-pyridylmethyl group, a 5-cyano-3-pyridylmethyl group, a 5-nitro-3-pyridylmethyl group, a 5-carboxyl-3-pyridylmethyl group, a 5-hydroxyl-3-pyridylmethyl group, a 5-(N-methylcarboamide)-3-pyridylmethyl group, a 5-(N,N-dimethylcarboamide)-3-pyridylmethyl group, a 5-methyl-3-pyridylmethyl group, a 5-trifluoromethyl-3-pyridylmethyl group, a 5-methoxy-3-pyridylmethyl group, a 5-trifluoromethoxy-3-pyridylmethyl group, a 5-methylthio-3-pyridylmethyl group, a 5-methylsulfinyl-3-pyridylmethyl group, a 5-methylsulfonyl-3-pyridylmethyl group, a 5-methoxycarbonyl-3-pyridylmethyl group, a 5-vinyl-3-pyridylmethyl group, a 5-(2',2'-difluorovinyl)-3-pyridylmethyl group, an 5-ethynyl-3-pyridylmethyl group, a 5-(2'-fluoroethynyl)-3-pyridylmethyl group, a 5-fluoro-3-pyridylmethyl group, a 5-chloro-3-pyridylmethyl group, a 6-cyano-3-pyridylmethyl group, a 6-nitro-3-pyridylmethyl group, a 6-carboxyl-3-pyridylmethyl group, a 6-hydroxyl-3-pyridylmethyl group, a 6-(N-methylcarboamide)-3-pyridylmethyl group, a 6-(N,N-dimethylcarboamide)-3-pyridylmethyl group, a 6-methyl-3-pyridylmethyl group, a 6-trifluoromethyl-3-pyridylmethyl group, a 6-methoxy-3-pyridylmethyl group, a 6-trifluoromethoxy-3-pyridylmethyl group, a 6-methylthio-3-pyridylmethyl group, a 6-methylsulfinyl-3-pyridylmethyl group, a 6-methylsulfonyl-3-pyridylmethyl group, a 6-methoxycarbonyl-3-pyridylmethyl group, a 6-vinyl-3-pyridylmethyl group, a 6-(2',2'-difluorovinyl)-3-pyridylmethyl group, an 6-ethynyl-3-pyridylmethyl group, a 6-(2'-fluoroethynyl)-3-pyridylmethyl group, a 6-fluoro-3-pyridylmethyl group, a 6-chloro-3-pyridylmethyl group, a 4-pyridylmethyl group, a 2-cyano-4-pyridylmethyl group, a 2-nitro-4-pyridylmethyl group, a 2-carboxyl-4-pyridyl methyl group, a 2-hydroxyl-4-pyridylmethyl group, a 2-(N-methylcarboamide)-4-pyridylmethyl group, a 2-(N,N-dimethylcarboamide)-4-pyridylmethyl group, a 2-methyl-4-pyridylmethyl group, a 2-trifluoromethyl-4-pyridylmethyl group, a 2-methoxy-4-pyridylmethyl group, a 2-trifluoromethoxy-4-pyridylmethyl group, a 2-methylthio-4-pyridylmethyl group, a 2-methylsulfinyl-4-pyridylmethyl group, a 2-methylsulfonyl-4-pyridylmethyl group, a 2-methoxycarbonyl-4-pyridylmethyl group, a 2-vinyl-4-pyridylmethyl group, a 2-(2',2'-difluorovinyl)-4-pyridylmethyl group, an 2-ethynyl-4-pyridylmethyl group, a 2-(2'-fluoroethynyl)-4-pyridylmethyl group, a 2-fluoro-4-pyridylmethyl group, a 2-chloro-4-pyridylmethyl group, a 6-cyano-4-pyridylmethyl group, a 6-nitro-4-pyridylmethyl group, a 6-carboxyl-4-pyridylmethyl group, a 6-hydroxyl-4-pyridylmethyl group, a 6-(N-methylcarboamide)-4-pyridylmethyl group, a 6-(N,N-dimethylcarboamide)-4-pyridylmethyl group, a 6-methyl-4-pyridylmethyl group, a 6-trifluoromethyl-4-pyridylmethyl group, a 6-methoxy-4-pyridylmethyl group, a 6-trifluoromethoxy-4-pyridylmethyl group, a 6-methylthio-4-pyridylmethyl group, a 6-methylsulfinyl-4-pyridylmethyl group, a 6-methylsulfonyl-4-pyridylmethyl group, a 6-methoxycarbonyl-4-pyridylmethyl group, a 6-vinyl-4-pyridylmethyl group, a 6-(2',2'-difluorovinyl)-4-pyridylmethyl group, an 6-ethynyl-4-pyridylmethyl group, a 6-(2'-fluoroethynyl)-4-pyridylmethyl group, a 6-fluoro-4-pyridylmethyl group, a 6-chloro-4-pyridylmethyl group, a 2-quinolylmethyl group, a 6-cyano-2-quinolylmethyl group, a 6-nitro-2-quinolylmethyl group, a 6-carboxyl-2-quinolylmethyl group, a 6-hydroxyl-2-quinolylmethyl group, a 6-(N-methylcarboamide)-2-quinolylmethyl group, a 6-(N,N-dimethylcarboamide)-2-quinolylmethyl group, a 6-methyl-2-quinolylmethyl group, a 6-trifluoromethyl-2-quinolylmethyl group, a 6-methoxy-2-quinolylmethyl group, a 6-trifluoromethoxy-2-quinolylmethyl group, a 6-methylthio-2-quinolylmethyl group, a 6-methylsulfinyl-2-quinolylmethyl group, a 6-methylsulfonyl-2-quinolylmethyl group, a 6-methoxycarbonyl-2-quinolylmethyl group, a 6-vinyl-2-quinolylmethyl group, a 6-(2',2'-difluorovinyl)-2-quinolylmethyl group, an 6-ethynyl-2-quinolylmethyl group, a 6-(2'-fluoroethynyl)-2-quinolylmethyl group, a 6-fluoro-2-quinolylmethyl group, a 6-chloro-2-quinolylmethyl group, a 3 quinolylmethyl group, a 6-cyano-3-quinolylmethyl group, a 6-nitro-3-quinolylmethyl group, a 6-carboxyl-3-quinolylmethyl group, a 6-hydroxyl-3-quinolylmethyl group, a 6-(N-methylcarboamide)-3-quinolylmethyl group, a 6-(N,N-dimethylcarboamide)-3-quinolylmethyl group, a 6-methyl-3-quinolylmethyl group, a 6-trifluoromethyl-3-quinolylmethyl group, a 6-methoxy-3-quinolylmethyl group, a 6-trifluoromethoxy-3-quinolylmethyl group, a 6-methylthio-3-quinolylmethyl group, a 6-methylsulfinyl-3-quinolylmethyl group, a 6-methylsulfonyl-3-quinolylmethyl group, a 6-methoxycarbonyl-3-quinolylmethyl group, a 6-vinyl-3-quinolylmethyl group, a 6-(2',2'-difluorovinyl)-3-quinolylmethyl group, an 6-ethynyl-3-quinolylmethyl group, a 6-(2'-fluoroethynyl)-3-quinolylmethyl group, a 6-fluoro-3-quinolylmethyl group, a 6-chloro-3-quinolylmethyl group, a 4-quinolylmethyl group, a 6-cyano-4-quinolylmethyl group, a 6-nitro-4-quinolylmethyl group, a 6-carboxyl-4-quinolylmethyl group, a 6-hydroxyl-4-quinolylmethyl group, a 6-(N-methylcarboamide)-4-quinolylmethyl group, a 6-(N,N-dimethylcarboamide)-4-quinolylmethyl group, a 6-methyl-4-quinolylmethyl group, a 6-trifluoromethyl-4-quinolylmethyl group, a 6-methoxy-4-quinolylmethyl group, a 6-trifluoromethoxy-4-quinolylmethyl group, a 6-methylthio-4-quinolylmethyl group, a 6-methylsulfinyl-4-quinolylmethyl group, a 6-methylsulfonyl-4-quinolylmethyl group, a 6-methoxycarbonyl-4-quinolylmethyl group, a 6-vinyl-4-quinolylmethyl group, a 6-(2',2'-difluorovinyl)-4-quinolylmethyl group, an 6-ethynyl-4-quinolylmethyl group, a 6-(2'-fluoroethynyl)-4-quinolylmethyl group, a 6-fluoro-4-quinolylmethyl group, a 6-chloro-4-quinolylmethyl group, a 2-furylmethyl group, a 4-cyano-2-furylmethyl group, a 4-nitro-2-furylmethyl group, a 4-carboxyl-2-furylmethyl group, a 4-hydroxyl-2-furylmethyl group, a 4-(N-methylcarboamide)-2-furylmethyl group, a 4-(N,N-dimethylcarboamide)-2-furylmethyl group, a 4-methyl-2-furylmethyl group, a 4-trifluoromethyl-2-furylmethyl group, a 4-methoxy-2-furylmethyl group, a 4-trifluoromethoxy-2-furylmethyl group, a 4-methylthio-2-furylmethyl group, a 4-methylsulfinyl-2-furylmethyl group, a 4-methylsulfonyl-2-furylmethyl group, a 4-methoxycarbonyl-2-furylmethyl group, a 4-vinyl-2-furylmethyl group, a 4-(2',2'-difluorovinyl)-2-furylmethyl group, an 4-ethynyl-2-furylmethyl group, a 4-(2'-fluoroethynyl)-2-furylmethyl group, a 4-fluoro-2-furylmethyl group, a 4-chloro-2-furylmethyl group, a 3-furylmethyl group, a 4-cyano-3-furylmethyl group, a 4-nitro-3-furylmethyl group, a 4-carboxyl-3-furylmethyl group, a 4-hydroxyl-3-furylmethyl group, a 4-(N-methylcarboamide)-3-furylmethyl group, a 4-(N,N-dimethylcarboamide)-3-furylmethyl group, a 4-methyl-3-furylmethyl group, a 4-trifluoromethyl-3-furylmethyl group, a 4-methoxy-3-furylmethyl group, a 4-trifluoromethoxy-3-furylmethyl group, a 4-methylthio-3-furylmethyl group, a 4-methylsulfinyl-3-furylmethyl group, a 4-methylsulfonyl-3-furylmethyl group, a 4-methoxycarbonyl-3-furylmethyl group, a 4-vinyl-3-furylmethyl group, a 4-(2',2'-difluorovinyl)-3-furylmethyl group, an 4-ethynyl-3-furylmethyl group, a 4-(2'-fluoroethynyl)-3-furylmethyl group, a 4-fluoro-3-furylmethyl group, a 4-chloro-3-furylmethyl group, a 2-thienylmethyl group, a 4-cyano-2-thienylmethyl group, a 4-nitro-2-thienylmethyl group, a 4-carboxyl-2-thienylmethyl group, a 4-hydroxyl-2-thienylmethyl group, a 4-(N-methylcarboamide)-2-thienylmethyl group, a 4-(N,N-dimethylcarboamide)-2-thienylmethyl group, a 4-methyl-2-thienylmethyl group, a 4-trifluoromethyl-2-thienylmethyl group, a 4-methoxy-2-thienylmethyl group, a 4-trifluoromethoxy-2-thienylmethyl group, a 4-methylthio-2-thienylmethyl group, a 4-methylsulfinyl-2-thienylmethyl group, a 4-methylsulfonyl-2-thienylmethyl group, a 4 methoxycarbonyl-2-thienylmethyl group, a 4-vinyl-2-thienylmethyl group, a 4-(2',2'-difluorovinyl)-2-thienylmethyl group, an 4-ethynyl-2-thienylmethyl group, a 4-(2'-fluoroethynyl)-2-thienylmethyl group, a 4-fluoro-2-thienylmethyl group, a 4-chloro-2-thienylmethyl group, a 3-thienylmethyl group, a 4-cyano-3-thienylmethyl group, a 4-nitro-3-thienylmethyl group, a 4-carboxyl-3-thienylmethyl group, a 4-hydroxyl-3-thienylmethyl group, a 4-(N-methylcarboamide)-3-thienylmethyl group, a 4-(N,N-dimethylcarboamide)-3-thienylmethyl group, a 4-methyl-3-thienylmethyl group, a 4-trifluoromethyl-3-thienylmethyl group, a 4-methoxy-3-thienylmethyl group, a 4-trifluoromethoxy-3-thienylmethyl group, a 4-methylthio-3-thienylmethyl group, a 4-methylsulfinyl-3-thienylmethyl group, a 4-methylsulfonyl-3-thienylmethyl group, a 4-methoxycarbonyl-3-thienylmethyl group, a 4-vinyl-3-thienylmethyl group, a 4-(2',2'-difluorovinyl)-3-thienylmethyl group, an 4-ethynyl-3-thienylmethyl group, a 4-(2'-fluoroethynyl)-3-thienylmethyl group, a 4-fluoro-3-thienylmethyl group, a 4-chloro-3-thienylmethyl group, a 2-(1-benzofuranyl)methyl group, a 5-cyano-2-(1-benzofuranyl)methyl group, a 5-nitro-2-(1-benzofuranyl)methyl group, a 5-carboxyl-2-(1-benzofuranyl)methyl group, a 5-hydroxyl-2-(1-benzofuranyl)methyl group, a 5-(N-methylcarboamide)-2-(1-benzofuranyl)methyl group, a 5-(N, N-dimethylcarboamide)-2-(1-benzofuranyl)methyl group, a 5-methyl-2-(1-benzofuranyl)methyl group, a 5-trifluoromethyl-2-(1-benzofuranyl)methyl group, a 5-methoxy-2-(1-benzofuranyl)methyl group, a 5-trifluoromethoxy-2-(1-benzofuranyl)methyl group, a 5-methylthio-2-(1-benzofuranyl)methyl group, a 5-methyl-sulfinyl-2-(1-benzofuranyl)methyl group, a 5-methylsulfonyl-2-(1-benzofuranyl)methyl group, a 5-methoxycarbonyl-2-(1-benzofuranyl)methyl group, a 5-vinyl-2-(1-benzofuranyl)methyl group, a 5-(2',2'-difluorovinyl)-2-(1-benzofuranyl)methyl group, an 5-ethynyl-2-(1-benzofuranyl)methyl group, a 5-(2'-fluoroethynyl)-2-(1-benzofuranyl)methyl group, a 5-fluoro-2-(1-benzofuranyl)methyl group, a 5-chloro-2-(1-benzofuranyl)methyl group, a 3-(1-benzofuranyl)methyl group, a 5-cyano-3-(1-benzofuranyl)methyl group, a 5-nitro-3-(1-benzofuranyl)methyl group, a 5-carboxyl-3-(1-benzofuranyl)methyl group, a 5-hydroxyl-3-(1-benzofuranyl)methyl group, a 5-(N-methylcarboamide)-3-(1-benzofuranyl)methyl group, a 5-(N,N-dimethylcarboamide)-3-(1-benzofuranyl)methyl group, a 5-methyl-3-(1-benzofuranyl)methyl group, a 5-trifluoromethyl-3-(1-benzofuranyl)methyl group, a 5-methoxy-3-(1-benzofuranyl)methyl group, a 5-trifluoromethoxy-3-(1-benzofuranyl)methyl group, a 5-methylthio-3-(1-benzofuranyl)methyl group, a 5-methyl-sulfinyl-3-(1-benzofuranyl)methyl group, a 5-methylsulfonyl-3-(1-benzofuranyl)methyl group, a 5-methoxycarbonyl-3-(1-benzofuranyl)methyl group, a 5-vinyl-3-(1-benzofuranyl)methyl group, a 5-(2',2'-difluorovinyl)-3-(1-benzofuranyl)methyl group, an 5-ethynyl-3-(1-benzofuranyl)methyl group, a 5-(2'-fluoroethynyl)-3-(1-benzofuranyl)methyl group, a 5-fluoro-3-(1-benzofuranyl)methyl group, a 5-chloro-3-(1-benzofuranyl)methyl group, a 2-(1-benzothienyl)methyl group, a 5-cyano-2-(1-benzothienyl)methyl group, a 5-nitro-2-(1-benzothienyl)methyl group, a 5-carboxyl-2-(1-benzothienyl)methyl group, a 5-hydroxyl-2-(1-benzothienyl)methyl group, a 5-(N-methylcarboamide)-2-(1-benzothienyl)methyl group, a 5-(N,N-dimethylcarboamide)-2-(1-benzothienyl)methyl group, a 5-methyl-2-(1-benzothienyl)methyl group, a 5-trifluoromethyl-2-(1-benzothienyl)methyl group, a 5-methoxy-2-(1-benzothienyl)methyl group, a 5-trifluoromethoxy-2-(1-benzothienyl)methyl group, a 5-methylthio-2-(1-benzothienyl)methyl group, a 5-methylsulfinyl-2-(1-benzothienyl)methyl group, a 5-methylsulfonyl-2-(1-benzothienyl)methyl group, a 5-methoxycarbonyl-2-(1-benzothienyl)methyl group, a 5-vinyl-2-(1-benzothienyl)methyl group, a 5-(2',2'-difluorovinyl)-2-(1-benzothienyl)methyl group, an 5-ethynyl-2-(1-benzothienyl)methyl group, a 5-(2'-fluoroethynyl)-2-(1-benzothienyl)methyl group, a 5-fluoro-2-(1-benzothienyl)methyl group, a 5-chloro-2-(1-benzothienyl)methyl group, a 3-(1-benzothienyl)methyl group, a 5-cyano-3-(1-benzothienyl)methyl group, a 5-nitro-3-(1-benzothienyl)methyl group, a 5-carboxyl-3-(1-benzothienyl)methyl group, a 5-hydroxyl-3-(1-benzothienyl)methyl group, a 5-(N-methylcarboamide)-3-(1-benzothienyl)methyl group, a 5-(N,N-dimethylcarboamide)-3-(1-benzothienyl)methyl group, a 5-methyl-3-(1-benzothienyl)methyl group, a 5-trifluoromethyl-3-(1-benzothienyl)methyl group, a 5-methoxy-3-(1-benzothienyl)methyl group, a 5-trifluoromethoxy-3-(1-benzothienyl)methyl group, 5-methylthio-3-(1-benzothienyl)methyl group, a 5-methylsulfinyl-3-(1-benzothienyl)methyl group, a 5-methylsulfonyl-3-(1-benzothienyl)methyl group, a 5-methoxycarbonyl-3-(1-benzothienyl)methyl group, a 5-vinyl-3-(1-benzothienyl)methyl group, a 5-(2',2'-difluorovinyl)-3-(1-benzothienyl)methyl group, an 5-ethynyl-3-(1-benzothienyl)methyl group, a 5-(2'-fluoroethynyl)-3-(1-benzothienyl)methyl group, a 5-fluoro-3-(1-benzothienyl)methyl group, a 5-chloro-3-(1-benzothienyl)methyl group, a (methoxycarbonyl)methyl group, a cyanomethyl group, a nitromethyl group, a (carboxy)methyl group, and a hydroxymethyl group.

Examples of the embodiment of the compound of the present invention include the following amide compounds.

In the formula (I-s), compounds wherein A is a group represented by formula (III-a):

(III-a)

$A^1$ is an oxygen atom or a sulfur atom, r is 0 or 1, and p is 0, 1 or 2, i.e., compounds represented by formula (I-S):

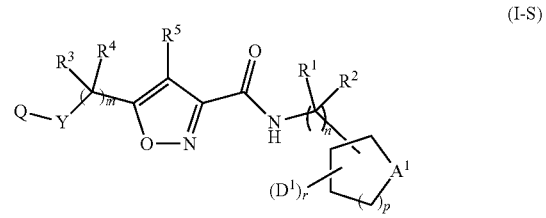

(I-S)

wherein Q, $R^1$, $R^2$, $R^3$, $R^4$, $R^5$, Y, $A^1$, $D^1$, m, n, p and r have the same meaning as described above;];

In the formula (I-S), compounds wherein n is 1, and $R^1$ and $R^2$ are a hydrogen atom;

In the formula (I-S), compounds wherein m is 1, Y is an oxygen atom, and Q is a C1 to C8 chain hydrocarbon group optionally having one or more atoms or groups selected from group G;

In the formula (I-S), compounds wherein m is 1, Y is an oxygen atom, and Q is a C1 to C8 chain hydrocarbon group optionally having a phenyl group optionally having one or more atoms or groups selected from group B;

In the formula (I-S), compounds wherein m is 1, Y is an oxygen atom, and Q is a C1 to C8 chain hydrocarbon group optionally having a naphthyl group optionally having one or more atoms or groups selected from group B;

In the formula (I-S), compounds wherein m is 1, Y is an oxygen atom, $R^3$ and $R^4$ are a hydrogen atom, and Q is a C1 to C8 chain hydrocarbon group optionally having one or more atoms or groups selected from group G;

In the formula (I-S), compounds wherein m is 1, Y is an oxygen atom, $R^3$ and $R^4$ are a hydrogen atom, and Q is a C1 to C8 chain hydrocarbon group optionally having a phenyl group optionally having one or more atoms or groups selected from group B;

In the formula (I-S), compounds wherein m is 1, Y is an oxygen atom, $R^3$ and $R^4$ are a hydrogen atom, and Q is a C1 to C8 chain hydrocarbon group optionally having a naphthyl group optionally having one or more atoms or groups selected from group B;

In the formula (I-S), compounds wherein n is 1, $R^1$ and $R^2$ are a hydrogen atom, and $R^5$ is a hydrogen atom;

In the formula (I-S), compounds wherein n is 1, $R^1$ and $R^2$ are a hydrogen atom, and $R^5$ is a C1 to C3 hydrocarbon group optionally having one or more atoms or groups selected from —$OR^7$ and halogen atoms;

In the formula (I-S), compounds wherein n is 1, $R^1$ and $R^2$ are a hydrogen atom, and $R^5$ is a methyl group;

In the formula (I-S), compounds wherein n is 1, $R^1$ and $R^2$ are a hydrogen atom, and $R^5$ is a hydroxymethyl group;

In the formula (I-S), compounds wherein n is 1, $R^1$ and $R^2$ are a hydrogen atom, and $R^5$ is a fluoromethyl group;

In the formula (I-S), compounds wherein m is 1, Y is an oxygen atom, $R^5$ is a hydrogen atom, and Q is a C1 to C8 chain hydrocarbon group optionally having one or more atoms or groups selected from group G;

In the formula (I-S), compounds wherein m is 1, Y is an oxygen atom, R is a hydrogen atom, and Q is a C1 to C8 chain hydrocarbon group optionally having a phenyl group optionally having one or more atoms or groups selected from group B;

In the formula (I-S), compounds wherein m is 1, Y is an oxygen atom, $R^5$ is a hydrogen atom, and Q is a C1 to C8 chain hydrocarbon group optionally having a naphthyl group optionally having one or more atoms or groups selected from group B;

In the formula (I-S), compounds wherein m is 1, Y is an oxygen atom, $R^3$, $R^4$ and $R^5$ are a hydrogen atom, and Q is a C1 to C8 chain hydrocarbon group optionally having one or more atoms or groups selected from group G;

In the formula (I-S), compounds wherein m is 1, Y is an oxygen atom, $R^3$, $R^4$ and $R^5$ are a hydrogen atom, and Q is a C1 to C8 chain hydrocarbon group optionally having a phenyl group optionally having one or more atoms or groups selected from group B;

In the formula (I-S), compounds wherein m is 1, Y is an oxygen atom, $R^3$, $R^4$ and $R^5$ are a hydrogen atom, and Q is a C1 to C8 chain hydrocarbon group optionally having a naphthyl group optionally having one or more atoms or groups selected from group B;

In the formula (I-S), compounds wherein m is 1, Y is an oxygen atom, $R^5$ is a C1 to C3 hydrocarbon atom optionally having one or more atoms or groups selected from the group consisting of —$OR^7$ and halogen atoms, and Q is a C1 to C8 chain hydrocarbon group optionally having one or more atoms or groups selected from group G;

In the formula (I-S), compounds wherein m is 1, Y is an oxygen atom, $R^5$ is a C1 to C3 hydrocarbon atom optionally having one or more atoms or groups selected from the group consisting of —$OR^7$ and halogen atoms, and Q is a C1 to C8 chain hydrocarbon group optionally having a phenyl group optionally having one or more atoms or groups selected from group B;

In the formula (I-S), compounds wherein m is 1, Y is an oxygen atom, $R^5$ is a C1 to C3 hydrocarbon atom optionally having one or more atoms or groups selected from the group consisting of —$OR^7$ and halogen atoms, and Q is a C1 to C8 chain hydrocarbon group optionally having a naphthyl group optionally having one or more atoms or groups selected from group B;

In the formula (I-S), compounds wherein m is 1, Y is an oxygen atom, $R^3$ and $R^4$ are a hydrogen atom, $R^5$ is a C1 to C3 hydrocarbon atom optionally having one or more atoms or groups selected from the group consisting of —$OR^7$ and halogen atoms, and Q is a C1 to C8 chain hydrocarbon group optionally having one or more atoms or groups selected from group G;

In the formula (I-S), compounds wherein m is 1, Y is an oxygen atom, $R^3$ and $R^4$ are a hydrogen atom, $R^5$ is a C1 to C3 hydrocarbon atom optionally having one or more atoms or groups selected from the group consisting of —$OR^7$ and halogen atoms, and Q is a C1 to C8 chain hydrocarbon group optionally having a phenyl group optionally having one or more atoms or groups selected from group B;

In the formula (I-S), compounds wherein m is 1, Y is an oxygen atom, $R^3$ and $R^4$ are a hydrogen atom, $R^5$ is a C1 to C3 hydrocarbon atom optionally having one or more atoms or groups selected from the group consisting of —$OR^7$ and halogen atoms, and Q is a C1 to C8 chain hydrocarbon group optionally having a naphthyl group optionally having one or more atoms or groups selected from group B;

In the formula (I-S), compounds wherein m is 1, Y is an oxygen atom, $R^5$ is a methyl group, and Q is a C1 to C8 chair, hydrocarbon group optionally having one or more atoms or groups selected from group G;

In the formula (I-S), compounds wherein m is 1, Y is an oxygen atom, $R^5$ is a methyl atom, and Q is a C1 to C8 chain hydrocarbon group optionally having a phenyl group optionally having one or more atoms or groups selected from group B;

In the formula (I-S), compounds wherein m is 1, Y is an oxygen atom, $R^5$ is a methyl atom, and Q is a C1 to C8 chain hydrocarbon group optionally having a naphthyl group optionally having one or more atoms or groups selected from group B;

In the formula (I-S), compounds wherein m is 1, Y is an oxygen atom, $R^3$ and $R^4$ are a hydrogen atom, $R^5$ is a methyl group, and Q is a C1 to C8 chain hydrocarbon group optionally having one or more atoms or groups selected from group G;

In the formula (I-S), compounds wherein m is 1, Y is an oxygen atom, $R^3$ and $R^4$ are a hydrogen atom, $R^5$ is a methyl group, and Q is a C1 to C8 chain hydrocarbon group optionally having a phenyl group optionally having one or more atoms or groups selected from group B;

In the formula (I-S), compounds wherein m is 1, Y is an oxygen atom, $R^3$ and $R^4$ are a hydrogen atom, $R^5$ is a methyl group, and Q is a C1 to C8 chain hydrocarbon group optionally having a naphthyl group optionally having one or more atoms or groups selected from group B;

In the formula (I-S), compounds wherein m is 1, Y is an oxygen atom, $R^5$ is a hydroxymethyl group, and Q is a C1 to C8 chain hydrocarbon group optionally having one or more atoms or groups selected from group G;

In the formula (I-S), compounds wherein m is 1, Y is an oxygen atom, $R^5$ is a hydroxymethyl atom, and Q is a C1 to C8 chain hydrocarbon group optionally having a phenyl group optionally having one or more atoms or groups selected from group B;

In the formula (I-S), compounds wherein m is 1, Y is an oxygen atom, $R^5$ is a hydroxymethyl atom, and Q is a C1 to C8 chain hydrocarbon group optionally having a naphthyl group optionally having one or more atoms or groups selected from group B;

In the formula (I-S), compounds wherein m is 1, Y is an oxygen atom, $R^3$ and $R^4$ are a hydrogen atom, $R^5$ is a hydroxymethyl group, and Q is a C1 to C8 chain hydrocarbon group optionally having one or more atoms or groups selected from group G;

In the formula (I-S), compounds wherein m is 1, Y is an oxygen atom, $R^3$ and $R^4$ are a hydrogen atom, $R^5$ is a hydroxymethyl group, and Q is a C1 to C8 chain hydrocarbon group optionally having a phenyl group optionally having one or more atoms or groups selected from group B;

In the formula (I-S), compounds wherein m is 1, Y is an oxygen atom, $R^3$ and $R^4$ are a hydrogen atom, $R^5$ is a hydroxymethyl group, and Q is a C1 to C8 chain hydrocarbon group optionally having a naphthyl group optionally having one or more atoms or groups selected from group B;

In the formula (I-S), compounds wherein m is 1, Y is an oxygen atom, $R^5$ is a fluoromethyl group, and Q is a C1 to C8 chain hydrocarbon group optionally having one or more atoms or groups selected from group G;

In the formula (I-S), compounds wherein m is 1, Y is an oxygen atom, $R^5$ is a fluoromethyl atom, and Q is a C1 to C8 chair, hydrocarbon group optionally having a phenyl group optionally having one or more atoms or groups selected from group B;

In the formula (I-S), compounds wherein m is 1, Y is an oxygen atom, $R^5$ is a fluoromethyl atom, and Q is a C1 to C8 chain hydrocarbon group optionally having a naphthyl group optionally having one or more atoms or groups selected from group B;

In the formula (I-S), compounds wherein m is 1, Y is an oxygen atom, $R^3$ and $R^4$ are a hydrogen atom, $R^5$ is a fluoromethyl group, and Q is a C1 to C8 chain hydrocarbon group optionally having one or more atoms or groups selected from group G;

In the formula (I-S), compounds wherein m is 1, Y is an oxygen atom, $R^3$ and $R^4$ are a hydrogen atom, $R^5$ is a fluoromethyl group, and Q is a C1 to C8 chain hydrocarbon group optionally having a phenyl group optionally having one or more atoms or groups selected from group B;

In the formula (I-S), compounds wherein m is 1, Y is an oxygen atom, $R^3$ and $R^4$ are a hydrogen atom, $R^5$ is a fluoromethyl group, and Q is a C1 to C8 chain hydrocarbon group optionally having a naphthyl group optionally having one or more atoms or groups selected from group B;

In the formula (I-S), compounds wherein m is 1, n is 1, Y is an oxygen atom, $R^1$, $R^2$ and $R^5$ are a hydrogen atom, and Q is a C1 to C8 chain hydrocarbon group optionally having one or more atoms or groups selected from group G;

In the formula (I-S), compounds wherein m is 1, n is 1, Y is an oxygen atom, $R^1$, $R^2$ and $R^5$ are a hydrogen atom, and Q is a C1 to C8 chain hydrocarbon group optionally having a phenyl group optionally having one or more atoms or groups selected from group B;

In the formula (I-S), compounds wherein m is 1, n is 1, Y is an oxygen atom, $R^1$, $R^2$ and $R^5$ are a hydrogen atom, and Q is a C1 to C8 chain hydrocarbon group optionally having a naphthyl group optionally having one or more atoms or groups selected from group B;

In the formula (I-S), compounds wherein in is 1, n is 1, Y is an oxygen atom, $R^1$, $R^2$, $R^3$, $R^4$ and $R^5$ are a hydrogen atom, and Q is a C1 to C8 chain hydrocarbon group optionally having one or more atoms or groups selected from group G;

In the formula (I-S), compounds wherein m is 1, n is 1, Y is an oxygen atom, $R^1$, $R^2$, $R^3$, $R^4$ and $R^5$ are a hydrogen atom, and Q is a C1 to C8 chain hydrocarbon group optionally having a phenyl group optionally having one or more atoms or groups selected from group B;

In the formula (I-S), compounds wherein m is 1, n is 1, Y is an oxygen atom, $R^1$, $R^2$, $R^3$, $R^4$ and $R^5$ are a hydrogen atom, and Q is a C1 to C8 chain hydrocarbon group optionally having a naphthyl group optionally having one or more atoms or groups selected from group B;

In the formula (I-S), compounds wherein m is 1, n is 1, Y is an oxygen atom, $R^1$, $R^2$ and $R^5$ are a C1 to C3 hydrocarbon atom optionally having one or more atoms or groups selected from the group consisting of —$OR^7$ and halogen atoms, and Q is a C1 to C8 chain hydrocarbon group optionally having one or more atoms or groups selected from group G;

In the formula (I-S), compounds wherein m is 1, n is 1, Y is an oxygen atom, $R^1$, $R^2$ and $R^5$ are a C1 to C3 hydrocarbon atom optionally having one or more atoms or groups selected from the group consisting of —$OR^7$ and halogen atoms, and Q is a C1 to C8 chain hydrocarbon group optionally having a phenyl group optionally having one or more atoms or groups selected from group B;

In the formula (I-S), compounds wherein m is 1, n is 1, Y is an oxygen atom, $R^1$, $R^2$ and $R^5$ are a C1 to C3 hydrocarbon atom optionally having one or more atoms or groups selected from the group consisting of —$OR^7$ and halogen atoms, and Q is a C1 to C8 chain hydrocarbon group optionally having a naphthyl group optionally having one or more atoms or groups selected from group B;

In the formula (I-S), compounds wherein m is 1, n is 1, Y is an oxygen atom, $R^1$, $R^2$, $R^3$ and $R^4$ are a hydrogen atom, $R^5$ is a C1 to C3 hydrocarbon atom optionally having one or more atoms or groups selected from the group consisting of —$OR^7$ and halogen atoms, and Q is a C1 to C8 chain hydrocarbon group optionally having one or more atoms or groups selected from group G;

In the formula (I-S), compounds wherein m is 1, n is 1, Y is an oxygen atom, $R^1$, $R^2$, $R^3$ and $R^4$ are a hydrogen atom, $R^5$ is a C1 to C3 hydrocarbon atom optionally having one or more atoms or groups selected from the group consisting of —$OR^7$ and halogen atoms, and Q is a C1 to C8 chain hydrocarbon group optionally having a phenyl group optionally having one or more atoms or groups selected from group B;

In the formula (I-S), compounds wherein m is 1, n is 1, Y is an oxygen atom, $R^1$, $R^2$, $R^3$ and $R^4$ are a hydrogen atom, $R^5$ is a C1 to C3 hydrocarbon atom optionally having one or more atoms or groups selected from the group consisting of —$OR^7$ and halogen atoms, and Q is a C1 to C8 chain hydrocarbon group optionally having a naphthyl group optionally having one or more atoms or groups selected from group B;

In the formula (I-S), compounds wherein m is 1, n is 1, Y is an oxygen atom, $R^1$, $R^2$ and $R^5$ are a methyl group, and Q is a C1 to C8 chain hydrocarbon group optionally having one or more atoms or groups selected from group G;

In the formula (I-S), compounds wherein m is 1, n is 1, Y is an oxygen atom, $R^1$, $R^2$ and $R^5$ are a methyl group, and Q is a C1 to C8 chain hydrocarbon group optionally having a phenyl group optionally having one or more atoms or groups selected from group B;

In the formula (I-S), compounds wherein m is 1, n is 1, Y is an oxygen atom, $R^1$, $R^2$ and $R^5$ are a methyl group, and Q is a C1 to C8 chain hydrocarbon group optionally having a naphthyl group optionally having one or more atoms or groups selected from group B;

In the formula (I-S), compounds wherein m is 1, n is 1, Y is an oxygen atom, $R^1$, $R^2$, $R^3$ and $R^4$ are a hydrogen atom, $R^5$ is a methyl group, and Q is a C1 to C8 chain hydrocarbon group optionally having one or more atoms or groups selected from group G;

In the formula (I-S), compounds wherein in is 1, n is 1, Y is an oxygen atom, $R^1$, $R^2$, $R^3$ and $R^4$ are a hydrogen atom, $R^5$ is a methyl group, and Q is a C1 to C8 chain hydrocarbon group optionally having a phenyl group optionally having one or more atoms or groups selected from group B;

In the formula (I-S), compounds wherein m is 1, n is 1, Y is an oxygen atom, $R^1$, $R^2$, $R^3$ and $R^4$ are a hydrogen atom, $R^5$ is a methyl group, and Q is a C1 to C8 chain hydrocarbon group optionally having a naphthyl group optionally having one or more atoms or groups selected from group B;

In the formula (I-S), compounds wherein m is 1, n is 1, Y is an oxygen atom, $R^1$, $R^2$ and $R^5$ are a hydroxymethyl group, and Q is a C1 to C8 chain hydrocarbon group optionally having one or more atoms or groups selected from group G;

In the formula (I-S), compounds wherein m is 1, n is 1, Y is an oxygen atom, $R^1$, $R^2$ and $R^5$ are a hydroxymethyl group, and Q is a C1 to C8 chain hydrocarbon group optionally having a phenyl group optionally having one or more atoms or groups selected from group B;

In the formula (I-S), compounds wherein m is 1, n is 1, Y is an oxygen atom, $R^1$, $R^2$ and $R^5$ are a hydroxymethyl group, and Q is a C1 to C8 chain hydrocarbon group optionally having a naphthyl group optionally having one or more atoms or groups selected from group B;

In the formula (I-S), compounds wherein in is 1, n is 1, Y is an oxygen atom, $R^1$, $R^2$, $R^3$ and $R^4$ are a hydrogen atom, $R^5$ is a hydroxymethyl group, and Q is a C1 to C8 chain hydrocarbon group optionally having one or more atoms or groups selected from group G;

In the formula (I-S), compounds wherein m is 1, n is 1, Y is an oxygen atom, $R^1$, $R^2$, $R^3$ and $R^4$ are a hydrogen atom, $R^5$ is a hydroxymethyl group, and Q is a C1 to C8 chain hydrocarbon group optionally having a phenyl group optionally having one or more atoms or groups selected from group B;

In the formula (I-S), compounds wherein m is 1, n is 1, Y is an oxygen atom, $R^1$, $R^2$, $R^3$ and $R^4$ are a hydrogen atom, $R^5$ is a hydroxymethyl group, and Q is a C1 to C8 chain hydrocarbon group optionally having a naphthyl group optionally having one or more atoms or groups selected from group B;

In the formula (I-S), compounds wherein m is 1, n is 1, Y is an oxygen atom, $R^1$, $R^2$ and $R^5$ are a fluoromethyl group, and Q is a C1 to C8 chain hydrocarbon group optionally having one or more atoms or groups selected from group G;

In the formula (I-S), compounds wherein m is 1, n is 1, Y is an oxygen atom, $R^1$, $R^2$ and $R^5$ are a fluoromethyl group, and Q is a C1 to C8 chain hydrocarbon group optionally having a phenyl group optionally having one or more atoms or groups selected from group B;

In the formula (I-S), compounds wherein m is 1, n is 1, Y is an oxygen atom, $R^1$, $R^2$ and $R^5$ are a fluoromethyl group, and Q is a C1 to C8 chain hydrocarbon group optionally having a naphthyl group optionally having one or more atoms or groups selected from group B;

In the formula (I-S), compounds wherein m is 1, n is 1, Y is an oxygen atom, $R^1$, $R^2$, $R^3$ and $R^4$ are a hydrogen atom, $R^5$ is a fluoromethyl group, and Q is a C1 to C8 chain hydrocarbon group optionally having one or more atoms or groups selected from group G;

In the formula (I-S), compounds wherein m is 1, n is 1, Y is an oxygen atom, $R^1$, $R^2$, $R^3$ and $R^4$ are a hydrogen atom, $R^5$ is a fluoromethyl group, and Q is a C1 to C8 chain hydrocarbon group optionally having a phenyl group optionally having one or more atoms or groups selected from group B;

In the formula (I-S), compounds wherein m is 1, n is 1, Y is an oxygen atom, $R^1$, $R^2$, $R^3$ and $R^4$ are a hydrogen atom, $R^5$ is a fluoromethyl group, and Q is a C1 to C8 chain hydrocarbon group optionally having a naphthyl group optionally having one or more atoms or groups selected from group B;

The compound of the present invention may have an isomer derived from an asymmetric carbon atom and an isomer derived from a double bond, and the present invention contains each isomer having an arthropod pest control activity and an isomer mixture in any ratio.

Next, the method for producing the compound of the present invention will be described.

The compound of the present invention can be produced, for example, according to the following (Production Method 1) to (Production Method 7).

(Production Method 1)

The compound of the present invention can be produced by reacting a compound represented by formula (1) with a compound represented by formula (2), in the presence of a condensing agent;

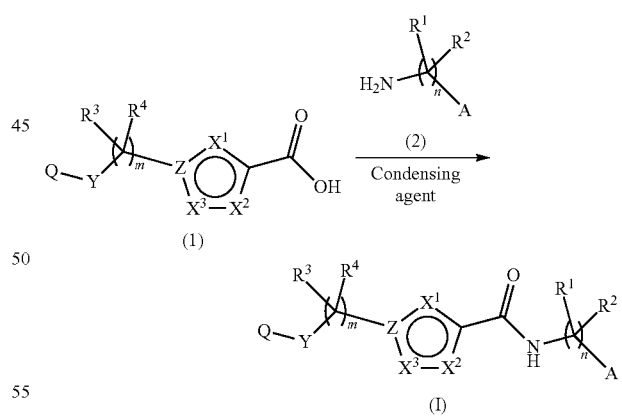

wherein $X^1$, $X^2$, $X^3$, Y, A, Z, Q, $R^1$, $R^2$, $R^3$, $R^4$, m and n have the same meaning as described above.

Examples of the condensing agent include dicyclohexylcarbodiimide, 1-ethyl-3-(3-dimethylaminopropyl) carbodiimide hydrochloride, benzotriazol-1-yloxytris(dimethylamino)phosphonium hexafluorophosphate, and (benzotriazol-1-yloxy)tripyrrolidinophosphonium hexafluorophosphate.

The reaction is usually carried out in a solvent, in the presence of a base as necessary.

Examples of the base include carbonates such as sodium carbonate and potassium carbonate, tertiary amines such as triethylamine, diisopropylethylamine, 1,8-diazabicyclo[5.4.0]undec-7-ene and 1,5-diazabicyclo[4.3.0]non-5-ene, and nitrogen-containing aromatic compounds such as pyridine and 4-dimethylaminopyridine.

Examples of the solvent include aromatic hydrocarbons such as benzene and toluene, hydrocarbons such as hexane, ethers such as diethyl ether and tetrahydrofuran, halogenated hydrocarbons such as dichloromethane, chloroform, 1,2-dichloroethane and chlorobenzene, acid amides such as N,N-dimethylformamide, esters such as ethyl acetate and butyl acetate, and the like.

The reaction can be also performed by further adding 1-hydroxybenzotriazole, 1-hydroxy-7-azabenzotriazole, N-hydroxysuccinimide or the like, usually in any ratio from 0.01 mol to 1 mol, and preferably in a ratio from 0.05 to 0.2 mol, based on 1 mol of the compound represented by the formula (1), as necessary.

The reaction time is usually within the range of 5 minutes to 72 hours, and the reaction temperature is usually within the range of −20 to 100° C. (with the proviso that, when the boiling point of the solvent to be used is less than 100° C., it is within the range of −20° C. to the boiling point of the solvent).

The compound represented by the formula (1) and the compound represented by the formula (2) can be used in any molar ratio, and are preferably equimolar or in a ratio close thereto, and for example, the ratio of the compound represented by the formula (2) is 1 to 3 mol, based on 1 mol of the compound represented by the formula (1).

The condensing agent can be used usually in any ratio from 1 mol to an excess amount, and the amount is preferably 1 to 3 mol, based on 1 mol of the compound represented by the formula (1).

The base can be used usually in any ratio from 1 mol to an excess amount, and the amount is preferably 1 to 3 mol, based on 1 mol of the compound represented by the formula (1).

After completion of the reaction, the compound of the present invention can be isolated by adding the reaction mixture to water and then subjecting it to an extraction with an organic solvent and concentration, as usual post-treatment operations.

The isolated compound of the present invention also can be purified by operations such as chromatography, recrystallization, and distillation.

(Production Method 2)

The compound of the present invention can be produced by reacting a compound represented by formula (3) with a compound represented by formula (2), in the presence of a base;

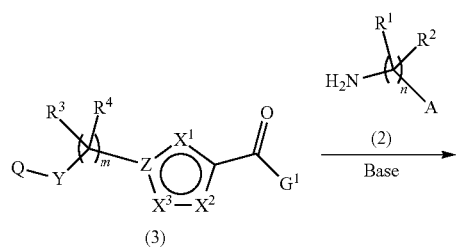
(3)

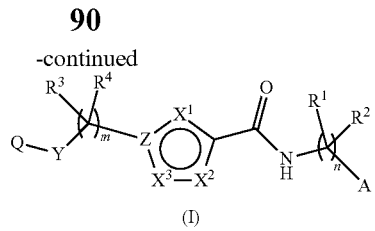
(I)

wherein $G^1$ represents a leaving group (for example, a chlorine atom, a bromine atom, etc.), and $X^1$, $X^2$, $X^3$, A, Y, Z, Q, $R^1$, $R^2$, $R^3$, $R^4$, m and n have the same meaning as described above.

Examples of the base include carbonates such as sodium carbonate and potassium carbonate, tertiary amines such as triethylamine, diisopropylethylamine, 1,8-diazabicyclo[5.4.0]undec-7-ene and 1,5-diazabicyclo[4.3.0]non-5-ene, and nitrogen-containing aromatic compounds such as pyridine and 4-dimethylaminopyridine.

The reaction is usually carried out in a solvent. Examples of the solvent include ethers such as 1,4-dioxane, tetrahydrofuran, ethylene glycol dimethyl ether and tert-butyl methyl ether, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile and butyronitrile, acid amides such as N,N-dimethylformamide, sulfoxides such as dimethyl sulfoxide, and mixtures thereof.

The reaction time is usually within the range of 5 minutes to 72 hours, and the reaction temperature is usually within the range of −20 to 100° C.

In the above reaction, the compound represented by the formula (3) and the compound represented by the formula (2) can be used in any molar ratio, and are preferably equimolar or in a ratio close thereto, and specifically, the compound represented by the formula (2) is 0.5 to 3 mol, based on 1 mol of the compound represented by the formula (5).

The amount of the base is usually in any ratio from 1 mol to an excess amount, and preferably in a ratio of 1 to 3 mol, based on 1 mol of the compound represented by the formula (3).

After completion of the reaction, the reaction mixture is added to water, then extracted with an organic solvent, and subjected to concentration as usual post-treatment operations, whereby the compound of the present invention can be isolated. The isolated compound of the present invention also can be purified by operations such as chromatography, recrystallization and distillation.

(Production Method 3)

A compound represented by formula (I-w) can be produced by reacting a compound represented by formula (4) with the compound represented by the formula (5), in the presence of a base;

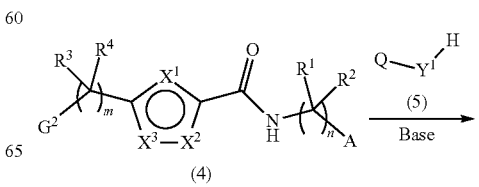
(4)

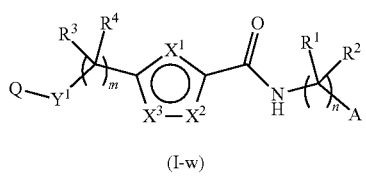

(I-w)

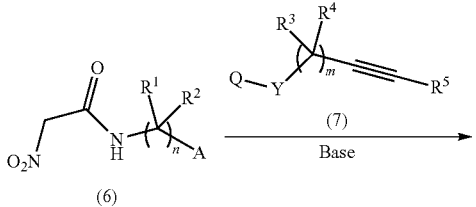

(6)

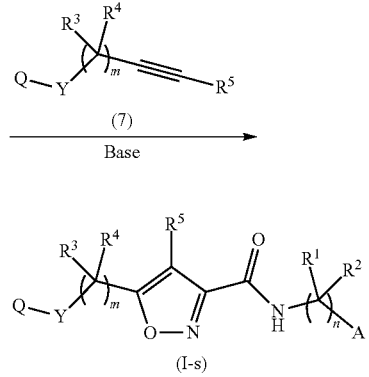

(I-s)

wherein G² represents a leaving group (for example, a chlorine atom, a bromine atom, an iodine atom, a methanesulfonyloxy group, a trifluoromethanesulfonyloxy group, a 4-toluenesulfonyloxy group, etc.), Y¹ represents an oxygen atom or a sulfur atom, and $X^1$, $X^2$, $X^3$, Q, A, $R^1$, $R^2$, $R^3$, $R^4$, m and n have the same meaning as described above.

Examples of the base include alkali metals such as sodium and potassium, alkyllithiums such as n-butyllithium, metal hydrides such as sodium hydride and potassium hydride, carbonates such as sodium carbonate and potassium carbonate, alkali metal alkoxides such as potassium-t-butoxide, tertiary amines such as triethylamine, diisopropylethylamine, 1,8-diazabicyclo[5.4.0]undec-7-ene and 1,5-diazabicyclo[4.3.0]non-5-ene, and nitrogen-containing aromatic compounds such as pyridine and 4-dimethylaminopyridine.

The reaction is usually carried out in a solvent. Examples of the solvent include ethers such as 1,4-dioxane, tetrahydrofuran, ethylene glycol dimethyl ether and tert-butyl methyl ether, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile and butyronitrile, acid amides such as N,N-dimethylformamide, sulfoxides such as dimethyl sulfoxide, and mixtures thereof.

The reaction time is usually within the range of 5 minutes to 72 hours, and the reaction temperature is usually within the range of −20 to 100° C.

In the above reaction, the compound represented by the formula (4) and the compound represented by the formula (5) can be used in any molar ratio, and are preferably equimolar or in a ratio close thereto, and specifically, the compound represented by the formula (5) is 0.5 to 3 mol, based on 1 mol of the compound represented by the formula (4).

The amount of the base is usually in any ratio from 1 mol to an excess amount, and preferably in a ratio of 1 to 3 mol, based on 1 mol of the compound represented by the formula (5).

After completion of the reaction, the reaction mixture is added to water, then extracted with an organic solvent, and subjected to concentration as usual post-treatment operations, whereby the compound of the present invention can be isolated. The isolated compound of the present invention also can be purified by operations such as chromatography, recrystallization and distillation.

(Production Method 4)

A compound represented by formula (I-s) can be produced, for example, by a route shown by the following scheme according to a method described in European Journal of Organic Chemistry, 4852 to 4860, (2006);

wherein Y, A, Q, $R^1$, $R^2$, $R^3$, $R^4$, $R^5$, m and n have the same meaning as described above.

(Production Method 5)

A compound represented by formula (I-t) can be produced, for example, by a route shown by the following scheme according to a method described in European Journal of Organic Chemistry, 4852 to 4860, (2006);

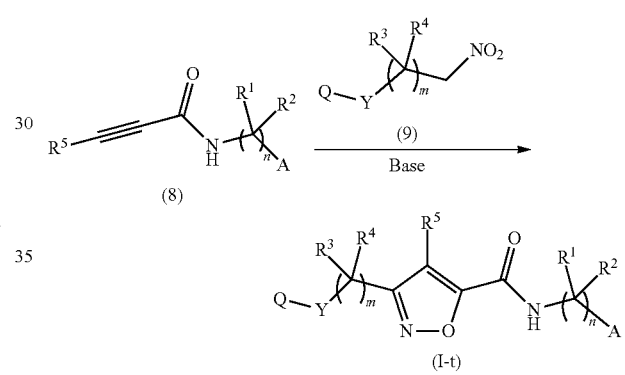

(I-t)

wherein Y, A, Q, $R^1$, $R^2$, $R^3$, $R^4$, $R^5$, m and n have the same meaning as described above.

(Production Method 6)

A compound represented by formula (I-x) can be produced, for example, by a route shown by the following scheme according to a method described in Phosphorus and Sulfur and the Related Elements, 15(2), 137-42 (1983);

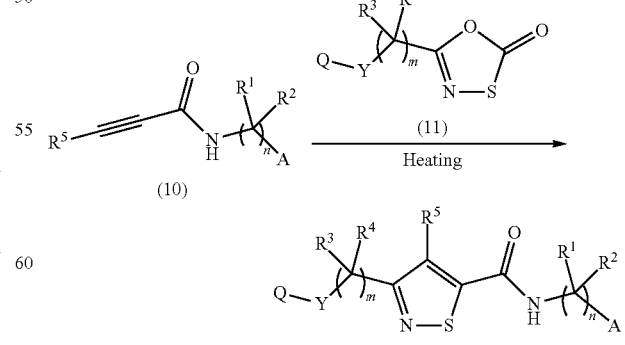

(I)

wherein Y, A, Q, $R^1$, $R^2$, $R^3$, $R^4$, $R^5$, m and n have the same meaning as described above.

(Production Method 7)

A compound represented by formula (I-w) can be produced by subjecting a compound represented by formula (12) to a coupling reaction;

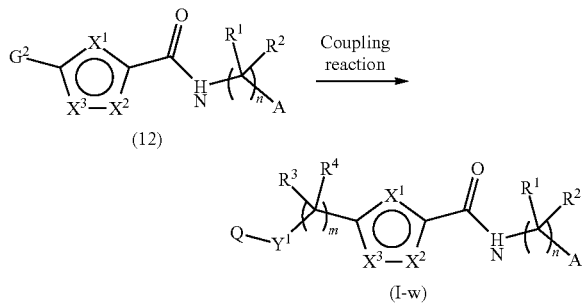

wherein $G^2$ represents a leaving group (for example, a chlorine atom, a bromine atom, an iodine atom, a methanesulfonyloxy group, a trifluoromethanesulfonyloxy group, a toluenesulfonyloxy group, etc.), and $X^1, X^2, X^3, Q, Y, A, R^1, R^2, R^3, R^4$, m and n have the same meaning as described above.

Examples of the coupling reaction include
(1) Negishi coupling reaction,
(2) Stille coupling reaction,
(3) Suzuki coupling reaction, and
(4) other methods using an organic metal reagent such as a Grignard Reagent, an organic copper reagent, or an organic lithium reagent.

As an example, the method by (1) Negishi coupling reaction will be specifically described.

The reaction is carried out in a solvent, in the presence of ligand as necessary, usually in the presence of a transition metal catalyst, an inorganic zinc salt and an organic metal reagent, and usually in an inert gas atmosphere such as nitrogen. Examples of the solvent include aromatic hydrocarbons such as benzene and toluene, hydrocarbons such as hexane, and ethers such as diethyl ether and tetrahydrofuran.

Examples of the transition metal catalyst include palladium catalysts such as palladium acetate, palladium dichloride, dichlorobis(triphenylphosphine)palladium and tetrakis(triphenylphosphine)palladium, and the like.

Examples of the ligand include phosphines such as trimethylphosphine, tricyclohexylphosphine and triphenylphosphine, imidazolium salts such as 1,3-bis(2,4,6-trimethylphenyl)imidazolium chloride, diketones such as acetylacetone and octafluoroacetylacetone, 1,1'-bis(diphenylphosphino)ferrocene and 2-dicyclohexylphosphino-2',6'-dimethoxybiphenyl, and the like.

Examples of the inorganic zinc salt include zinc chloride and the like.

Examples of the organic metal reagent include organic magnesium halides such as methylmagnesium chloride, ethylmagnesium chloride, propylmagnesium chloride, butylmagnesium chloride, pentylmagnesium bromide and hexylmagnesium chloride, and organic lithium compounds such as methyllithium and ethyllithium, and the like.

The reaction time is usually within the range of 5 minutes to 72 hours, and the reaction temperature is usually within the range of –20 to 100° C. (with the proviso that, when the boiling point of the solvent to be used is less than 100° C., it is within the range of –20° C. to the boiling point of the solvent).

The amount of the transition metal catalyst used in the reaction is usually at a ratio of 0.001 to 0.5 mol, based on 1 mol of the compound represented by the formula (12). The amount of the ligand is usually at a ratio of 0.001 to 0.5 mol, based on 1 mol of the compound represented by the formula (12). The amount of the inorganic zinc salt is usually in any ratio from 1 mol to an excess amount, and preferably in a ratio of 1 mol to 3 mol, based on 1 mol of the compound represented by the formula (12). The amount of the organic metal reagent is usually in any ratio from 1 mol to an excess amount, and preferably in a ratio of 1 mol to 3 mol, based on 1 mol of the compound represented by the formula (12).

After completion of the reaction, the compound of the present invention can be isolated by adding the reaction mixture to water and then subjecting it to an extraction with an organic solvent and concentration, as usual post-treatment operations. The isolated compound of the present invention also can be purified by operations such as chromatography, recrystallization, and distillation.

Next, the method for producing a production intermediate of the compound of the present invention will be described.
(Production Method 8)

A compound represented by formula (I-y) can be produced by reacting a compound represented by formula (1-x) with a base and then reacting an electrophile;

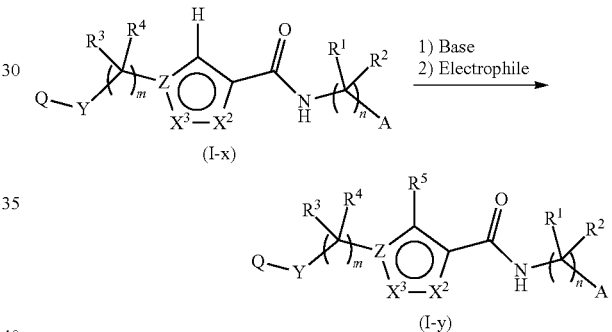

wherein $R^x$ represents a halogen atom, a formyl group, a carboxyl group, or a C1 to C3 hydrocarbon group optionally having one or more atoms or groups selected from the group consisting of hydroxyl groups and halogen atoms, and $X^2, X^3, Y, A, Z, Q, R^1, R^2, R^3, R^4$, m and n have the same meaning as described above.

The reaction is carried out in a solvent, usually in an inert gas atmosphere such as nitrogen.

Examples of the base include metal amides such as sodium amide, lithium diisopropylamide and sodium bis(trimethylsilyl)amide, alkali metal alkoxides such as potassium tert-butoxide, organic lithium compounds such as methyllithium, ethyllithium, n-butyllithium, sec-butyllithium, tert-butyllithium and 2,4,6-trimethylphenyllithium, organic magnesium halides such as methylmagnesium chloride, ethylmagnesium chloride, propylmagnesium chloride, butylmagnesium chloride, pentylmagnesium bromide and hexylmagnesium chloride, and 2,2,6,6-tetramethylpiperidinylmagnesium chloride lithium chloride complex.

Examples of the electrophile include N,N-dimethylformamide, formaldehyde, paraformaldehyde, acetaldehyde, propionaldehyde, iodomethane, iodoethane, 1,2-dibromoethane, 1-bromo-2-chloroethane, 1-chloropropane, 1-bromopropane, 1-iodopropane, dimethyl sulfate, diethyl sulfate, methyl tosylate, bromine, iodine, N-bromosuccinimide, N-chlorosuccinimide, N-iodosuccinimide, carbon dioxide, N-fluoropyridinium salts such as N-fluoro-2,4,6-trimethylpyridinium triflate, and electrophilic fluorinating agents such as N-fluoro-N'-(chloromethyl)triethylenediamine bis(tetrafluoroborate) and N-fluorobenzenesulfonimide.

Examples of the solvent include hydrocarbons such as hexane, aromatic hydrocarbons such as benzene, toluene and xylene, ethers such as diethyl ether and tetrahydrofuran, and mixtures thereof.

The reaction time is usually within the range of 5 minutes to 72 hours, and the reaction temperature is usually within the range of −100 to 40° C. (with the proviso that, when the boiling point of the solvent to be used is less than 40° C., it is within the range of −100° C. to the boiling point of the solvent).

The amount of the base used in the reaction is usually in any ratio from 1 mol to an excess amount, and preferably 2 mol to 3 mol, based on 1 mol of the compound represented by the formula (I-y).

The amount of the electrophile used in the reaction is usually in any ratio from 1 mol to an excess amount, and preferably 1 mol to 3 mol, based on 1 mol of the compound represented by the formula (I-y).

After completion of the reaction, the compound of the present invention can be isolated by adding the reaction mixture to water and then subjecting it to an extraction with an organic solvent and concentration, as usual post-treatment operations. The isolated compound of the present invention also can be purified by operations such as chromatography, recrystallization and distillation.

(Production Method 9)

A compound represented by formula (I-u) can be produced by reacting a compound represented by formula (1-t) with a halogenating agent, and then reacting it with a nucleophilic agent;

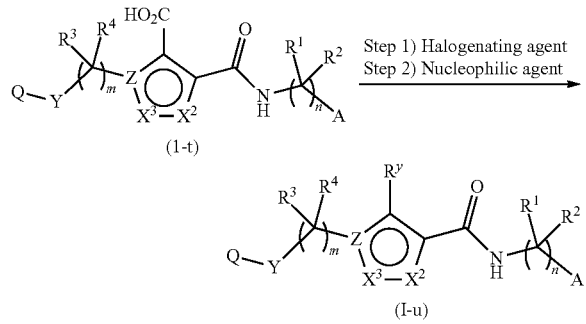

wherein $R^y$ represents a C1 to C4 alkoxycarbonyl group optionally having one or more halogen atoms or a carbamoyl group, and $X^2$, $X^3$, Y, A, Z, Q, $R^1$, $R^2$, $R^3$, $R^4$, m and n have the same meaning as described above.

The reaction is carried out in a solvent, in the presence of N,N-dimethylformamide as necessary, usually in an inert gas atmosphere such as nitrogen.

Examples of the halogenating agent include thionyl chloride, oxalyl chloride and phosphorus oxychloride.

Examples of the nucleophilic agent include C1 to C4 alcohols such as methyl alcohol, ethyl alcohol, propyl alcohol, and butyl alcohol, ammonia, and ammonium hydroxide.

Examples of the solvent include esters such as ethyl acetate and butyl acetate, ethers such as 1,4-dioxane, tetrahydrofuran, ethylene glycol dimethyl ether and tert-butyl methyl ether, aliphatic hydrocarbons such as hexane and heptane, aromatic hydrocarbons such as toluene and xylene, halogenated hydrocarbons such as chlorobenzene, and mixtures thereof.

The reaction time is usually within the range of 5 minutes to 24 hours, and the reaction temperature is usually within the range of 0 to 100° C. (with the proviso that, when the boiling point of the solvent to be used is less than 100° C., it is within the range of 0° C. to the boiling point of the solvent).

The amount of the halogenating agent used in the reaction is usually in any ratio from 1 mol to an excess amount, and preferably 1 to 5 mol, based on 1 mol of the compound represented by the formula (1-t).

The amount of the N,N-dimethylformamide used as necessary is usually in any ratio from 0.01 mol to an excess amount, and preferably in a ratio of 0.01 to 0.1 mol, based on 1 mol of the compound represented by the formula (1-t).

The amount of the nucleophilic agent used in the reaction is usually in any ratio from 1 mol to an excess amount, and preferably 1 mol to 5 mol, based on 1 mol of the compound represented by the formula (I-t).

After completion of the reaction, the compound of the present invention can be isolated by adding the reaction mixture to water and then subjecting it to an extraction with an organic solvent and concentration, as usual post-treatment operations. The isolated compound of the present invention also can be purified by operations such as chromatography, recrystallization and distillation.

(Production Method 10)

A compound represented by formula (I-m) can be produced by reacting a compound represented by formula (1-l) with a nucleophilic agent;

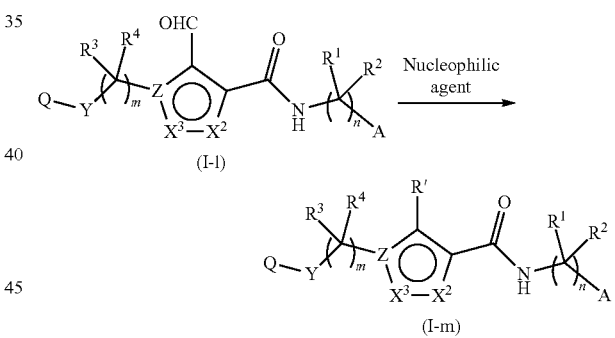

wherein $R^z$ represents a C1 to C3 hydrocarbon group having one or more atoms or groups selected from the group consisting of hydroxyl groups and halogen atoms, and $X^2$, $X^3$, Y, A, Z, Q, $R^1$, $R^2$, $R^3$, $R^4$, m and n have the same meaning as described above.

The reaction is usually carried out in a solvent.

Examples of the nucleophilic agent include organic magnesium halides such as methylmagnesium chloride, ethylmagnesium chloride and propylmagnesium chloride, organic lithium compounds such as methyllithium, ethyllithium and propyllithium, metal hydrides such as sodium borohydride, organic zinc reagents such as dimethylzinc and diethylzinc, nucleophilic fluorinating agents such as (diethylamino)sulfur trifluoride and bis(2-methoxyethyl)aminosulfur trifluoride.

Examples of the solvent include ethers such as 1,4-dioxane, tetrahydrofuran, ethylene glycol dimethyl ether and tert-butyl methyl ether, aliphatic hydrocarbons such as hexane, heptane and octane, aromatic hydrocarbons such as toluene and xylene, halogenated hydrocarbons such as chlorobenzene, alcohols such as methyl alcohol and ethyl alcohol, and mixtures thereof.

The reaction time is usually within the range of 5 minutes to 72 hours, and the reaction temperature is usually within the range of −40 to 60° C. (with the proviso that, when the boiling point of the solvent to be used is less than 60° C., it is within the range of −40° C. to the boiling point of the solvent).

The amount of the nucleophilic agent used in the reaction is usually in any ratio from 1 mol to an excess amount, and preferably 1 to 5 mol, based on 1 mol of the compound represented by the formula (1-l).

After completion of the reaction, the reaction mixture is added to water, then extracted with an organic solvent, and subjected to concentration as usual post-treatment operations, whereby the compound of the present invention can be isolated. The isolated compound of the present invention also can be purified by operations such as chromatography, recrystallization and distillation.

(Production Method 11)

A compound represented by formula (I-o) can be produced by reacting a compound represented by formula (I-n) with a fluorinating agent;

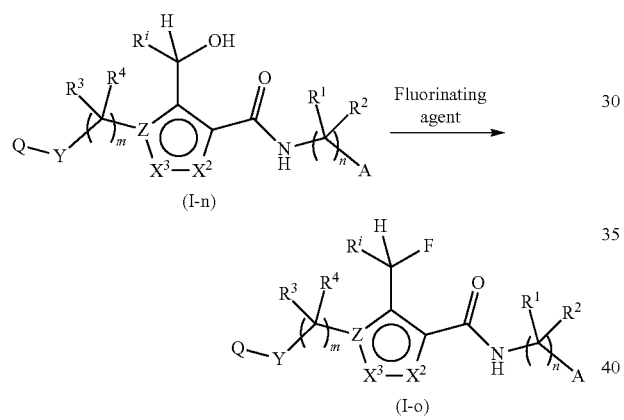

wherein $R^1$ represents a C1 to C2 hydrocarbon group optionally having one or more halogen atoms or a hydrogen atom, and $X^2$, $X^3$, Y, A, Z, Q, $R^1$, $R^2$, $R^3$, $R^4$, m and n have the same meaning as described above.

The reaction is usually carried out in a solvent.

Examples of the fluorinating agent include 4-tert-butyl-2,6-dimethylphenylsulfur trifluoride (Fluolead), bis(2-methoxyethyl)amino sulfur trifluoride (Deoxo-Fluor), (diethylamino)sulfur trifluoride (DAST), (diethylamino)difluorosulfonium tetrafluoroborate (XtalFluor-E), and difluoro(morpholino)sulfonium tetrafluoroborate (Xtal-Fluor-M).

Examples of the solvent include ethers such as 1,4-dioxane, tetrahydrofuran, ethylene glycol dimethyl ether and tert-butyl methyl ether, aliphatic hydrocarbons such as hexane, heptane and octane, aromatic hydrocarbons such as toluene and xylene, halogenated hydrocarbons such as dichloromethane, chloroform and chlorobenzene, esters such as ethyl acetate and butyl acetate, nitriles such as acetonitrile and butyronitrile, acid amides such as N,N-dimethylformamide, sulfoxides such as dimethyl sulfoxide, and mixtures thereof.

The reaction time is usually within the range of 5 minutes to 72 hours, and the reaction temperature is usually within the range of −78 to 100° C. (with the proviso that, when the boiling point of the solvent to be used is less than 100° C., it is within the range of −78° C. to the boiling point of the solvent).

The amount of the reducing agent used in the reaction is usually in any ratio from 1 mol to an excess amount, and preferably 1 to 5 mol, based on 1 mol of the compound represented by the formula (I-n).

After completion of the reaction, the compound of the present invention can be isolated by adding the reaction mixture to dilute hydrochloric acid or water and then subjecting it to an extraction with an organic solvent and concentration, as usual post-treatment operations. The isolated compound of the present invention also can be purified by operations such as chromatography, recrystallization and distillation.

(Production Method 12)

Compounds represented by formula (I-p) and formula (I-q) can be produced, for example, by a route shown by the following scheme according to a method described in Journal of Organic Chemistry, 63, 4011 to 4017 (1998);

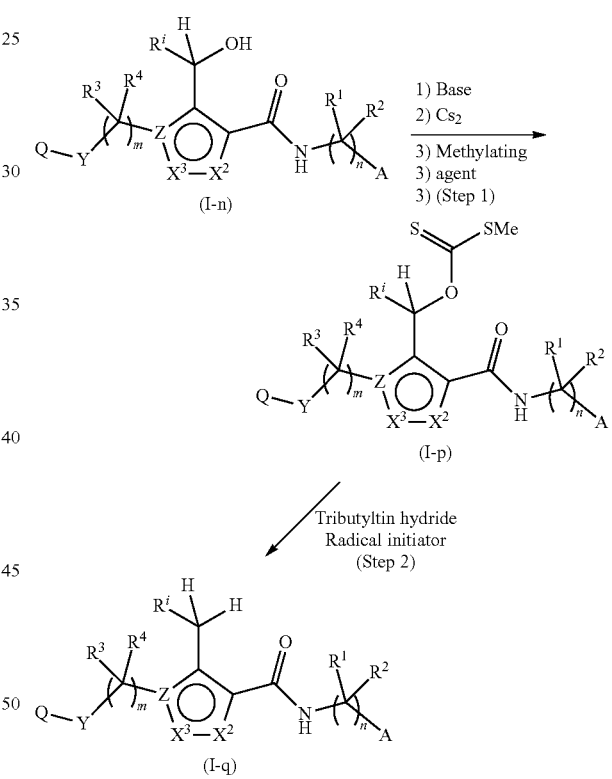

wherein $R^1$ represents a C1 to C2 hydrocarbon group optionally having one or more halogen atoms or a hydrogen atom, and $X^2$, $X^3$, Y, A, Z, Q, $R^1$, $R^2$, $R^3$, $R^4$, m and n have the same meaning as described above.

(Step 1)

The reaction is carried out in a solvent, in the presence of a base and carbon bisulfide, usually in an inert gas atmosphere such as nitrogen, and further the post treatment with a methylating agent is carried out.

Examples of the base include organic lithium compounds such as n-butyllithium, sec-butyllithium, tert-butyllithium and 2,4,6-trimethylphenyllithium, lithium diisopropylamide, lithium hexamethyldisilazide, and sodium hydride.

Examples of the methylating agent include methyl iodide, dimethyl sulfate, and methyl tosylate.

Examples of the solvent include aromatic hydrocarbons such as benzene and toluene, hydrocarbons such as hexane, and ethers such as diethyl ether and tetrahydrofuran.

The reaction time is usually within the range of 1 minute to 72 hours, and the reaction temperature is usually within the range of −78 to 100° C. (with the proviso that, when the boiling point of the solvent to be used is less than 100° C., it is within the range of −78° C. to the boiling point of the solvent).

The amount of the base used in the reaction is usually in any ratio from 1 mol to an excess amount, and preferably 1 mol to 3 mol, based on 1 mol of the compound represented by the formula (I-n).

The amount of the carbon bisulfide used in the reaction is usually in any ratio from 1 mol to an excess amount, and preferably 1 mol to 5 mol, based on 1 mol of the compound represented by the formula (I-n).

The amount of the methylating agent used in the reaction is usually in any ratio from 1 mol to an excess amount, and preferably in a ratio of 1 to 5 mol, based on 1 mol of the compound represented by the formula (I-n).

After completion of the reaction, the compound represented by the formula (I-p) can be isolated by adding the reaction mixture to dilute hydrochloric acid or water and then subjecting it to an extraction with an organic solvent and concentration, as usual post-treatment operations. The isolated compound represented by the formula (I-p) also can be purified by operations such as chromatography, recrystallization and distillation.

(Step 2)

The reaction is carried out in a solvent, in the presence of tributyltin hydride and a radical initiator, usually in an inert gas atmosphere such as nitrogen.

Examples of the radical initiator include azo compounds such as azobisisobutyronitrile (AIBN) and 1,1'-azobis(cyclohexanecarbonitrile) (ABCN), organic peroxides such as di-tert-butyl peroxide and benzoyl peroxide (BPO), triethyl borane, and diethyl zinc.

Examples of the solvent include aromatic hydrocarbons such as benzene and toluene, halogenated hydrocarbons such as chloroform and chlorobenzene, hydrocarbons such as hexane, and ethers such as diethyl ether and tetrahydrofuran.

The reaction time is usually within the range of 1 minute to 72 hours, and the reaction temperature is usually within the range of 0 to 100° C.

The amount of the tributyltin hydride used in the reaction is usually in any ratio from 1 mol to an excess amount, and preferably 1 mol to 3 mol, based on 1 mol of the compound represented by the formula (I-p).

The amount of the radical initiator used in the reaction is usually in any ratio from 0.01 mol to an excess amount, and preferably 0.1 mol to 1 mol, based on 1 mol of the compound represented by the formula (I-p).

After completion of the reaction, the reaction mixture is subjected to usual post-treatment operations such as concentration, whereby the compound represented by the formula (I-p) can be isolated. The isolated compound represented by the formula (I-p) also can be purified by operations such as chromatography, recrystallization and distillation.

(Production Method 13)

A compound represented by formula (I-f) can be produced by subjecting a compound represented by formula (I-e) and an aryl halide to Sonogashira reaction;

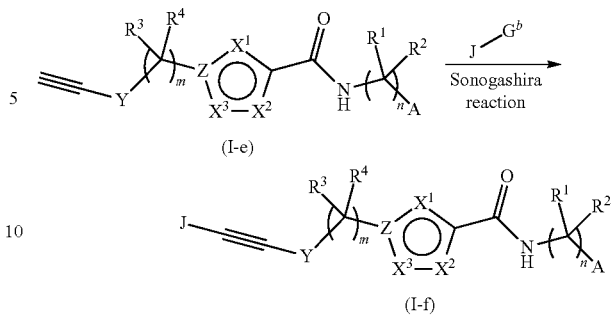

wherein J represents a group selected form group I, $G^b$ represents a leaving group (for example, a chlorine atom, a bromine atom, an iodine atom, etc.), and $X^1$, $X^2$, $X^3$, Y, A, Z, $R^1$, $R^2$, $R^3$, $R^4$, m and n have the same meaning as described above.

Group I: A group consisting of indanyl groups optionally having one or more atoms or groups selected from group B, 1,2,3,4-tetrahydronaphthyl groups optionally having one or more atoms or groups selected from group B, phenyl groups optionally having one or more atoms or groups selected from group B, naphthyl groups optionally having one or more atoms or groups selected from group B, pyridyl groups optionally having one or more atoms or groups selected from group B, quinolyl groups optionally having one or more atoms or groups selected from group B, furyl groups optionally having one or more atoms or groups selected from group B, thienyl groups optionally having one or more atoms or groups selected from group B, benzofuranyl groups optionally having one or more atoms or groups selected from group B, and benzothienyl groups optionally having one or more atoms or groups selected from group B.

The reaction is carried out in a solvent, in the presence of a transition metal catalyst, an inorganic copper salt, an alkyne and a base, usually in an inert gas atmosphere such as nitrogen.

Examples of the transition metal catalyst include palladium catalysts such as palladium acetate, palladium dichloride, dichlorobis(triphenylphosphine)palladium, and tetrakis(triphenylphosphine)palladium.

Examples of the inorganic copper salt include copper(I) bromide and copper(I) iodide.

Examples of the base include carbonates such as sodium carbonate and potassium carbonate, tertiary amines such as triethylamine, diisopropylethylamine, 1,8-diazabicyclo[5.4.0]undec-7-ene and 1,5-diazabicyclo[4.3.0]non-5-ene, and nitrogen-containing aromatic compounds such as pyridine and 4-dimethylaminopyridine.

Examples of the solvent include aromatic hydrocarbons such as benzene and toluene, hydrocarbons such as hexane, ethers such as diethyl ether and tetrahydrofuran, halogenated hydrocarbons such as dichloromethane, 1,2-dichloroethane and chlorobenzene, acid amides such as N,N-dimethylformamide, and esters such as ethyl acetate and butyl acetate.

The reaction time is usually within the range of 5 minutes to 72 hours, and the reaction temperature is usually within the range of −20 to 100° C. (with the proviso that, when the boiling point of the solvent to be used is less than 100° C., it is within the range of −20° C. to the boiling point of the solvent).

The amount of the transition metal catalyst used in the reaction is usually at a ratio of 0.001 to 0.5 mol, based on 1 mol of the compound represented by the formula (I-e).

The amount of the inorganic copper salt used in the reaction is usually at a ratio of 0.001 to 0.5 mol, based on 1 mol of the compound represented by the formula (I-e).

The amount of the alkyne used in the reaction is usually in any ratio from 1 mol to an excess amount, and preferably 1 mol to 5 mol, based on 1 mol of the compound represented by the formula (I-e).

The amount of the base used in the reaction is usually in any ratio from 1 mol to an excess amount, and preferably 1 mol to 3 mol, based on 1 mol of the compound represented by the formula (I-e).

After completion of the reaction, the compound represented by the formula (I-f) can be isolated by adding the reaction mixture to water and then subjecting it to an extraction with an organic solvent and concentration, as usual post-treatment operations. The obtained compound represented by the formula (I-f) also can be purified by operations such as chromatography, recrystallization and distillation.

(Reference Production Method 1)

A compound represented by formula (1) can be produced by subjecting a compound represented by formula (13) to a hydrolysis reaction, in the presence of a base;

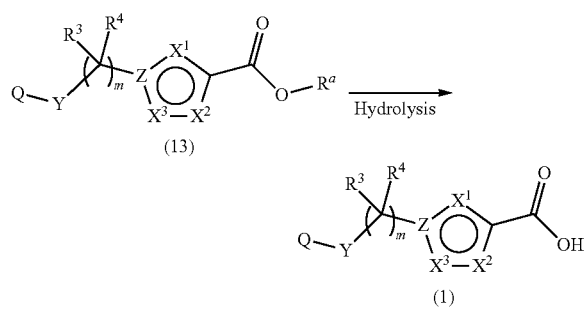

wherein $R^a$ represents a methyl group or an ethyl group, and $X^1$, $X^2$, $X^3$, Y, Z, Q, $R^3$, $R^4$ and m have the same meaning as described above.

The reaction is carried out in an organic solvent, in the presence of water. Examples of the organic solvent include ethers such as 1,4-dioxane, tetrahydrofuran, ethylene glycol dimethyl ether and tert-butyl methyl ether, aromatic hydrocarbons such as toluene and xylene, halogenated hydrocarbons such as chlorobenzene, nitriles such as acetonitrile and butyronitrile, alcohols such as methanol, ethanol and propanol, and mixtures thereof.

Examples of the base include alkali metal hydroxides such as lithium hydroxide, sodium hydroxide and potassium hydroxide.

The reaction time is usually within the range of 5 minutes to 72 hours, and the reaction temperature is usually within the range of 0 to 100° C. (with the proviso that, when the boiling point of the solvent to be used is less than 10000, it is within the range of 0° C. to the boiling point of the solvent).

The amount of the base used in the reaction is usually in any ratio from 1 mol to an excess amount, and preferably in a ratio of 1 mol to 5 mol, based on 1 mol of the compound represented by the formula (13).

After completion of the reaction, the reaction mixture is added to water and washed with an organic solvent, then the aqueous layer is neutralized by an acid water (hydrochloric acid, etc.) and the mixture is subjected to an extraction with an organic solvent and concentration as post-treatment operations, whereby the compound represented by the formula (1) can be obtained. Also, the obtained compound represented by the formula (1) is usually used for the reaction in the next step without purification, but also can be purified by operations such as chromatography and recrystallization as necessary.

(Reference Production Method 2)

A compound represented by formula (3) can be produced, for example, by reacting a compound represented by formula (1) with a halogenating agent;

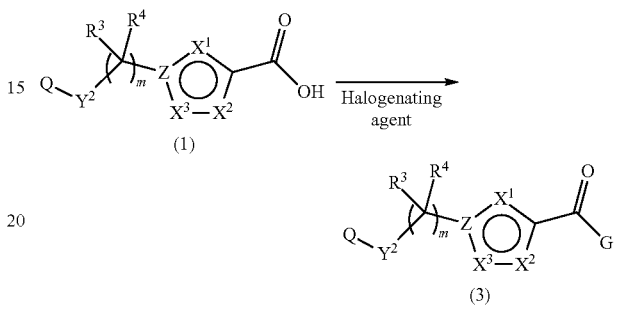

wherein G represents a chlorine atom or a bromine atom, $Y^2$ represents $—CR^8R^9—$, an oxygen atom or $—S(O)_2—$, and $X^1$, $X^2$, $X^3$, Q, Z, $R^3$, $R^4$ and m have the same meaning as described above.

Examples of the halogenating agent include thionyl chloride, oxalyl chloride and phosphorus oxychloride.

The reaction is usually carried out in a solvent as necessary. Examples of the solvent include ethers such as 1,4-dioxane, tetrahydrofuran, ethylene glycol dimethyl ether and tert-butyl methyl ether, aliphatic hydrocarbons such as hexane and heptane, aromatic hydrocarbons such as toluene and xylene, halogenated hydrocarbons such as chlorobenzene, and mixtures thereof.

The reaction time is usually within the range of 5 minutes to 24 hours, and the reaction temperature is usually within the range of 0 to 100° C.

The amount of the halogenating agent used in the reaction is usually in any ratio from 1 mol to an excess amount, and preferably in a ratio of 1 to 5 mol, based on 1 mol of the compound represented by the formula (1).

After completion of the reaction, the reaction mixture is subjected to post-treatment operations such as direct concentration, whereby the compound represented by the formula (3) can be isolated. The isolated compound represented by the formula (3) is usually used for the reaction in the next step without purification, but can be purified by distillation or the like as necessary.

(Reference Production Method 3)

Compound (13-a) among compounds (13) can be produced, for example, by a route shown by the following scheme according to a method described in Journal of Chemical Society, Perkin Trans., 14, 1716, (2001);

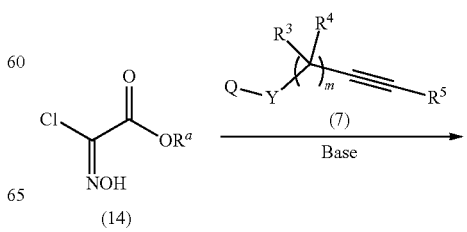

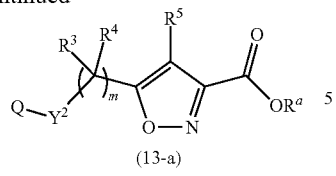

(13-a)

wherein $R^a$ represents a methyl group or an ethyl group, and Y, Q, $R^3$, $R^4$, $R^5$ and m have the same meaning as described above.

(Reference Production Method 4)

Compound (13-b) among compounds (13) can be produced, for example, by a route shown by the following scheme according to a method described in Journal of Chemical Society, Perkin Trans., 14, 1716, (2001);

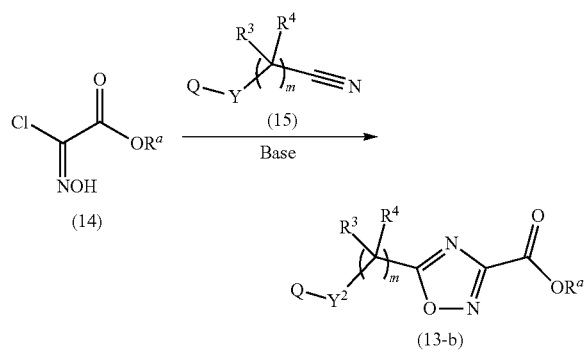

wherein $R^a$ represents a methyl group or an ethyl group, and Y, Q, $R^3$, $R^4$ and m have the same meaning as described above.

(Reference Production Method 5)

Compound (13-a) among compounds (13) can be produced, for example, by a route shown by the following scheme according to a method described in European Journal of Organic Chemistry, 4852 to 4860, (2006);

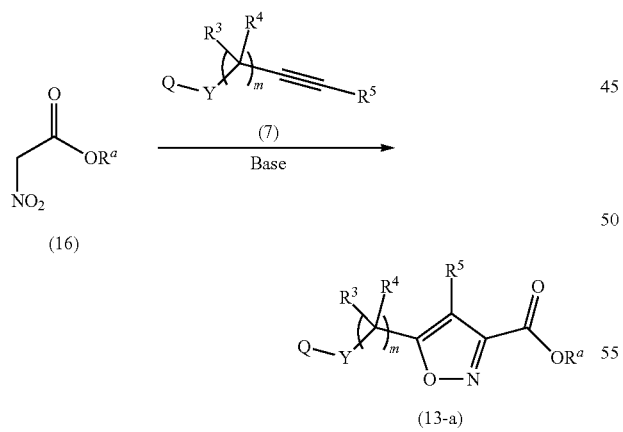

wherein $R^a$ represents a methyl group or an ethyl group, and Y, Q, $R^3$, $R^4$, $R^5$ and m have the same meaning as described above.

(Reference Production Method 6)

Compound (13-c) among compounds (13) can be produced, for example, by a route shown by the following scheme according to a method described in European Journal of Organic Chemistry, 4852 to 4860, (2006);

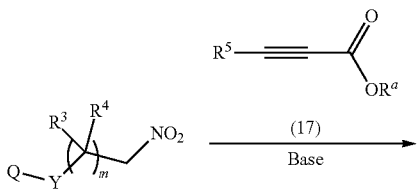

wherein $R^a$ represents a methyl group or an ethyl group, and Y, Q, $R^3$, $R^4$, $R^5$ and m have the same meaning as described above.

(Reference Production Method 7)

Compound (13-e) among compounds (13) can be produced, for example, by a route shown by the following scheme according to a method described in Phosphorus and Sulfur and the Related Elements, 15(2), 137-42 (1983);

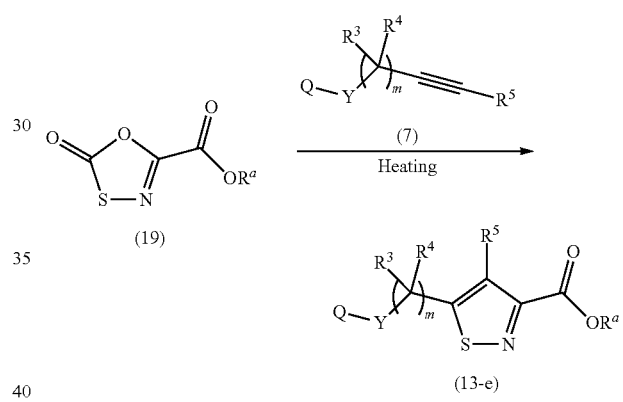

wherein $R^a$ represents a methyl group or an ethyl group, and Y, Q, $R^3$, $R^4$, $R^5$ and m have the same meaning as described above.

(Reference Production Method 8)

Compound (13-f) among compounds (13) can be produced, for example, by a route shown by the following scheme according to a method described in Journal of Organic Chemistry, 39, 962 to 964, (1974);

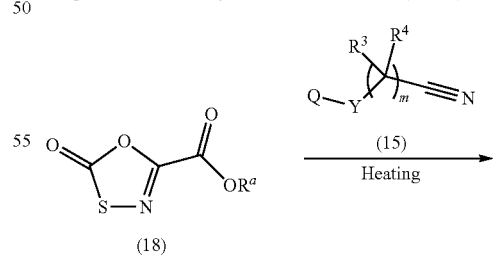

wherein $R^a$ represents a methyl group or an ethyl group, and Y, Q, $R^3$, $R^4$ and m have the same meaning as described above.

(Reference Production Method 9)

Compound (13-f) among compounds (13) can be produced, for example, by a route shown by the following scheme according to a method described in Phosphorus and Sulfur and the Related Elements, 15(2), 137-42 (1983);

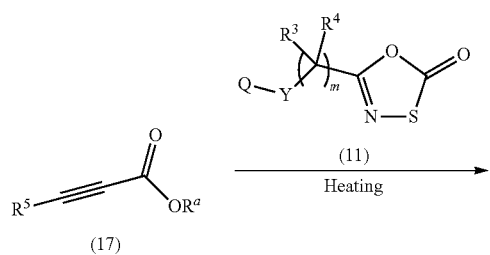

wherein $R^a$ represents a methyl group or an ethyl group, and Y, Q, $R^3$, $R^4$, $R^5$ and m have the same meaning as described above.

(Reference Production Method 10)

Compound (13-h) among compounds (13) can be produced, for example, by a route shown by the following scheme according to a method described in Tetrahedron, 69, 8564 to 8571 (2013);

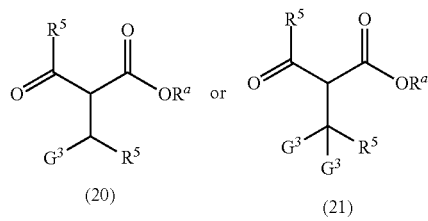

wherein $G^3$ represents a methoxy group or an ethoxy group, $R^a$ represents a methyl group or an ethyl group, and $G^2$, Y, Q, $R^3$, $R^4$, $R^5$ and m have the same meaning as described above.

(Reference Production Method 11)

Compound (1-a) among compounds (1) can be produced, for example, by a route shown by the following scheme, for example, by producing compound (27) according to a method described in WO2005068432 and then subjecting the compound (27) to an oxidation process according to a method described in Advanced organic chemistry, fourth edition, part B, 747 to 809 (2001, Kluwer Academic/Plenum Publishers);

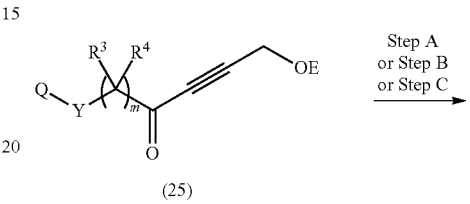

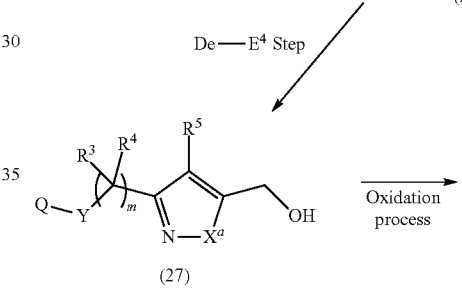

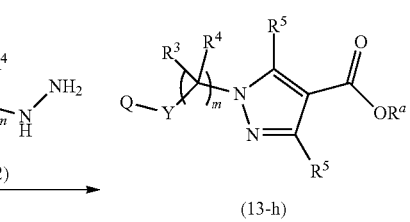

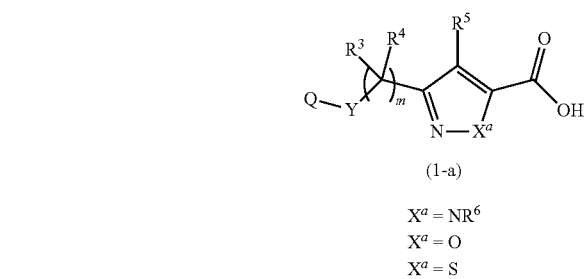

(1-a)

$X^a = NR^6$
$X^a = O$
$X^a = S$

Step A: $R^6NHNH_2$
Step B: $NH_2OH$, Base
Step C: $NH_2OSO_3H$, Base, NaSH

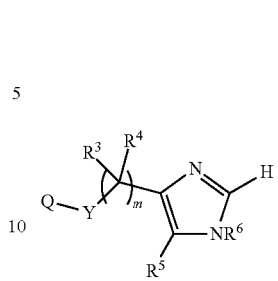

(30)

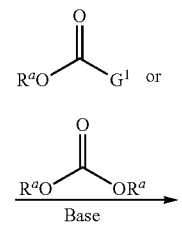

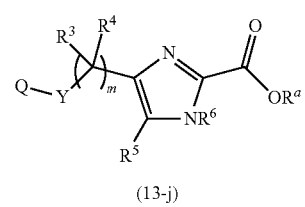

(13-j)

wherein E represents a protecting group (for example, tetrahydropyran-2-yl group, t-butyldimethylsilyl group, etc.), $X^a$ represents an oxygen atom, a nitrogen atom or $NR^6$, and $R^a$, $X^2$, Y, Q, $R^3$, $R^4$, $R^5$ and m have the same meaning as described above.

(Reference Production Method 12)

Compound (13-i) among compounds (13) can be produced, for example, according to a route shown by the following scheme according to a method described in Bioorganic & Medicinal Chemistry Letters, 23, 273 to 280 (2013);

wherein $G^1$, $R^a$, Y, Q, $R^3$, $R^4$, $R^5$, $R^6$ and m have the same meaning as described above.

(Reference Production Method 14)

Compound (13-k) among compounds (13) can be produced, for example, according to a route shown by the following scheme according to a method described in JP-A-2001-58979;

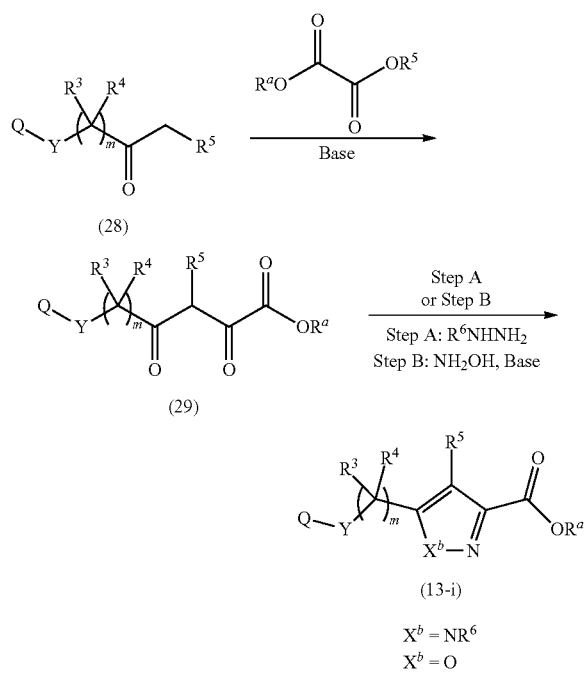

(28)

(29)

(13-i)

$X^b = NR^6$
$X^b = O$

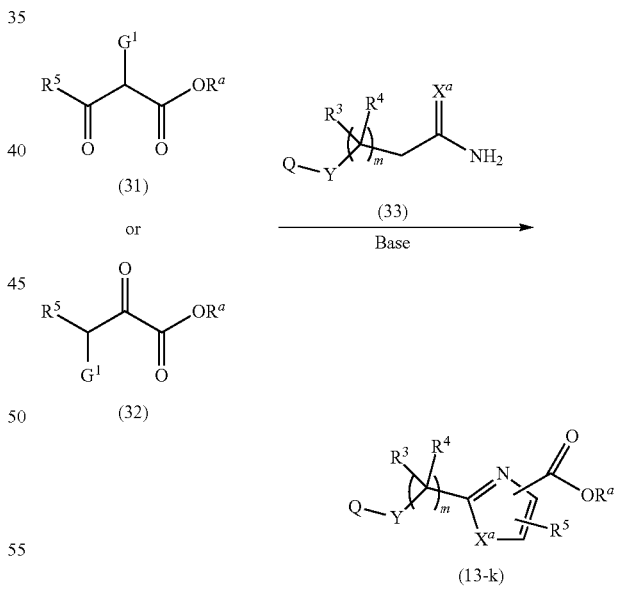

(31)

(33)

or (32)

(13-k)

wherein $X^b$ represents an oxygen group or $NR^6$, and $R^a$, Y, Q, $R^3$, $R^4$, $R^5$, $R^6$ and m have the same meaning as described above.

(Reference Production Method 13)

Compound (13-j) among compounds (13) can be produced, for example, according to a route shown by the following scheme according to a method described in Heterocycles, 23, 1759, (1985);

wherein $G^1$, $R^a$, $X^a$, Y, Q, $R^3$, $R^4$, $R^5$, $R^6$ and m have the same meaning as described above.

(Reference Production Method 15)

A compound represented by formula (13) can be produced by reacting a compound represented by formula (35) with the compound represented by the formula (5), in the presence of a base;

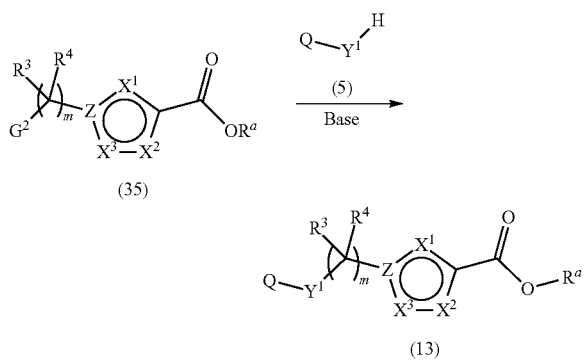

(35)

(13)

wherein $X^1$, $X^2$, $X^3$, $Y^1$, Z, $G^2$, Q, $R^a$, $R^3$, $R^4$ and m have the same meaning as described above.

The reaction is carried out usually in a solvent, in the presence of a base.

Examples of the base include alkali metals such as sodium and potassium, alkyllithiums such as n-butyllithium, metal hydrides such as sodium hydride and potassium hydride, carbonates such as sodium carbonate and potassium carbonate, alkali metal alkoxides such as potassium-t-butoxide, tertiary amines such as triethylamine, diisopropylethylamine, 1,8-diazabicyclo[5.4.0]undec-7-ene and 1,5-diazabicyclo[4.3.0]non-5-ene, and nitrogen-containing aromatic compounds such as pyridine and 4-dimethylaminopyridine.

Examples of the solvent include ethers such as 1,4-dioxane, tetrahydrofuran, ethylene glycol dimethyl ether and tert-butyl methyl ether, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile and butyronitrile, acid amides such as N,N-dimethylformamide, sulfoxides such as dimethyl sulfoxide, and mixtures thereof.

The reaction time is usually within the range of 5 minutes to 72 hours, and the reaction temperature is usually within the range of −20 to 100° C.

In the above reaction, the compound represented by the formula (35) and the compound represented by the formula (5) can be used in any molar ratio, and are preferably equimolar or in a ratio close thereto, and specifically, the compound represented by the formula (5) is at a ratio of 0.5 to 3 mol, based on 1 mol of the compound represented by the formula (35).

The amount of the base used in the reaction is usually in any ratio from 1 mol to an excess amount, and preferably 1 to 3 mol, based on 1 mol of the compound represented by the formula (35).

After completion of the reaction, the reaction mixture is added to water, then extracted with an organic solvent, and subjected to concentration as usual post-treatment operations, whereby the compound of the present invention can be isolated. The isolated compound of the present invention also can be purified by operations such as chromatography, recrystallization and distillation.

(Reference Production Method 16)

Compound (35-a) among compounds (35) can be produced, for example, by a route shown by the following scheme according to a method described in Journal of Chemical Society, Parkin Transl, 206 to 215 (2001);

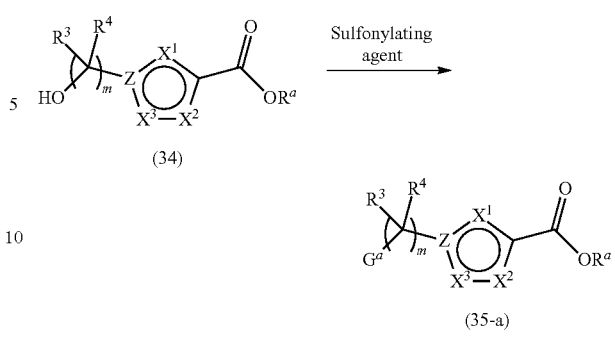

(34)

(35-a)

wherein $G^a$ represents a leaving group (for example, a methanesulfonyloxy group, a trifluoromethanesulfonyloxy group, a 4-toluenesulfonyloxy group, etc.), and $X^1$, $X^2$, $X^3$, Z, $R^a$, $R^3$, $R^4$ and m have the same meaning as described above.

(Reference Production Method 17)

Compound (35-b) among compounds (35) can be produced, for example, by a route shown by the following scheme according to a method described in Chemistry-A European Journal, 993 to 1005 (2001);

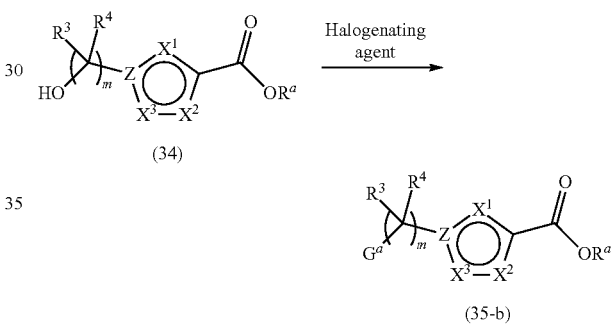

(34)

(35-b)

wherein $X^1$, $X^2$, $X^3$, Z, $G^b$, $R^a$, $R^3$, $R^4$ and m have the same meaning as described above.

(Reference Production Method 18)

Compound (36) can be produced, for example, by Mitsunobu reaction shown by the following scheme according to a method described in Strategic applications of named reactions in organic synthesis, 294 to 295 (2005, Elsevier Academic Press);

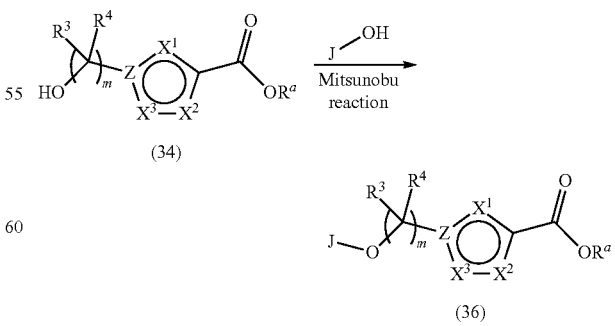

(34)

(36)

wherein $X^1$, $X^2$, $X^3$, Z, J, $R^a$, $R^3$, $R^4$ and m have the same meaning as described above.

(Reference Production Method 19)

A compound represented by formula (1) can be produced by converting a compound represented by formula (35) into a compound represented by formula (13) according to a method described in Reference Production Method 15 and then subjecting it to a hydrolysis reaction according to the method described in Reference Production Method 1. At that time, it is not necessary to purify the compound represented by the formula (13);

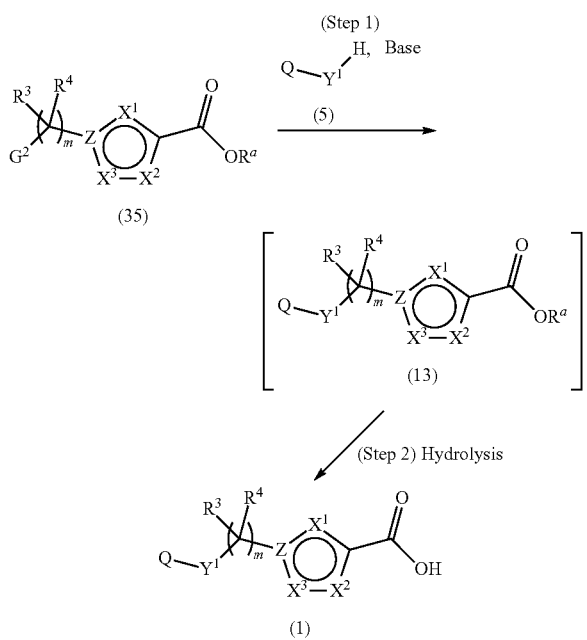

wherein $X^1$, $X^2$, $X^3$, $Y^1$, Z, $G^2$, Q, $R^a$, $R^3$, $R^a$ and m have the same meaning as described above.

The arthropod pest on which the composition of the present invention has a control effect includes pest insects and pest mites. More specifically, examples include those shown below.

Hemiptera pests: Delphacidae such as *Laodelphax striatellus*, *Nilaparvata lugens*, and *Sogatella furcifera*, Deltocephalidae such as *Nephotettix cincticeps* and *Nephotettix virescens*, Aphididae such as *Aphis gossypii* and *Myzus persicae*, Pentatomidae such as *Nezara antennata*, *Riptortus clavetus*, *Eysarcoris lewisi*, *Eysarcoris parvus*, *Plautia stali*, *Halyomorpha mista*, *Stenotus rubrovittatus*, and *Trigonotylus ruficornis*, Aleyrodidae such as *Trialeurodes vaporariorum* and *Bemisia argentifolii*, Coccoidea such as *Aonidiella aurantii*, *Comstockaspis perniciosa*, *Unaspis citri*, *Ceroplastes rubens*, and *Icerya purchasi*, Tingidae, Cimicidae such as *Cimex lectularius*, Psyliidae, etc.;

Lepidoptera pests: Pyralidae such as *Chilo suppressalis*, *Cnaphalocrocis medinalis*, *Notarcha derogata*, and *Plodia interpunctella*, Noctuidae such as *Spodoptera litura*, *Pseudaletia separata*, *Trichoplusia* spp., *Heliothis* spp., and *Helicoverpa* spp., Pieridae such as *Pieris rapae*, Tortricidae such as *Adoxophyes* spp., *Grapholita molesta* and *Cydia pomonella*, Carposinidae such as *Carposina niponensis*, Lyonetiidae such as *Lyonetia* spp., Lymantriidae such as *Lymantria* spp. and *Euproctis* spp., Yponomeutidae such as *Plutella xylostella*, Gelechiidae such as *Pectinophora gossypiella*, Arctiidae such as *Hyphantria cunea*, Tineidae such as *Tinea translucens* and *Tineola bisselliella*, etc.;

Diptera pests: *Culex* spp. such as *Culex pipiens pallens*, *Culex tritaeniorhynchus*, and *Culex quinquefasciatus*, *Aedes* spp. such as *Aedes aegypti* and *Aedes albopictus*, *Anopheles* spp. such as *Anopheles sinensis*, Chironomidae, Muscidae such as *Musca domestica* and *Muscina stabulans*, Calliphoridae, Sarcophagidae, *Fannia canicularis*, Anthomyiidae such as *Delia platura* and *Delia antiqua*, Agromyzidae such as *Liriomyza trifolii*, Tephritidae, Drosophilidae, Phoridae such as *Megaselia spiracularis*, Psychodidae such as *Clogmia albipunctata*, Simuliidae, Tabanidae, Stomoxyidae, etc.;

Coleoptera pests: *Diabrotica* spp. such as *Diabrotica virgifera virgifera* and *Diabrotica undecimpunctata howardi*, Scarabaeidae such as *Anomala cuprea* and *Anomala rufocuprea*, Curculionidae such as *Sitophilus zeamais*, *Lissorhoptrus oryzophilus*, and *Callosobruchuys chienensis*, Tenebrionidae such as *Tenebrio molitor* and *Tribolium castaneum*, Chrysomelidae such as *Oulerna oryzae*, *Aulacophora fernoralis*, *Phyllotreta striolata*, and *Leptinotarsa decemlineata*, Dermestidae such as *Dermestes maculates*, Anobiidae, *Epilachna* such as *Epilachna vigintioctopunctata*, Lyctidae, Bostrychidae, Ptinidae, Cerambycidae, and *Paederus fuscipes*, etc.;

Dictyoptera pests: *Blattella germanica*, *Periplaneta fuliginosa*, *Periplaneta americana*, *Periplaneta brunnea*, *Blatta orientalis*, etc.

Thysanoptera pests: *Thrips palmi*, *Thrips tabaci*, *Frankliniella occidentalis*, *Frankliniella intonsa*, etc.;

Hymenoptera pests: Formicidae such as *Monomorium pharaosis*, *Formica fusca japonica*, *Ochetellus glaber*, *Pristomyrmex pungens*, and *Pheidole noda*, Vespidae, Bethylidae, Tenthredinidae such as *Athalia japonica*, etc.;

Orthoptera pests: Gryllotalpidae, Acrididae, Gryllidae, etc.;

Siphonaptera pests: *Ctenocephalides felis*, *Ctenocephalides canis*, *Pulex irritans*, *Xenopsylla cheopis*, etc.

Anoplura pests: *Pediculus humanus corporis*, *Phthirus pubis*, *Haematopinus eurysternus*, *Dalmalinia ovis*, *Haematopinus suis*, etc.;

Isoptera pests: Subterranean termites such as *Reticulitermes speratus*, *Coptotermes formosanus*, *Reticulitermes flavipes*, *Reticulitermes hesperus*, *Reticulitermes virginicus*, *Reticulitermes tibialis*, and *Heterotermes aureus*, Drywood termites such as *Incisitermes minor*, Dampwood termites such as *Zootermopsis nevadensis*, etc.;

Acarina pests: Tetranychidae such as *Tetranychus urticae*, *Tetranychus kanzawai*, *Panonychus citri*, *Panonychus ulmi*, and *Oligonychus* spp., Eriophyidae such as *Aculops lycopers*, *Aculops pelekassi*, and *Aculus schlechtendali*, Tarsonemidae such as *Polyphagotarsonemus latus*, Tenuipalpidae, Tuckerellidae, Ixodidae such as *Haemaphysalis longicornis*, *Haemaphysalis flava*, *Dermacentor variabilis*, *Haemaphysalis flava*, *Dermacentor taiwanicus*, *Ixodes ovatus*, *Ixodes persulcatus*, *Ixodes scapularis*, *Boophilus microplus*, *Amblyomma americanum*, and *Rhipicephalus sanguineus*, Acaridae such as *Tyrophagus putrescentiae*, Dermatophagoides such as *Dermatophagoides farinae* and *Dermatophagoides ptrenyssnus*, Cheyletidae such as *Cheyletus eruditus*, *Cheyletus malaccensis*, and *Cheyletus moorei*, Ornithonyssus bacoti, Ornithonyssus sylvairum, Dermanyssidae such as *Dermanyssus gallinae*, Trombiculidae such as *Leptotrombidium akamushi*, etc.;

Araneae: *Chiracanthium japonicum*, *Latrodectus hasseltii*, etc.;

Chilopoda: *Thereuonema hilgendorfi*, *Scolopendra subspinipes*, etc.;

Diplopoda: *Oxidus gracilis*, *Nedyopus tambanus*, etc.;

Isopoda: *Armadillidium vulgare*, etc.

The arthropod pest control agent of the present invention contains the compound of the present invention and an inert carrier. In the present invention, an inert carrier refers to an extender, a diluent and the like used in epidemic prevention and in the agricultural field. The arthropod pest control agent of the present invention is usually obtained by mixing the compound of the present invention and an inert carrier such as a solid carrier, a liquid carrier or a gaseous carrier, and adding a surfactant or other auxiliaries for formulation as necessary, to be formulated into emulsifiable concentrates, oil formulations, dust formulations, granules, wettable powder, flowable, microcapsule formulations, aerosols, smoking agents, poisonous baits, resin formulations, and the like. These formulations usually contain the compound of the present invention in an amount of 0.01 to 95% by weight.

Examples of the solid carrier which is used in the formulation include fine powder and granules of clays (kaolin clay, diatomaceous earth, bentonite, Fubasami clay, acid clay, etc.), synthetic hydrated silicon oxide, talc, ceramics, other inorganic minerals (sericite, quartz, sulfur, activated carbon, calcium carbonate, hydrated silica, etc.), fine powder and granulated substances of chemical fertilizers (ammonium sulfate, ammonium phosphate, ammonium nitrate, urea, ammonium chloride, etc.) and the like.

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), and propylene carbonate and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants such as alkyl sulfonates, alkylbenzene sulfonates and alkylsulfates.

The other auxiliaries for formulation include such as fixing agents, dispersants, colorants and stabilizers, specifically, for example, casein, gelatin, polysaccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

The arthropod pest control agent of the present invention is used, for example, by being applied to an arthropod pest directly and/or an arthropod pest-infested area.

The method for controlling arthropod pest is carried out, for example, by applying an effective amount of the compound of the present invention to an arthropod pest or an arthropod pest-infested area, while the method is not particularly limited as long as it is in a form which the compound of the present invention can be substantially applied. In the method for controlling arthropod pests of the present invention, the compound of the present invention is usually used in the form of the arthropod pest control agent of the present invention.

The arthropod pest-infested area includes rice fields, fields, orchards, non-agricultural lands, house, and the like.

The application can be carried out by an application method which is the same as a conventional case, as long as the compound of the present invention can be contacted to or taken by an arthropod pest.

Examples of the application method include spray treatment, soil treatment, seed treatment and hydroponic liquid treatment.

When the arthropod pest control agent of the present invention is used in arthropod pest controlling in the agricultural field, the application amount is usually 1 to 10000 g per the amount of the compound of the present invention per 10000 $m^2$. When the arthropod pest control agent of the present invention is formulated into an emulsifiable concentrate, wettable powder, flowable or the like, the pest control agent is usually diluted with water for an application so as to have a concentration of the active ingredient of 0.01 to 10000 ppm, and dust formulations, granules and the like are usually applied as they are.

These formulations and formulation solutions diluted with water may be directly applied by being sprayed on an arthropod pest or a plant such as crops which should be protected from arthropod pests, and also may be applied on a soil in order to control an arthropod pest that infests the soil of cultivated land.

The resin formulation processed into a sheet or string can be also applied by a method such as winding it around crops, spreading it in the vicinity of crops, or spreading it to the soil around crop roots.

When the arthropod pest control agent of the present invention is used in controlling the arthropod pest that inhabits in the house, the application amount is usually 0.01 to 1000 mg in an amount of the compound of the present invention per 1 $m^2$ of an area to be treated, in the case of using it on a planar area, and is usually 0.01 to 500 mg in an amount of the compound of the present invention per 1 $m^3$ of a space to be treated, in the case of using it in a space. When the arthropod pest control agent of the present invention is formulated into an emulsifiable concentrate, wettable powder, flowable or the like, the pest control agent is usually diluted with water for an application so as to have a concentration of the active ingredient of 0.1 to 1000 ppm, and oil formulations, aerosols, smoking agents, poisonous baits and the like are applied as they are.

The compound of the present invention can be used in the farmland where the following crops are grown.

Crops: corn, rice, wheat, barley, rye, oat, sorghum, cotton, soybean, peanut, sarrazin, sugar beet, rapeseed, sunflower, sugar cane, tobacco, etc., Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese mint, mint, basil, etc.), strawberry, sweat potato, yam, aroid, etc., Flowers;

Ornamental foliage plants;

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruits, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, etc., Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew), etc.

The above crops also contain genetically modified crops.

The arthropod control agent of the present invention can be used as a mixture with or in combination with other insecticide, miticide, nematicide, fungicide, plant growth regulator, herbicide or synergist. Examples of the active ingredient of said insecticide, miticide, nematicide, fungicide, plant growth regulator, herbicide and synergist are shown below.

Active Ingredients of Insecticide (1) Organic Phosphorus Compounds acephate, Aluminium phosphide, butathiofos, cadusafos, chlorethoxyfos, chlorfenvinphos, chlorpyrifos, chlorpyrifos-methyl, cyanophos, diazinon, DCIP(dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, ozydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.

(2) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur, XMC, thiodicarb, xylylcarb, and aldicarb.

(3) Pyrethroid Compounds acrinathrin, allethrin, benfluthrin, beta-cyfluthrin, bifenthrin, cyclopropthrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS, 3RS; 1RS, 3SR)-2,2-dimethyl-3-prop-1-enylcyclopropanecarboxylate, 2,3,5,6-tetrafluoro-4-methylbenzyl (EZ)-(1RS, 3RS; 1RS, 3SR)-2,2-dimethyl-3-prop-1-enylcyclopropanecarboxylate, and 2,3,5,6-tetrafluoro-4-(methoxymethyl) benzyl (1RS, 3RS; 1RS, 3SR)-2,2-dimethyl-3-(2-methyl-1-propenyl)cyclopropanecarboxylate.

(4) Nereistoxin Compounds cartap, bensultap, thiocyclam, monosultap, and bisultap.

(5) Neonicotinoid Compounds imidacloprid, nitenpyram, acetamiprid, thiamethoxam, thiacloprid, dinotefuran, and clothianidin.

(6) Benzoyl Urea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole-Based Compounds acetoprole, ethiprole, fipronil, vaniliprole, pyriprole, and pyrafluprole.

(8) Bt Toxins

Living spores derived from *Bacillus thuringiensis* and produced crystalline toxins and mixtures thereof;

(9) Hydrazine Compounds chromafenozide, halofenozide, methoxyfenozide, and tebufenozide.

(10) Organic Chlorine Compounds aldrin, dieldrin, dienochlor, endosulfan, and methoxychlor.

(11) Other Active Ingredients of Insecticide machine oil, nicotine-sulfate; avermectin-B, bromopropylate, buprofezin, chlorphenapyr, cyantraniliprole, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, chlorantraniliprole, tralopyril, cyantraniliprole, Active Ingredients of Miticide acequinocyl, amitraz, benzoximate, bifenaate, bromopropylate, chinomethionat, chlorobenzilate, CPCBS (chlorfenson), clofentezine, cyflumetofen, dicofol, etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Active Ingredients of Nematicide

DCIP, fosthiazate, levamisol, methyisothiocyanate, morantel tartarate, and imicyafos.

Active Ingredients of Fungicide azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol; Cyclic amine fungicidal compounds such as fenpropimorph, tridemorph, and fenpropidin; Benzimidazole fungicidal compounds such as carbendezim, benomyl, thiabendazole, and thiophanate-methyl; procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhezamid; famoxadone; fenamidone; zoxamide; ethaboxam; amisulbrom; iprovalicarb; benthiavalicarb; cyazofamid;

mandipropamid; boscalid; penthiopyrad; metrafenone; fluopiran; bixafen; cyflufenamid; proquinazid; isotianil and tiadinil.

Active Ingredients of Herbicide (1) Phenoxy Fatty Acid Herbicidal Compounds
  2,4-PA, MCP, MCPB, phenothiol, mecoprop, fluroxypyr, triclopyr, clomeprop, and naproanilide.

(2) Benzoate Herbicidal Compounds
  2,3,6-TBA, dicamba, clopyralid, picloram, aminopyralid, quinclorac, and quinmerac.

(3) Urea Herbicidal Compounds
  diuron, linuron, chlortoluron, isoproturon, fluometuron, isouron, tebuthiuron, methabenzthiazuron, curnyluron, daimuron, and methyl-daimuron.

(4) Triazine Herbicidal Compounds
  atrazine, ametoryn, cyanazine, simazine, propazine, simetryn, dimethametryn,
prometryn, metribuzin, triaziflam, and indaziflam.

(5) Bipyridinium Herbicidal Compounds
  paraquat, and diquat.

(6) Hydroxybenzonitrile Herbicidal Compounds
  bromoxynil, and ioxynil.

(7) Dinitroaniline Herbicidal Compounds
  pendimethalin, prodiamine, and trifluralin.

(8) Organophosphorus Herbicidal Compounds
  amiprofos-methyl, butamifos, bensulide, piperophos, anilofos, glyphosate, glufosinate, glufosinate-P, and bialaphos.

(9) Carbamate Herbicidal Compounds
  di-allate, tri-allate, EPTC, butylate, benthiocarb, esprocarb, molinate, dimepiperate, swep, chlorpropham, phenmedipham, phenisopham, pyributicarb, and asulam.

(10) Acid Amide Herbicidal Compounds
  propanil, propyzamide, bromobutide, and etobenzanid.

(11) Chloroacetanilide Herbicidal Compounds
  acetochlor, alachlor, butachlor, dimethenamid, propachlor, metazachlor, metolachlor, pretilachlor, thenylchlor, and pethoxamid.

(12) Diphenyl Ether Herbicidal Compounds
  acifluorfen-sodium, bifenoz, oxyfluorfen, lactofen, fomesafen, chlomethoxynil, and aclonifen.

(13) Cyclic Imide Herbicidal Compounds
  oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.

(14) Pyrazole Herbicidal Compounds
  benzofenap, pyrazolate, pyrazoxyfen, topramezone, and pyrasulfotole.

(15) Triketone Herbicidal Compounds
  isoxaflutole, benzobicyclon, sulcotrione, mesotrione, tembotrione, and tefuryltrione.

(16) Aryloxyphenoxypropionate Herbicidal Compounds
  clodinafop-propargyl, cyhalofop-butyl, diclofop-methyl, fenoxaprop-ethyl, fluazifop-butyl, haloxyfop-methyl, and quizalofop-ethyl, metamifop.

(17) Trione Oxime Herbicidal Compounds
  alloxydim-sodium, sethoxydim, butroxydim, clethodim, cloproxydim, cycloxydim, tepraloxydim, tralkoxydim, and profoxydim.

(18) Sulfonyl Urea Herbicidal Compounds
  chlorsulfuron, sulfometuron-methyl, metsulfuron-methyl, chlorimuron-ethyl, tribenuron-methyl, triasulfuron, metsulfuron-methyl, thifensulfuron-methyl, pyrazosulfuron-ethyl, primisulfuron-methyl, nicosulfuron, amidosulfuron, cinosulfurorn, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.

(19) Imidazolinone Herbicidal Compounds
  imazamethabenz-methyl, imazamethapyr, imazamox, imazapyr, imazaquin, and imazethapyr.

(20) Sulfonamide Herbicidal Compounds
  flumetsulam, metosulam, diclosulam, florasulam, cloransulam-methyl, penozsulam, and pyroxsulam.

(21) Pyrimidinyloxybenzoate Herbicidal Compounds
  pyrithiobac-sodium, bispyribac-sodium, pyriminobac-methyl, pyribenzoxim, pyriftalid, and pyrimisulfan.

(22) Other Herbicidal Compounds
  bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of Synergist piperonyl butoxide, sesamex, sulfoxide, N-(2-ethylhexyl)-8,9,10-trinorborn-5-ene-2,3-dicarboximide (MGK 264), N-declyimidazole), WARF-antiresistant, TBPT, TPP, IBP, PSCP, Methyl iodide ($CH_3I$), t-phenylbutenone, diethylmaleate, DMC, FDMC, ETP, and ETN.

Active Ingredients of Plant Growth Regulator ethephon, chlormequat-chloride, mepiquat-chloride, Gibberellin A represented by Gibberellin A3, abscisic acid, Kinetin, benzyladenine, 1,3-diphenylurea, forchlorfenuron, thidiazuron, 4-oxo-4-(2-phenylethyl)aminobutyric acid, methyl 5-(trifluoromethyl)benzo[b]thiophene-2-carboxylate, and 5-(trifluoromethyl)benzo[b]thiophene-2-carboxylic acid.

EXAMPLES

Hereinbelow, the present invention will be further described in detail by production examples, formulation examples, test examples, and the like. However, the present invention is not limited to these examples.

First, production examples of the compound of the present invention are shown below.

Production Example 1

N-(Tetrahydrofuran-3-ylmethyl)-5-(pent-1-ynyl)-1,3,4-thiadiazole-2-carboxamide (400 mg, 1.43 mmol) and palladium-carbon (100 mg) were added to ethanol (20 mL). Under a hydrogen atmosphere, the mixture was stirred at room temperature for 6 hours, and then the insoluble matter was removed by filtration using celite. The resulting filtrate was concentrated under reduced pressure conditions, and the residue was applied to a silica gel column chromatography to obtain 330 mg of N-(tetrahydrofuran-3-ylmethyl)-5-pentyl-1,3,4-thiadiazole-2-carboxamide (hereinafter, referred to as Compound of Present Invention (1)) represented by the following formula.

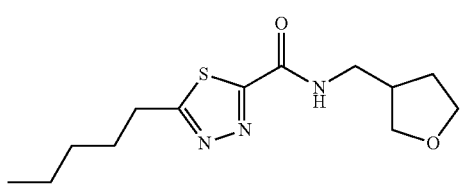

(1)

$^1$H-NMR (CDCl$_3$, TMS) δ(ppm): 0.91 (t, 3H), 1.32-1.45 (m, 4H), 1.66-1.74 (m, 18), 1.78-1.88 (m, 2H), 2.04-2.15 (m, 1H), 2.54-2.66 (m, 1H), 3.14 (t, 2H), 3.50 (t, 2H), 3.60 (dd, 1H), 3.74-3.81 (m, 1H), 3.84-3.96 (m, 2H), 7.45 (br s, 1H)

Production Example 2

N-(Tetrahydrofuran-3-ylmethyl)-5-(pent-1-ynyl)-1,3,4-thiadiazole-2-carboxamide (400 mg, 1.43 mmol), palladium-carbon (100 mg) and 1-hexene (1 mL) were added to ethanol (20 mL). Under a hydrogen atmosphere, the mixture was stirred at room temperature for 1 hour, and then the insoluble matter was removed by filtration using celite. The resulting filtrate was concentrated under reduced pressure, and the residue was applied to a silica gel column chromatography to obtain 300 mg of N-(tetrahydrofuran-3-ylmethyl)-5-(Z-pent-1-enyl)-1,3,4-thiadiazole-2-carboxamide (hereinafter, referred to as Compound of Present Invention (2)) represented by the following formula.

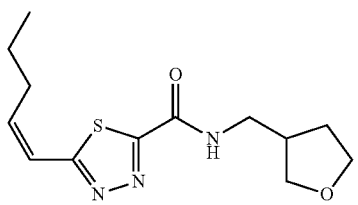

(2)

$^1$H-NMR (CDCl$_3$, TMS) δ(ppm): 0.98-1.03 (m, 3H), 1.57-1.75 (m, 4H), 2.06-2.16 (m, 1H), 2.46-2.54 (m, 1H), 2.56-2.66 (m, 1H), 3.47-3.54 (m, 2H), 3.58-3.63 (m, 1H), 3.74-3.81 (m, 1H), 3.84-3.96 (m, 2H), 6.28 (dt, 1H), 6.84 (dt, 1H), 7.46 (brs, 1H)

Production Example 3

1-Methyl-3-propyl-1H-pyrazole-5-carboxylic acid (1.68 g, 10 mmol), tetrahydrofuran-3-ylmethylamine hydrochloride (1.38 g, 10 mmol), triethylamine (1.01 g, 10 mmol) and 1-hydroxybenzotriazole (0.15 g, 1.0 mmol) were added to chloroform (amylene addition product) (60 mL). 1-Ethyl-3-(3-dimethylaminopropyl) carbodiimide hydrochloride (1.92 g, 10 mmol) was added to the mixture at room temperature, and the mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 2.02 g of N-(tetrahydrofuran-3-ylmethyl)-1-methyl-3-propyl-1H-pyrazole-5-carboxamide (hereinafter, referred to as Compound of Present Invention (3)) represented by the following formula.

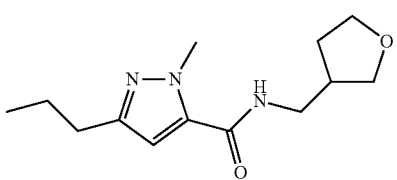

(3)

$^1$H-NMR (CDCl$_3$, TMS, δ(ppm)): 0.96 (3H, t), 1.64-1.68 (3H, m), 2.05-2.14 (1H, m), 2.56-2.58 (3H, m), 3.41-3.43 (2H, m), 3.61-3.63 (1H, m), 3.75-3.77 (1H, m), 3.82-3.84 (1H, m), 3.92-3.94 (1H, m), 4.11 (3H, s), 6.15 (1H, s), 6.26 (1H, s)

Production Example 4

1-Methyl-3-butyl-1H-pyrazole-5-carboxylic acid (1.82 g, 10 mmol), tetrahydrofuran-3-ylmethylamine hydrochloride (1.38 g, 10 mmol), triethylamine (1.01 g, 10 mmol) and 1-hydroxybenzotriazole (0.15 g, 1.0 mmol) were added to chloroform (amylene addition product) (60 mL). 1-Ethyl-3-(3-dimethylaminopropyl) carbodiimide hydrochloride (1.92 g, 10 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 2.31 g of N-(tetrahydrofuran-3-ylmethyl)-1-methyl-3-butyl-1H-pyrazole-5-carboxamide (hereinafter, referred to as Compound of Present Invention (4)) represented by the following formula.

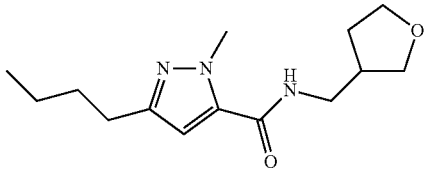

(4)

$^1$H-NMR (CDCl$_3$, TMS, δ(ppm)): 0.93 (3H, t), 1.35-1.39 (2H, m), 1.57-1.72 (3H, m), 2.05-2.14 (1H, m), 2.53-2.62 (3H, m), 3.42 (2H, t), 3.61-3.63 (1H, m), 3.74-3.78 (1H, m), 3.82-3.84 (1H, m), 3.92-3.94 (1H, m), 4.10 (3H, s), 6.17 (1H, br s), 6.26 (1H, s)

Production Example 5

1-Methyl-3-pentyl-1H-pyrazole-5-carboxylic acid (1.82 g, 10 mmol), tetrahydrofuran-3-ylmethylamine hydrochloride (1.38 g, 10 mmol), triethylamine (1.01 g, 10 mmol) and 1-hydroxybenzotriazole (0.15 g, 1.0 mmol) were added to chloroform (amylene addition product) (60 mL). 1-Ethyl-3-(3-dimethylaminopropyl) carbodiimide hydrochloride (1.92 g, 10 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 2.61 g of N-(tetrahydrofuran-3-ylmethyl)-1-methyl-3-pentyl-1H-pyrazole-5-carboxamide (hereinafter, referred to as Compound of Present Invention (5)) represented by the following formula.

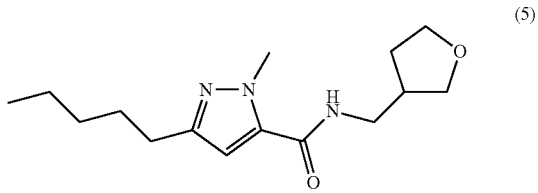 [SMILES: CCCCCc1cc(C(=O)NCC2CCOC2)n(C)n1]

(5)

¹H-NMR (CDCl₃, TMS, δ(ppm)): 0.90 (3H, t), 1.29-1.39 (3H, m), 1.59-1.72 (5H, m), 2.05-2.14 (1H, m), 2.53-2.62 (2H, m), 3.42 (2H, t), 3.61-3.63 (1H, m), 3.74-3.76 (1H, m), 3.79-3.85 (1H, m), 3.92-3.94 (1H, m), 4.11 (3H, s), 6.15 (1H, br s), 6.26 (1H, s)

Production Example 6

1-Butyl-5-methyl-1H-pyrazole-4-carboxylic acid (1.82 g, 10 mmol), tetrahydrofuran-3-ylmethylamine hydrochloride (1.38 g, 10 mmol), triethylamine (1.01 g, 10 mmol) and 1-hydroxybenzotriazole (0.15 g, 1.0 mmol) were added to chloroform (amylene addition product) (60 mL). 1-Ethyl-3-(3-dimethylaminopropyl) carbodiimide hydrochloride (1.92 g, 10 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 2.11 g of N-(tetrahydrofuran-3-ylmethyl)-1-butyl-5-methyl-1H-pyrazole-4-carboxamide (hereinafter, referred to as Compound of Present Invention (6)) represented by the following formula.

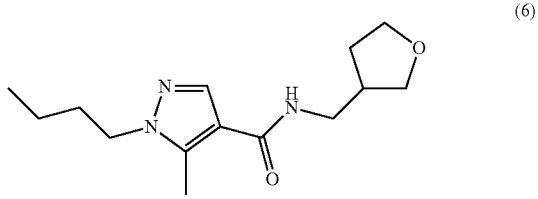 [SMILES: CCCCn1ncc(C(=O)NCC2CCOC2)c1C]

(6)

¹H-NMR (CDCl₃, TMS, δ(ppm)): 0.97 (3H, t), 1.33-1.37 (2H, m), 1.65-1.73 (1H, m), 1.77-1.81 (2H, m), 2.02-2.12 (1H, m), 2.28 (3H, s), 2.56-2.61 (1H, m), 3.40-3.45 (2H, m), 3.57-3.60 (1H, m), 3.73-3.79 (1H, m), 3.86-3.90 (2H, m), 4.00 (2H, t), 6.52 (1H, s), 6.96 (1H, br s)

Production Example 7

1-Methyl-5-propoxy-1H-pyrazole-3-carboxylic acid (1.82 g, 10 mmol), tetrahydrofuran-3-ylmethylamine hydrochloride (1.38 g, 10 mmol), triethylamine (1.01 g, 10 mmol) and 1-hydroxybenzotriazole (0.15 g, 1.0 mmol) were added to chloroform (amylene addition product) (60 mL). 1-Ethyl-3-(3-dimethylaminopropyl) carbodiimide hydrochloride (1.92 g, 10 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 1.62 g of N-(tetrahydrofuran-3-ylmethyl)-1-methyl-5-propoxy-1H-pyrazole-le-3-carboxamide (hereinafter, referred to as Compound of Present Invention (7)) represented by the following formula.

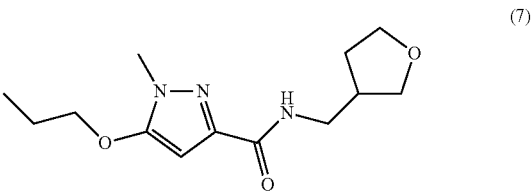 [SMILES: CCCOc1cc(C(=O)NCC2CCOC2)nn1C]

(7)

¹H-NMR (CDCl₃, TMS, δ(ppm)): 1.03 (3H, t), 1.66-1.71 (1H, m), 1.75-1.86 (2H, m), 2.05-2.08 (1H, m), 2.53-2.60 (1H, m), 3.39-3.45 (2H, m), 3.57-3.59 (1H, m), 3.65 (3H, s), 3.75-3.77 (1H, m), 3.86-3.90 (2H, m), 4.02 (2H, t), 6.04 (1H, s), 6.96 (1H, br s)

Production Example 8

1-Butyl-1H-pyrazole-3-carboxylic acid (0.82 g, 4.8 mmol), tetrahydrofuran-3-ylmethylamine hydrochloride (0.66 g, 4.8 mmol), triethylamine (0.48 g, 4.8 mmol) and 1-hydroxybenzotriazole (0.07 g, 0.48 mmol) were added to chloroform (amylene addition product) (30 mL). 1-Ethyl-3-(3-dimethylaminopropyl) carbodiimide hydrochloride (0.92 g, 4.8 mmol) was added to the mixture at room temperature, and the mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.86 g of N-(tetrahydrofuran-3-ylmethyl)-1-butyl-1H-pyrazole-3-carboxamide (hereinafter, referred to as Compound of Present Invention (8)) represented by the following formula.

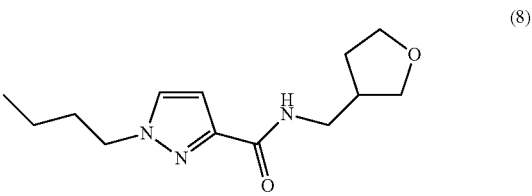 [SMILES: CCCCn1ccc(C(=O)NCC2CCOC2)n1]

(8)

¹H-NMR (CDCl₃, TMS, δ(ppm)): 0.93 (3H, t), 1.31-1.35 (2H, m), 1.68-1.70 (1H, m), 1.79-1.86 (2H, m), 2.05-2.14 (1H, m), 2.54-2.64 (1H, m), 3.44 (2H, t), 3.63 (1H, dd), 3.75-3.77 (1H, m), 3.81-3.86 (1H, m), 3.92-3.94 (1H, m), 4.55 (2H, t), 6.22 (1H, br s), 6.46 (1H, d), 7.46 (1H, d)

Production Example 9

1-Benzyl-1H-1,2,3-triazole-4-carboxylic acid (0.96 g, 4.7 mmol), tetrahydrofuran-3-ylmethylamine hydrochloride (0.71 g, 5.2 mmol), triethylamine (1.01 g, 10 mmol) and 1-hydroxybenzotriazole (0.08 g, 0.52 mmol) were added to chloroform (amylene addition product) (30 mL). 1-Ethyl-3-(3-dimethylaminopropyl) carbodiimide hydrochloride (1.00 g, 4.2 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.86 g of 1-benzyl-1H-1,2,3-triazole-4-carboxamide (hereinafter, referred to as Compound of Present Invention (9)) represented by the following formula.

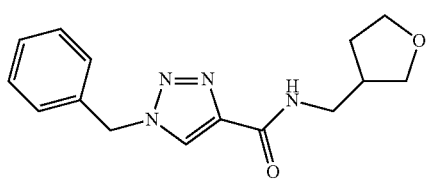

(9)

$^1$H-NMR (CDCl$_3$, TMS, δ(ppm)): 1.64-1.72 (1H, m), 2.03-2.11 (1H, m), 2.54-2.59 (1H, m), 3.46 (2H, dd), 3.58 (1H, dd), 3.75 (1H, q), 3.93-3.94 (2H, m), 5.55 (2H, s), 7.41-7.27 (5H, m), 7.97 (1H, s)

Production Example 10

5-Propylisoxazole-3-carboxylic acid (0.25 g, 1.6 mmol), tetrahydrofuran-3-ylmethyl amine hydrochloride (0.27 g, 1.9 mmol), triethylamine (0.19 g, 1.9 mmol) and 1-hydroxybenzotriazole (0.03 g, 0.19 mmol) were added to chloroform (amylene addition product) (10 mL). 1-Ethyl-3-(3-dimethylaminopropyl) carbodiimide hydrochloride (0.36 g, 1.9 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.10 g of N-(tetrahydrofuran-3-ylmethyl)-5-propylisoxazole-3-carboxamide (hereinafter, referred to as Compound of Present Invention (10)) represented by the following formula.

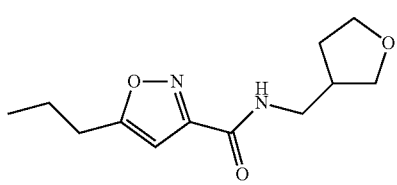

(10)

$^1$H-NMR (CDCl$_3$, TMS, δ(ppm)): 1.01 (3H, t), 1.65-1.82 (3H, m), 2.05-2.13 (1H, m), 2.54-2.64 (1H, m), 2.79 (2H, t), 3.41-3.52 (2H, m), 3.60-3.62 (1H, m), 3.76-3.96 (3H, m), 6.46 (1H, s), 7.04 (1H, br s)

Production Example 11

5-Butylisoxazole-3-carboxylic acid (0.50 g, 3.0 mmol), tetrahydrofuran-3-ylmethylamine hydrochloride (0.50 g, 3.6 mmol), triethylamine (0.36 g, 3.6 mmol) and 1-hydroxybenzotriazole (0.05 g, 0.36 mmol) were added to chloroform (amylene addition product) (20 mL). 1-Ethyl-3-(3-dimethylaminopropyl) carbodiimide hydrochloride (0.69 g, 3.6 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.28 g of N-(tetrahydrofuran-3-ylmethyl)-5-butylisoxazole-3-carboxamide (hereinafter, referred to as Compound of Present Invention (11)) represented by the following formula.

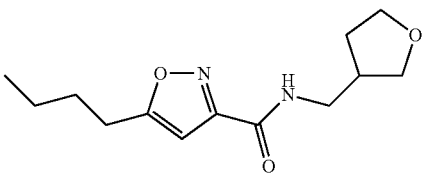

(11)

$^1$H-NMR (CDCl$_3$, TMS, δ(ppm)): 0.92 (3H, t), 1.34-1.36 (2H, m), 1.69-1.73 (3H, m), 2.08-2.10 (1H, m), 2.59-2.63 (1H, m), 2.77-2.79 (2H, m), 3.46-3.48 (2H, m), 3.62 (1H, dd), 3.79 (1H, dd), 3.86-3.97 (2H, m), 6.46 (1H, s), 7.10 (1H, br s)

Production Example 12

5-Pentylisoxazole-3-carboxylic acid (0.28 g, 1.5 mmol), tetrahydrofuran-3-ylmethylamine hydrochloride (0.25 g, 1.8 mmol), triethylamine (0.18 g, 1.8 mmol) and 1-hydroxybenzotriazole (0.03 g, 0.18 mmol) were added to chloroform (amylene addition product) (10 mL). 1-Ethyl-3-(3-dimethylaminopropyl) carbodiimide hydrochloride (0.35 g, 1.8 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.10 g of N-(tetrahydrofuran-3-ylmethyl)-5-pentylisoxazole-3-carboxamide (hereinafter, referred to as Compound of Present Invention (12)) represented by the following formula.

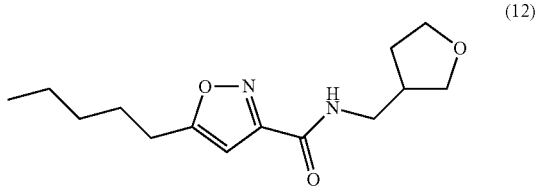 [SMILES: CCCCCc1cc(C(=O)NCC2CCOC2)no1]

(12)

$^1$H-NMR (CDCl$_3$, TMS, δ(ppm)): 0.96-0.89 (3H, m), 1.40-1.31 (4H, m) 1.77-1.65 (3H, m), 2.09 (1H, tt), 2.61 (1H, td), 2.84-2.76 (2H, t), 3.47 (2H, dt), 3.62 (1H, dd), 3.79 (1H, dd), 3.97-3.86 (2H, m), 6.46 (1H, s), 7.10 (1H, br s)

Production Example 13

5-Benzyloxymethylisoxazole-3-carboxylic acid (0.59 g, 2.5 mmol), tetrahydrofuran-3-ylmethylamine hydrochloride (0.39 g, 2.8 mmol), triethylamine (0.28 g, 2.8 mmol) and 1-hydroxybenzotriazole (0.04 g, 0.28 mmol) were added to chloroform (amylene addition product) (15 mL). 1-Ethyl-3-(3-dimethylaminopropyl) carbodiimide hydrochloride (0.54 g, 2.8 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.35 g of N-(tetrahydrofuran-3-ylmethyl)-5-benzyloxymethyl-isoxazole-3-carboxamide (hereinafter, referred to as Compound of Present Invention (13)) represented by the following formula.

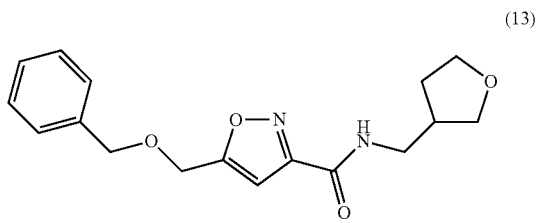 [SMILES: O=C(NCC1CCOC1)c1cc(COCc2ccccc2)on1]

(13)

$^1$H-NMR (CDCl$_3$, TMS, δ(ppm)): 1.66-1.69 (1H, m), 2.05-2.13 (1H, m), 2.53-2.63 (1H, m), 3.47-3.49 (2H, m), 3.58-3.60 (1H, m), 3.76-3.78 (1H, m), 3.84-3.95 (2H, m), 4.61 (2H, s), 4.65 (2H, s), 6.73 (1H, d), 6.95 (1H, br s), 7.31-7.40 (5H, m)

Production Example 14

5-Benzyloxymethylisoxazole-3-carboxylic acid (0.35 g, 1.5 mmol), tetrahydropyran-2-ylmethylamine (0.21 g, 1.8 mmol), and 1-hydroxybenzotriazole (0.02 g, 0.15 mmol) were added to chloroform (amylene addition product) (7.5 mL). 1-Ethyl-3-(3-dimethylaminopropyl) carbodiimide hydrochloride (0.35 g, 1.8 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.36 g of N-(tetrahydropyran-2-ylmethyl)-5-benzyloxymethylisoxazole-3-carboxamide (hereinafter, referred to as Compound of Present Invention (14)) represented by the following formula.

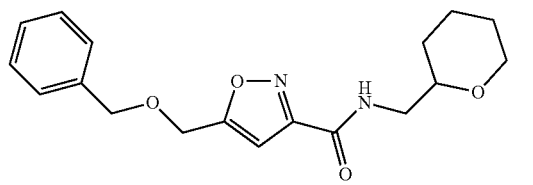

(14)

$^1$H-NMR (CDCl$_3$, TMS, δ(ppm)): 1.30-1.39 (1H, m), 1.45-1.70 (4H, m), 1.84-1.86 (1H, m), 3.23-3.26 (1H, m), 3.40-3.50 (2H, m), 3.68-3.71 (1H, m), 3.98-4.00 (1H, m), 4.60 (2H, s), 4.64 (2H, s), 6.72 (1H, s), 7.18 (1H, br s), 7.30-7.39 (5H, m)

Production Example 15

5-Benzyloxymethylisoxazole-3-carboxylic acid (0.35 g, 1.5 mmol), tetrahydropyran-4-ylmethylamine (0.21 g, 1.8 mmol), and 1-hydroxybenzotriazole (0.02 g, 0.15 mmol) were added to chloroform (amylene addition product) (7.5 mL). 1-Ethyl-3-(3-dimethylaminopropyl) carbodiimide hydrochloride (0.35 g, 1.8 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.36 g of N-(tetrahydropyran-4-ylmethyl)-5-benzyloxymethylisoxazole-3-carboxamide (hereinafter, referred to as Compound of Present Invention (15)) represented by the following formula.

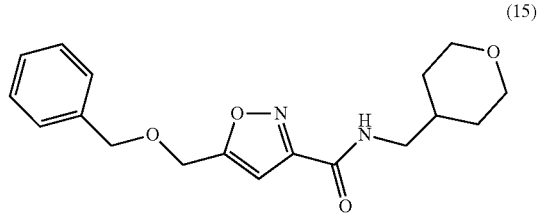 [SMILES: O=C(NCC1CCOCC1)c1cc(COCc2ccccc2)on1]

(15)

$^1$H-NMR (CDCl$_3$, TMS, δ(ppm)): 1.36-1.40 (2H, m), 1.64-1.67 (2H, m), 1.81-1.92 (1H, m), 3.35-3.40 (4H, m), 3.98-4.00 (2H, m), 4.62 (2H, s), 4.65 (2H, s), 6.73 (1H, s), 6.89 (1H, br s), 7.34-7.38 (5H, m)

Production Example 16

5-Benzyloxymethylisoxazole-3-carboxylic acid (0.35 g, 1.5 mmol), 1,3-dioxolanyl-2-ylmethylamine (0.19 g, 1.8 mmol), and 1-hydroxybenzotriazole (0.02 g, 0.15 mmol) were added to chloroform (amylene addition product) (3.5 mL). 1-Ethyl-3-(3-dimethylaminopropyl) carbodiimide hydrochloride (0.35 g, 15 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.44 g of N-(1,3-dioxolanyl-2-ylmethyl)-5-benzyloxymethylisoxazole-3-carboxamide (hereinafter, referred to as Compound of Present Invention (16)) represented by the following formula.

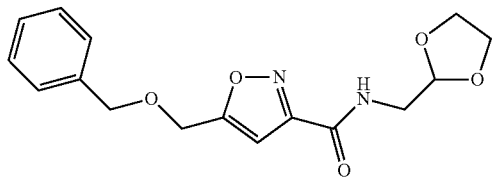

(16)

$^1$H-NMR (CDCl$_3$, TMS, δ(ppm)): 3.69-3.70 (2H, m), 3.88-3.96 (2H, m), 4.00-4.02 (2H, m), 4.60 (2H, s), 4.65 (2H, s), 5.07 (1H, td), 6.73 (1H, d), 7.03 (1H, s), 7.33-7.38 (5H, m)

Production Example 17

5-Benzyloxymethylisoxazole-3-carboxylic acid (0.35 g, 1.5 mmol), 2-(tetrahydrofuran-2-yl)ethylamine (0.21 g, 1.8 mmol), and 1-hydroxybenzotriazole (0.02 g, 0.15 mmol) were added to chloroform (amylene addition product) (7.5 mL). 1-Ethyl-3-(3-dimethylaminopropyl) carbodiimide hydrochloride (0.35 g, 1.8 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.34 g of N-[2-(tetrahydrofuran-2-yl)ethyl]-5-benzyloxymethylisoxazole-3-carboxamide (hereinafter, referred to as Compound of Present Invention (17)) represented by the following formula.

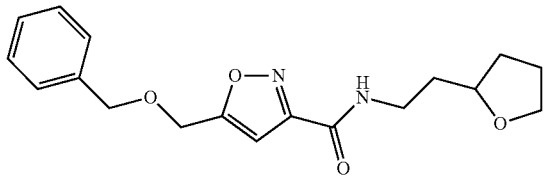

(17)

$^1$H-NMR (CDCl$_3$, TMS, δ(ppm)): 1.50-1.55 (1H, m), 1.69-1.78 (1H, m), 1.85-1.94 (3H, m), 2.00-2.08 (1H, m), 3.43-3.48 (1H, m), 3.66-3.79 (2H, m), 3.92-3.96 (2H, m), 4.60 (2H, s), 4.64 (2H, s), 6.71 (1H, s), 7.29-7.39 (5H, m), 7.53 (1H, br s)

Production Example 18

5-Benzyloxymethylisoxazole-3-carboxylic acid (0.35 g, 1.5 mmol), 2-(tetrahydropyran-4-yl)ethylamine (0.23 g, 1.8 mmol), and 1-hydroxybenzotriazole (0.02 g, 0.15 mmol) were added to chloroform (amylene addition product) (7.5 mL). 1-Ethyl-3-(3-dimethylaminopropyl) carbodiimide hydrochloride (0.35 g, 1.8 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.43 g of N-[2-(tetrahydropyran-4-yl)ethyl]-5-benzyloxymethylisoxazole-3-carboxamide (hereinafter, referred to as Compound of Present Invention (18)) represented by the following formula.

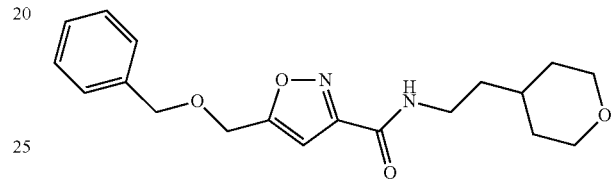

(18)

$^1$H-NMR (CDCl$_3$, TMS, δ(ppm)): 1.31-1.34 (2H, m), 1.57-1.64 (5H, m), 3.36-3.39 (2H, m), 3.48-3.50 (2H, m), 3.95 (2H, dd), 4.61 (2H, s), 4.64 (2H, s), 6.72 (1H, s), 6.83 (1H, s), 7.30-7.39 (5H, m)

Production Example 19

5-Cyclopentyloxymethylisoxazole-3-carboxylic acid (0.26 g, 1.2 mmol), tetrahydrofuran-3-ylmethylamine hydrochloride (0.20 g, 1.5 mmol), triethylamine (0.15 g, 1.5 mmol) and 1-hydroxybenzotriazole (0.02 g, 0.15 mmol) were added to chloroform (amylene addition product) (15 mL). 1-Ethyl-3-(3-dimethylaminopropyl) carbodiimide hydrochloride (0.28 g, 1.5 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.10 g of N-(tetrahydrofuran-3-ylmethyl)-5-cyclopentyloxymethylisoxazole-3-carboxamide (hereinafter, referred to as Compound of Present Invention (19)) represented by the following formula.

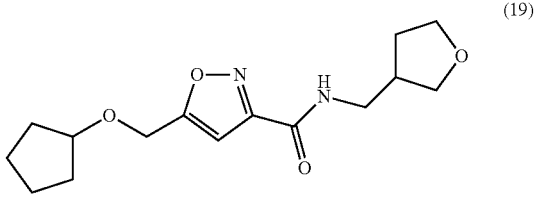 [SMILES: O=C(NCC1CCOC1)c1cc(COC2CCCC2)on1]

(19)

$^1$H-NMR(CDCl$_3$, TMS, δ(ppm)): 1.54-1.59 (2H, m), 1.68-1.72 (7H, m), 2.04-2.13 (1H, m), 2.56-2.58 (1H, m), 3.46 (2H, t), 3.57-3.60 (1H, m), 3.75-3.78 (1H, m), 3.84-3.94 (2H, m), 4.03-4.04 (1H, m), 4.58 (2H, s), 6.69 (1H, s), 6.93 (1H, br s)

Production Example 20

5-(2-Naphthylmethoxymethyl)isoxazole-3-carboxylic acid (0.57 g, 2.0 mmol), tetrahydrofuran-3-ylmethylamine hydrochloride (0.33 g, 2.4 mmol), triethylamine (0.24 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.37 g of N-(tetrahydrofuran-3-ylmethyl)-5-(2-naphthylmethoxymethyl)isoxazole-3-carboxamide (hereinafter, referred to as Compound of Present Invention (20)) represented by the following formula.

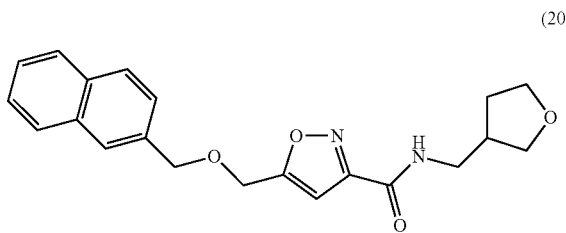

(20)

$^1$H-NMR (CDCl$_3$, TMS, δ(ppm)): 1.67-1.70 (1H, m), 2.05-2.14 (1H, m), 2.56-2.60 (1H, m), 3.47 (2H, t), 3.58-3.60 (1H, m), 3.76-3.78 (1H, m), 3.84-3.95 (2H, m), 4.69 (2H, s), 4.77 (2H, s), 6.76 (1H, s), 6.94 (1H, br s), 7.46-7.53 (3H, m), 7.80-7.87 (4H, m)

Production Example 21

5-(2-Naphthylmethoxymethyl)isoxazole-3-carboxylic acid (0.53 g, 2.0 mmol), tetrahydropyran-4-ylmethylamine (0.28 g, 2.4 mmol), and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.74 g of N-(tetrahydropyran-4-ylmethyl)-5-(2-naphthylmethoxymethyl)isoxazole-3-carboxamide (hereinafter, referred to as Compound of Present Invention (21)) represented by the following formula.

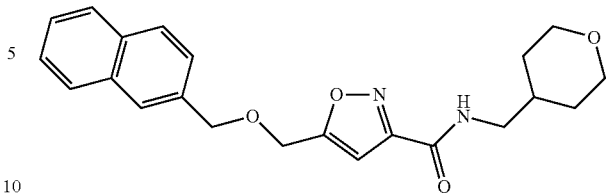

(21)

$^1$H-NMR (CDCl$_3$, TMS, δ(ppm)): 1.35-1.41 (2H, m), 1.65-1.69 (2H, m), 1.85-1.88 (1H, m), 3.34-3.42 (4H, m), 3.99 (2H, dd), 4.69 (2H, d), 4.77 (2H, s), 6.75 (1H, s), 6.88 (1H, br s), 7.46-7.52 (3H, m), 7.80-7.87 (4H, m)

Production Example 22

5-(3-Phenylpropyl)isoxazole-3-carboxylic acid (0.46 g, 2.0 mmol), tetrahydrofuran-3-ylmethylamine hydrochloride (0.33 g, 2.4 mmol), triethylamine (0.24 g, 2.4 mmol) and 1-hydroxybenzotriazole (0.04 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.49 g of N-(tetrahydrofuran-3-ylmethyl)-5-(3-phenylpropyl)isoxazole-3-carboxamide (hereinafter, referred to as Compound of Present Invention (22)) represented by the following formula.

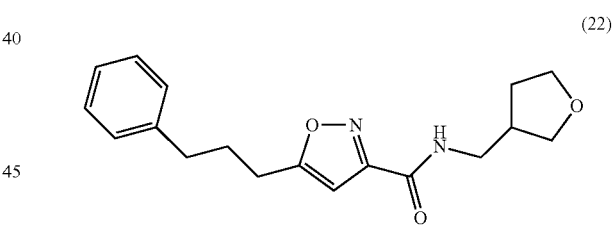

(22)

$^1$H-NMR (CDCl$_3$, TMS, δ(ppm)): 1.62-1.72 (1H, m), 2.02-2.13 (3H, m), 2.52-2.62 (1H, m), 2.69 (2H, t), 2.80 (2H, t), 3.44-3.47 (2H, m), 3.57-3.60 (1H, m), 3.75-3.78 (1H, m), 3.84-3.94 (2H, m), 6.46 (1H, s), 6.93 (1H, br s), 7.18-7.22 (3H, m), 7.29-7.32 (2H, m)

Production Example 23

5-Phenyloxymethylisoxazole-3-carboxylic acid (0.31 g, 1.4 mmol), tetrahydrofuran-3-ylmethylamine hydrochloride (0.24 g, 1.7 mmol), triethylamine (0.17 g, 1.7 mmol) and 1-hydroxybenzotriazole (0.02 g, 0.17 mmol) were added to chloroform (amylene addition product) (3 mL). 1-Ethyl-3-(3-dimethylaminopropyl) carbodiimide hydrochloride (0.33 g, 1.7 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.15 g of N-(tetrahydrofuran-3-ylmethyl)-5-phenyloxymethyl-isoxazole-3-carboxamide (hereinafter, referred to as Compound of Present Invention (23)) represented by the following formula.

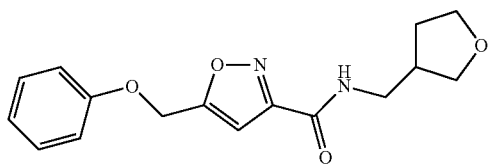

(23)

¹H-NMR (CDCl₃, TMS, δ(ppm)): 1.66-1.69 (1H, m), 2.06-2.14 (1H, m), 2.56-2.60 (1H, m), 3.46 (2H, t), 3.60 (1H, dd), 3.76-3.78 (1H, m), 3.85-3.87 (1H, m), 3.91-3.93 (1H, m), 5.20 (2H, s), 6.80 (1H, s), 6.94-6.97 (3H, m), 7.00-7.05 (1H, m), 7.29-7.34 (2H, m)

Production Example 24

5-(2-Phenylethyl)isoxazole-3-carboxylic acid (0.43 g, 2.0 mmol), tetrahydrofuran-3-ylmethylamine hydrochloride (0.33 g, 2.4 mmol), triethylamine (0.24 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.15 g of N-(tetrahydrofuran-3-ylmethyl)-5-(2-phenylethyl)isoxazole-3-carboxamide (hereinafter, referred to as Compound of Present Invention (24)) represented by the following formula.

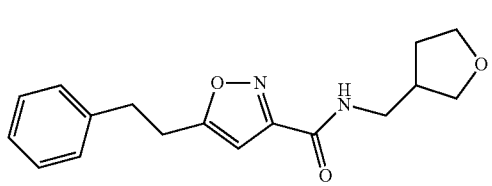

(24)

¹H-NMR (CDCl₃, TMS, δ(ppm)): 1.65-1.69 (1H, m), 2.04-2.13 (1H, m), 2.53-2.60 (1H, m), 3.01-3.05 (2H, m), 3.10-3.14 (2H, m), 3.43-3.47 (2H, m), 3.57-3.59 (1H, m), 3.75-3.78 (1H, m), 3.85-3.87 (1H, m), 3.90-3.92 (1H, m), 6.41 (1H, s), 6.91 (1H, br s), 7.18-7.19 (2H, m), 7.22-7.24 (1H, m), 7.29-7.31 (2H, m)

Production Example 25

5-(2-Phenylethyl)oxymethylisoxazole-3-carboxylic acid (0.50 g, 2.0 mmol), tetrahydrofuran-3-ylmethylamine hydrochloride (0.33 g, 2.4 mmol), triethylamine (0.24 g, 2.4 mmol) and 1-hydroxybenzotriazole (0.04 g, 0.24 mmol) were added to chloroform (amylene addition product) (5 mL). 1-Ethyl-3-(3-dimethylaminopropyl) carbodiinmide hydrochloride (0.46 g, 2.4 mmol) was added to the mixture at room temperature, then the mixture was stirred overnight and concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.36 g of N-(tetrahydrofuran-3-ylmethyl)-5-(2-phenylethyl)oxymethylisoxazole-3-carboxamide (hereinafter, referred to as Compound of Present Invention (25)) represented by the following formula.

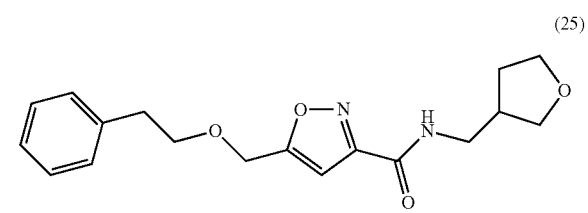 [SMILES: O=C(NCC1CCOC1)c1cc(COCCc2ccccc2)on1]

(25)

¹H-NMR (CDCl₃, TMS, δ(ppm)): 1.65-1.69 (1H, m), 2.08-2.11 (1H, m), 2.54-2.61 (1H, m), 2.92 (2H, t), 3.47 (2H, dt), 3.59 (1H, dd), 3.75-3.77 (3H, m), 3.84-3.94 (2H, m), 4.62 (2H, d), 6.64 (1H, s), 6.92 (1H, br s), 7.21-7.24 (3H, m), 7.29-7.31 (2H, m)

Production Example 26

5-Benzylisoxazole-3-carboxylic acid (0.27 g, 1.3 mmol), tetrahydrofuran-3-ylmethylamine hydrochloride (0.22 g, 1.6 mmol), triethylamine (0.16 g, 1.6 mmol) and 1-hydroxybenzotriazole (0.02 g, 0.16 mmol) were added to chloroform (amylene addition product) (3 mL). 1-Ethyl-3-(3-dimethylaminopropyl) carbodiimide hydrochloride (0.31 g, 1.6 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.32 g of N-(tetrahydrofuran-3-ylmethyl)-5-benzylisoxazole-3-carboxamide (hereinafter, referred to as Compound of Present Invention (26)) represented by the following formula.

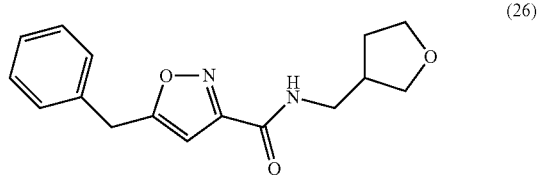 [SMILES: O=C(NCC1CCOC1)c1cc(Cc2ccccc2)on1]

(26)

¹H-NMR (CDCl₃, TMS, δ(ppm)): 1.63-1.68 (1H, m), 2.03-2.11 (1H, m), 2.52-2.59 (1H, m), 3.44 (2H, dd), 3.57 (1H, dd), 3.74-3.77 (1H, m), 3.82-3.93 (2H, m), 4.12 (2H, s), 6.39 (1H, s), 6.90 (18, br s), 7.24-7.37 (5H, m)

Production Example 27

5-(1-Naphthylmethoxymethyl)isoxazole-3-carboxylic acid (0.46 g, 1.6 mmol), tetrahydrofuran-3-ylmethylamine hydrochloride (0.26 g, 1.9 mmol), triethylamine (0.19 g, 1.9 mmol) and 1-hydroxybenzotriazole (0.02 g, 0.19 mmol) were added to chloroform (amylene addition product) (3 mL). 1-Ethyl-3-(3-dimethylaminopropyl) carbodiimide hydrochloride (0.37 g, 1.9 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydrofuran-3-ylmethyl)-5-(1-naphthylmethoxymethyl)isoxazole-3-carboxamide (hereinafter, referred to as Compound of Present Invention (27)) represented by the following formula.

(27)

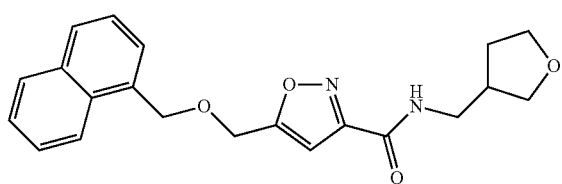

$^1$H-NMR (CDCl$_3$, TMS, δ(ppm)): 1.66-1.69 (1H, m), 2.04-2.13 (1H, m), 2.53-2.63 (1H, m), 3.46 (2H, t), 3.58-3.60 (1H, m), 3.75-3.79 (1H, m), 3.84-3.94 (2H, m), 4.68 (2H, s), 5.06 (2H, s), 6.72 (1H, s), 6.95 (1H, br s), 7.43-7.58 (4H, m), 7.84-7.89 (2H, m), 8.11 (1H, d)

Production Example 28

5-[1-(2-Naphthyl)ethyl]oxymethylisoxazole-3-carboxylic acid (0.59 g, 2.0 mmol), tetrahydrofuran-3-ylmethylamine hydrochloride (0.33 g, 2.4 mmol), triethylamine (0.24 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.42 g of N-(tetrahydrofuran-3-ylmethyl)-5-[1-(2-naphthyl)ethyl]oxymethylisoxazole-3-carboxamide (hereinafter, referred to as Compound of Present Invention (28)) represented by the following formula.

(28)

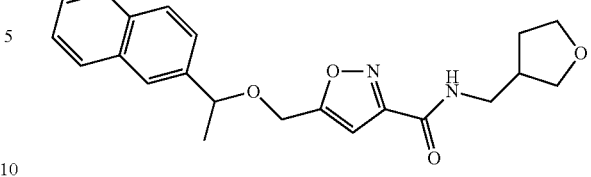

$^1$H-NMR (CDCl$_3$, TMS, δ(ppm)): 1.57 (3H, d), 1.66-1.69 (1H, m), 2.04-2.13 (1H, m), 2.56-2.61 (1H, m), 3.46 (2H, t), 3.59 (1H, dd), 3.77 (1H, dd), 3.84-3.95 (2H, m), 4.49 (2H, dd), 4.70 (1H, q), 6.69 (1H, s), 6.93 (1H, br s), 7.48-7.52 (3H, m), 7.76 (1H, s), 7.84-7.89 (3H, m)

Production Example 29

5-(4-Methoxymethyl-2,3,5,6-tetrafluorobenzyl)oxymethylisoxazole-3-carboxylic acid (0.20 g, 0.6 mmol), tetrahydrofuran-3-ylmethylamine hydrochloride (0.10 g, 0.9 mmol), triethylamine (0.07 g, 0.7 mmol) and 1-hydroxybenzotriazole (0.01 g, 0.07 mmol) were added to chloroform (amylene addition product) (2 mL). 1-Ethyl-3-(3-dimethylaminopropyl) carbodiimide hydrochloride (0.13 g, 0.7 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.12 g of N-(tetrahydrofuran-3-ylmethyl)-5-(4-methoxymethyl-2,3,5,6-tetrafluorobenzyl)oxymethylisoxazole-3-carboxamide (hereinafter, referred to as Compound of Present Invention (29)) represented by the following formula.

(29)

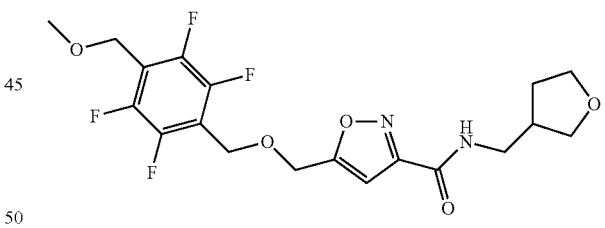

$^1$H-NMR (CDCl$_3$, TMS, δ(ppm)): 1.63-1.68 (1H, m), 2.03-2.12 (1H, m), 2.51-2.61 (1H, m), 3.39 (3H, s), 3.45 (2H, t), 3.58 (1H, dd), 3.75 (1H, dd), 3.83-3.85 (1H, m), 3.89-3.91 (1H, m), 4.57 (2H, t), 4.68 (2H, s), 4.71 (2H, t), 6.74 (1H, s), 6.94 (1H, br s)

Production Example 30

5-Benzyloxymethylisoxazole-3-carboxylic acid (0.35 g, 1.5 mmol), 2-(tetrahydrofuran-3-yl)ethylamine hydrochloride (0.27 g, 1.8 mmol), and 1-hydroxybenzotriazole (0.02 g, 0.15 mmol) were added to chloroform (amylene addition product) (7.5 mL). 1-Ethyl-3-(3-dimethylaminopropyl) carbodiimide hydrochloride (0.35 g, 1.8 mmol) was added to the mixture at room temperature, and the mixture was stirred overnight and then concentrated under reduced pressure.

Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.34 g of N-[2-(tetrahydrofuran-3-yl)ethyl]-5-benzyloxymethylisoxazole-3-carboxamide (hereinafter, referred to as Compound of Present Invention (30)) represented by the following formula.

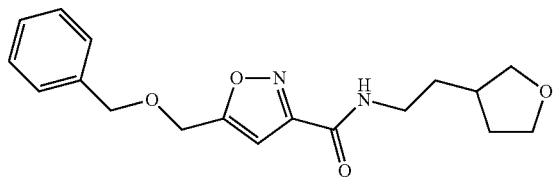

(30)

$^1$H-NMR (CDCl$_3$, TMS, δ(ppm)): 1.53-1.60 (1H, m), 1.64-1.78 (2H, m), 2.05-2.15 (1H, m), 2.21-2.32 (1H, m), 3.39 (1H, t), 3.43-3.54 (2H, m), 3.76 (1H, q), 3.86-3.89 (1H, m), 3.94 (1H, t), 4.61 (2H, s), 4.65 (2H, s), 6.72 (1H, s), 6.85 (1H, brs), 7.32-7.37 (5H, m)

Production Example 31

5-Benzyloxymethylisoxazole-3-carboxylic acid (0.35 g, 1.5 mmol), (1,4-dioxan-2-yl)methylamine (0.21 g, 1.8 mmol), and 1-hydroxybenzotriazole (0.02 g, 0.15 mmol) were added to chloroform (amylene addition product) (7.5 mL). 1-Ethyl-3-(3-dimethylaminopropyl) carbodiimide hydrochloride (0.35 g, 1.8 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.34 g of N-[1,4-dioxan-2-yl)methyl]-5-benzyloxymethyl isoxazole-3-carboxamide (hereinafter, referred to as Compound of Present Invention (31)) represented by the following formula.

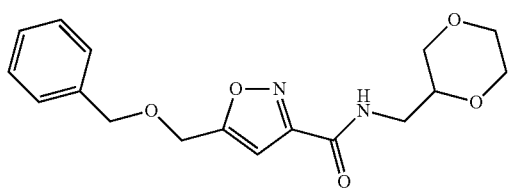

(31)

$^1$H-NMR (CDCl$_3$, TMS, δ(ppm)): 3.31-3.40 (2H, m), 3.57-3.66 (2H, m), 3.70-3.83 (5H, m), 4.61 (2H, s), 4.65 (2H, s), 6.73 (1H, t), 7.14 (1H, br s), 7.30-7.40 (5H, m)

Production Example 32

5-Benzyloxymethylisoxazole-3-carboxylic acid (0.30 g, 1.3 mmol), tetrahydrofuran-2-ylmethylamine (0.16 g, 1.5 mmol), and 1-hydroxybenzotriazole (0.02 g, 0.01 mmol) were added to chloroform (amylene addition product) (3 mL). 1-Ethyl-3-(3-dimethylaminopropyl) carbodiimide hydrochloride (0.30 g, 1.5 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.33 g of N-(tetrahydrofuran-2-ylmethyl)-5-benzyloxymethylisoxazole-3-carboxamide (hereinafter, referred to as Compound of Present Invention (32)) represented by the following formula.

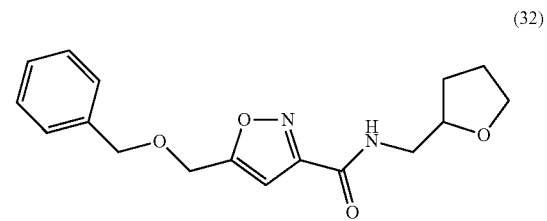 [SMILES: O=C(NCC1CCCO1)c1cc(COCc2ccccc2)on1]

(32)

$^1$H-NMR (CDCl$_3$, TMS, δ(ppm)): 1.59-1.62 (1H, m), 1.88-1.95 (2H, m), 1.99-2.01 (1H, m), 3.40-3.43 (1H, m), 3.68-3.71 (1H, m), 3.74-3.80 (1H, m), 3.88-3.91 (1H, m), 4.03-4.08 (1H, m), 4.60 (2H, s), 4.64 (2H, s), 6.72 (1H, s), 7.13 (1H, br s), 7.30-7.39 (5H, m)

Production Example 33

5-Benzyloxymethylisoxazole-3-carboxylic acid (0.24 g, 1.0 mmol), (R)-tetrahydrofuran-3-ylmethylamine (0.13 g, 1.2 mmol), and 1-hydroxybenzotriazole (0.01 g, 0.1 mmol) were added to chloroform (amylene addition product) (2.5 mL). 1-Ethyl-3-(3-dimethylaminopropyl) carbodiimide hydrochloride (0.24 g, 1.2 mmol) was added to the mixture at room temperature, and the mixture was stirred overnight. Then, dilute hydrochloric acid was added thereto, and the mixture was extracted twice with chloroform. The organic layer was passed through a short column of silica gel to remove impurities, and then concentrated under reduced pressure. The residue was applied to a silica gel column chromatography to obtain 0.26 g of N—[(R)-tetrahydrofuran-3-ylmethyl]-5-benzyloxymethylisoxazole-3-carboxamide (hereinafter, referred to as Compound of Present Invention (33)) represented by the following formula.

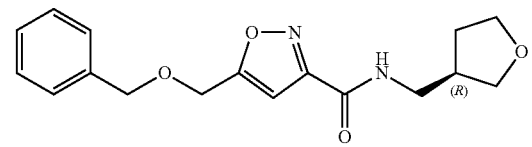

(33)

$^1$H-NMR (CDCl$_3$, TMS, δ(ppm)): 1.63-1.72 (1H, m), 2.04-2.13 (1H, m), 2.53-2.63 (1H, m), 3.47-3.49 (2H, m), 3.57-3.61 (1H, m), 3.74-3.80 (1H, m), 3.84-3.94 (2H, m), 4.61 (2H, s), 4.65 (2H, s), 6.73 (1H, s), 6.99 (1H, br s), 7.31-7.40 (5H, m)

Production Example 34

5-Benzyloxymethylisoxazole-3-carboxylic acid (0.24 g, 1.0 mmol), (S)-tetrahydrofuran-3-ylmethylamine (0.13 g, 1.2 mmol), and 1-hydroxybenzotriazole (0.01 g, 0.1 mmol) were added to chloroform (amylene addition product) (2.5 mL). 1-Ethyl-3-(3-dimethylaminopropyl) carbodiimide hydrochloride (0.24 g, 1.2 mmol) was added to the mixture at room temperature, and the mixture was stirred overnight. Then, dilute hydrochloric acid was added thereto, and the mixture was extracted twice with chloroform. The organic layer was passed through a short column of silica gel to remove impurities, and then concentrated under reduced pressure. The residue was applied to a silica gel column chromatography to obtain 0.23 g of N—[(S)-tetrahydrofuran-3-ylmethyl]-5-benzyloxymethylisoxazole-3-carboxamide (hereinafter, referred to as Compound of Present Invention (34)) represented by the following formula.

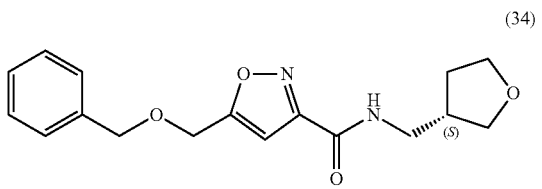

(34)

¹H-NMR (CDCl₃, TMS, (ppm)): 1.63-1.72 (1H, m), 2.05-2.13 (1H, m), 2.53-2.63 (1H, m), 3.45-3.48 (2H, m), 3.57-3.61 (1H, m), 3.74-3.80 (1H, m), 3.84-3.94 (2H, m), 4.61 (2H, s), 4.65 (2H, s), 6.73 (1H, s), 6.98 (1H, br s), 7.31-7.40 (5H, m)

Production Example 35

5-Benzyloxymethylisoxazole-3-carboxylic acid (0.24 g, 1.0 mmol), 1,3-dioxolan-4-ylmethylamine (0.13 g, 1.2 mmol), and 1-hydroxybenzotriazole (0.01 g, 0.1 mmol) were added to chloroform (amylene addition product) (2.5 mL). 1-Ethyl-3-(3-dimethylaminopropyl) carbodiimide hydrochloride (0.24 g, 1.2 mmol) was added to the mixture at room temperature, and the mixture was stirred overnight. Then, dilute hydrochloric acid was added thereto, and the mixture was extracted twice with chloroform. The organic layer was passed through a short column of silica gel to remove impurities, and then concentrated under reduced pressure. The residue was applied to a silica gel column chromatography to obtain 0.22 g of N-[4-(1,3-dioxolyl) methyl]-5-benzyloxymethylisoxazole-3-carboxamide (hereinafter, referred to as Compound of Present Invention (35)) represented by the following formula.

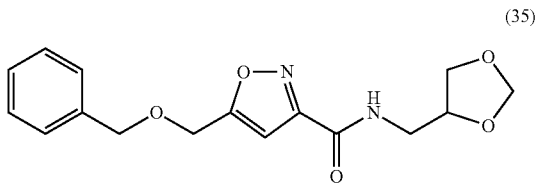 [SMILES: O=C(NCC1COCO1)c1cc(COCc2ccccc2)on1]

(35)

¹H-NMR (CDCl₃, TMS, δ(ppm)): 4.00 (4H, s), 4.13-4.16 (1H, m), 4.61 (2H, s), 4.66 (2H, s), 4.80 (1H, d), 5.02 (1H, d), 6.73 (1H, s), 7.31-7.40 (5H, m), 7.62 (1H, br s)

Production Example 36

5-Benzyloxymethylisoxazole-3-carboxylic acid (0.24 g, 1.0 mmol), (3-methyltetrahydrofuran-3-yl)methylamine (0.14 g, 1.2 mmol), and 1-hydroxybenzotriazole (0.01 g, 0.1 mmol) were added to chloroform (amylene addition product) (2.5 mL). 1-Ethyl-3-(3-dimethylaminopropyl) carbodiimide hydrochloride (0.24 g, 1.2 mmol) was added to the mixture at room temperature, and the mixture was stirred overnight. Then, dilute hydrochloric acid was added thereto, and the mixture was extracted twice with chloroform. The organic layer was passed through a short column of silica gel to remove impurities, and then concentrated under reduced pressure. The residue was applied to a silica gel column chromatography to obtain 0.31 g of N-(3-methyltetrahydrofuran-3-ylmethyl)-5-benzyloxymethylisoxazole-3-carboxamide (hereinafter, referred to as Compound of Present Invention (36)) represented by the following formula.

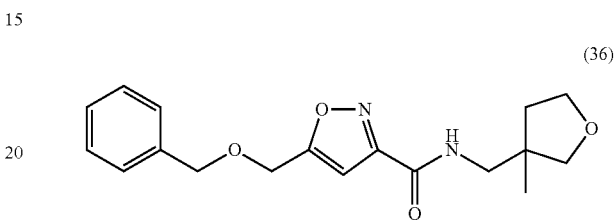

(36)

¹H-NMR (CDCl₃, TMS, δ(ppm)): 1.17 (3H, s), 1.67-1.74 (1H, m), 1.86-1.93 (1H, m), 3.45 (1H, d), 3.46-3.48 (2H, m), 3.70 (1H, d), 3.85-3.91 (1H, m), 3.94-3.99 (1H, m), 4.61 (2H, s), 4.65 (2H, s), 6.73 (1H, s), 7.05 (1H, brs), 7.31-7.40 (5H, m)

Production Example 37

5-Benzyloxymethylisoxazole-3-carboxylic acid (0.15 g, 0.65 mmol), tetrahydropyran-3-ylmethylamine (0.09 g, 0.78 mmol), and 1-hydroxybenzotriazole (0.008 g, 0.06 mmol) were added to chloroform (amylene addition product) (1.5 mL). 1-Ethyl-3-(3-dimethylaminopropyl) carbodiimide hydrochloride (0.15 g, 0.78 mmol) was added to the mixture at room temperature, and the mixture was stirred at room temperature overnight. Then, dilute hydrochloric acid was added thereto, and the mixture was extracted twice with chloroform. The organic layer was passed through a short column of silica gel to remove impurities, and then concentrated under reduced pressure. The residue was applied to a silica gel column chromatography to obtain 0.19 g of N-(tetrahydropyran-3-ylmethyl)-5-benzyloxymethylisoxazole-3-carboxamide (hereinafter, referred to as Compound of Present Invention (37)) represented by the following formula.

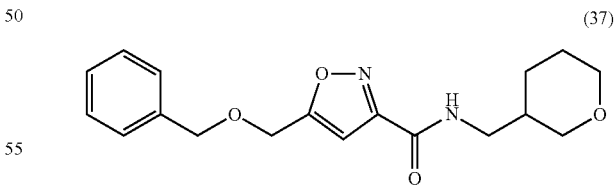

(37)

¹H-NMR (CDCl₃, TMS, δ(ppm)): 1.28-1.38 (1H, m), 1.55-1.71 (2H, m), 1.86-1.98 (2H, m), 3.23-3.28 (1H, m), 3.35 (2H, t), 3.41-3.47 (1H, m), 3.82-3.86 (1H, m), 3.88-3.92 (1H, m), 4.61 (2H, s), 4.65 (2H, s), 6.72 (1H, d), 6.86 (1H, brs), 7.30-7.40 (5H, m)

Production Example 38

5-Benzyloxymethylisoxazole-3-carboxylic acid (0.24 g, 1.0 mmol), 5-ethyl-1,3-dioxane-5-ylmethylamine (0.45 g, 1.2 mmol), and 1-hydroxybenzotriazole (0.01 g, 0.1 mmol) were added to chloroform (amylene addition product) (2.5 mL). 1-Ethyl-3-(3-dimethylaminopropyl) carbodiimide hydrochloride (0.24 g, 1.2 mmol) was added to the mixture at room temperature, and the mixture was stirred overnight. Then, dilute hydrochloric acid was added thereto, and the mixture was extracted twice with chloroform. The organic layer was passed through a short column of silica gel to remove impurities, and then concentrated under reduced pressure. The residue was applied to a silica gel column chromatography to obtain 0.26 g of N-[5-ethyl-5-(1,3-dioxanylmethyl)]-5-benzyloxymethylisoxazole-3-carboxamide (hereinafter, referred to as Compound of Present Invention (38)) represented by the following formula.

(38)

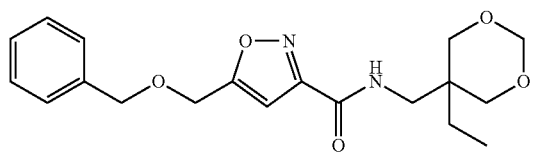

¹H-NMR (CDCl₃, TMS, δ(ppm)): 0.91 (3H, t), 1.29 (2H, q), 3.55 (2H, d), 3.70 (2H, d), 3.84 (2H, d), 4.61 (2H, s), 4.65 (2H, s), 4.67 (1H, d), 5.01 (1H, d), 6.73 (1H, s), 7.11 (1H, br s), 7.30-7.40 (5H, m)

Production Example 39

5-Benzyloxymethylisoxazole-3-carboxylic acid (0.24 g, 1.0 mmol), 3-aminomethylthiolane-1,1-dione (0.18 g, 1.2 mmol), and 1-hydroxybenzotriazole (0.01 g, 0.1 mmol) were added to chloroform (amylene addition product) (2.5 mL). 1-Ethyl-3-(3-dimethylaminopropyl) carbodiimide hydrochloride (0.24 g, 1.2 mmol) was added to the mixture at room temperature, and the mixture was stirred overnight. Then, dilute hydrochloric acid was added thereto, and the mixture was extracted twice with chloroform. The organic layer was passed through a short column of silica gel to remove impurities, and then concentrated under reduced pressure. The residue was applied to a silica gel column chromatography to obtain 0.30 g of N-(1,1-dioxotetrahydrothiophen-3-ylmethyl)-5-benzyloxymethylisoxazole-3-carboxamide (hereinafter, referred to as Compound of Present Invention (39)) represented by the (39)

¹H-NMR (CDCl₃, TMS, δ(ppm)): 1.96-2.04 (1H, m), 2.34-2.42 (1H, m), 2.77-2.89 (2H, m), 3.03-3.11 (1H, m), 3.22-3.29 (2H, m), 3.51-3.65 (2H, m), 4.61 (2H, s), 4.66 (2H, s), 6.72 (1H, d), 7.14 (1H, br s), 7.30-7.40 (5H, m)

Production Example 40

Thietan-3-ylamine hydrobromide (0.21 g, 1.2 mmol) and triethylamine (0.17 mL, 1.2 mmol) were added to chloroform (amylene addition product) (2.5 mL). 5-Benzyloxymethylisoxazole-3-carboxylic acid (0.24 g, 1.0 mmol), 1-hydroxybenzotriazole (0.01 g, 0.1 mmol), and 1-ethyl-3-(3-dimethylaminopropyl) carbodiimide hydrochloride (0.24 g, 1.2 mmol) were added to the mixture, and the mixture was stirred at room temperature overnight. Then, dilute hydrochloric acid was added thereto, and the mixture was extracted twice with chloroform. The organic layer was passed through a short column of silica gel to remove impurities, and then concentrated under reduced pressure. The residue was applied to a silica gel column chromatography to obtain 0.22 g of N-(thietan-3-yl)-5-benzyloxymethylisoxazole-3-carboxamide (hereinafter, referred to as Compound of Present Invention (40)) represented by the following formula.

(40)

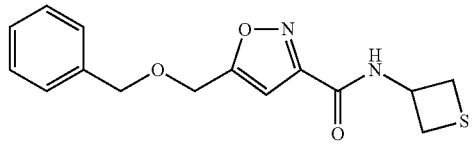

¹H-NMR (CDCl₃, TMS, δ(ppm)): 3.39-3.49 (4H, m), 4.61 (2H, s), 4.65 (2H, s), 5.36-5.47 (1H, m), 6.71 (1H, s), 7.22 (1H, br s), 7.31-7.40 (5H, m)

Production Example 41

N-(Thietan-3-yl)-5-benzyloxymethylisoxazole-3-carboxamide (0.13 g, 0.43 mmol) was dissolved in chloroform (5 mL), and 70% m-chloroperbenzoic acid (0.16 g, 0.65 mmol) was added thereto under ice cooling, and then the mixture was stirred for 2 hours. A 5% aqueous sodium sulfite solution (10 mL) was added to the mixture, and the mixture was stirred for 15 minutes. The fractionated organic layer was washed with a saturated aqueous sodium bicarbonate solution, dried over anhydrous magnesium sulfate, and then concentrated under reduced pressure. The residue was applied to a silica gel column chromatography to obtain 0.06 g of N-(1-oxothietan-3-yl)-5-benzyloxymethylisoxazole-3-carboxamide (hereinafter, referred to as Compound of Present Invention (41)) represented by the following formula:

(41)

and 0.03 g of N1-(1,1-dioxothietan-3-yl)-5-benzyloxymethylisoxazole-3-carboxamide (hereinafter, referred to as Compound of Present Invention (42)) represented by the following formula.

(42)

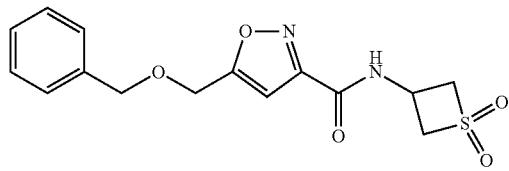

Compound of Present Invention (41)
¹H-NMR (CDCl₃, TMS, δ(ppm)): 3.30-3.37 (2H, m), 4.13-4.19 (2H, m), 4.56-4.63 (1H, m), 4.61 (2H, s), 4.66 (2H, s), 6.72 (1H, s), 7.31-7.40 (6H, m)

Compound of Present Invention (42)
¹H-NMR (CDCl₃, TMS, δ(ppm)): 4.13-4.19 (2H, m), 4.57-4.65 (2H, m), 4.62 (2H, s), 4.66 (2H, s), 4.82-4.90 (1H, m), 6.72 (1H, s), 7.31-7.40 (5H, m), 7.43 (1H, br s)

Production Example 42

5-Benzyloxymethylisoxazole-3-carboxylic acid (0.24 g, 1.0 mmol), a 0.1 M tetrahydropyran-4-ylamine tetrahydrofuran solution (12 mL, 1.2 mmol), and 1-hydroxybenzotriazole (0.01 g, 0.1 mmol) were added to chloroform (amylene addition product) (2.5 mL). 1-Ethyl-3-(3-dimethylaminopropyl) carbodiimide hydrochloride (0.24 g, 1.2 mmol) was added to the mixture at room temperature, and the mixture was stirred overnight. Then, dilute hydrochloric acid was added thereto, and the mixture was extracted twice with chloroform. The organic layer was passed through a short column of silica gel to remove impurities, and then concentrated under reduced pressure. The residue was applied to a silica gel column chromatography to obtain 0.18 g of N-(tetrahydropyran-4-yl)-5-benzyloxymethylisoxazole-3-carboxamide (hereinafter, referred to as Compound of Present Invention (43)) represented by the following formula.

(43)

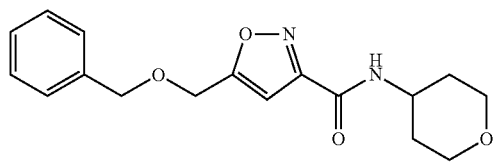

¹H-NMR (CDCl₃, TMS, δ(ppm)): 1.56-1.66 (2H, m), 1.96-2.01 (2H, m), 3.49-3.55 (2H, m), 3.98-4.02 (2H, m), 4.11-4.22 (1H, m), 4.61 (2H, s), 4.66 (2H, s), 6.71 (1H, br s), 6.73 (1H, s), 7.30-7.40 (5H, m)

Production Example 43

5-Phenoxymethythiazole-2-carboxylic acid (0.28 g, 1.1 mmol), tetrahydrofuran-3-ylmethylamine hydrochloride (0.19 g, 1.4 mmol), triethylamine (0.14 g, 1.4 mmol) and 1-hydroxybenzotriazole (0.02 g, 0.14 mmol) were added to chloroform (amylene addition product) (5 mL). 1-Ethyl-3-(3-dimethylaminopropyl) carbodiimide hydrochloride (0.27 g, 1.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.22 g of N-(tetrahydrofuran-3-ylmethyl)-5-phenoxymethythiazole-2-carboxamide (hereinafter, referred to as Compound of Present Invention (47)) represented by the following formula.

(47)

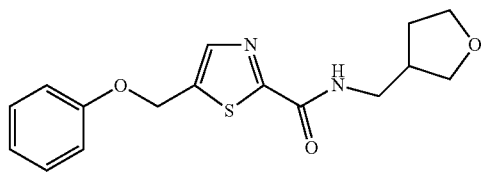

¹H-NMR (CDCl₃, TMS, δ(ppm)): 1.69-1.73 (1H, m), 2.05-2.15 (1H, m), 2.58-2.65 (1H, m), 3.45-3.51 (2H, m), 3.62 (1H, dd), 3.78 (1H, dd), 3.86-3.95 (2H, m), 5.20 (2H, s), 6.99-7.01 (3H, m), 7.31-7.33 (2H, m), 7.39 (1H, s), 7.58 (1H, s)

Production Example 44

5-Benzyloxymethylisoxazole-2-carboxylic acid (0.11 g, 0.43 mmol), tetrahydrofuran-3-ylmethylamine hydrochloride (0.07 g, 0.51 mmol), triethylamine (0.05 g, 0.51 mmol) and 1-hydroxybenzotriazole (0.01 g, 0.05 mmol) were added to chloroform (amylene addition product) (2 mL). 1-Ethyl-3-(3-dimethylaminopropyl) carbodiimide hydrochloride (0.10 g, 0.51 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.11 g of N-(tetrahydrofuran-3-ylmethyl)-5-benzyloxymethythiazole-2-carboxamide (hereinafter, referred to as Compound of Present Invention (48)) represented by the following formula.

(48)

¹H-NMR (CDCl₃, TMS, δ(ppm)): 1.67-1.72 (1H, m), 2.05-2.13 (1H, m), 2.56-2.63 (1H, m), 3.46-3.49 (2H, m), 3.60 (1H, dd), 3.77 (1H, dd), 3.85-3.94 (2H, m), 4.65 (2H, s), 4.67 (2H, s), 7.33-7.37 (6H, m), 7.48 (1H, s)

Production Example 45

3-Benzyloxymethylisoxazole-5-carboxylic acid (0.46 g, 2.0 mmol), tetrahydrofuran-3-ylmethylamine hydrochloride (0.33 g, 2.4 mmol), triethylamine (0.25 g, 2.4 mmol) and 1-hydroxybenzotriazole (0.03 g, 0.24 mmol) were added to chloroform (amylene addition product) (5 mL). 1-Ethyl-3-

(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.42 g of N-(tetrahydrofuran-3-ylmethyl)-3-benzyloxymethyl-isoxazole-5-carboxamide (hereinafter, referred to as Compound of Present Invention (49)) represented by the following formula.

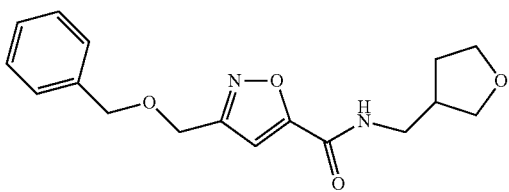

(49)

$^1$H-NMR (CDCl$_3$, TMS, δ(ppm)): 1.66-1.72 (1H, m), 2.05-2.15 (1H, m), 2.57-2.61 (1H, m), 3.48 (2H, dd), 3.61 (1H, dd), 3.75-3.79 (1H, m), 3.85-3.87 (1H, m), 3.92-3.94 (1H, m), 4.58 (2H, s), 4.65 (2H, s), 6.68 (1H, s), 6.99 (1H, s), 7.34-7.36 (5H, m)

Production Example 46

5-Benzyloxymethyl-1H-pyrazole-3-carboxylic acid (0.50 g, 2.0 mmol), tetrahydrofuran-3-ylmethylamine hydrochloride (0.33 g, 2.0 mmol), triethylamine (0.24 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.51 g of N-(tetrahydrofuran-3-ylmethyl)-5-benzyloxymethyl-1H-pyrazole-3-carboxamide (hereinafter, referred to as Compound of Present Invention (50)) represented by the following formula.

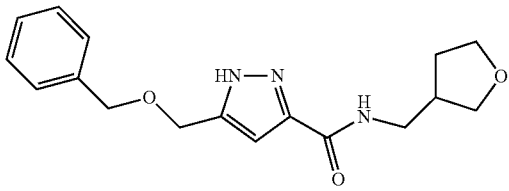

(50)

$^1$H-NMR (CDCl$_3$, TMS, δ(ppm)): 1.66-1.71 (1H, m), 2.06-2.09 (1H, m), 2.56-2.62 (1H, m), 3.39-3.51 (2H, m), 3.62 (1H, dd), 3.75-3.77 (1H, m), 3.84-3.94 (2H, m), 4.57 (2H, s), 4.63 (2H, s), 6.71 (1H, s), 7.01 (1H, s), 7.33-7.38 (5H, m)

Production Example 47

1-Butyl-1H-pyrazole-4-carboxylic acid (0.34 g, 2.0 mmol), tetrahydrofuran-3-ylmethylamine hydrochloride (0.35 g, 2.5 mmol), triethylamine (0.25 g, 2.5 mmol) and 1-hydroxybenzotriazole (0.03 g, 0.25 mmol) were added to chloroform (amylene addition product) (5 mL). 1-Ethyl-3-(3-dimethylaminopropyl) carbodiimide hydrochloride (0.48 g, 2.5 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.32 g of N-(tetrahydrofuran-3-ylmethyl)-1-butyl-1H-pyrazole-4-carboxamide (hereinafter, referred to as Compound of Present Invention (51)) represented by the following formula.

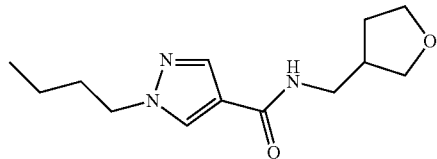

(51)

$^1$H-NMR (CDCl$_3$, TMS, δ(ppm)): 0.94 (3H, t), 1.27-1.37 (2H, m), 1.65-1.70 (1H, m), 1.85 (2H, tt), 2.04-2.13 (1H, m), 2.55-2.61 (1H, m), 3.43 (2H, t), 3.62 (1H, dd), 3.75-3.77 (1H, m), 3.84 (1H, dd), 3.92 (1H, td), 4.13 (2H, t), 5.93 (1H, s), 7.71 (1H, s), 7.85 (1H, s)

Production Example 48

The 56:44 mixture of 3-benzyloxymethyl-1-methyl-1H-pyrazole-5-carboxylic acid and 5-benzyloxymethyl-1-methyl-1H-pyrazole-3-carboxylic acid obtained in Reference Production Example 292 (1.47 g, 6.0 mmol), tetrahydrofuran-3-ylmethylamine hydrochloride (0.96 g, 7.0 mmol), triethylamine (0.71 g, 7.0 mmol) and 1-hydroxybenzotriazole (0.1 g, 0.7 mmol) were added to chloroform (amylene addition product) (10 mL). 1-Ethyl-3-(3-dimethylaminopropyl) carbodiimide hydrochloride (1.34 g, 7.0 mmol) was added to the mixed liquid at room temperature, and then the mixture was stirred at room temperature overnight. Thereafter, the resulting mixture was concentrated under reduced pressure. Dilute hydrochloric acid was added to the reaction mixture, and the mixture was extracted twice with ethyl acetate. The organic layer was washed with saturated saline water, dried over anhydrous sodium sulfate and then filtered, and the filtrate was concentrated under reduced pressure. The residue was applied to a silica gel column chromatography to obtain 0.71 g of N-(tetrahydrofuran-3-ylmethyl)-3-benzyloxymethyl-1-methyl-1H-pyrazole-5-carboxamide (hereinafter, referred to as Compound of Present Invention (52)) represented by the following formula:

(52)

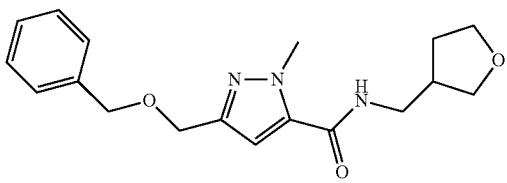

and 0.61 g of N-(tetrahydrofuran-3-ylmethyl)-5-benzyloxymethyl-1-methyl-1H-pyrazole-3-carboxamide (hereinafter, referred to as Compound of Present Invention (53)) represented by the following formula.

(53)

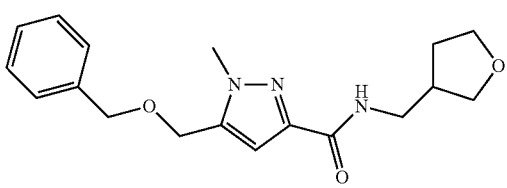

Compound of Present Invention (52)
$^1$H-NMR (CDCl$_3$, TMS, δ(ppm)): 1.66-1.68 (1H, m), 2.08-2.11 (1H, m), 2.56-2.59 (1H, m), 3.42 (2H, tz), 3.61 (1H, dd), 3.73-3.79 (1H, m), 3.83 (1H, dd), 3.90-3.97 (1H, m), 4.15 (3H, s), 4.54 (2H, s), 4.58 (2H, s), 6.19 (1H, s), 6.52 (1H, s), 7.28-7.38 (5H, m)

Compound of Present Invention (53)
$^1$H-NMR (CDCl$_3$, TMS, δ(ppm)): 1.68-1.71 (1H, m), 2.03-2.12 (1H, m), 2.56-2.62 (1H, m), 3.41-3.47 (2H, m), 3.59 (1H, dd), 3.77 (1H, dd), 3.85-3.93 (5H, m), 4.50 (2H, s), 4.53 (2H, s), 6.76 (1H, s), 6.97 (1H, s), 7.32-7.37 (5H, m)

Production Example 49

Tetrahydrofuran-3-ylmethylamine hydrochloride (0.54 g, 3.96 mmol) and triethylamine (0.40 g, 3.96 mmol) were added to chloroform (amylene addition product) (13 mL). 1-Butyl-1H-1,2,3-triazole-4-carboxylic acid (0.56 g, 3.30 mmol), 1-hydroxybenzotriazole (0.05 g, 0.33 mmol) and 1-ethyl-3-(3-dimethylaminopropyl) carbodiimide hydrochloride (0.76 g, 3.96 mmol) were added to the mixture at room temperature, and the mixture was stirred for 3 hours. Then, dilute hydrochloric acid was added thereto, and the mixture was extracted twice with chloroform. The organic layer was washed with a saturated aqueous sodium bicarbonate solution, dried over anhydrous magnesium sulfate, and then concentrated under reduced pressure. The residue was applied to a silica gel column chromatography to obtain 0.63 g of N-(tetrahydrofuran-3-ylmethyl)-1-butyl-1H-1,2,3-triazole-4-carboxamide (hereinafter, referred to as Compound of Present Invention (54)) represented by the following formula.

(54)

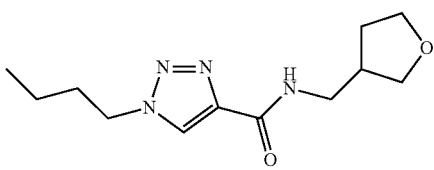

$^1$H-NMR (CDCl$_3$, TMS, δ(ppm)): 0.96 (3H, t), 1.30-1.39 (2H, m), 1.65-1.74 (1H, m), 1.92-1.99 (2H, m), 2.05-2.13 (1H, m), 2.54-2.63 (1H, m), 3.41-3.52 (2H, m), 3.59-3.63 (1H, m), 3.74-3.80 (1H, m), 3.85-3.95 (2H, m), 4.43 (2H, t), 6.85 (1H, br s), 8.03 (1H, s)

Production Example 50

Tetrahydrofuran-3-ylmethylamine hydrochloride (0.20 g, 1.20 mmol) and triethylamine (0.12 g, 1.20 mmol) were added to chloroform (amylene addition product) (4 mL). 2-Butyl-2H-1,2,3-triazole-4-carboxylic acid (0.17 g, 1.00 mmol), 1-hydroxybenzotriazole (0.01 g, 0.10 mmol) and 1-ethyl-3-(3-dimethylaminopropyl) carbodiimide hydrochloride (0.23 g, 1.20 mmol) were added to the mixture at room temperature, and the mixture was stirred for 3 hours. Then, dilute hydrochloric acid was added thereto, and the mixture was extracted twice with chloroform. The organic layer was washed with a saturated aqueous sodium bicarbonate solution, and the filtrate was concentrated under reduced pressure. The residue was applied to a silica gel column chromatography to obtain 0.11 g of N-(tetrahydrofuran-3-ylmethyl)-2-butyl-2H-1,2,3-triazole-4-carboxamide (hereinafter, referred to as Compound of Present Invention (55)) represented by the following formula.

(55)

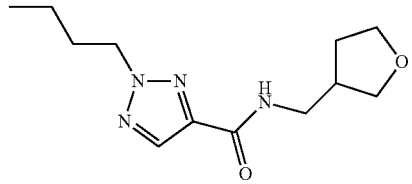

$^1$H-NMR (CDCl$_3$, TMS, δ(ppm)): 0.97 (3H, t), 1.31-1.41 (2H, m), 1.65-1.74 (1H, m), 1.87-1.95 (2H, m), 2.05-2.13 (1H, m), 2.54-2.64 (1H, m), 3.46-3.50 (2H, m), 3.58-3.61 (1H, m), 3.74-3.80 (1H, m), 3.86-3.94 (2H, m), 4.40 (2H, t), 7.28 (1H, br s), 8.04 (1H, s)

Production Example 51

Tetrahydrofuran-3-ylmethylamine hydrochloride (0.38 g, 2.75 mmol) and triethylamine (0.28 g, 2.75 mmol) were added to chloroform (amylene addition product) (8 mL). 2-Butyl-2H-tetrazole-5-carboxylic acid (0.39 g, 2.29 mmol), 1-hydroxybenzotriazole (0.03 g, 0.23 mmol) and 1-ethyl-3-(3-dimethylaminopropyl) carbodiimide hydrochloride (0.53 g, 2.75 mmol) were added to the mixture at room temperature, and the mixture was stirred overnight. Then, dilute hydrochloric acid was added thereto, and the mixture was extracted twice with chloroform. The organic layer was washed with a saturated aqueous sodium bicarbonate solution, dried over anhydrous magnesium sulfate, and then concentrated under reduced pressure. The residue was applied to a silica gel column chromatography to obtain 0.51 g of N-(tetrahydrofuran-3-ylmethyl)-2-butyl-2H-tetrazole-5-carboxamide (hereinafter, referred to as Compound of Present Invention (56)) represented by the following formula.

(56)

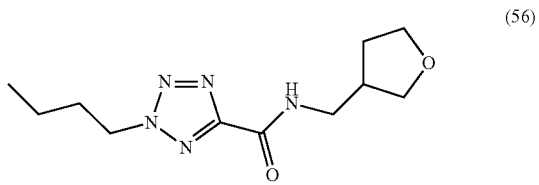 [SMILES: CCCCn1nnc(C(=O)NCC2CCOC2)n1]

(58)

¹H-NMR (CDCl₃, TMS, δ(ppm)): 0.97 (3H, t), 1.32-1.41 (2H, m), 1.66-1.75 (1H, m), 2.01-2.13 (3H, m), 2.58-2.68 (1H, m), 3.53-3.56 (2H, m), 3.61-3.64 (1H, m), 3.75-3.80 (1H, m), 3.85-3.96 (2H, m), 4.69 (2H, t), 7.31 (1H, br s)

¹H-NMR (CDCl₃, TMS, δ(ppm)): 0.96 (3H, t), 1.36-1.46 (2H, m), 1.64-1.79 (3H, m), 2.07-2.16 (1H, m), 2.58-2.65 (1H, m), 2.79 (2H, t), 3.45-3.55 (2H, m), 3.62 (1H, dd), 3.74-3.81 (1H, m), 3.85 (1H, dd), 3.93 (1H, td), 7.19 (1H, brs)

Production Example 52

5-Butyl-1,2,4-oxadiazole-3-carboxylic acid (1.36 g, 8 mmol), tetrahydrofuran-3-ylmethylamine hydrochloride (1.65 g, 12 mmol), triethylamine (1.21 g, 12 mmol) and 1-hydroxybenzotriazole (0.11 g, 0.8 mmol) were added to chloroform (amylene addition product) (16 mL). 1-Ethyl-3-(3-dimethylaminopropyl) carbodiimide hydrochloride (1.83 g, 12 mmol) was added to the mixture at room temperature, and the mixture was stirred overnight. Then, water was added thereto, and the mixture was extracted three times with chloroform. The organic layer was washed with saturated saline water, dried over anhydrous sodium sulfate, and then concentrated under reduced pressure. The residue was applied to a silica gel column chromatography to obtain 0.76 g of N-(tetrahydrofuran-3-ylmethyl)-5-butyl-1,2,4-oxadiazole-3-carboxamide (hereinafter, referred to as Compound of Present Invention (57)) represented by the following formula.

Production Example 54

2-Butyloxazole-5-carboxylic acid (0.10 g, 0.6 mmol), tetrahydrofuran-3-ylmethylamine hydrochloride (0.12 g, 0.9 mmol), triethylamine (0.09 g, 0.9 mmol) and 1-hydroxybenzotriazole (0.01 g, 0.1 mmol) were added to chloroform (amylene addition product) (1.2 mL). 1-Ethyl-3-(3-dimethylaminopropyl) carbodiimide hydrochloride (0.14 g, 0.7 mmol) was added to the mixture at room temperature, and the mixture was stirred overnight. Then, water was added thereto, and the mixture was extracted three times with ethyl acetate. The organic layer was washed with saturated saline water, dried over anhydrous sodium sulfate, and then concentrated under reduced pressure. The residue was applied to a silica gel column chromatography to obtain 0.13 g of N-(tetrahydrofuran-3-ylmethyl)-2-butyloxazole-5-carboxamide (hereinafter, referred to as Compound of Present Invention (59)) represented by the following formula.

(57)

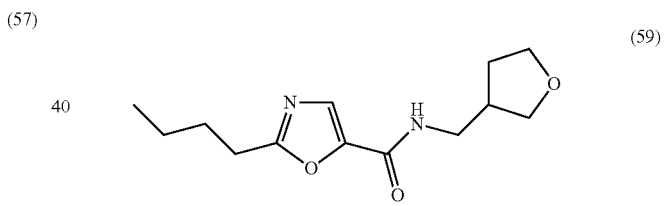

(59)

¹H-NMR (CDCl₃, TMS, δ(ppm)): 0.96 (3H, t), 1.38-1.49 (2H, m), 1.62-1.73 (1H, m), 1.80-1.87 (2H, m), 2.05-2.15 (1H, m), 2.55-2.67 (1H, m), 2.95 (2H, t), 3.45-3.55 (2H, m), 3.61 (1H, dd), 3.73-3.80 (1H, m), 3.85 (1H, dd), 3.92 (1H, td), 7.10 (1H, brs)

¹H-NMR (CDCl₃, TMS, δ(ppm)): 0.95 (3H, t), 1.36-1.45 (2H, m), 1.63-1.80 (3H, m), 2.03-2.13 (1H, m), 2.50-2.63 (1H, m), 2.76 (2H, t), 3.37-3.50 (2H, m), 3.59 (1H, dd), 3.73-3.80 (1H, m), 3.84-3.94 (2H, m), 7.02 (1H, brs), 8.08 (1H, s)

Production Example 53

Ethyl 3-butyl-1,2,4-oxadiazole-5-carboxylate (0.40 g, 2 mmol), tetrahydrofuran-3-ylmethylamine hydrochloride (2.75 g, 20 mmol) and diisopropylethylamine (2.58 g, 20 mmol) were added to ethanol (40 mL), and the mixture was stirred at room temperature for 2 hours. The reaction mixture was concentrated under reduced pressure, then water was added to the residue, and the mixture was extracted three times with ethyl acetate. The organic layer was washed with saturated saline water, dried over anhydrous sodium sulfate, and then concentrated under reduced pressure. The residue was applied to a silica gel column chromatography to obtain 0.43 g of N-(tetrahydrofuran-3-ylmethyl)-3-butyl-1,2,4-oxadiazole-5-carboxamide (hereinafter, referred to as Compound of Present Invention (58)) represented by the following formula.

Production Example 55

Ethyl 5-butyloxazole-2-carboxylate (0.39 g, 2 mmol), tetrahydrofuran-3-ylmethylamine hydrochloride (2.75 g, 20 mmol) and diisopropylethylamine (2.58 g, 20 mmol) were added to ethanol (40 mL), and the mixture was stirred under heating and refluxing for 10 hours, and then concentrated under reduced pressure. Water was added to the residue, and the mixture was extracted three times with ethyl acetate. The organic layer was washed with saturated saline water, dried over anhydrous sodium sulfate, and then concentrated under reduced pressure. The residue was applied to a silica gel column chromatography to obtain 0.39 g of N-(tetrahydrofuran-3-ylmethyl)-5-butyloxazole-2-carboxamide (hereinafter, referred to as Compound of Present Invention (60)) represented by the following formula.

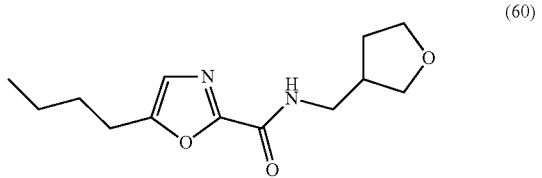 [SMILES: CCCCc1cnc(C(=O)NCC2CCOC2)o1]

(60)

¹H-NMR (CDCl₃, TMS, δ(ppm)): 0.94 (3H, t), 1.33-1.44 (2H, m), 1.63-1.73 (3H, m), 2.04-2.13 (1H, m), 2.52-2.63 (1H, m), 2.73 (2H, t), 3.40-3.51 (2H, m), 3.59 (1H, dd), 3.73-3.80 (1H, m), 3.83-3.95 (2H, m), 6.83 (1H, brs), 7.12 (1H, s)

Production Example 56

Tetrahydrofuran-3-ylmethylamine hydrochloride (0.13 g, 0.93 mmol) was dissolved in 1 mL of chloroform (amylene addition product), and triethylamine (0.13 mL, 0.93 mmol) was added thereto. Then, the mixture was stirred at room temperature for 30 minutes. 2.0 ml of a chloroform (amylene addition product) solution of 5-benzylisoxathiazole-3-carboxylic acid (0.17 g, 0.77 mmol), 1-ethyl-3-(3-dimethylaminopropyl) carbodiimide hydrochloride (0.23 g, 0.93 mmol) and 1-hydroxybenzotriazole (0.01 g, 0.08 mmol) were added to the mixture at room temperature, and the mixture was stirred overnight. Then, 2 ml of 1 N hydrochloric acid was added thereto, and the mixture was extracted with chloroform. The organic layer was washed with saturated saline water, dried over anhydrous magnesium sulfate, and then concentrated under reduced pressure. The resulting residue was applied to a silica gel column chromatography to obtain 0.12 g of N-(tetrahydrofuran-3-ylmethyl)-5-benzylisozathiazole-3-carboxamide (hereinafter, referred to as Compound of Present Invention (61)) represented by the following formula.

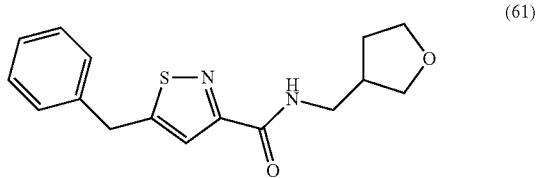 [SMILES: O=C(NCC1CCOC1)c1cc(Cc2ccccc2)sn1]

(61)

¹H-NMR (CDCl₃, TMS) δ(ppm): 7.57 (1H, t), 7.39-7.21 (6H, m), 4.24 (2H, s), 3.90 (1H, td), 3.86 (1H, dd), 3.76 (1H, dd), 3.59 (1H, dd), 3.44 (2H, td), 2.60-2.54 (1H, m), 2.12-2.03 (1H, m), 1.74-1.60 (1H, m)

Production Example 57

Tetrahydrofuran-3-ylmethylamine hydrochloride (0.07 g, 0.48 mmol) was dissolved in 0.8 mL of chloroform (amylene addition product), and triethylamine (0.07 mL, 0.48 mmol) was added thereto. Then, the mixture was stirred at room temperature for 30 minutes. 1.2 ml of a chloroform (amylene addition product) solution of 5-butylisoxazole-3-carboxylic acid (0.08 g, 0.40 mmol), 1-ethyl-3-(3-dimethylaminopropyl) carbodiimide hydrochloride (0.09 g, 0.48 mmol) and 1-hydroxybenzotriazole (0.005 g, 0.04 mmol) were added to the mixture at room temperature, and the mixture was stirred at room temperature overnight. Then, 2 ml of 1 N hydrochloric acid was added thereto, and the mixture was extracted with chloroform. The organic layer was washed with saturated saline water, dried over anhydrous magnesium sulfate, and then concentrated under reduced pressure. The resulting residue was applied to a silica gel column chromatography to obtain 0.03 g of N-(tetrahydrofuran-3-ylmethyl)-5-butylisoxathiazole-3-carboxamide (hereinafter, referred to as Compound of Present Invention (62)) represented by the following formula.

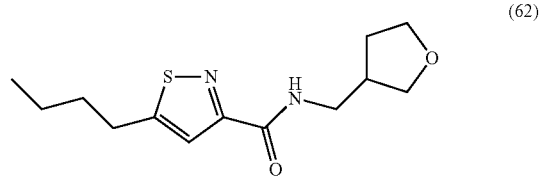 [SMILES: CCCCc1cc(C(=O)NCC2CCOC2)ns1]

(62)

¹H-NMR (CDCl₃, TMS) δ(ppm): 7.58-7.56 (1H, m), 7.47-7.32 (1H, m), 3.96-3.85 (2H, m), 3.77 (1H, dd), 3.60 (1H, dd), 3.45 (2H, td), 2.93 (2H, t), 2.64-2.53 (1H, m), 2.13-2.04 (1H, m), 1.70 (3H, tt), 1.41 (2H, td), 0.95 (3H, t)

Production Example 58

5-(4-Trifluoromethylbenzyloxymethyl)isoxazole-3-carboxylic acid (0.60 g, 2.0 mmol), tetrahydrofuran-3-ylmethylamine hydrochloride (0.33 g, 2.4 mmol), triethylamine (0.25 g, 2.4 mmol) and 1-hydroxybenzotriazole (0.03 g, 0.24 mmol) were added to 5 mL of chloroform (amylene addition product). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.40 g of N-(tetrahydrofuran-3-ylmethyl)-5-(4-trifluoromethylbenzyloxymethyl)isoxazole-3-carboxamide (hereinafter, referred to as Compound of Present Invention (63)) represented by the following formula.

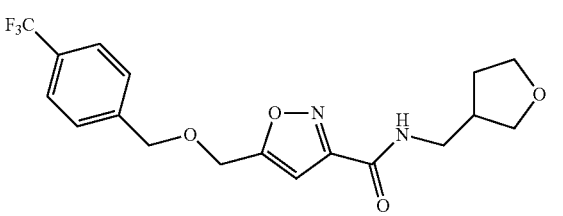

(63)

¹H-NMR (CDCl₃, TMS, δ(ppm)): 1.65-1.70 (1H, m), 2.05-2.13 (1H, m), 2.55-2.61 (1H, m), 3.47 (2H, dd), 3.60 (1H, dd), 3.77 (1H, dd,), 3.86 (1H, dd), 3.91-3.93 (1H, m), 4.67 (2H, s), 4.69 (2H, s), 6.75 (1H, s), 6.94 (1H, s), 7.47 (2H, d), 7.63 (2H, d)

Production Example 59

5-(3-Trifluoromethylbenzyloxymethyl)isoxazole-3-carboxylic acid (0.60 g, 2.0 mmol), tetrahydrofuran-3-ylmethylamine hydrochloride (0.33 g, 2.4 mmol), triethylamine (0.25 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.20 g of N-(tetrahydrofuran-3-ylmethyl)-5-(3-trifluoromethylbenzyloxymethyl) isoxazole-3-carboxamide (hereinafter, referred to as Compound of Present Invention (64)) represented by the following formula.

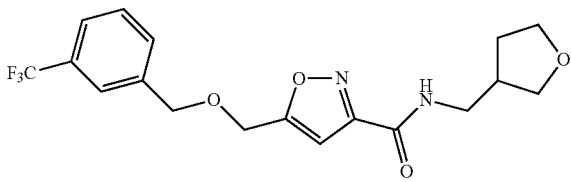

(64)

$^1$H-NMR (CDCl$_3$, TMS, δ(ppm)): 1.64-1.72 (1H, mL), 2.08-2.11 (1H, m), 2.55-2.63 (1H, m), 3.47 (2H, t), 3.59 (1H, dd), 3.77 (1H, dd), 3.84-3.95 (2H, m), 4.66 (2H, s), 4.70 (2H, s), 6.75 (1H, s), 6.95 (1H, s), 7.50-7.58 (4H, m)

Production Example 60

5-(3-Trifluoromethylbenzyloxymethyl)isoxazole-3-carboxylic acid (0.30 g, 1.0 mmol), tetrahydropyran-4-ylmethylamine (0.14 g, 1.2 mmol), and 1-hydroxybenzotriazole (0.02 g, 0.12 mmol) were added to chloroform (amylene addition product) (2 mL). 1-Ethyl-3-(3-dimethylaminopropyl) carbodiimide hydrochloride (0.23 g, 1.2 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.21 g of N-(tetrahydropyran-4-ylmethyl)-5-[3-trifluoromethylbenzyl)oxymethyl]isoxazole-3-carboxamide (hereinafter, referred to as Compound of Present Invention (65)) represented by the following formula.

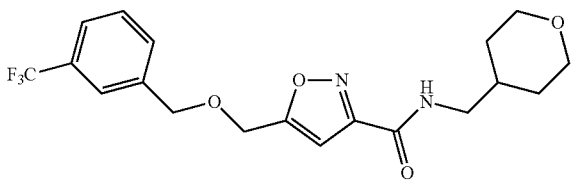

(65)

$^1$H-NMR(CDCl$_3$, TMS, δ(ppm)): 1.35-1.41 (2H, m), 1.66-1.68 (2H, m), 1.84-1.88 (1H, m), 3.34-3.42 (4H, m), 3.99 (2H, dd), 4.66 (2H, s), 4.70 (2H, s), 6.75 (1H, s), 6.89 (1H, s), 7.50-7.58 (4H, m)

Production Example 61

5-(2-Chlorobenzyloxymethyl)isoxazole-3-carboxylic acid (500 mg, 1.87 mmol) and tetrahydrofuran-3-ylmethylamine (208 mg, 2.05 mmol) were added to dehydrated tetrahydrofuran (20 ml). The mixture was cooled to 0° C., (benzotriazol-1-yloxy)tripyrrolidinophosphonium hexafluorophosphate (1.46 g, 2.80 mmol) was added thereto, and the mixture was stirred at 0° C. for 16 hours. Then, the reaction mixture was added to water, and extracted twice with ethyl acetate. The organic layer was washed with saturated saline water, dried over anhydrous sodium sulfate, and then concentrated under reduced pressure. The residue was applied to a silica gel column chromatography to obtain 305 mg of N-(tetrahydrofuran-3-ylmethyl)-5-(2-chlorobenzyloxymethyl)isoxazole-3-carboxamide (hereinafter, referred to as Compound of Present Invention (66)) represented by the following formula.

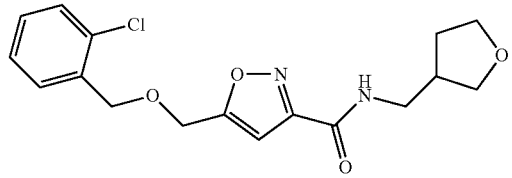

(66)

$^1$H-NMR (CDCl$_3$, TMS, δ(ppm)): 1.70-1.62 (1H, m), 2.11-2.06 (1H, m), 2.58 (1H, t), 3.46 (2H, t), 3.60-3.57 (1H, m), 3.79-3.73 (1H, m), 3.94-3.83 (2H, m), 4.72 (4H, d), 6.76 (1H, s), 6.94 (NH, s), 7.30-7.27 (2H, m), 7.37 (1H, d), 7.47 (1H, d)

Production Example 62

5-(2-Chlorobenzyloxymethyl)isoxazole-3-carboxylic acid (500 mg, 1.87 mmol) and tetrahydropyran-4-ylmethylamine (237 mg, 2.05 mmol) were added to dehydrated tetrahydrofuran (20 ml). The mixture was cooled to 0° C., (benzotriazol-1-yloxy)tripyrrolidinophosphonium hexafluorophosphate (1.46 g, 2.80 mmol) was added thereto, and the mixture was stirred at 0° C. for 16 hours. Then, the reaction mixture was added to water, and extracted twice with ethyl acetate. The organic layer was washed with saturated saline water, dried over anhydrous sodium sulfate, and then concentrated under reduced pressure. The residue was applied to a silica gel column chromatography to obtain 320 mg of N-(tetrahydropyran-4-ylmethyl)-5-(2-chlorobenzyloxymethyl)isoxazole-3-carboxamide (hereinafter, referred to as Compound of Present Invention (67)) represented by the following formula.

(67)

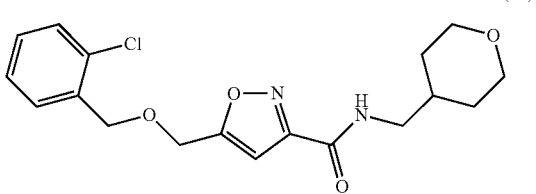

¹H-NMR (CDCl₃, TMS, δ(ppm)): 1.43-1.32 (2H, m), 1.67 (2H, d), 1.89-1.83 (1H, m), 3.41-3.33 (4H, M), 3.99 (2H, d), 4.72 (4H, d), 6.76 (1H, s), 6.89 (NH, s), 7.30-7.23 (2H, m), 7.37 (1H, d), 7.47 (1H, d)

Production Example 63

5-(3-Chlorobenzyloxymethyl)isoxazole-3-carboxylic acid (500 mg, 1.87 mmol) and tetrahydrofuran-3-ylmethylamine (208 mg, 2.05 mmol) were added to dehydrated tetrahydrofuran (20 ml). The mixture was cooled to 0° C., (benzotriazol-1-yloxy)tripyrrolidinophosphonium hexafluorophosphate (1.46 g, 2.80 mmol) was added thereto, and the mixture was stirred at 0° C. for 16 hours. Then, the reaction mixture was added to water, and extracted twice with ethyl acetate. The organic layer was washed with saturated saline water, dried over anhydrous sodium sulfate, and then concentrated under reduced pressure. The residue was applied to a silica gel column chromatography to obtain 350 mg of N-(tetrahydrofuran-3-ylmethyl)-5-(2-chlorobenzyloxymethyl)isoxazole-3-carboxamide (hereinafter, referred to as Compound of Present Invention (68)) represented by the following formula.

(68)

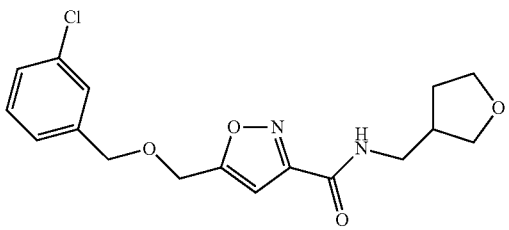

¹H-NMR (CDCl₃, TMS, δ(ppm)): 1.70-1.65 (1H, m), 2.11-2.06 (1H, m), 2.59-2.56 (1H, m), 3.47 (2H, t), 3.61-3.58 (1H, m), 3.79-3.75 (1H, m), 3.94-3.83 (2H, m), 4.58 (2H, s), 4.66 (2H, s), 6.73 (1H, s), 6.93 (1H, br.s), 7.23-7.20 (1H, m), 7.29 (2H, d), 7.34 (1H, s)

Production Example 64

5-(3-Chlorobenzyloxymethyl)isoxazole-3-carboxylic acid (500 mg, 1.87 mmol) and tetrahydropyran-4-ylmethylamine (237 mg, 2.05 mmol) were added to dehydrated tetrahydrofuran (20 ml). The mixture was cooled to 0° C., (benzotriazol-1-yloxy)tripyrrolidinophosphonium hexafluorophosphate (1.46 g, 2.80 mmol) was added thereto, and the mixture was stirred at 0° C. for 16 hours. The mixture was added to water, and extracted twice with ethyl acetate. The organic layer was washed with saturated saline water, dried over anhydrous sodium sulfate, and then concentrated under reduced pressure. The residue was applied to a silica gel column chromatography to obtain 400 mg of N-(tetrahydropyran-4-ylmethyl)-5-(3-chlorobenzyloxymethyl)isoxazole-3-carboxamide (hereinafter, referred to as Compound of Present Invention (69)) represented by the following formula.

(69)

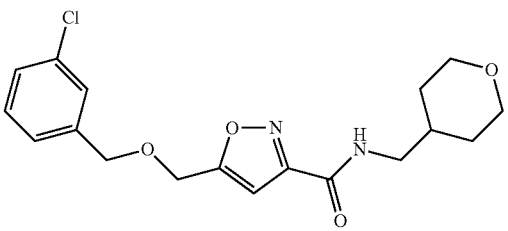

¹H-NMR (CDCl₃, TMS, δ(ppm)): 1.47-1.36 (2H, m), 1.68-1.57 (2H, m), 1.86 (1H, s), 3.40-3.35 (4H, m), 3.98 (2H, d), 4.57 (2H, s), 4.65 (2H, s), 6.73 (1H, s), 6.88 (1H, s), 7.21 (1H, s), 7.34-7.29 (3H, d)

Production Example 65

5-(4-Chlorobenzyloxymethyl)isoxazole-3-carboxylic acid (0.50 g, 1.8 mmol) was added to chloroform (amylene addition product) (15 mL), and cooled to 0° C. Triethylamine (0.39 ml, 2.2 mmol), 1-ethyl-3-(3-dimethylaminopropyl)carbodiimide hydrochloride (0.49 g, 2.2 mmol) and 1-hydroxybenzotriazole (0.30 g, 2.2 mmol) were added thereto, and the mixture was stirred for 10 minutes. Tetrahydrofuran-3-ylmethylamine (0.21 g, 2.1 mmol) was added to the mixture, and the mixture was stirred at room temperature for 12 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.40 g of N-(tetrahydrofuran-3-ylmethyl)-5-(4-chlorobenzyloxymethyl)isoxazole-3-carboxamide (hereinafter, referred to as Compound of Present Invention (70)) represented by the following formula.

(70)

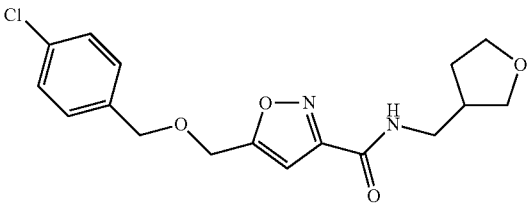

¹H-NMR (CDCl₃, TMS, δ(ppm)): 1.68 (1H, m), 2.08 (1H, m), 2.57 (1H, m), 3.46 (2H, t), 3.59 (1H, q), 3.80 (1H, q), 3.94-3.83 (2H, m), 4.56 (2H, s), 4.64 (2H, s), 6.73 (1H, s), 6.92 (1H, s), 7.27 (2H, d), 7.34 (2H, d)

Production Example 66

5-(4-Chlorobenzyloxymethyl)isoxazole-3-carboxylic acid (0.50 g, 1.8 mmol) was added to chloroform (amylene addition product) (15 mL), and cooled to 0° C. Triethylamine (0.39 ml, 2.2 mmol), 1-ethyl-3-(3-dimethylaminopropyl)carbodiimide hydrochloride (0.49 g, 2.2 mmol) and 1-hydroxybenzotriazole (0.30 g, 2.2 mmol) were added thereto, and the mixture was stirred for 10 minutes. Tetrahydropyran-4-ylmethylamine (0.21 g, 2.1 mmol) was added to the mixture, and the mixture was stirred at room temperature for 12 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.23 g of N-(tetrahydropyran-4-ylmethyl)-5-(4-chlorobenzyloxymethyl)isoxazole-3-carboxamide (hereinafter, referred to as Compound of Present Invention (71)) represented by the following formula.

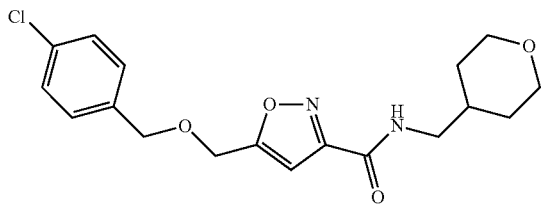

(71)

¹H-NMR (CDCl₃, TMS, δ(ppm)): 1.36 (2H, q), 1.66 (2H, d), 1.84 (1H, m), 3.37 (4H, m), 3.98 (2H, d), 4.56 (2H, s), 4.63 (2H, s), 6.72 (1H, s), 6.87 (1H, Brs), 7.27 (2H, d), 7.36 (2H, d)

Production Example 67

5-(3,4-Dichlorobenzyloxymethyl)isoxazole-3-carboxylic acid (0.50 g, 1.6 mmol) was added to chloroform (amylene addition product) (12 mL), and cooled to 0° C. Triethylamine (0.38 ml, 2.0 mmol), 1-ethyl-3-(3-dimethylaminopropyl)carbodiimide hydrochloride (0.38 g, 2.0 mmol) and 1-hydroxybenzotriazole (0.27 g, 1.8 mmol) were added thereto, and the mixture was stirred for 10 minutes. Tetrahydrofuran-3-ylmethylamine (0.18 g, 1.8 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.30 g of N-(tetrahydrofuran-3-ylmethyl)-5-(3,4-dichlorobenzyloxymethyl)isoxazole-3-carboxamide (hereinafter, referred to as Compound of Present Invention (72)) represented by the following formula.

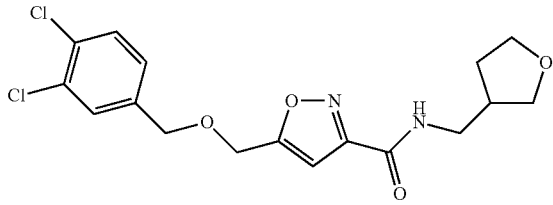

(72)

¹H-NMR (CDCl₃, TMS, δ(ppm)): 1.70-1.65 (1H, m), 2.11-2.06 (1H, m), 2.59-2.56 (1H, m), 3.48-3.45 (2H, m), 3.73-3.57 (1H, m), 3.79-3.75 (1H, m), 3.93-3.83 (2H, m), 4.55 (2H, s), 4.66 (2H, s), 6.73 (1H, s), 6.92 (1H, s), 7.19-7.16 (1H, m), 7.43 (2H, d)

Production Example 68

5-(3,4-Dichlorobenzyloxymethyl)isoxazole-3-carboxylic acid (0.50 g, 1.6 mmol) was added to chloroform (amylene addition product) (12 mL), and cooled to 0° C. Triethylamine (0.34 ml, 2.5 mmol), 1-ethyl-3-(3-dimethylaminopropyl)carbodiimide hydrochloride (0.38 g, 2.0 mmol) and 1-hydroxybenzotriazole (0.27 g, 2.0 mmol) were added thereto, and the mixture was stirred for 10 minutes. Tetrahydropyran-4-ylmethylamine (0.21 g, 2.1 mmol) was added to the mixture, and the mixture was stirred at room temperature for 12 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.34 g of N-(tetrahydropyran-4-ylmethyl)-5-(3,4-dichlorobenzyloxymethyl)isoxazole-3-carboxamide (hereinafter, referred to as Compound of Present Invention (73)) represented by the following formula.

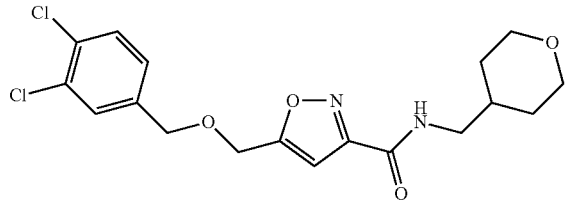

(73)

¹H-NMR (CDCl₃, TMS, δ(ppm)): 1.43-1.33 (2H, m), 1.67 (2H, d), 1.89-1.83 (1H, m), 3.41-3.33 (4H, m), 4.55 (2H, s), 4.66 (2H, s), 6.73 (1H, s), 6.87 (1H, s), 7.18-7.16 (1H, m), 7.43 (2H, d)

Production Example 69

5-(3-Fluorobenzyloxymethyl)isoxazole-3-carboxylic acid (0.50 g, 2.0 mmol) was added to chloroform (amylene addition product) (12 mL), and cooled to 0° C. Triethylamine (0.40 ml, 3.0 mmol), 1-ethyl-3-(3-dimethylaminopropyl)carbodiimide hydrochloride (0.46 g, 2.4 mmol) and 1-hydroxybenzotriazole (0.32 g, 2.4 mmol) were added thereto, and the mixture was stirred for 10 minutes. Tetrahydrofuran-3-ylmethylamine (0.22 g, 2.2 mmol) was added to the mixture, and the mixture was stirred at room temperature for 12 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydrofuran-3-ylmethyl)-5-(3-fluorobenzyloxyethyl)isoxazole-3-carboxamide (hereinafter, referred to as Compound of Present Invention (74)) represented by the following formula.

(74)

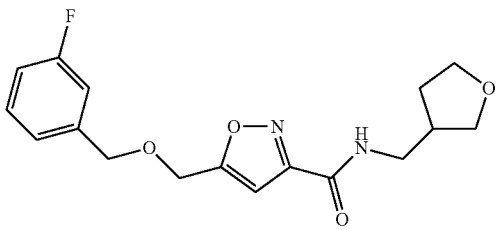

¹H-NMR (CDCl₃, TMS, δ(ppm)): 1.70-1.65 (1H, m), 2.11-2.06 (1H, m), 2.59-2.56 (1H, m), 3.48-3.45 (2H, m), 3.60-3.57 (1H, m), 3.79-3.73 (1H, m), 3.94-3.83 (2H, m), 4.59 (2H, s), 4.66 (2H, s), 6.73 (1H, s), 6.93 (1H, s), 7.11-6.98 (3H, m), 7.35-7.30 (1H, m)

Production Example 70

5-(3-Fluorobenzyloxymethyl)isoxazole-3-carboxylic acid (0.50 g, 2.0 mmol) was added to chloroform (amylene addition product) (12 mL), and cooled to 0° C. Triethylamine (0.40 ml, 3.0 mmol), 1-ethyl-3-(3-dimethylaminopropyl) carbodiimide hydrochloride (0.46 g, 2.4 mmol) and 1-hydroxybenzotriazole (0.32 g, 2.4 mmol) were added thereto, and the mixture was stirred for 10 minutes. Tetrahydropyran-4-ylmethylamine (0.25 g, 2.2 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.35 g of N-(tetrahydropyran-4-ylmethyl)-5-(3-fluorobenzyloxymethyl)isoxazole-3-carboxamide (hereinafter, referred to as Compound of Present Invention (75)) represented by the following formula.

(75)

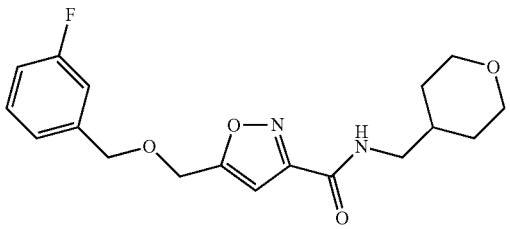

¹H-NMR (CDCl₃, TMS, δ(ppm)): 1.43-1.32 (2H, m), 1.68-1.65 (2H, m), 1.89-1.82 (1H, m), 3.41-3.33 (4H, m), 4.00-3.97 (2H, m), 4.59 (2H, s), 4.66 (2H, s), 6.73 (1H, s), 6.87 (1H, s), 7.11-6.98 (3H, m), 7.35-7.30 (1H, m)

Production Example 71

5-(3-Bromobenzyloxymethyl)isoxazole-3-carboxylic acid (0.50 g, 1.6 mmol) was added to chloroform (amylene addition product) (12 mL), and cooled to 0° C. Triethylamine (0.33 ml, 2.4 mmol), 1-ethyl-3-(3-dimethylaminopropyl) carbodiimide hydrochloride (0.37 g, 1.9 mmol) and 1-hydroxybenzotriazole (0.26 g, 1.9 mmol) were added thereto, and the mixture was stirred for 10 minutes. Tetrahydrofuran-3-ylmethylamine (0.16 g, 1.6 mmol) was added to the mixture, and the mixture was stirred at room temperature for 12 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydrofuran-3-ylmethyl)-5-[(3-bromobenzyl)oxymethyl]isoxazole-3-carboxamide (hereinafter, referred to as Compound of Present Invention (76)) represented by the following formula.

(76)

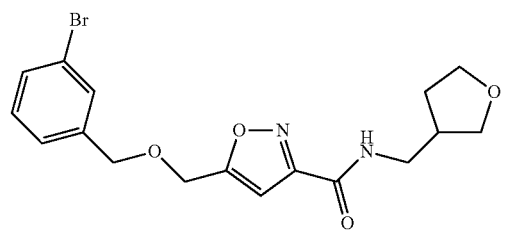

¹H-NMR (CDCl₃, TMS, δ(ppm)): 1.68 (1H, m), 2.08 (1H, m), 2.57 (1H, m), 3.47 (2H, t), 3.59 (1H, t), 3.77 (1H, q), 3.85 (2H, m), 4.57 (2H, s), 4.66 (2H, s), 6.73 (1H, s), 6.93 (1H, s), 7.23 (2H, m), 7.44 (1H, m), 7.50 (1H, s)

Production Example 72

5-(3-Bromobenzyloxymethyl)isoxazole-3-carboxylic acid (0.50 g, 2.0 mmol) was added to chloroform (amylene addition product) (12 mL), and cooled to 0° C. Triethylamine (0.40 ml, 3.0 mmol), 1-ethyl-3-(3-dimethylaminopropyl) carbodiimide hydrochloride (0.46 g, 2.4 mmol) and 1-hydroxybenzotriazole (0.32 g, 2.4 mmol) were added thereto, and the mixture was stirred for 10 minutes. Tetrahydropyran-4-ylmethylamine (0.25 g, 2.2 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.26 g of N-(tetrahydropyran-4-ylmethyl)-5-(3-bromobenzyloxymethyl)isoxazole-3-carboxamide (hereinafter, referred to as Compound of Present Invention (77)) represented by the following formula.

(77)

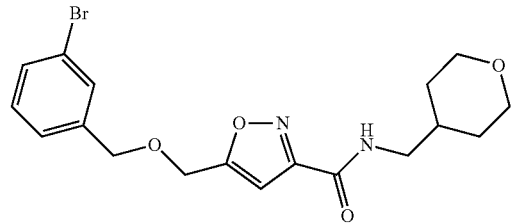

¹H-NMR (CDCl₃, TMS, δ(ppm)): 1.40 (2H, q), 1.67 (2H, d), 1.85 (1H, m), 3.38 (4H, m), 3.98 (2H, s), 4.57 (2H, s), 4.65 (2H, s), 6.72 (1H, s), 6.87 (1H, br.s), 7.21-7.26 (2H, m), 7.45 (1H, d), 7.51 (1H, s)

Production Example 73

5-[3-Trifluoromethoxybenzyl)oxymethyl]isoxazole-3-carboxylic acid (0.70 g, 2.2 mmol) was added to chloroform (amylene addition product) (15 mL), and cooled to 0° C. Triethylamine (0.61 ml, 4.4 mmol), 1-ethyl-3-(3-dimethylaminopropyl) carbodiimide hydrochloride (0.51 g, 2.6 mmol) and 1-hydroxybenzotriazole (0.36 g, 2.6 mmol) were added thereto, and the mixture was stirred for 10 minutes. Tetrahydrofuran-3-ylmethylamine (0.24 g, 2.4 mmol) was added to the mixture, and the mixture was stirred at room temperature for 12 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.30 g of N-(tetrahydrofuran-3-ylmethyl)-5-(3-trifluoromethoxybenzyloxymethyl)isoxazole-3-carboxamide (hereinafter, referred to as Compound of Present Invention (78)) represented by the following formula.

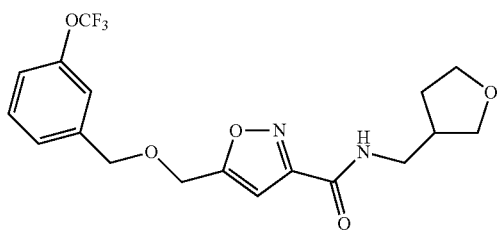

(78)

$^1$H-NMR (CDCl$_3$, TMS, δ(ppm)): 1.64-1.73 (m, 1H), 2.08 (m, 1H), 2.57 (m, 1H), 3.47 (t, 2H), 3.58 (m, 1H), 3.95-3.75 (m, 2H), 4.16 (s, 2H), 4.67 (s, 2H), 6.73 (s, 1H), 6.93 (s, 1H), 6.72 (s, 1H), 7.18 (m, 2H), 7.28 (d, 1H), 7.39 (t, 1H)

Production Example 74

5-(3-Trifluoromethoxybenzyloxymethyl)isoxazole-3-carboxylic acid (0.50 g, 1.6 mmol) was added to chloroform (amylene addition product) (12 mL), and cooled to 0° C. Triethylamine (0.44 ml, 3.2 mmol), 1-ethyl-3-(3-dimethylaminopropyl) carbodiimide hydrochloride (0.36 g, 1.9 mmol) and 1-hydroxybenzotriazole (0.26 g, 1.9 mmol) were added thereto, and the mixture was stirred for 10 minutes. Tetrahydropyran-4-ylmethylamine (0.20 g, 1.7 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.35 g of N-(tetrahydropyran-4-ylmethyl)-5-[3-trifluoromethoxybenzyl)oxymethyl]isoxazole-3-carboxamide (hereinafter, referred to as Compound of Present Invention (79)) represented by the following formula.

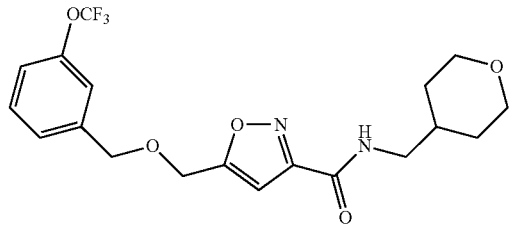

(79)

$^1$H-NMR (CDCl$_3$, TMS, δ(ppm)): 1.39 (q, 2H), 1.66 (d, 2H), 1.86 (m, 1H), 3.34-3.33 (m, 4H), 3.98 (dd, 2H), 4.61 (s, 2H), 4.67 (s, 2H), 6.73 (s, 1H), 6.88 (brs, 1H), 7.18 (m, 2H), 7.26 (d, 1H), 7.39 (t, 1H)

Production Example 75

5-(3-Trifluoromethylthiobenzyloxymethyl)isoxazole-3-carboxylic acid (0.30 g, 0.9 mmol) was added to chloroform (amylene addition product) (12 mL), and cooled to 0° C. Triethylamine (0.18 ml, 1.4 mmol), 1-ethyl-3-(3-dimethylaminopropyl) carbodiimide hydrochloride (0.26 g, 1.4 mmol) and 1-hydroxybenzotriazole (0.18 g, 1.4 mmol) were added thereto, and the mixture was stirred for 10 minutes. Tetrahydrofuran-3-ylmethylamine (0.10 g, 1.0 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.15 g of N-(tetrahydrofuran-3-ylmethyl)-5-(3-trifluoromethylthiobenzyloxymethyl)isoxazole-3-carboxamide (hereinafter, referred to as Compound of Present Invention (80)) represented by the following formula.

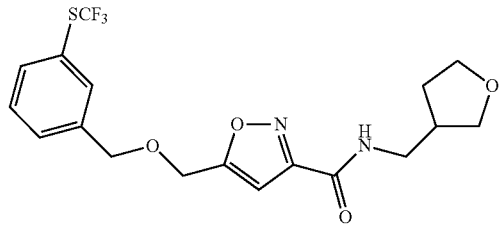

(80)

$^1$H-NMR (CDCl$_3$, TMS, δ(ppm)): 1.70-1.65 (m, 1H), 2.11-2.06 (m, 1H), 2.59-2.56 (m, 1H), 3.47 (t, 2H), 3.61-3.57 (m, 1H), 3.79-3.73 (m, 1H), 3.92-3.83 (m, 2H), 4.63 (s, 2H), 4.68 (s, 2H), 6.73 (s, 1H), 6.93 (s, 1H), 7.48-7.41 (m, 2H), 7.63-7.60 (m, 2H)

Production Example 76

5-(3-Trifluoromethylthiobenzyloxymethyl)isoxazole-3-carboxylic acid (0.30 g, 0.9 mmol) was added to chloroform (amylene addition product) (12 mL), and cooled to 0° C. Triethylamine (0.18 ml, 1.4 mmol), 1-ethyl-3-(3-dimethylaminopropyl) carbodiimide hydrochloride (0.26 g, 1.4 mmol) and 1-hydroxybenzotriazole (0.18 g, 1.4 mmol) were added thereto, and the mixture was stirred for 10 minutes.

Tetrahydropyran-4-ylmethylamine (0.11 g, 1.0 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.23 g of N-(tetrahydropyran-4-ylmethyl)-5-(3-trifluoromethylthiobenzyloxymethyl)isoxazole-3-carboxamide (hereinafter, referred to as Compound of Present Invention (81)) represented by the following formula.

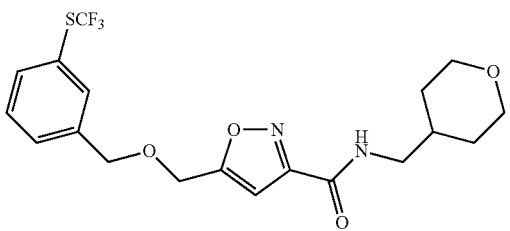

(81)

$^1$H-NMR (CDCl$_3$, TMS, δ(ppm)): 1.42-1.36 (m, 2H), 1.68-1.65 (m, 2H), 1.87-1.84 (m, 1H), 3.41-3.33 (m, 4H), 4.00-3.97 (m, 2H), 4.62 (s, 2H), 4.68 (s, 2H), 6.73 (s, 1H), 6.87 (s, 1H), 7.48-7.41 (m, 2H), 7.63-7.60 (m, 2H)

Production Example 77

5-(3-Methylbenzyloxymethyl)isoxazole-3-carboxylic acid (0.50 g, 2.0 mmol) was added to chloroform (amylene addition product) (12 mL), and cooled to 0° C. Triethylamine (0.40 ml, 3.0 mmol), 1-ethyl-3-(3-dimethylaminopropyl) carbodiimide hydrochloride (0.58 g, 3.0 mmol) and 1-hydroxybenzotriazole (0.41 g, 3.0 mmol) were added thereto, and the mixture was stirred for 10 minutes. Tetrahydrofuran-3-ylmethylamine (0.22 g, 2.2 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.15 g of N-(tetrahydrofuran-3-ylmethyl)-5-(3-methylbenzyloxymethyl)isoxazole-3-carboxamide (hereinafter, referred to as Compound of Present Invention (82)) represented by the following formula.

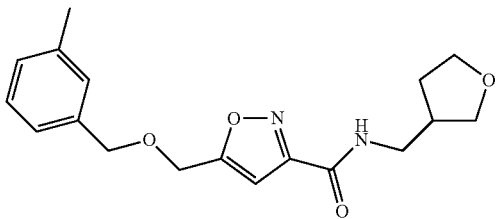

(82)

$^1$H-NMR (CDCl$_3$, TMS, δ(ppm)): 1.71-1.63 (1H, m), 2.12-2.05 (1H, m), 2.36 (3H, s), 2.60-2.54 (1H, m), 3.46 (2H, t), 3.60-3.57 (1H, m), 3.79-3.73 (1H, m), 3.93-3.85 (2H, m), 4.56 (2H, s), 4.63 (2H, s), 6.72 (1H, s), 6.95 (1H, s), 7.16-7.12 (3H, m), 7.27-7.23 (1H, m)

Production Example 78

5-(3-Methylbenzyloxymethyl)isoxazole-3-carboxylic acid (0.50 g, 2.0 mmol) was added to chloroform (amylene addition product) (12 mL), and cooled to 0° C. Triethylamine (0.40 ml, 3.0 mmol), 1-ethyl-3-(3-dimethylaminopropyl) carbodiimide hydrochloride (0.58 g, 3.0 mmol) and 1-hydroxybenzotriazole (0.41 g, 3.0 mmol) were added thereto, and the mixture was stirred for 10 minutes. Tetrahydropyran-4-ylmethylamine (0.26 g, 2.2 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.30 g of N-(tetrahydropyran-4-ylmethyl)-5-(3-methylbenzyloxymethyl)isoxazole-3-carboxamide (hereinafter, referred to as Compound of Present Invention (83)) represented by the following formula.

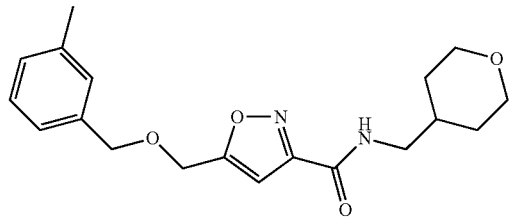

(83)

$^1$H-NMR (CDCl$_3$, TMS, δ(ppm)): 1.43-1.32 (2H, m), 1.65-1.57 (2H, m), 1.88-1.83 (1H, m), 2.36 (3H, s), 3.41-3.33 (4H, m), 4.00-3.96 (2H, m), 4.56 (2H, s), 4.64 (2H, s), 6.72 (1H, s), 6.87 (1H, s), 7.16-7.12 (3H, m), 7.27-7.23 (1H, m)

Production Example 79

5-(3-Methoxybenzyloxymethyl)isoxazole-3-carboxylic acid (0.50 g, 1.9 mmol) was added to chloroform (amylene addition product) (12 mL), and cooled to 0° C. Triethylamine (0.40 ml, 3.0 mmol), 1-ethyl-3-(3-dimethylaminopropyl) carbodiimide hydrochloride (0.54 g, 2.9 mmol) and 1-hydroxybenzotriazole (0.38 g, 2.9 mmol) were added thereto, and the mixture was stirred for 10 minutes. Tetrahydrofuran-3-ylmethylamine (0.21 g, 2.1 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydrofuran-3-ylmethyl)-5-(3-methoxybenzyloxymethyl)isoxazole-3-carboxamide (hereinafter, referred to as Compound of Present Invention (84)) represented by the following formula.

(84)

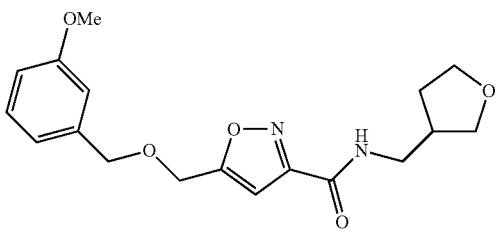

¹H-NMR(CDCl₃, TMS, δ(ppm)): 1.70-1.63 (1H, m), 2.10-2.06 (1H, m), 2.59-2.56 (1H, m), 3.46 (2H, t), 3.60-3.57 (1H, m), 3.94-3.73 (6H, m), 4.58 (2H, s), 4.64 (2H, s), 6.72 (1H, s), 6.94-6.85 (4H, m), 7.29 (1H, d)

Production Example 80

5-(3-Methoxybenzyloxymethyl)isoxazole-3-carboxylic acid (0.50 g, 1.9 mmol) was added to chloroform (amylene addition product) (12 mL), and cooled to 0° C. Triethylamine (0.40 ml, 3.0 mmol), 1-ethyl-3-(3-dimethylaminopropyl)carbodiimide hydrochloride (0.54 g, 2.9 mmol) and 1-hydroxybenzotriazole (0.38 g, 2.9 mmol) were added thereto, and the mixture was stirred for 10 minutes. Tetrahydropyran-4-ylmethylamine (0.26 g, 2.2 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.32 g of N-(tetrahydropyran-4-ylmethyl)-5-(3-methoxybenzyloxymethyl)isoxazole-3-carboxamide (hereinafter, referred to as Compound of Present Invention (85)) represented by the following formula.

(85)

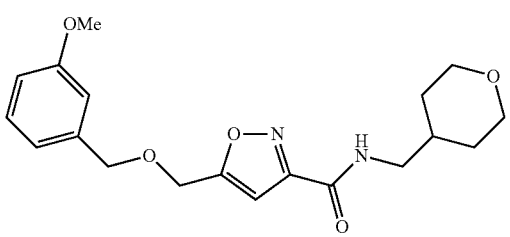

¹H-NMR (CDCl₃, TMS, δ(ppm)): 1.43-1.32 (2H, m), 1.68 (2H, d), 1.88-1.83 (1H, m), 3.41-3.33 (4H, m), 3.81 (3H, s), 4.00-3.96 (2H, m), 4.58 (2H, s), 4.64 (2H, s), 6.72 (1H, s), 6.92-6.85 (4H, m), 7.29 (1H, d)

Production Example 81

5-(3-Cyanobenzyloxymethyl)isoxazole-3-carboxylic acid (0.50 g, 1.9 mmol) was added to chloroform (amylene addition product) (12 mL), and cooled to 0° C. Triethylamine (0.40 ml, 3.0 mmol), 1-ethyl-3-(3-dimethylaminopropyl)carbodiimide hydrochloride (0.54 g, 2.9 mmol) and 1-hydroxybenzotriazole (0.38 g, 2.9 mmol) were added thereto, and the mixture was stirred for 10 minutes. Tetrahydrofuran-3-ylmethylamine (0.21 g, 2.1 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydrofuran-3-ylmethyl)-5-(3-cyanobenzyloxymethyl)isoxazole-3-carboxamide (hereinafter, referred to as Compound of Present Invention (86)) represented by the following formula.

(86)

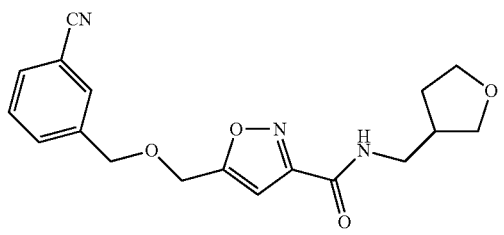

¹H-NMR (CDCl₃, TMS, δ(ppm)): 1.70-1.67 (m, 1H), 2.11-2.06 (m, 1H), 2.59-2.56 (m, 1H), 3.47 (t, 2H), 3.61-3.57 (m, 1H), 3.79-3.75 (m, 1H), 3.94-3.83 (m, 2H), 4.63 (s, 2H), 4.70 (s, 2H), 6.74 (s, 1H), 6.93 (s, 1H), 7.50-7.46 (m, 1H), 7.64-7.57 (m, 3H)

Production Example 82

5-(3-Cyanobenzyloxymethyl)isoxazole-3-carboxylic acid (0.50 g, 1.9 mmol) was added to chloroform (amylene addition product) (12 mL), and cooled to 0° C. Triethylamine (0.40 ml, 3.0 mmol), 1-ethyl-3-(3-dimethylaminopropyl)carbodiimide hydrochloride (0.54 g, 2.9 mmol) and 1-hydroxybenzotriazole (0.38 g, 2.9 mmol) were added thereto, and the mixture was stirred for 10 minutes. Tetrahydropyran-4-ylmethylamine (0.26 g, 2.2 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.40 g of N-(tetrahydropyran-4-ylmethyl)-5-(3-cyanobenzyloxymethyl)isoxazole-3-carboxamide (hereinafter, referred to as Compound of Present Invention (87)) represented by the following formula.

(87)

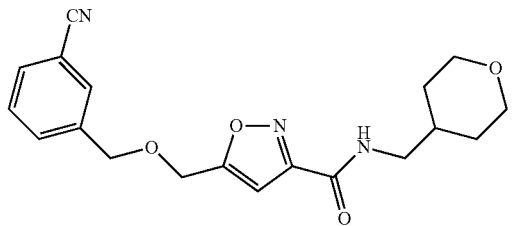

¹H-NMR (CDCl₃, TMS, δ(ppm)): 1.43-1.33 (m, 2H), 1.69-1.65 (m, 2H), 1.87-1.84 (m, 1H), 3.41-3.34 (m, 4H), 4.01-3.97 (m, 2H), 4.63 (s, 2H), 4.70 (s, 2H), 6.74 (s, 1H), 6.88 (s, 1H), 7.50-7.46 (m, 1H), 7.64-7.57 (m, 3H)

Production Example 83

5-(3-Methylthiobenzyloxymethyl)isoxazole-3-carboxylic acid (0.35 g, 1.3 mmol) was added to chloroform (amylene addition product) (12 mL), and cooled to 0° C. Triethylamine (0.26 ml, 1.9 mmol), 1-ethyl-3-(3-dimethylaminopropyl)carbodiimide hydrochloride (0.36 g, 1.9 mmol) and 1-hydroxybenzotriazole (0.25 g, 1.9 mmol) were added thereto, and the mixture was stirred for 10 minutes. Tetrahydrofuran-3-ylmethylamine (0.14 g, 1.4 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.05 g of N-(tetrahydrofuran-3-ylmethyl)-5-(3-methylthiobenzyloxymethyl)isoxazole-3-carboxamide (hereinafter, referred to as Compound of Present Invention (88)) represented by the following formula.

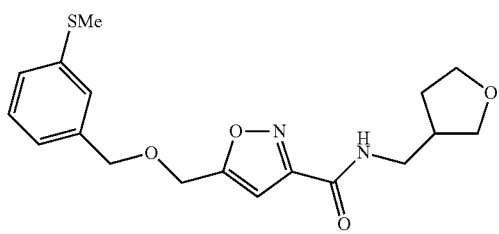

(88)

$^1$H-NMR(CDCl$_3$, TMS, δ(ppm)): 1.69 (m, 1H), 2.09 (q, 1H), 2.49 (s, 3H), 2.61-2.54 (m, 1H), 3.48-3.42 (m, 2H), 3.60-3.53 (m, 1H), 3.79-3.73 (m, 1H), 3.95-3.83 (m, 2H), 4.57 (s, 2H), 4.61 (s, 2H), 6.72 (s, 1H), 6.94 (brs, 1H), 7.11 (d, 1H), 7.23-7.19 (m, 2H), 7.30 (m, 1H)

Production Example 84

5-(4-Fluorobenzyloxymethyl)isoxazole-3-carboxylic acid (0.60 g, 2.4 mmol) was added to chloroform (amylene addition product) (12 mL), and cooled to 0° C. Triethylamine (0.50 ml, 3.6 mmol), 1-ethyl-3-(3-dimethylaminopropyl)carbodiimide hydrochloride (0.68 g, 3.6 mmol) and 1-hydroxybenzotriazole (0.48 g, 3.6 mmol) were added thereto, and the mixture was stirred for 10 minutes. Tetrahydrofuran-3-ylmethylamine (0.36 g, 3.6 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydrofuran-3-ylmethyl)-5-(4-fluorobenzyloxymethyl)isoxazole-3-carboxamide (hereinafter, referred to as Compound of Present Invention (89)) represented by the following formula.

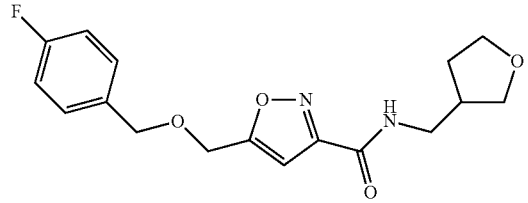

(89)

$^1$H-NMR (CDCl$_3$, TMS, δ(ppm)): 1.69-1.65 (m, 1H), 2.11-2.06 (m, 1H), 2.59-2.56 (m, 1H), 3.46 (t, 2H), 3.60-3.57 (m, 1H), 3.79-3.75 (m, 1H), 3.94-3.83 (m, 2H), 4.56 (s, 2H), 4.64 (s, 2H), 6.72 (s, 1H), 6.92 (s, 1H), 7.07-7.03 (m, 2H), 7.33-7.31 (m, 2H)

Production Example 85

5-(4-Fluorobenzyloxymethyl)isoxazole-3-carboxylic acid (0.60 g, 2.4 mmol) was added to chloroform (amylene addition product) (12 mL), and cooled to 0° C. Triethylamine (0.50 ml, 3.6 mmol), 1-ethyl-3-(3-dimethylaminopropyl)carbodiimide hydrochloride (0.68 g, 3.6 mmol) and 1-hydroxybenzotriazole (0.48 g, 3.6 mmol) were added thereto, and the mixture was stirred for 10 minutes. Tetrahydropyran-4-ylmethylamine (0.30 g, 2.6 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.39 g of N-(tetrahydropyran-4-ylmethyl)-5-(4-fluorobenzyloxymethyl)isoxazole-3-carboxamide (hereinafter, referred to as Compound of Present Invention (90)) represented by the following formula.

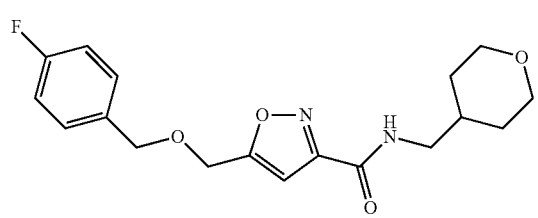

(90)

$^1$H-NMR (CDCl$_3$, TMS, δ(ppm)): 1.43-1.32 (m, 2H), 1.68-1.64 (m, 2H), 1.89-1.82 (m, 1), 3.41-3.33 (m, 4H), 4.00-3.97 (m, 2H), 4.56 (s, 2H), 4.64 (s, 2H), 6.72 (s, 1H), 6.88 (s, 1H), 7.07-7.03 (m, 2H), 7.33-7.30 (m, 2H)

Production Example 86

5-(4-Bromobenzyloxyethyl)isoxazole-3-carboxylic acid (0.60 g, 1.9 mmol) was added to chloroform (amylene addition product) (12 mL), and cooled to 0° C. Triethylamine (0.54 ml, 3.8 mmol), 1-ethyl-3-(3-dimethylaminopropyl)carbodiimide hydrochloride (0.44 g, 2.3 mmol) and 1-hydroxybenzotriazole (0.31 g, 2.3 mmol) were added thereto, and the mixture was stirred for 10 minutes. Tetrahydrofuran-3-ylmethylamine (0.21 g, 2.1 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.50 g of N-(tetrahydrofuran-3-ylmethyl)-5-(4-bromobenzyloxymethyl)isoxazole-3-carboxamide (hereinafter, referred to as Compound of Present Invention (91)) represented by the following formula.

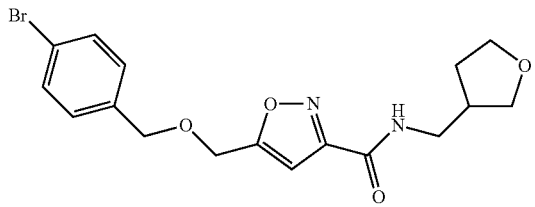

(91)

$^1$H-NMR (CDCl$_3$, TMS, δ(ppm)): 1.71-1.63 (m, 1H), 2.13-2.04 (m, 1H), 2.61-2.54 (m, 1H), 3.48-3.45 (t, 2H), 3.60-3.57 (m, 1H), 3.79-3.73 (m, 1H), 3.94-3.83 (m, 2H), 4.55 (s, 1H), 4.64 (s, 2H), 6.72 (s, 1H), 6.94 (br, s, 1H), 7.22-7.20 (d, 2H), 7.26 (s, 1H), 7.50-7.48 (d, 2H)

Production Example 87

5-(4-Bromobenzyloxymethyl)isoxazole-3-carboxylic acid (0.60 g, 1.9 mmol) was added to chloroform (amylene addition product) (12 mL), and cooled to 0° C. Triethylamine (0.54 ml, 3.8 mmol), 1-ethyl-3-(3-dimethylaminopropyl) carbodiimide hydrochloride (0.44 g, 2.3 mmol) and 1-hydroxybenzotriazole (0.31 g, 2.3 mmol) were added thereto, and the mixture was stirred for 10 minutes. Tetrahydropyran-4-ylmethylamine (0.24 g, 2.1 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.40 g of N-(tetrahydropyran-4-ylmethyl)-5-(4-bromobenzyloxymethyl)isoxazole-3-carboxamide (hereinafter, referred to as Compound of Present Invention (92)) represented by the following formula.

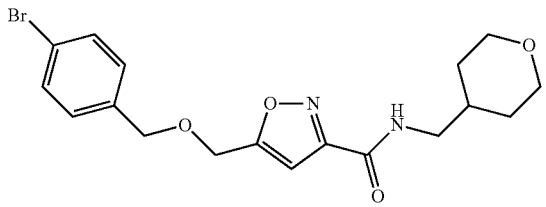

(92)

$^1$H-NMR (CDCl$_3$, TMS, δ(ppm)): 1.43-1.32 (m, 2H), 1.68-1.59 (m, 2H), 1.89-1.83 (m, 1H), 3.41-3.34 (m, 4H), 4.00-3.96 (dd, 2H), 4.55 (s, 1H), 4.64 (s, 2H), 6.72 (s, 1H), 6.88 (brs, 1H), 7.23-7.21 (d, 2H), 7.26 (s, 1H), 7.50-7.48 (d, 2H)

Production Example 88

5-(4-Trifluoromethoxybenzyloxymethyl)isoxazole-3-carboxylic acid (0.30 g, 0.9 mmol) was added to chloroform (amylene addition product) (10 mL), and cooled to 0° C. Triethylamine (0.20 ml, 1.4 mmol), 1-ethyl-3-(3-dimethylaminopropyl) carbodiimide hydrochloride (0.27 g, 1.4 mmol) and 1-hydroxybenzotriazole (0.19 g, 1.4 mmol) were added thereto, and the mixture was stirred for 10 minutes. Tetrahydrofuran-3-ylmethylamine (0.11 g, 1.1 mmol) was added to the mixture, and the mixture was stirred at room temperature for 16 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.17 g of N-(tetrahydrofuran-3-ylmethyl)-5-(4-trifluoromethoxybenzyloxymethyl)isoxazole-3-carboxamide (hereinafter, referred to as Compound of Present Invention (93)) represented by the following formula.

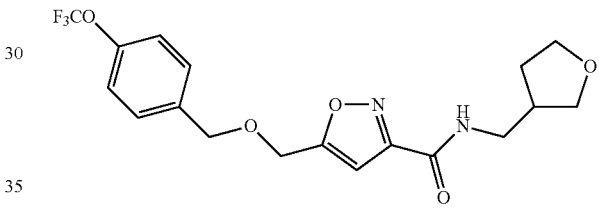

(93)

$^1$H-NMR (CDCl$_3$, TMS, δ(ppm)): 1.70-1.65 (m, 1H), 2.11-2.06 (m, 1H), 2.59-2.56 (m, 1H), 3.46 (t, 2H), 3.60-3.57 (m, 1H), 3.79-3.73 (m, 1H), 3.94-3.83 (m, 2H), 4.60 (s, 2H), 4.66 (s, 2H), 6.73 (s, 1H), 6.93 (s, 1H), 7.21 (d, 2H), 7.37 (d, 2H)

Production Example 89

5-(4-Trifluoromethoxybenzyloxybenzyloxymethyl)isoxazole-3-carboxylic acid (0.30 g, 0.9 mmol) was added to chloroform (amylene addition product) (10 mL), and cooled to 0° C. Triethylamine (0.20 ml, 1.4 mmol), 1-ethyl-3-(3-dimethylaminopropyl) carbodiimide hydrochloride (0.27 g, 1.4 mmol) and 1-hydroxybenzotriazole (0.19 g, 1.4 mmol) were added thereto, and the mixture was stirred for 10 minutes. Tetrahydropyran-4-ylmethylamine (0.12 g, 1.0 mmol) was added to the mixture, and the mixture was stirred at room temperature for 16 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.19 g of N-(tetrahydropyran-4-ylmethyl)-5-(4-trifluoromethoxybenzyloxymethyl)isoxazole-3-carboxamide (hereinafter, referred to as Compound of Present Invention (94)) represented by the following formula.

(94)

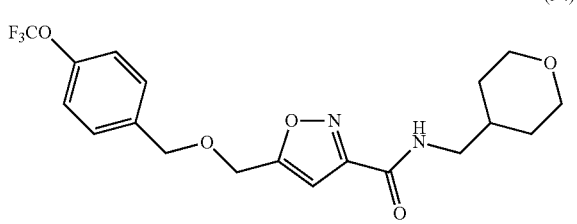

¹H-NMR (CDCl₃, TMS, δ(ppm)): 1.42-1.34 (m, 2H), 1.68-1.65 (m, 2H), 1.87-1.84 (m, 1H), 3.41-3.33 (m, 4H), 4.00-3.97 (m, 2H), 4.60 (s, 2H), 4.66 (s, 2H), 6.73 (s, 1H), 6.87 (s, 1H), 7.21 (d, 2H), 7.37 (d, 2H)

Production Example 90

5-(4-Trifluoromethylthiobenzyloxymethyl)isoxazole-3-carboxylic acid (0.50 g, 1.5 mmol) was added to chloroform (amylene addition product) (10 mL), and cooled to 0° C. Triethylamine (0.30 ml, 2.3 mmol), 1-ethyl-3-(3-dimethylaminopropyl) carbodiimide hydrochloride (0.43 g, 2.3 mmol) and 1-hydroxybenzotriazole (0.30 g, 2.3 mmol) were added thereto, and the mixture was stirred for 10 minutes. Tetrahydrofuran-3-ylmethylamine (0.17 g, 1.7 mmol) was added to the mixture, and the mixture was stirred at room temperature for 16 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.11 g of N-(tetrahydrofuran-3-ylmethyl)-5-(4-trifluoromethylthiobenzyloxymethyl)isoxazole-3-carboxamide (hereinafter, referred to as Compound of Present Invention (95)) represented by the following formula.

(95)

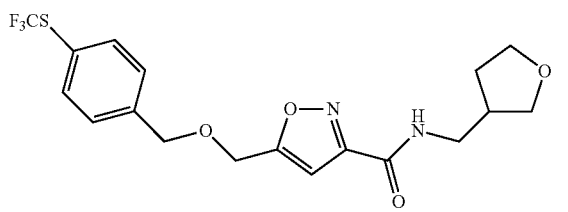

¹H-NMR (CDCl₃, TMS, δ(ppm)): 1.70-1.65 (m, 1H), 2.11-2.06 (m, 1H), 2.59-2.56 (m, 1H), 3.47 (t, 2H), 3.60-3.57 (m, 1H), 3.79-3.73 (m, 1H), 3.94-3.83 (m, 2H), 4.64 (s, 2H), 4.69 (s, 2H), 6.74 (s, 1H), 6.92 (s, 1H), 7.40 (d, 2H), 7.65 (d, 2H)

Production Example 91

5-(4-Trifluoromethylthiobenzyloxymethyl)isoxazole-3-carboxylic acid (0.50 g, 1.5 mmol) was added to chloroform (amylene addition product) (10 mL), and cooled to 0° C. Triethylamine (0.30 ml, 2.3 mmol), 1-ethyl-3-(3-dimethylaminopropyl) carbodiimide hydrochloride (0.43 g, 2.3 mmol) and 1-hydroxybenzotriazole (0.30 g, 2.3 mmol) were added thereto, and the mixture was stirred for 10 minutes. Tetrahydropyran-4-ylmethylamine (0.19 g, 1.7 mmol) was added to the mixture, and the mixture was stirred at room temperature for 16 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.12 g of N-(tetrahydropyran-4-ylmethyl)-5-(4-trifluoromethylthiobenzyloxymethyl)isoxazole-3-carboxamide (hereinafter, referred to as Compound of Present Invention (96)) represented by the (96)

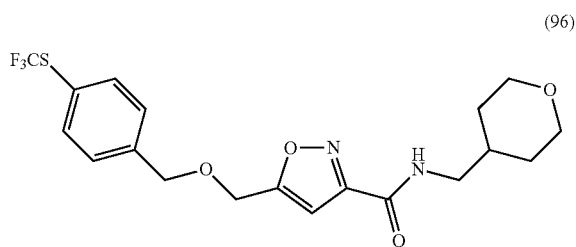

¹H-NMR (CDCl₃, TMS, δ(ppm)): 1.42-1.34 (m, 2H), 1.65-1.60 (m, 2H), 1.87-1.84 (m, 1H), 3.41-3.33 (m, 4H), 4.00-3.96 (m, 2H), 4.64 (s, 2H), 4.69 (s, 2H), 6.74 (s, 1H), 6.92 (s, 1H), 7.40 (d, 2H), 7.65 (d, 2H)

Production Example 92

5-(4-Methylbenzyloxymethyl)isoxazole-3-carboxylic acid (0.70 g, 2.8 mmol) was added to chloroform (amylene addition product) (20 mL), and cooled to 0° C. Triethylamine (0.79 ml, 5.7 mmol), 1-ethyl-3-(3-dimethylaminopropyl) carbodiimide hydrochloride (0.65 g, 3.4 mmol) and 1-hydroxybenzotriazole (0.46 g, 3.4 mmol) were added thereto, and the mixture was stirred for 10 minutes. Tetrahydrofuran-3-ylmethylamine (0.31 g, 3.1 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.44 g of N-(tetrahydrofuran-3-ylmethyl)-5-(4-methylbenzyloxymethyl)isoxazole-3-carboxamide (hereinafter, referred to as Compound of Present Invention (97)) represented by the following formula.

(97)

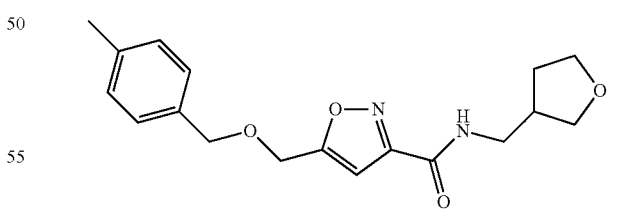

¹H-NMR (CDCl₃, TMS, δ(ppm)): 1.66 (m, 1H), 2.08 (m, 1H), 2.35 (s, 3H), 2.57 (m, 1H), 3.46 (t, 2H), 3.59 (m, 1H), 3.85 (m, 3H), 4.56 (s, 2H), 4.61 (s, 2H), 6.71 (s, 1H), 6.95 (brs, 1H), 7.17 (d, 2H), 7.25 (d, 2H)

Production Example 93

5-(4-Methylbenzyloxymethyl)isoxazole-3-carboxylic acid (0.70 g, 2.8 mmol) was added to chloroform (amylene addition product) (20 mL), and cooled to 0° C. Triethylamine (0.79 ml, 5.7 mmol), 1-ethyl-3-(3-dimethylaminopropyl)carbodiimide hydrochloride (0.65 g, 3.4 mmol) and 1-hydroxybenzotriazole (0.46 g, 3.4 mmol) were added thereto, and the mixture was stirred for 10 minutes. Tetrahydropyran-4-ylmethylamine (0.49 g, 4.2 mmol) was added to the mixture, and the mixture was stirred at room temperature for 16 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.45 g of N-(tetrahydropyran-4-ylmethyl)-5-(4-methylbenzyloxymethyl)isoxazole-3-carboxamide (hereinafter, referred to as Compound of Present Invention (98)) represented by the following formula.

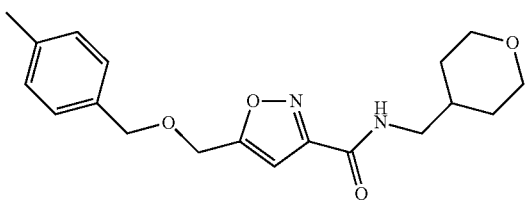

(98)

$^1$H-NMR(CDCl$_3$, TMS, δ(ppm)): 1.38 (q, 2H), 1.66 (d, 2H), 1.86 (m, 1H), 2.35 (s, 3H), 3.36 (q, 4H), 3.98 (dd, 2H), 4.56 (s, 2H), 4.61 (s, 2H), 6.70 (s, 1H), 6.81 (brs, 1H), 7.16 (d, 2H), 7.24 (d, 2H)

Production Example 94

5-(4-Methoxybenzyloxymethyl)isoxazole-3-carboxylic acid (0.50 g, 1.9 mmol) was added to chloroform (amylene addition product) (15 mL), and cooled to 0° C. Triethylamine (0.40 ml, 2.8 mmol), 1-ethyl-3-(3-dimethylaminopropyl)carbodiimide hydrochloride (0.44 g, 2.3 mmol) and 1-hydroxybenzotriazole (0.31 g, 2.3 mmol) were added thereto, and the mixture was stirred for 10 minutes. Tetrahydrofuran-3-ylmethylamine (0.31 g, 3.1 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.30 g of N-(tetrahydrofuran-3-ylmethyl)-5-(4-methoxybenzyloxymethyl)isoxazole-3-carboxamide (hereinafter, referred to as Compound of Present Invention (99)) represented by the following formula.

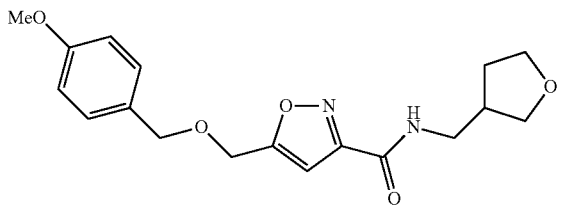

(99)

$^1$H-NMR (CDCl$_3$, TMS, δ(ppm)): 1.75-1.6 (m, 1H), 2.15-2.0 (m, 1H), 2.6 (t, 1H), 3.45 (t, 2H), 3.4 (dd, 1H), 4.0-3.7 (m, 6H), 4.5 (s, 2H), 4.65 (s, 2H), 6.7 (s, 1H), 6.9 (d, 3H), 7.30 (d, 2H)

Production Example 95

5-[(4-Methoxybenzyl)oxymethyl]isoxazole-3-carboxylic acid (0.50 g, 1.9 mmol) was added to chloroform (amylene addition product) (15 mL), and cooled to 0° C. Triethylamine (0.40 ml, 2.8 mmol), 1-ethyl-3-(3-dimethylaminopropyl)carbodiimide hydrochloride (0.44 g, 2.3 mmol) and 1-hydroxybenzotriazole (0.31 g, 2.3 mmol) were added thereto, and the mixture was stirred for 10 minutes. Tetrahydropyran-4-ylmethylamine (0.49 g, 4.2 mmol) was added to the mixture, and the mixture was stirred at room temperature for 16 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydropyran-4-ylmethyl)-5-(4-methoxybenzyloxymethyl)isoxazole-3-carboxamide (hereinafter, referred to as Compound of Present Invention (100)) represented by the following formula.

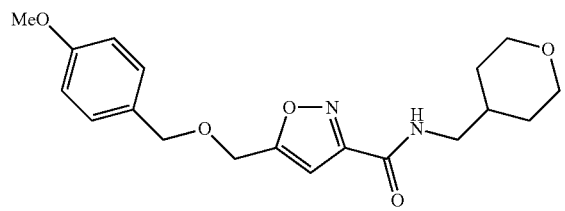

(100)

$^1$H-NMR (CDCl$_3$, TMS, δ(ppm)): 1.45-1.3 (q, 2H), 1.65 (d, 2H), 1.95-1.8 (m, 1H), 3.45-3.30 (t, 4H), 3.8 (s, 3H), 4.0 (dd, 2H), 4.5 (s, 2H), 4.65 (s, 2H), 6.7 (s, 1H), 6.9 (d, 3H), 7.30 (d, 2H)

Production Example 96

5-(4-Cyanobenzyloxymethyl)isoxazole-3-carboxylic acid (0.60 g, 2.3 mmol) was added to chloroform (amylene addition product) (15 mL), and cooled to 0° C. Triethylamine (0.48 ml, 3.5 mmol), 1-ethyl-3-(3-dimethylaminopropyl)carbodiimide hydrochloride (0.58 g, 3.1 mmol) and 1-hydroxybenzotriazole (0.41 g, 3.1 mmol) were added thereto, and the mixture was stirred for 10 minutes. Tetrahydrofuran-3-ylmethylamine (0.26 g, 2.6 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.35 g of N-(tetrahydrofuran-3-ylmethyl)-5-(4-cyanobenzyloymethyl)isoxazole-3-carboxamide (hereinafter, referred to as Compound of Present Invention (101)) represented by the following formula.

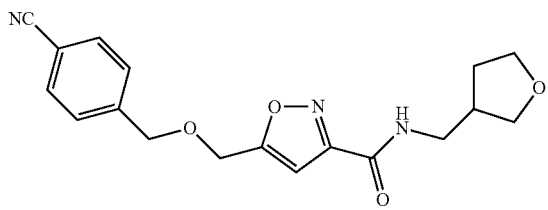

(101)

¹H-NMR (CDCl₃, TMS, δ(ppm)): 1.72-1.63 (m, 1H), 2.13-2.04 (m, 1H), 2.58 (t, 1H), 3.47 (t, 2H), 3.60 (q, 1H), 3.75 (q, 1H), 3.94-3.83 (m, 2H), 4.68 (d, 4H), 6.75 (s, 1H), 6.93 (brs, 1H), 7.45 (d, 2H), 7.66 (d, 2H)

Production Example 97

5-(4-Cyanobenzyloxymethyl)isoxazole-3-carboxylic acid (0.60 g, 2.3 mmol) was added to chloroform (amylene addition product) (15 mL), and cooled to 0° C. Triethylamine (0.48 ml, 3.5 mmol), 1-ethyl-3-(3-dimethylaminopropyl) carbodiimide hydrochloride (0.58 g, 3.1 mmol) and 1-hydroxybenzotriazole (0.41 g, 3.1 mmol) were added thereto, and the mixture was stirred for 10 minutes. Tetrahydropyran-4-ylmethylamine (0.29 g, 2.6 mmol) was added to the mixture, and the mixture was stirred at room temperature for 16 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.45 g of N-(tetrahydropyran-4-ylmethyl)-5-(4-cyanobenzyloxymethyl)isoxazole-3-carboxamide (hereinafter, referred to as Compound of Present Invention (102)) represented by the following formula.

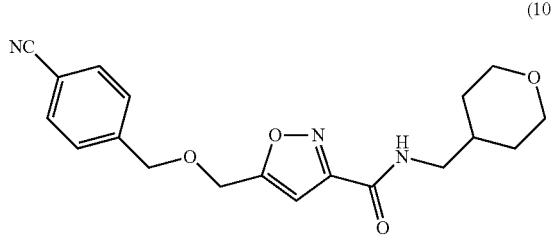

(102)

¹H-NMR (CDCl₃, TMS, δ(ppm)): 1.43-1.33 (dd, 2H), 1.66 (dd, 2H), 1.88-1.84 (m, 1H), 3.41-3.34 (m, 4H), 3.99 (dd, 2H), 4.65 (s, 2H), 4.7 (s, 2H), 6.74 (s, 1H), 6.87 (brs, 1H), 7.45 (d, 2H), 7.66 (d, 2H)

Production Example 98

5-(4-Methylthiobenzyloxymethyl)isoxazole-3-carboxylic acid (0.50 g, 1.8 mmol) was added to chloroform (amylene addition product) (15 mL), and cooled to 0° C. Triethylamine (0.50 ml, 2.7 mmol), 1-ethyl-3-(3-dimethylaminopropyl) carbodiimide hydrochloride (0.51 g, 2.1 mmol) and 1-hydroxybenzotriazole (0.36 g, 2.7 mmol) were added thereto, and the mixture was stirred for 10 minutes. Tetrahydrofuran-3-ylmethylamine (0.31 g, 3.1 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.11 g of N-(tetrahydrofuran-3-ylmethyl)-5-(4-methylthiobenzyloxymethyl)isoxazole-3-carboxamide (hereinafter, referred to as Compound of Present Invention (103)) represented by the following formula.

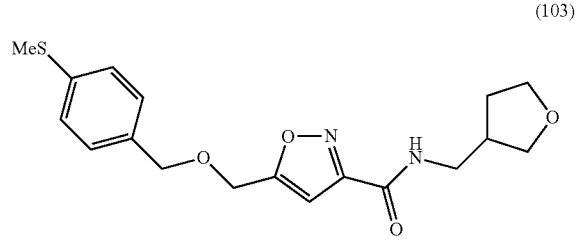 [SMILES: CSc1ccc(COCc2cc(C(=O)NCC3CCOC3)no2)cc1]

(103)

¹H-NMR (CDCl₃, TMS, δ(ppm)): 1.61-1.56 (m, 1H), 1.95-1.89 (m, 1H), 2.49-2.46 (m, 4H), 3.22 (t, 2H), 3.46-3.42 (m, 1H), 3.73-3.59 (m, 3H), 4.52 (s, 2H), 4.68 (s, 2H), 6.81 (s, 1H), 7.30-7.23 (m, 4H), 8.90 (t, 1H)

Production Example 99

5-(4-Methylthiobenzyloxymethyl)isoxazole-3-carboxylic acid (0.50 g, 1.8 mmol) was added to chloroform (amylene addition product) (15 mL), and cooled to 0° C. Triethylamine (0.50 ml, 2.7 mmol), 1-ethyl-3-(3-dimethylaminopropyl) carbodiimide hydrochloride (0.51 g, 2.1 mmol) and 1-hydroxybenzotriazole (0.36 g, 2.7 mmol) were added thereto, and the mixture was stirred for 10 minutes. Tetrahydropyran-4-ylmethylamine (0.49 g, 4.2 mmol) was added to the mixture, and the mixture was stirred at room temperature for 16 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.17 g of N-(tetrahydropyran-4-ylmethyl)-5-(4-methylthiobenzyloxymethyl)isoxazole-3-carboxamide (hereinafter, referred to as Compound of Present Invention (104)) represented by the following formula.

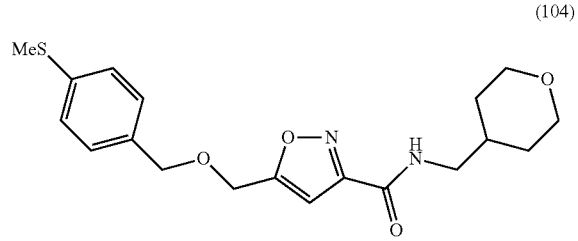 [SMILES: CSc1ccc(COCc2cc(C(=O)NCC3CCOCC3)no2)cc1]

(104)

¹H-NMR (CDCl₃, TMS, δ(ppm)): 1.23-1.10 (m, 2H), 1.58-1.53 (m, 2H), 1.82-1.75 (m, 1H), 2.49 (s, 3H), 3.13 (t, 2H), 3.31-3.21 (m, 2H), 3.85-3.80 (m, 2H), 4.52 (s, 2H), 4.68 (s, 2H), 6.80 (s, 1H), 7.30-7.23 (m, 4H), 8.89 (t, 1H)

Production Example 100

5-(3,4-Methylenedioxybenzyloxymethyl)isoxazole-3-carboxylic acid (0.70 g, 2.5 mmol) was added to chloroform (amylene addition product) (12 mL), and cooled to 0° C.

Triethylamine (0.70 ml, 5.1 mmol), 1-ethyl-3-(3-dimethylaminopropyl) carbodiimide hydrochloride (0.58 g, 3.0 mmol) and 1-hydroxybenzotriazole (0.41 g, 3.0 mmol) were added thereto, and the mixture was stirred for 10 minutes. Tetrahydrofuran-3-ylmethylamine (0.28 g, 2.8 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.30 g of N-(tetrahydrofuran-3-ylmethyl)-5-(3,4-methylenedioxybenzyloxymethyl)isoxazole-3-carboxamide (hereinafter, referred to as Compound of Present Invention (105)) represented by the following formula.

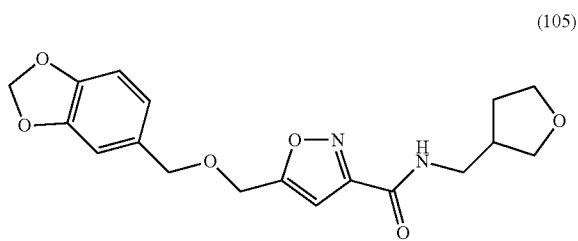 [SMILES: O=C(NCC1CCOC1)c1cc(COCc2ccc3c(c2)OCO3)on1]

(105)

$^1$H-NMR (CDCl$_3$, TMS, δ(ppm)): 1.66 (m, 1H), 2.08 (m, 1H), 2.57 (m, 1H), 3.46 (t, 2H), 3.59 (m, 1H), 3.77 (q, 1H), 3.94-3.83 (m, 2H), 4.49 (s, 2H), 4.61 (s, 2H), 5.96 (s, 2H), 6.70 (d, 1H), 6.79 (s, 2H), 6.84 (d, 1H), 6.90 (brs, 1H)

Production Example 101

5-(3,4-Methylenedioxybenzyloxymethyl)isoxazole-3-carboxylic acid (0.70 g, 2.5 mmol) was added to chloroform (amylene addition product) (12 mL), and cooled to 0° C. Triethylamine (0.70 ml, 5.1 mmol), 1-ethyl-3-(3-dimethylaminopropyl) carbodiimide hydrochloride (0.58 g, 3.0 mmol) and 1-hydroxybenzotriazole (0.41 g, 3.0 mmol) were added thereto, and the mixture was stirred for 10 minutes. Tetrahydropyran-4-ylmethylamine (0.32 g, 2.8 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.45 g of N-(tetrahydropyran-4-ylmethyl)-5-(3,4-methylenedioxybenzyloxymethyl)isoxazole-3-carboxamide (hereinafter, referred to as Compound of Present Invention (106)) represented by the following formula.

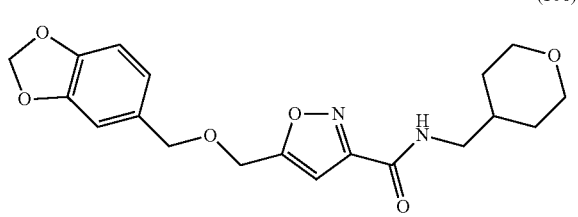

(106)

$^1$H-NMR (CDCl$_3$, TMS, δ(ppm)): 1.38 (m, 2H), 1.65 (d, 2H), 1.86 (m, 1H), 3.37 (m, 4H), 3.99 (d, 2H), 4.49 (s, 2H), 4.60 (s, 2H), 5.96 (s, 2H), 6.70 (s, 1H), 6.79 (d, 2H), 6.87-6.84 (m, 2H)

Production Example 102

5-(Thiophen-3-ylmethoxymethyl)isoxazole-3-carboxylic acid (0.50 g, 2.1 mmol) was added to chloroform (amylene addition product) (10 mL), and cooled to 0° C. Triethylamine (0.42 ml, 3.1 mmol), 1-ethyl-3-(3-dimethylaminopropyl) carbodiimide hydrochloride (0.60 g, 3.1 mmol) and 1-hydroxybenzotriazole (0.41 g, 3.0 mmol) were added thereto, and the mixture was stirred for 10 minutes. Tetrahydrofuran-3-ylmethylamine (0.23 g, 2.3 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydrofuran-3-ylmethyl)-5-(thiophen-3-ylmethoxymethyl)isoxazole-3-carboxamide (hereinafter, referred to as Compound of Present Invention (107)) represented by the following formula.

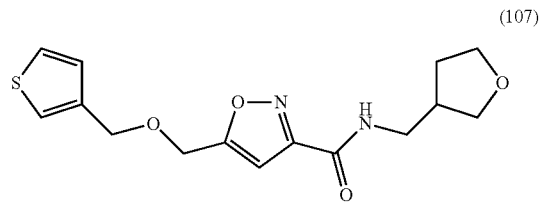 [SMILES: O=C(NCC1CCOC1)c1cc(COCc2ccsc2)on1]

(107)

$^1$H-NMR (CDCl$_3$, TMS, δ(ppm)): 1.71-1.56 (1H, m), 2.12-2.05 (1H, m), 2.60-2.54 (1H, m), 3.46 (2H, t), 3.60-3.57 (1H, m), 3.79-3.75 (1H, m), 3.94-3.83 (2H, m), 4.53-4.51 (4H, m), 6.70 (1H, s), 6.92 (1H, s), 7.09 (1H, d), 7.26 (1H, s), 7.34-7.32 (1H, m)

Production Example 103

5-(Thiophen-3-ylmethoxymethyl)isoxazole-3-carboxylic acid (0.50 g, 2.1 mmol) was added to chloroform (amylene addition product) (10 mL), and cooled to 0° C. Triethylamine (0.42 ml, 3.1 mmol), 1-ethyl-3-(3-dimethylaminopropyl) carbodiimide hydrochloride (0.60 g, 3.1 mmol) and 1-hydroxybenzotriazole (0.41 g, 3.0 mmol) were added thereto, and the mixture was stirred for 10 minutes. Tetrahydropyran-4-ylmethylamine (0.26 g, 2.3 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.32 g of N-(tetrahydropyran-4-ylmethyl)-5-(thiophen-3-ylmethoxymethyl)isoxazole-3-carboxamide (hereinafter, referred to as Compound of Present Invention (108)) represented by the following formula.

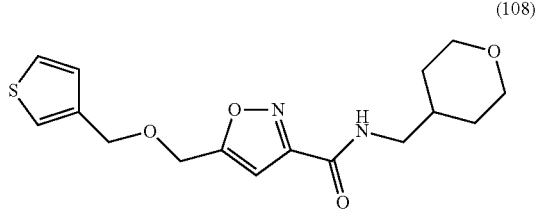 [SMILES: O=C(NCC1CCOCC1)c1cc(COCc2ccsc2)on1]

(108)

¹H-NMR (CDCl₃, TMS, δ(ppm)): 1.42-1.32 (2H, m), 1.68 (2H, d), 1.90-1.81 (1H, m), 3.41-3.33 (4H, m), 4.00-3.96 (2H, m), 4.63-4.61 (4H, m), 6.70 (1H, s), 6.88 (1H, s), 7.08 (1H, d), 7.26 (1H, s), 7.34-7.32 (1H, m)

Production Example 104

5-(2-Chlorothiophen-5-ylmethoxymethyl)isoxazole-3-carboxylic acid (0.50 g, 2.0 mmol) was added to chloroform (amylene addition product) (12 mL), and cooled to 0° C. Triethylamine (0.40 ml, 2.9 mmol), 1-ethyl-3-(3-dimethylaminopropyl) carbodiimide hydrochloride (0.56 g, 2.9 mmol) and 1-hydroxybenzotriazole (0.40 g, 2.9 mmol) were added thereto, and the mixture was stirred for 10 minutes. Tetrahydrofuran-3-ylmethylamine (0.22 g, 2.2 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.15 g of N-(tetrahydrofuran-3-ylmethyl)-5-(2-chlorothiophen-5-ylmethoxymethyl)isoxazole-3-carboxamide (hereinafter, referred to as Compound of Present Invention (109)) represented by the following formula.

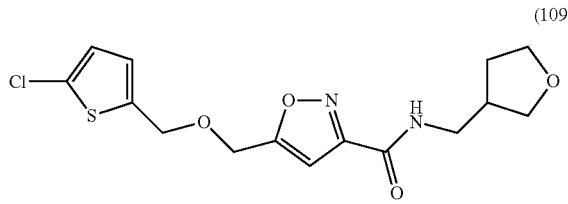

(109)

¹H-NMR (CDCl₃, TMS, δ(ppm)): 1.71-1.63 (m, 1H), 2.10-2.04 (m, 1H), 2.59-2.56 (m, 1H), 3.48-3.45 (m, 2H), 3.60-3.58 (m, 1H), 3.94-3.83 (m, 3H), 4.65-4.63 (m, 4H), 6.71 (s, 1H), 6.80 (s, 2H), 6.94 (s, 1H)

Production Example 105

5-[2-Chlorothiophen-5-ylmethyl)oxymethyl]isoxazole-3-carboxylic acid (0.50 g, 2.0 mmol) was added to chloroform (amylene addition product) (12 mL), and cooled to 0° C. Triethylamine (0.40 ml, 2.9 mmol), 1-ethyl-3-(3-dimethylaminopropyl) carbodiimide hydrochloride (0.56 g, 2.9 mmol) and 1-hydroxybenzotriazole (0.40 g, 2.9 mmol) were added thereto, and the mixture was stirred for 10 minutes. Tetrahydropyran-4-ylmethylamine (0.25 g, 2.2 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.14 g of N-(tetrahydropyran-4-ylmethyl)-5-(2-chlorothiophen-5-ylmethoxymethyl)isoxazole-3-carboxamide (hereinafter, referred to as Compound of Present Invention (110)) represented by the following formula.

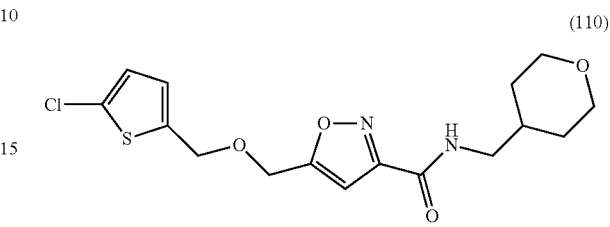

(110)

¹H-NMR (CDCl₃, TMS, δ(ppm)): 1.32-1.43 (m, 2H), 1.65-1.68 (m, 2H), 1.84-1.89 (m, 1H), 3.33-3.41 (m, 4H), 3.96-3.584.01 (m, 2H), 4.64 (s, 2H), 4.65 (s, 2H), 6.71 (s, 1H), 6.80 (s, 2H), 6.87 (br.s, 1H)

Production Example 106

5-(Benzofuran-2-ylmethoxymethyl)isoxazole-3-carboxylic acid (0.35 g, 1.3 mmol) was added to chloroform (amylene addition product) (10 mL), and cooled to 0° C. Triethylamine (0.27 ml, 1.9 mmol), 1-ethyl-3-(3-dimethylaminopropyl) carbodiimide hydrochloride (0.29 g, 1.5 mmol) and 1-hydroxybenzotriazole (0.21 g, 1.5 mmol) were added thereto, and the mixture was stirred for 10 minutes. Tetrahydrofuran-3-ylmethylamine (0.14 g, 1.1 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.15 g of N-(tetrahydrofuran-3-ylmethyl)-5-(benzofuran-2-ylmethoxymethyl))isoxazole-3-carboxamide (hereinafter, referred to as Compound of Present Invention (111)) represented by the

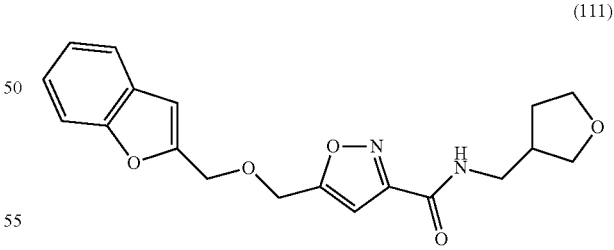

(111)

¹H-NMR(CDCl₃, TMS, δ(ppm)): 1.71-1.63 (m, 1H), 2.12-2.04 (m, 1H), 2.60-2.54 (m, 1H), 3.46 (t, 2H), 3.6-3.57 (m, 1H), 3.74 (q, 1H), 3.94-3.83 (m, 2H), 4.72 (d, 4H), 6.75 (s, 2H), 6.91 (brs, 1H), 7.23 (d, 1H), 7.30 (t, 1H), 7.5 (d, 1H), 7.56 (d, 1H)

Production Example 107

5-(Benzothiophen-2-ylmethoxymethyl)isoxazole-3-carboxylic acid (0.52 g, 1.8 mmol) was added to chloroform (amylene addition product) (10 mL), and cooled to 0° C. Triethylamine (0.38 ml, 2.7 mmol), 1-ethyl-3-(3-dimethylaminopropyl) carbodiimide hydrochloride (0.41 g, 2.2 mmol) and 1-hydroxybenzotriazole (0.29 g, 2.2 mmol) were added thereto, and the mixture was stirred for 10 minutes. Tetrahydrofuran-3-ylmethylamine (0.20 g, 2.0 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.23 g of N-(tetrahydrofuran-3-ylmethyl)-5-(benzothiophen-2-ylmethoxymethyl)isoxazole-3-carboxamide (hereinafter, referred to as Compound of Present Invention (112)) represented by the following formula.

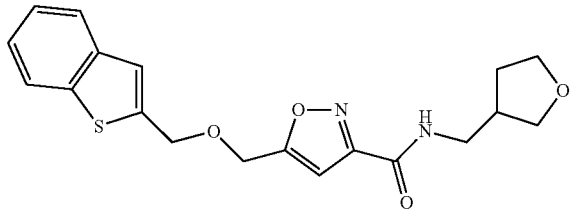

(112)

¹H-NMR (CDCl₃, TMS, δ(ppm)): 1.71-1.19 (m, 1H), 2.13-2.04 (m, 1H), 2.54-2.60 (m, 1H), 3.48-3.42 (m, 2H), 3.6-3.54 (m, 1H), 3.74 (q, 1H), 3.94-3.84 (m, 2H), 4.69 (s, 2H), 4.86 (s, 2H), 6.75 (s, 1H), 6.92 (brs, 1H), 7.38-7.32 (m, 3H), 7.75 (dd, 1H), 7.84-7.81 (m, 1H)

Production Example 108

Tetrahydrofuran-3-ylmethylamine hydrochloride (0.16 g, 1.2 mmol) and triethylamine (0.12 g, 1.2 mmol) were added to chloroform (amylene addition product) (5 mL). 5-(3-Phenylbenzyloxymethyl)isoxazole-3-carboxylic acid (0.25 g, 0.8 mmol), 1-hydroxybenzotriazole (0.01 g, 0.08 mmol) and 1-ethyl-3-(3-dimethylaminopropyl) carbodiimide hydrochloride (0.22 g, 1.2 mmol) were added to the mixture at room temperature, and the mixture was stirred for 3 hours. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.21 g of N1-(tetrahydrofuran-3-ylmethyl)-5-(3-phenylbenzyloxymethyl)isoxazole-3-carboxamide (hereinafter, referred to as Compound of Present Invention (113)) represented by the following formula.

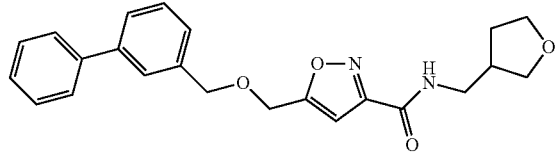

(113)

¹H-NMR (CDCl₃, TMS, δ(ppm)): 1.63-1.71 (1H, m), 2.04-2.13 (1H, m), 2.52-2.63 (1H, m), 3.45-3.48 (2H, m), 3.57-3.61 (1H, m), 3.74-3.79 (1H, m), 3.84-3.94 (2H, m), 4.68 (2H, s), 4.69 (2H, s), 6.74 (1H, s), 6.95 (1H, br s), 7.32-7.38 (2H, m), 7.43-7.47 (3H, m), 7.55-7.61 (4H, m)

Production Example 109

Tetrahydrofuran-3-ylmethylamine hydrochloride (0.23 g, 1.69 mmol) and triethylamine (0.17 g, 1.69 mmol) were added to chloroform (amylene addition product) (10 mL). 5-(3-Phenoxybenzyloxymethyl)isoxazole-3-carboxylic acid (0.46 g, 1.41 mmol), 1-hydroxybenzotriazole (0.02 g, 0.14 mmol) and 1-ethyl-3-(3-dimethylaminopropyl) carbodiimide hydrochloride (0.32 g, 1.69 mmol) were added to the mixture at room temperature, and the mixture was stirred overnight. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.54 g of N-(tetrahydrofuran-3-ylmethyl)-5-(3-phenoxybenzyloxymethyl)isoxazole-3-carboxamide (hereinafter, referred to as Compound of Present Invention (114)) represented by the following formula.

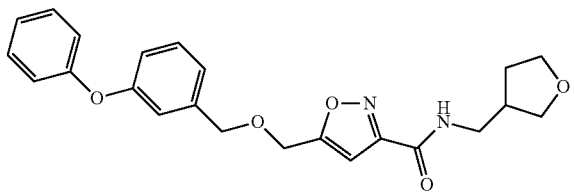

(114)

¹H-NMR (CDCl₃, TMS, δ(ppm)): 1.63-1.72 (1H, m), 2.04-2.11 (1H, m), 2.53-2.63 (1H, m), 3.45-3.48 (2H, m), 3.57-3.61 (1H, m), 3.74-3.79 (1H, m), 3.84-3.94 (2H, m), 4.57 (2H, s), 4.65 (2H, s), 6.71 (1H, s), 6.94-7.03 (5H, m), 7.07-7.14 (2H, m), 7.30-7.37 (3H, m)

Production Example 110

Tetrahydrofuran-3-ylmethylamine hydrochloride (0.24 g, 1.78 mmol) and triethylamine (0.18 g, 1.78 mmol) were added to chloroform (amylene addition product) (10 mL). 5-(4-Phenylbenzyl)oxymethylisoxazole-3-carboxylic acid (0.40 g, 1.19 mmol), 1-hydroxybenzotriazole (0.02 g, 0.18 mmol) and 1-ethyl-3-(3-dimethylaminopropyl) carbodiimide hydrochloride (0.34 g, 1.78 mmol) were added to the mixture at room temperature, and the mixture was stirred overnight. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.42 g of N-(tetrahydrofuran-3-ylmethyl)-5-(4-phenylbenzyloxymethyl)isoxazole-3-carboxamide (hereinafter, referred to as Compound of Present Invention (115)) represented by the following formula.

(115)

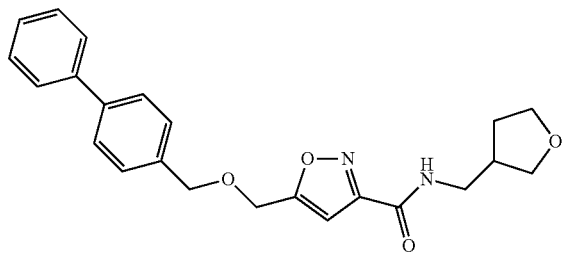

¹H-NMR (CDCl₃, TMS, δ(ppm)): 1.64-1.72 (1H, m), 2.05-2.13 (1H, m), 2.53-2.63 (18, m), 3.45-3.49 (2H, m), 3.57-3.61 (1H, m), 3.74-3.80 (1H, m), 3.84-3.95 (2H, m), 4.65 (2H, s), 4.69 (2H, s), 6.75 (1H, s), 6.94 (1H, br s), 7.34-7.38 (1H, m), 7.42-7.47 (4H, m), 7.58-7.61 (4H, m)

Production Example 111

Tetrahydrofuran-3-ylmethylamine hydrochloride (0.24 g, 1.78 mmol) and triethylamine (0.18 g, 1.78 mmol) were added to chloroform (amylene addition product) (10 mL). 5-(2-Phenylbenzyloxymethyl)isoxazole-3-carboxylic acid (0.40 g, 1.19 mmol), 1-hydroxybenzotriazole (0.02 g, 0.18 mmol) and 1-ethyl-3-(3-dimethylaminopropyl) carbodiimide hydrochloride (0.34 g, 1.78 mmol) were added to the mixture at room temperature, and the mixture was stirred overnight. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.40 g of N-(tetrahydrofuran-3-ylmethyl)-5-(2-phenylbenzyl)oxymethylisoxazole-3-carboxamide (hereinafter, referred to as Compound of Present Invention (116)) represented by the following formula.

(116)

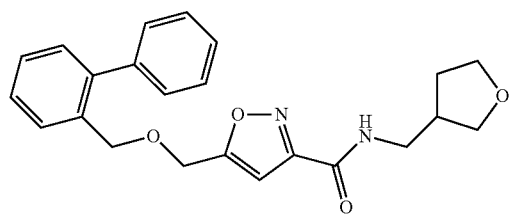

¹H-NMR (CDCl₃, TMS, δ(ppm)): 1.63-1.72 (1H, m), 2.05-2.13 (1H, m), 2.53-2.63 (1H, m), 3.45-3.48 (2H, m), 3.57-3.61 (1H, m), 3.74-3.80 (1H, m), 3.84-3.95 (2H, m), 4.50 (2H, s), 4.56 (2H, s), 6.61 (1H, s), 6.92 (1H, br s), 7.30-7.44 (8H, m), 7.51-7.55 (1H, m)

Production Example 112

Tetrahydrofuran-3-ylmethylamine hydrochloride (0.23 g, 1.69 mmol) and triethylamine (0.17 g, 1.69 mmol) were added to chloroform (amylene addition product) (10 mL). 5-(4-Phenoxybenzyloxymethyl)isoxazole-3-carboxylic acid (0.46 g, 1.41 mmol), 1-hydroxybenzotriazole (0.02 g, 0.14 mmol) and 1-ethyl-3-(3-dimethylaminopropyl) carbodiimide hydrochloride (0.32 g, 1.69 mmol) were added to the mixture at room temperature, and the mixture was stirred at room temperature for 5 hours. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.29 g of N-(tetrahydrofuran-3-ylmethyl)-5-(4-phenoxybenzyloxymethyl)isoxazole-3-carboxamide (hereinafter, referred to as Compound of Present Invention (117)) represented by the following formula.

(117)

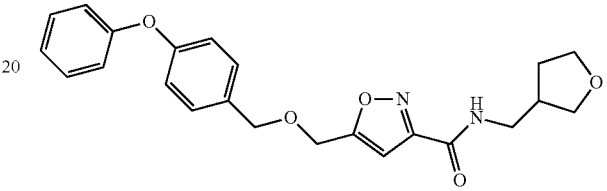

¹H-NMR (CDCl₃, TMS, δ(ppm)): 1.63-1.72 (1, m), 2.05-2.13 (1H, m), 2.53-2.63 (1H, m), 3.45-3.49 (2H, m), 3.57-3.61 (1H, m), 3.74-3.80 (1H, m), 3.84-3.94 (2H, m), 4.57 (2H, s), 4.66 (2H, s), 6.73 (1H, s), 6.94 (1H, br s), 6.99-7.03 (4H, m), 7.10-7.14 (1H, m), 7.30-7.37 (4H, m)

Production Example 113

Tetrahydrofuran-3-ylmethylamine hydrochloride (0.29 g, 2.09 mmol) and triethylamine (0.21 g, 2.09 mmol) were added to chloroform (amylene addition product) (8 mL). 5-(1,2,3,4-Tetrahydronaphthalen-2-ylmethoxymethyl)isoxazole-3-carboxylic acid (0.40 g, 1.39 mmol), 1-hydroxybenzotriazole (0.02 g, 0.14 mmol) and 1-ethyl-3-(3-dimethylaminopropyl) carbodiimide hydrochloride (0.40 g, 2.09 mmol) were added to the mixture at room temperature, and the mixture was stirred at room temperature for 6 hours. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.50 g of N-(tetrahydrofuran-3-ylmethyl)-5-(1,2,3,4-tetrahydronaphthalen-2-ylmethoxymethyl)isoxazole-3-carboxamide (hereinafter, referred to as Compound of Present Invention (118)) represented by the following formula.

(118)

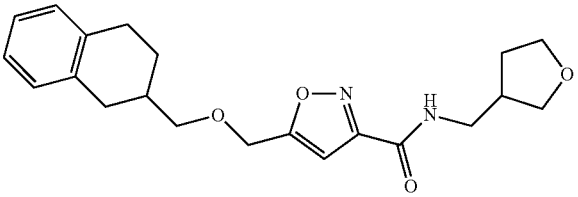

¹H-NMR (CDCl₃, TMS, δ(ppm)): 1.41-1.51 (1H, m), 1.63-1.70 (1H, m), 1.97-2.05 (1H, m), 2.07-2.11 (2H, m), 2.47-2.63 (2H, m), 2.80-2.91 (3H, m), 3.45-3.51 (4H, m), 3.58-3.61 (1H, m), 3.74-3.80 (1H, m), 3.84-3.95 (2H, m), 4.66 (2H, s), 6.72 (1H, s), 6.96 (1H, br s), 7.07-7.11 (4H, m)

Production Example 114

Tetrahydrofuran-3-ylmethylamine hydrochloride (0.55 g, 3.97 mmol) and triethylamine (0.40 g, 3.97 mmol) were added to chloroform (amylene addition product) (15 mL). 5-(5,6,7,8-Tetrahydronaphthalen-2-ylmethoxymethyl)isoxazole-3-carboxylic acid (0.76 g, 2.65 mmol), 1-hydroxybenzotriazole (0.04 g, 0.26 mmol) and 1-ethyl-3-(3-dimethylaminopropyl) carbodiimide hydrochloride (0.76 g, 3.97 mmol) were added to the mixture at room temperature, and the mixture was stirred at room temperature for 5 hours. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.80 g of N-(tetrahydrofuran-3-ylmethyl)-5-(5,6,7,8-tetrahydronaphthalen-2-ylmethoxymethyl)isoxazole-3-carboxamide (hereinafter, referred to as Compound of Present Invention (119)) represented by the following formula.

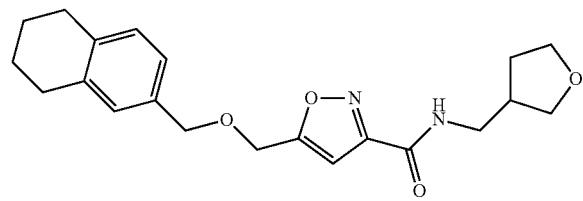

(119)

$^1$H-NMR (CDCl$_3$, TMS, δ(ppm)): 1.64-1.72 (1H, m), 1.78-1.81 (4H, m), 2.04-2.13 (1H, m), 2.53-2.63 (1H, m), 2.76 (4H, br s), 3.45-3.48 (2H, m), 3.57-3.61 (1H, m), 3.74-3.80 (1H, m), 3.84-3.94 (2H, m), 4.53 (2H, s), 4.62 (2H, s), 6.71 (1H, s), 6.96 (1H, br s), 7.04 (1H, s), 7.06 (2H, s)

Production Example 115

Tetrahydrofuran-3-ylmethylamine hydrochloride (0.07 g, 0.49 mmol) and triethylamine (0.05 g, 0.49 mmol) were added to chloroform (amylene addition product) (3 mL). 5-(1,4-Benzodioxan-2-ylmethoxymethyl)isoxazole-3-carboxylic acid (0.12 g, 0.41 mmol), 1-hydroxybenzotriazole (0.01 g, 0.04 mmol) and 1-ethyl-3-(3-dimethylaminopropyl) carbodiimide hydrochloride (0.10 g, 0.49 mmol) were added to the mixture at room temperature, and the mixture was stirred at room temperature for 6 hours. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.08 g of N-(tetrahydrofuran-3-ylmethyl)-5-(1,4-benzodioxan-2-ylmethoxymethyl)isoxazole-3-carboxamide (hereinafter, referred to as Compound of Present Invention (120)) represented by the following formula.

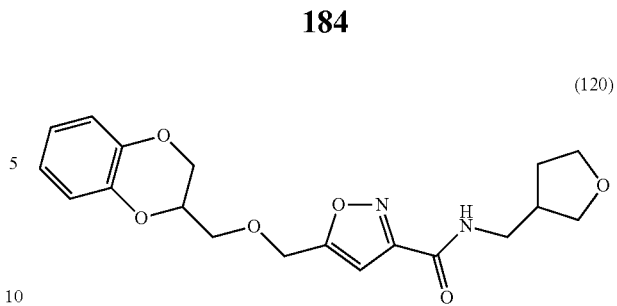

(120)

$^1$H-NMR (CDCl$_3$, TMS, δ(ppm)): 1.63-1.72 (1H, m), 2.05-2.13 (1H, m), 2.53-2.63 (1H, m), 3.45-3.48 (2H, m), 3.58-3.61 (1H, m), 3.74-3.94 (5H, m), 4.07-4.11 (1H, m), 4.27-4.30 (1H, m), 4.34-4.39 (1H, m), 4.73 (2H, s), 6.74 (1H, s), 6.83-6.90 (4H, m), 7.03 (1H, br s)

Production Example 116

Tetrahydrofuran-3-ylmethylamine hydrochloride (0.19 g, 1.13 mmol) and triethylamine (0.14 g, 1.36 mmol) were added to chloroform (amylene addition product) (8 mL). 5-(3-Benzyloxymethylbenzyloxymethyl)isoxazole-3-carboxylic acid (0.40 g, 1.22 mmol), 1-hydroxybenzotriazole (0.02 g, 0.11 mmol) and 1-ethyl-3-(3-dimethylaminopropyl) carbodiimide hydrochloride (0.26 g, 1.36 mmol) were added to the mixture at room temperature, and the mixture was stirred overnight. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.43 g of N-(tetrahydrofuran-3-ylmethyl)-5-(3-benzyloxymethylbenzyloxymethyl)isoxazole-3-carboxamide (hereinafter, referred to as Compound of Present Invention (121)) represented by the following formula.

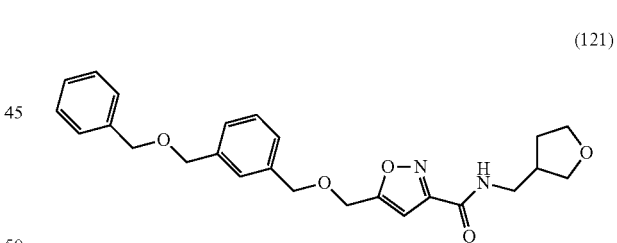

(121)

$^1$H-NMR (CDCl$_3$, TMS, δ(ppm)): 1.62-1.70 (1H, m), 2.02-2.11 (1H, m), 2.51-2.62 (1H, m), 3.43-3.47 (2H, m), 3.56-3.60 (1H, m), 3.72-3.78 (1H, m), 3.82-3.93 (2H, m), 4.56 (2H, s), 4.57 (2H, s), 4.60 (2H, s), 4.64 (2H, s), 6.73 (1H, s), 7.07 (1H, br s), 7.26-7.37 (9H, m)

Production Example 117

Tetrahydrofuran-3-ylmethylamine hydrochloride (0.06 g, 0.41 mmol) and triethylamine (0.04 g, 0.41 mmol) were added to chloroform (amylene addition product) (2 mL). 5-(1,3-Benzodioxolan-2-ylmethoxymethyl)isoxazole-3-carboxylic acid (0.10 g, 0.34 mmol), 1-hydroxybenzotriazole (0.01 g, 0.03 mmol) and 1-ethyl-3-(3-dimethylaminopropyl) carbodiimide hydrochloride (0.08 g, 0.41 mmol) were added to the mixture at room temperature, and the mixture was stirred overnight. Then, dilute hydrochloric acid was added thereto, and the mixture was extracted twice with chloroform. The organic layer was washed with a saturated aqueous sodium bicarbonate solution, dried over anhydrous magnesium sulfate, and then concentrated under reduced pressure. The residue was applied to a silica gel column chromatography to obtain 0.10 g of N-(tetrahydrofuran-3-ylmethyl)-5-(1,3-benzodioxolan-2-ylmethoxymethyl)isoxazole-3-carboxamide (hereinafter, referred to as Compound of Present Invention (122)) represented by the following formula.

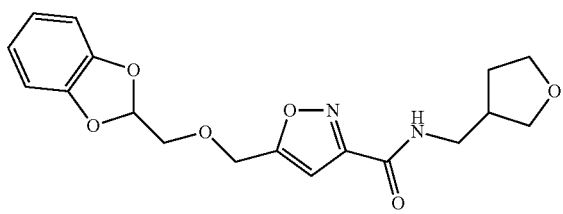

(122)

$^1$H-NMR (CDCl$_3$, TMS, δ(ppm)): 1.63-1.71 (1H, m), 2.05-2.13 (1H, m), 2.53-2.63 (1H, m), 3.44-3.48 (2H, m), 3.57-3.60 (1H, m), 3.73-3.79 (1H, m), 3.83-3.94 (4H, m), 4.10-4.15 (1H, m), 4.78 (2H, s), 6.23-6.25 (1H, t), 6.72 (1H, s), 6.82 (4H, br s), 6.96 (1H, br s)

Production Example 118

Tetrahydrofuran-3-ylmethylamine hydrochloride (0.20 g, 1.48 mmol) and triethylamine (0.15 g, 1.48 mmol) were added to chloroform (amylene addition product) (8 mL). 5-(2-Methyl-3-phenylbenzyloxymethyl)isoxazole-3-carboxylic acid (0.40 g, 1.24 mmol), 1-hydroxybenzotriazole (0.02 g, 0.12 mmol) and 1-ethyl-3-(3-dimethylaminopropyl) carbodiimide hydrochloride (0.28 g, 1.48 mmol) were added to the mixture at room temperature, and the mixture was stirred for 3 hours. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.38 g of N-(tetrahydrofuran-3-ylmethyl)-5-(2-methyl-3-phenylbenzyloxymethyl)isoxazole-3-carboxamide (hereinafter, referred to as Compound of Present Invention (123)) represented by the following formula.

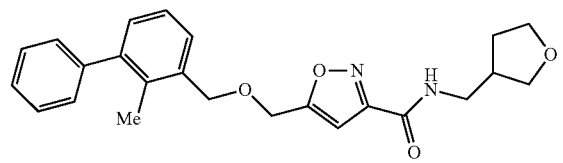

(123)

$^1$H-NMR (CDCl$_3$, TMS, δ(ppm)): 1.63-1.72 (1H, m), 2.04-2.13 (1H, m), 2.21 (3H, s), 2.52-2.63 (1H, m), 3.45-3.48 (2H, m), 3.57-3.61 (1H, m), 3.74-3.79 (1H, m), 3.83-3.94 (2H, m), 4.67 (2H, s), 4.71 (2H, s), 6.74 (1H, s), 6.96 (1H, brs), 7.21-7.30 (4H, m), 7.32-7.36 (2H, m), 7.39-7.43 (2H, m)

Production Example 119

Tetrahydrofuran-3-ylmethylamine hydrochloride (0.22 g, 1.60 mmol) and triethylamine (0.16 g, 1.60 mmol) were added to chloroform (amylene addition product) (8 mL). 5-(5-Phenylfurfuryloxymethyl)isoxazole-3-carboxylic acid (0.40 g, 1.34 mmol), 1-hydroxybenzotriazole (0.02 g, 0.13 mmol) and 1-ethyl-3-(3-dimethylaminopropyl) carbodiimide hydrochloride (0.31 g, 1.60 mmol) were added to the mixture at room temperature, and the mixture was stirred for 3 hours. Then, dilute hydrochloric acid was added thereto, and the mixture was extracted twice with chloroform. The organic layer was washed with a saturated aqueous sodium bicarbonate solution, and concentrated under reduced pressure. The residue was applied to a silica gel column chromatography to obtain 0.35 g of N-(tetrahydrofuran-3-ylmethyl)-5-(5-phenylfurfuryloxymethyl)isoxazole-3-carboxamide (hereinafter, referred to as Compound of Present Invention (124)) represented by the following formula.

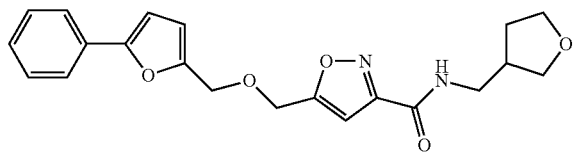

(124)

$^1$H-NMR (CDCl$_3$, TMS, δ(ppm)): 1.64-1.71 (1H, m), 2.03-2.12 (1H, m), 2.51-2.61 (1H, m), 3.43-3.46 (2H, m), 3.56-3.60 (1H, m), 3.73-3.79 (1H, m), 3.83-3.94 (2H, m), 4.60 (2H, s), 4.69 (2H, s), 6.46 (1H, d), 6.62 (1H, d), 6.72 (1H, s), 6.91 (1H, br s), 7.26-7.29 (1H, m), 7.37-7.41 (2H, m), 7.66-7.68 (2H, m)

Production Example 120

5-[1-Phenylethyl)oxymethyl]isoxazole-3-carboxylic acid (0.50 g, 2.0 mmol), tetrahydrofuran-3-ylmethylamine hydrochloride (0.33 g, 2.4 mmol), triethylamine (0.24 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.51 g of N-(tetrahydrofuran-3-ylmethyl)-5-[(1-phenylethyl)oxymethyl]isoxazole-3-carboxamide (hereinafter, referred to as Compound of Present Invention (125)) represented by the following formula.

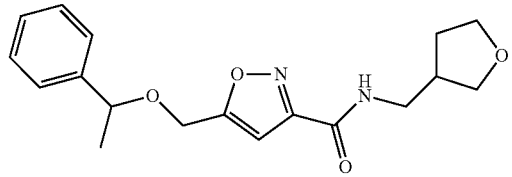

(125)

¹H-NMR(CDCl₃, TMS, δ(ppm)): 1.49 (3H, d), 1.66-1.69 (1H, m), 2.04-2.13 (1H, m), 2.53-2.63 (1H, m), 3.46 (2H, t), 3.59 (1H, dd), 3.77 (1H, dd), 3.86 (1H, dd), 3.92 (1H, td), 4.48 (3H, ddd), 6.67 (1H, s), 6.94 (1H, s), 7.29-7.40 (5H, m)

Production Example 121

5-Diphenylmethoxymethylisoxazole-3-carboxylic acid (0.62 g, 2.0 mmol), tetrahydrofuran-3-ylmethylamine hydrochloride (0.33 g, 2.4 mmol), triethylamine (0.25 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.37 g of N-(tetrahydrofuran-3-ylmethyl)-5-diphenylmethoxymethylisoxazole-3-carboxamide (hereinafter, referred to as Compound of Present Invention (126)) represented by the following formula.

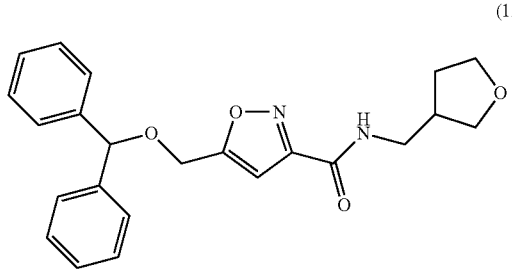

(126)

¹H-NMR (CDCl₃, TMS, δ(ppm)): 1.63-1.72 (1H, m), 2.06-2.13 (1H, m), 2.56-2.59 (1H, m), 3.45-3.48 (2H, m), 3.59 (1H, dd), 3.76-3.78 (1H, m), 3.84-3.94 (2H, m), 4.64 (2H, s), 5.49 (1H, s), 6.73 (1H, s), 6.94 (1H, s), 7.27-7.37 (10H, m)

Production Example 122

5-[1-Phenyl-2,2,2-trifluoroethyl)oxymethyl]isoxazole-3-carboxylic acid (0.50 g, 2.0 mmol), tetrahydrofuran-3-ylmethylamine hydrochloride (0.33 g, 2.4 mmol), triethylamine (0.24 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.51 g of N-(tetrahydrofuran-3-ylmethyl)-5-[(1-phenyl-2,2,2-trifluoroethyl)oxymethyl]isoxazole-3-carboxamide (hereinafter, referred to as Compound of Present Invention (127)) represented by the following formula.

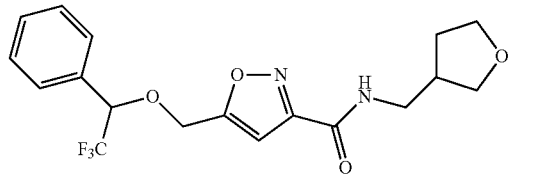

(127)

¹H-NMR (CDCl₃, TMS, δ(ppm)): 1.65-1.72 (1H, m), 2.06-2.13 (1H, m), 2.56-2.60 (1H, m), 3.47 (2H, t), 3.59 (1H, dd), 3.74-3.80 (1H, m), 3.86 (1H, dd), 3.91-3.93 (1H, m), 4.62-4.76 (3H, m), 6.70-6.80 (1H, m), 6.96 (1H, brs), 7.41-7.49 (5H, m)

Production Example 123

5-[2,2,2-Trifluoroethyl)oxymethyl]isoxazole-3-carboxylic acid (0.30 g, 1.3 mmol), tetrahydrofuran-3-ylmethylamine hydrochloride (0.22 g, 1.6 mmol), triethylamine (0.16 g, 1.6 mmol) and 1-hydroxybenzotriazole (0.02 g, 0.16 mmol) were added to chloroform (amylene addition product) (4 mL). 1-Ethyl-3-(3-dimethylaminopropyl) carbodiimide hydrochloride (0.31 g, 1.6 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.32 g of N-(tetrahydrofuran-3-ylmethyl)-5-[2,2,2-Trifluoroethyl)oxymethyl]isoxazole-3-carboxamide (hereinafter, referred to as Compound of Present Invention (128)) represented by the following formula.

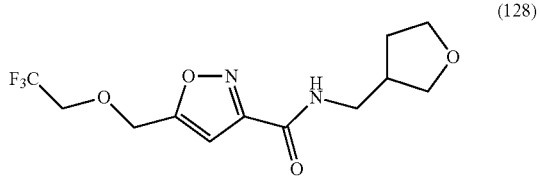 [SMILES: O=C(NCC1CCOC1)c1cc(COCC(F)(F)F)on1]

(128)

¹H-NMR (CDCl₃, TMS, δ(ppm)): 1.64-1.72 (1H, m), 2.06-2.13 (1H, m), 2.53-2.64 (1H, m), 3.47 (2H, t), 3.60 (1H, dd), 3.74-3.80 (1H, m), 3.84-3.96 (4H, m), 4.80 (2H, s), 6.78 (1H, brs), 7.00 (1H, s)

Production Example 124

5-[1-(Benzyloxy)ethyl]isoxazole-3-carboxylic acid (0.60 g, 2.0 mmol), tetrahydrofuran-3-ylmethylamine hydrochloride (0.33 g, 2.4 mmol), triethylamine (0.24 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.58 g of N-(tetrahydrofuran-3-ylmethyl)-5-[1-(benzyloxy)ethyl]isoxazole-3-carboxamide (hereinafter, referred to as Compound of Present Invention (129)) represented by the following formula.

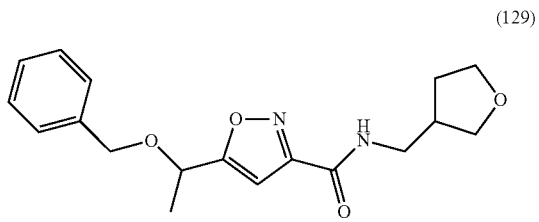 [SMILES: CC(OCc1ccccc1)c1cc(C(=O)NCC2CCOC2)no1]

(129)

$^1$H-NMR (CDCl$_3$, TMS, δ(ppm)): 1.59 (3H, d), 1.63-1.73 (1H, m), 2.07-2.12 (1H, m), 2.55-2.62 (1H, m), 3.47 (2H, t), 3.60 (1H, dd), 3.76-3.78 (1H, m), 3.86 (1H, dd), 3.91-3.93 (1H, m), 4.47 (1H, d), 4.60 (1H, d), 4.70-4.75 (1H, m), 6.69 (1H, d), 6.95 (1H, s), 7.30-7.38 (5H, m)

Production Example 125

5-[1-Benzyloxy-1-phenylmethyl]isoxazole-3-carboxylic acid (0.44 g, 1.4 mmol), tetrahydrofuran-3-ylmethylamine hydrochloride (0.23 g, 1.7 mmol), triethylamine (0.17 g, 1.7 mmol) and 1-hydroxybenzotriazole (0.02 g, 0.17 mmol) were added to chloroform (amylene addition product) (4 mL). 1-Ethyl-3-(3-dimethylaminopropyl) carbodiimide hydrochloride (0.32 g, 1.7 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.45 g of N-(tetrahydrofuran-3-ylmethyl)-5-[1-benzyloxy-1-phenylmethyl]isoxazole-3-carboxamide (hereinafter, referred to as Compound of Present Invention (130)) represented by the following formula.

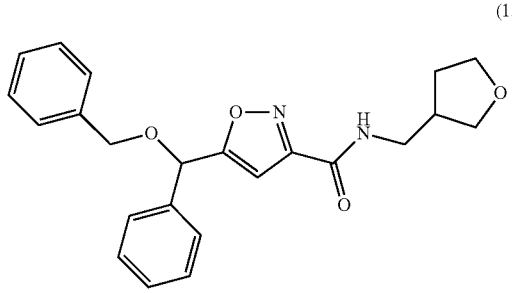

(130)

$^1$H-NMR (CDCl$_3$, TMS, δ(ppm)): 1.63-1.68 (1H, m), 2.02-2.11 (1H, m), 2.55-2.56 (1H, m), 3.42-3.46 (2H, m), 3.57 (1H, dd), 3.75 (1H, dd), 3.84 (1H, dd), 3.89-3.91 (1H, m), 4.60 (2H, dd), 5.57 (1H, s), 6.62 (1H, s), 6.91 (1H, s), 7.32-7.44 (10H, m)

Production Example 126

Tetrahydrofuran-3-ylmethylamine hydrochloride (0.20 g, 1.44 mmol) and triethylamine (0.15 g, 1.44 mmol) were added to chloroform (amylene addition product) (6 mL). 5-Cyclopentylmethoxymethylisoxazole-3-carboxylic acid (0.27 g, 1.20 mmol), 1-hydroxybenzotriazole (0.02 g, 0.12 mmol) and 1-ethyl-3-(3-dimethylaminopropyl) carbodiimide hydrochloride (0.28 g, 1.44 mmol) were added to the mixture at room temperature, and the mixture was stirred for 5 hours. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.33 g of N-(tetrahydrofuran-3-ylmethyl)-5-cyclopentylmethoxymethylisoxazole-3-carboxamide (hereinafter, referred to as Compound of Present Invention (131)) represented by the following formula.

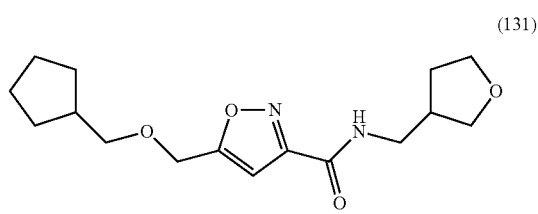 [SMILES: O=C(NCC1CCOC1)c1cc(COCC2CCCC2)on1]

(131)

$^1$H-NMR (CDCl$_3$, TMS, δ(ppm)): 1.18-1.28 (2H, m), 1.50-1.60 (4H, m), 1.64-1.78 (3H, m), 2.05-2.23 (2H, m), 2.53-2.63 (1H, m), 3.39 (2H, d), 3.45-3.48 (2H, m), 3.57-3.61 (1H, m), 3.74-3.80 (1H, m), 3.84-3.94 (2H, m), 4.62 (2H, s), 6.70 (1H, s), 6.96 (1H, br s)

Production Example 127

Tetrahydrofuran-3-ylmethylamine hydrochloride (0.45 g, 3.26 mmol) and triethylamine (0.33 g, 3.26 mmol) were added to chloroform (amylene addition product) (13 mL). 5-(2-Cyclopentylethyl)oxymethylisoxazole-3-carboxylic acid (0.65 g, 2.72 mmol), 1-hydroxybenzotriazole (0.04 g, 0.27 mmol) and 1-ethyl-3-(3-dimethylaminopropyl) carbodiimide hydrochloride (0.63 g, 3.26 mmol) were added to the mixture at room temperature, and the mixture was stirred overnight. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.85 g of N-(tetrahydrofuran-3-ylmethyl)-5-(2-cyclopentylethyl)oxymethylisoxazole-3-carboxamide (hereinafter, referred to as Compound of Present Invention (132)) represented by the following formula.

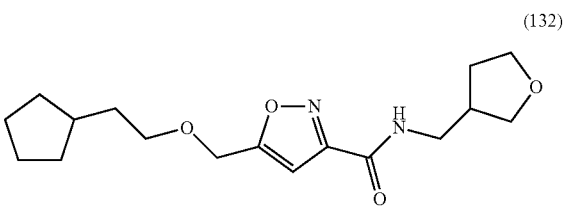 [SMILES: O=C(NCC1CCOC1)c1cc(COCCC2CCCC2)on1]

(132)

$^1$H-NMR (CDCl$_3$, TMS, δ(ppm)): 1.05-1.13 (2H, m), 1.46-1.90 (10H, m), 2.05-2.13 (1H, m), 2.53-2.63 (1H, m), 3.45-3.48 (2H, m), 3.52-3.56 (2H, m), 3.57-3.61 (1H, m), 3.74-3.80 (1H, m), 3.84-3.94 (2H, m), 4.61 (2H, s), 6.70 (1H, s), 6.94 (1H, br s)

Production Example 128

5-(3-Phenylpropoyrnethyl)isoxazole-3-carboxylic acid (0.60 g, 2.3 mmol) was added to chloroform (amylene addition product) (12 mL), and cooled to 0° C. Triethylamine (0.48 ml, 3.4 mmol), 1-ethyl-3-(3-dimethylaminopropyl) carbodiimide hydrochloride (0.66 g, 3.4 mmol) and 1-hydroxybenzotriazole (0.47 g, 3.4 mmol) were added thereto, and the mixture was stirred for 10 minutes. Tetrahydrofuran-3-ylmethylamine (0.26 g, 2.5 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydrofuran-3-ylmethyl)-5-(3-phenylpropoxymethyl)isoxazole-3-carboxamide (hereinafter, referred to as Compound of Present Invention (132)) represented by the following formula.

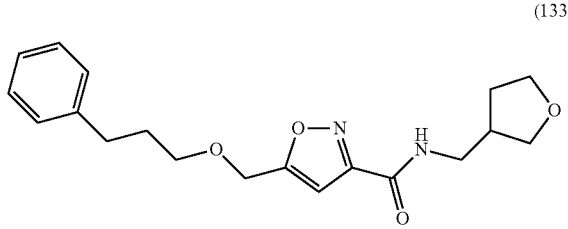

(133)

$^1$H-NMR (CDCl$_3$, TMS, δ(ppm)): 1.70-1.65 (m, 1H), 1.96-1.89 (m, 2H), 2.10-2.06 (m, 1H), 2.59-2.56 (m, 1H), 2.69 (t, 2H), 3.46 (t, 2H), 3.52 (t, 2H), 3.59-3.57 (m, 1H), 3.77-3.73 (m, 1H), 3.94-3.79 (m, 2H), 4.60 (s, 2H), 6.69 (s, 1H), 6.94 (s, 1H), 7.20-7.16 (m, 3H), 7.29-7.27 (m, 2H)

Production Example 129

5-(3-Phenylpropoxymethyl)isoxazole-3-carboxylic acid (0.60 g, 2.3 mmol) was added to chloroform (amylene addition product) (12 mL), and cooled to 0° C. Triethylamine (0.48 ml, 3.4 mmol), 1-ethyl-3-(3-dimethylaminopropyl) carbodiimide hydrochloride (0.66 g, 3.4 mmol) and 1-hydroxybenzotriazole (0.47 g, 3.4 mmol) were added thereto, and the mixture was stirred for 10 minutes. Tetrahydropyran-4-ylmethylamine (0.29 g, 2.5 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydropyran-4-ylmethyl)-5-(3-phenylpropoxymethyl)isoxazole-3-carboxamide (hereinafter, referred to as Compound of Present Invention (134)) represented by the following formula.

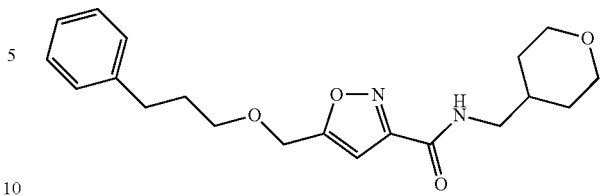

(134)

$^1$H-NMR (CDCl$_3$, TMS, δ(ppm)): 1.43-1.32 (m, 2H), 1.68-1.65 (m, 2H), 1.96-1.83 (m, 3H), 2.69 (t, 2H), 3.40-3.33 (m, 4H), 3.52 (t, 2H), 4.00-3.96 (m, 2H), 4.60 (s, 2H), 6.69 (s, 1H), 6.88 (s, 1H), 7.20-7.16 (m, 3H), 7.29-7.27 (m, 2H)

Production Example 130

5-(4-Phenylbutoxymethyl)isoxazole-3-carboxylic acid (0.50 g, 1.8 mmol) was added to chloroform (amylene addition product) (12 mL), and cooled to 0° C. Triethylamine (0.51 ml, 3.6 mmol), 1-ethyl-3-(3-dimethylaminopropyl) carbodiimide hydrochloride (0.42 g, 2.2 mmol) and 1-hydroxybenzotriazole (0.29 g, 2.2 mmol) were added thereto, and the mixture was stirred for 10 minutes. Tetrahydrofuran-3-ylmethylamine (0.20 g, 2.0 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.50 g of N-(tetrahydrofuran-3-ylmethyl)-5-(4-phenylbutoxymethyl)isoxazole-3-carboxylic acid-3-carboxamide (hereinafter, referred to as Compound of Present Invention (135)) represented by the following formula.

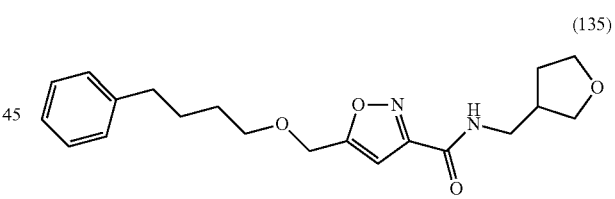

(135)

$^1$H-NMR (CDCl$_3$, TMS, δ(ppm)): 1.68 (m, 5H), 2.08 (q, 1H), 2.64-2.53 (m, 3H), 3.46 (t, 2H), 3.54 (m, 3H), 3.75 (q, 1H), 3.93-3.79 (m, 2H), 4.59 (s, 2H), 6.68 (s, 1H), 6.94 (brs, 1H), 7.17 (dd, 3H), 7.27 (dd, 1H), 7.29 (d, 1H)

Production Example 131

5-(4-Phenylbutoxymethyl)isoxazole-3-carboxylic acid (0.50 g, 1.8 mmol) was added to chloroform (amylene addition product) (12 mL), and cooled to 0° C. Triethylamine (0.51 ml, 3.6 mmol), 1-ethyl-3-(3-dimethylaminopropyl) carbodiimide hydrochloride (0.42 g, 2.2 mmol) and 1-hydroxybenzotriazole (0.29 g, 2.2 mmol) were added thereto, and the mixture was stirred for 10 minutes. Tetrahydropyran-4-ylmethylamine (0.23 g, 2.0 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.32 g of N-(tetrahydropyran-4-ylmethyl)-5-(4-phenylbutoxymethyl)isoxazole-3-carboxamide (hereinafter, referred to as Compound of Present Invention (136)) represented by the following formula.

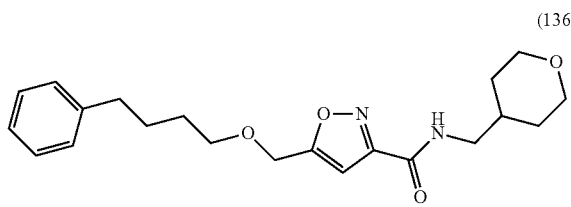

(136)

¹H-NMR (CDCl₃, TMS, δ(ppm)): 1.38 (q, 2H), 1.66 (m, 6H), 1.82 (m, 1H), 2.62 (t, 2H), 3.36 (m, 4H), 3.51 (t, 2H), 4.00 (d, 2H), 4.59 (s, 2H), 6.68 (s, 1H), 6.87 (brs, 1H), 7.17 (d, 3H), 7.27 (d, 1H), 7.29 (d, 1H)

Production Example 132

5-(5-Phenylpentyloxymethyl)isoxazole-3-carboxylic acid (0.50 g, 1.7 mmol) was added to chloroform (amylene addition product) (12 mL), and cooled to 0° C. Triethylamine (0.49 ml, 3.5 mmol), 1-ethyl-3-(3-dimethylaminopropyl) carbodiimide hydrochloride (0.40 g, 2.1 mmol) and 1-hydroxybenzotriazole (0.28 g, 2.1 mmol) were added thereto, and the mixture was stirred for 10 minutes. Tetrahydrofuran-3-ylmethylamine (0.19 g, 1.9 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.30 g of N-(tetrahydrofuran-3-ylmethyl)-5-(5-phenylpentyloxymethyl)isoxazole-3-carboxylic acid-3-carboxamide (hereinafter, referred to as Compound of Present Invention (137)) represented by the following formula.

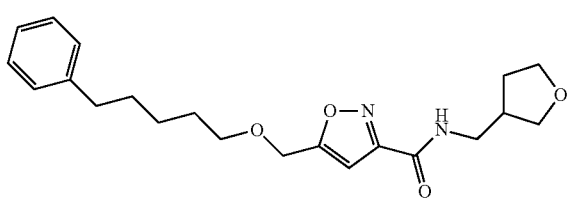

(137)

¹H-NMR (CDCl₃, TMS, δ(ppm)): 1.43-1.36 (m, 2H), 1.68-1.54 (m, 5H), 2.12-1.71 (m, 1H), 2.63-2.54 (m, 3H), 3.52-3.44 (m, 4H), 3.60-3.56 (m, 1H), 3.77-3.73 (m, 1H), 4.00-3.79 (m, 2H), 4.59 (s, 2H), 6.68 (s, 1H), 6.91 (m, 1H), 7.18-7.15 (m, 3H), 7.29-7.25 (m, 2H)

Production Example 133

5-(5-Phenylpentyloxymethyl)isoxazole-3-carboxylic acid (0.50 g, 1.7 mmol) was added to chloroform (amylene addition product) (12 mL), and cooled to 0° C. Triethylamine (0.49 ml, 3.5 mmol), 1-ethyl-3-(3-dimethylaminopropyl) carbodiimide hydrochloride (0.40 g, 2.1 mmol) and 1-hydroxybenzotriazole (0.28 g, 2.1 mmol) were added thereto, and the mixture was stirred for 10 minutes. Tetrahydropyran-4-ylmethylamine (0.22 g, 1.9 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.42 g of N-(tetrahydropyran-4-ylmethyl)-5-(5-phenylpentyloymethyl)isoxazole-3-carboxamide (hereinafter, referred to as Compound of Present Invention (138)) represented by the following formula.

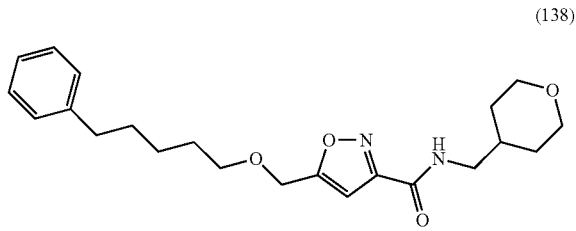 [SMILES: O=C(NCC1CCOCC1)c1cc(COCCCCCc2ccccc2)on1]

(138)

¹H-NMR (CDCl₃, TMS, δ(ppm)): 1.43-1.32 (m, 4H), 1.68-1.58 (m, 6H), 1.88-1.68 (m, 1H), 2.62-2.59 (t, 2H), 3.40-3.33 (m, 4H), 3.50-3.49 (m, 2H), 4.00-3.52 (m, 2H), 4.59 (s, 2H), 6.68 (s, 1H), 6.87 (m, 1H), 7.18-7.15 (m, 3H), 7.29-7.25 (m, 2H)

Production Example 134

5-(3-Benzyloxypropyl)isoxazole-3-carboxylic acid (0.65 g, 2.5 mmol), tetrahydrofuran-3-ylmethylamine hydrochloride (0.43 g, 3.1 mmol), triethylamine (0.32 g, 3.1 mmol) and 1-hydroxybenzotriazole (0.04 g, 0.30 mmol) were added to chloroform (amylene addition product) (5 mL). 1-Ethyl-3-(3-dimethylaminopropyl) carbodiimide hydrochloride (0.60 g, 3.1 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.44 g of N-(tetrahydrofuran-3-ylmethyl)-5-(3-benzyloxypropyl)isoxazole-3-carboxamide (hereinafter, referred to as Compound of Present Invention (139)) represented by the following formula.

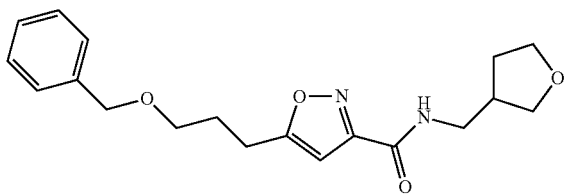

(139)

¹H-NMR (CDCl₃, TMS, δ(ppm)): 1.64-1.71 (1H, m), 2.00-2.03 (2H, m), 2.08-2.11 (1H, m), 2.54-2.60 (1H, m), 2.93 (2H, t), 3.43-3.47 (2H, m), 3.52 (2H, t), 3.58 (1H, dd), 3.76 (1H, dd), 3.84-3.94 (2H, m), 4.51 (2H, s), 6.43 (1H, s), 6.93 (1H, s), 7.28-7.40 (5H, m)

Production Example 135

5-(4-Benzyloxybutyl)isoxazole-3-carboxylic acid (0.42 g, 1.5 mmol), tetrahydrofuran-3-ylmethylamine hydrochloride (0.26 g, 1.9 mmol), triethylamine (0.19 g, 1.9 mmol) and 1-hydroxybenzotriazole (0.03 g, 0.19 mmol) were added to chloroform (amylene addition product) (3 mL). 1-Ethyl-3-(3-dimethylaminopropyl) carbodiimide hydrochloride (0.37 g, 1.9 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.62 g of N-(tetrahydrofuran-3-ylmethyl)-5-(4-benzyloxybutyl)isoxazole-3-carboxamide (hereinafter, referred to as Compound of Present Invention (140)) represented by the following formula.

(140)

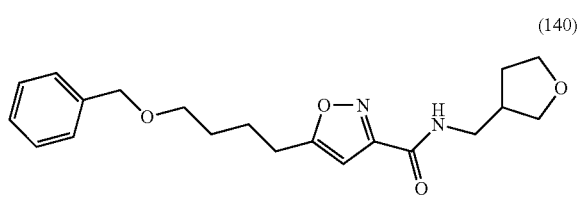 [SMILES: O=C(NCC1CCOC1)c1cc(CCCCOCc2ccccc2)on1]

¹H-NMR (CDCl₃, TMS, δ(ppm)): 1.67-1.70 (4H, m), 1.79-1.87 (1H, m), 2.02-2.13 (1H, m), 2.56-2.61 (1H, m), 2.81 (2H, t), 3.45 (2H, dt), 3.48-3.52 (2H, m), 3.59 (1H, dd), 3.77 (1H, dd), 3.84-3.95 (2H, m), 4.51 (2H, s), 6.45 (1H, d), 6.93 (1H, s), 7.30-7.41 (5H, m)

Production Example 136

A mixture of 5-(5-benzyloxypentyl)isoxazole-3-carboxylic acid and 5-(5-hydroxypentyl)isoxazole-3-carboxylic acid (1.33 g), tetrahydrofuran-3-ylmethylamine hydrochloride (1.10 g, 8.0 mmol), triethylamine (0.81 g, 8.0 mmol) and 1-hydroxybenzotriazole (0.11 g, 0.80 mmol) were added to chloroform (amylene addition product) (25 mL). 1-Ethyl-3-(3-dimethylaminopropyl) carbodiimide hydrochloride (1.54 g, 8.0 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.59 g of N-(tetrahydrofuran-3-ylmethyl)-5-(5-benzyloxypentyl)isoxazole-3-carboxamide (hereinafter, referred to as Compound of Present Invention (141)) represented by the following formula:

(141)

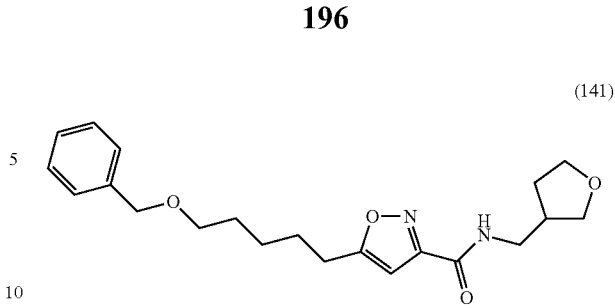

and 0.43 g of N-(tetrahydrofuran-3-ylmethyl)-5-(5-hydroxypentyl)isoxazole-3-carboxamide (hereinafter, referred to as Compound of Present Invention (142)) represented by the following formula.

(142)

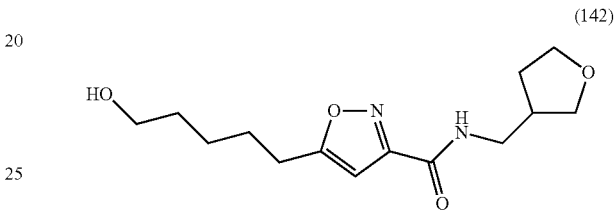

Compound of Present Invention 141

¹H-NMR (CDCl₃, TMS, δ(ppm)): 1.39-1.40 (4H, m), 1.61-1.64 (1H, m), 1.68-1.73 (2H, m), 2.06-2.11 (1H, m), 2.53-2.60 (1H, m), 2.78 (2H, t), 3.45-3.47 (4H, m), 3.58 (1H, dd), 3.77 (1H, t), 3.86 (1H, dd), 3.88-3.93 (1H, m), 4.50 (2H, s), 6.43 (1H, s), 6.92 (1H, s), 7.34-7.35 (5H, m)

Compound of Present Invention 142

¹H-NMR (CDCl₃, TMS, δ(ppm)): 1.38-1.41 (4H, m)), 1.62-1.66 (1H, m), 1.70-1.73 (2H, m), 2.09-2.10 (1H, m), 2.56-2.61 (1H, m), 2.80 (2H, t), 3.46 (2H, t), 3.59 (1H, dd), 3.76 (1H, dd), 3.84-3.94 (2H, m), 4.05 (2H, t), 6.44 (1H, s), 6.93 (1H, s)

Production Example 137

A mixture of 5-(6-benzyloxyhexyl)isoxazole-3-carboxylic acid and 5-(6-hydroxyhexyl)isoxazole-3-carboxylic acid (1.23 g), tetrahydrofuran-3-ylmethylamine hydrochloride (1.10 g, 8.0 mmol), triethylamine (0.81 g, 8.0 mmol) and 1-hydroxybenzotriazole (0.11 g, 0.80 mmol) were added to chloroform (amylene addition product) (25 mL). 1-Ethyl-3-(3-dimethylaminopropyl) carbodiimide hydrochloride (1.54 g, 8.0 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.32 g of N-(tetrahydrofuran-3-ylmethyl)-5-(6-benzyloxyhexyl)isoxazole-3-carboxamide (hereinafter, referred to as Compound of Present Invention (143)) represented by the following formula:

(143)

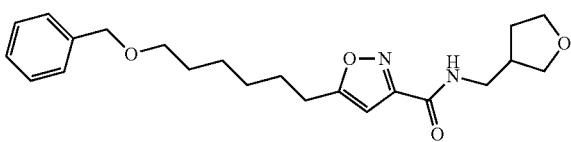

and 0.14 g of N-(tetrahydrofuran-3-ylmethyl)-5-(6-hydroxyhexyl)isoxazole-3-carboxamide (hereinafter, referred to as Compound of Present Invention (144)) represented by the following formula.

(144)

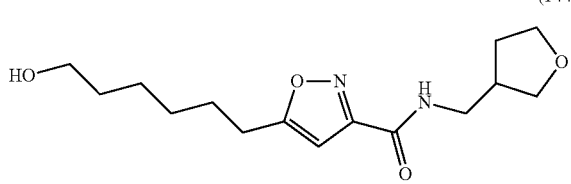

Compound of Present Invention 143
$^1$H-NMR (CDCl$_3$, TMS, δ(ppm)): 1.37-1.45 (4H, m), 1.56-1.65 (3H, m), 1.66-1.75 (2H, m), 2.04-2.13 (1H, m), 2.54-2.60 (1H, m), 2.78 (2H, t), 3.45-3.47 (4H, m), 3.58 (1H, dd), 3.76 (1H, dd), 3.86 (1H, dd), 3.90-3.92 (1H, m), 4.51 (2H, s), 6.43 (1H, s), 6.94 (1H, s), 7.28-7.37 (5H, m)
Compound of Present Invention 144
$^1$H-NMR (CDCl$_3$, TMS, δ(ppm)): 1.38 (4H, td), 1.57-1.68 (3H, m), 1.71-1.75 (2H, m), 2.04-2.13 (1H, m), 2.52-2.62 (1H, m), 2.80 (2H, t), 3.46 (2H, t), 3.59 (1H, dd), 3.77 (1H, dd), 3.86 (1H, dd), 3.91 (1H, td), 4.05 (2H, t), 6.46 (1H, s), 6.95 (1H, s)

Production Example 138

5-(3-Phenoxypropyl)isoxazole-3-carboxylic acid (0.50 g, 2.0 mmol), tetrahydrofuran-3-ylmethylamine hydrochloride (0.33 g, 2.4 mmol), triethylamine (0.25 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.51 g of N-(tetrahydrofuran-3-ylmethyl)-5-(3-phenoxypropyl)isoxazole-3-carboxamide (hereinafter, referred to as Compound of Present Invention (145)) represented by the following formula.

(145)

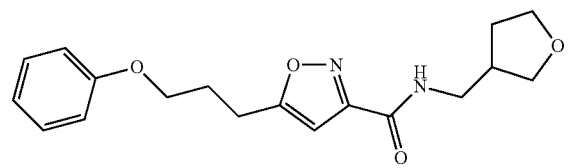

$^1$H-NMR (CDCl$_3$, TMS, δ(ppm)): 1.64-1.70 (1H, m), 2.04-2.12 (1H, m), 2.18-2.22 (2H, m), 2.52-2.62 (1H, m), 3.03 (2H, t), 3.43-3.47 (2H, m), 3.59 (1H, dd), 3.76 (1H, dd), 3.83-3.94 (2H, m), 4.02 (2H, t), 6.50 (1H, s), 6.88-6.90 (2H, m), 6.94-6.98 (1H, m), 7.00 (1H, s), 7.28-7.30 (2H, m)

Production Example 139

5-(4-Phenoxybutyl)isoxazole-3-carboxylic acid (0.52 g, 2.0 mmol), tetrahydrofuran-3-ylmethylamine hydrochloride (0.33 g, 2.4 mmol), triethylamine (0.25 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.51 g of N-(tetrahydrofuran-3-ylmethyl)-5-(4-phenoxybutyl)isoxazole-3-carboxamide (hereinafter, referred to as Compound of Present Invention (146)) represented by the following formula.

(146)

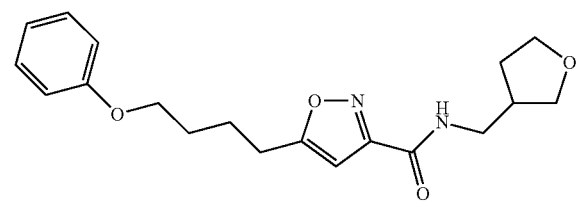

$^1$H-NMR (CDCl$_3$, TMS, δ(ppm)): 1.66-1.69 (1H, m), 1.63-1.98 (4H, m), 2.08-2.11 (1H, m), 2.54-2.61 (1H, m), 2.89 (2H, t), 3.44-3.47 (2H, m), 3.59 (1H, dd), 3.77 (1H, dd), 3.84-3.94 (2H, m), 3.99 (2H, t), 6.48 (1H, s), 6.89 (2H, ddd), 6.95 (2H, dq), 7.27-7.31 (2H, m)

Production Example 140

5-(5-Phenoxypentyl)isoxazole-3-carboxylic acid (0.70 g, 2.5 mmol), tetrahydrofuran-3-ylmethylamine hydrochloride (0.42 g, 3.0 mmol), triethylamine (0.31 g, 3.0 mmol) and 1-hydroxybenzotriazole (0.04 g, 0.30 mmol) were added to chloroform (amylene addition product) (8 mL). 1-Ethyl-3-(3-dimethylaminopropyl) carbodiimide hydrochloride (0.58 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.81 g of N1-(tetrahydrofuran-3-ylmethyl)-5-(5-phenoxypentyl)isoxazole-3-carboxamide (hereinafter, referred to as Compound of Present Invention (147)) represented by the following formula.

(147)

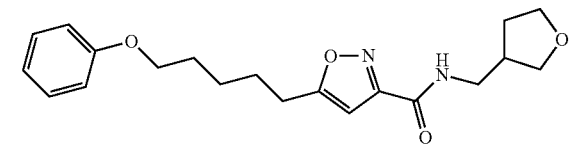

$^1$H-NMR (CDCl$_3$, TMS, δ(ppm)): 1.55-1.59 (2H, m), 1.65-1.71 (1H, m), 1.76-1.86 (4H, m), 2.04-2.13 (1H, m), 2.52-2.62 (1H, m), 2.83 (2H, t), 3.46 (2H, dd), 3.59 (1H, dd), 3.76 (1H, dd), 3.86 (1H, dd), 3.91 (1H, td), 3.96 (2H, t), 6.46 (1H, s), 6.87-6.96 (4H, m), 7.27-7.29 (2H, m)

Production Example 141

5-(6-Phenoxyhexyl)isoxazole-3-carboxylic acid (0.72 g, 2.5 mmol), tetrahydrofuran-3-ylmethylamine hydrochloride (0.42 g, 3.0 mmol), triethylamine (0.31 g, 3.0 mmol) and 1-hydroxybenzotriazole (0.04 g, 0.30 mmol) were added to chloroform (amylene addition product) (8 mL). 1-Ethyl-3-(3-dimethylaminopropyl) carbodiimide hydrochloride (0.58 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.77 g of N-(tetrahydrofuran-3-ylmethyl)-5-(6-phenoxyhexyl)isoxazole-3-carboxamide (hereinafter, referred to as Compound of Present Invention (148)) represented by the following formula.

(148)

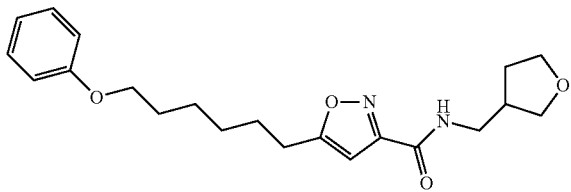

$^1$H-NMR (CDCl$_3$, TMS, δ(ppm)): 1.40-1.56 (4H, m), 1.64-1.68 (1H, m), 1.72-1.82 (4H, m), 2.04-2.13 (1H, m), 2.52-2.62 (1H, m), 2.81 (2H, t), 3.46 (2H, dt), 3.58 (1H, dd), 3.73-3.79 (1H, m), 3.86 (1H, dd), 3.88-3.93 (1H, m), 3.95 (2H, t), 6.45 (1H, s), 6.87-6.95 (4H, m), 7.27-7.29 (2H, m)

Production Example 142

5-(2-Phenoxyethoxymethyl)isoxazole-3-carboxylic acid (1.40 g, 5.3 mmol), tetrahydrofuran-3-ylmethylamine hydrochloride (0.88 g, 6.4 mmol), triethylamine (0.65 g, 6.4 mmol) and 1-hydroxybenzotriazole (0.08 g, 0.64 mmol) were added to chloroform (amylene addition product) (20 mL). 1-Ethyl-3-(3-dimethylaminopropyl) carbodiimide hydrochloride (1.23 g, 6.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 1.60 g of N-(tetrahydrofuran-3-ylmethyl)-5-(2-phenoxyethoxymethyl)isoxazole-3-carboxamide (hereinafter, referred to as Compound of Present Invention (149)) represented by the following formula.

(149)

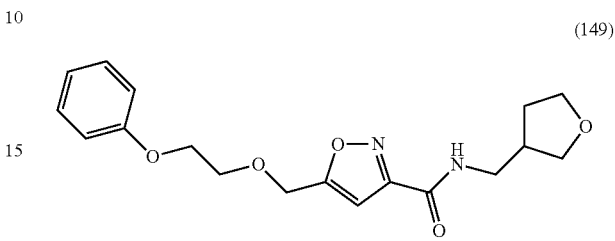

$^1$H-NMR (CDCl$_3$, TMS, δ(ppm)): 1.66-1.69 (1H, m), 2.05-2.13 (1H, m), 2.56-2.60 (1H, m), 3.47 (2H, t), 3.56-3.61 (1H, m), 3.74-3.80 (1H, m), 3.84-3.88 (1H, m), 3.91-3.93 (3H, m), 4.15-4.17 (2H, m), 4.77 (2H, s), 6.76 (1H, s), 6.90-7.00 (4H, m), 7.27-7.32 (2H, m)

Production Example 143

5-[7-(2-Quinolyloxy)heptyl]isoxazole-3-carboxylic acid (0.50 g, 1.4 mmol), tetrahydrofuran-3-ylmethylamine hydrochloride (0.33 g, 2.4 mmol), triethylamine (0.24 g, 2.4 mmol) and 11-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.51 g of N-(tetrahydrofuran-3-ylmethyl)-5-[7-(2-quinolyloxy)heptyl]isoxazole-3-carboxamide (hereinafter, referred to as Compound of Present Invention (150)) represented by the following formula.

(150)

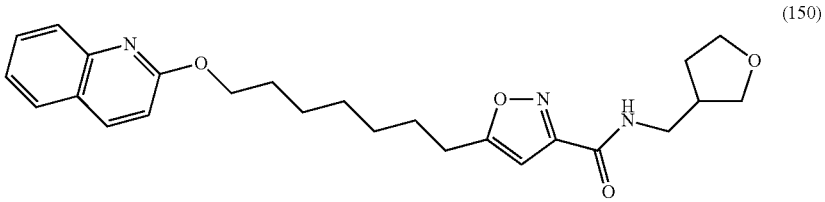 [SMILES: O=C(NCC1CCOC1)c1cc(CCCCCCCOc2ccc3ccccc3n2)on1]

$^1$H-NMR(CDCl$_3$, TMS, δ(ppm)): 1.40-1.44 (4H, m), 1.47-1.51 (2H, m), 1.66-1.74 (3H, m), 1.79-1.86 (2H, m), 2.04-2.12 (1H, m), 2.52-2.60 (1H, m), 2.79 (2H, t), 3.43-3.47 (2H, m), 3.58 (1H, dd), 3.73-3.79 (1H, m), 3.84-3.94 (2H, m), 4.46 (2H, t), 6.44 (1H, s), 6.89 (1H, d), 6.92 (1H, s), 7.34-7.38 (1H, m), 7.59-7.63 (18, m), 7.71 (1H, dd), 7.82 (1H, d), 7.97 (1H, d)

Production Example 144

5-(1-Fluorobutyl)isoxazole-3-carboxylic acid (120 mg, 0.64 mmol), tetrahydrofuran-3-ylmethylamine hydrochloride (114 mg, 0.83 mmol), triethylamine (0.23 mL, 1.65 mmol) and 1-hydroxybenzotriazole (9 mg, 0.06 mmol) were added to chloroform (amylene addition product) (3 mL). 1-Ethyl-3-(3-dimethylaminopropyl) carbodiimide hydrochloride (160 mg, 0.83 mmol) was added to the mixture at room temperature, and the mixture was stirred overnight and then concentrated under reduced pressure. The residue was applied to a silica gel column chromatography to obtain 166 mg of N-(tetrahydrofuran-3-ylmethyl)-5-(1-fluorobutyl)isoxazole-3-carboxamide (hereinafter, referred to as Compound of Present Invention (151)) represented by the following formula.

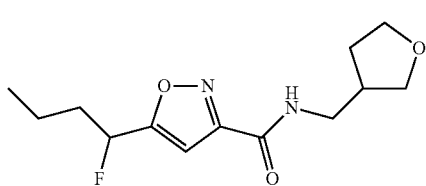

(151)

$^1$H-NMR (CDCl$_3$, TMS, δ(ppm)): 1.00 (t, 3H), 1.43-1.56 (m, 2H), 1.63-1.72 (m, 1H), 1.87-2.15 (m, 3H), 2.54-2.63 (m, 1H), 3.45-3.50 (m, 2H), 3.59 (dd, 1H), 3.73-3.80 (m, 1H), 3.83-3.95 (m, 2H), 5.59 (ddd, 1H), 6.75-6.77 (m, 1H), 6.94 (brs, 1H)

Production Example 145

5-(Hydroxyphenylmethyl)isoxazole-3-carboxylic acid (2.56 g, 10.4 mmol), tetrahydrofuran-3-ylmethylamine hydrochloride (1.77 g, 13.0 mmol), triethylamine (1.31 g, 13.0 mmol) and 1-hydroxybenzotriazole (0.18 g, 1.3 mmol) were added to chloroform (amylene addition product) (13 mL). 1-Ethyl-3-(3-dimethylaminopropyl) carbodiimide hydrochloride (2.42 g, 13.0 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 2.78 g of N-(tetrahydrofuran-3-ylmethyl)-5-(1-phenyl-1-hydroxymethyl)isoxazole-3-carboxamide (hereinafter, referred to as Compound of Present Invention (152)) represented by the following formula.

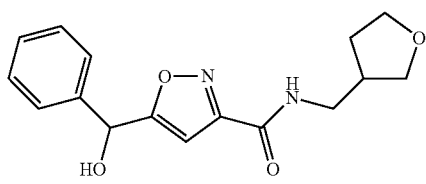

(152)

$^1$H-NMR (CDCl$_3$, TMS, δ(ppm)): 1.64-1.67 (1H, m), 2.03-2.12 (1H, m), 2.53-2.59 (1H, m), 3.43-3.46 (2H, m), 3.58 (1H, dd), 3.76 (1H, dd), 3.84 (1H, dd), 3.89-3.91 (1H, m), 5.97 (1H, s), 6.61 (1H, s), 6.95 (1H, s), 7.37-7.45 (5H, m)

Production Example 146

5-(1-Fluoro-1-phenylmethyl)isoxazole-3-carboxylic acid (250 mg, 1.13 mmol), tetrahydrofuran-3-ylmethylamine hydrochloride (202 mg, 1.47 mmol), triethylamine (0.41 mL, 2.94 mmol) and 1-hydroxybenzotriazole (15 mg, 0.11 mmol) were added to chloroform (amylene addition product) (5 mL). 1-Ethyl-3-(3-dimethylaminopropyl) carbodiimide hydrochloride (282 mg, 1.47 mmol) was added to the mixture at room temperature, and the mixture was stirred overnight. Then, water was added thereto, and the mixture was extracted with ethyl acetate. The organic layer was sequentially washed with water and saturated saline water, dried over anhydrous sodium sulfate, and then concentrated under reduced pressure. The residue was applied to a silica gel column chromatography to obtain 200 mg of N-(tetrahydrofuran-3-ylmethyl)-5-(1-fluoro-1-phenylmethyl)isoxazole-3-carboxamide (hereinafter, referred to as Compound of Present Invention (154)) represented by the following formula.

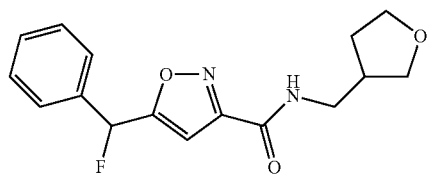

(154)

$^1$H-NMR (CDCl$_3$, TMS, δ(ppm)): 1.61-1.77 (m, 1H), 2.03-2.13 (m, 1H), 2.52-2.62 (m, 1H), 3.43-3.48 (m, 2H), 3.58 (dd, 1H), 3.72-3.79 (m, 1H), 3.82-3.95 (m, 2H), 6.54 (d, 1H), 6.64-6.67 (m, 1H), 6.92 (brs, 1H), 7.42-7.45 (m, 5H)

Production Example 147

Tetrahydrofuran-3-ylmethylamine hydrochloride (200 mg, 1.45 mmol) and a 1 mol/L aqueous sodium hydroxide solution (10 mL) were simultaneously added to a toluene solution (10 mL) of 5-(1,1-difluoro-1-phenylmethyl)isoxazole-3-carboxylic acid chloride (<0.60 mmol), under ice-water cooling. The mixture was vigorously stirred under ice-water cooling for 1 hour, and then the reaction mixture was extracted twice with ethyl acetate. The organic layer was washed with saturated saline water, dried over anhydrous sodium sulfate, and then concentrated under reduced pressure. The residue was applied to a silica gel column chromatography to obtain 190 mg of N-(tetrahydrofuran-3-ylmethyl)-5-(1,1-difluoro-1-phenylmethyl)isoxazole-3-carboxamide (hereinafter, referred to as Compound of Present Invention (155)) represented by the following formula.

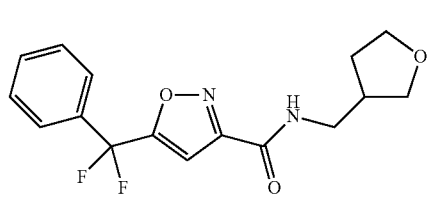

(155)

¹H-NMR (CDCl₃, TMS, δ(ppm)): 1.61-1.72 (m, 1H), 2.03-2.14 (m, 1H), 2.52-2.62 (m, 1H), 3.44-3.49 (m, 2H), 3.58 (dd, J=8.8, 5.2 Hz, 1H), 3.72-3.79 (m, 1H), 3.82-3.86 (m, 1H), 3.88-3.94 (m, 1H), 6.86-6.88 (m, 1H), 6.92 (brs, 1H), 7.46-7.61 (m, 5H)

Production Example 148

Tetrahydrofuran-3-ylmethylamine hydrochloride (250 mg, 1.82 mmol) and a 1 mol/L aqueous sodium hydroxide solution (20 mL) were simultaneously added to a toluene solution (20 mL) of 5-(1-phenylcyclopropyl)isoxazole-3-carboxylic acid chloride (<1.83 mmol), under ice-water cooling. The mixture was vigorously stirred for 30 minutes under ice-water cooling, and then the reaction mixture was extracted twice with ethyl acetate. The organic layer was washed with saturated saline water, dried over anhydrous sodium sulfate, and then concentrated under reduced pressure. The residue was applied to a silica gel column chromatography to obtain 504 mg of N-(tetrahydrofuran-3-ylmethyl)-5-(1-phenylcyclopropyl)isoxazole-3-carboxamide (hereinafter, referred to as Compound of Present Invention (156)) represented by the following formula.

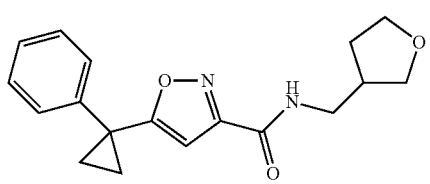

(156)

¹H-NMR (CDCl₃, TMS, δ(ppm)): 1.41-1.46 (m, 2H), 1.60-1.70 (m, 3H), 2.01-2.11 (m, 1H), 2.49-2.59 (m, 1H), 3.39-3.44 (m, 2H), 3.56 (dd, J=8.9, 5.3 Hz, 1H), 3.71-3.78 (m, 1H), 3.80-3.92 (m, 2H), 6.13 (s, 1H), 6.86 (brs, 1H), 7.29-7.42 (m, 5H)

Production Example 149

5-(2-Trifluoromethylbenzyl)isoxazole-3-carboxylic acid (380 mg, 1.40 mmol), tetrahydrofuran-3-ylmethylamine hydrochloride (239 mg, 1.74 mmol), triethylamine (0.46 mL, 3.28 mmol) and 1-hydroxybenzotriazole (18 mg, 0.13 mmol) were added to chloroform (amylene addition product) (5 mL). 1-Ethyl-3-(3-dimethylaminopropyl) carbodiimide hydrochloride (295 mg, 1.54 mmol) was added to the mixture at room temperature, and the mixture was stirred for 5.5 hours and then concentrated under reduced pressure. Water was added to the concentrate, and the mixture was extracted once with ethyl acetate. The organic layer was washed with saturated saline water, dried over anhydrous sodium sulfate, and then concentrated under reduced pressure. The residue was applied to a silica gel column chromatography to obtain 130 mg of N-(tetrahydrofuran-3-ylmethyl)-5-(2-trifluoromethylbenzyl)isoxazole-3-carboxamide (hereinafter, referred to as Compound of Present Invention (157)) represented by the following formula.

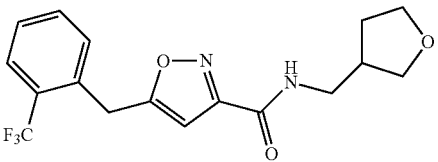

(157)

¹H-NMR (CDCl₃, TMS, δ(ppm)): 1.61-1.73 (m, 1H), 2.01-2.14 (m, 1H), 2.49-2.63 (m, 1H), 3.41-3.46 (m, 2H), 3.57 (dd, J=8.9, 5.3 Hz, 1H), 3.72-3.79 (m, 1H), 3.82-3.94 (m, 2H), 4.31 (s, 2H), 6.34 (s, 1H), 6.90 (brs, 1H), 7.34-7.38 (m, 1H), 7.39-7.45 (m, 1H), 7.51-7.56 (m, 1H), 7.68-7.72 (m, 1H).

Production Example 150

5-(3-Trifluoromethylbenzyl)isoxazole-3-carboxylic acid (242 mg, 0.89 mmol), tetrahydrofuran-3-ylmethylamine hydrochloride (155 mg, 1.15 mmol), triethylamine (0.32 mL, 2.30 mmol) and 1-hydroxybenzotriazole (15 mg, 0.11 mmol) were added to chloroform (amylene addition product) (5 mL). 1-Ethyl-3-(3-dimethylaminopropyl) carbodiimide hydrochloride (220 mg, 1.15 mmol) was added to the mixture at room temperature, and the mixture was stirred overnight and then concentrated under reduced pressure. The residue was applied to a silica gel column chromatography to obtain 130 mg of N-(tetrahydrofuran-3-ylmethyl)-5-(3-trifluoromethylbenzyl)isoxazole-3-carboxamide (hereinafter, referred to as Compound of Present Invention (158)) represented by the following formula.

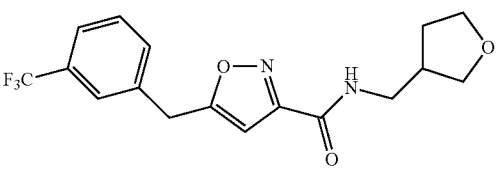

(158)

¹H-NMR (CDCl₃, TMS, δ(ppm)): 1.61-1.71 (m, 1H), 2.03-2.12 (m, 1H), 2.52-2.61 (m, 1H), 3.45 (dd, J=6.6, 6.6 Hz, 2H), 3.58 (dd, J=8.7, 5.3 Hz, 1H), 3.72-3.79 (m, 1H), 3.82-3.94 (m, 2H), 4.19 (s, 2H), 6.43 (s, 1H), 6.90 (brs, 1H), 7.43-7.59 (m, 4H)

Production Example 151

5-(Naphthalen-2-ylmethyl)isoxazole-3-carboxylic acid (204 mg, 0.81 mmol), tetrahydrofuran-3-ylmethylamine hydrochloride (204 mg, 1.48 mmol), triethylamine (0.38 mL, 2.75 mmol) and 1-hydroxybenzotriazole (14 mg, 0.11 mmol) were added to chloroform (amylene addition product) (5 mL). 1-Ethyl-3-(3-dimethylaminopropyl) carbodiimide hydrochloride (264 mg, 1.38 mmol) was added to the mixture at room temperature, and the mixture was stirred overnight and then concentrated under reduced pressure. The residue was applied to a silica gel column chromatography to obtain 166 mg of N-(tetrahydrofuran-3-ylmethyl)-5-(naphthalen-2-ylmethyl)isoxazole-3-carboxamide (hereinafter, referred to as Compound of Present Invention (159)) represented by the following formula.

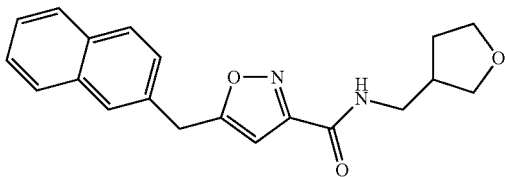

(159)

¹H-NMR (CDCl₃, TMS, δ(ppm)): 1.60-1.72 (m, 1H), 2.02-2.12 (m, 1H), 2.52-2.61 (m, 1H), 3.41-3.46 (m, 2H), 3.57 (dd, J=9.0, 5.3 Hz, 1H), 3.72-3.79 (m, 1H), 3.82-3.93 (m, 2H), 4.29 (s, 2H), 6.43 (d, J=3.9 Hz, 1H), 6.90 (brs, 1H), 7.34-7.38 (m, 1H), 7.46-7.53 (m, 2H), 7.71 (s, 1H), 7.78-7.86 (m, 3H)

Production Example 152

5-(Naphthalen-1-ylmethyl)isoxazole-3-carboxylic acid (123 mg, 0.49 mmol), tetrahydrofuran-3-ylmethylamine hydrochloride (123 mg, 0.90 mmol), triethylamine (0.23 mL, 1.66 mmol) and 1-hydroxybenzotriazole (9 mg, 0.06 mmol) were added to chloroform (amylene addition product) (5 mL). 1-Ethyl-3-(3-dimethylaminopropyl) carbodiimide hydrochloride (159 mg, 0.83 mmol) was added to the mixture at room temperature, and the mixture was stirred overnight and then concentrated under reduced pressure. The residue was applied to a silica gel column chromatography to obtain 95 mg of N-(tetrahydrofuran-3-ylmethyl)-5-(naphthalen-1-ylmethyl)isoxazole-3-carboxamide (hereinafter, referred to as Compound of Present Invention (160)) represented by the following formula.

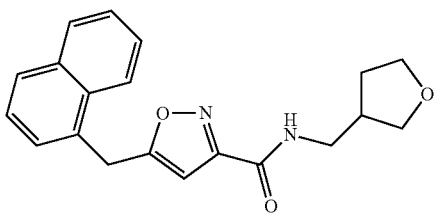

(160)

¹H-NMR (CDCl₃, TMS, δ(ppm)): 1.57-1.67 (m, 1H), 1.99-2.08 (m, 1H), 2.48-2.60 (m, 1H), 3.36-3.44 (m, 2H), 3.52-3.57 (m, 1H), 3.69-3.93 (m, 3H), 4.55 (s, 2H), 6.27 (s, 1H), 6.96 (brs, 1H), 7.37-7.54 (m, 4H), 7.80-7.85 (m, 1H), 7.86-7.92 (m, 2H)

Production Example 153

Tetrahydrofuran-3-ylmethylamine hydrochloride (150 mg, 1.09 mmol) and a 1 mol/L aqueous sodium hydroxide solution (8 mL) were simultaneously added to a toluene solution (10 mL) of 5-(benzo[b]thiophen-2-ylmethy)isoxazole-3-carboxylic acid chloride (<0.38 mmol), under ice-water cooling. The mixture was vigorously stirred for 30 minutes under ice-water cooling, and then the reaction mixture was extracted once with ethyl acetate. The organic layer was washed with saturated saline water, dried over anhydrous sodium sulfate, and then concentrated under reduced pressure. The residue was applied to a silica gel column chromatography to obtain 104 mg of N-(tetrahydrofuran-3-ylmethyl)-5-(benzo[b]thiophen-2-ylmethy)isoxazole-3-carboxamide (hereinafter, referred to as Compound of Present Invention (161)) represented by the following formula.

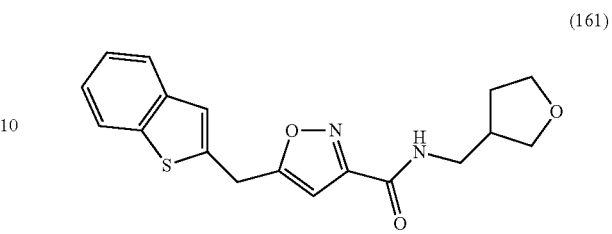

(161)

¹H-NMR (CDCl₃, TMS, δ(ppm)): 1.62-1.71 (m, 1H), 2.03-2.13 (m, 1H), 2.50-2.63 (m, 1H), 3.43-3.48 (m, 2H), 3.58 (dd, J=8.9, 5.3 Hz, 1H), 3.72-3.79 (m, 1H), 3.82-3.94 (m, 2H), 4.41 (s, 2H), 6.58 (s, 1H), 6.91 (s, 1H), 7.16 (s, 1H), 7.29-7.37 (m, 2H), 7.69-7.73 (m, 1H), 7.76-7.81 (m, 1H)

Production Example 154

Tetrahydrofuran-3-ylmethylamine hydrochloride (0.20 g, 1.46 mmol) and triethylamine (0.15 g, 1.46 mmol) were added to chloroform (amylene addition product) (7 mL). 5-(4-Phenoxybenzyl)isoxazole-3-carboxylic acid (0.36 g, 1.22 mmol), 1-hydroxybenzotriazole (0.02 g, 0.12 mmol) and 1-ethyl-3-(3-dimethylaminopropyl) carbodiimide hydrochloride (0.28 g, 1.46 mmol) were added to the mixture at room temperature, and the mixture was stirred overnight. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.34 g of N-(tetrahydrofuran-3-ylmethyl)-5-(4-phenoxybenzyl)isoxazole-3-carboxamide (hereinafter, referred to as Compound of Present Invention (162)) represented by the following formula.

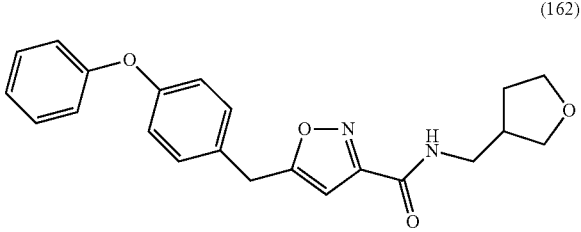 [SMILES: O=C(NCC1CCOC1)c1cc(Cc2ccc(Oc3ccccc3)cc2)on1]

(162)

¹H-NMR (CDCl₃, TMS, δ(ppm)): 1.62-1.70 (1H, m), 2.03-2.12 (1H, m), 2.51-2.61 (1H, m), 3.43-3.46 (2H, m), 3.56-3.60 (1H, m), 3.73-3.79 (1H, m), 3.83-3.92 (2H, m), 4.09 (2H, s), 6.41 (1H, s), 6.96-7.02 (5H, m), 7.09-7.14 (1H, m), 7.20-7.22 (2H, m) 7.32-7.37 (2H, m)

Production Example 155

Tetrahydrofuran-3-ylmethylamine hydrochloride (0.17 g, 1.22 mmol) and triethylamine (0.12 g, 1.22 mmol) were added to chloroform (amylene addition product) (6 mL). 5-(3-Phenoxybenzyl)isoxazole-3-carboxylic acid (0.30 g, 1.02 mmol), 1-hydroxybenzotriazole (0.01 g, 0.10 mmol)

and 1-ethyl-3-(3-dimethylaminopropyl) carbodiimide hydrochloride (0.23 g, 1.22 mmol) were added to the mixture at room temperature, and the mixture was stirred overnight. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.31 g of N-(tetrahydrofuran-3-ylmethyl)-5-(3-phenoxybenzyl)isoxazole-3-carboxamide (hereinafter, referred to as Compound of Present Invention (163)) represented by the following formula.

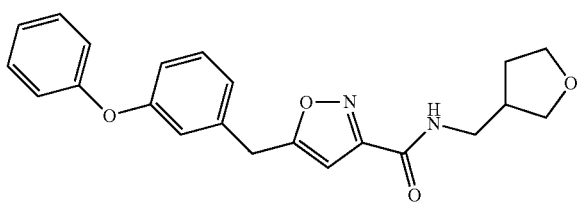

(163)

$^1$H-NMR (CDCl$_3$, TMS, δ(ppm)): 1.62-1.71 (1H, m), 2.03-2.11 (1H, m), 2.51-2.61 (1H, m), 3.43-3.46 (2H, m), 3.56-3.59 (1H, m), 3.73-3.79 (1H, m), 3.82-3.94 (2H, m), 4.08 (2H, s), 6.41 (1H, s), 6.90-7.02 (6H, m), 7.10-7.14 (1H, m), 7.28-7.37 (3H, m)

Production Example 156

A 1.64 mol/L-n-butyllithium hexane solution (15.2 mL, 25.0 mmol) was added dropwise to a tetrahydrofuran (50 mL) solution of N-(tetrahydrofuran-3-ylmethyl)-(5-benzyloxymethyl)isoxazole-3-carboxamide (3.16 g, 9.99 mmol) at −50° C. or less under a nitrogen atmosphere. After stirring at −60° C. or less for 1 hour, an N,N-dimethylformamide (3 mL) solution was added to the reaction mixture, and the mixture was stirred at a temperature in the range of −60° C. to 10° C. for 1.5 hours. Then, 1 mol/L hydrochloric acid (about 20 mL) was poured thereinto under ice cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 2.46 g of N-(tetrahydrofuran-3-ylmethyl)-(5-benzyloxymethyl-4-formyl)isoxazole-3-carboxamide (hereinafter, referred to as Compound of Present Invention (165)) represented by the following formula.

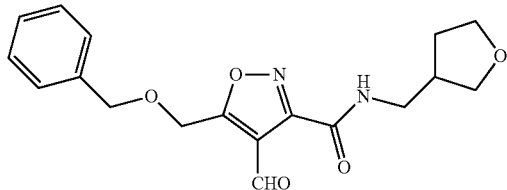

(165)

$^1$H-NMR (CDCl$_3$, TMS, δ(ppm)): 1.65-1.75 (m, 1H), 2.07-2.16 (m, 1H), 2.56-2.68 (m, 1H), 3.47-3.54 (m, 2H), 3.62 (dd, J=9.0, 5.1 Hz, 1H), 3.74-3.82 (m, 1H), 3.84-3.97 (m, 2H), 4.67 (s, 2H), 4.97 (s, 2H), 7.30-7.43 (m, 6H), 10.40 (s, 1H)

Production Example 157

A 1.58 mol/L-n-butyllithium hexane solution (12.5 mL, 19.8 mmol) was added dropwise to a tetrahydrofuran (40 mL) solution of N-(tetrahydrofuran-3-ylmethyl)-(5-benzyloxymethyl)isoxazole-3-carboxamide (2.50 g, 7.90 mmol) at −50° C. or less under a nitrogen atmosphere, and the mixture was stirred at −60° C. or less for 30 minutes. Then, carbon dioxide was introduced to the reaction mixture, and the mixture was further stirred at −60° C. to 10° C. for 2 hours. Subsequently, 1 mol/L hydrochloric acid (about 20 mL) was poured thereinto under ice cooling, and the mixture was extracted twice with ethyl acetate. The organic layer was washed with saturated saline water, dried over anhydrous magnesium sulfate, and then concentrated under reduced pressure. The residue was suspended in diisopropyl ether, and filtered to obtain 2.00 g of 5-benzyloxymethyl-3-[N-(3-tetrahydrofuranylmethyl)carbamoyl]isoxazole-4-carboxylic acid (hereinafter, referred to as Compound of Present Invention (166)) represented by the following formula.

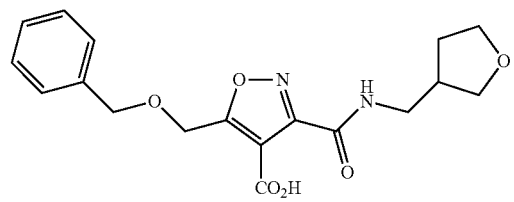

(166)

$^1$H-NMR (CDCl$_3$, TMS, δ(ppm)): 1.64-1.77 (m, 1H), 2.09-2.20 (m, 1H), 2.58-2.70 (m, 1H), 3.52-3.57 (m, 2H), 3.64 (dd, J=9.2, 4.6 Hz, 1H), 3.75-3.88 (m, 2H), 3.92-3.99 (m, 1H), 4.69 (s, 2H), 5.13 (s, 2H), 7.28-7.40 (m, 6H), 7.56 (brs, 1H)

Production Example 158

N,N-dimethylformamide (7 mg, 0.10 mmol) and oxalyl chloride (0.17 mL, 2.00 mmol) were added to an ethyl acetate solution (15 mL) of 5-benzyloxymethyl-3-[N-(3-tetrahydrofuranylmethyl) carbamoyl]isoxazole-4-carboxylic acid (<1.00 mmol), and the mixture was stirred at room temperature for 10 minutes. Then, methanol (5 mL) was added thereto, and the mixture was further stirred for 10 minutes and concentrated under reduced pressure. The concentrate was diluted with ethyl acetate, sequentially washed with water and saturated saline water, dried over anhydrous sodium sulfate, and then concentrated under reduced pressure. The residue was applied to a silica gel column chromatography to obtain 223 mg of N-(tetrahydrofuran-3-ylmethyl)-(5-benzyloxymethyl-4-methoxycarbonyl) isoxazole-3-carboxamide (hereinafter, referred to as Compound of Present Invention (167)) represented by the following formula.

(167)

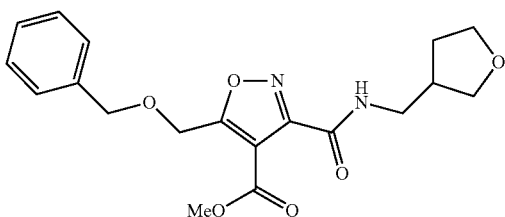

¹H-NMR (CDCl₃, TMS, δ(ppm)): 1.65-1.75 (m, 1H), 2.06-2.15 (m, 1H), 2.55-2.66 (m, 1H), 3.47-3.53 (m, 2H), 3.60 (dd, J=8.7, 5.5 Hz, 1H), 3.74-3.81 (m, 1H), 3.87 (s, 3H), 3.85-3.95 (m, 2H), 4.64 (s, 2H), 4.88 (s, 2H), 7.30-7.40 (m, 5H), 7.95 (brs, 1H)

Production Example 159

N,N-dimethylformamide (7 mg, 0.10 mmol) and oxalyl chloride (0.17 mL, 2.00 mmol) were added to an ethyl acetate solution (15 mL) of 5-benzyloxymethyl-3-[N-(3-tetrahydrofuranylmethyl) carbamoyl]isoxazole-4-carboxylic acid (<1.00 mmol), and the mixture was stirred at room temperature for 10 minutes. Then, a 28% aqueous ammonia solution (10 mL) was added thereto, and the mixture was further stirred for 10 minutes and diluted with ethyl acetate. The organic layer was sequentially washed with water and saturated saline water, dried over anhydrous sodium sulfate, and then concentrated under reduced pressure. The residue was applied to a silica gel column chromatography to obtain 265 mg of N-(tetrahydrofuran-3-ylmethyl)-(5-benzyloxymethyl-4-carbamoyl)isoxazole-3-carboxamide (hereinafter, referred to as Compound of Present Invention (168)) represented by the following formula.

(168)

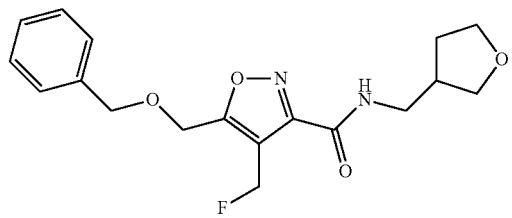

¹H-NMR (CDCl₃, TMS, δ(ppm)): 1.63-1.73 (m, 1H), 2.07-2.17 (m, 1H), 2.55-2.66 (m, 1H), 3.46-3.51 (m, 2H), 3.62 (dd, J=8.9, 5.0 Hz, 1H), 3.74-3.81 (m, 1H), 3.83-3.88 (m, 1H), 3.90-3.97 (m, 1H), 4.68 (s, 2H), 5.14 (s, 2H), 5.61 (brs, 1H), 7.29-7.43 (m, 6H), 9.81 (brs, 1H)

Production Example 160

Tributyltin hydride (544 mg, 1.87 mmol) and azobisisobutyronitrile (51 mg, 0.32 mmol) were added to a toluene (20 mL) solution of dithiocarboxylic acid 4-O-{5-benzyloxymethyl-3-[N-(3-tetrahydrofuranylmethyl) carbamoyl]isoxazolylmethyl}ester S-methyl ester (680 mg, 1.56 mmol). The mixture was stirred at 90° C. for 30 minutes, and then concentrated under reduced pressure. The residue was applied to a silica gel column chromatography to obtain 400 mg of N-(tetrahydrofuran-3-ylmethyl)-(5-benzyloxymethyl-4-methyl)isoxazole-3-carboxamide (hereinafter, referred to as Compound of Present Invention (169)) represented by the following formula.

(169)

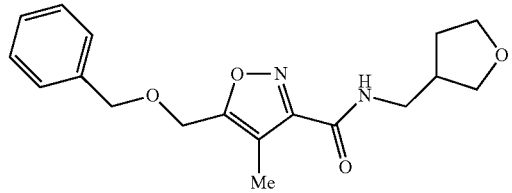

¹H-NMR (CDCl₃, TMS, δ(ppm)): 1.63-1.72 (m, 1H), 2.04-2.14 (m, 1H), 2.24 (s, 3H), 2.53-2.61 (m, 1H), 3.42-3.47 (m, 2H), 3.58 (dd, 1H), 3.74-3.80 (m, 1H), 3.84-3.95 (m, 2H), 4.57 (s, 2H), 4.59 (s, 2H), 6.95 (brs, 1H), 7.29-7.40 (m, 5H)

Production Example 161

Bis(2-methoxyethyl)aminosulfur trifluoride (0.28 mL, 1.50 mmol) was added to a toluene (8 mL) solution of N-(tetrahydrofuran-3-ylmethyl)-(5-benzyloxymethyl-4-hydroxymethyl)isoxazole-3-carboxamide (400 mg, 1.16 mmol) under ice-water cooling. The mixture was stirred for 30 minutes under ice-water cooling, and then diluted with ethyl acetate. The organic layer was sequentially washed with water and saturated saline water, dried over anhydrous sodium sulfate, and then concentrated under reduced pressure. The residue was applied to a silica gel column chromatography to obtain 124 mg of N-(tetrahydrofuran-3-ylmethyl)-(5-benzyloxymethyl-4-fluoromethyl)isoxazole-3-carboxamide (hereinafter, referred to as Compound of Present Invention (170)) represented by the following formula.

(170)

¹H-NMR (CDCl₃, TMS, δ(ppm)): 1.62-1.73 (m, 1H), 2.02-2.14 (m, 1H), 2.52-2.63 (m, 1H), 3.43-3.48 (m, 2H), 3.59 (dd, 1H), 3.73-3.80 (m, 1H), 3.85 (dd, 1H), 3.88-3.95 (m, 1H), 4.61 (s, 2H), 4.72 (d, 2H), 5.62 (d, 2H), 6.98 (brs, 1H), 7.29-7.41 (m, 5H)

Production Example 162

Bis(2-methoxyethyl)aminosulfur trifluoride (0.64 mL, 3.49 mmol) was added to a toluene (4 mL) solution of N-(tetrahydrofuran-3-ylmethyl)-(5-benzyloxymethyl-4-formyl)isoxazole-3-carboxamide (400 mg, 1.16 mmol). The mixture was stirred at room temperature for 2 hours, and then diluted with ethyl acetate. The organic layer was sequentially washed with water and saturated saline water, dried over anhydrous sodium sulfate, and then concentrated under reduced pressure. The residue was applied to a silica gel column chromatography to obtain 340 mg of N-(tetrahydrofuran-3-ylmethyl)-(5-benzyloxymethyl-4-difluoromethyl)isoxazole-3-carboxamide (hereinafter, referred to as Compound of Present Invention (171)) represented by the following formula.

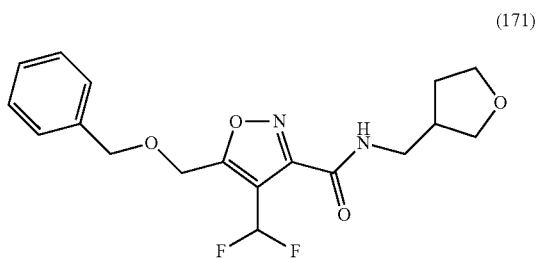 [SMILES: O=C(NCC1CCOC1)c1noc(COCc2ccccc2)c1C(F)F]

(171)

¹H-NMR (CDCl₃, TMS, δ(ppm)): 1.63-1.72 (m, 1H), 2.05-2.15 (m, 1H), 2.53-2.65 (m, 1H), 3.44-3.49 (m, 2H), 3.60 (dd, 1H), 3.74-3.80 (m, 1H), 3.83-3.87 (m, 1H), 3.89-3.95 (m, 1H), 4.63 (s, 2H), 4.80-4.81 (m, 2H), 6.97 (brs, 1H), 7.28 (t, 1H), 7.29-7.40 (m, 5H)

Production Example 163

Bis(2-methoxyethyl)aminosulfur trifluoride (0.42 mL, 2.29 mmol) was added to a dichloromethane (10 mL) solution of N-(tetrahydrofuran-3-ylmethyl)-[5-benzyloxymethyl-4-(1-hydroxyethyl)]isoxazole-3-carboxamide (550 mg, 1.53 mmol). The mixture was stirred at room temperature for 4 hours and 30 minutes, and then diluted with ethyl acetate. The organic layer was sequentially washed with an aqueous sodium bicarbonate solution and saturated saline water and dried over anhydrous sodium sulfate, and then concentrated under reduced pressure. The residue was applied to a silica gel column chromatography to obtain 460 mg of N-(tetrahydrofuran-3-ylmethyl)-[5-benzyloxymethyl-4-(1-fluoroethyl)]isoxazole-3-carboxamide (hereinafter, referred to as Compound of Present Invention (172)) represented by the following formula.

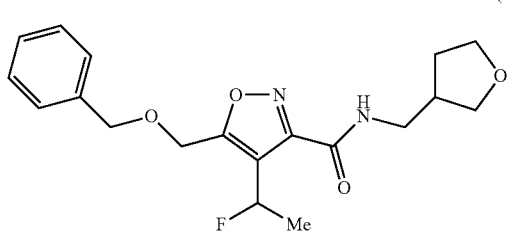

(172)

¹H-NMR (CDCl₃, TMS, δ(ppm)): 1.62-1.74 (m, 1H), 2.06-2.14 (m, 1H), 2.52-2.62 (m, 1H), 3.41-3.47 (m, 2H), 3.58 (dd, 1H), 3.73-3.80 (m, 1H), 3.82-3.96 (m, 2H), 4.61 (s, 2H), 4.71 (d, 1H), 4.79 (d, 1H), 6.19 (m, 1H), 6.98 (brs, 1H), 7.35 (m, 5H)

Production Example 164

60% Sodium hydride (108 mg, 2.70 mmol) was added to a tetrahydrofuran (20 mL) solution of N-(tetrahydrofuran-3-ylmethyl)-(5-benzyloxymethyl-4-hydroxymethyl)isoxazole-3-carboxamide (780 mg, 2.25 mmol) under ice-water cooling. After stirring for 15 minutes, under ice-water cooling, carbon bisulfide (0.8 mL) was added thereto. The mixture was further stirred for 10 minutes, and then, methyl iodide (0.8 mL) was added thereto. After stirring for 10 minutes, under ice-water cooling, water was added, and the mixture was extracted once with a mixed solution of ethyl acetate and hexane. The organic layer was sequentially washed with water and saturated saline water, dried over anhydrous sodium sulfate, and then concentrated under reduced pressure. The residue was applied to a silica gel column chromatography to obtain 840 mg of dithiocarboxylic acid 4-O-{5-benzyloxymethyl-3-[N-(3-tetrahydrofuranylmethyl)carbamoyl]isoxazolylmethyl}ester S-methyl ester (hereinafter, referred to as Compound of Present Invention (173)) represented by the following formula.

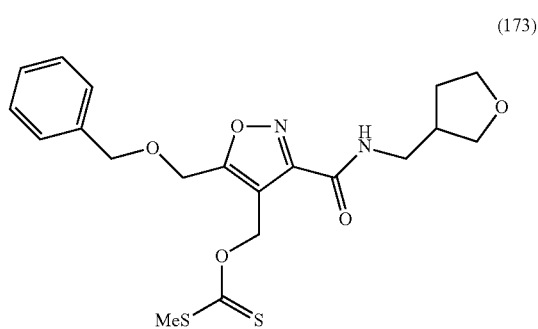 [SMILES: CSC(=S)OCc1c(C(=O)NCC2CCOC2)noc1COCc1ccccc1]

(173)

¹H-NMR (CDCl₃, TMS, δ(ppm)): 1.62-1.72 (m, 1H), 2.06-2.14 (m, 1H), 2.54 (s, 3H), 2.56-2.62 (m, 1H), 3.43-3.48 (m, 2H), 3.59 (dd, 1H), 3.73-3.80 (m, 1H), 3.83-3.95 (m, 2H), 4.60 (s, 2H), 4.72 (s, 2H), 5.80 (s, 2H), 6.94 (brs, 1H), 7.29-7.39 (m, 5H)

Production Example 165

Sodium borohydride (400 mg, 10.6 mmol) was added to a methanol (16 mL) solution of N-(tetrahydrofuran-3-ylmethyl)-(5-benzyloxymethyl-4-formyl)isoxazole-3-carboxamide (800 mg, 2.32 mmol) under ice-water cooling. The mixture was stirred for 30 minutes under ice-water cooling, and then the reaction mixture was diluted with toluene, and concentrated under reduced pressure. A 1 mol/L aqueous sodium hydroxide solution was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 640 mg of N-(tetrahydrofuran-3-ylmethyl)-(5-benzyloxymethyl-4-hydroxymethyl)isoxazole-3-carboxamide (hereinafter, referred to as Compound of Present Invention (174)) represented by the following formula.

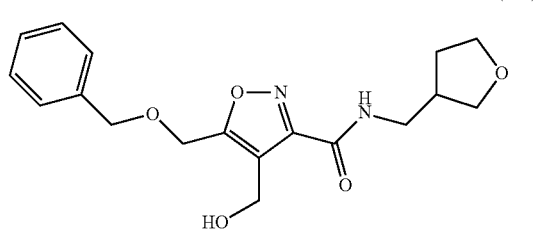

(174)

¹H-NMR (CDCl₃, TMS, δ(ppm)): 1.63-1.73 (m, 1H), 2.06-2.16 (m, 18H), 2.55-2.65 (m, 1H), 3.46-3.51 (m, 2H), 3.61 (dd, 1H), 3.74-3.81 (m, 1H), 3.83-3.88 (m, 1H), 3.90-3.96 (m, 1H), 4.56-4.66 (m, 7H), 7.15 (brs, 1H), 7.30-7.41 (m, 5H)

Production Example 166

A 0.98 mol/L-methylmagnesium bromide tetrahydrofuran solution (8.0 mL, 7.84 mmol) was added to a tetrahydrofuran (20 mL) solution of N-(tetrahydrofuran-3-ylmethyl)-(5-benzyloxymethyl-4-formyl)isoxazole-3-carboxamide (900 mg, 2.61 mmol) under ice-water cooling. The reaction mixture stirred at room temperature for 1 hour was poured into ice and dilute hydrochloric acid, and the mixture was extracted twice with ethyl acetate. The organic layer was washed with saturated saline water, dried over anhydrous sodium sulfate, and then concentrated under reduced pressure. The residue was applied to a silica gel column chromatography to obtain 751 mg of N-(tetrahydrofuran-3-ylmethyl)-[5-benzyloxymethyl-4-(1-hydroxyethyl)]isoxazole-3-carboxamide (hereinafter, referred to as Compound of Present Invention (175)) represented by the following formula.

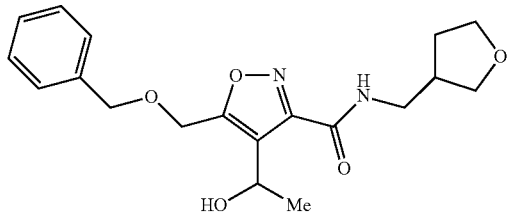

(175)

¹H-NMR (CDCl₃, TMS, δ(ppm)): 1.50 (d, J=6.6 Hz, 3H), 1.64-1.73 (m, 1H), 2.06-2.16 (m, 1H), 2.53-2.65 (m, 1H), 3.46-3.51 (m, 2H), 3.58-3.63 (m, 1H), 3.74-3.81 (m, 1H), 3.83-3.88 (m, 1H), 3.90-3.97 (m, 1H), 4.53-4.67 (m, 4H), 4.85-4.93 (m, 1H), 5.23-5.26 (m, 1H), 7.22 (brs, 1H), 7.30-7.42 (m, 5H)

Production Example 167

5-(2-Chlorophenoxymethyl)isoxazole-3-carboxylic acid (1.0 g, 4.0 mmol) was added to dehydrated N,N-dimethylformamide (5 mL), and cooled to 0° C. Triethylamine (1.10 ml, 7.9 mmol), 1-ethyl-3-(3-dimethylaminopropyl) carbodiimide hydrochloride (1.50 g, 7.9 mmol) and 1-hydroxybenzotriazole (1.07 g, 7.9 mmol) were added thereto, and the mixture was stirred for 10 minutes. Tetrahydrofuran-3-ylmethylamine (0.44 g, 4.0 mmol) was added to the mixture, and the mixture was stirred at room temperature for 4 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.27 g of N-(tetrahydrofuran-3-ylmethyl)-5-(2-chlorophenoxymethyl)isoxazole-3-carboxamide (hereinafter, referred to as Compound of Present Invention (176)) represented by the following formula.

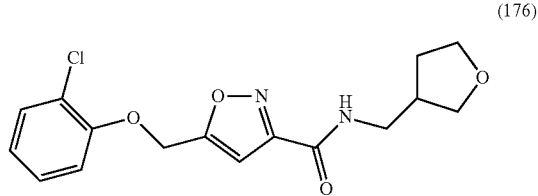 [SMILES: O=C(NCC1CCOC1)c1cc(COc2ccccc2Cl)on1]

(176)

¹H-NMR (CDCl₃, TMS, δ(ppm)): 1.56 (1H, m), 1.91 (1H, m), 2.44 (1H, m), 3.22 (2H, t), 3.45 (1H, m), 3.76-3.65 (3H, m), 5.45 (2H, s), 6.92 (1H, s), 7.03 (1H, m), 7.32 (2H, m), 7.47 (1H, d), 8.97 (1H, t)

Production Example 168

5-(2-Chlorophenoxymethyl)isoxazole-3-carboxylic acid (1.2 g, 4.7 mmol) was added to dehydrated N,N-dimethylformamide (6 mL), and cooled to 0° C. Triethylamine (1.33 ml, 9.5 mmol), 1-ethyl-3-(3-dimethylaminopropyl) carbodiimide hydrochloride (1.08 g, 5.7 mmol) and 1-hydroxybenzotriazole (0.77 g, 7.9 mmol) were added thereto, and the mixture was stirred for 10 minutes. Tetrahydropyran-4-ylmethylamine (0.60 g, 5.9 mmol) was added to the mixture, and the mixture was stirred at room temperature for 4 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.40 g of N-(tetrahydropyran-4-ylmethyl)-5-(2-chlorophenoxymethyl)isoxazole-3-carboxamide (hereinafter, referred to as Compound of Present Invention (177)) represented by the following formula.

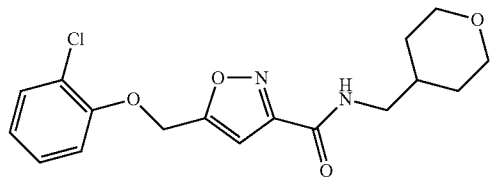

(177)

¹H-NMR (CDCl₃, TMS, δ(ppm)): 1.18 (2H, m), 1.54 (2H, d), 1.77 (1H, m), 3.13 (2H, t), 3.24 (2H, t), 3.84 (2H, d), 5.49 (2H, s), 6.91 (1H, s), 7.02 (1H, m), 7.33 (2H, m), 7.47 (1H, d), 8.84 (1H, t)

Production Example 169

5-(3-Chlorophenoxymethyl)isoxazole-3-carboxylic acid (1.0 g, 4.0 mmol) was added to N,N-dimethylformamide (10 mL), and cooled to 0° C. Triethylamine (1.10 ml, 7.9 mmol), 1-ethyl-3-(3-dimethylaminopropyl) carbodiimide hydrochloride (1.50 g, 7.9 mmol) and 1-hydroxybenzotriazole (1.07 g, 7.9 mmol) were added thereto, and the mixture was stirred for 10 minutes. Tetrahydrofuran-3-ylmethylamine (0.44 g, 4.0 mmol) was added to the mixture, and the mixture was stirred at room temperature for 4 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.25 g of N-(tetrahydrofuran-3-ylmethyl)-5-(3-chlorophenoxymethyl)isoxazole-3-carboxamide (hereinafter, referred to as Compound of Present Invention (178)) represented by the following formula.

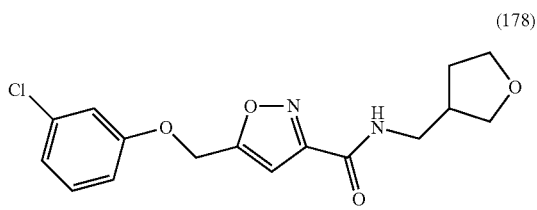 [SMILES: O=C(NCC1CCOC1)c1cc(COc2cccc(Cl)c2)on1]

(178)

¹H-NMR (CDCl₃, TMS, δ(ppm)): 1.64 (1H. m), 2.09 (1H, m), 2.57 (1H, m), 3.46 (2H, t), 3.58 (1H, q), 3.95-3.72 (3H, m), 5.18 (2H, s), 6.84 (2H, m), 6.96 (2H, m), 7.22 (1H, d)

Production Example 170

5-(3-Chlorophenoxymethyl)isoxazole-3-carboxylic acid (1.0 g, 4.0 mmol) was added to N,N-dimethylformamide (10 mL), and cooled to 0° C. Triethylamine (1.10 ml, 7.9 mmol), 1-ethyl-3-(3-dimethylaminopropyl) carbodiimide hydrochloride (1.50 g, 7.9 mmol) and 1-hydroxybenzotriazole (1.07 g, 7.9 mmol) were added thereto, and the mixture was stirred for 10 minutes. Tetrahydropyran-4-ylmethylamine (0.50 g, 4.3 mmol) was added to the mixture, and the mixture was stirred at room temperature for 4 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.40 g of N-(tetrahydropyran-4-ylmethyl)-5-(3-chlorophenoxymethyl)isoxazole-3-carboxamide (hereinafter, referred to as Compound of Present Invention (179)) represented by the following formula.

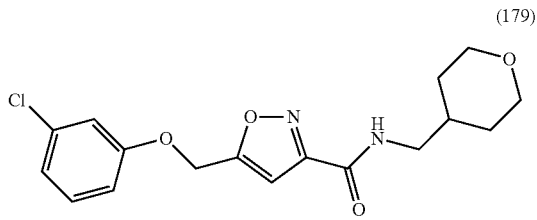 [SMILES: O=C(NCC1CCOCC1)c1cc(COc2cccc(Cl)c2)on1]

(179)

¹H-NMR (CDCl₃, TMS, δ(ppm)): 1.44-1.30 (2H, m), 1.66 (2H, d), 1.83 (1H, m), 3.37 (4H, m), 4.0 (2H, d), 5.17 (2H, s), 6.84 (2H, m), 6.99 (2H, t), 7.22 (1H, d)

Production Example 171

5-[4-Chlorophenoxy)methyl]isoxazole-3-carboxylic acid (500 mg, 1.87 mmol) and tetrahydrofuran-3-ylmethylamine (208 mg, 2.05 mmol) were added to dehydrated tetrahydrofuran (20 ml), and cooled to 0° C. (Benzotriazol-1-yloxy)tripyrrolidinophosphonium hexafluorophosphate (1.46 g, 2.80 mmol) was added thereto, and the mixture was stirred at 0° C. for 16 hours. The mixture was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 305 mg of N-(tetrahydrofuran-3-ylmethyl)-5-[4-chlorophenoxy)methyl]isoxazole-3-carboxamide (hereinafter, referred to as Compound of Present Invention (180)) represented by the following formula.

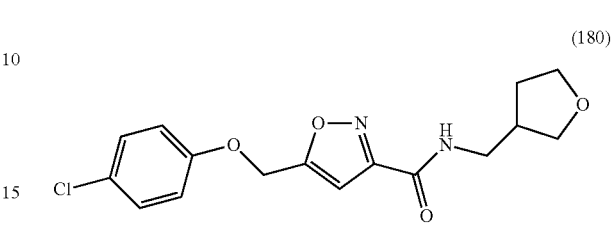

(180)

¹H-NMR (CDCl₃, TMS, δ(ppm)): 1.64-1.70 (1H. m), 2.06-2.12 (1H, m), 2.55-2.60 (1H, m), 3.46 (2H, t), 3.58 (1H, dd), 3.75-3.95 (3H, m), 5.26 (2H, s), 6.78 (1H, s), 6.87-6.91 (3H, m), 7.25-7.28 (2H, m)

Production Example 172

5-[4-Chlorophenoxy)methyl]isoxazole-3-carboxylic acid (500 mg, 1.87 mmol) and tetrahydropyran-4-ylmethylamine (237 mg, 2.05 mmol) were added to dehydrated tetrahydrofuran (20 ml), and cooled to 0° C. (Benzotriazol-1-yloxy)tripyrrolidinophosphonium hexafluorophosphate (1.46 g, 2.80 mmol) was added thereto, and the mixture was stirred at 0° C. for 16 hours. The mixture was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 320 mg of N-(tetrahydropyran-4-ylmethyl)-5-[(4-chlorophenoxy)methyl]isoxazole-3-carboxamide (hereinafter, referred to as Compound of Present Invention (181)) represented by the following formula.

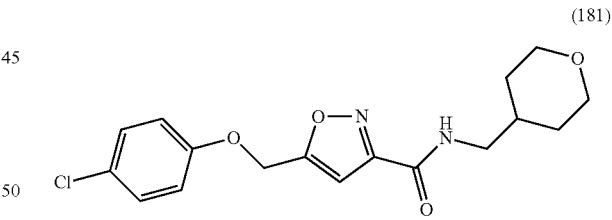

(181)

¹H-NMR (CDCl₃, TMS, δ(ppm)): 1.42-1.35 (2H, m), 1.6 (2H, d), 1.85 (1H, m), 3.37 (4H, m), 4.0 (2H, d), 5.18 (2H, s), 6.77 (1H, s), 6.87-6.89 (3H, m), 7.26 (2H, d)

Production Example 173

5-[3,4-Dichlorophenoxy)methyl]isoxazole-3-carboxylic acid (500 mg, 1.74 mmol) and tetrahydrofuran-3-ylmethylamine (211 mg, 2.09 mmol) were added to dehydrated tetrahydrofuran (30 mL), and cooled to 0° C. (Benzotriazol-1-yloxy)tripyrrolidinophosphonium hexafluorophosphate (1.35 g, 2.61 mmol) was added thereto, and then mixture was stirred at 0° C. for 16 hours. The mixture was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 400 mg of N-(tetrahydrofuran-3-ylmethyl)-5-[3,4-dichlorophenoxy)methyl]isoxazole-3-carboxamide (hereinafter, referred to as Compound of Present Invention (182)) represented by the

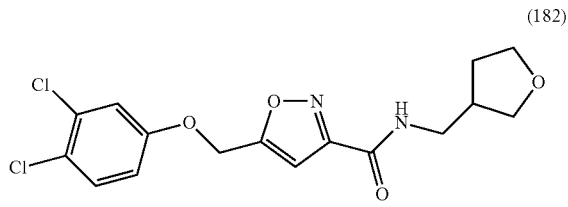

(182)

$^1$H-NMR (CDCl$_3$, TMS, δ(ppm)): 1.70-1.60 (1H, m), 2.20-2.0 (1H, m), 2.6 (1H, t), 3.45 (1H, t), 3.62 (1H, m), 3.75 (1H, q), 3.95-3.80 (2H, m), 5.20 (2H, 8), 6.85-6.78 (2H, m), 6.98-6.88 (1H, Brs), 7.08 (1H, d), 7.36 (1H, d)

Production Example 174

5-[3,4-Dichlorophenoxy)methyl]isoxazole-3-carboxylic acid (400 mg, 1.39 mmol) and tetrahydropyran-4-ylmethylamine (193 mg, 1.67 mmol) were added to dehydrated tetrahydrofuran (30 mL), and cooled to 0° C. (Benzotriazol-1-yloxy)tripyrrolidinophosphonium hexafluorophosphate (1.00 g, 2.00 mmol) was added thereto, and then the mixture was stirred at 0° C. for 16 hours. The mixture was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 300 mg of N-(tetrahydropyran-4-ylmethyl)-5-[3,4-dichlorophenoxy)methyl]isoxazole-3-carboxamide (hereinafter, referred to as Compound of Present Invention (183)) represented by the following formula.

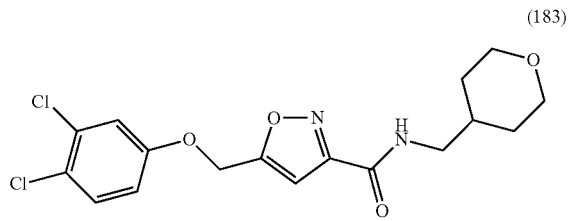

(183)

$^1$H-NMR (CDCl$_3$, TMS, δ(ppm)): 1.35-1.48 (2H, m), 1.65-1.68 (2H, d), 1.85-86 (1H, m), 3.33-3.41 (4H, m), 4.00 (2H, dd), 5.16 (2H, s), 6.83 (2H, m), 6.86 (1H, br.s), 7.06 (1H, d)

Production Example 175

5-[4-Fluorophenoxy)methyl]isoxazole-3-carboxylic acid (500 mg, 2.18 mmol) and tetrahydrofuran-3-ylmethylamine (211 mg, 2.09 mmol) were added to dehydrated tetrahydrofuran (30 mL), and cooled to 0° C. (Benzotriazol-1-yloxy)tripyrrolidinophosphonium hexafluorophosphate (1.35 g, 2.61 mmol) was added thereto, and the mixture was stirred at 0° C. for 16 hours. The mixture was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 320 mg of N-(tetrahydrofuran-3-ylmethyl)-5-[4-fluorophenoxy)methyl]isoxazole-3-carboxamide (hereinafter, referred to as Compound of Present Invention (184)) represented by the following formula.

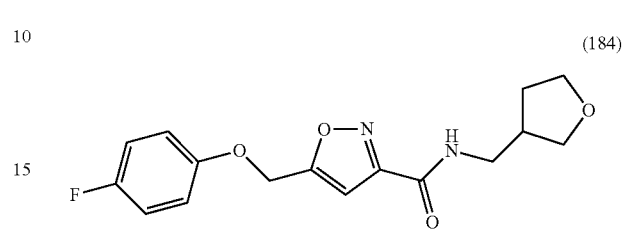

(184)

$^1$H-NMR (CDCl$_3$, TMS, δ(ppm)): 1.78-1.60 (1H, m), 2.18-2.0 (1H, m), 2.6 (1H, t), 3.48 (2H, t), 3.66-3.52 (1H, m), 3.80-3.70 (3H, m), 5.16 (2H, s), 6.78 (1H, s), 7.60-6.60 (5H, m)

Production Example 176

5-[4-Fluorophenoxy)methyl]isoxazole-3-carboxylic acid (500 mg, 2.18 mmol) and tetrahydropyran-4-ylmethylamine (660 mg, 6.60 mmol) were added to dehydrated tetrahydrofuran (30 mL), and cooled to 0° C. (Benzotriazol-1-yloxy)tripyrrolidinophosphonium hexafluorophosphate (1.80 g, 3.50 mmol) was added thereto, and the mixture was stirred at 0° C. for 16 hours. The mixture was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 250 mg of N-(tetrahydropyran-4-ylmethyl)-5-[4-fluorophenoxy)methyl]isoxazole-3-carboxamide (hereinafter, referred to as Compound of Present Invention (185)) represented by the following formula.

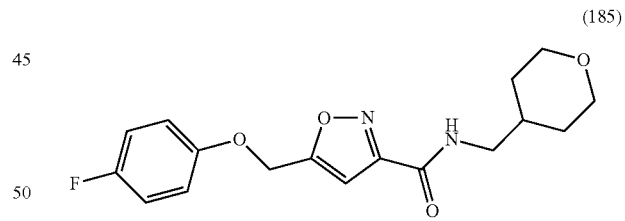

(185)

$^1$H-NMR (CDCl$_3$, TMS, δ(ppm)): 1.45-1.30 (2H, m), 1.65 (2H, d), 1.95-1.8 (1H, m), 3.45-3.30 (4H, m), 4.0 (2H, dd), 5.3 (2H, s), 6.78 (1H, s), 6.96-6.82 (3H, m), 7.06-6.98 (2H, m)

Production Example 177

5-(4-Bromophenoxymethyl)isoxazole-3-carboxylic acid (0.50 g, 1.7 mmol) was added to chloroform (amylene addition product) (10 mL), and cooled to 0° C. Triethylamine (0.30 ml, 2.5 mmol), 1-ethyl-3-(3-dimethylaminopropyl)carbodiimide hydrochloride (0.48 g, 2.5 mmol) and 1-hydroxybenzotriazole (0.34 g, 2.5 mmol) were added thereto, and the mixture was stirred for 10 minutes. Tetrahydrofuran-3-ylmethylamine (0.19 g, 1.8 mmol) was added to the mixture, and the mixture was stirred at room temperature for 4 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.25 g of N-(tetrahydrofuran-3-ylmethyl)-5-(4-bromophenoxymethyl)isoxazole-3-carboxamide (hereinafter, referred to as Compound of Present Invention (186)) represented by the following formula.

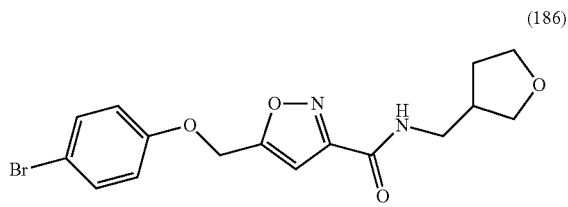 [SMILES: O=C(NCC1CCOC1)c1cc(COc2ccc(Cl)cc2)on1]

(186)

$^1$H-NMR (CDCl$_3$, TMS, δ(ppm)): 1.58 (1H, m), 1.91 (1H, m), 2.46 (1H, m), 3.22 (2H, t), 3.44 (1H, dd), 3.68 (3H, m), 5.53 (2H, s), 6.91 (1H, S), 7.04 (2H, d), 7.49 (2H, d), 8.92 (1H, t)

Production Example 178

5-(4-Bromophenoxymethyl)isoxazole-3-carboxylic acid (1.1 g, 3.7 mmol) was added to N,N-dimethylformamide (6 mL), and cooled to 0° C. Triethylamine (1.03 ml, 7.4 mmol), 1-ethyl-3-(3-dimethylaminopropyl) carbodiimide hydrochloride (0.85 g, 4.4 mmol) and 1-hydroxybenzotriazole (0.60 g, 4.4 mmol) were added thereto, and the mixture was stirred for 10 minutes. Tetrahydropyran-4-ylmethylamine (0.47 g, 4.1 mmol) was added to the mixture, and the mixture was stirred at room temperature for 4 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.29 g of N-(tetrahydropyran-4-ylmethyl)-5-(4-bromophenoxymethyl)isoxazole-3-carboxamide (hereinafter, referred to as Compound of Present Invention (187)) represented by the following formula.

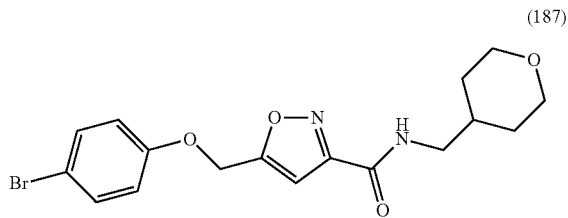 [SMILES: O=C(NCC1CCOCC1)c1cc(COc2ccc(Cl)cc2)on1]

(187)

$^1$H-NMR (CDCl$_3$, TMS, δ(ppm)): 1.18 (2H, m), 1.53 (2H, d), 1.78 (1H, m), 3.13 (2H, t), 3.20 (2H, t), 3.84 (2H, d), 5.35 (2H, s), 6.90 (1H, s), 7.04 (2H, d), 7.49 (2H, d), 8.82 (1H, t)

Production Example 179

5-(4-Trifluoromethylphenoxymethyl)isoxazole-3-carboxylic acid (0.60 g, 2.1 mmol) was added to chloroform (amylene addition product) (12 mL), and cooled to 0° C. Triethylamine (0.43 ml, 3.1 mmol), 1-ethyl-3-(3-dimethylaminopropyl) carbodiimide hydrochloride (0.60 g, 3.1 mmol) and 1-hydroxybenzotriazole (0.42 g, 3.1 mmol) were added thereto, and the mixture was stirred for 10 minutes. Tetrahydrofuran-3-ylmethylamine (0.23 g, 2.3 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.16 g of N-(tetrahydrofuran-3-ylmethyl)-5-(4-trifluorophenoxymethyl)isoxazole-3-carboxamide (hereinafter, referred to as Compound of Present Invention (188)) represented by the following formula.

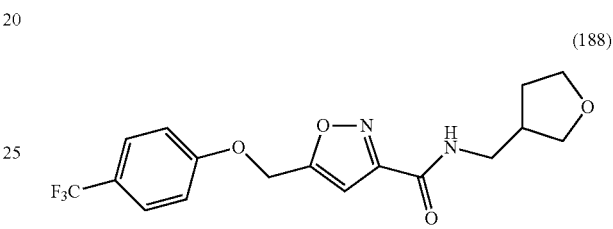

(188)

$^1$H-NMR (CDCl$_3$, TMS, δ(ppm)): 1.69-1.65 (m, 1H), 2.11-2.06 (m, 1H), 2.59-2.56 (m, 1H), 3.46 (t, 2H), 3.61-3.57 (m, 1H), 3.79-3.75 (m, 1H), 3.92-3.83 (m, 2H), 5.24 (s, 2H), 6.81 (s, 1H), 6.92 (s, 1H), 7.03 (d, 2H), 7.58 (d, 2H)

Production Example 180

5-(4-Trifluoromethylphenoxymethyl)isoxazole-3-carboxylic acid (0.60 g, 2.1 mmol) was added to chloroform (amylene addition product) (12 mL), and cooled to 0° C. Triethylamine (0.43 ml, 3.1 mmol), 1-ethyl-3-(3-dimethylaminopropyl) carbodiimide hydrochloride (0.60 g, 3.1 mmol) and 1-hydroxybenzotriazole (0.42 g, 3.1 mmol) were added thereto, and the mixture was stirred for 10 minutes. Tetrahydropyran-4-ylmethylamine (0.26 g, 2.3 mmol) was added to the mixture, and the mixture was stirred at room temperature for 4 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.25 g of N-(tetrahydropyran-4-ylmethyl)-5-(4-trifluoromethylphenoxymethyl) isoxazole-3-carboxamide (hereinafter, referred to as Compound of Present Invention (189)) represented by the following formula.

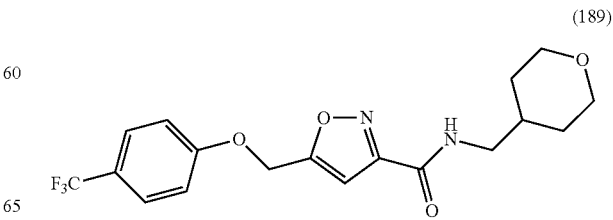

(189)

¹H-NMR (CDCl₃, TMS, δ(ppm)): 1.43-1.32 (m, 2H), 1.68-1.64 (m, 2H), 1.88-1.83 (m, 1H), 3.41-3.33 (m, 4H), 4.00-3.96 (m, 2H), 5.24 (s, 2H), 6.80 (s, 1H), 6.86 (s, 1H), 7.02 (d, 2H), 7.58 (d, 2H)

Production Example 181

5-(4-Trifluoromethoxyphenoxymethyl)isoxazole-3-carboxylic acid (0.60 g, 2.0 mmol) was added to chloroform (amylene addition product) (15 mL), and cooled to 0° C. Triethylamine (0.40 ml, 3.0 mmol), 1-ethyl-3-(3-dimethylaminopropyl) carbodiimide hydrochloride (0.45 g, 2.4 mmol) and 1-hydroxybenzotriazole (0.32 g, 2.4 mmol) were added thereto, and the mixture was stirred for 10 minutes. Tetrahydrofuran-3-ylmethylamine (0.22 g, 2.2 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.40 g of N-(tetrahydrofuran-3-ylmethyl)-5-(4-trifluoromethoxyphenoxymethyl) isoxazole-3-carboxamide (hereinafter, referred to as Compound of Present Invention (190)) represented by the following formula.

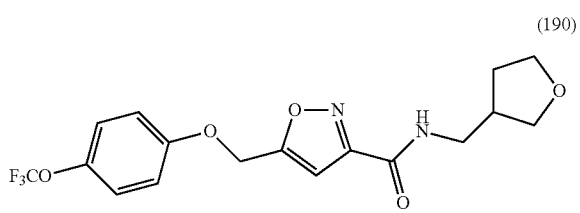 [SMILES: O=C(NCC1CCOC1)c1cc(COc2ccc(OC(F)(F)F)cc2)on1]

(190)

¹H-NMR (CDCl₃, TMS, δ(ppm)): 1.25-1.1 (m, 1H), 2.15-2.0 (m, 1H), 2.6-2.5 (m, 1H), 3.45 (t, 2H), 3.6 (q, 1H), 3.8-3.6 (m, 1H), 4.0-3.8 (m, 2H), 5.2 (s, 2H), 6.8 (s, 1H), 7.0-6.86 (m, 3H), 7.18 (d, 2H)

Production Example 182

5-(4-Trifluoromethoxyphenoxymethyl)isoxazole-3-carboxylic acid (0.10 g, 0.33 mmol) was added to chloroform (amylene addition product) (3 mL), and cooled to 0° C. Triethylamine (0.069 ml, 0.5 mmol), 1-ethyl-3-(3-dimethylaminopropyl) carbodiimide hydrochloride (0.76 g, 0.40 mmol) and 1-hydroxybenzotriazole (0.053 g, 0.40 mmol) were added thereto, and the mixture was stirred for 10 minutes. Tetrahydropyran-4-ylmethylamine (0.042 g, 0.37 mmol) was added to the mixture, and the mixture was stirred at room temperature for 4 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.066 g of N-(tetrahydropyran-4-ylmethyl)-5-(4-trifluoromethoxyphenoxymethyl)isoxazole-3-carboxamide (hereinafter, referred to as Compound of Present Invention (191)) represented by the following formula.

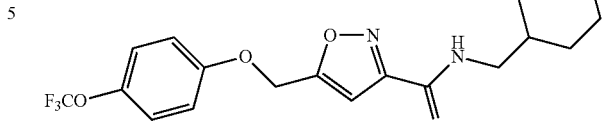

(191)

¹H-NMR (CDCl₃, TMS, δ(ppm)): 1.43-1.32 (2H, m), 1.67 (2H, d), 1.85 (1H, m), 3.37 (4H, m), 3.98 (2H, d), 5.19 (2H, s), 6.79 (1H, s), 6.87 (1H, t), 6.93 (2H, d), 7.17 (2H, d)

Production Example 183

5-(4-Trifluoromethylthiophenoxymethyl)isoxazole-3-carboxylic acid (0.50 g, 1.6 mmol) was added to chloroform (amylene addition product) (10 mL), and cooled to 0° C. Triethylamine (0.30 ml, 2.4 mmol), 1-ethyl-3-(3-dimethylaminopropyl) carbodiimide hydrochloride (0.45 g, 2.4 mmol) and 1-hydroxybenzotriazole (0.32 g, 2.4 mmol) were added thereto, and the mixture was stirred for 10 minutes. Tetrahydrofuran-3-ylmethylamine (0.17 g, 1.7 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydrofuran-3-ylmethyl)-5-(4-trifluoromethylthiophenoxymethyl) isoxazole-3-carboxamide (hereinafter, referred to as Compound of Present Invention (192)) represented by the following formula.

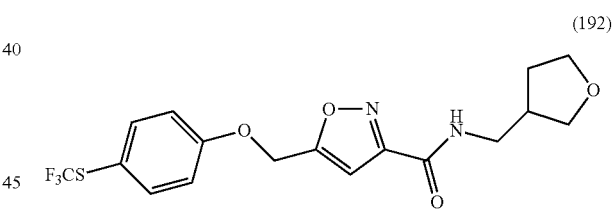

(192)

¹H-NMR (CDCl₃, TMS, δ(ppm)): 1.71-1.61 (1H, m), 2.11-2.04 (1H, m), 2.61-2.54 (1H, m), 3.47 (2H, t), 3.61-3.57 (1H, m), 3.79-3.73 (1H, m), 3.94-3.83 (2H, m), 5.21 (2H, s), 6.81 (1H, s), 6.95 (1H, Brs), 7.00-6.97 (2H, d), 7.61 (2H, d)

Production Example 184

5-(4-Trifluoromethylthiophenoxymethyl)isoxazole-3-carboxylic acid (0.50 g, 1.6 mmol) was added to chloroform (amylene addition product) (10 mL), and cooled to 0° C. Triethylamine (0.30 ml, 2.4 mmol), 1-ethyl-3-(3-dimethylaminopropyl) carbodiimide hydrochloride (0.45 g, 2.4 mmol) and 1-hydroxybenzotriazole (0.32 g, 2.4 mmol) were added thereto, and the mixture was stirred for 10 minutes. Tetrahydropyran-4-ylmethylamine (0.20 g, 1.7 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydropyran-4-ylmethyl)-5-(4-trifluoromethylthiophenoxymethyl)isoxazole-3-carboxamide (hereinafter, referred t as Compound of Present Invention (191)) represented by the following formula.

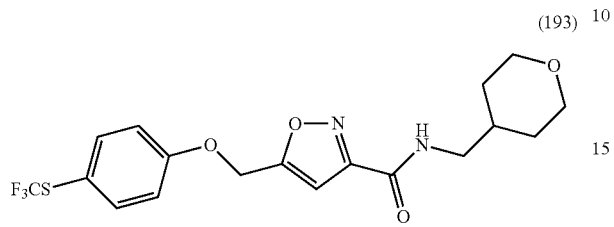

(193)

$^1$H-NMR (CDCl$_3$, TMS, δ(ppm)): 1.43-1.32 (2H, m), 1.58 (2H, d), 1.89-1.83 (1H, m), 3.41-3.33 (4H, m), 4.00-3.96 (2H, m), 5.21 (2H, s), 6.81 (1H, s), 6.88 (1H, s), 6.99 (2H, d), 7.61 (2H, d)

Production Example 185

5-(3-Fluorophenoxymethyl)isoxazole-3-carboxylic acid (0.70 g, 3.0 mmol) was added to chloroform (amylene addition product) (12 mL), and cooled to 0° C. Triethylamine (0.82 ml, 5.9 mmol), 1-ethyl-3-(3-dimethylaminopropyl) carbodiimide hydrochloride (0.68 g, 3.5 mmol) and 1-hydroxybenzotriazole (0.48 g, 3.5 mmol) were added thereto, and the mixture was stirred for 10 minutes. Tetrahydrofuran-3-ylmethylamine (0.33 g, 3.2 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.51 g of N-(tetrahydrofuran-3-ylmethyl)-5-(3-fluorophenoxymethyl)isoxazole-3-carboxamide (hereinafter, referred to as Compound of Present Invention (194)) represented by the following formula.

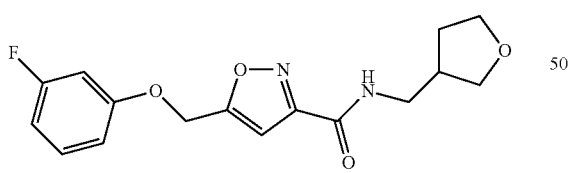

(194)

$^1$H-NMR (CDCl$_3$, TMS, δ(ppm)): 1.68(m, 1H), 2.09(m, 1H), 2.57(m, 1H), 3.46(q, 2H), 3.59(q, 1H), 3.77(q, 1H), 3.88(m, 2H), 5.17(s, 2H), 6.67(dd, 1H), 6.73(m, 2H), 6.79(s, 1H), 6.93(brs, 1H), 7.26(d, 1H)

Production Example 186

5-(3-Fluorophenoxymethyl)isoxazole-3-carboxylic acid (0.70 g, 3.0 mmol) was added to chloroform (amylene addition product) (12 mL), and cooled to 0° C. Triethylamine (0.82 ml, 5.9 mmol), 1-ethyl-3-(3-dimethylaminopropyl) carbodiimide hydrochloride (0.68 g, 3.5 mmol) and 1-hydroxybenzotriazole (0.48 g, 3.5 mmol) were added thereto, and the mixture was stirred for 10 minutes. Tetrahydropyran-4-ylmethylamine (0.37 g, 3.2 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.53 g of N-(tetrahydropyran-4-ylmethyl)-5-(3-fluorophenoxymethyl)isoxazole-3-carboxamide (hereinafter, referred to as Compound of Present Invention (195)) represented by the following formula.

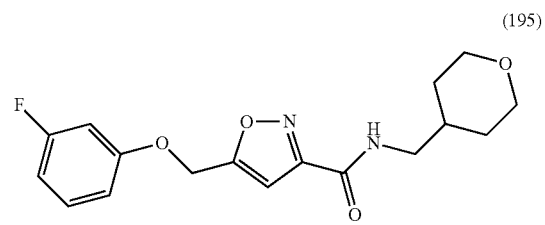 [SMILES: O=C(NCC1CCOCC1)c1cc(COc2cccc(F)c2)on1]

(195)

$^1$H-NMR (CDCl$_3$, TMS, δ(ppm)): 1.38(q, 2H), 1.65(m, 2H), 1.86(m, 1H), 3.37(m, 4H), 3.98(dd, 2H), 5.17(s, 2H), 6.67(dd, 1H), 6.72(m, 2H), 6.79(s, 1H), 6.88(brs, 1H), 7.26(d, 1H)

Production Example 187

5-(3-Bromophenoxymethyl)isoxazole-3-carboxylic acid (0.60 g, 1.9 mmol) was added to chloroform (amylene addition product) (15 mL), and cooled to 0° C. Triethylamine (0.53 ml, 3.8 mmol), 1-ethyl-3-(3-dimethylaminopropyl) carbodiimide hydrochloride (0.44 g, 2.3 mmol) and 1-hydroxybenzotriazole (0.31 g, 2.3 mmol) were added thereto, and the mixture was stirred for 10 minutes. Tetrahydrofuran-3-ylmethylamine (0.21 g, 2.1 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.44 g of N-(tetrahydrofuran-3-ylmethyl)-5-(3-bromophenoxymethyl)isoxazole-3-carboxamide (hereinafter, referred to as Compound of Present Invention (196)) represented by the following formula.

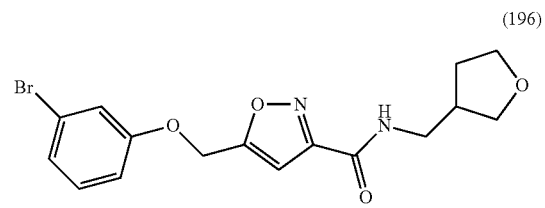 [SMILES: O=C(NCC1CCOC1)c1cc(COc2cccc(Br)c2)on1]

(196)

$^1$H-NMR (CDCl$_3$, TMS, δ(ppm)): 1.70-1.64(m, 1H), 2.12-2.06(m, 1H), 2.60-2.55(m, 1H), 3.49-3.44(t, 2H), 3.61-3.56(m, 1H), 3.95-3.72(m, 3H), 5.17(s, 2H), 6.79(s, 1H), 6.92-6.87(m, 2H), 7.18-7.11(m, 3H)

Production Example 188

5-(3-Bromophenoxymethyl)isoxazole-3-carboxylic acid (0.60 g, 1.9 mmol) was added to chloroform (amylene addition product) (15 mL), and cooled to 0° C. Triethylamine (0.53 ml, 3.8 mmol), 1-ethyl-3-(3-dimethylaminopropyl) carbodiimide hydrochloride (0.44 g, 2.3 mmol) and 1-hydroxybenzotriazole (0.31 g, 2.3 mmol) were added thereto, and the mixture was stirred for 10 minutes. Tetrahydropyran-4-ylmethylamine (0.24 g, 2.1 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.52 g of N-(tetrahydropyran-4-ylmethyl)-5-(3-bromophenoxymethyl)isoxazole-3-carboxamide (hereinafter, referred to as Compound of Present Invention (197)) represented by the following formula.

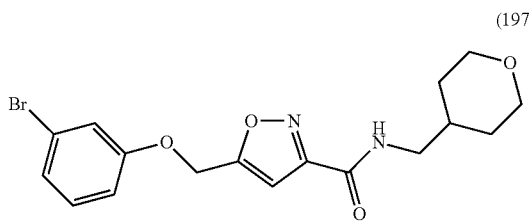

(197)

$^1$H-NMR (CDCl$_3$, TMS, δ(ppm)): 1.38(q, 2H), 1.68-1.64 (dd, 2H), 1.86(m, 1H), 3.41-3.32(m, 4H), 4.01-3.96(dd, 2H), 5.17(s, 2H), 6.78(s, 1H), 6.89-6.87(d, 2H), 7.17-7.11(m, 3H)

Production Example 189

5-(3-Trifluoromethylphenoxymethyl)isoxazole-3-carboxylic acid (0.50 g, 1.7 mmol) was added to chloroform (amylene addition product) (15 mL), and cooled to 0° C. Triethylamine (0.36 ml, 2.6 mmol), 1-ethyl-3-(3-dimethylaminopropyl) carbodiimide hydrochloride (0.40 g, 2.1 mmol) and 1-hydroxybenzotriazole (0.28 g, 2.1 mmol) were added thereto, and the mixture was stirred for 10 minutes. Tetrahydrofuran-3-ylmethylamine (0.19 g, 1.9 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.34 g of N-(tetrahydrofuran-3-ylmethyl)-5-(3-trifluoromethylphenoxymethyl) isoxazole-3-carboxamide (hereinafter, referred to as Compound of Present Invention (198)) represented by the following formula.

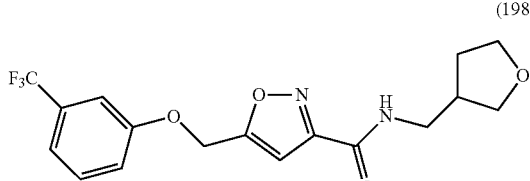

(198)

$^1$H-NMR (CDCl$_3$, TMS, δ(ppm)): 1.7-1.6(m,1H),2.15-2.0 (m,1H),2.6(q,1H),3.45(t,2H),3.6(dd,1H),3.75(q,1H).4.0-3.8 (m,2H),5.3(s,2H), 6.8(s,1H),6.94(brs,1H),7.14(d,1H),7.2(s,1H),7.3(d,1H),7.44(t,1H)

Production Example 190

5-(3-Trifluoromethylphenoxymethyl)isoxazole-3-carboxylic acid (0.50 g, 1.7 mmol) was added to chloroform (amylene addition product) (15 mL), and cooled to 0° C. Triethylamine (0.36 ml, 2.6 mmol), 1-ethyl-3-(3-dimethylaminopropyl) carbodiimide hydrochloride (0.40 g, 2.1 mmol) and 1-hydroxybenzotriazole (0.28 g, 2.1 mmol) were added thereto, and the mixture was stirred for 10 minutes. Tetrahydropyran-4-ylmethylamine (0.22 g, 1.9 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.34 g of N-(tetrahydropyran-4-ylmethyl)-5-(3-trifluoromethylphenoxymethyl) isoxazole-3-carboxamide (hereinafter, referred to as Compound of Present Invention (199)) represented by the following formula.

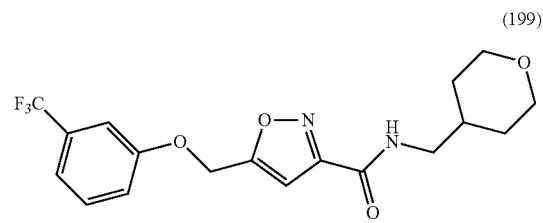 [SMILES: O=C(NCC1CCOCC1)c1cc(COc2cccc(C(F)(F)F)c2)on1]

(199)

$^1$H-NMR (CDCl$_3$, TMS, δ(ppm)): 1.45-1.3(m, 2H), 1.65 (d, 2H), 1.9-1.8(m, 1H), 3.4-3.3(m, 4H).4.0(dd, 2H), 5.25(s, 2H), 6.8(s, 1H), 6.84(brs, 1H), 7.14(d, 1H), 7.2(s, 1H), 7.3(d, 1H), 7.44(t, 1H)

Production Example 191

5-(3-Trifluoromethoxyphenoxymethyl)isoxazole-3-carboxylic acid (0.60 g, 2.0 mmol) was added to chloroform (amylene addition product) (15 mL), and cooled to 0° C. Triethylamine (0.56 ml, 4.0 mmol), 1-ethyl-3-(3-dimethylaminopropyl) carbodiimide hydrochloride (0.46 g, 2.4 mmol) and 1-hydroxybenzotriazole (0.32 g, 2.4 mmol) were added thereto, and the mixture was stirred for 10 minutes. Tetrahydrofuran-3-ylmethylamine (0.22 g, 2.2 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.32 g of N-(tetrahydrofuran-3-ylmethyl)-5-(3-trifluoromethoxyphenoxymethyl) isoxazole-3-carboxamide (hereinafter, referred to as Compound of Present Invention (200)) represented by the following formula.

(200)

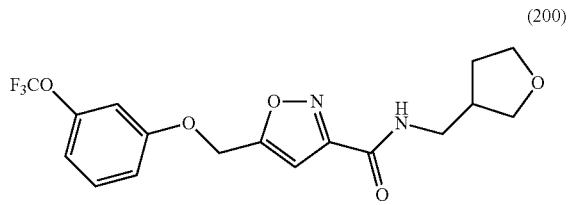 [SMILES: O=C(NCC1CCOC1)c1cc(COc2cccc(OC(F)(F)F)c2)on1]

¹H-NMR (CDCl₃, TMS, δ(ppm)): 1.67(m, 1H), 2.08(m, 1H), 2.57(m, 1H), 3.46(t, 2H), 3.58(m, 1H), 3.85(m, 3H), 5.19(s, 2H), 6.82(d, 2H), 6.88(d, 3H), 7.32(t, 1H)

Production Example 192

5-(3-Trifluoromethoxyphenoxymethyl)isoxazole-3-carboxylic acid (0.60 g, 2.0 mmol) was added to chloroform (amylene addition product) (15 mL), and cooled to 0° C. Triethylamine (0.56 ml, 4.0 mmol), 1-ethyl-3-(3-dimethylaminopropyl) carbodiimide hydrochloride (0.46 g, 2.4 mmol) and 1-hydroxybenzotriazole (0.32 g, 2.4 mmol) were added thereto, and the mixture was stirred for 10 minutes. Tetrahydropyran-4-ylmethylamine (0.34 g, 3.0 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of N-(tetrahydropyran-4-ylmethyl)-5-(3-trifluoromethoxyphenoxymethyl) isoxazole-3-carboxamide (hereinafter, referred to as Compound of Present Invention (201)) represented by the following formula.

(201)

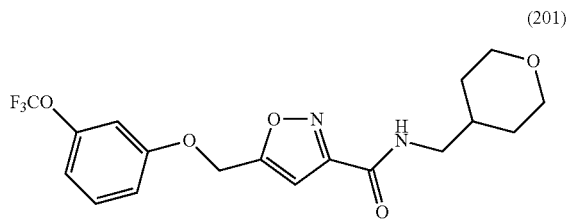 [SMILES: O=C(NCC1CCOCC1)c1cc(COc2cccc(OC(F)(F)F)c2)on1]

¹H-NMR (CDCl₃, TMS, δ(ppm)): 1.37(m, 2H), 1.66(d, 2H), 1.86(m, 1H), 3.36(s, 4H), 4.0(d, 2H), 5.19(s, 2H), 6.80(s, 1H), 6.82-6.91(m, 4H), 7.32(t, 1H)

Production Example 193

5-(3-Trifluoromethylthiophenoxymethyl)isoxazole-3-carboxylic acid (0.60 g, 1.9 mmol) was added to chloroform (amylene addition product) (15 mL), and cooled to 0° C. Triethylamine (0.40 ml, 2.8 mmol), 1-ethyl-3-(3-dimethylaminopropyl) carbodiimide hydrochloride (0.43 g, 2.3 mmol) and 1-hydroxybenzotriazole (0.31 g, 2.3 mmol) were added thereto, and the mixture was stirred for 10 minutes. Tetrahydrofuran-3-ylmethylamine (0.21 g, 2.1 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.40 g of N-(tetrahydrofuran-3-ylmethyl)-5-(3-trifluoromethylthiophenoxymethyl) isoxazole-3-carboxamide (hereinafter, referred to as Compound of Present Invention (202)) represented by the following formula.

(202)

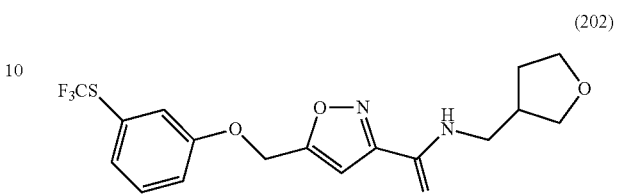

¹H-NMR (CDCl₃, TMS, δ(ppm)): 1.67(1H, q), 2.09(q, 1H), 2.57(t, 1H), 3.47(t, 2H), 3.61-3.57(m, 1H), 3.76(q, 1H), 3.94-3.79(m, 2H), 5.2(s, 2H), 6.8(s, 1H), 6.94(brs, 1H), 7.09-7.07(m, 1H), 7.26-7.24(m, 1H), 7.39-7.30(m, 2H)

Production Example 194

5-(3-Trifluoromethylthiophenoxymethyl)isoxazole-3-carboxylic acid (0.60 g, 1.9 mmol) was added to chloroform (amylene addition product) (15 mL), and cooled to 0° C. Triethylamine (0.40 ml, 2.8 mmol), 1-ethyl-3-(3-dimethylaminopropyl) carbodiimide hydrochloride (0.43 g, 2.3 mmol) and 1-hydroxybenzotriazole (0.31 g, 2.3 mmol) were added thereto, and the mixture was stirred for 10 minutes. Tetrahydropyran-4-ylmethylamine (0.24 g, 2.1 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.30 g of N-(tetrahydropyran-4-ylmethyl)-5-(3-trifluoromethylthiophenoxymethyl) isoxazole-3-carboxamide (hereinafter, referred to as Compound of Present Invention (203)) represented by the following formula.

(203)

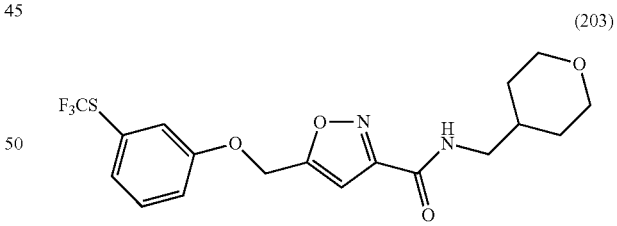

¹H-NMR (CDCl₃, TMS, δ(ppm)): 1.45-1.3(m, 2H), 1.75-1.65(m, 2H), 1.95-1.8(m, 1H), 3.5-3.3(m, 4H), 4.0(dd, 2H), 5.2(s, 2H), 6.8(s, 1H), 6.9(brs, 1H), 7.1-7.06(m, 1H), 7.27-7.22(m, 1H), 7.4-7.30(m, 2H)

Production Example 195

5-(5-(1,3-Benzodioxolanyl)oxymethyl)isoxazole-3-carboxylic acid (0.60 g, 2.2 mmol) was added to chloroform (amylene addition product) (12 mL), and cooled to 0° C. Triethylamine (0.48 ml, 3.4 mmol), 1-ethyl-3-(3-dimethylaminopropyl) carbodiimide hydrochloride (0.52 g, 2.7 mmol) and 1-hydroxybenzotriazole (0.37 g, 2.7 mmol) were added thereto, and the mixture was stirred for 10 minutes. Tetrahydrofuran-3-ylmethylamine (0.25 g, 2.5 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.30 g of N-(tetrahydrofuran-3-ylmethyl)-5-(5-(1,3-benzodioxolanyl)oxymethyl)isoxazole-3-carboxamide (hereinafter, referred to as Compound of Present Invention (204)) represented by the following formula.

(204)

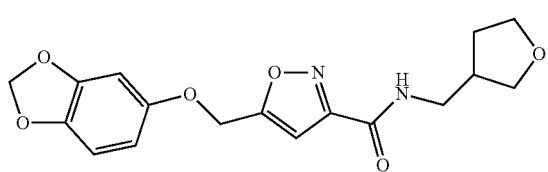

$^1$H-NMR (CDCl$_3$, TMS, δ(ppm)): 1.69-1.64(1H, m), 2.10-2.06(1H, m), 2.59-2.55(1H, m), 3.46(2H, t), 3.60-3.56(1H, m), 3.79-3.75(1H, m), 3.94-3.83(2H, m), 5.11(2H, s), 5.93(2H, s), 6.38-6.35(1H, m), 6.53(1H, d), 6.70(1H, d), 6.76(1H, s), 6.95(1H, s)

Production Example 196

5-(5-(1,3-Benzodioxolanyl)oxymethyl)isoxazole-3-carboxylic acid (0.60 g, 2.2 mmol) was added to chloroform (amylene addition product) (12 mL), and cooled to 0° C. Triethylamine (0.48 ml, 3.4 mmol), 1-ethyl-3-(3-dimethylaminopropyl) carbodiimide hydrochloride (0.52 g, 2.7 mmol) and 1-hydroxybenzotriazole (0.37 g, 2.7 mmol) were added thereto, and the mixture was stirred for 10 minutes. Tetrahydropyran-4-ylmethylamine (0.28 g, 2.5 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.38 g of N-(tetrahydropyran-4-ylmethyl)-5-(5-(1,3-benzodioxolanyl)oxymethyl)isoxazole-3-carboxamide (hereinafter, referred to as Compound of Present Invention (205)) represented by the following formula.

(205)

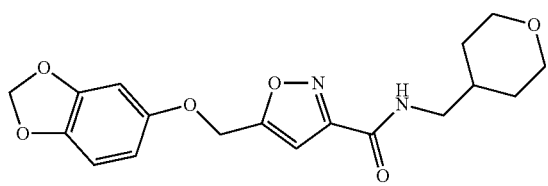

$^1$H-NMR (CDCl$_3$, TMS, δ(ppm)): 1.42-1.32(2H, m), 1.66 (2H, d), 1.87-1.83(1H, m), 3.41-3.33(4H, m), 4.00-3.96(2H, m), 5.11(2H, s), 5.93(2H, s), 6.38-6.35(1H, m), 6.52(1H, d), 6.70(1H, d), 6.75(1H, s), 6.86(1H, s)

Production Example 197

5-(3,4-Dimethoxyphenoxymethyl)isoxazole-3-carboxylic acid (0.60 g, 2.1 mmol) was added to chloroform (amylene addition product) (12 mL), and cooled to 0° C. Triethylamine (0.45 ml, 3.2 mmol), 1-ethyl-3-(3-dimethylaminopropyl) carbodiimide hydrochloride (0.49 g, 2.6 mmol) and 1-hydroxybenzotriazole (0.35 g, 2.6 mmol) were added thereto, and the mixture was stirred for 10 minutes. Tetrahydrofuran-3-ylmethylamine (0.24 g, 2.4 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.40 g of N-(tetrahydrofuran-3-ylmethyl)-5-(3,4-dimethoxyphenoxymethyl)isoxazole-3-carboxamide (hereinafter, referred to as Compound of Present Invention (206)) represented by the following formula.

(206)

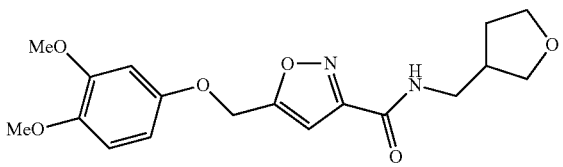

$^1$H-NMR (CDCl$_3$, TMS, δ(ppm)): 1.67(q, 1H), 2.08(q, 1H), 2.57(t, 1H), 3.46(t, 2H), 3.58(q, 1H), 3.76(q, 1H), 3.94-3.83(m, 8H), 5.15(s, 2H), 6.45-6.43(dd, 1H), 6.57(d, 1H), 6.78-6.76(m, 2H), 6.93(s, 1H)

Production Example 198

5-(3,4-Dimethoxyphenoxymethyl)isoxazole-3-carboxylic acid (0.60 g, 2.1 mmol) was added to chloroform (amylene addition product) (12 mL), and cooled to 0° C. Triethylamine (0.45 ml, 3.2 mmol), 1-ethyl-3-(3-dimethylaminopropyl) carbodiimide hydrochloride (0.49 g, 2.6 mmol) and 1-hydroxybenzotriazole (0.35 g, 2.6 mmol) were added thereto, and the mixture was stirred for 10 minutes. Tetrahydropyran-4-ylmethylamine (0.27 g, 2.4 mmol) was added to the mixture, and the mixture was stirred at room temperature for 18 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.42 g of N-(tetrahydropyran-4-ylmethyl)-5-(3,4-dimethoxyphenoxymethyl)isoxazole-3-carboxamide (hereinafter, referred to as Compound of Present Invention (207)) represented by the following formula.

(207)

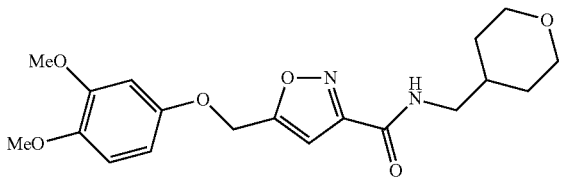

$^1$H-NMR (CDCl$_3$, TMS, δ(ppm)): 1.43-1.32(qd, 2H), 1.68-1.65(dd, 2H), 1.88-1.83(m, 1H), 3.41-3.33(m, 4H), 3.84(s, 3H), 3.86(s, 3H), 4.00-3.97(dd, 2H), 5.14(s, 2H), 6.45-6.43 dd, 1H), 6.65(d, 1H), 6.78-6.76(m, 2H), 6.87(brs, 1H)

Production Example 199

A 1.64 mol/L-n-butyllithium hexane solution (8.3 mL, 13.7 mmol) was added dropwise to a tetrahydrofuran (40 mL) solution of N-(tetrahydrofuran-3-ylmethyl)-5-(2-naphthylmethoxymethyl)isoxazole-3-carboxamide (2.00 g, 5.46 mmol) at −60° C. or less under a nitrogen atmosphere. After stirring at −60° C. or less for 30 minutes, N,N-dimethylformamide (5 mL) was added thereto, and the mixture was stirred at a temperature of −60° C. to 20° C. for 2 hours. Then, the reaction mixture was poured into 1 mol/L hydrochloric acid under ice cooling, and the mixture was extracted twice with ethyl acetate. The organic layer was sequentially washed with water and saturated saline water, dried over anhydrous sodium sulfate, and then concentrated under reduced pressure. The residue was applied to a silica gel column chromatography to obtain 1.81 g of N-(tetrahydrofuran-3-ylmethyl)-4-formyl-5-(2-naphthylmethoxymethyl)isoxazole-3-carboxamide (hereinafter, referred to as Compound of Present Invention (208)) represented by the following formula.

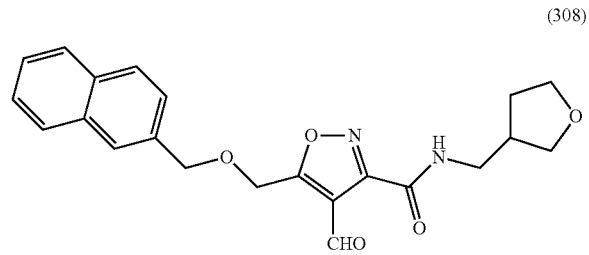 [SMILES: O=Cc1c(C(=O)NCC2CCOC2)noc1COCc1ccc2ccccc2c1]

(308)

$^1$H-NMR (CDCl$_3$, TMS, δ(ppm)): 1.64-1.74(m, 1H), 2.06-2.16(m, 1H), 2.54-2.65(m, 1H), 3.45-3.51(m, 2H), 3.60 (dd, 1H), 3.74-3.81(m, 1H), 3.84-3.97(m, 2H), 4.83(s, 2H), 5.01(s, 2H), 7.31(brs, 1H), 7.45-7.52(m, 3H), 7.79-7.88(m, 4H), 10.38(s, 1H)

Production Example 200

Sodium borohydride (580 mg, 15.3 mmol) was added to a methanol (15 mL) solution of N-(tetrahydrofuran-3-ylmethyl)-4-formyl-5-(2-naphthylmethoxymethyl)isoxazole-3-carboxamide (1.51 g, 3.83 mmol) under ice-water cooling. The mixture was stirred for 15 minutes under ice-water cooling, and further stirred at room temperature for 1 hour and 15 minutes, then the reaction mixture was diluted with toluene, and concentrated under reduced pressure. The concentrate was added to 1 mol/L hydrochloric acid under ice-water cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 1.40 g of N-(tetrahydrofuran-3-ylmethyl)-4-hydroxymethyl-5-(2-naphthylmethoxymethyl)isoxazole-3-carboxamide (hereinafter, referred to as Compound of Present Invention (209)) represented by the following formula.

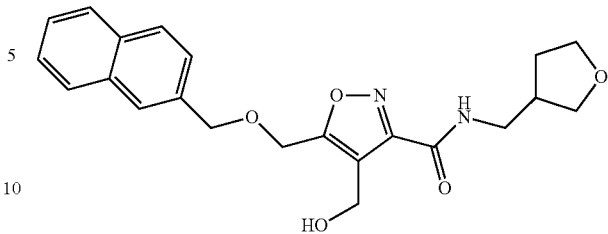

(209)

$^1$H-NMR (CDCl$_3$, TMS, δ(ppm)): 1.63-1.73(m, 1H), 2.06-2.15(m, 1H), 2.53-2.64(m, 1H), 3.46-3.50(m, 2H), 3.61 (dd, 1H), 3.74-3.81(m, 1H), 3.83-3.88(m, 1H), 3.90-3.96(m, 1H), 4.56-4.64(m, 3H), 4.68(s, 2H), 4.74(s, 2H), 7.14(brs, 1H), 7.45-7.52(m, 3H), 7.79(s, 1H), 7.82-7.88(m, 3H)

Production Example 201

A 0.98 mol/L-methylmagnesium bromide tetrahydrofuran solution (2.8 mL, 2.66 mmol) was added to a tetrahydrofuran (15 mL) solution of N-(tetrahydrofuran-3-ylmethyl)-4-formyl-5-(2-naphthylmethoxymethyl)isoxazole-3-carboxamide (300 mg, 0.76 mmol) under ice-water cooling. The mixture was stirred at room temperature for 1.5 hours and then poured into 1 mol/L hydrochloric acid, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 260 mg of N-(tetrahydrofuran-3-ylmethyl)-1-hydroxyethyl-5-(2-naphthylmethoxymethyl)isoxazole-3-carboxamide (hereinafter, referred to as Compound of Present Invention (210)) represented by the following formula.

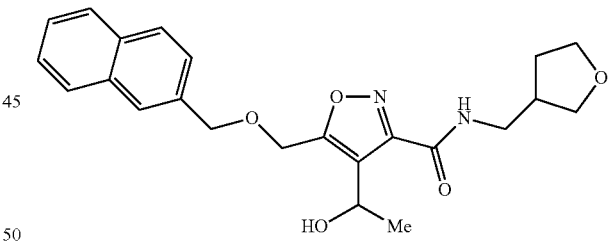

(210)

$^1$H-NMR (CDCl$_3$, TMS, (ppm)): 1.51(d, J=6.6 Hz, 3H), 1.63-1.75(m, 1H), 2.07-2.15(m, 1H), 2.54-2.64(m, 1H), 3.47-3.51(m, 2H), 3.59-3.63(m, 1H), 3.74-3.97(m, 3H), 4.63-5.01(m, 5H), 5.26(d, J=11.0 Hz, 1H), 7.22(brs, 1H), 7.45-7.52(m, 3H), 7.79(s, 1H), 7.82-7.89(m, 3H)

Production Example 202

Bis(2-methoxyethyl)aminosulfur trifluoride (0.24 mL, 1.31 mmol) was added to a toluene (10 mL) solution of N-(tetrahydrofuran-3-ylmethyl)-4-hydroxymethyl-5-(2-naphthylmethoxymethyl)isoxazole-3-carboxamide (400 mg, 1.01 mmol). The mixture was stirred at room temperature for 1.5 hours and then poured into 1 mol/L hydrochloric acid under ice-water cooling, and the mixture was extracted twice with ethyl acetate. The organic layer was sequentially washed with water and saturated saline water, dried over anhydrous sodium sulfate, and then concentrated under reduced pressure. The residue was applied to a silica gel column chromatography to obtain 180 mg of N-(tetrahydrofuran-3-ylmethyl)-4-fluoromethyl-5-(2-naphthylmethoxymethyl)isoxazole-3-carboxamide (hereinafter, referred to as Compound of Present Invention (211)) represented by the following formula.

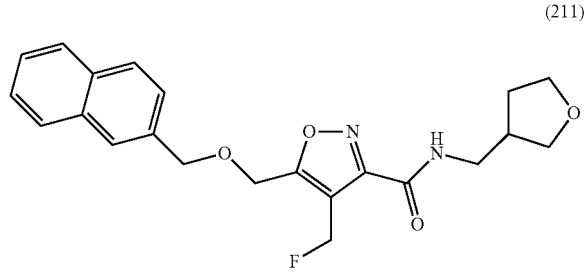 [SMILES: O=C(NCC1CCOC1)c1noc(COCc2ccc3ccccc3c2)c1CF]

(211)

$^1$H-NMR (CDCl$_3$, TMS, δ(ppm)): 1.61-1.75(m, 1H), 2.06-2.14(m, 1H), 2.52-2.64(m, 1H), 3.42-3.48(m, 2H), 3.56-3.61(m, 1H), 3.73-3.80(m, 1H), 3.83-3.96(m, 2H), 4.76 (d, 2H), 4.77(s, 2H), 5.64(d, 2H), 6.94(brs, 1H), 7.45-7.53 (m, 3H), 7.79-7.88(m, 4H)

Production Example 203

55% Sodium hydride (106 mg, 2.42 mmol) was added to a tetrahydrofuran (20 mL) solution of N-(tetrahydrofuran-3-ylmethyl)-4-hydroxymethyl-5-(2-naphthylmethoxymethyl)isoxazole-3-carboxamide (800 mg, 2.02 mmol), and the mixture was stirred at room temperature for 15 minutes. After stirring under ice-water cooling, carbon bisulfide (0.8 mL) was added to the reaction mixture. The mixture was stirred for 10 minutes, then, methyl iodide (0.8 mL) was added thereto, and the mixture was further stirred for 10 minutes. The reaction mixture was diluted with toluene, and concentrated under reduced pressure. The concentrate was added to 1 mol/L hydrochloric acid under ice-water cooling, and the mixture was extracted twice with ethyl acetate. The organic layer was washed with saturated saline water, dried over anhydrous sodium sulfate, and then concentrated under reduced pressure. The residue was applied to a silica gel column chromatography to obtain 884 mg of dithiocarboxylic acid O-{5-(2-naphthylmethoxymethyl)-3-[3-tetrahydrofuranylmethyl)carbamoyl]isoxazolyl-4-ylmethyl}-S-methyl ester (hereinafter, referred to as Compound of Present Invention (212)) represented by the following formula.

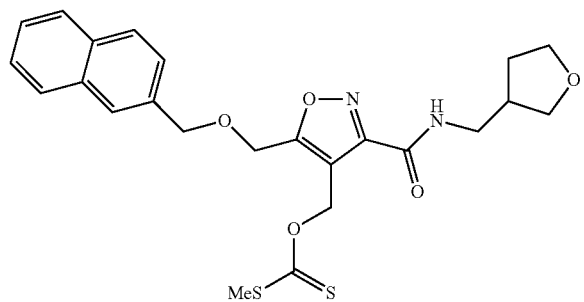

(212)

$^1$H-NMR (CDCl$_3$, TMS, δ(ppm)): 1.62-1.72(m, 1H), 2.06-2.13(m, 1H), 2.50(s, 3H), 2.53-2.63(m, 1H), 3.43-3.48 (m, 2H), 3.58(dd, 1H), 3.73-3.80(m, 1H), 3.83-3.95(m, 2H), 4.76(s, 4H), 5.81(s, 2H), 6.91(brs, 1H), 7.44-7.52(m, 3H), 7.78(s, 1H), 7.81-7.86(m, 3H)

Production Example 204

Tributyltin hydride (632 mg, 2.17 mmol) and azobisisobutyronitrile (59 mg, 0.36 mmol) were added to a toluene (20 mL) solution of dithiocarboxylic acid O-{5-(2-naphthylmethoxymethyl-3-[3-tetrahydrofuranylmethyl)carbamoyl]isoxazolyl-4-ylmethyl}-S-methyl ester (880 mg, 1.81 mmol). The mixture was stirred at 90° C. to 95° C. for 30 minutes, and then concentrated under reduced pressure. The residue was applied to a silica gel column chromatography to obtain 400 mg of N-(tetrahydrofuran-3-ylmethyl)-4-methyl-5-(2-naphthylmethoxymethyl)isoxazole-3-carboxamide (hereinafter, referred to as Compound of Present Invention (213)) represented by the following formula.

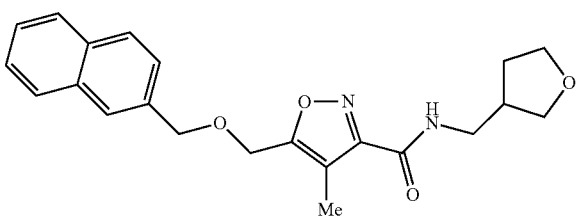

(213)

$^1$H-NMR (CDCl$_3$, TMS, δ(ppm)): 1.63-1.74(m, 1H), 2.06-2.14(m, 1H), 2.25(s, 3H), 2.53-2.62(m, 1H), 3.41-3.48 (m, 2H), 3.56-3.61(m, 1H), 3.74-3.81(m, 1H), 3.84-3.96(m, 2H), 4.63(s, 2H), 4.74(s, 2H), 6.94(brs, 1H), 7.45-7.54(m, 3H), 7.79(s, 1H), 7.82-7.88(m, 3H)

Production Example 205

A 1.58 mol/L-n-butyllithium hexane solution (9.7 mL, 15.3 mmol) was added dropwise to a tetrahydrofuran (70 mL) solution of N-(tetrahydrofuran-3-ylmethyl)-5-(3-fluorobenzyloxymethyl)isoxazole-3-carboxamide (2.38 g, 7.12 mmol) at −65° C. or less, under a nitrogen atmosphere. After stirring at −60° C. or less for 30 minutes, N,N-dimethylformamide (5 mL) was added thereto, and the mixture was stirred at a temperature of −65° C. to −60° C. for 30 minutes. Then, the reaction mixture was poured into 1 mol/L hydrochloric acid under cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 2.30 g of N-(tetrahydrofuran-3-ylmethyl)-5-(3-fluorobenzyloxymethyl)-4-formylisoxazole-3-carboxamide (hereinafter, referred to as Compound of Present Invention (214)) represented by the following formula.

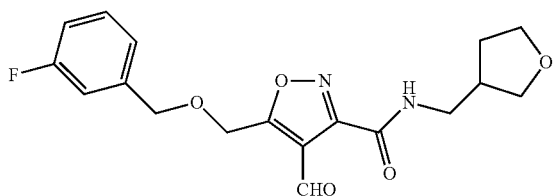

(214)

¹H-NMR (CDCl₃, TMS, δ(ppm)): 1.65-1.74(m, 1H), 2.07-2.17(m, 1H), 2.57-2.66(m, 1H), 3.48-3.54(m, 2H), 3.62 (dd, 1H), 3.75-3.81(m, 1H), 3.84-3.98(m, 2H), 4.66(s, 2H), 4.99(s, 2H), 6.98-7.14(m, 3H), 7.30-7.36(m, 2H), 10.42(s, 1H)

Production Example 206

Sodium borohydride (500 mg, 13.2 mmol) was added to a methanol (23 mL) solution of N-(tetrahydrofuran-3-ylmethyl)-5-(3-fluorobenzyloxymethyl)-4-formylisoxazole-3-carboxamide (2.30 g, 6.38 mmol) under ice-water cooling. The mixture was stirred for 30 minutes under ice-water cooling, and then the reaction mixture was diluted with toluene, and concentrated under reduced pressure. The concentrate was poured into 1 mol/L hydrochloric acid, and the mixture was extracted twice with ethyl acetate. The organic layer was sequentially washed with a saturated aqueous sodium bicarbonate solution and saturated saline water, dried over anhydrous magnesium sulfate, and then concentrated under reduced pressure. The residue was applied to a silica gel column chromatography to obtain 1.46 g of N-(tetrahydrofuran-3-ylmethyl)-5-(3-fluorobenzyloxymethyl)-4-hydroxymethylisoxazole-3-carboxamide (hereinafter, referred to as Compound of Present Invention (215)) represented by the following formula.

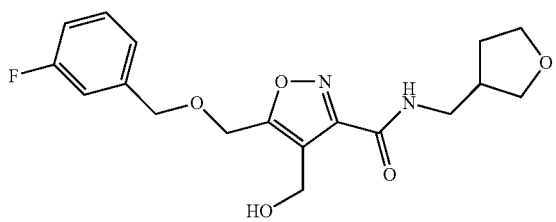

(215)

MS (ESI) m/z 365 ([M+H]⁺)

Production Example 207

55% Sodium hydride (211 mg, 4.83 mmol) was added to a tetrahydrofuran (25 mL) solution of N-(tetrahydrofuran-3-ylmethyl)-5-(3-fluorobenzyloxymethyl)-4-hydroxymethylisoxazole-3-carboxamide (1.46 g, 4.03 mmol) under water cooling, and the mixture was stirred for 25 minutes. Carbon bisulfide (1.2 mL) was added under ice-water cooling, and the mixture was stirred for 20 minutes, and then, methyl iodide (1.2 mL) was further added thereto. After stirring for 30 minutes under ice-water cooling, the reaction mixture was poured into 1 mol/L hydrochloric acid, and the mixture was extracted once with ethyl acetate. The organic layer was washed with saturated saline water, dried over anhydrous magnesium sulfate, and then concentrated under reduced pressure. The residue was applied to a silica gel column chromatography to obtain 1.40 g of dithiocarboxylic acid O-{5-(3-fluorobenzyloxymethyl)-3-[(tetrahydrofuran-3-ylmethyl)carbamoyl]isoxazol-4-ylmethyl}-S-methyl ester (hereinafter, referred to as Compound of Present Invention (216)) represented by the following formula.

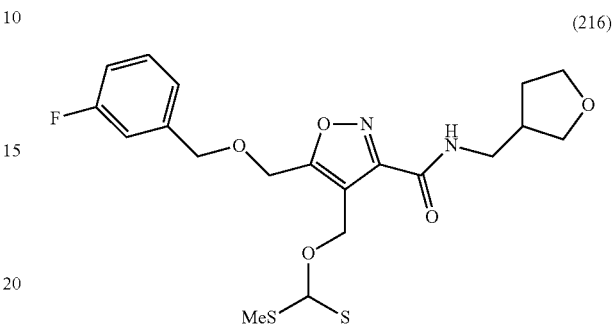

(216)

¹H-NMR (CDCl₃, TMS, δ(ppm)): 1.63-1.72(m, 1H), 2.06-2.14(m, 1H), 2.55(s, 3H), 2.56-2.62(m, 1H), 3.44-3.49 (m, 2H), 3.56-3.61(m, 1H), 3.73-3.81(m, 1H), 3.83-3.95(m, 2H), 4.59(s, 2H), 4.74(s, 2H), 5.82(s, 2H), 6.90-7.15(m, 4H), 7.29-7.36(m, 1H)

Production Example 208

Tributyltin hydride (1.33 g, 4.55 mmol) and azobisisobutyronitrile (50 mg, 0.30 mmol) were added to a toluene (20 mL) solution of dithiocarboxylic acid O-{5-(3-fluorobenzyloxymethyl)-3-[(tetrahydrofuran-3-ylmethyl)carbamoyl] isoxazol-4-ylmethyl}-S-methyl ester (1.38 g, 3.04 mmol). The mixture was stirred at a temperature in the range of 95° C. to 100° C. for 2 hours and 30 minutes, and then concentrated under reduced pressure. The residue was applied to a silica gel column chromatography to obtain 500 mg of N-(tetrahydrofuran-3-ylmethyl)-5-(3-fluorobenzyloxymethyl)-4-methylisoxazole-3-carboxamide (hereinafter, referred to as Compound of Present Invention (217)) represented by the following formula.

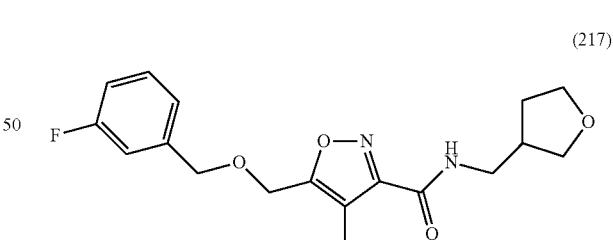

(217)

¹H-NMR (CDCl₃, TMS, δ(ppm)): 1.63-1.73(m, 1H), 2.04-2.13(m, 1H), 2.25(s, 3H), 2.53-2.63(m, 1H), 3.42-3.48 (m, 2H), 3.59(dd, 1H), 3.74-3.80(m, 1H), 3.84-3.95(m, 2H), 4.56(s, 2H), 4.61(s, 2H), 6.92-7.13(m, 4H), 7.29-7.36(m, 1H)

Production Example 209

A 1.58 mol/L-n-butyllithium hexane solution (4.4 mL, 7.00 mmol) was added dropwise to a tetrahydrofuran (20 mL) solution of N-(tetrahydrofuran-3-ylmethyl)-5-(3-phenylpropyl)isoxazole-3-carboxamide (1.02 g, 2.80 mmol) at −45° C. or less under a nitrogen atmosphere. After stirring at −45° C. to −60° C. for 30 minutes, N,N-dimethylformamide (2.5 mL) was added thereto, and the mixture was further stirred at a temperature of −60° C. to room temperature for 11.5 hours. Then, the reaction mixture was poured into 1 mol/L hydrochloric acid under cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 1.00 g of N-(tetrahydrofuran-3-ylmethyl)-4-formyl-5-(3-phenylpropyl)isoxazole-3-carboxamide (hereinafter, referred to as Compound of Present Invention (218)) represented by the following formula.

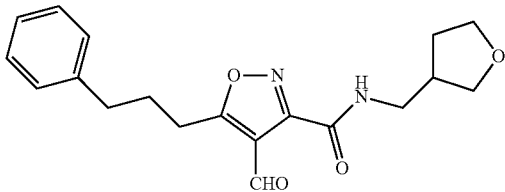

(218)

$^1$H-NMR (CDCl$_3$, TMS, δ(ppm)): 1.64-1.75(m, 1H), 2.07-2.16(m, 3H), 2.55-2.65(m, 1H), 2.67-2.74(m, 2H), 3.14-3.19(m, 2H), 3.47-3.52(m, 2H), 3.61(dd, 1H), 3.74-3.81(m, 1H), 3.84-3.97(m, 2H), 7.15-7.34(m, 6H), 10.37(s, 1H)

Production Example 210

Sodium borohydride (250 mg, 6.61 mmol) was added to a methanol (15 mL) solution of N-(tetrahydrofuran-3-ylmethyl)-4-formyl-5-(3-phenylpropyl)isoxazole-3-carboxamide (1.00 g, 2.55 mmol) under water cooling. The mixture was stirred for 1.5 hours under water cooling, and diluted with toluene, and then concentrated under reduced pressure. The concentrate was diluted with ethyl acetate, sequentially washed with a saturated aqueous sodium bicarbonate solution and saturated saline water, dried over anhydrous magnesium sulfate, and then concentrated under reduced pressure. The residue was applied to a silica gel column chromatography to obtain 890 mg of N-(tetrahydrofuran-3-ylmethyl)-4-hydroxymethyl-5-(3-phenylpropyl)isoxazole-3-carboxamide (hereinafter, referred to as Compound of Present Invention (219)) represented by the following formula.

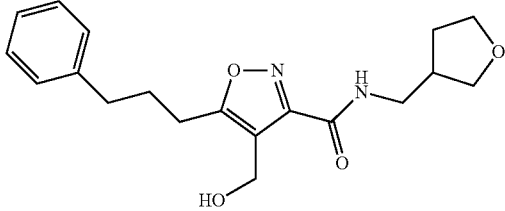

(219)

MS (ESI) m/z 345 ([M+H]$^+$)

Production Example 211

55% Sodium hydride (117 mg, 2.69 mmol) was added to a tetrahydrofuran (20 mL) solution of N-(tetrahydrofuran-3-ylmethyl)-4-hydroxymethyl-5-(3-phenylpropyl)isoxazole-3-carboxamide (890 mg, 2.24 mmol) under water cooling, and the mixture was stirred for 25 minutes. Carbon bisulfide (0.8 mL) was added under ice-water cooling, the mixture was stirred for 15 minutes, then methyl iodide (0.8 mL) was added thereto, and the mixture was further stirred for 15 minutes under ice-water cooling. Then, the reaction mixture was poured into 1 mol/L hydrochloric acid, and the mixture was extracted once with ethyl acetate. The organic layer was washed with saturated saline water, dried over anhydrous magnesium sulfate, and then concentrated under reduced pressure. The residue was applied to a silica gel column chromatography to obtain 869 mg of dithiocarboxylic acid O-{5-(3-phenylpropyl)-3-[(tetrahydrofuran-3-ylmethyl)carbamoyl]isoxazolyl-4-ylmethyl}-S-methyl ester (hereinafter, referred to as Compound of Present Invention (220)) represented by the following formula.

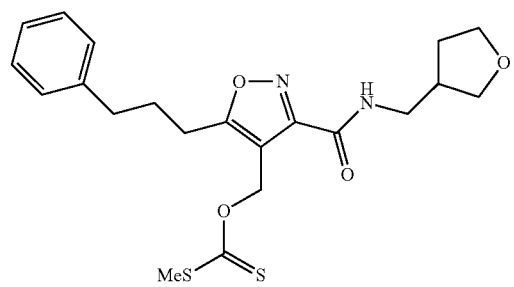

(220)

$^1$H-NMR (CDCl$_3$, TMS, δ(ppm)): 1.63-1.73(m, 1H), 2.01-2.14(m, 3H), 2.55(s, 3H), 2.56-2.62(m, 1H), 2.65-2.73(m, 2H), 2.84-2.90(m, 2H), 3.42-3.48(m, 2H), 3.56-3.61(m, 1H), 3.73-3.80(m, 1H), 3.83-3.95(m, 2H), 5.72(s, 2H), 6.91 (brs, 1H), 7.16-7.23(m, 3H), 7.27-7.32(m, 2H)

Production Example 212

Tributyltin hydride (938 mg, 2.69 mmol) and azobisisobutyronitrile (29 mg, 0.18 mmol) were added to a toluene (20 mL) solution of dithiocarboxylic acid O-{5-(3-phenylpropyl)-3-[(tetrahydrofuran-3-ylmethyl)carbamoyl] isoxazolyl-4-ylmethyl}ester-S-methyl ester (869 mg, 1.79 mmol). The mixture was stirred at 95° C. to 100° C. for 2 hours, and then concentrated under reduced pressure. The residue was applied to a silica gel column chromatography to obtain 290 mg of N-(tetrahydrofuran-3-ylmethyl)-4-methyl-5-(3-phenylpropyl)isoxazole-3-carboxamide (hereinafter, referred to as Compound of Present Invention (221)) represented by the following formula.

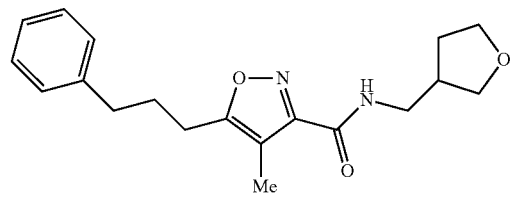

(221)

¹H-NMR (CDCl₃, TMS, δ(ppm)): 1.62-1.73(m, 1H), 1.99-2.12(m, 3H), 2.14(s, 3H), 2.52-2.62(m, 1H), 2.63-2.69 (m, 2H), 2.70-2.76(m, 2H), 3.38-3.49(m, 2H), 3.58(d, 1H), 3.73-3.80(m, 1H), 3.83-3.94(m, 2H), 6.93(brs, 1H), 7.16-7.23(m, 3H), 7.27-7.32(m, 2H)

Production Example 213

A 1.58 mol/L-n-butyllithium hexane solution (4.2 mL, 6.57 mmol) was added dropwise to a tetrahydrofuran (20 mL) solution of N-(tetrahydropyran-4-ylmethyl)-5-(2-naphthylmethoxymethyl)isoxazole-3-carboxamide (1.00 g, 2.63 mmol) at −45° C. or less under a nitrogen atmosphere. After stirring at −50° C. to −60° C. for 40 minutes, N,N-dimethylformamide (5 mL) was added thereto, and the mixture was further stirred at a temperature of −60° C. to room temperature for 1 hour. Then, the reaction mixture was poured into 1 mol/L hydrochloric acid under cooling, and the mixture was extracted twice with ethyl acetate. The organic layer was sequentially washed with water and saturated saline water, dried over anhydrous magnesium sulfate, and then concentrated under reduced pressure to obtain 1.33 g of N-(tetrahydropyran-4-ylmethyl)-4-formyl-5-(2-naphthylmethoxymethyl)isoxazole-3-carboxamide (hereinafter, referred to as Compound of Present Invention (222)) represented by the following formula, as a crude product.

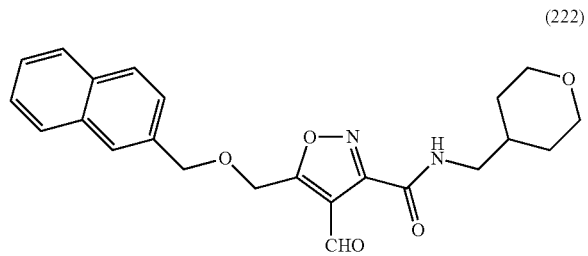 [SMILES: O=Cc1c(C(=O)NCC2CCOCC2)noc1COCc1ccc2ccccc2c1]

(222)

¹H-NMR (CDCl₃, TMS, δ(ppm)): 1.30-1.45(m, 2H), 1.60-1.71(m, 2H), 1.80-1.91(m, 1H), 3.34-3.40(m, 4H), 3.95-4.03(m, 2H), 4.60(s, 2H), 4.67(s, 2H), 6.76(brs, 1H), 7.46-7.53(m, 3H), 7.80-7.88(m, 4H), 10.39(s, 1H)

Production Example 214

Sodium borohydride (580 mg, 15.3 mmol) was added to a methanol (20 mL) solution of the unpurified N-(tetrahydropyran-4-ylmethyl)-4-formyl-5-(2-naphthylmethoxymethyl)isoxazole-3-carboxamide (1.33 g, <3.26 mmol) obtained in Production Example 213 under ice-water cooling. The mixture was stirred for 1 hour, and then the reaction mixture was diluted with toluene, and concentrated under reduced pressure. The concentrate was poured into 1 mol/L hydrochloric acid under cooling, and the mixture was extracted twice with ethyl acetate. The organic layer was sequentially washed with a saturated aqueous sodium bicarbonate solution and saturated saline water, dried over anhydrous magnesium sulfate, and then concentrated under reduced pressure. The residue was applied to a silica gel column chromatography to obtain 950 mg of N-(tetrahydropyran-4-ylmethyl)-4-hydroxymethyl-5-(2-naphthylmethoxymethyl)isoxazole-3-carboxamide (hereinafter, referred to as Compound of Present Invention (223)) represented by the following formula.

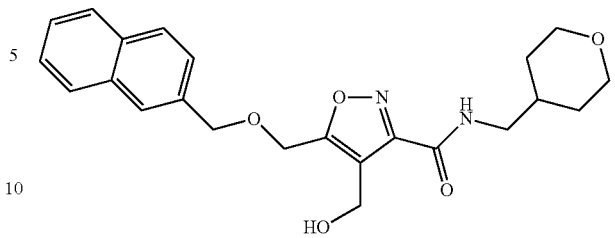

(223)

¹H-NMR (CDCl₃, TMS, δ(ppm)): 1.32-1.45(m, 2H), 1.59 (s, 1H), 1.63-1.71(m, 2H), 1.82-1.94(m, 1H), 3.33-3.43(m, 4H), 3.97-4.04(m, 2H), 4.62(s, 2H), 4.67(s, 2H), 4.74(s, 2H), 7.08(brs, 1H), 7.45-7.53(m, 3H), 7.78-7.88(m, 4H)

Production Example 215

55% Sodium hydride (121 mg, 2.78 mmol) was added to a tetrahydrofuran (20 mL) solution of N-(tetrahydropyran-4-ylmethyl)-4-hydroxymethyl-5-(2-naphthylmethoxymethyl)isoxazole-3-carboxamide (950 mg, 2.31 mmol), and the mixture was stirred at room temperature for 20 minutes. Then, carbon bisulfide (1 mL) was added under ice-water cooling, and the mixture was further stirred for 15 minutes. Methyl iodide (1 mL) was added to the reaction mixture, and the mixture was stirred for 30 minutes, then poured into 1 mol/L hydrochloric acid under ice-water cooling, and extracted twice with ethyl acetate. The organic layer was washed with saturated saline water, dried over anhydrous magnesium sulfate, and then concentrated under reduced pressure. The residue was applied to a silica gel column chromatography to obtain 1.06 g of dithiocarboxylic acid O-{5-(2-naphthylmethoxymethyl)-3-[(tetrahydropyran-4-ylmethyl)carbamoyl]isoxazol-4-ylmethyl}-S-methyl ester (hereinafter, referred to as Compound of Present Invention (224)) represented by the following formula.

(224)

¹H-NMR (CDCl₃, TMS, δ(ppm)): 1.30-1.44(m, 2H), 1.62-1.71(m, 2H), 1.80-1.93(m, 1H), 2.50(s, 3H), 3.30-3.42 (m, 4H), 3.95-4.02(m, 2H), 4.76(s, 4H), 5.81(s, 2H), 6.86 (brs, 1H), 7.44-7.53(m, 3H), 7.77-7.88(m, 4H)

Production Example 216

Tributyltin hydride (740 mg, 2.54 mmol) and azobisisobutyronitrile (70 mg, 0.42 mmol) were added to a toluene (20 mL) solution of dithiocarboxylic acid O-{5-(2-naphthylmethoxymethyl)-3-[(tetrahydropyran-4-ylmethyl) carbamoyl]isoxazol-4-ylmethyl}-S-methyl ester (1.06 g, 2.12 mmol). The mixture was stirred at 90° C. to 100° C. for 1 hour, and concentrated under reduced pressure. The residue was applied to a silica gel column chromatography to obtain 380 mg of N-(tetrahydropyran-4-ylmethyl)-4-methyl-5-(2-naphthylmethoxymethyl)isoxazole-3-carboxamide (hereinafter, referred to as Compound of Present Invention (225)) represented by the following formula.

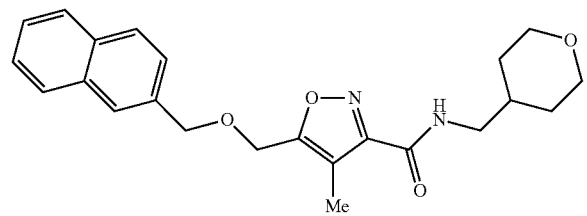

(225)

¹H-NMR (CDCl₃, TMS, δ(ppm)): 1.32-1.43(m, 2H), 1.64-1.70(m, 2H), 1.80-1.91(m, 1H), 2.25(s, 3H), 3.33-3.43 (m, 4H), 3.96-4.02(m, 2H), 4.63(s, 2H), 4.73(s, 2H), 6.90 (brs, 1H), 7.45-7.52(m, 3H), 7.78-7.88(m, 4H)

Production Example 217

5-[2-Methylbenzyl)oxymethyl]isoxazole-3-carboxylic acid (1.15 g, 4.7 mmol) was added to chloroform (amylene addition product) (10 mL), and cooled to 0° C. Triethylamine (0.57 ml, 5.6 mmol), 1-ethyl-3-(3-dimethylaminopropyl) carbodiimide hydrochloride (1.08 g, 5.6 mmol) and 1-hydroxybenzotriazole (0.08 g, 0.6 mmol) were added thereto, and the mixture was stirred for 10 minutes. Tetrahydropyran-4-ylmethylamine (0.77 g, 5.6 mmol) was added to the mixture, and the mixture was stirred at room temperature for 16 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.96 g of N-(tetrahydrofuran-3-ylmethyl)-5-[2-methylbenzyl)oxymethyl]isoxazole-3-carboxamide (hereinafter, referred to as Compound of Present Invention (226)) represented by the following formula.

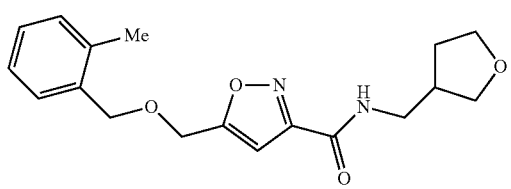

(226)

¹H-NMR (CDCl₃, TMS, δ(ppm)): 1.63-1.72(1H, m), 2.08-2.11(1H, m), 2.34(3H, s), 2.55-2.61(1H, m), 3.47(2H, t), 3.59(1H, dd), 3.75-3.79(1H, m), 3.85-3.87(1H, m), 3.91-3.93(1H, m), 4.61(2H, s), 4.65(2H, s), 6.72(1H, s), 6.96(1H, s), 7.20-7.23(3H, m), 7.30-7.31(1H, m)

Production Example 218

5-[2-Methoxybenzyl)oxymethyl]isoxazole-3-carboxylic acid (1.13 g, 4.7 mmol) was added to chloroform (amylene addition product) (10 mL), and cooled to 0° C. Triethylamine (0.57 ml, 5.6 mmol), 1-ethyl-3-(3-dimethylaminopropyl) carbodiimide hydrochloride (1.08 g, 5.6 mmol) and 1-hydroxybenzotriazole (0.08 g, 0.6 mmol) were added thereto, and the mixture was stirred for 10 minutes. Tetrahydropyran-4-ylmethylamine (0.77 g, 5.6 mmol) was added to the mixture, and the mixture was stirred at room temperature for 16 hours. Then, water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 1.02 g of N-(tetrahydrofuran-3-ylmethyl)-5-(2-methoxybenzyloxymethyl)isoxazole-3-carboxamide (hereinafter, referred to as Compound of Present Invention (227)) represented by the following formula.

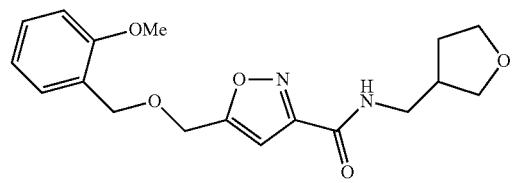

(227)

¹H-NMR (CDCl₃, TMS, δ(ppm)): 1.67-1.72(1H, m), 2.08-2.11(1H, m), 2.55-2.62(1H, m), 3.47(2H, t), 3.59(1H, dd), 3.74-3.80(1H, m), 3.85-3.87(4H, m), 3.91-3.93(1H, m), 4.65(2H, s), 4.69(2H, s), 6.75(1H, s), 6.89(1H, d), 6.96-6.98 (2H, m), 7.28-7.37(2H, m)

Production Example 219

5-[3-(2-Naphthyl)propyl]isoxazole-3-carboxylic acid (0.56 g, 2.0 mmol), tetrahydrofuran-3-ylmethylamine hydrochloride (0.33 g, 2.4 mmol), triethylamine (0.25 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.49 g of N-(tetrahydrofuran-3-ylmethyl)-5-[3-(2-naphthyl) propyl]isoxazole-3-carboxamide (hereinafter, referred to as Compound of Present Invention (228)) represented by the following formula.

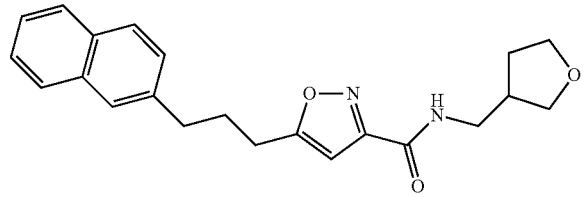

(228)

¹H-NMR (CDCl₃, TMS, δ(ppm)): 1.66-1.73(1H, m), 2.06-2.19(3H, m), 2.54-2.61(1H, m), 2.83-2.87(4H, m), 3.46 (2H, t), 3.58-3.60(1H, m), 3.75-3.79(1H, m), 3.84-3.94(2H, m), 6.48(1H, s), 6.93(1H, s), 7.32(1H, dd), 7.42-7.49(2H, m), 7.62(1H, s), 7.78-7.83(3H, m)

Production Example 220

5-[3-(2-Naphthyl)propyl]isoxazole-3-carboxylic acid (0.56 g, 2.0 mmol), 1,3-dioxolan-4-ylmethylamine (0.24 g, 2.4 mmol), triethylamine (0.25 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.51 g of N-(1,3-dioxolan-4-ylmethyl)-5-[3-(2-naphthyl)propyl] isoxazole-3-carboxamide (hereinafter, referred to as Compound of Present Invention (229)) represented by the following formula.

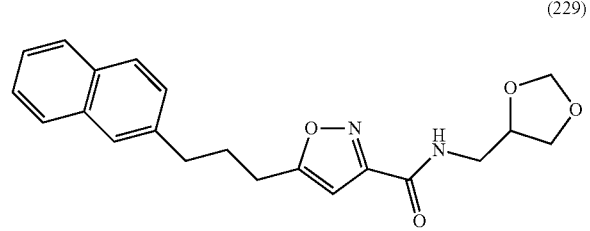 [SMILES: O=C(NCC1COCO1)c1cc(CCCc2ccc3ccccc3c2)on1]

(229)

¹H-NMR (CDCl₃, TMS, δ(ppm)): 2.13-2.18(2H, m), 2.84-2.88(4H, m), 3.99-4.00(4H, m), 4.11-4.16(1H, 1nm), 4.80(1H, d), 5.02(1H, d), 6.48(1H, s), 7.33(1H, dd), 7.42-7.49(2H, m), 7.60-7.62(2H, m), 7.78-7.83(3H, m)

Production Example 221

5-[3-(2-Naphthyl)propyl]isoxazole-3-carboxylic acid (0.56 g, 2.0 mmol), 1,4-dioxan-2-ylmethylamine (0.24 g, 2.4 mmol), triethylamine (0.25 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.57 g of N-(1,4-dioxan-2-ylmethyl)-5-[3-(2-naphthyl)propyl] isoxazole-3-carboxamide (hereinafter, referred to as Compound of Present Invention (230)) represented by the following formula.

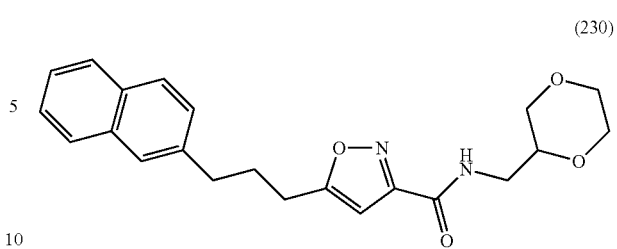

(230)

¹H-NMR (CDCl₃, TMS, δ(ppm)): 2.12-2.17(2H, m), 2.85 (4H, q), 3.33-3.38(2H, m), 3.58-3.66(2H, m), 3.73-3.80(5H, m), 6.47(1H, s), 7.10(1H, s), 7.32(1H, dd), 7.41-7.49(2H, m), 7.62(1H, s), 7.78-7.93(3H, m).

Production Example 222

5-[3-(5-(2,2-Difluoro-1,3-benzodioxolanyl)propyl]isoxazole-3-carboxylic acid (0.58 g, 2.0 mmol), tetrahydrofuran-3-ylmethylamine hydrochloride (0.33 g, 2.4 mmol), triethylamine (0.25 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.57 g of N-(tetrahydrofuran-3-ylmethyl)-5-[5-(2,2-difluoro-1,3-benzodioxolanyl)propyl]isoxazole-3-carboxamide (hereinafter, referred to as Compound of Present Invention (231)) represented by the following formula.

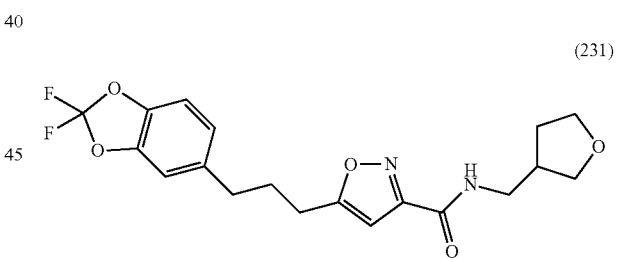

(231)

¹H-NMR (CDCl₃, TMS, δ(ppm)): 1.66-1.69(1H, m), 1.99-2.13(3H, m), 2.53-2.63(1H, m), 2.68(2H, t), 2.81(2H, t), 3.46(2H, t), 3.59(1H, dd), 3.76(1H, q), 3.84-3.94(2H, m), 6.46(1H, s), 6.86-6.99(4H, m)

Production Example 223

5-[3-(5-(2,2-Difluoro-1,3-benzodioxolanyl))propyl]isoxazole-3-carboxylic acid (0.52 g, 1.8 mmol), 1,4-dioxan-2-ylmethylamine (0.24 g, 2.4 mmol), triethylamine (0.25 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.50 g of N-(1,4-dioxan-2-ylmethyl)-5-[3-(5-(2,2-difluoro-1,3-benzodioxolanyl))propyl]isoxazole-3-carboxamide (hereinafter, referred to as Compound of Present Invention (232)) represented by the following formula.

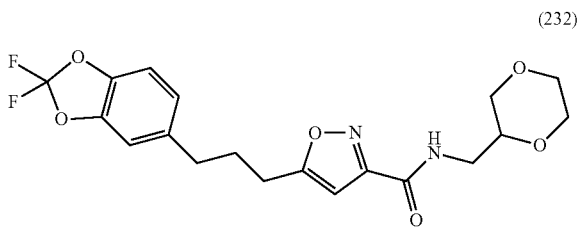 [SMILES: O=C(NCC1COCCO1)c1cc(CCCc2ccc3c(c2)OC(F)(F)O3)on1]

(232)

$^1$H-NMR (CDCl$_3$, TMS, δ(ppm)): 1.99-2.06(2H, m), 2.67-2.71(2H, m), 2.80(2H, t), 3.30-3.40(2H, m), 3.57-3.66 (2H, m), 3.70-3.83(5H, m), 6.46(1H, d), 6.87(2H, td), 6.97 (1H, d), 7.10(1H, s)

Production Example 224

5-(2-Naphthylmethoxymethyl)isoxazole-3-carboxylic acid (0.57 g, 2.0 mmol), 1,4-dioxan-2-ylmethylamine (0.24 g, 2.4 mmol), and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.51 g of N-(1,4-dioxan-2-ylmethyl)-5-(2-naphthylmethoxymethyl)isoxazole-3-carboxamide (hereinafter, referred to as Compound of Present Invention (233)) represented by the following formula.

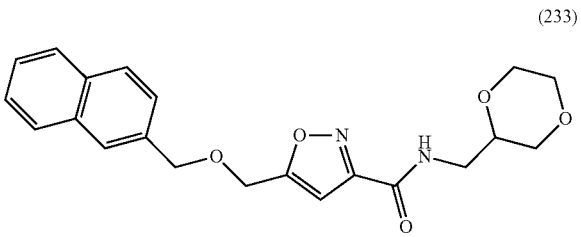 [SMILES: O=C(NCC1COCCO1)c1cc(COCc2ccc3ccccc3c2)on1]

(233)

$^1$H-NMR (CDCl$_3$, TMS, δ(ppm)): 3.31-3.41(2H, m), 3.58-3.67(2H, m), 3.70-3.83(5H, m), 4.69(2H, d), 4.77(2H, s), 6.75(1H, s), 7.13(1H, s), 7.46-7.53(3H, m), 7.82-7.84 (4H, m)

Production Example 225

5-[3-(1,3-Benzodioxolan-5-yl)propyl]isoxazole-3-carboxylic acid (0.55 g, 2.0 mmol), tetrahydrofuran-3-ylmethylamine hydrochloride (0.33 g, 2.4 mmol), triethylamine (0.25 g, 2.4 mmol) and 1-hydroxybenzotriazole (0.03 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.57 g of N-(tetrahydrofuran-3-ylmethyl)-5-[3-(1,3-benzodioxolan-5-yl)propyl]isoxazole-3-carboxamide (hereinafter, referred to as Compound of Present Invention (234)) represented by the following formula.

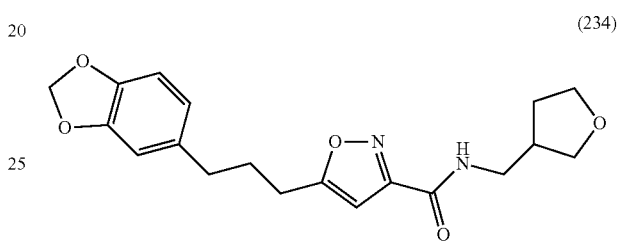

(234)

$^1$H-NMR (CDCl$_3$, TMS, δ(ppm)): 1.63-1.72(1H, m), 1.95-2.03(2H, m), 2.04-2.11(1H, m), 2.55-2.62(3H, m), 2.78 (2H, t), 3.44-3.46(2H, m), 3.58-3.60(1H, m), 3.72-3.78(1H, m), 3.82-3.93(2H, m), 5.92(2H, s), 6.46(1H, s), 6.61-6.65 (2H, m), 6.73(1H, d), 7.22(1H, s)

Production Example 226

5-(3-Phenylpropyl)isoxazole-3-carboxylic acid (0.46 g, 2.0 mmol), tetrahydropyran-4-ylmethylamine (0.29 g, 2.5 mmol), triethylamine (0.24 g, 2.4 mmol) and 1-hydroxybenzotriazole (0.04 g, 0.24 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.49 g of N-(tetrahydropyran-4-ylmethyl)-5-(3-phenylpropyl)isoxazole-3-carboxamide (hereinafter, referred to as Compound of Present Invention (235)) represented by the following formula.

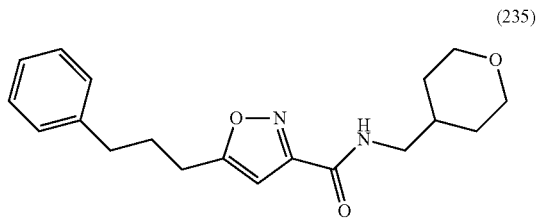 [SMILES: O=C(NCC1CCOCC1)c1cc(CCCc2ccccc2)on1]

(235)

¹H-NMR (CDCl₃, TMS, δ(ppm)): 1.34-1.41(2H, m), 1.65-1.69(2H, m), 1.81-1.91(1H, m), 2.02-2.09(2H, m), 2.69 (2H, t), 2.80(2H, t), 3.34-3.39(4H, m), 3.97-4.00(2H, m), 6.46(1H, s), 6.89(1H, s), 7.17-7.23(3H, m), 7.29-7.31(2H, m)

Production Example 227

5-[5-(2,2-Difluoro-1,3-benzodioxolanyl)methoxymethyl]isoxazole-3-carboxylic acid (0.69 g, 2.2 mmol), tetrahydrofuran-3-ylmethylamine hydrochloride (0.36 g, 2.7 mmol), triethylamine (0.27 g, 2.7 mmol) and 1-hydroxybenzotriazole (0.03 g, 0.27 mmol) were added to chloroform (amylene addition product) (7 mL). 1-Ethyl-3-(3-dimethylaminopropyl) carbodiimide hydrochloride (0.52 g, 2.7 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.74 g of N-(tetrahydrofuran-3-ylmethyl)-5-[5-(2,2-difluoro-1,3-benzodioxolanyl)methoxymethyl]isoxazole-3-carboxamide (hereinafter, referred to as Compound of Present Invention (236)) represented by the following formula.

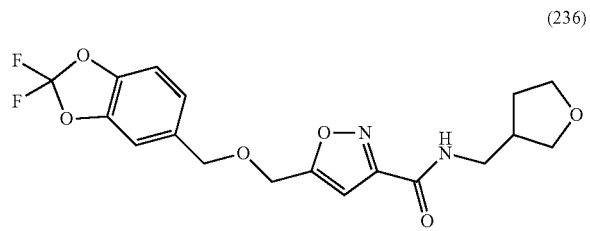 [SMILES: O=C(NCC1CCOC1)c1cc(COCc2ccc3c(c2)OC(F)(F)O3)on1]

(236)

¹H-NMR (CDCl₃, TMS, δ(ppm)): 1.66-1.71(1H, m), 2.05-2.15(1H, m), 2.55-2.62(1H, m), 3.46-3.49(2H, m), 3.60 (1H, dd), 3.74-3.80(1H, m), 3.86(1H, dd), 3.93(1H, td), 4.57(2H, s), 4.66(2H, s), 6.74(1H, s), 6.97(1H, brs), 7.04-7.10(3H, m)

Production Example 228

5-[5-(2,2-Difluoro-1,3-benzodioxolanyl)methoxymethyl]isoxazole-3-carboxylic acid (0.69 g, 2.2 mmol), tetrahydropyran-4-ylmethylamine (0.31 g, 2.7 mmol), triethylamine (0.27 g, 2.7 mmol) and 1-hydroxybenzotriazole (0.03 g, 0.27 mmol) were added to chloroform (amylene addition product) (7 mL). 1-Ethyl-3-(3-dimethylaminopropyl) carbodiimide hydrochloride (0.52 g, 2.7 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.64 g of N-(tetrahydropyran-4-ylmethyl)-5-[5-(2,2-difluoro-1,3-benzodioxolanyl) methoxymethyl]isoxazole-3-carboxamide (hereinafter, referred to as Compound of Present Invention (237)) represented by the following formula.

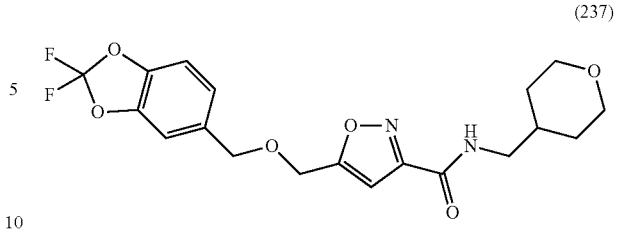

(237)

¹H-NMR (CDCl₃, TMS, δ(ppm)): 1.37-1.42(2H, m), 1.68-1.69(2H, m), 1.83-1.89(1H, m), 3.34-3.42(4H, m), 3.99 (2H, dd), 4.57(2H, s), 4.65(2H, d), 6.73(1H, s), 6.90(1H, s), 7.04-7.10(3H, m)

Production Example 229

5-[5-(2,2-Difluoro-1,3-benzodioxolanyl)methoxymethyl]isoxazole-3-carboxylic acid (0.69 g, 2.2 mmol), 3-methyloxetan-3-ylmethylamine (0.31 g, 2.7 mmol), triethylamine (0.27 g, 2.7 mmol) and 1-hydroxybenzotriazole (0.03 g, 0.27 mmol) were added to chloroform (amylene addition product) (7 mL). 1-Ethyl-3-(3-dimethylaminopropyl) carbodiimide hydrochloride (0.52 g, 2.7 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.64 g of N-(3-methyloxetan-3-ylmethyl)-5-[5-(2,2-difluoro-1,3-benzodioxolanyl)methoxymethyl]isoxazole-3-carboxamide (hereinafter, referred to as Compound of Present Invention (238)) represented by the following formula.

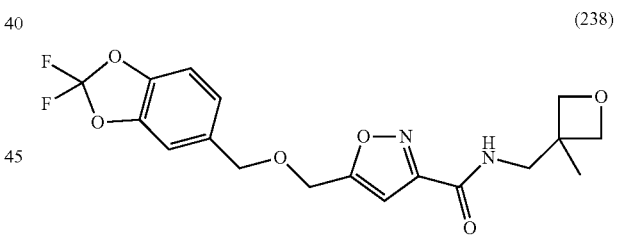

(238)

¹H-NMR (CDCl₃, TMS, δ(ppm)): 1.37(3H, s), 3.66(2H, d), 4.43(2H, d), 4.54(2H, d), 4.57(2H, s), 4.66(2H, s), 6.75(1H, s), 7.07(4H, t)

Production Example 230

Tetrahydrofuran-3-ylmethylamine hydrochloride (0.24 g, 1.75 mmol) and triethylamine (0.18 g, 1.75 mmol) were added to chloroform (amylene addition product) (8 mL). 5-(5,6,7,8-Tetrahydronaphthalen-2-yl)oxymethylisoxazole-3-carboxylic acid (0.40 g, 1.46 mmol), 1-hydroxybenzotriazole (0.02 g, 0.18 mmol) and 1-ethyl-3-(3-dimethylaminopropyl) carbodiimide hydrochloride (0.34 g, 1.75 mmol) were added to the mixture at room temperature, and the mixture was stirred for 5 hours. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.40 g of N-(tetrahydrofuran-3-ylmethyl)-5-(5,6,7,8-tetrahydronaphthalen-2-yl) oxymethylisoxazole-3-carboxamide (hereinafter, referred to as Compound of Present Invention (239)) represented by the following formula.

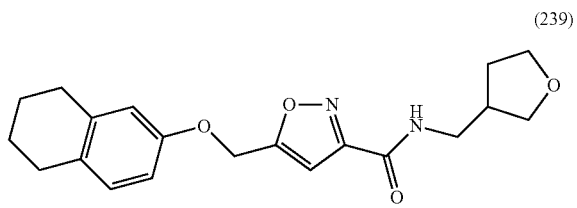 [SMILES: O=C(NCC1CCOC1)c1cc(COc2ccc3c(c2)CCCC3)on1]

(239)

¹H-NMR (CDCl₃, TMS, δ(ppm)): 1.61-1.71(1H, m), 1.76-1.79(4H, br m), 2.04-2.13(1H, m), 2.52-2.62(1H, m), 2.70-2.73(4H, br m), 3.44-3.48(2H, m), 3.57-3.60(1H, m), 3.73-3.79(1H, m), 3.83-3.94(2H, m), 5.15(2H, s), 6.65(1H, br s), 6.69(1H, dd), 6.77(1H, s), 6.96(1H, br s), 6.99(1H, d)

Production Example 231

Iodobenzene (0.66 g, 3.22 mmol) and dichlorobistriphenylphosphine palladium (0.11 g, 0.16 mmol) were added to tetrahydrofuran (25 mL). Copper iodide (0.06 g, 0.32 mmol), diisopropylamine (0.39 g, 3.86 mmol) and N-(tetrahydrofuran-3-ylmethyl)-5-propargyloxymethylisoxazole-3-carboxamide (0.85 g, 3.22 mmol) were added to the mixture at room temperature, and the mixture was stirred for 5 hours. Then, dilute hydrochloric acid was added thereto, and the mixture was extracted twice with chloroform. The organic layer was washed with a saturated aqueous sodium bicarbonate solution, and concentrated under reduced pressure. The residue was applied to a silica gel column chromatography to obtain 0.76 g of N-(tetrahydrofuran-3-ylmethyl)-5-(3-phenyl-2-propionyl)oxymethylisoxazole-3-carboxamide (hereinafter, referred to as Compound of Present Invention (240)) represented by the following formula.

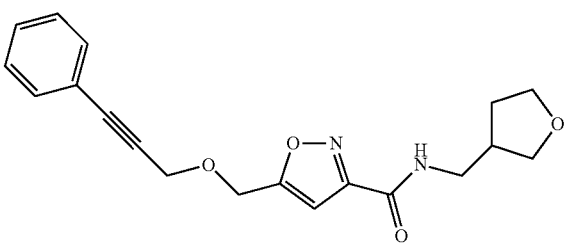

(240)

¹H-NMR (CDCl₃, TMS, δ(ppm)): 1.63-1.71(1H, m), 2.04-2.12(1H, m), 2.54-2.61(1H, m), 3.44-3.48(2H, m), 3.57-3.61(1H, m), 3.74-3.79(1H, m), 3.83-3.92(2H, m), 4.47 (2H, s), 4.81(2H, s), 6.78(1H, s), 6.99(1H, br s), 7.32-7.36 (3H, m), 7.44-7.47(2H, m)

Production Example 232

Tetrahydrofuran-3-ylmethylamine hydrochloride (0.13 g, 0.95 mmol) and triethylamine (0.10 g, 0.95 mmol) were added to chloroform (amylene addition product) (5 mL). 5-(5-Phenyl-2-thienylmethoxymethyl)isoxazole-3-carboxylic acid (0.25 g, 0.79 mmol), 1-hydroxybenzotriazole (0.01 g, 0.08 mmol) and 1-ethyl-3-(3-dimethylaminopropyl) carbodiimide hydrochloride (0.18 g, 0.95 mmol) were added to the mixture at room temperature, and the mixture was stirred overnight. Then, dilute hydrochloric acid was added thereto, and the mixture was extracted twice with chloroform. The organic layer was washed with a saturated aqueous sodium bicarbonate solution, dried over anhydrous magnesium sulfate, and then concentrated under reduced pressure. The residue was applied to a silica gel column chromatography to obtain 0.25 g of N-(tetrahydrofuran-3-ylmethyl)-5-(5-phenyl-2-thienylmethoxymethyl)isoxazole-3-carboxamide (hereinafter, referred to as Compound of Present Invention (241)) represented by the following formula.

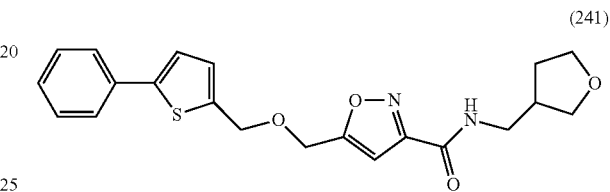

(241)

¹H-NMR (CDCl₃, TMS, δ(ppm)): 1.63-1.72(1H, m), 2.04-2.13(1H, m), 2.52-2.62(1H, m), 3.45-3.48(2H, m), 3.57-3.61(1H, m), 3.74-3.79(1H, m), 3.84-3.94(2H, m), 4.68 (2H, s), 4.76(2H, s), 6.74(1H, s), 6.94(1H, br), 6.01(1H, d), 7.19(1H, d), 7.28-7.31(1H, m), 7.36-7.40(2H, m), 7.56-7.60 (2H, m)

Production Example 233

Tetrahydrofuran-3-ylmethylamine hydrochloride (0.16 g, 1.16 mmol) and triethylamine (0.12 g, 1.16 mmol) were added to chloroform (amylene addition product) (5 mL). 5-(3-Phenyl-(E)-2-propenyloxymethyl)isoxazole-3-carboxylic acid (0.25 g, 0.96 mmol), 1-hydroxybenzotriazole (0.01 g, 0.10 mmol) and 1-ethyl-3-(3-dimethylaminopropyl) carbodiimide hydrochloride (0.22 g, 1.16 mmol) were added to the mixture at room temperature, and the mixture was stirred at room temperature overnight. Then, dilute hydrochloric acid was added thereto, and the mixture was extracted twice with chloroform. The organic layer was washed with a saturated aqueous sodium bicarbonate solution, dried over anhydrous sodium sulfate, and then concentrated under reduced pressure. The residue was applied to a silica gel column chromatography to obtain 0.25 g of N-(tetrahydrofuran-3-ylmethyl)-5-(3-phenyl-(E)-2-propenyloxymethyl) isoxazole-3-carboxamide (hereinafter, referred to as Compound of Present Invention (242)) represented by the following formula.

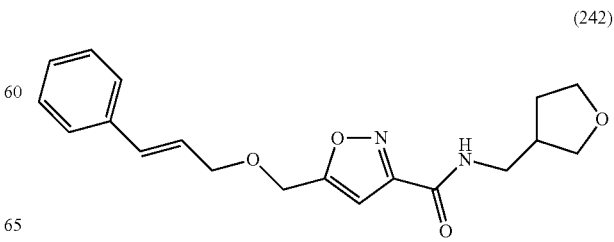

(242)

¹H-NMR (CDCl₃, TMS, δ(ppm)): 1.64-1.72(1H, m), 2.05-2.13(1H, m), 2.53-2.63(1H, m), 3.45-3.48(2H, m), 3.57-3.61(1H, m), 3.74-3.80(1H, m), 3.84-3.95(2H, m), 4.25 (2H, d), 4.68(2H, s), 6.24-6.31(1H, m), 6.65(1H, d), 6.74 (1H, s), 6.95(1H, br s), 7.25-7.28(1H, m), 7.32-7.35(2H, m), 7.39-7.41(2H, m)

Production Example 234

5-(3-quinolyl)pentan-2-one (3.60 g, 16.9 mmol) and diethyl oxalate (2.71 g, 18.6 mmol) were dissolved in ethanol (37 mL), and the mixture was cooled to 0° C. under a nitrogen atmosphere. Sodium ethoxide (20% ethanol solution, 6.37 g, 18.6 mmol) was added dropwise to the mixture over 30 minutes, and the mixture was stirred at room temperature overnight and then concentrated under reduced pressure. A saturated aqueous ammonium chloride solution was poured into the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 1.05 g of ethyl 7-(3-quinolyl)-2,4-dioxoheptanoate represented by the following formula.

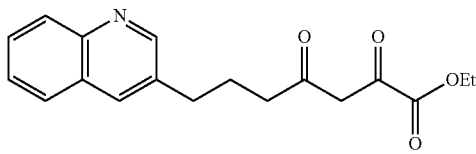 [SMILES: CCOC(=O)C(=O)CC(=O)CCCc1cnc2ccccc2c1]

Ethyl 7-(3-quinolyl)-2,4-dioxoheptanoate (1.05 g, 3.3 mmol) was dissolved in ethanol (10 ml), and hydroxylamine hydrochloride (0.47 g, 6.7 mmol) was added thereto, and the mixture was heated and refluxed for 8 hours, under a nitrogen atmosphere. The reaction mixture was cooled to room temperature, 10 ml of water and potassium hydroxide (0.94 g, 16.8 mmol) were added thereto, and the mixture was stirred at room temperature for 4 hours. 20 ml of a 1 N aqueous hydrochloric acid solution was added thereto, and then the mixture was concentrated under reduced pressure. Chloroform (amylene addition product) (10 mL) and triethylamine (0.68 g, 6.7 mmol) were added to the obtained solid, and the mixture was dried over anhydrous sodium sulfate. Tetrahydrofuran-3-ylmethylamine hydrochloride (0.51 g, 3.7 mmol) and 1-hydroxybenzotriazole (0.05 g, 0.37 mmol) were added to a chloroform solution, and 1-ethyl-3-(3-dimethylaminopropyl) carbodiimide hydrochloride (0.71 g, 3.7 mmol) was further added to the mixture at room temperature. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.16 g of N-(tetrahydrofuran-3-ylmethyl)-5-[3-(3-quinolyl)propyl]isoxazole-3-carboxamide (hereinafter, referred to as Compound of Present Invention (243)) represented by the following formula.

(243)

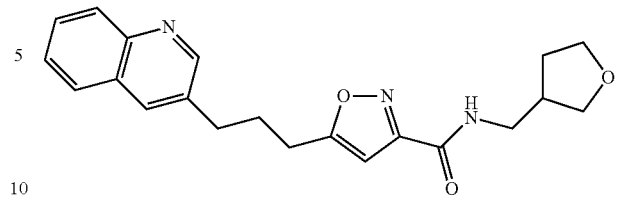

¹H-NMR (CDCl₃, TMS, δ(ppm)): 1.65-1.72(1H, m), 2.06-2.14(1H, m), 2.19(2H, dd), 2.54-2.61(1H, m), 2.88-2.90(4H, m), 3.46(2H, t), 3.58-3.60(1H, m), 3.74-3.80(1H, m), 3.84-3.95(2H, m), 6.50(1H, s), 6.93(1H, s), 7.54-7.56 (1H, m), 7.67-7.71(1H, m), 7.79(1H, d), 7.95(1H, d), 8.10 (1H, d), 8.79(1H, d)

Production Example 235

4-Chloro-3-(2-naphthylmethoxymethyl)-1-methyl-1H-pyrazole-5-carboxylic acid (0.72 g, 2.2 mmol), tetrahydrofuran-3-ylmethylamine hydrochloride (0.36 g, 2.6 mmol), triethylamine (0.27 g, 2.6 mmol) and 1-hydroxybenzotriazole (0.04 g, 0.26 mmol) were added to chloroform (amylene addition product) (5.4 mL). 1-Ethyl-3-(3-dimethylaminopropyl) carbodiimide hydrochloride (0.50 g, 2.6 mmol) was added to the mixture at room temperature, and the mixture was stirred overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain N-(tetrahydrofuran-3-ylmethyl)-4-chloro-3-(2-naphthylmethoxymethyl)-1-methyl-1H-pyrazole-5-carboxamide (hereinafter, referred to as Compound of Present Invention (244)) in the following formula.

(244)

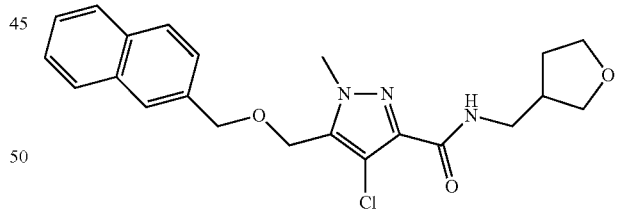

¹H-NMR (CDCl₃, TMS, δ(ppm)): 1.64-1.72(1H, m), 2.01-2.08(1H, m), 2.55-2.61(1H, m), 3.36-3.49(2H, m), 3.59 (1H, dd), 3.77(1H, q), 3.83-3.94(5H, dd), 4.59(2H, s), 4.65 (2H, s), 6.89(1H, br.s), 7.41-7.44(1H, m), 7.47-7.51(2H, m), 7.77-7.85(4H, m)

Production Example 236

Tetrahydrofuran-3-ylmethylamine hydrochloride (1.32 g, 9.6 mmol) and triethylamine (1.34 mL, 9.6 mmol) were added to chloroform (amylene addition product) (20 mL), and the mixture was stirred at room temperature for 30 minutes. 5-[3-(2-Fluorophenyl)propyl]isoxazole-3-carboxylic acid (2.0 g, 8.0 mmol), 1-hydroxybenzotriazole (0.1 g, 0.8 mmol) and 1-ethyl-3-(3-dimethylaminopropyl) carbodiimide hydrochloride (1.8 g, 9.6 mmol) were added to the mixture at room temperature, and the mixture was stirred overnight. Then, dilute hydrochloric acid was added thereto, and the mixture was extracted twice with chloroform. The organic layer was washed with a saturated aqueous sodium bicarbonate solution and saturated saline water, and concentrated under reduced pressure. The residue was applied to a silica gel column chromatography to obtain 1.94 g of N-(tetrahydrofuran-3-ylmethyl)-5-[3-(2-fluorophenyl)propyl]isoxazole-3-carboxamide (hereinafter, referred to as Compound of Present Invention (245)) represented by the following formula.

(245)

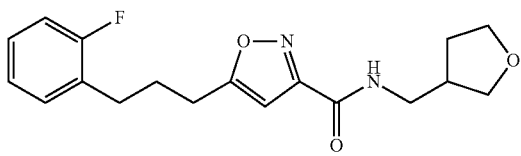

¹H-NMR (CDCl₃, TMS, δ(ppm)): 1.63-1.72(1H, m), 2.01-2.12(3H, m), 2.52-2.63(1H, m), 2.71-2.75(2H, m), 2.80-2.84(2H, m), 3.44-3.47(2H, m), 3.57-3.60(1H, m), 3.73-3.79(1H, m), 3.84-3.94(2H, m), 6.47(1H, s), 6.98(1H, brs), 7.00-7.09(2H, m), 7.16-7.22(2H, m)

Production Example 237

5-[3-(3,4-dichlorophenyl)propyl]isoxazole-3-carboxylic acid (0.60 g, 2.0 mmol), tetrahydrofuran-3-ylmethylamine hydrochloride (0.41 g, 3.0 mmol), triethylamine (0.30 g, 3.0 mmol) and 1-hydroxybenzotriazole (0.03 g, 0.2 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.33 g of N-(tetrahydrofuran-3-ylmethyl)-5-[3-(3,4-dichlorophenyl)propyl]isoxazole-3-carboxamide (hereinafter, referred to as Compound of Present Invention (246)) represented by the following formula.

(246)

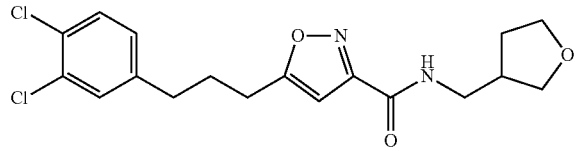

¹H-NMR (CDCl₃, TMS, δ(ppm)): 1.62-1.73(1H, m), 2.05-2.14(3H, m), 2.52-2.62(1H, m), 2.65(2H, t), 2.81(2H, t), 3.46(2H, t), 3.59(1H, dd), 3.73-3.80(1H, m), 3.83-3.95(2H, m), 6.46(1H, s), 6.92(1H, br s), 7.01(1H, dd), 7.26-7.29(1H, m), 7.36(1H, d)

Production Example 238

5-[3-(6-Methoxy-2-naphthyl)propyl]isoxazole-3-carboxylic acid (0.62 g, 2.0 mmol), tetrahydrofuran-3-ylmethylamine hydrochloride (0.41 g, 3.0 mmol), triethylamine (0.30 g, 3.0 mmol) and 1-hydroxybenzotriazole (0.03 g, 0.2 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.48 g of N-(tetrahydrofuran-3-ylmethyl)-5-[3-(6-methoxy-2-naphthyl)propyl]isoxazole-3-carboxamide (hereinafter, referred to as Compound of Present Invention (247)) represented by the following formula.

(247)

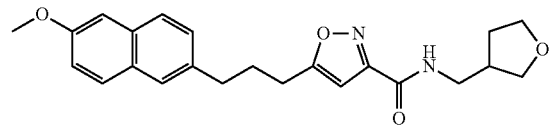

¹H-NMR (CDCl₃, TMS, δ(ppm)): 1.61-1.72(1H, m), 2.01-2.17(3H, m), 2.50-2.63(1H, m), 2.82(4H, t), 3.45(2H, t), 3.59(1H, dd), 3.73-3.80(1H, m), 3.83-3.95(2H, m), 3.92 (3H, s), 6.47(1H, s), 6.93(1H, br s), 7.10-7.16(2H, m), 7.26-7.30(1H, m), 7.54(1H, s), 7.66-7.71(2H, m)

Production Example 239

Tetrahydrofuran-3-ylmethylamine hydrochloride (0.65 g, 4.70 mmol) and triethylamine (0.48 g, 4.70 mmol) were added to chloroform (amylene addition product) (20 mL). 5-(3-Bromopropyl)isoxazole-3-carboxylic acid (1.00 g, 4.27 mmol), 1-hydroxybenzotriazole (0.06 g, 0.43 mmol) and 1-ethyl-3-(3-dimethylaminopropyl) carbodiimide hydrochloride (0.98 g, 5.13 mmol) were added to the mixture at room temperature, and the mixture was stirred overnight. Then, dilute hydrochloric acid was added thereto, and the mixture was extracted twice with chloroform. The organic layer was washed with a saturated aqueous sodium bicarbonate solution, dried over anhydrous magnesium sulfate, and then concentrated under reduced pressure. The residue was applied to a silica gel column chromatography to obtain 0.91 g of N-(tetrahydrofuran-3-ylmethyl)-5-(3-bromopropyl)isoxazole-3-carboxamide (hereinafter, referred to as Compound of Present Invention (248)) represented by the following formula.

(248)

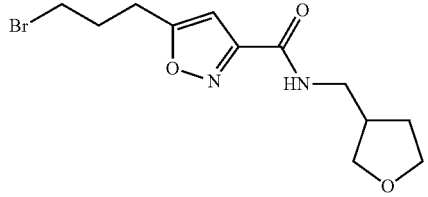

¹H-NMR (CDCl₃, TMS, δ(ppm)): 1.63-1.72(1H, m), 2.04-2.13(1H, m), 2.24-2.30(2H, m), 2.52-2.63(1H, m), 2.99-3.03(2H, t), 3.45-3.48(4H, m), 3.57-3.61(1H, m), 3.74-3.79(1H, m), 3.84-3.94(2H, m), 6.51(1H, s), 6.93(1H, br s)

Production Example 240

Potassium carbonate (0.2 g, 1.44 mmol) was added to a methanol (10 mL) solution of N-(tetrahydrofuran-3-ylmethyl)-5-(2-fluorobenzyloxymethyl)-4-trimethylsilanylethynyl isoxazole-3-carboxamide (0.29 g, 0.67 mmol). The mixture was stirred at room temperature for 1 hour and poured into 1 mol/L hydrochloric acid, and the mixture was extracted twice with ethyl acetate. The organic layer was washed with saturated saline water, dried over anhydrous magnesium sulfate, and then concentrated under reduced pressure. The resulting solid was washed with hexane, and the washed solid was collected by suction filtration to obtain 0.20 g of N-(tetrahydrofuran-3-ylmethyl)-5-(2-fluorobenzyloxymethyl)-4-ethynylisoxazole-3-carboxamide (hereinafter, referred to as Compound of Present Invention (249)) represented by the following formula.

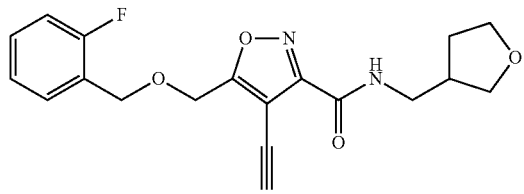

(249)

¹H-NMR (CDCl₃, TMS, δ(ppm)): 1.64-1.72(m, 1H), 2.04-2.13(m, 1H), 2.56-2.63(m, 1H), 3.39(s, 1H), 3.42-3.53 (m, 2H), 3.57-3.61(m, 1H), 3.73-3.79(m, 1H), 3.83-3.94(m, 2H), 4.69(s, 2H), 4.76(s, 2H), 6.90(brs, 1H), 7.04-7.09(m, 1H), 7.13-7.17(m, 1H), 7.28-7.34(m, 1H), 7.41-7.45(m, 1H)

Production Example 241

Potassium carbonate (0.22 g, 1.59 mmol) was added to a methanol (10 mL) solution of N-(tetrahydrofuran-3-ylmethyl)-5-(2-naphthylmethoxymethyl)-4-trimethylsilanylethynyl isoxazole-3-carboxamide (0.35 g, 0.76 mmol). The mixture was stirred at room temperature for 1 hour and poured into 1 mol/L hydrochloric acid, and the mixture was extracted twice with ethyl acetate. The organic layer was washed with saturated saline water, dried over anhydrous magnesium sulfate, and then concentrated under reduced pressure. The resulting solid was washed with hexane, and the washed solid was collected by suction filtration to obtain 0.20 g of N-(tetrahydrofuran-3-ylmethyl)-5-(2-naphthylmethoxymethyl)-4-ethynylisoxazole-3-carboxamide (hereinafter, referred to as Compound of Present Invention (250)) represented by the following formula.

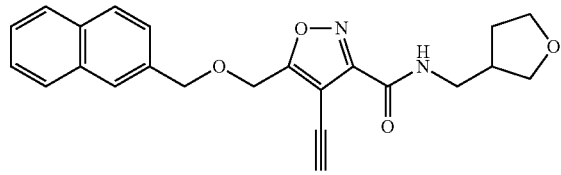

(250)

¹H-NMR (CDCl₃, TMS, δ(ppm)): 1.63-1.72(m, 1H), 2.04-2.12(m, 1H), 2.56-2.63(m, 1H), 3.37(s, 1H), 3.41-3.52 (m, 2H), 3.57-3.61(m, 1H), 3.73-3.79(m, 1H), 3.83-3.94(m, 2H), 4.75(s, 2H), 4.78(s, 2H), 6.87(brs, 1H), 7.47-7.52(m, 3H), 7.82-7.86(m, 4H)

Production Example 242

5-[3-(3-Fluorophenyl)propyl]isoxazole-3-carboxylic acid (0.25 g, 1.0 mmol), tetrahydrofuran-3-ylmethylamine hydrochloride (0.21 g, 1.5 mmol), triethylamine (0.15 g, 1.5 mmol) and 1-hydroxybenzotriazole (0.01 g, 0.1 mmol) were added to chloroform (amylene addition product) (2.5 mL). 1-Ethyl-3-(3-dimethylaminopropyl) carbodiimide hydrochloride (0.23 g, 1.2 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.22 g of N-(tetrahydrofuran-3-ylmethyl)-5-[3-(3-fluorophenyl)propyl]isoxazole-3-carboxamide (hereinafter, referred to as Compound of Present Invention (251)) represented by the following formula.

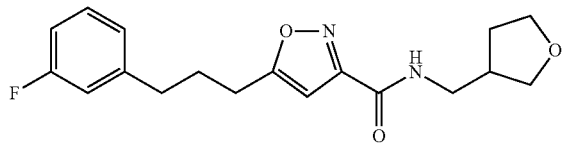

(251)

¹H-NMR (CDCl₃, TMS, δ(ppm)): 1.63-1.73(1H, m), 2.00-2.13(3H, m), 2.52-2.62(1H, m), 2.69(2H, t), 2.81(2H, t), 3.46(2H, t), 3.59(1H, dd), 3.73-3.80(1H, m), 3.83-3.95 (2H, m), 6.46(1H, s), 6.85-6.98(4H, m), 7.22-7.29(1H, m)

Production Example 243

5-[3-(4-Chlorophenyl)propyl]isoxazole-3-carboxylic acid (0.78 g, 2.9 mmol), tetrahydrofuran-3-ylmethyl amine hydrochloride (0.60 g, 4.4 mmol), triethylamine (0.44 g, 4.4 mmol) and 1-hydroxybenzotriazole (0.04 g, 0.3 mmol) were added to a mixed solvent of chloroform (amylene addition product) (4 mL) and tetrahydrofuran (4 mL). 1-Ethyl-3-(3-dimethylaminopropyl) carbodiimide hydrochloride (0.67 g, 3.5 mmol) was added to the mixture at room temperature, and the mixture was stirred at room temperature overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.78 g of N-(tetrahydrofuran-3-ylmethyl)-5-[3-(4-chlorophenyl]propyl)isoxazole-3-carboxamide (hereinafter, referred to as Compound of Present Invention (252)) represented by the following formula.

(252)

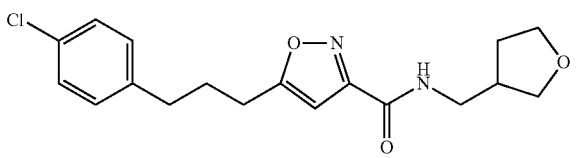

¹H-NMR (CDCl₃, TMS, δ(ppm)): 1.62-1.73(1H, m), 1.99-2.15(3H, m), 2.53-2.63(1H, m), 2.66(2H, t), 2.80(2H, t), 3.46(2H, t), 3.59(1H, dd), 3.73-3.80(1H, m), 3.83-3.95 (2H, m), 6.46(1H, s), 6.92(1H, br s), 7.11(2H, d), 7.27(2H, d)

Production Example 244

Tetrahydrofuran-3-ylmethylamine hydrochloride (1.00 g, 7.26 mmol) and a 1 mol/L aqueous sodium hydroxide solution (16 mL) were simultaneously added at room temperature to the ethyl acetate solution (30 mL) of 5-[2-naphthylmethy)thiomethyl]isoxazole-3-carboxylic acid chloride (<3.67 mmol) obtained in Reference Production Example 197. After vigorously stirring the mixture at room temperature for 1 hour, a 1 mol/L aqueous sodium hydroxide solution was added to the mixture. The fractionated organic layer was sequentially washed with water and saturated saline water, dried over anhydrous magnesium sulfate, and then concentrated under reduced pressure. The residue was applied to a silica gel column chromatography to obtain 480 mg of N-(tetrahydrofuran-3-ylmethyl)-5-[2-naphthylmethyl)thiomethyl]isoxazole-3-carboxamide (hereinafter, referred to as Compound of Present Invention (253)) represented by the following formula.

(253)

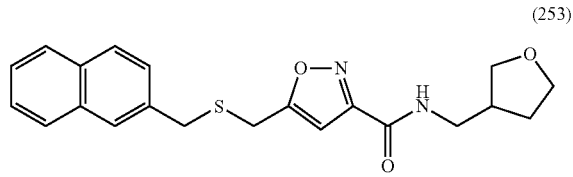 [SMILES: O=C(NCC1CCOC1)c1cc(CSCc2ccc3ccccc3c2)on1]

¹H-NMR (CDCl₃, TMS, δ(ppm)): 1.63-1.75(1H, m), 2.04-2.15(1H, m), 2.52-2.62(1H, m), 3.42-3.50(2H, m), 3.57-3.67(3H, m), 3.73-3.98(5H, m), 6.59(1H, s), 6.89(1H, br s), 7.45-7.56(3H, m), 7.69(1H, s), 7.79-7.88(3H, m)

Production Example 245

5-Benzylthiomethylisoxazole-3-carboxylic acid (510 mg, 2.05 mmol) was added to chloroform (amylene addition product) (5 mL). Triethylamine (0.86 mL, 6.14 mmol), 1-ethyl-3-(3-dimethylaminopropyl) carbodiimide hydrochloride (451 mg, 2.36 mmol), 1-hydroxybenzotriazole (28 mg, 0.21 mmol) and tetrahydrofuran-3-ylmethylamine hydrochloride (366 mg, 2.66 mmol) were added to the mixture, and the mixture was stirred at room temperature for 11 hours. Then, water was added thereto, and the mixture was extracted twice with ethyl acetate. The organic layer was sequentially washed with 1 mol/L hydrochloric acid, an aqueous sodium bicarbonate solution and saturated saline water and dried over anhydrous sodium sulfate, and then concentrated under reduced pressure. The residue was applied to a silica gel column chromatography to obtain 360 mg of N-(tetrahydrofuran-3-ylmethyl)-5-benzylthiomethyl-isoxazole-3-carboxamide (hereinafter, referred to as Compound of Present Invention (254)) represented by the following formula.

(254)

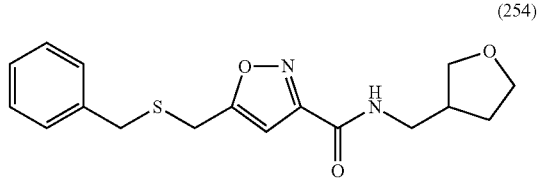

¹H-NMR (CDCl₃, TMS, δ(ppm)): 1.64-1.73(1H, m), 2.05-2.15(1H, m), 2.54-2.63(1H, m), 3.45-3.50(2H, m), 3.60 (1H, dd), 3.64(2H, s), 3.74(2H, s), 3.76-3.81(1H, m), 3.84-3.96(2H, m), 6.57(1H, s), 6.95(1H, s) 7.27-7.37(5H, m)

Production Example 246

A 1.6 mol/L-n-butyllithium hexane solution (1.9 mL, 3.00 mmol) was added dropwise to a tetrahydrofuran (6 mL) solution of N-(tetrahydrofuran-3-ylmethyl)-5-(2-naphthyl-methoxymethyl)isoxazole-3-carboxamide (0.5 g, 1.36 mmol) at −65° C. or less under a nitrogen atmosphere. After stirring at −60° C. or less for 1 hour, a tetrahydrofuran (4 mL) solution of N-fluorobenzenesulfonimide (1.29 g, 4.09 mmol) was added thereto, and the mixture was stirred overnight while slowly returning to room temperature. The reaction mixture was poured into 1 mol/L hydrochloric acid under ice cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.08 g of N-(tetrahydrofuran-3-ylmethyl)-5-(2-naphthyl-methoxymethyl)-4-fluoroisoxazole-3-carboxamide (hereinafter, referred to as Compound of Present Invention (255)) represented by the following formula.

(255)

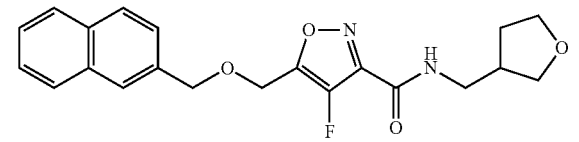

¹H-NMR (CDCl₃, TMS, δ(ppm)): 1.63-1.71(m, 1H), 2.03-2.12(m, 1H), 2.54-2.61(m, 1H), 3.42-3.50(m, 2H), 3.57-3.61(m, 1H), 3.73-3.79(m, 1H), 3.82-3.94(m, 2H), 4.68 (s, 2H), 4.75(s, 2H), 6.86(brs, 1H), 7.45-7.51(m, 3H), 7.79-7.86(m, 4H)

Production Example 247

A 1.6 mol/L-n-butyllithium hexane solution (1.9 mL, 3.00 mmol) was added dropwise to a tetrahydrofuran (6 mL) solution of N-(tetrahydrofuran-3-ylmethyl)-5-(2-naphthyl-methoxymethyl)isoxazole-3-carboxamide (0.5 g, 1.36 mmol) at −65° C. or less under a nitrogen atmosphere. After stirring at −60° C. or less for 1 hour, a tetrahydrofuran (1 mL) solution of bromotrichloromethane (0.40 mL, 4.09 mmol) was added thereto, and the mixture was stirred at −65° C. to −60° C. for 3 hours. The reaction mixture was poured into 1 mol/L hydrochloric acid under ice cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.36 g of N-(tetrahydrofuran-3-ylmethyl)-5-(2-naphthylmethoxymethyl)-4-bromoisoxazole-3-carboxamide (hereinafter, referred to as Compound of Present Invention (256)) represented by the following formula.

(256)

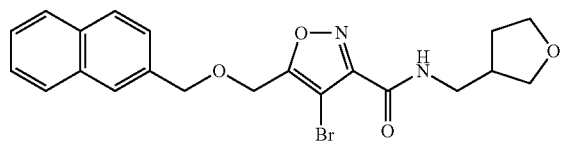

$^1$H-NMR (CDCl$_3$, TMS, δ(ppm)): 1.65-1.71(m, 1H), 2.04-2.13(m, 1H), 2.55-2.61(m, 1H), 3.40-3.51(m, 2H), 3.57-3.61(m, 1H), 3.73-3.79(m, 1H), 3.83-3.94(m, 2H), 4.70 (s, 2H), 4.76(s, 2H), 6.87(brs, 1H), 7.47-7.51(m, 3H), 7.81-7.86(m, 4H)

Production Example 248

5-(3-Fluoro-2-naphthylmethoxymethyl)isoxazole-3-carboxylic acid (0.48 g, 1.6 mmol), tetrahydrofuran-3-ylmethylamine hydrochloride (0.83 g, 6.0 mmol), triethylamine (0.61 g, 6.0 mmol) and 1-hydroxybenzotriazole (0.06 g, 0.4 mmol) were added to a mixed solvent of chloroform (amylene addition product) (4 mL) and tetrahydrofuran (4 mL). 1-Ethyl-3-(3-dimethylaminopropyl) carbodiimide hydrochloride (0.92 g, 4.8 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.06 g of N-(tetrahydrofuran-3-ylmethyl)-5-(3-fluoro-2-naphthylmethoxymethyl)isoxazole-3-carboxamide (hereinafter, referred to as Compound of Present Invention (257)) represented by the following formula.

(257)

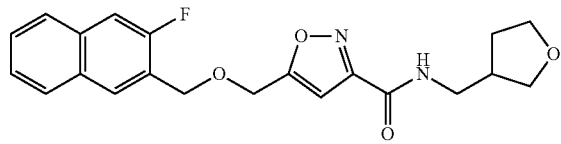

$^1$H-NMR (CDCl$_3$, TMS, δ(ppm)): 1.62-1.73(1H, m), 2.05-2.13(1H, m), 2.52-2.64(1H, m), 3.47(2H, t), 3.59(1H, dd), 3.73-3.80(1H, m), 3.83-3.95(2H, m), 4.76(2H, s), 4.83 (2H, s), 6.78(1H, s), 6.95(1H, br s), 7.43-7.55(3H, m), 7.76-7.90(3H, m)

Production Example 249

5-(1-Fluoro-2-naphthylmethoxymethyl)isoxazole-3-carboxylic acid (0.59 g, 1.5 mmol), tetrahydrofuran-3-ylmethylamine hydrochloride (0.83 g, 6.0 mmol), triethylamine (0.61 g, 6.0 mmol) and 1-hydroxybenzotriazole (0.06 g, 0.4 mmol) were added to a mixed solvent of chloroform (amylene addition product) (4 mL) and tetrahydrofuran (4 mL). 1-Ethyl-3-(3-dimethylaminopropyl) carbodiimide hydrochloride (0.92 g, 4.8 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.07 g of N-(tetrahydrofuran-3-ylmethyl)-5-(1-fluoro-2-naphthylmethoxymethyl)isoxazole-3-carboxamide (hereinafter, referred to as Compound of Present Invention (258)) represented by the following formula.

(258)

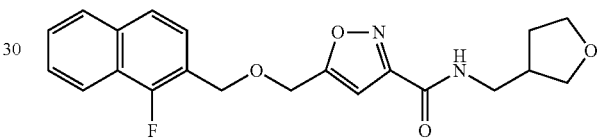

$^1$H-NMR (CDCl$_3$, TMS, δ(ppm)): 1.60-1.73(1H, m), 2.03-2.14(1H, m), 2.52-2.63(1H, m), 3.46(2H, t), 3.59(1H, dd), 3.73-3.80(1H, m), 3.83-3.95(2H, m), 4.69(2H, s), 4.86 (2H, s), 6.76(1H, s), 6.93(1H, br s), 7.46-7.52(1H, m), 7.52-7.59(2H, m), 7.66(1H, d), 7.81-7.88(1H, m), 8.07-8.14 (1H, m)

Production Example 250

5-(2,5-Difluorobenzyloxymethyl)isoxazole-3-carboxylic acid (0.54 g, 2.0 mmol), tetrahydrofuran-3-ylmethylamine hydrochloride (0.41 g, 3.0 mmol), triethylamine (0.30 g, 3.0 mmol) and 1-hydroxybenzotriazole (0.03 g, 0.2 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.17 g of N-(tetrahydrofuran-3-ylmethyl)-5-(2,5-difluorobenzyloxymethyl)isoxazole-3-carboxamide (hereinafter, referred to as Compound of Present Invention (259)) represented by the following formula.

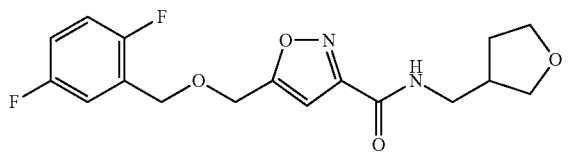

(259)

¹H-NMR (CDCl₃, TMS, δ(ppm)): 1.63-1.73(1H, m), 2.05-2.14(1H, m), 2.53-2.64(1H, m), 3.47(2H, t), 3.59(1H, dd), 3.73-3.80(1H, m), 3.83-3.95(2H, m), 4.65(2H, s), 4.71 (2H, s), 6.76(1H, s), 6.95(1H, br s), 6.95-7.06(2H, m), 7.12-7.17(1H, m)

Production Example 251

5-(4-Chloro-2-fluorobenzyloxymethyl)isoxazole-3-carboxylic acid (1.30 g, 4.6 mmol), tetrahydrofuran-3-ylmethylamine hydrochloride (0.94 g, 6.8 mmol), triethylamine (0.95 mL, 6.8 mmol) and 1-hydroxybenzotriazole (0.06 g, 0.5 mmol) were added to chloroform (amylene addition product) (10 mL). 1-Ethyl-3-(3-dimethylaminopropyl) carbodiimide hydrochloride (1.05 g, 5.5 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.85 g of N-(tetrahydrofuran-3-ylmethyl)-5-(4-chloro-2-fluorobenzyloxymethyl)isoxazole-3-carboxamide (hereinafter, referred to as Compound of Present Invention (260)) represented by the following formula.

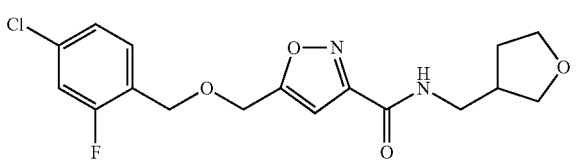

(260)

¹H-NMR (CDCl₃, TMS, δ(ppm)): 1.62-1.72(1H, m), 2.05-2.14(1H, m), 2.52-2.63(1H, m), 3.47(2H, t), 3.59(1H, dd), 3.73-3.80(1H, m), 3.83-3.95(2H, m), 4.63(2H, s), 4.68 (2H, s), 6.74(1H, s), 6.94(1H, br s), 7.10(1H, dd), 7.16(1H, dd), 7.36(1H, t)

Production Example 252

5-(3-Chloro-4-fluorobenzyloxymethyl)isoxazole-3-carboxylic acid (2.55 g, 8.9 mmol), tetrahydrofuran-3-ylmethylamine hydrochloride (1.84 g, 13.4 mmol), triethylamine (1.87 mL, 13.4 mmol) and 1-hydroxybenzotriazole (0.12 g, 0.9 mmol) were added to chloroform (amylene addition product) (20 mL). 1-Ethyl-3-(3-dimethylaminopropyl) carbodiimide hydrochloride (2.05 g, 10.7 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.29 g of N-(tetrahydrofuran-3-ylmethyl)-5-(3-chloro-4-fluorobenzyloxymethyl)isoxazole-3-carboxamide (hereinafter, referred to as Compound of Present Invention (261)) represented by the following formula.

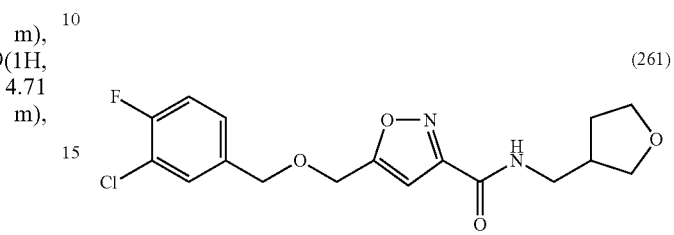

(261)

¹H-NMR (CDCl₃, TMS, δ(ppm)): 1.62-1.73(1H, m), 2.04-2.15(1H, m), 2.53-2.63(1H, m), 3.47(2H, t), 3.59(1H, dd), 3.73-3.80(1H, m), 3.84-3.95(2H, m), 4.54(2H, s), 4.66 (2H, s), 6.73(1H, s), 6.93(1H, br s), 7.13(1H, t), 7.18-7.24 (1H, m), 7.40(1H, dd)

Production Example 253

5-(3,5-Dibromobenzyloxymethyl)isoxazole-3-carboxylic acid (3.25 g, 8.3 mmol), tetrahydrofuran-3-ylmethylamine hydrochloride (1.37 g, 10.0 mmol), triethylamine (1.74 mL, 12.5 mmol) and 1-hydroxybenzotriazole (0.11 g, 0.8 mmol) were added to chloroform (amylene addition product) (20 mL). 1-Ethyl-3-(3-dimethylaminopropyl) carbodiimide hydrochloride (1.91 g, 10.0 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.46 g of N-(tetrahydrofuran-3-ylmethyl)-5-(3,5-dibromobenzyloxymethyl)isoxazole-3-carboxamide (hereinafter, referred to as Compound of Present Invention (262)) represented by the following formula.

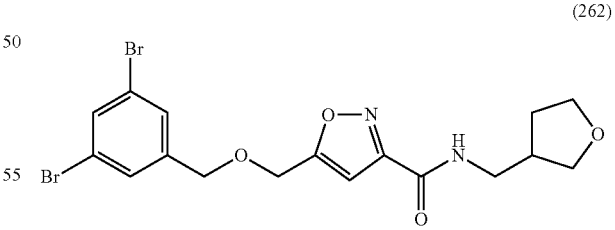

(262)

¹H-NMR (CDCl₃, TMS, δ(ppm)): 1.62-1.73(1H, m), 2.04-2.14(1H, m), 2.53-2.64(1H, m), 3.47(2H, t), 3.59(1H, dd), 3.72-3.81(1H, m), 3.83-3.96(2H, m), 4.54(2H, s), 4.67 (2H, s), 6.74(1H, s), 6.95(1H, br s), 7.42(2H, s), 7.61(1H, s)

Production Example 254

5-(3,4-Difluorobenzyloxymethyl)isoxazole-3-carboxylic acid (0.54 g, 2.0 mmol), tetrahydrofuran-3-ylmethylamine hydrochloride (0.41 g, 3.0 mmol), triethylamine (0.30 g, 3.0 mmol) and 1-hydroxybenzotriazole (0.03 g, 0.2 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.36 g of N-(tetrahydrofuran-3-ylmethyl)-5-(3,4-difluorobenzyloxymethyl)isoxazole-3-carboxamide (hereinafter, referred to as Compound of Present Invention (263)) represented by the following formula.

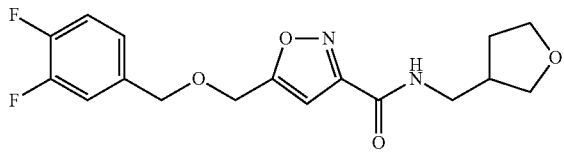

(263)

$^1$H-NMR (CDCl$_3$, TMS, δ(ppm)): 1.62-1.75(1H, m), 2.05-2.14(1H, m), 2.52-2.64(1H, m), 3.47(2H, t), 3.59(1H, dd), 3.73-3.80(1H, m), 3.83-3.95(2H, m), 4.55(2H, s), 4.66 (2H, s), 6.74(1H, s), 6.94(1H, br s), 7.03-7.08(1H, m), 7.11-7.22(2H, m)

Production Example 255

5-(2-Fluorobenzyloxylmethyl)isoxazole-3-carboxylic acid (0.75 g, 3.0 mmol), tetrahydrofuran-3-ylmethyl amine hydrochloride (0.62 g, 4.5 mmol), triethylamine (0.46 g, 4.5 mmol) and 1-hydroxybenzotriazole (0.04 g, 0.3 mmol) were added to chloroform (amylene addition product) (7.5 mL). 1-Ethyl-3-(3-dimethylaminopropyl) carbodiimide hydrochloride (0.69 g, 3.6 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.44 g of N-(tetrahydrofuran-3-ylmethyl)-5-(2-fluorobenzyloxymethyl)isoxazole-3-carboxamide (hereinafter, referred to as Compound of Present Invention (264)) represented by the following formula.

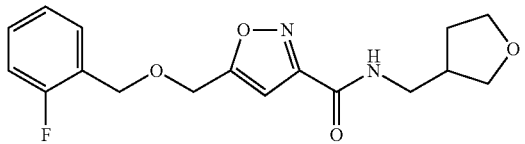

(264)

$^1$H-NMR (CDCl$_3$, TMS, δ(ppm)): 1.62-1.73(1H, m), 2.05-2.14(1H, m), 2.52-2.63(1H, m), 3.47(2H, t), 3.59(1H, dd), 3.73-3.80(1H, m), 3.83-3.95(2H, m), 4.68(2H, s), 4.69 (2H, s), 6.74(1H, s), 6.95(1H, br s), 7.03-7.10(1H, m), 7.13-7.19(1H, m), 7.28-7.35(1H, m), 7.38-7.45(1H, m)

Production Example 256

5-(2-Bromsobenzyloxymethyl)isoxazole-3-carboxylic acid (0.94 g, 3.0 mmol), tetrahydrofuran-3-ylmethylamine hydrochloride (0.62 g, 4.5 mmol), triethylamine (0.46 g, 4.5 mmol) and 1-hydroxybenzotriazole (0.04 g, 0.3 mmol) were added to chloroform (amylene addition product) (7.5 mL). 1-Ethyl-3-(3-dimethylaminopropyl) carbodiimide hydrochloride (0.69 g, 3.6 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.23 g of N-(tetrahydrofuran-3-ylmethyl)-5-(2-bromobenzyloxymethyl)isoxazole-3-carboxamide (hereinafter, referred to as Compound of Present Invention (265)) represented by the following formula.

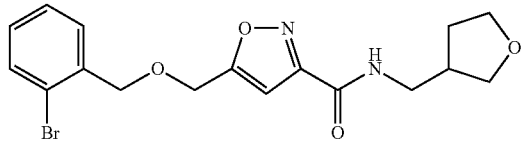

(265)

$^1$H-NMR (CDCl$_3$, TMS, δ(ppm)): 1.62-1.73(1H, m), 2.05-2.14(1H, m), 2.53-2.63(1H, m), 3.47(2H, t), 3.59(1H, dd), 3.73-3.80(1H, m), 3.83-3.95(2H, m), 4.69(2H, s), 4.74 (2H, s), 6.77(1H, s), 6.95(1H, br s), 7.18(1H, dt), 7.34(1H, dt), 7.47(1H, dd), 7.56(1H, dd)

Production Example 257

5-(3,5-Difluorobenzyloxymethyl)isoxazole-3-carboxylic acid (1.35 g, 5.0 mmol), tetrahydrofuran-3-ylmethylamine hydrochloride (1.03 g, 7.5 mmol), triethylamine (0.76 g, 7.5 mmol) and 1-hydroxybenzotriazole (0.07 g, 0.5 mmol) were added to chloroform (amylene addition product) (12.5 mL). 1-Ethyl-3-(3-dimethylaminopropyl) carbodiimide hydrochloride (1.15 g, 6.0 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.26 g of N-(tetrahydrofuran-3-ylmethyl)-5-(3,5-difluorobenzyloxymethyl)isoxazole-3-carboxamide (hereinafter, referred to as Compound of Present Invention (266)) represented by the following formula.

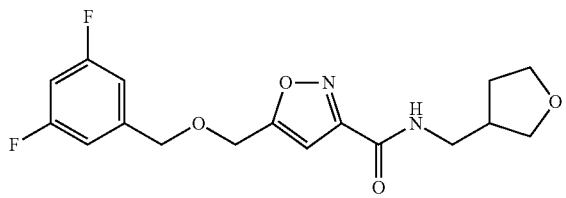

(266)

¹H-NMR (CDCl₃, TMS, δ(ppm)): 1.62-1.74(1H, m), 2.06-2.14(1H, m), 2.53-2.64(1H, m), 3.47(2H, t), 3.59(1H, dd), 3.73-3.80(1H, m), 3.83-3.95(2H, m), 4.58(2H, s), 4.68 (2H, s), 6.72-6.79(1H, m), 6.75(1H, s), 6.84-6.91(2H, m), 6.94(1H, br s)

Production Example 258

5-(3,4,5-Trifluorobenzyloxymethyl)isoxazole-3-carboxylic acid (0.86 g, 3.0 mmol), tetrahydrofuran-3-ylmethylamine hydrochloride (0.62 g, 4.5 mmol), triethylamine (0.46 g, 4.5 mmol) and 1-hydroxybenzotriazole (0.04 g, 0.3 mmol) were added to chloroform (amylene addition product) (7.5 mL). 1-Ethyl-3-(3-dimethylaminopropyl) carbodiimide hydrochloride (0.69 g, 3.6 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.25 g of N-(tetrahydrofuran-3-ylmethyl)-5-(3,4,5-trifluorobenzyloxymethyl)isoxazole-3-carboxamide (hereinafter, referred to as Compound of Present Invention (267)) represented by the following formula.

(267)

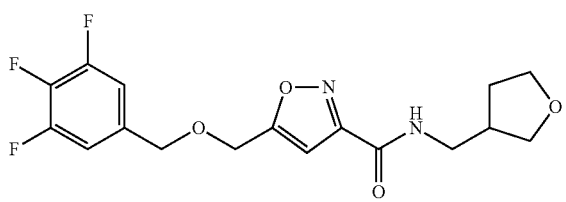

¹H-NMR (CDCl₃, TMS, δ(ppm)): 1.62-1.73(1H, m), 2.04-2.14(1H, m), 2.53-2.64(1H, m), 3.47(2H, t), 3.59(1H, dd), 3.73-3.81(1H, m), 3.83-3.95(2H, m), 4.53(2H, s), 4.68 (2H, s), 6.75(1H, s), 6.93-7.02(2H, m), 6.96(1H, br s)

Production Example 259

5-(3-Chloro-5-fluorobenzyloxymethyl)isoxazole-3-carboxylic acid (1.04 g, 3.6 mmol), tetrahydrofuran-3-ylmethylamine hydrochloride (0.75 g, 5.5 mmol), triethylamine (0.76 mL, 5.5 mmol) and 1-hydroxybenzotriazole (0.05 g, 0.4 mmol) were added to chloroform (amylene addition product) (10 mL). 1-Ethyl-3-(3-dimethylaminopropyl) carbodiimide hydrochloride (0.84 g, 4.4 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.40 g of N-(tetrahydrofuran-3-ylmethyl)-5-(3-chloro-5-fluorobenzyloxymethyl) isoxazole-3-carboxamide (hereinafter, referred to as Compound of Present Invention (268)) represented by the following formula.

(268)

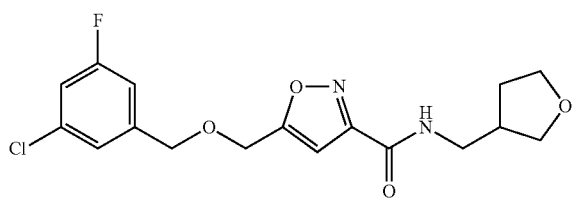

¹H-NMR (CDCl₃, TMS, δ(ppm)): 1.63-1.72(1H, m), 2.07-2.13(1H, m), 2.53-2.63(1H, m), 3.47(2H, t), 3.59(1H, dd), 3.73-3.80(1H, m), 3.84-3.94(2H, m), 4.57(2H, s), 4.68 (2H, s), 6.74(1H, s), 6.93(1H, br s), 6.97(1H, d), 7.04(1H, dt), 7.13(1H, s)

Production Example 260

5-(2,3,5,6-Tetrafluorobenzyloxymethyl)isoxazole-3-carboxylic acid (0.18 g, 0.6 mmol), tetrahydrofuran-3-ylmethylamine hydrochloride (0.21 g, 1.5 mmol), triethylamine (0.15 g, 1.5 mmol) and 1-hydroxybenzotriazole (0.01 g, 0.1 mmol) were added to chloroform (amylene addition product) (2.5 mL). 1-Ethyl-3-(3-dimethylaminopropyl) carbodiimide hydrochloride (0.23 g, 1.2 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.06 g of N-(tetrahydrofuran-3-ylmethyl)-5-(2,3,5,6-tetrafluorobenzyloxymethyl) isoxazole-3-carboxamide (hereinafter, referred to as Compound of Present Invention (269)) represented by the following formula.

(269)

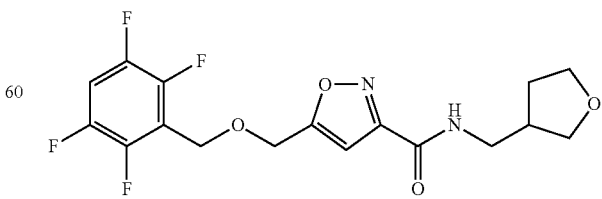

¹H-NMR (CDCl₃, TMS, δ(ppm)): 1.63-1.73(1H, m), 2.05-2.14(1H, m), 2.52-2.63(1H, m), 3.47(2H, t), 3.59(1H, dd), 3.73-3.80(1H, m), 3.83-3.95(2H, m), 4.70(2H, s), 4.72 (2H, dt), 6.76(1H, s), 6.94(1H, br s), 7.04-7.16(1H, m)

Production Example 261

5-(2,3,4-Trifluorobenzyloxymethyl)isoxazole-3-carboxylic acid (0.57 g, 2.0 mmol), tetrahydrofuran-3-ylmethylamine hydrochloride (0.41 g, 3.0 mmol), triethylamine (0.30 g, 3.0 mmol) and 1-hydroxybenzotriazole (0.03 g, 0.2 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred at room temperature overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.24 g of N-(tetrahydrofuran-3-ylmethyl)-5-(2,3,4-trifluorobenzyloxymethyl)isoxazole-3-carboxamide (hereinafter, referred to as Compound of Present Invention (270)) represented by the following formula.

(270)

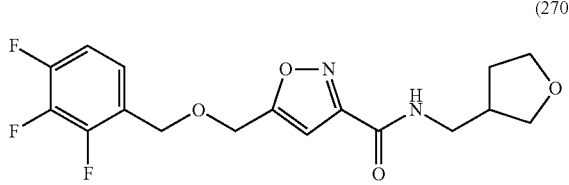

$^1$H-NMR (CDCl$_3$, TMS, δ(ppm)): 1.62-1.73(1H, m), 2.05-2.14(1H, m), 2.52-2.64(1H, m), 3.47(2H, t), 3.59(1H, dd), 3.73-3.80(1H, m), 3.83-3.95(2H, m), 4.64(2H, s), 4.69 (2H, s), 6.75(1H, s), 6.95(1H, br s), 6.95-7.01(1H, m), 7.10-7.18(1H, m)

Production Example 262

5-(3,5-Dimethylbenzyloxymethyl)isoxazole-3-carboxylic acid (1.06 g, 4.1 mmol), tetrahydrofuran-3-ylmethylamine hydrochloride (0.84 g, 6.1 mmol), triethylamine (0.85 mL, 6.1 mmol) and 1-hydroxybenzotriazole (0.05 g, 0.4 mmol) were added to chloroform (amylene addition product) (10 mL). 1-Ethyl-3-(3-dimethylaminopropyl) carbodiimide hydrochloride (0.93 g, 4.9 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.31 g of N-(tetrahydrofuran-3-ylmethyl)-5-(3,5-dimethylbenzyloxymethyl)isoxazole-3-carboxamide (hereinafter, referred to as Compound of Present Invention (271)) represented by the following formula.

(271)

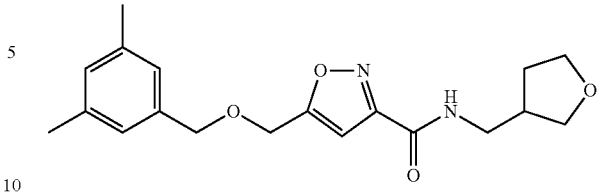

$^1$H-NMR (CDCl$_3$, TMS, δ(ppm)): 1.63-1.72(1H, m), 2.05-2.12(1H, m), 2.32(6H, s), 2.55-2.61(1H, m), 3.47(2H, t), 3.59(1H, dd), 3.73-3.79(1H, m), 3.84-3.94(2H, m), 4.53 (2H, s), 4.63(2H, s), 6.72(1H, s), 6.93(1H, br s), 6.96(3H, s)

Production Example 263

5-(4-Bromo-3-fluorobenzyloxymethyl)isoxazole-3-carboxylic acid (1.42 g, 4.3 mmol), tetrahydrofuran-3-ylmethylamine hydrochloride (0.89 g, 6.5 mmol), triethylamine (0.90 mL, 6.5 mmol) and 1-hydroxybenzotriazole (0.06 g, 0.4 mmol) were added to chloroform (amylene addition product) (10 mL). 1-Ethyl-3-(3-dimethylaminopropyl) carbodiimide hydrochloride (0.99 g, 5.2 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.59 g of N-(tetrahydrofuran-3-ylmethyl)-5-(4-bromo-3-fluorobenzyloxymethyl) isoxazole-3-carboxamide (hereinafter, referred to as Compound of Present Invention (272)) represented by the following formula.

(272)

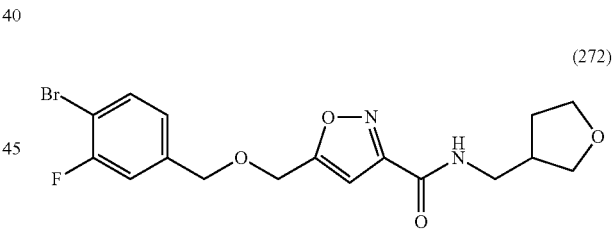

$^1$H-NMR (CDCl$_3$, TMS, δ(ppm)): 1.60-1.75(1H, m), 2.04-2.14(1H, m), 2.52-2.64(1H, m), 3.48(2H, t), 3.59(1H, dd), 3.73-3.80(1H, m), 3.82-3.94(2H, m), 4.56(2H, s), 4.66 (2H, s), 6.73(1H, s), 6.92(1H, br s), 7.01(1H, d), 7.13(1H, d), 7.53(1H, t)

Production Example 264

5-(4-Methyl-2,3,5,6-tetrafluorobenzyloxymethyl)isoxazole-3-carboxylic acid (0.29 g, 0.9 mmol), tetrahydrofuran-3-ylmethylamine hydrochloride (0.21 g, 1.5 mmol), triethylamine (0.15 g, 1.5 mmol) and 1-hydroxybenzotriazole (0.01 g, 0.1 mmol) were added to chloroform (amylene addition product) (2.5 mL). 1-Ethyl-3-(3-dimethylaminopropyl) carbodiimide hydrochloride (0.23 g, 1.2 mmol) was added to the mixture at room temperature, and the mixture was stirred at room temperature overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.06 g of N-(tetrahydrofuran-3-ylmethyl)-5-(4-methyl-2,3,5,6-tetrafluorobenzyloxymethyl)isoxazole-3-carboxamide (hereinafter, referred to as Compound of Present Invention (273)) represented by the following formula.

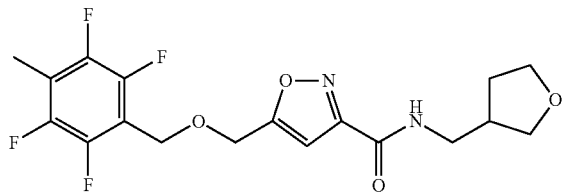

(273)

$^1$H-NMR (CDCl$_3$, TMS, δ(ppm)): 1.63-1.74(1H, m), 2.04-2.15(1H, m), 2.29(3H, s), 2.53-2.65(1H, m), 3.47(2H, t), 3.61(1H, dd), 3.74-3.82(1H, m), 3.84-3.97(2H, m), 4.68 (2H, s), 4.71(2H, s), 6.76(1H, s), 7.01(1H, br s)

Production Example 265

5-(2,3-Difluorobenzyloxymethyl)isoxazole-3-carboxylic acid (0.54 g, 2.0 mmol), tetrahydrofuran-3-ylmethylamine hydrochloride (0.41 g, 3.0 mmol), triethylamine (0.30 g, 3.0 mmol) and 1-hydroxybenzotriazole (0.03 g, 0.2 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.25 g of N-(tetrahydrofuran-3-ylmethyl)-5-(2,3-difluorobenzyloxymethyl)isoxazole-3-carboxamide (hereinafter, referred to as Compound of Present Invention (274)) represented by the following formula.

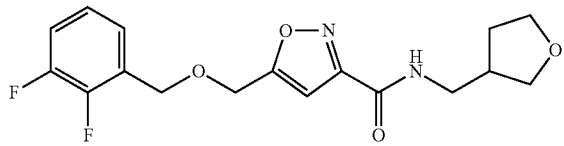

(274)

$^1$H-NMR (CDCl$_3$, TMS, δ(ppm)): 1.63-1.73(1H, m), 2.05-2.15(1H, m), 2.53-2.64(1H, m), 3.47(2H, t), 3.59(1H, dd), 3.73-3.81(1H, m), 3.83-3.96(2H, m), 4.69(2H, s), 4.70 (2H, s), 6.75(1H, s), 6.94(1H, br s), 7.07-7.22(3H, m)

Production Example 266

5-(2,6-Difluorobenzyloxymethyl)isoxazole-3-carboxylic acid (0.54 g, 2.0 mmol), tetrahydrofuran-3-ylmethylamine hydrochloride (0.41 g, 3.0 mmol), triethylamine (0.30 g, 3.0 mmol) and 1-hydroxybenzotriazole (0.03 g, 0.2 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.34 g of N-(tetrahydrofuran-3-ylmethyl)-5-(2,6-difluorobenzyloxymethyl)isoxazole-3-carboxamide (hereinafter, referred to as Compound of Present Invention (275)) represented by the following formula.

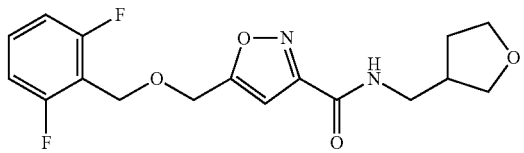

(275)

$^1$H-NMR (CDCl$_3$, TMS, δ(ppm)): 1.62-1.73(1H, m), 2.04-2.14(1H, m), 2.52-2.63(1H, m), 3.46(2H, t), 3.59(1H, dd), 3.73-3.80(1H, m), 3.83-3.95(2H, m), 4.68(2H, s), 4.70 (2H, s), 6.74(1H, s), 6.93(1H, br s), 6.93(2H, t), 7.28-7.3 (1H, m)

Production Example 267

5-(4-Chloro-3-fluorobenzyloxymethyl)isoxazole-3-carboxylic acid (0.54 g, 2.0 mmol), tetrahydrofuran-3-ylmethylamine hydrochloride (0.41 g, 3.0 mmol), triethylamine (0.30 g, 3.0 mmol) and 1-hydroxybenzotriazole (0.03 g, 0.2 mmol) were added to chloroform (amylene addition product) (5 mL). 1-Ethyl-3-(3-dimethylaminopropyl) carbodiimide hydrochloride (0.46 g, 2.4 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.18 g of N-(tetrahydrofuran-3-ylmethyl)-5-(4-chloro-3-fluorobenzyloxymethyl)isoxazole-3-carboxamide (hereinafter, referred to as Compound of Present Invention (276)) represented by the following formula.

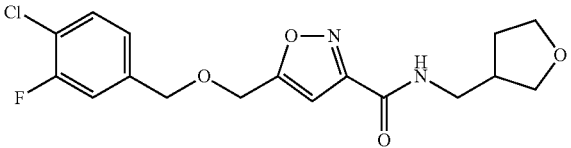

(276)

$^{1}$H-NMR (CDCl$_3$, TMS, δ(ppm)): 1.62-1.74(1H, m), 2.05-2.14(1H, m), 2.52-2.64(1H, m), 3.47(2H, t), 3.59(1H, dd), 3.73-3.80(1H, m), 3.83-3.95(2H, m), 4.57(2H, s), 4.67(2H, s), 6.74(1H, s), 6.94(1H, br s), 7.04-7.08(1H, m), 7.16(1H, dd), 7.38(1H, t)

Production Example 268

5-(3-Fluoro-4-methoxybenzyloxymethyl)isoxazole-3-carboxylic acid (1.10 g, 3.9 mmol), tetrahydrofuran-3-ylmethylamine hydrochloride (0.81 g, 5.9 mmol), triethylamine (0.82 mL, 5.9 mmol) and 1-hydroxybenzotriazole (0.05 g, 0.4 mmol) were added to chloroform (amylene addition product) (10 mL). 1-Ethyl-3-(3-dimethylaminopropyl) carbodiimide hydrochloride (0.90 g, 4.7 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.38 g of N-(tetrahydrofuran-3-ylmethyl)-5-(3-fluoro-4-methoxybenzyloxymethyl)isoxazole-3-carboxamide (hereinafter, referred to as Compound of Present Invention (277)) represented by the following formula.

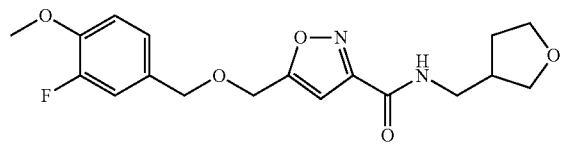

(277)

$^{1}$H-NMR (CDCl$_3$, TMS, δ(ppm)): 1.62-1.73(1H, m), 2.04-2.14(1H, m), 2.52-2.63(1H, m), 3.47(2H, t), 3.59(1H, dd), 3.73-3.80(1H, m), 3.83-3.95(2H, m), 3.89(3H, s), 4.52(2H, s), 4.63(2H, s), 6.72(1H, s), 6.93(1H, br s), 6.94(1H, t), 7.04(1H, d), 7.09(1H, dd)

Production Example 269

5-(2,4-Difluorobenzyloxymethyl)isoxazole-3-carboxylic acid (1.20 g, 4.5 mmol), tetrahydrofuran-3-ylmethylamine hydrochloride (0.92 g, 6.7 mmol), triethylamine (0.93 mL, 6.7 mmol) and 1-hydroxybenzotriazole (0.06 g, 0.4 mmol) were added to chloroform (amylene addition product) (10 mL). 1-Ethyl-3-(3-dimethylaminopropyl) carbodiimide hydrochloride (1.03 g, 5.4 mmol) was added to the mixture at room temperature, and the mixture was stirred overnight and then concentrated under reduced pressure. Dilute hydrochloric acid was added to the residue, and the mixture was extracted three times with ethyl acetate. The organic layer was washed with a saturated aqueous sodium bicarbonate solution and saturated saline water and dried over anhydrous sodium sulfate, and then concentrated under reduced pressure. The residue was applied to a silica gel column chromatography to obtain 0.78 g of N-(tetrahydrofuran-3-ylmethyl)-5-(2,4-difluorobenzyloxymethyl)isoxazole-3-carboxamide (hereinafter, referred to as Compound of Present Invention (278)) represented by the following formula.

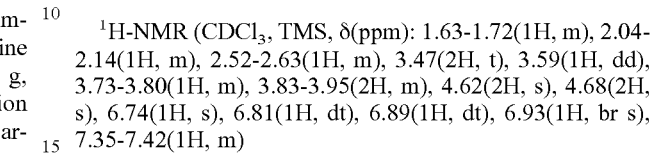

(278)

$^{1}$H-NMR (CDCl$_3$, TMS, δ(ppm): 1.63-1.72(1H, m), 2.04-2.14(1H, m), 2.52-2.63(1H, m), 3.47(2H, t), 3.59(1H, dd), 3.73-3.80(1H, m), 3.83-3.95(2H, m), 4.62(2H, s), 4.68(2H, s), 6.74(1H, s), 6.81(1H, dt), 6.89(1H, dt), 6.93(1H, br s), 7.35-7.42(1H, m)

Production Example 270

A 1.6 mol/L-n-butyllithium hexane solution (7.2 mL, 11.55 mmol) was added dropwise to a tetrahydrofuran (26 mL) solution of N-(tetrahydrofuran-3-ylmethyl)-5-[3-(2-fluorophenyl)propyl]isoxazole-3-carboxamide (1.75 g, 5.25 mmol) at −45° C. or less under a nitrogen atmosphere, and the mixture was stirred at −45° C. to −60° C. for 1 hour. Then, N,N-dimethylformamide (1.2 mL) was added thereto, and the mixture was further stirred at −60° C. to room temperature for 11.5 hours. The reaction mixture was poured into 1 mol/L hydrochloric acid under ice cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.82 g of N-(tetrahydrofuran-3-ylmethyl)-4-formyl-5-[3-(2-fluorophenyl)propyl]isoxazole-3-carboxamide (hereinafter, referred to as Compound of Present Invention (279)) represented by the following formula.

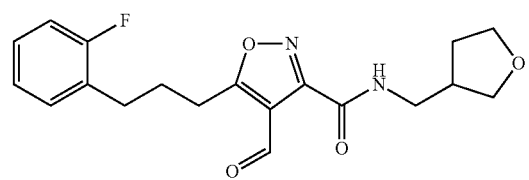

(279)

$^{1}$H-NMR (CDCl$_3$, TMS, δ(ppm)): 1.67-1.73(m, 1H), 2.06-2.16(m, 3H), 2.55-2.66(m, 1H), 2.72-2.76(m, 2H), 3.17-3.21(m, 2H), 3.48-3.51(m, 2H), 3.60-3.63(m, 1H), 3.75-3.79(m, 1H), 3.81-3.96(m, 2H), 6.99-7.08(m, 2H), 7.17-7.22(m, 2H), 10.39(s, 1H)

Production Example 271

Sodium borohydride (0.25 g, 6.55 mmol) was added to a methanol (4.5 mL) solution of N-(tetrahydrofuran-3-ylmethyl)-4-formyl-5-[3-(2-fluorophenyl)propyl]isoxazole-3-carboxamide (0.78 g, 2.18 mmol) under ice cooling. The mixture was stirred for 1.5 hours under ice cooling and then poured into 1 mol/L hydrochloric acid, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.68 g of N-(tetrahydrofuran-3- ylmethyl)-4-hydroxymethyl-5-[3-(2-fluorophenyl)propyl]isoxazole-3-carboxamide (hereinafter, referred to as Compound of Present Invention (280)) represented by the following formula.

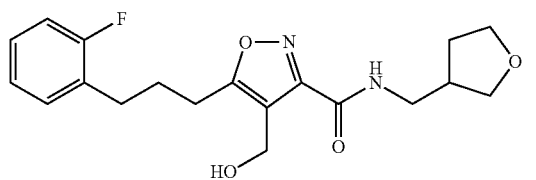

(280)

¹H-NMR (CDCl₃, TMS, δ(ppm)): 1.67-1.71(m, 1H), 2.00-2.13(m, 3H), 2.57-2.61(m, 1H), 2.68-2.72(m, 2H), 2.79-2.82(m, 2H), 3.46-3.49(m, 2H), 3.59-3.62(m, 1H), 3.74-3.80(m, 1H), 3.83-3.86(m, 1H), 3.87-3.95(m, 1H), 4.49-4.50(m, 2H), 4.58-4.62(m, 1H), 7.00-7.09(m, 2H), 7.15-7.22(m, 3H)

Production Example 272

60% Sodium hydride (0.08 g, 2.06 mmol) was added to a tetrahydrofuran (8 mL) solution of N-(tetrahydrofuran-3-ylmethyl)-4-hydroxymethyl-5-[3-(2-fluorophenyl)propyl]isoxazole-3-carboxamide (0.67 g, 1.87 mmol) under ice cooling, and the mixture was stirred for about 30 minutes. Carbon bisulfide (0.28 mL) was added under ice-water cooling, and subsequently, methyl iodide (0.35 mL) was added thereto, and the mixture was diluted with toluene, and concentrated under reduced pressure. Then, the residue was added to 1 mol/L hydrochloric acid, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.67 g of dithiocarboxylic acid 4-O-{5-[3-(2-fluorophenyl)propyl]-3-[3-tetrahydrofurylmethyl)carbamoyl]isoxazoylmethyl}ester S-methyl ester (hereinafter, referred to as Compound of Present Invention (281)) represented by the following formula.

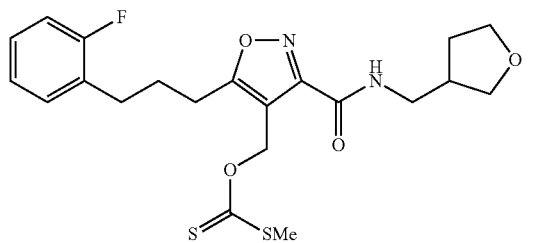

(281)

¹H-NMR (CDCl₃, TMS, δ(ppm)): 1.65-1.71(m, 1H), 2.01-2.13(m, 3H), 2.54(s, 3H), 2.56-2.60(m, 1H), 2.70-2.74(m, 2H), 2.87-2.91(m, 2H), 3.43-3.47(m, 2H), 3.57-3.60(m, 1H), 3.73-3.79(m, 1H), 3.84-3.94(m, 2H), 5.74(s, 2H), 6.93(brs, 1H), 7.02-7.05(m, 1H), 7.07-7.08(m, 1H), 7.16-7.22(m, 2H)

Production Example 273

Tributyltin hydride (0.52 mL, 1.95 mmol) and azobisisobutyronitrile (0.04 g, 0.26 mmol) were added to a toluene (5 mL) solution of dithiocarboxylic acid 4-O-{5-[3-(2-fluorophenyl)propyl]-3-[3-tetrahydrofurylmethyl)carbamoyl]isoxazoylmethyl}ester S-methyl ester (0.59 g, 1.30 mmol). The mixture was stirred at 95° C. to 100° C. for 3 hours, and then concentrated under reduced pressure. The residue was applied to a silica gel column chromatography to obtain 0.30 g of N-(tetrahydrofuran-3-ylmethyl)-4-methyl-5-[3-(2-fluorophenyl)propyl]isoxazole-3-carboxamide (hereinafter, referred to as Compound of Present Invention (282)) represented by the following formula.

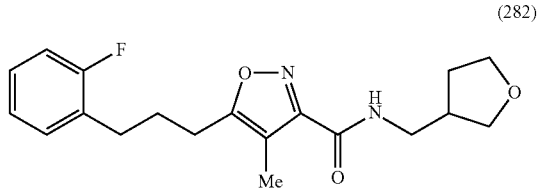 [SMILES: Cc1c(C(=O)NCC2CCOC2)noc1CCCc1ccccc1F]

(282)

¹H-NMR (CDCl₃, TMS, δ(ppm)): 1.63-1.72(m, 1H), 1.99-2.12(m, 3H), 2.15(s, 3H), 2.54-2.61(m, 1H), 2.68-2.71(m, 2H), 2.73-2.77(m, 2H), 3.42-3.46(m, 2H), 3.56-3.60(m, 1H), 3.74-3.79(m, 1H), 3.84-3.94(m, 2H), 6.96(brs, 1H), 7.00-7.08(m, 2H), 7.15-7.22(m, 2H)

Production Example 274

A 1.6 mol/L-n-butyllithium hexane solution (4.9 mL, 7.89 mmol) was added dropwise to a tetrahydrofuran (18 mL) solution of N-(tetrahydrofuran-3-ylmethyl)-5-(2-fluorobenzyloxymethyl)isoxazole-3-carboxamide (1.2 g, 3.58 mmol) at −65° C. or less under a nitrogen atmosphere. After stirring at −60° C. or less for 30 minutes, N,N-dimethylformamide (0.84 mL) was added thereto, and the mixture was further stirred at a temperature of −65° C. to −60° C. for 5 hours. The reaction mixture was poured into 1 mol/L hydrochloric acid under ice cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.53 g of N-(tetrahydrofuran-3-ylmethyl)-5-(2-fluorobenzyloxymethyl)-4-formylisoxazole-3-carboxamide (hereinafter, referred to as Compound of Present Invention (283)) represented by the following formula.

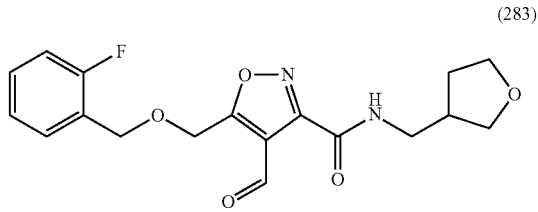 [SMILES: O=Cc1c(C(=O)NCC2CCOC2)noc1COCc1ccccc1F]

(283)

¹H-NMR (CDCl₃, TMS, δ(ppm)): 1.65-1.74(m, 1H), 2.08-2.16(m, 1H), 2.58-2.64(m, 1H), 3.49-3.52(m, 2H), 3.60-3.64(m, 1H), 3.75-3.81(m, 1H), 3.85-3.96(m, 2H), 4.74(s, 2H), 5.01(s, 2H), 7.04-7.09(m, 1H), 7.14-7.17(m, 1H), 7.29-7.44(m, 3H), 10.41(s, 1H)

Production Example 275

Sodium borohydride (0.16 g, 4.14 mmol) was added to a methanol (3 mL) solution of N-(tetrahydrofuran-3-ylmethyl)-5-(2-fluorobenzyloxymethyl)-4-formylisoxazole-3-carboxamide (0.5 g, 1.38 mmol) under ice-water cooling. After stirring for 3 hours under ice-water cooling, the reaction mixture was poured into 1 mol/L hydrochloric acid, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.45 g of N-(tetrahydrofuran-3-ylmethyl)-5-(2-fluorobenzyloxymethyl)-4-hydroxymethylisoxazole-3-carboxamide (hereinafter, referred to as Compound of Present Invention (284)) represented by the following formula.

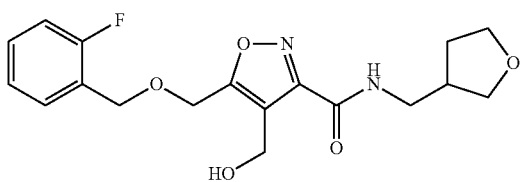

(284)

$^1$H-NMR (CDCl$_3$, TMS, δ(ppm)): 1.64-1.72(m, 1H), 2.06-2.15(m, 1H), 2.56-2.62(m, 1H), 3.46-3.50(m, 2H), 3.59-3.62(m, 1H), 3.74-3.80(m, 1H), 3.83-3.87(m, 1H), 3.90-3.96(m, 1H), 4.58-4.65(m, 5H), 4.69(s, 2H), 7.05-7.09 (m, 1H), 7.14-7.15(m, 1H), 7.17(brs, 1H), 7.22-7.35(m, 1H), 7.38-7.41(m, 1H)

Production Example 276

60% Sodium hydride (0.05 g, 1.34 mmol) was added to a tetrahydrofuran (5 mL) solution of N-(tetrahydrofuran-3-ylmethyl)-5-(2-fluorobenzyloxymethyl)-4-hydroxymethyl-isoxazole-3-carboxamide (0.45 g, 1.2 mmol) under water cooling, and the mixture was stirred for 25 minutes. Carbon bisulfide (0.18 mL) was added under ice-water cooling, and methyl iodide (0.23 mL) was subsequently added thereto. The mixture was stirred for 2 hours under ice-water cooling, and then the reaction mixture was diluted with toluene, and concentrated under reduced pressure. The residue was poured into 1 mol/L hydrochloric acid, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.39 g of dithiocarboxylic acid 4-O-{5-(2-fluorobenzyloxymethyl)-3-[(tetrahydrofuran-3-ylmethyl)carbamoyl]isoxazolylmethyl}ester S-methyl ester (hereinafter, referred to as Compound of Present Invention (285)) represented by the following formula.

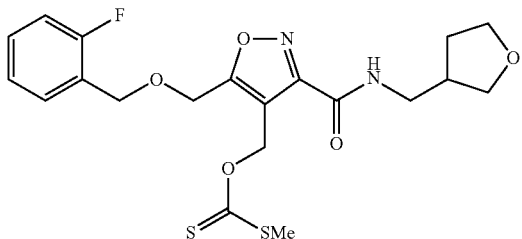

(285)

$^1$H-NMR (CDCl$_3$, TMS, δ(ppm)): 1.63-1.71(m, 1H), 2.06-2.13(m, 1H), 2.53(s, 3H), 2.56-2.61(m, 1H), 3.44-3.47 (m, 2H), 3.57-3.61(m, 1H), 3.74-3.79(m, 1H), 3.83-3.94(m, 2H), 4.67(s, 2H), 4.78(s, 2H), 5.82(s, 2H), 6.98(brs, 1H), 7.03-7.08(m, 1H), 7.12-7.16(m, 1H), 7.28-7.33(m, 1H), 7.38-7.42(m, 1H)

Production Example 277

Tributyltin hydride (0.32 mL, 1.22 mmol) and azobisisobutyronitrile (0.03 g, 0.16 mmol) were added to a toluene (3 mL) solution of dithiocarboxylic acid 4-O-{5-(2-fluorobenzyloxymethyl)-3-[(tetrahydrofuran-3-ylmethyl)carbamoyl]isoxazolylmethyl}ester S-methyl eater (0.37 g, 0.81 mmol). The mixture was stirred at 95° C. to 100° C. for 2 hours, and then concentrated under reduced pressure. The residue was applied to a silica gel column chromatography to obtain 0.22 g of N-(tetrahydrofuran-3-ylmethyl)-5-(2-fluorobenzyloxymethyl)-4-methylisoxazole-3-carboxamide (hereinafter, referred to as Compound of Present Invention (286)) represented by the following formula.

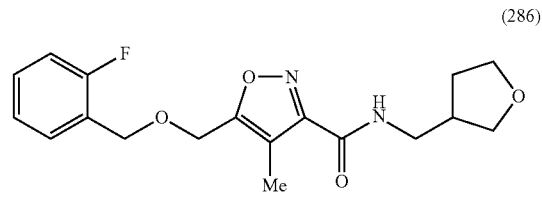 [SMILES: Cc1c(C(=O)NCC2CCOC2)noc1COCc1ccccc1F]

(286)

$^1$H-NMR (CDCl$_3$, TMS, δ(ppm)): 1.63-1.72(m, 1H), 2.04-2.13(m, 1H), 2.25(s, 3H), 2.54-2.61(m, 1H), 3.43-3.46 (m, 2H), 3.57-3.60(m, 1H), 3.74-3.80(m, 1H), 3.84-3.94(m, 2H), 4.63(s, 4H), 7.00(brs, 1H), 7.04-7.09(m, 1H), 7.13-7.17 (m, 1H), 7.28-7.34(m, 1H), 7.38-7.42(m, 1H)

Production Example 278

A 2.6 mol/L-n-butyllithium hexane solution (5.2 mL, 13.4 mmol) was added dropwise to a tetrahydrofuran (30 mL) solution of N-(tetrahydrofuran-3-ylmethyl)-5-[3-(2-naphthyl)propyl]isoxazole-3-carboxamide (2.22 g, 6.09 mmol) at −60° C. or less under a nitrogen atmosphere, and the mixture was stirred at −30° C. to −60° C. for 30 minutes. Then, the mixture was further stirred at 0° C. to −30° C. for 30 minutes. N,N-Dimethylformamide (1.4 mL) was added to the reaction mixture at −60° C. or less, and the mixture was stirred at a temperature of −60° C. to room temperature for 2 hours. Then, the mixture was cooled to −40° C., 30 mL of 1 mol/L hydrochloric acid was poured thereto, and the mixture was extracted with ethyl acetate. The organic layer was washed with saturated saline water, dried over anhydrous magnesium sulfate, and then concentrated under reduced pressure. The residue was applied to a silica gel column chromatography to obtain 1.88 g of N-(tetrahydrofuran-3-ylmethyl)-4-formyl-5-[3-(2-naphthyl)propyl]isoxazole-3-carboxamide (hereinafter, referred to as Compound of Present Invention (287)) represented by the following formula.

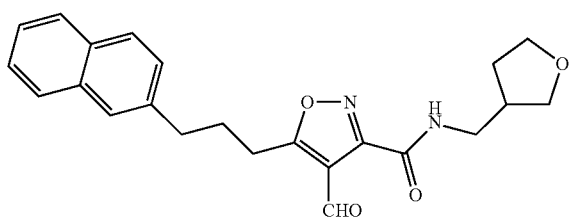

(287)

¹H-NMR (CDCl₃, TMS, δ(ppm)): 10.35(1H, s), 7.78(3H, d), 7.61(1H, s), 7.45(2H, ddd), 7.32(1H, dd), 7.20-7.10(1H, m), 3.93(1H, td), 3.86(1H, dd), 3.77(1H, dd), 3.60(1H, dd), 3.47(2H, t), 3.21(2H, t), 2.88 (2H, t), 2.62-2.55 (1H, m), 2.21 (2H, dt), 2.15-2.06 (1H, m), 1.72-1.61 (1H, m)

Production Example 279

Sodium borohydride (648 mg, 17.1 mmol) was added to a methanol (11 mL) solution of N-(tetrahydrofuran-3-ylmethyl)-4-formyl-5-[3-(2-naphthyl)propyl]isoxazole-3-carboxamide (1.88 g, 4.79 mmol) under ice-water cooling. The mixture was stirred for 30 minutes under ice-water cooling, and then stirred at room temperature for 30 minutes. 1 mol/L Hydrochloric acid was poured into the reaction mixture under ice-water cooling, and the mixture was extracted with ethyl acetate. The organic layer was washed with saturated saline water, dried over anhydrous magnesium sulfate, and then concentrated under reduced pressure to obtain 1.81 g of a crude product of N-(tetrahydrofuran-3-ylmethyl)-4-hydroxymethyl-5-[3-(2-naphthyl)propyl]isoxazole-3-carboxamide (hereinafter, referred to as Compound of Present Invention (288)) represented by the following formula.

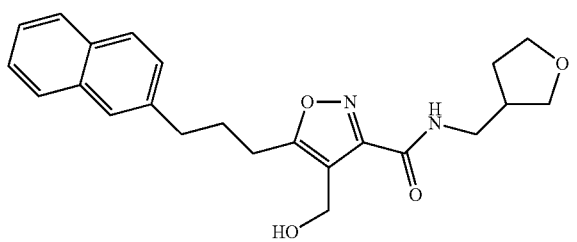

(288)

¹H-NMR (CDCl₃, TMS, δ(ppm)): 7.84-7.76 (3H, m), 7.61 (1H, s), 7.45 (2H, dtd), 7.33-7.30 (1H, m), 7.16-7.06 (1H, m), 4.59 (1H, t), 4.48 (2H, d), 3.93 (1H, td), 3.85 (1H, dd), 3.77 (1H, dt), 3.60 (1H, dd), 3.47 (2H, dd), 2.85-2.80 (4H, m), 2.63-2.53 (1H, m), 2.21-2.07 (3H, m), 1.75-1.62 (1H, m)

Production Example 280

55% Sodium hydride (220 mg, 5.05 mmol) was added to a tetrahydrofuran (20 mL) solution of N-(tetrahydrofuran-3-ylmethyl)-4-formyl-5-[3-(2-naphthyl)propyl]isoxazole-3-carboxamide (1.81 g, 4.59 mmol) under ice-water cooling, and the mixture was stirred for 30 minutes under ice-water cooling. Carbon bisulfide (0.7 mL) was added under ice-water cooling, and the mixture was stirred for 40 minutes, and then methyl iodide (0.86 mL) was added thereto. The mixture was stirred under ice-water cooling for 40 minutes, diluted with toluene, and concentrated under reduced pressure. 1 mol/L Hydrochloric acid was added to the concentrate, and the mixture was extracted with ethyl acetate. The organic layer was dried over anhydrous magnesium sulfate, and then concentrated under reduced pressure. The residue was applied to a silica gel column chromatography to obtain 1.84 g of dithiocarboxylic acid 4-O-{5-[3-(2-naphthyl)propyl]-3-[(tetrahydrofuran-3-ylmethyl)carbamoyl]isoxazoylmethyl}ester S-methyl ester (hereinafter, referred to as Compound of Present Invention (289)) represented by the following formula.

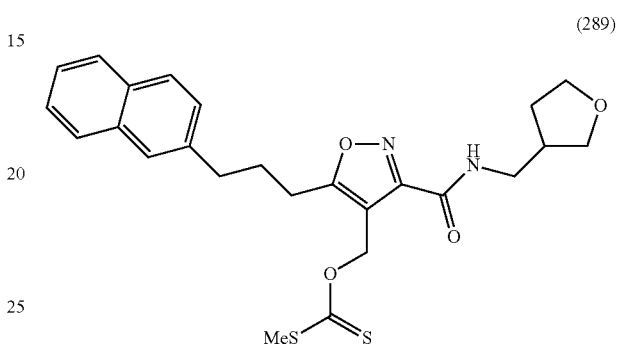

(289)

¹H-NMR (CDCl₃, TMS, δ(ppm)): 7.82-7.77 (3H, m), 7.61 (1H, s), 7.48-7.41 (2H, m), 7.32 (1H, dd), 6.94-6.83 (1H, m), 5.73 (2H, s), 3.91 (1H, td), 3.85 (1H, dd), 3.76 (1H, td), 3.58 (1H, dd), 3.46-3.43 (2H, m), 2.88 (4H, td), 2.57 (1H, dt), 2.52 (3H, s), 2.19-2.11 (2H, m), 2.12-2.06 (1H, m), 1.67 (1H, tt)

Production Example 281

Tributyltin hydride (1.5 mL, 6.05 mmol) and azobisisobutyronitrile (132 mg, 0.81 mmol) were added to a toluene (13 mL) solution of dithiocarboxylic acid 4-O-{5-[3-(2-naphthyl)propyl]-3-[(tetrahydrofuran-3-ylmethyl)carbamoyl]isoxazolylmethyl}ester S-methyl ester (1.84 g, 4.03 mmol). The mixture was stirred at 90° C. to 100° C. for 2 hours, and then concentrated under reduced pressure. The residue was applied to a silica gel column chromatography to obtain 1.00 g of N-(tetrahydrofuran-3-ylmethyl)-4-methyl-5-[3-(2-naphthyl)propyl]isoxazole-3-carboxamide (hereinafter, referred to as Compound of Present Invention (290)) represented by the

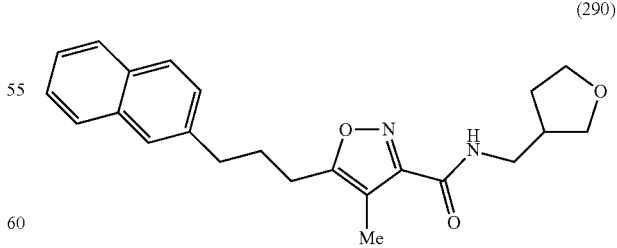

(290)

¹H-NMR (CDCl₃, TMS, δ(ppm)): 7.84-7.74 (3H, m), 7.61 (1H, s), 7.45 (2H, dtd), 7.32 (1H, dd), 6.96-6.85 (1H, m), 3.91 (1H, td), 3.86 (1H, dd), 3.80-3.74 (1H, m), 3.58 (1H, dd), 3.43 (2H, dq), 2.82 (2H, t), 2.76 (2H, t), 2.62-2.52 (1H, m), 2.14 (3H, s), 2.12-2.06 (3H, m), 1.68 (1H, dt)

Production Example 282

A 1.64 mol/L-n-butyllithium hexane solution (5.5 mL, 8.8 mmol) was added dropwise to a tetrahydrofuran (20 mL) solution of N-(tetrahydrofuran-3-ylmethyl)-5-(3-fluorobenzyl)isoxazole-3-carboxamide (1.22 g, 4.0 mmol) at −60° C. or less over 10 minutes, under a nitrogen atmosphere, and the mixture was stirred at −60° C. or less for 30 minutes. Then, N,N-dimethylformamide (1.0 mL) was added thereto, and the mixture was further stirred at −60° C. to 20° C. for 2 hours. 16 mL of 1 mol/L hydrochloric acid was poured into the reaction mixture under ice cooling, and the mixture was extracted with ethyl acetate. The organic layer was washed with saturated saline water, dried over anhydrous magnesium sulfate, and then concentrated under reduced pressure. The residue was applied to a silica gel column chromatography to obtain 154 mg of N-(tetrahydrofuran-3-ylmethyl)-4-formyl-5-(3-fluorobenzyl)isoxazole-3-carboxamide (hereinafter, referred to as Compound of Present Invention (291)) represented by the following formula.

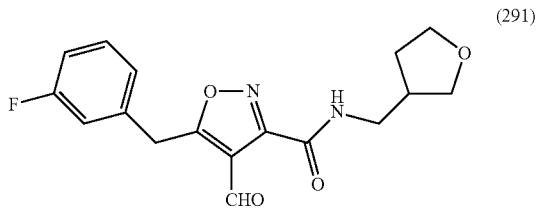 [SMILES: O=Cc1c(C(=O)NCC2CCOC2)noc1Cc1cccc(F)c1]

(291)

$^1$H-NMR (CDCl$_3$, TMS, δ(ppm)): 10.47 (1H, s), 7.29 (1H, td), 7.12 (2H, dt) 7.05 (1H, dt), 6.97 (1H, tdd), 4.48 (2H, s), 3.93 (1H, td), 3.85 (1H, dd), 3.77 (1H, td), 3.61 (1H, dd), 3.48 (2H, t), 2.64-2.54 (1H, m), 2.15-2.06 (1H, m), 1.73-1.63 (1H, m)

Production Example 283

Sodium borohydride (80 mg, 3.0 mmol) was added to a methanol (1.4 mL) solution of N-(tetrahydrofuran-3-ylmethyl)-4-formyl-5-(3-fluorobenzyl)isoxazole-3-carboxamide (230 mg, 1.0 mmol) under ice-water cooling. The mixture was stirred under ice-water cooling to room temperature for 1 hour. 1 mol/L Hydrochloric acid was poured into the reaction mixture under ice-water cooling, and the mixture was extracted with ethyl acetate. The organic layer was dried over anhydrous magnesium sulfate, and then concentrated under reduced pressure to obtain 245 mg of a crude product of N-(tetrahydrofuran-3-ylmethyl)-4-hydroxymethyl-5-(3-fluorobenzyl)isoxazole-3-carboxamide (hereinafter, referred to as Compound of Present Invention (292)) represented by the following formula.

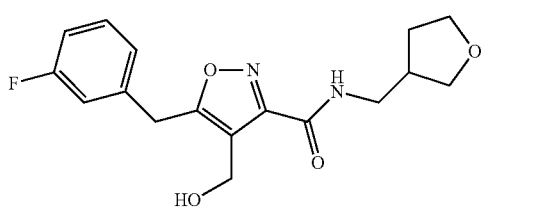

(292)

$^1$H-NMR (CDCl$_3$, TMS, δ(ppm)): 7.29 (2H, dd), 7.18-7.10 (1H, m), 7.00-6.98 (1H, m), 6.96 (1H, dd), 6.93-6.90 (1H, m), 4.56 (2H, s), 4.13 (2H, s), 3.93 (1H, td), 3.85 (1H, dd), 3.77 (1H, dd), 3.60 (1H, dd), 3.48 (2H, dd), 2.62-2.55 (1H, m), 2.11 (1H, tt), 1.73-1.63 (1H, m).

Production Example 284

55% Sodium hydride (34 mg, 0.77 mmol) was added to a tetrahydrofuran (3.0 mL) solution of N-(tetrahydrofuran-3-ylmethyl)-4-hydroxymethyl-5-(3-fluorobenzyl)isoxazole-3-carboxamide (245 mg, 0.70 mmol) under ice-water cooling, and the mixture was stirred for 40 minutes under ice-water cooling. Carbon bisulfide (0.1 mL) was added thereto, under ice-water cooling, and the mixture was stirred at the same temperature for 30 minutes. Then, methyl iodide (0.13 mL) was added thereto, and the mixture was further stirred for 30 minutes. The reaction mixture was diluted with toluene, and concentrated under reduced pressure. 1 mol/L Hydrochloric acid was added to the concentrate, and the mixture was extracted with ethyl acetate. The organic layer was dried over anhydrous magnesium sulfate, and then concentrated under reduced pressure. The residue was applied to a silica gel column chromatography to obtain 220 mg of dithiocarboxylic acid 4-O-{5-(3-fluorobenzyl)-3-[3-tetrahydrofurylmethyl) carbamoyl]isoxazolylmethyl}ester S-methyl ester (hereinafter, referred to as Compound of Present Invention (293)) represented by the following formula.

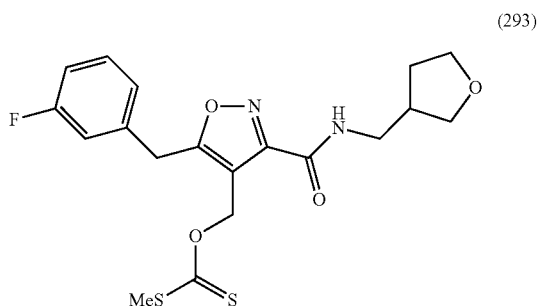 [SMILES: CSC(=S)OCc1c(C(=O)NCC2CCOC2)noc1Cc1cccc(F)c1]

(293)

$^1$H-NMR (CDCl$_3$, TMS, δ(ppm)): 7.34-7.27 (1H, m), 7.08-6.89 (4H, m), 5.77 (2H, s), 4.21 (2H, s), 3.91 (1H, td), 3.85 (1H, dd), 3.76 (1H, td), 3.58 (1H, dd), 3.45 (2H, t), 2.58 (1H, tt), 2.54 (3H, s), 2.13-2.04 (1H, m), 1.72-1.62 (1H, m)

Production Example 285

Tributyltin hydride (0.2 mL, 0.777 mmol) and azobisisobutyronitrile (17 mg, 0.104 mmol) were added to a toluene (1.7 mL) solution of dithiocarboxylic acid 4-O-{5-(3-fluorobenzyl)-3-[3-tetrahydrofurylmethyl)carbamoyl]isoxazolylmethyl}ester S-methyl ester (220 mg, 0.518 mmol). After stirring at 90° C. to 95° C. for 2 hours, tributyltin hydride (0.2 mL, 0.777 mmol) and azobisisobutyronitrile (34 mg, 0.208 mmol) were added thereto. The mixture was stirred at 90° C. to 95° C. for 1 hour, and then concentrated under reduced pressure. The residue was applied to a silica gel column chromatography to obtain 92 mg of N-(tetrahydrofuran-3-ylmethyl)-4-methyl-5-(3-fluorobezyl)isoxazole-3-carboxamide (hereinafter, referred to as Compound of Present Invention (294)) represented by the following formula.

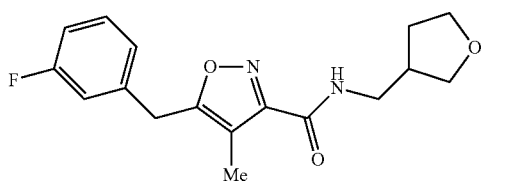

(294)

¹H-NMR (CDCl₃, TMS, δ(ppm)): 7.31-7.25 (1H, m), 7.01-6.87 (4H, m), 4.07 (2H, s), 3.91 (1H, td), 3.85 (1H, dd), 3.76 (1H, dd), 3.58 (1H, dd), 3.49-3.38 (2H, m), 2.62-2.51 (1H, m), 2.20 (3H, s), 2.14-2.03 (1H, m), 1.67 (1H, tt)

Production Example 286

A 1.6 mol/L-n-butyllithium hexane solution (5.6 mL, 9.00 mmol) was added dropwise to a tetrahydrofuran (15 mL) solution of N-(tetrahydrofuran-3-ylmethyl)-5-(2-naphthylmethoxymethyl)isoxazole-3-carboxamide (1.5 g, 4.09 mmol) at −65° C. or less, under a nitrogen atmosphere. After stirring at −60° C. or less for 1 hour, a tetrahydrofuran (5 mL) solution of iodine (3.11 g, 12.28 mmol) was added thereto, and the mixture was stirred overnight while slowly returning to room temperature. The reaction mixture was poured into 1 mol/L hydrochloric acid under ice cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.78 g of N-(tetrahydrofuran-3-ylmethyl)-5-(2-naphthylmethoxymethyl)-4-iodoisoxazole-3-carboxamide (hereinafter, referred to as Compound of Present Invention (295)) represented by the following formula.

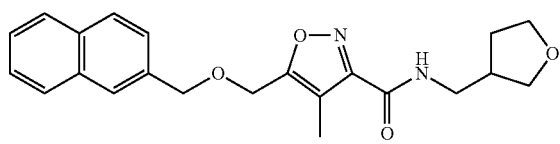

(295)

¹H-NMR (CDCl₃, TMS, δ(ppm)): 1.63-1.71 (m, 1H), 2.04-2.15 (m, 1H), 2.55-2.62 (m, 1H), 3.43-3.47 (m, 2H), 3.57-3.61 (m, 1H), 3.74-3.80 (m, 1H), 3.83-3.95 (m, 2H), 4.73 (s, 2H), 4.77 (s, 2H), 6.91 (brs, 1H), 7.48-7.52 (m, 3H), 7.82-7.87 (m, 4H)

Production Example 287

A 1.6 mol/L-n-butyllithium hexane solution (1.6 mL, 2.63 mmol) was added dropwise to a tetrahydrofuran (5 mL) solution of N-(tetrahydrofuran-3-ylmethyl)-5-(2-fluorobenzyloxymethyl)isoxazole-3-carboxamide (0.4 g, 1.19 mmol) at −65° C. or less, under a nitrogen atmosphere, and the mixture was stirred at −60° C. or less for 1 hour. Then, a tetrahydrofuran (1 mL) solution of bromotrichloromethane (0.35 mL, 3.58 mmol) was added thereto, and the mixture was stirred at −65° C. to −60° C. for 3 hours. The reaction mixture was poured into 1 mol/L hydrochloric acid under ice cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.25 g of N-(tetrahydrofuran-3-ylmethyl)-5-(2-fluorobenzyloxymethyl)-4-bromoisoxazole-3-carboxamide (hereinafter, referred to as Compound of Present Invention (296)) represented by the following formula.

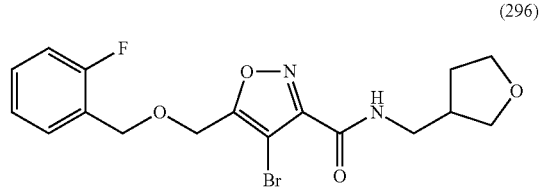 [SMILES: O=C(NCC1CCOC1)c1noc(COCc2ccccc2F)c1Br]

(296)

¹H-NMR (CDCl₃, TMS, δ(ppm)): 1.64-1.72 (m, 1H), 2.06-2.13 (m, 1H), 2.56-2.63 (m, 1H), 3.45-3.51 (m, 2H), 3.58-3.61 (m, 1H), 3.74-3.79 (m, 1H), 3.83-3.95 (m, 2H), 4.70 (s, 2H), 4.71 (s, 2H), 6.93 (brs, 1H), 7.04-7.09 (m, 1H), 7.13-7.17 (m, 1H), 7.28-7.34 (m, 1H), 7.40-7.44 (m, 1H)

Production Example 288

A 1.6 mol/L-n-butyllithium hexane solution (1.6 mL, 2.63 mmol) was added dropwise to a tetrahydrofuran (5 mL) solution of N-(tetrahydrofuran-3-ylmethyl)-5-(2-fluorobenzyloxymethyl)isoxazole-3-carboxamide (0.4 g, 1.19 mmol) at −65° C. or less, under a nitrogen atmosphere, and the mixture was stirred at −60° C. or less for 1 hour. Then, a tetrahydrofuran (1 mL) solution of iodine (0.91 g, 3.58 mmol) was added thereto, and the mixture was stirred at −65° C. to −60° C. for 3 hours. The reaction mixture was poured into 1 mol/L hydrochloric acid under ice cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.19 g of N-(tetrahydrofuran-3-ylmethyl)-5-(2-fluorobenzyloxymethyl)-4-iodoisoxazole-3-carboxamide (hereinafter, referred to as Compound of Present Invention (297)) represented by the following formula.

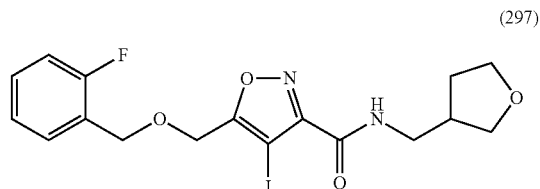

(297)

¹H-NMR (CDCl₃, TMS, δ(ppm)): 1.64-1.72 (m, 1H), 2.06-2.13 (m, 1H), 2.56-2.63 (m, 1H), 3.44-3.48 (m, 2H), 3.58-3.61 (m, 1H), 3.74-3.79 (m, 1H), 3.83-3.95 (m, 2H), 4.68 (s, 2H), 4.74 (s, 2H), 6.97 (brs, 1H), 7.04-7.09 (m, 1H), 7.14-7.17 (m, 1H), 7.28-7.34 (m, 1H), 7.41-7.46 (m, 1H)

Production Example 289

A 1.6 mol/L-n-butyllithium hexane solution (1.6 mL, 2.63 mmol) was added dropwise to a tetrahydrofuran (5 mL) solution of N-(tetrahydrofuran-3-ylmethyl)-5-(2-fluorobenzyloxymethyl)isoxazole-3-carboxamide (0.4 g, 1.19 mmol) at −65° C. or less, under a nitrogen atmosphere, and the mixture was stirred at −60° C. or less for 1 hour. Then, a tetrahydrofuran (3 mL) solution of N-fluorobenzenesulfonimide (1.13 g, 3.58 mmol) was added thereto, and the mixture was stirred at −65° C. to −60° C. for 3 hours. The reaction mixture was poured into 1 mol/L hydrochloric acid under ice cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.06 g of N-(tetrahydrofuran-3-ylmethyl)-5-(2-fluorobenzyloxymethyl)-4-fluoroisoxazole-3-carboxamide (hereinafter, referred to as Compound of Present Invention (298)) represented by the following formula.

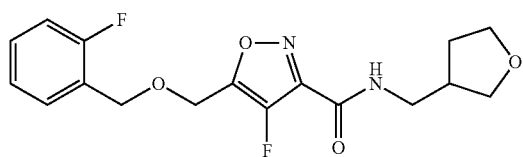

(298)

$^1$H-NMR (CDCl$_3$, TMS, δ(ppm)): 1.64-1.72 (m, 1H), 2.05-2.14 (m, 1H), 2.56-2.62 (m, 1H), 3.46-3.50 (m, 2H), 3.58-3.62 (m, 1H), 3.74-3.80 (m, 1H), 3.83-3.95 (m, 2H), 4.68 (s, 2H), 4.70 (s, 2H), 6.83 (brs, 1H), 7.05-7.09 (m, 1H), 7.13-7.17 (m, 1H), 7.29-7.34 (m, 1H), 7.39-7.42 (m, 1H)

Production Example 290

5-(1,3-Benzodioxolan-5-ylmethyl)isoxazole-3-carboxylic acid (600 mg, 2.42 mmol), tetrahydrofuran-3-ylmethylamine (270 mg, 2.67 mmol) and 1-hydroxybenzotriazole (393 mg, 2.91 mmol) were added to dichloromethane (15 mL), and the mixture was stirred at 0° C. for 30 minutes. 1-Ethyl-3-(3-dimethylaminopropyl) carbodiimide hydrochloride (556 mg, 2.91 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 530 mg of N-(tetrahydrofuran-3-ylmethyl)-5-(1,3-benzodioxolan-5-ylmethyl)isoxazole-3-carboxamide (hereinafter, referred to as Compound of Present Invention (299)) represented by the following formula.

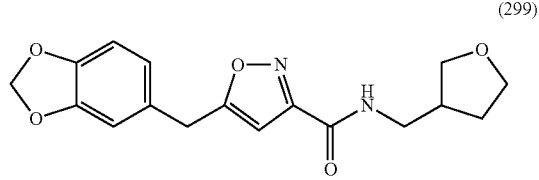 [SMILES: O=C(NCC1CCOC1)c1cc(Cc2ccc3c(c2)OCO3)on1]

(299)

$^1$H-NMR (CDCl$_3$, TMS, δ(ppm)): 1.60-1.71 (1H, m), 2.02-2.12 (1H, m), 2.50-2.62 (1H, m), 3.44 (2H, dd), 3.52 (1H, dd), 3.76 (1H, dd), 3.81-3.92 (2H, m), 4.02 (2H, s), 5.95 (2H, s), 6.39 (1H, s), 6.68-6.73 (2H, m), 6.75-6.95 (1H, m), 6.89 (1H, br s)

Production Example 291

5-(3,5-Difluorobenzyl)isoxazole-3-carboxylic acid (600 mg, 2.51 mmol), tetrahydrofuran-3-ylmethylamine (279 mg, 2.76 mmol) and 1-hydroxybenzotriazole (407 mg, 3.01 mmol) were added to dichloromethane (15 mL), and the mixture was stirred at 0° C. for 30 minutes. 1-Ethyl-3-(3-dimethylaminopropyl) carbodiimide hydrochloride (577 mg, 3.01 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 460 mg of N-(tetrahydrofuran-3-ylmethyl)-5-(3,5-difluorobenzyl)isoxazole-3-carboxamide (hereinafter, referred to as Compound of Present Invention (305)) represented by the following formula.

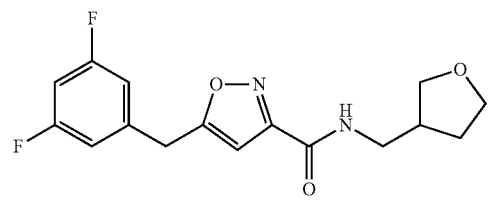

(305)

$^1$H-NMR (CDCl$_3$, TMS, δ(ppm)): 1.60-1.71 (1H, m), 2.02-2.14 (1H, m), 2.50-2.62 (1H, m), 3.45 (2H, dd), 3.58 (1H, dd), 3.76 (1H, dd), 3.81-3.95 (2H, m), 4.11 (2H, s), 6.47 (1H, s), 6.71-6.82 (3H, m), 6.90 (1H, br s)

Production Example 292

5-(3,4-Difluorobenzyl)isoxazole-3-carboxylic acid (600 mg, 2.51 mmol), tetrahydrofuran-3-ylmethylamineamine (279 mg, 2.76 mmol) and 1-hydroxybenzotriazole (407 mg, 3.01 mmol) were added to dichloromethane (15 mL), and the mixture was stirred at 0° C. for 30 minutes. 1-Ethyl-3-(3-dimethylaminopropyl) carbodiimide hydrochloride (577 mg, 3.01 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 510 mg of N-(tetrahydrofuran-3-ylmethyl)-5-(3,4-difluorobenzyl)isoxazole-3-carboxamide (hereinafter, referred to as Compound of Present Invention (306)) represented by the following formula.

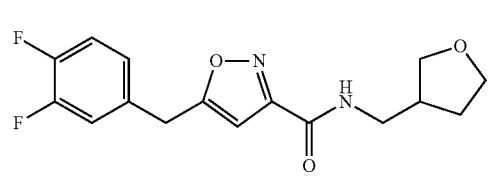

(306)

¹H-NMR (CDCl₃, TMS, δ(ppm)): 1.61-1.71 (1H, m), 2.02-2.12 (1H, m), 2.50-2.61 (1H, m), 3.45 (2H, dd), 3.58 (1H, dd), 3.76 (1H, dd), 3.80-3.92 (2H, m), 4.09 (2H, s), 6.43 (1H, s), 6.89 (1H, br s), 6.94-7.00 (1H, m), 7.03-7.18 (2H, m)

Production Example 293

5-(3,5-Dichlorobenzyl)isoxazole-3-carboxylic acid (600 mg, 2.2 mmol), 3-tetrahydrofurylmethylamine (245 mg, 2.42 mmol) and 1-hydroxybenzotriazole (357 mg, 2.65 mmol) were added to dichloromethane (15 mL), and the mixture was stirred at 0° C. for 30 minutes. 1-Ethyl-3-(3-dimethylaminopropyl) carbodiimide hydrochloride (506 mg, 2.65 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 505 mg of N-(tetrahydrofuran-3-ylmethyl)-5-(3,5-dichlorobenzyl)isoxazole-3-carboxamide (hereinafter, referred to as Compound of Present Invention (307)) represented by the following formula.

(307)

¹H-NMR (CDCl₃, TMS, δ(ppm)): 1.61-1.72 (1H, m), 2.02-2.12 (1H, m), 2.50-2.62 (1H, m), 3.45 (2H, dd), 3.58 (1H, dd), 3.76 (1H, dd), 3.81-3.93 (2H, m), 4.08 (2H, s), 6.45 (1H, s), 6.90 (1H, br s), 7.14 (2H, d), 7.30 (1H, dd)

Production Example 294

5-(2-Thienylmethyl)isoxazole-3-carboxylic acid (500 mg, 2.09 mmol), tetrahydrofuran-3-ylmethylamine (232 mg, 2.3 mmol) and 1-hydroxybenzotriazole (339 mg, 2.5 mmol) were added to dichloromethane (15 mL), and the mixture was stirred at 0° C. for 30 minutes. 1-Ethyl-3-(3-dimethylaminopropyl) carbodiimide hydrochloride (480 mg, 2.5 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 350 mg of N-(tetrahydrofuran-3-ylmethyl)-5-(2-thienylmethyl)isoxazole-3-carboxamide (hereinafter, referred to as Compound of Present Invention (308)) represented by the following formula.

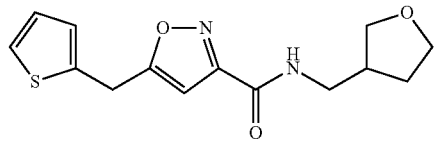
(308)

¹H-NMR (CDCl₃, TMS, δ(ppm)): 1.60-1.72 (1H, m), 2.00-2.14 (1H, m), 2.49-2.62 (1H, m), 3.45 (2H, dd), 3.57 (1H, dd), 3.76 (1H, dd), 3.85-3.95 (2H, m), 4.33 (2H, s), 6.49 (1H, s), 6.90 (1H, br s), 6.92-7.01 (2H, m), 7.20-7.25 (1H, m)

Production Example 296

5-(3-Thienylmethyl)isoxazole-3-carboxylic acid (600 mg, 2.87 mmol), tetrahydrofuran-3-ylmethylamine (319 mg, 2.3 mmol) and 1-hydroxybenzotriazole (465 mg, 3.44 mmol) were added to dichloromethane (15 mL), and the mixture was stirred at 0° C. for 30 minutes. 1-Ethyl-3-(3-dimethylaminopropyl) carbodiimide hydrochloride (657 mg, 3.44 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 520 mg of N-(tetrahydrofuran-3-ylmethyl)-5-(3-thienylmethyl)isoxazole-3-carboxamide (hereinafter, referred to as Compound of Present Invention (309)) represented by the following formula.

(309)

¹H-NMR (CDCl₃, TMS, δ(ppm)): 1.59-1.72 (1H, m), 2.00-2.15 (1H, m), 2.50-2.60 (1H, m), 3.45 (2H, dd), 3.57 (1H, dd), 3.73 (1H, dd), 3.81-3.95 (2H, m), 4.15 (2H, s), 6.43 (1H, s), 6.90 (1H, br s), 6.95-7.02 (1H, m), 7.08-7.16 (1H, m), 7.29-7.36 (1H, m)

Production Example 297

5-(2-Furylmethyl)isoxazole-3-carboxylic acid (500 mg, 2.59 mmol), tetrahydrofuran-3-ylmethylamine (288 mg, 2.84 mmol) and 1-hydroxybenzotriazole (420 mg, 3.1 mmol) were added to dichloromethane (20 mL), and the mixture was stirred at 0° C. for 30 minutes. 1-Ethyl-3-(3-dimethylaminopropyl) carbodiimide hydrochloride (601 mg, 3.1 mmol) was added to the mixture at room temperature, and the mixture was stirred for 18 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 330 mg of N-(tetrahydrofuran-3-ylmethyl)-5-(2-furylmethyl)isoxazole-3-carboxamide (hereinafter, referred to as Compound of Present Invention (310)) represented by the following formula.

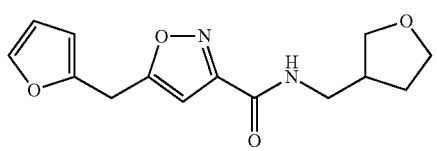
(310)

$^1$H-NMR (CDCl$_3$, TMS, δ(ppm)): 1.60-1.71 (1H, m), 2.02-2.12 (1H, m), 2.50-2.61 (1H, m), 3.45 (2H, dd), 3.57 (1H, dd), 3.76 (1H, dd), 3.81-3.92 (2H, m), 4.33 (2H, s), 6.49 (1H, s), 6.89 (1H, brs), 6.92-7.00 (2H, m), 7.20-7.22 (1H, m)

Production Example 298

5-(3-Furylmethyl)isoxazole-3-carboxylic acid (500 mg, 2.59 mmol), tetrahydrofuran-3-ylmethylamine (288 mg, 2.84 mmol) and 1-hydroxybenzotriazole (420 mg, 3.1 mmol) were added to dichloromethane (20 mL), and the mixture was stirred at 0° C. for 30 minutes. 1-Ethyl-3-(3-dimethylaminopropyl) carbodiimide hydrochloride (601 mg, 3.1 mmol) was added to the mixture at room temperature, and the mixture was stirred for 18 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 310 mg of N-(tetrahydrofuran-3-ylmethyl)-5-(3-furylmethyl)isoxazole-3-carboxamide (hereinafter, referred to as Compound of Present Invention (311)) represented by the following formula.

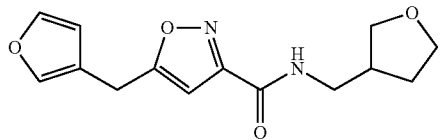
(311)

$^1$H-NMR (CDCl$_3$, TMS, δ(ppm)): 1.60-1.71 (1H, rm), 2.02-2.12 (1H, m), 2.50-2.61 (1H, m), 3.45 (2H, dd), 3.57 (1H, dd), 3.76 (1H, dd), 3.81-3.92 (2H, m), 4.15 (2H, s), 6.43 (1H, s), 6.89 (1H, brs), 6.96-7.02 (1H, m), 7.10-7.14 (1H, m), 7.30-7.34 (1H, m)

Production Example 299

5-(3-Methoxybenzyl)isoxazole-3-carboxylic acid (100 mg, 0.43 mmol), tetrahydrofuran-3-ylmethylamine (279 mg, 2.76 mmol), 1-hydroxybenzotriazole (69 mg, 0.51 mmol), 1-ethyl-3-(3-dimethylaminopropyl) carbodiimide hydrochloride (98 mg, 0.51 mmol) and triethylamine (0.09 mL, 0.68 mmol) were added to chloroform (amylene addition product) (4 mL) at 0° C., and the mixture was stirred at the same temperature for 10 minutes. Then, the mixture was stirred at room temperature for 18 hours. Water was added to the reaction mixture, and the mixture was extracted twice with ethyl acetate. The organic layer was sequentially washed with water and saturated saline water, dried over anhydrous sodium sulfate, and then concentrated under reduced pressure. The residue was applied to a silica gel column chromatography to obtain 60 mg of N-(tetrahydrofuran-3-ylmethyl)-5-(3-methoxybenzyl)isoxazole-3-carboxamide (hereinafter, referred to as Compound of Present Invention (312)) represented by the following formula.

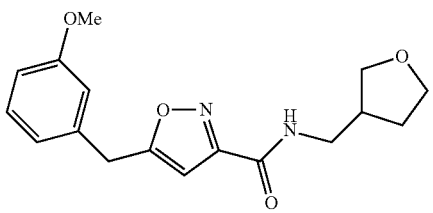
(312)

$^1$H-NMR (CDCl$_3$, TMS, δ(ppm)): 1.60-1.71 (1H, m), 2.01-2.12 (1H, m), 2.50-2.61 (1H, m), 3.44 (2H, dd), 3.57 (1H, dd), 3.71-3.94 (3H, m), 3.80 (3H, s), 4.08 (2H, s), 6.41 (1H, s), 6.76-6.85 (3H, m), 6.89 (1H, br s), 7.21-7.30 (1H, m)

Production Example 300

5-(3-Trifluoromethoxybenzyl)isoxazole-3-carboxylic acid (100 mg, 0.35 mmol), tetrahydrofuran-3-ylmethylamine (39 mg, 0.38 mmol) and 1-hydroxybenzotriazole (55 mg, 0.41 mmol) were added to dichloromethane (5 mL), and the mixture was stirred at 0° C. for 30 minutes. 1-Ethyl-3-(3-dimethylaminopropyl) carbodiimide hydrochloride (65 mg, 0.41 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 78 mg of N-(tetrahydrofuran-3-ylmethyl)-5-(3-trifluoromethoxybenzyl)isoxazole-3-carboxamide (hereinafter, referred to as Compound of Present Invention (313)) represented by the following formula.

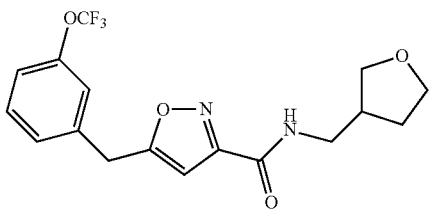
(313)

$^1$H-NMR (CDCl$_3$, TMS, δ(ppm)): 1.60-1.74 (1H, m), 2.00-2.15 (1H, m), 2.50-2.62 (1H, m), 3.45 (2H, dd), 3.57 (1H, dd), 3.70-3.95 (3H, m), 4.14 (2H, s), 6.43 (1H, s), 6.90 (1H, br s), 7.08-7.22 (3H, m), 7.33-7.42 (1H, m)

Production Example 301

5-(4-Methoxybenzyl)isoxazole-3-carboxylic acid (600 mg, 2.57 mmol), tetrahydrofuran-3-ylmethylamine (286 mg, 2.83 mmol) and 1-hydroxybenzotriazole (416 mg, 3.08 mmol) were added to dichloromethane (15 mL), and the mixture was stirred at 0° C. for 30 minutes. 1-Ethyl-3-(3-dimethylaminopropyl) carbodiimide hydrochloride (588 mg, 3.08 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 480 mg of N-(tetrahydrofuran-3-ylmethyl)-5-(4-methoxybenzyl)isoxazole-3-carboxamide (hereinafter, referred to as Compound of Present Invention (314)) represented by the following formula.

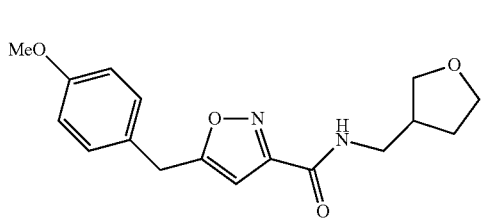

(314)

$^1$H-NMR (CDCl$_3$, TMS, δ(ppm)): 1.60-1.71 (1H, m), 2.02-2.12 (1H, m), 2.50-2.61 (1H, m), 3.44 (2H, dd), 3.56 (1H, dd), 3.71-3.93 (3H, m), 3.80 (3H, s), 4.05 (2H, s), 6.36 (1H, s), 6.84-6.92 (3H, m), 7.13-7.19 (2H, m)

Production Example 302

5-(4-Trifluoromethoxybenzyl)isoxazole-3-carboxylic acid (500 mg, 1.74 mmol), tetrahydrofuran-3-ylmethylamine (194 mg, 1.91 mmol) and 1-hydroxybenzotriazole (282 mg, 2.09 mmol) were added to dichloromethane (15 mL), and the mixture was stirred at 00° C. for 30 minutes. 1-Ethyl-3-(3-dimethylaminopropyl) carbodiimide hydrochloride (399 mg, 2.1 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 320 mg of N-(tetrahydrofuran-3-ylmethyl)-5-(4-trifluoromethoxybenzyl)isoxazole-3-carboxamide (hereinafter, referred to as Compound of Present Invention (315)) represented by the following formula.

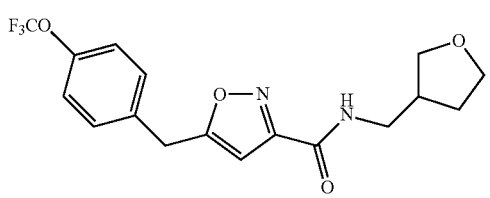

(315)

$^1$H-NMR (CDCl$_3$, TMS, δ(ppm)): 1.60-1.71 (1H, m), 2.00-2.12 (1H, m), 2.50-2.61 (1H, m), 3.45 (2H, dd), 3.57 (1H, dd), 3.76 (1H, dd), 3.80-3.92 (2H, m), 4.13 (2H, s), 6.42 (1H, s), 6.89 (1H, br s), 7.16-7.22 (2H, m), 7.25-7.32 (2H, m)

Production Example 303

5-(4-Trifluoromethylbenzyl)isoxazole-3-carboxylic acid (600 mg, 2.20 mmol), tetrahydrofuran-3-ylmethylamine (245 mg, 2.40 mmol) and 1-hydroxybenzotriazole (505 mg, 2.65 mmol) were added to dichloromethane (10 mL), and the mixture was stirred at 0° C. for 30 minutes. 1-Ethyl-3-(3-dimethylaminopropyl) carbodiimide hydrochloride (577 mg, 3.01 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water. The organic layer was dried over anhydrous sodium sulfate, and then concentrated under reduced pressure. The residue was applied to a silica gel column chromatography to obtain 510 mg of N-(tetrahydrofuran-3-ylmethyl)-5-(4-trifluoromethylbenzyl)isoxazole-3-carboxamide (hereinafter, referred to as Compound of Present Invention (316)) represented by the following formula.

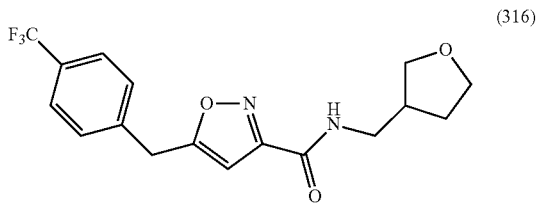 [SMILES: O=C(NCC1CCOC1)c1cc(Cc2ccc(C(F)(F)F)cc2)on1]

(316)

$^1$H-NMR (CDCl$_3$, TMS, δ(ppm)): 1.60-1.71 (1H, m), 2.02-2.12 (1H, m), 2.50-2.61 (1H, m), 3.45 (2H, dd), 3.57 (1H, dd), 3.76 (1H, dd), 3.80-3.95 (2H, m), 4.19 (2H, s), 6.43 (1H, s), 6.89 (1H, br s), 7.35-7.40 (2H, m), 7.58-7.64 (2H, m)

Production Example 304

5-(2-Methoxybenzyl)isoxazole-3-carboxylic acid (600 mg, 2.57 mmol), tetrahydrofuran-3-ylmethylamine (286 mg, 2.83 mmol) and 1-hydroxybenzotriazole (416 mg, 3.08 mmol) were added to dichloromethane (15 mL), and the mixture was stirred at 0° C. for 30 minutes. 1-Ethyl-3-(3-dimethylaminopropyl) carbodiimide hydrochloride (588 mg, 3.08 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water. The organic layer was dried over anhydrous sodium sulfate, and then concentrated under reduced pressure. The residue was applied to a silica gel column chromatography to obtain 536 mg of N-(tetrahydrofuran-3-ylmethyl)-5-(2-methoxybenzyl)isoxazole-3-carboxamide (hereinafter, referred to as Compound of Present Invention (317)) represented by the following formula.

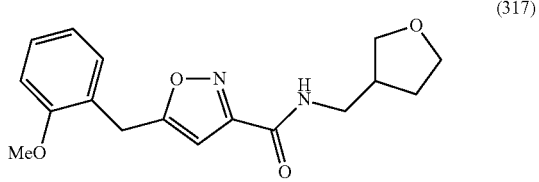 [SMILES: COc1ccccc1Cc1cc(C(=O)NCC2CCOC2)no1]

(317)

$^1$H-NMR (CDCl$_3$, TMS, δ(ppm)): 1.60-1.71 (1H, m), 2.00-2.12 (1H, m), 2.48-2.62 (1H, m), 3.43 (2H, dd), 3.56

(1H, dd), 3.70-3.95 (3H, m), 3.82 (3H, s), 4.10 (2H, s), 6.33 (1H, s), 6.82-6.95 (3H, m), 7.12-7.20 (1H, m), 7.26-7.32 (1H, m)

Production Example 305

5-(3-Fluorobenzyl)isoxazole-3-carboxylic acid (100 mg, 0.45 mmol), 1-hydroxybenzotriazole (73 mg, 0.54 mmol), 1-ethyl-3-(3-dimethylaminopropyl) carbodiimide hydrochloride (103 mg, 0.50 mmol) and triethylamine (0.09 mL, 0.68 mmol) were added to chloroform (amylene addition product) (4 mL) at 0° C., and the mixture was stirred at the same temperature for 10 minutes. Tetrahydrofuran-3-ylmethylamine (50 mg, 0.50 mmol) was added to the mixture at room temperature, and the mixture was stirred for 18 hours. Then, water was added thereto, and the mixture was extracted twice with ethyl acetate. The organic layer was sequentially washed with water and saturated saline water, dried over anhydrous sodium sulfate, and then concentrated under reduced pressure. The residue was applied to a silica gel column chromatography to obtain 62 mg of N-(tetrahydrofuran-3-ylmethyl)-5-(3-fluorobenzyl)isoxazole-3-carboxamide (hereinafter, referred to as Compound of Present Invention (318)) represented by the following formula.

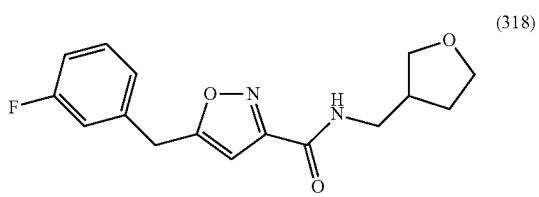 [SMILES: O=C(NCC1CCOC1)c1cc(Cc2cccc(F)c2)on1]

(318)

¹H-NMR (CDCl₃, TMS, δ(ppm)): 1.60-1.72 (1H, m), 2.01-2.13 (1H, m), 2.48-2.63 (1H, m), 3.40-3.50 (2H, m), 3.55-3.60 (1H, m), 3.72-3.80 (1H, m), 3.81-3.95 (2H, m), 4.11 (2H, s), 6.43 (1H, s), 6.91 (1H, br s), 6.92-7.06 (3H, m), 7.27-7.36 (1H, m)

Production Example 306

5-(4-Fluorobenzyl)isoxazole-3-carboxylic acid (100 mg, 0.45 mmol), 1-hydroxybenzotriazole (73 mg, 0.54 mmol), 1-ethyl-3-(3-dimethylaminopropyl) carbodiimide hydrochloride (103 mg, 0.50 mmol) and triethylamine (0.09 mL, 0.68 mmol) were added to chloroform (amylene addition product) (4 mL) at 0° C., and the mixture was stirred at the same temperature for 10 minutes. Tetrahydrofuran-3-ylmethylamine (50 mg, 0.50 mmol) was added to the mixture at room temperature, and the mixture was stirred for 18 hours. Then, water was added thereto, and the mixture was extracted twice with ethyl acetate. The organic layer was sequentially washed with water and saturated saline water, dried over anhydrous sodium sulfate, and then concentrated under reduced pressure. The residue was applied to a silica gel column chromatography to obtain 80 mg of N-(tetrahydrofuran-3-ylmethyl)-5-(4-fluorobenzyl)isoxazole-3-carboxamide (hereinafter, referred to as Compound of Present Invention (319)) represented by the following formula.

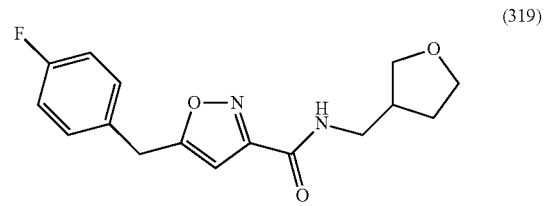 [SMILES: O=C(NCC1CCOC1)c1cc(Cc2ccc(F)cc2)on1]

(319)

¹H-NMR (CDCl₃, TMS, δ(ppm)): 1.60-1.72 (1H, m), 2.01-2.13 (1H, m), 2.48-2.63 (1H, m), 3.40-3.48 (2H, m), 3.55-3.60 (1H, m), 3.70-3.79 (1H, m), 3.80-3.95 (2H, m), 4.09 (2H, s), 6.39 (1H, s), 6.89 (1H, br s), 7.00-7.06 (2H, m), 7.18-7.24 (2H, m)

Production Example 307

5-(2-Fluorobenzyl)isoxazole-3-carboxylic acid (600 mg, 2.71 mmol), 1-hydroxybenzotriazole (438 mg, 3.25 mmol), 1-ethyl-3-(3-dimethylaminopropyl) carbodiimide hydrochloride (621 mg, 3.25 mmol) and triethylamine (0.57 mL, 4.07 mmol) were added to chloroform (amylene addition product) (10 mL) at 0° C., and the mixture was stirred at the same temperature for 10 minutes. Tetrahydrofuran-3-ylmethylamine (301 mg, 2.98 mmol) was added to the mixture at room temperature, and the mixture was stirred for 18 hours. Then, water was added thereto, and the mixture was extracted twice with ethyl acetate. The organic layer was sequentially washed with water and saturated saline water, dried over anhydrous sodium sulfate, and then concentrated under reduced pressure. The residue was applied to a silica gel column chromatography to obtain 450 mg of N-(tetrahydrofuran-3-ylmethyl)-5-(2-fluorobenzyl)isoxazole-3-carboxamide (hereinafter, referred to as Compound of Present Invention (320)) represented by the following formula.

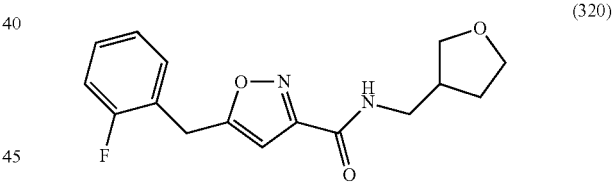

(320)

¹H-NMR (CDCl₃, TMS, δ(ppm)): 1.60-1.72 (1H, m), 2.01-2.13 (1H, m), 2.48-2.63 (1H, m), 3.40-3.48 (2H, m), 3.55-3.60 (1H, m), 3.70-3.79 (1H, m), 3.80-3.95 (2H, m), 4.15 (2H, s), 6.41 (1H, s), 6.90 (1H, br s), 7.04-7.16 (2H, m), 7.21-7.35 (2H, m)

Production Example 308

5-(3-Chlorobenzyl)isoxazole-3-carboxylic acid (100 mg, 0.42 mmol), 1-hydroxybenzotriazole (69 mg, 0.51 mmol), 1-ethyl-3-(3-dimethylaminopropyl) carbodiimide hydrochloride (98 mg, 0.51 mmol) and triethylamine (0.09 mL, 0.64 mmol) were added to chloroform (amylene addition product) (4 mL) at 0° C., and the mixture was stirred at the same temperature for 10 minutes. Tetrahydrofuran-3-ylmethylamine (48 mg, 0.47 mmol) was added to the mixture at room temperature, and the mixture was stirred for 18 hours. Then, water was added thereto, and the mixture was extracted twice with ethyl acetate. The organic layer was sequentially washed with water and saturated saline water, dried over anhydrous sodium sulfate, and then concentrated under reduced pressure. The residue was applied to a silica gel column chromatography to obtain 47 mg of N-(tetrahydrofuran-3-ylmethyl)-5-(3-chlorobenzyl)isoxazole-3-carboxamide (hereinafter, referred to as Compound of Present Invention (321)) represented by the following formula.

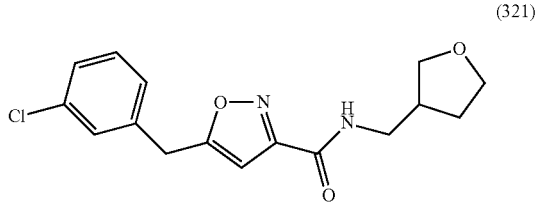 [SMILES: O=C(NCC1CCOC1)c1cc(Cc2cccc(Cl)c2)on1]

(321)

$^1$H-NMR (CDCl$_3$, TMS, δ(ppm)): 1.60-1.72 (1H, m), 2.05-2.13 (1H, m), 2.50-2.62 (1H, m), 3.40-3.50 (2H, m), 3.55-3.62 (1H, m), 3.72-3.80 (1H, m), 3.80-3.95 (2H, m), 4.10 (2H, s), 6.43 (1H, s), 6.89 (1H, br s), 7.10-7.17 (1H, m), 7.22-7.32 (3H, m)

Production Example 309

5-(4-Chlorobenzyl)isoxazole-3-carboxylic acid (100 mg, 0.42 mmol), tetrahydrofuran-3-ylmethylamine (52 mg, 0.50 mmol) and 1-hydroxybenzotriazole (6 mg, 0.04 mmol) were added to chloroform (amylene addition product) (3 mL) at 0° C., and the mixture was stirred at the same temperature for 10 minutes. 1-Ethyl-3-(3-dimethylaminopropyl) carbodiimide hydrochloride (97 mg, 0.50 mmol) was added to the mixture at room temperature, and the mixture was stirred for 18 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 70 rag of N-(tetrahydrofuran-3-ylmethyl)-5-(4-chlorobenzyl)isoxazole-3-carboxamide (hereinafter, referred to as Compound of Present Invention (322)) represented by the following formula.

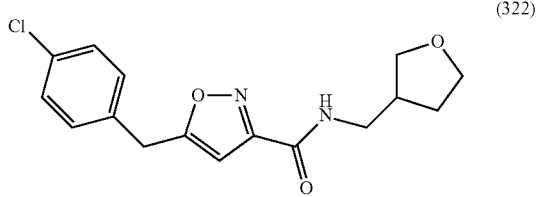 [SMILES: O=C(NCC1CCOC1)c1cc(Cc2ccc(Cl)cc2)on1]

(322)

$^1$H-NMR (CDCl$_3$, TMS, δ(ppm)): 1.58-1.71 (1H, m), 2.00-2.12 (1H, m), 2.50-2.62 (1H, m), 3.40-3.49 (2H, m), 3.53-3.60 (1H, m), 3.70-3.80 (1H, m), 3.81-3.95 (2H, m), 4.09 (2H, s), 6.40 (1H, s), 6.89 (1H, br s), 7.18 (2H, d), 7.31 (2H, d)

Production Example 310

5-(2-Chlorobenzyl)isoxazole-3-carboxylic acid (100 mg, 0.42 mmol), tetrahydrofuran-3-ylmethylamine (52 mg, 0.50 mmol) and 1-hydroxybenzotriazole (6 mg, 0.04 mmol) were added to chloroform (amylene addition product) (3 mL) at 0° C., and the mixture was stirred at the same temperature for 10 minutes. 1-Ethyl-3-(3-dimethylaminopropyl) carbodiimide hydrochloride (97 mg, 0.50 mmol) was added to the mixture at room temperature, and the mixture was stirred for 18 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 67 rag of N-(tetrahydrofuran-3-ylmethyl)-5-(2-chlorobenzyl)isoxazole-3-carboxamide (hereinafter, referred to as Compound of Present Invention (323)) represented by the following formula.

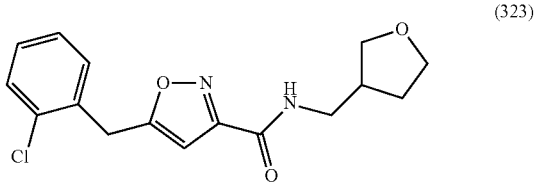 [SMILES: O=C(NCC1CCOC1)c1cc(Cc2ccccc2Cl)on1]

(323)

$^1$H-NMR (CDCl$_3$, TMS, δ(ppm)): 1.60-1.72 (1H, m), 2.01-2.12 (1H, m), 2.50-2.62 (1H, m), 3.40-3.48 (2H, m), 3.54-3.60 (1H, m), 3.71-3.80 (1H, m), 3.80-3.95 (2H, m), 4.25 (2H, s), 6.39 (1H, s), 6.90 (1H, br s), 7.21-7.32 (3H, m), 7.37-7.45 (1H, m)

Production Example 311

5-(2,3,4-Trifluorobenzyl)isoxazole-3-carboxylic acid (450 mg, 1.75 mmol), tetrahydrofuran-3-ylmethylamine (195 mg, 1.93 mmol) and 1-hydroxybenzotriazole (284 mg, 2.1 mmol) were added to dichloromethane (10 mL), and the mixture was stirred at 0° C. for 30 minutes. 1-Ethyl-3-(3-dimethylaminopropyl) carbodiimide hydrochloride (401 mg, 2.10 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 320 mg of N-(tetrahydrofuran-3-ylmethyl)-5-(2,3,4-trifluorobenzyl)isoxazole-3-carboxamide (hereinafter, referred to as Compound of Present Invention (324)) represented by the following formula.

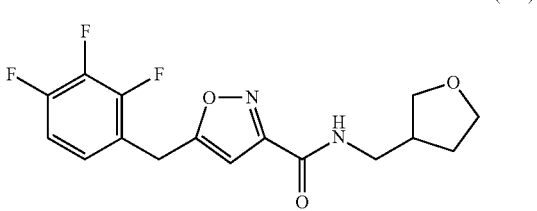

(324)

$^1$H-NMR (CDCl$_3$, TMS, δ(ppm)): 1.60-1.71 (1H, m), 2.02-2.12 (1H, m), 2.50-2.62 (1H, m), 3.45 (2H, dd), 3.57 (1H, dd), 3.76 (1H, dd), 3.81-3.93 (2H, m), 4.15 (2H, s), 6.45 (1H, m), 6.89 (1H, br s), 6.91-7.02 (2H, m)

Production Example 312

5-(3,4-Dichlorobenzyl)isoxazole-3-carboxylic acid (600 mg, 2.20 mmol), tetrahydrofuran-3-ylmethylamine (245 mg, 2.42 mmol) and 1-hydroxybenzotriazole (357 mg, 2.64 mmol) were added to dichloromethane (15 mL), and the mixture was stirred at 0° C. for 30 minutes. 1-Ethyl-3-(3-dimethylaminopropyl) carbodiimide hydrochloride (505 mg, 2.64 mmol) was added to the mixture at room temperature, and the mixture was stirred for 16 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 520 mg of N-(tetrahydrofuran-3-ylmethyl)-5-(3,4-dichlorobenzyl)isoxazole-3-carboxamide (hereinafter, referred to as Compound of Present Invention (325)) represented by the following formula.

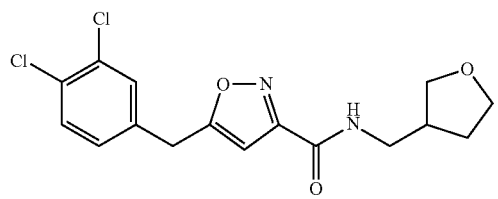

(325)

$^1$H-NMR (CDCl$_3$, TMS, δ(ppm)): 1.60-1.71 (1H, m), 2.05-2.12 (1H, m), 2.50-2.61 (1H, m), 3.45 (2H, dd), 3.57 (1H, dd), 3.76 (1H, dd), 3.81-3.92 (2H, m), 4.08 (2H, s), 6.44 (1H, s), 6.89 (1H, br s), 7.09 (1H, dd), 7.34 (1H, d), 7.42 (1H, d)

Production Example 313

5-(2-Phenylbenzyl)isoxazole-3-carboxylic acid (500 mg, 1.79 mmol), 1-hydroxybenzotriazole (290 mg, 2.15 mmol), 1-ethyl-3-(3-dimethylaminopropyl) carbodiimide hydrochloride (410 mg, 2.15 mmol) and triethylamine (0.37 mL, 2.68 mmol) were added to chloroform (amylene addition product) (20 mL) at 0° C., and the mixture was stirred at the same temperature for 10 minutes. Tetrahydrofuran-3-ylmethylamine (199 mg, 1.97 mmol) was added to the mixture at room temperature, and the mixture was stirred for 18 hours. Then, water was added thereto, and the mixture was extracted twice with ethyl acetate. The organic layer was sequentially washed with water and saturated saline water, dried over anhydrous sodium sulfate, and then concentrated under reduced pressure. The residue was applied to a silica gel column chromatography to obtain 300 mg of N-(tetrahydrofuran-3-ylmethyl)-5-(2-phenylbenzyl)isoxazole-3-carboxamide (hereinafter, referred to as Compound of Present Invention (326)) represented by the following formula.

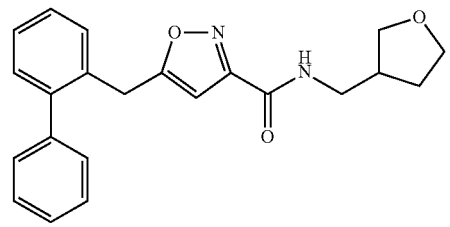

(326)

$^1$H-NMR (CDCl$_3$, TMS, δ(ppm)): 1.60-1.71 (1H, m), 2.00-2.12 (1H, m), 2.48-2.61 (1H, m), 3.43 (2H, dd), 3.56 (1H, dd), 3.75 (1H, dd), 3.81-3.92 (2H, m), 4.06 (2H, s), 6.22 (1H, s), 6.86 (1H, br s), 7.20-7.46 (9H, m)

Production Example 314

5-(3-Phenylbenzyl)isoxazole-3-carboxylic acid (500 mg, 1.79 mmol), 1-hydroxybenzotriazole (290 ng, 2.15 mmol), 1-ethyl-3-(3-dimethylaminopropyl) carbodiimide hydrochloride (410 mg, 2.15 mmol) and triethylamine (0.37 mL, 2.68 mmol) were added to chloroform (amylene addition product) (12 mL) at 0° C., and the mixture was stirred at the same temperature for 10 minutes. Tetrahydrofuran-3-ylmethylamine (199 mg, 1.97 mmol) was added to the mixture at room temperature, and the mixture was stirred for 18 hours. Then, water was added thereto, and the mixture was extracted twice with ethyl acetate. The organic layer was sequentially washed with water and saturated saline water, dried over anhydrous sodium sulfate, and then concentrated under reduced pressure. The residue was applied to a silica gel column chromatography to obtain 300 mg of N-(tetrahydrofuran-3-ylmethyl)methyl-5-(3-phenylbenzyl)isoxazole-3-carboxamide (hereinafter, referred to as Compound of Present Invention (327)) represented by the following formula.

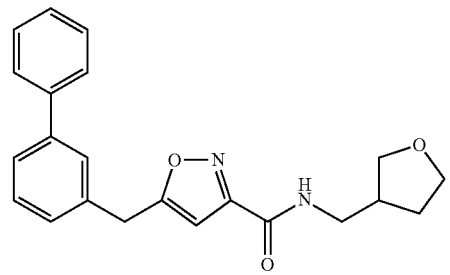

(327)

$^1$H-NMR (CDCl$_3$, TMS, δ(ppm)): 1.58-1.72 (1H, m), 1.98-2.12 (1H, m), 2.45-2.62 (1H, m), 3.38-3.49 (2H, m), 3.52-3.62 (1H, m), 3.70-3.95 (3H, m), 4.18 (2H, s), 6.44 (1H, s), 6.89 (1H, br s), 7.20-7.60 (9H, m)

Production Example 315

5-(3-Methylbenzyl)isoxazole-3-carboxylic acid (100 mg, 0.42 mmol), tetrahydrofuran-3-ylmethylamine (52 mg, 0.50 mmol), triethylamine (0.15 mL, 1.05 mmol) and 1-hydroxybenzotriazole (6 mg, 0.04 mmol) were added to chloroform (amylene addition product) (3 mL) at 0° C., and the mixture was stirred at the same temperature for 10 minutes. 1-Ethyl-3-(3-dimethylaminopropyl) carbodiimide hydrochloride (97 mg, 0.50 mmol) was added to the mixture at room temperature, and the mixture was stirred for 18 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 53 mg of N-(tetrahydrofuran-3-ylmethyl)-5-(3-methylbenzyl)isoxazole-3-carboxamide (hereinafter, referred to as Compound of Present Invention (328)) represented by the following formula.

(328)

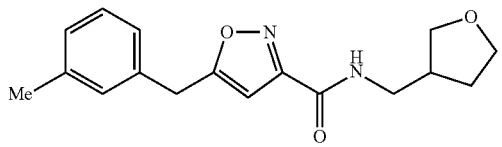

¹H-NMR (CDCl₃, TMS, δ(ppm)): 1.60-1.72 (1H, m), 2.00-2.12 (1H, m), 2.34 (3H, s), 2.48-2.62 (1H, m), 3.40-3.48 (2H, m), 3.52-3.60 (1H, m), 3.70-3.80 (1H, m), 3.81-3.95 (2H, m), 4.07 (2H, s), 6.39 (1H, s), 6.89 (1H, br s), 7.00-7.15 (3H, m), 7.20-7.26 (1H, m)

Production Example 316

5-(4-Methylbenzyl)isoxazole-3-carboxylic acid (100 mg, 0.42 mmol), tetrahydrofuran-3-ylmethylamine (52 mg, 0.50 mmol), triethylamine (0.15 mL, 1.05 mmol) and 1-hydroxybenzotriazole (6 mg, 0.04 mmol) were added to chloroform (amylene addition product) (3 mL) at 0° C., and the mixture was stirred at the same temperature for 10 minutes. 1-Ethyl-3-(3-dimethylaminopropyl) carbodiimide hydrochloride (97 mg, 0.50 mmol) was added to the mixture at room temperature, and the mixture was stirred for 18 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 49 mg of N-(tetrahydrofuran-3-ylmethyl)-5-(4-methylbenzyl)isoxazole-3-carboxamide (hereinafter, referred to as Compound of Present Invention (329)) represented by the following formula.

(329)

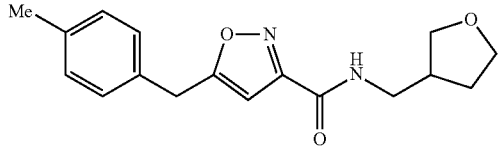

¹H-NMR (CDCl₃, TMS, δ(ppm)): 1.60-1.70 (1H, m), 2.01-2.12 (1H, m), 2.34 (3H, s), 2.50-2.62 (1H, m), 3.40-3.48 (2H, m), 3.55-3.60 (1H, m), 3.72-3.80 (1H, m), 3.81-3.92 (2H, m), 4.07 (2H, s), 6.37 (1H, s), 6.89 (1H, br s), 7.10-7.18 (4H, m)

Production Example 317

5-(2-Methylbenzyl)isoxazole-3-carboxylic acid (100 mg, 0.42 mmol), tetrahydrofuran-3-ylmethylamine (52 mg, 0.50 mmol), triethylamine (0.15 mL, 1.05 mmol) and 1-hydroxybenzotriazole (6 mg, 0.04 mmol) were added to chloroform (amylene addition product) (3 mL) at 0° C., and the mixture was stirred at the same temperature for 10 minutes. 1-Ethyl-3-(3-dimethylaminopropyl) carbodiimide hydrochloride (97 mg, 0.50 mmol) was added to the mixture at room temperature, and the mixture was stirred for 18 hours. Then, water was added thereto, and the mixture was extracted twice with ethyl acetate. The organic layer was sequentially washed with 0.5 mol/L hydrochloric acid and saturated saline water, dried over anhydrous sodium sulfate, and then concentrated under reduced pressure. The residue was applied to a silica gel column chromatography to obtain 45 mg of N-(tetrahydrofuran-3-ylmethyl)-5-(2-methylbenzyl)isoxazole-3-carboxamide (hereinafter, referred to as Compound of Present Invention (330)) represented by the following formula.

(330)

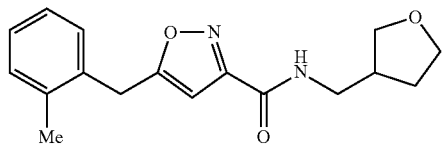

¹H-NMR (CDCl₃, TMS, δ(ppm)): 1.60-1.71 (1H, m), 2.00-2.12 (1H, m), 2.29 (3H, s), 2.48-2.60 (1H, m), 3.40-3.48 (2H, m), 3.55-3.60 (1H, m), 3.72-3.80 (1H, m), 3.81-3.93 (2H, m), 4.10 (2H, s), 6.28 (1H, s), 6.89 (1H, br s), 7.14-7.22 (4H, m)

Production Example 318

5-[3-(2-Naphthyl)propyl]isoxazole-3-carboxylic acid (0.42 g, 1.5 mmol), (3-methyloxetan-3-yl)methylamine (0.18 g, 1.8 mmol) and 1-hydroxybenzotriazole (0.02 g, 0.15 mmol) were added to chloroform (amylene addition product) (5.0 mL). 1-Ethyl-3-(3-dimethylaminopropyl) carbodiimide hydrochloride (0.34 g, 1.8 mmol) was added to the mixture at room temperature, and the mixture was stirred overnight. Then, dilute hydrochloric acid was added thereto, and the mixture was extracted twice with chloroform. The organic layer was passed through a short column to remove impurities, and then concentrated under reduced pressure. The residue was applied to a silica gel column chromatography to obtain 0.49 g of N-(3-methyloxetan-3-ylmethyl)-5-[3-(2-naphthyl)propyl]isoxazole-3-carboxamide (hereinafter, referred to as Compound of Present Invention (332)) represented by the following formula.

(332)

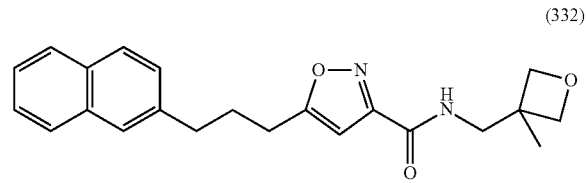 [SMILES: CC1(CNC(=O)c2cc(CCCc3ccc4ccccc4c3)on2)COC1]

¹H-NMR (CDCl₃, TMS, δ(ppm)): 1.36 (3H, s), 2.10-2.18 (2H, m), 2.82-2.88 (4H, m), 3.65 (2H, d), 4.41 (2H, d), 4.54 (2H, d), 6.49 (1H, s), 7.07 (1H, brs), 7.31-7.33 (1H, m), 7.41-7.49 (2H, m), 7.62 (1H, s), 7.77-7.82 (3H, m)

Production Example 319

5-(2-Naphthylmethoxymethyl)isoxazole-3-carboxylic acid (0.57 g, 2.0 mmol), (3-methyloxetan-3-yl)methylamine (0.24 g, 2.4 mmol) and 1-hydroxybenzotriazole (0.03 g, 0.2 mmol) were added to chloroform (amylene addition product) (6.0 mL). 1-Ethyl-3-(3-dimethylaminopropyl) carbodiimide hydrochloride (0.46 g, 2.4 mmol) was added to the mixture at room temperature, and the mixture was stirred overnight. Then, dilute hydrochloric acid was added thereto, and the mixture was extracted twice with chloroform. The organic layer was passed through a short column to remove impurities, and then concentrated under reduced pressure. The residue was applied to a silica gel column chromatography to obtain 0.67 g of N-(3-methyloxetan-3-ylmethyl)-5-(2-naphthylmethoxymethyl)isoxazole-3-carboxamide (hereinafter, referred to as Compound of Present Invention (333)) represented by the following formula.

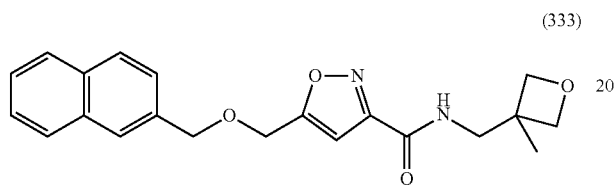

(333)

$^1$H-NMR (CDCl$_3$, TMS, δ(ppm)): 1.36 (3H, s), 3.66 (2H, d), 4.42 (2H, d), 4.54 (2H, d), 4.68 (2H, s), 4.77 (2H, s), 6.76 (1H, s), 7.10 (1H, brs), 7.46-7.52 (3H, m), 7.79 (1H, s), 7.83-7.87 (3H, m)

Production Example 320

5-Benzyloxymethylisoxazole-3-carboxylic acid (0.24 g, 1.0 mmol), (3-methyloxetan-3-yl)methylamine (0.12 g, 1.2 mmol) and 1-hydroxybenzotriazole (0.01 g, 0.1 mmol) were added to chloroform (amylene addition product) (2.5 mL). 1-Ethyl-3-(3-dimethylaminopropyl) carbodiimide hydrochloride (0.24 g, 1.2 mmol) was added to the mixture at room temperature, and the mixture was stirred overnight. Then, dilute hydrochloric acid was added thereto, and the mixture was extracted twice with chloroform. The organic layer was passed through a short column to remove impurities, and then concentrated under reduced pressure. The residue was applied to a silica gel column chromatography to obtain 0.29 g of N-(3-methyloxetan-3-ylmethyl)-5-benzyloxymethylisoxazole-3-carboxamide (hereinafter, referred to as Compound of Present Invention (334)) represented by the following formula.

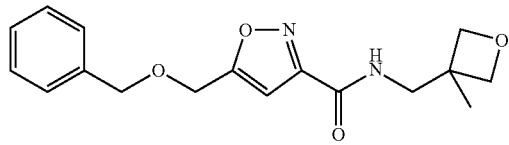

(334)

$^1$H-NMR (CDCl$_3$, TMS, δ(ppm)): 1.37 (3H, s), 3.66 (2H, d), 4.42 (2H, d), 4.54 (2H, d), 4.61 (2H, s), 4.65 (2H, s), 6.74 (1H, s), 7.08 (1H, brs), 7.31-7.40 (5H, m)

Production Example 321

5-Benzyloxymethylisoxazole-3-carboxylic acid (0.24 g, 1.0 mmol), 4-amino-2,2-dimethyltetrahydropyran (0.18 ml, 1.2 mmol) and 1-hydroxybenzotriazole (0.01 g, 0.1 mmol) were added to chloroform (amylene addition product) (2.5 mL). 1-Ethyl-3-(3-dimethylaminopropyl) carbodiimide hydrochloride (0.24 g, 1.2 mmol) was added to the mixture at room temperature, and the mixture was stirred overnight. Then, dilute hydrochloric acid was added thereto, and the mixture was extracted twice with chloroform. The organic layer was passed through a short column to remove impurities, and then concentrated under reduced pressure. The residue was applied to a silica gel column chromatography to obtain 0.29 g of N-(2,2-dimethyltetrahydropyran-4-yl)-5-benzyloxymethylisoxazole-3-carboxamide (hereinafter, referred to as Compound of Present Invention (335)) represented by the following formula.

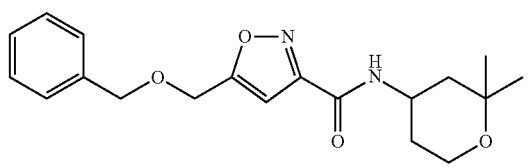

(335)

$^1$H-NMR (CDCl$_3$, TMS, δ(ppm)): 1.26 (3H, s), 1.29 (3H, s), 1.33-1.40 (1H, m), 1.41-1.52 (1H, m), 1.89-2.00 (2H, m), 3.72-3.84 (2H, m), 4.27-4.38 (1H, m), 4.61 (2H, s), 4.65 (2H, s), 6.62 (1H, br s), 6.72 (1H, s), 7.30-7.40 (5H, m)

Production Example 322

1-Hydroxybenzotriazole (0.01 g, 0.08 mmol) was added to 2.0 ml of a chloroform (amylene addition product) solution of 5-[(5-benzothiophenyl)methoxymethyl]isoxazole-3-carboxylic acid (0.24 g, 0.83 mmol), and the mixture was stirred at room temperature for 15 minutes. Tetrahydrofuran-3-ylmethylamine hydrochloride (0.14 g, 1.0 mmol) and triethylamine (0.14 mL, 1.0 mmol) were added to the mixture at room temperature, and the mixture was stirred for 30 minutes. 1-Ethyl-3-(3-dimethylaminopropyl) carbodiimide hydrochloride (0.19 g, 1.0 mmol) was further added thereto at room temperature, and the mixture was stirred overnight. Then, 1 N hydrochloric acid was added thereto, and the mixture was extracted with chloroform. The organic layer was dried over anhydrous magnesium sulfate, and then concentrated under reduced pressure. The residue was applied to a silica gel column chromatography to obtain 0.13 g of N-(tetrahydrofuran-3-ylmethyl)-5-[(5-benzothiophenyl)methoxymethyl]isoxazole-3-carboxamide (hereinafter, referred to as Compound of Present Invention (336)) represented by the following formula.

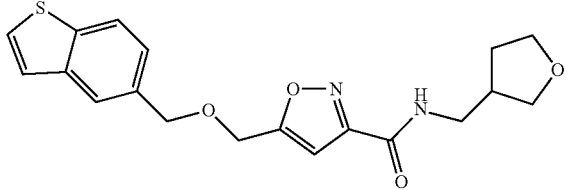

(336)

$^1$H-NMR (CDCl$_3$, TMS) δ(ppm): 7.88 (1H, d), 7.80 (1H, s), 7.48 (1H, d), 7.34 (2H, dt), 6.97-6.90 (1H, m), 6.74 (1H, s), 4.73 (2H, s), 4.67 (2H, s), 3.92 (1H, td), 3.86 (1H, dd), 3.77 (1H, dd), 3.59 (1H, dd), 3.47 (2H, t), 2.63-2.53 (1H, m), 2.10 (1H, tt), 1.68 (1H, tt)

Production Example 323

3-Aminomethyloxetane hydrochloride (0.15 g, 1.2 mmol) and triethylamine (0.17 mL, 1.2 mmol) were added to chloroform (amylene addition product) (2.5 mL), and the mixture was stirred at room temperature for 30 minutes. 5-Benzyloxymethylisoxazole-3-carboxylic acid (0.24 g, 1.0 mmol), 1-hydroxybenzotriazole (0.01 g, 0.1 mmol) and 1-ethyl-3-(3-dimethylaminopropyl) carbodiimide hydrochloride (0.24 g, 1.2 mmol) were added to the mixture at room temperature, and the mixture was stirred overnight. Then, dilute hydrochloric acid was added thereto, and the mixture was extracted twice with chloroform. The organic layer was passed through a short column to remove impurities, and then concentrated under reduced pressure. The residue was applied to a silica gel column chromatography to obtain 0.19 g of N-(oxetan-3-ylmethyl)-5-benrzyloxymethylisoxazole-3-carboxamide (hereinafter, referred to as Compound of Present Invention (337)) represented by the following formula.

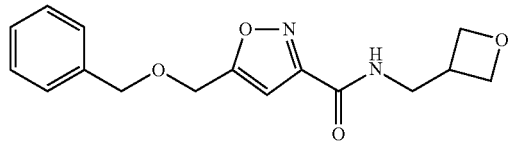

(337)

$^1$H-NMR (CDCl$_3$, TMS, δ(ppm)): 3.23-3.33 (1H, m), 3.75 (2H, t), 4.47 (2H, t), 4.61 (2H, s), 4.65 (2H, s), 4.81-4.84 (2H, m), 6.73 (1H, s), 7.05 (1H, brs), 7.30-7.40 (5H, m)

Production Example 324

A 1.6 mol/L-n-butyllithium hexane solution (1.9 mL, 3.00 mmol) was added dropwise to a tetrahydrofuran (7 mL) solution of N-(tetrahydrofuran-3-ylmethyl)-5-(2-naphthylmethoxymethyl)isoxazole-3-carboxamide (0.5 g, 1.36 mmol) at −65° C. or less, under a nitrogen atmosphere, and the mixture was stirred at −60° C. or less for 1 hour. Then, iodomethane (0.14 mL, 1.77 mL) was added thereto, and the mixture was stirred overnight while slowly returning to room temperature. The reaction mixture was poured into 1 mol/L hydrochloric acid under ice cooling, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 0.016 g of N-(tetrahydrofuran-3-ylmethyl)-5-(2-naphthylmethoxymethyl)-4-ethyl-isoxazole-3-carboxamide (hereinafter, referred to as Compound of Present Invention (338)) represented by the following formula.

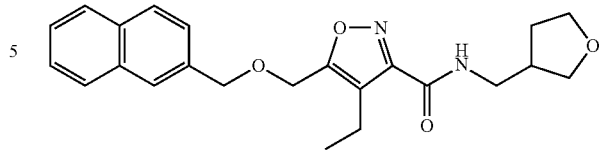

(338)

$^1$H-NMR(CDCl$_3$, TMS, δ(ppm)): 1.19 (t, 3H), 1.65-1.72 (m, 1H), 2.04-2.13 (m, 1H), 2.56-2.61 (m, 1H), 2.71 (q, 2H), 3.44-3.49 (m, 2H), 3.57-3.62 (m, 1H), 3.74-3.80 (m, 1H), 3.84-3.94 (m, 2H), 4.63 (s, 2H), 4.74 (s, 2H), 6.97 (brs, 1H), 7.44-7.51 (m, 3H), 7.75-7.87 (m, 4H)

Production Example 325

5-Propargyloxymethylisoxazole-3-carboxylic acid (2.88 g, 15.9 mmol), tetrahydrofuran-3-ylmethylamine hydrochloride (2.72 g, 19.8 mmol), triethylamine (1.94 g, 19.8 mmol) and 1-hydroxybenzotriazole (0.22 g, 1.59 mmol) were added to chloroform (amylene addition product) (30 mL). 1-Ethyl-3-(3-dimethylaminopropyl) carbodiimide hydrochloride (3.80 g, 19.8 mmol) was added to the mixed liquid at room temperature, and then the mixture was stirred at room temperature overnight. Thereafter, the resulting mixture was concentrated under reduced pressure. Dilute hydrochloric acid was added to the reaction mixture, and the mixture was extracted twice with ethyl acetate. The organic layer was washed with saturated saline water, dried over anhydrous sodium sulfate and then filtered, and the filtrate was concentrated under reduced pressure. The residue was applied to a silica gel column chromatography to obtain 2.95 g of N-(tetrahydrofuran-3-ylmethyl)-5-propargyloxymethylisoxazole-3-carboxamide (hereinafter, referred to as Compound of Present Invention (339)) represented by the following formula.

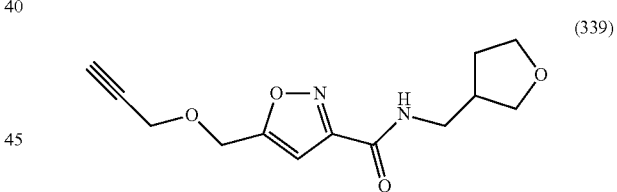

(339)

$^1$H-NMR (CDCl$_3$, TMS, δ(ppm)): 1.62-1.73 (m, 1H), 2.04-2.14 (m, 1H), 2.52-2.63 (m, 2H), 3.44-3.49 (m, 2H), 3.59 (dd, 1H), 3.73-3.80 (m, 1H), 3.83-3.95 (m, 2H), 4.25 (d, 2H), 4.75 (d, 2H), 6.75 (s, 1H), 6.94 (br s, 1H)

Next, production examples of intermediate compounds are shown as reference production examples. Herein, Et represents an ethyl group.

Reference Production Example 1

Triethylamine (1.6 mL) and tetrahydrofuran-3-ylmethylamine hydrochloride (1.12 g, 8.14 mmol) were added to an N,N-dimethylformamide (6 mL) solution of ethyl 5-pent-1-ynyl-1,3,4-thiadiazole-2-carboxylate (950 mg, 4.24 mmol). The mixture was stirred at 40° C. for 20 minutes under ultrasonic irradiation, and cooled. Then, the mixture was diluted with ethyl acetate, and sequentially washed with 3% hydrochloric acid and saturated saline water, and then the organic layer was dried over anhydrous sodium sulfate. The dried matter was concentrated under reduced pressure, and the residue was applied to a silica gel column chromatography to obtain 850 mg of N-(tetrahydrofuran-3-ylmethyl)-5-(pent-1-ynyl)-1,3,4-thiadiazole-2-carboxamide represented by the following formula:

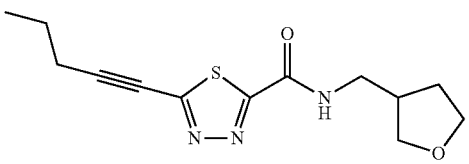 [SMILES: CCCC#Cc1nnc(C(=O)NCC2CCOC2)s1]

as a crude product. The crude product was subjected to a next reaction as it was.

Reference Production Example 2

5-Chloro-1,3,4-thiadiazole-2-carboxylic acid ethyl ester (1.00 g, 5.19 mmol), 1-pentyne (530 mg, 7.79 mmol), triethylamine (2.9 mL, 20.8 mmol), copper iodide (20 mg, 0.10 mmol) and dichlorobis(triphenylphosphine)palladium (73 mg, 0.10 mmol) were added, and the mixture was stirred at room temperature for 7 hours and 30 minutes, under a nitrogen atmosphere. Water was added to the reaction mixture, and the mixture was extracted with ethyl acetate. The organic layer was sequentially washed with aqueous ammonia, 1.5% hydrochloric acid and saturated saline water, and then dried over anhydrous sodium sulfate. The residue was applied to a silica gel column chromatography to obtain 0.95 g of ethyl 5-pent-1-ynyl-1,3,4-thiadiazole-2-carboxylate represented by the following formula.

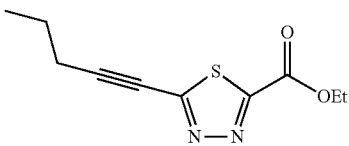

$^1$H-NMR (CDCl$_3$, TMS) δ(ppm): 1.07 (t, 3H), 1.46 (t, 3H), 1.70 (m, 2H), 2.51 (t, 2H), 4.52 (q, 2H)

Reference Production Example 3

Ethyl 2-chloro-2-(hydroxyimino) acetate (4.54 g, 30 mmol) and 1-pentyne (1.70 g, 25 mmol) were added to N,N-dimethylformamide (50 mL), and triethylamine (3.03 g, 30 mmol) was further added thereto at room temperature. Then, the mixture was stirred at room temperature overnight. Dilute hydrochloric acid was added to the reaction mixture, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.66 g of ethyl 5-propyl-isoxazole-3-carboxylate represented by the following formula.

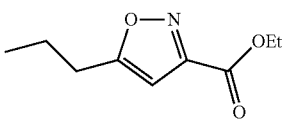

$^1$H-NMR (CDCl$_3$, TMS, δ(ppm)): 1.00 (3H, t), 1.42 (3H, t), 1.76 (2H, dt), 2.78 (2H, t), 4.43 (2H, q), 6.42 (1H, s)

Reference Production Example 4

Ethyl 5-propylisoxazole-3-carboxylate (0.66 g, 3.6 mmol) was added to ethanol (20 mL), and potassium hydroxide (0.40 g, 7.2 mmol) and water (10 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 0.27 g of 5-propylisoxazole-3-carboxylic acid represented by the following formula.

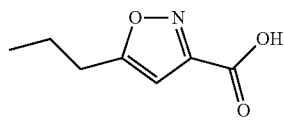

The resulting carboxylic acid was subjected to a next reaction without purification.

Reference Production Example 5

Ethyl 2-chloro-2-(hydroxyimino) acetate (4.54 g, 30 mmol) and 1-hexyne (2.05 g, 25 mmol) were added to N,N-dimethylformamide (50 mL). Triethylamine (3.03 g, 30 mmol) was added to the mixture at room temperature, and the mixture was stirred overnight. Then, dilute hydrochloric acid was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.71 g of ethyl 5-butylisoxazole-3-carboxylate represented by the following formula.

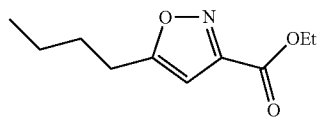

$^1$H-NMR (CDCl$_3$, TMS, δ(ppm)): 0.95 (3H, t), 1.40 (5H, m), 1.74-1.67 (2H, m), 2.80 (2H, t), 4.43 (2H, q), 6.40 (1H, s)

Reference Production Example 6

Ethyl 5-butylisoxazole-3-carboxylate (0.71 g, 3.6 mmol) was added to ethanol (20 mL), and potassium hydroxide (0.40 g, 7.2 mmol) and water (10 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 0.50 g of 5-butylisoxazole-3-carboxylic acid represented by the following formula.

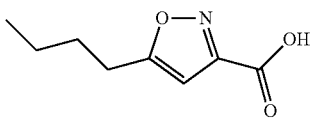

The resulting carboxylic acid was subjected to a next reaction without purification.

Reference Production Example 7

Ethyl 2-chloro-2-(hydroxyimino) acetate (4.54 g, 30 mmol) and 1-heptyne (2.40 g, 25 mmol) were added to N,N-dimethylformamide (50 mL). Triethylamine (3.03 g, 30 mmol) was added to the mixture at room temperature, and the mixture was stirred overnight. Then, dilute hydrochloric acid was added thereto, and the mixture was extracted twice with ethyl acetate. The organic layer was washed with saturated saline water, dried over anhydrous sodium sulfate, and then concentrated under reduced pressure to obtain ethyl 5-pentylisoxazole-3-carboxylate represented by the following formula:

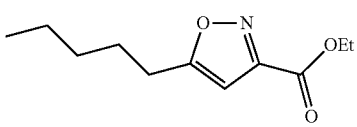

as a crude product. The crude product was added to ethanol (80 mL), and potassium hydroxide (1.68 g, 30 mmol) and water (40 mL) were added thereto, and then the mixture was stirred at room temperature overnight. Thereafter, the resulting mixture was concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 0.28 g of 5-pentylisoxazole-3-carboxylic acid represented by the following formula.

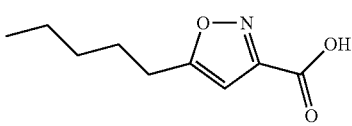

The resulting carboxylic acid was subjected to a next reaction without purification.

Reference Production Example 8

Ethyl nitroacetate (4.80 g, 40 mmol), benzylpropargylether (3.55 g, 27 mmol) and 1,4-diazabicyclo[2.2.2]octane (0.61 g, 5.4 mmol) were added to chloroform (amylene addition product) (10 mL). The mixture was heated and refluxed for 48 hours, and then cooled to room temperature. Dilute hydrochloric acid was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 5.37 g of ethyl 5-benzyloxymaethylisoxazole-3-carboxylate represented by the following formula.

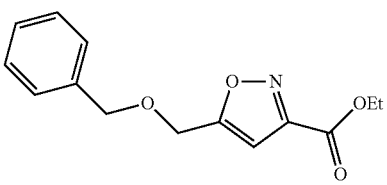 [SMILES: CCOC(=O)c1cc(COCc2ccccc2)on1]

$^1$H-NMR (CDCl$_3$, TMS, δ(ppm)): 1.42 (3H, t), 4.45 (2H, q), 4.62 (2H, s), 4.67 (2H, s), 6.70 (1H, d), 7.33-7.39 (5H, m)

Reference Production Example 9

Ethyl 5-benzyloxymethylisoxazole-3-carboxylate (10.9 g, 42 mmol) was added to ethanol (80 mL), and potassium hydroxide (3.49 g, 62.3 mmol) and water (40 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography and crystallized with t-butyl methyl ether/hexane to obtain 8.27 g of 5-benzyloxymethylisoxazole-3-carboxylic acid represented by the following formula.

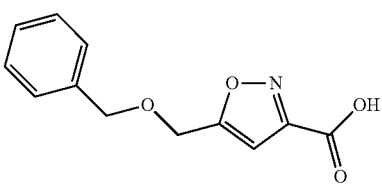 [SMILES: O=C(O)c1cc(COCc2ccccc2)on1]

$^1$H-NMR (CDCl$_3$, TMS, δ(ppm)): 7.40-7.32 (5H, m), 6.75 (1H, d), 4.69 (2H, s), 4.64 (2H, s)

Reference Production Example 10

Ethyl nitroacetate (0.96 g, 8.2 mmol), cyclopentylpropargyl ether (0.81 g, 6.5 mmol) and 1,4-diazabicyclo[2.2.2]octane (0.18 g, 1.6 mmol) were added to chloroform (amylene addition product) (2 mL). The mixture was heated and refluxed for 24 hours and cooled to room temperature, then dilute hydrochloric acid was added thereto, and the mixture was extracted twice with ethyl acetate. The organic layer was washed with saturated saline water, dried over anhydrous sodium sulfate, and then concentrated under reduced pressure to obtain 0.36 g of ethyl 5-cyclopentyloxymethylisoxazole-3-carboxylate represented by the following formula.

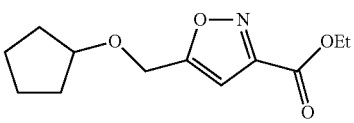 [SMILES: CCOC(=O)c1cc(COC2CCCC2)on1]

The resulting carboxylic acid was subjected to a next reaction without purification.

Reference Production Example 11

Ethyl 5-cyclopentyloxymethylisoxazole-3-carboxylate (0.36 g) was added to ethanol (2 mL), and potassium hydroxide (0.18 g, 1.5 mmol) and water (1 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.26 g of 5-cyclopentyloxymethylisoxazole-3-carboxylic acid represented by the following formula.

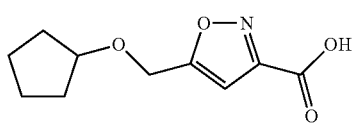 [SMILES: O=C(O)c1cc(COC2CCCC2)on1]

$^1$H-NMR (CDCl$_3$, TMS, δ(ppm)): 1.55-1.57 (2H, m), 1.68-1.80 (6H, m), 4.05-4.06 (1H, m), 4.62 (2H, s), 6.72 (1H, s)

Reference Production Example 12

Ethyl nitroacetate (1.49 g, 12.5 mmol), (2-naphthylmethyl)propargyl ether (1.96 g, 10 mmol) and 1,4-diazabicyclo[2.2.2]octane (0.56 g, 5 mmol) were added to chloroform (amylene addition product) (3 mL). The mixture was heated and refluxed for 24 hours and cooled to room temperature, then dilute hydrochloric acid was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 1.58 g of ethyl 5-(2-naphthylmethoxymethyl)isoxazole-3-carboxylate represented by the following formula.

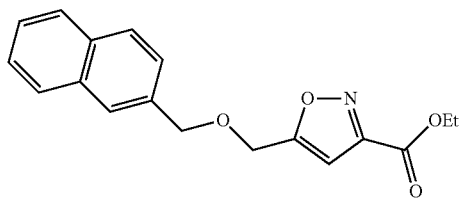 [SMILES: CCOC(=O)c1cc(COCc2ccc3ccccc3c2)on1]

$^1$H-NMR (CDCl$_3$, TMS, δ(ppm)): 1.42 (3H, t), 4.45 (2H, q), 4.70 (2H, d), 4.78 (2H, s), 6.72 (1H, s), 7.46-7.51 (3H, m), 7.83-7.85 (4H, m)

Reference Production Example 13

Ethyl 5-(2-naphthylmethoxymethyl)isoxazole-3-carboxylate (1.58 g, 5.1 mmol) was added to ethanol (60 mL), and potassium hydroxide (0.58 g, 10.2 mmol) and water (10 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography and crystallized with t-butyl methyl ether/hexane to obtain 1.23 g of 5-(2-naphthylmethoxymethyl)isoxazole-3-carboxylic acid represented by the following formula.

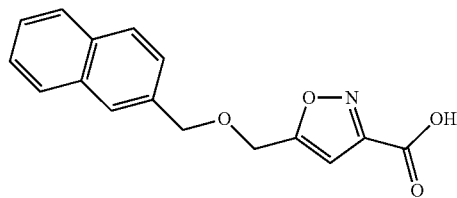

$^1$H-NMR (CDCl$_3$, TMS, δ(ppm)): 4.72 (2H, d), 4.80 (2H, s), 6.77 (1H, s), 7.47-7.52 (3H, m), 7.83-7.86 (4H, m)

Reference Production Example 14

Ethyl nitroacetate (1.49 g, 40 mmol), 5-phenyl-1-pentyne (1.44 g, 10.0 mmol) and 1,4-diazabicyclo[2.2.2]octane (0.56 g, 5.0 mmol) were added to chloroform (amylene addition product) (3 mL), and the mixture was heated and refluxed for 12 hours. Ethyl nitroacetate (1.49 g, 40 mmol) was added to the mixture, and the mixture was further heated and refluxed for 12 hours and then cooled to room temperature. Dilute hydrochloric acid was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 1.15 g of ethyl 5-(3-phenylpropyl)isoxazole-3-carboxylate represented by the following formula.

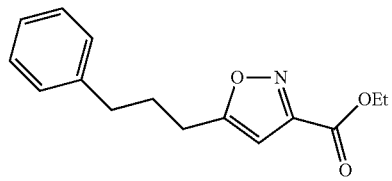 [SMILES: CCOC(=O)c1cc(CCCc2ccccc2)on1]

$^1$H-NMR (CDCl$_3$, TMS, δ(ppm)): 1.42 (3H, t), 2.04-2.08 (2H, m), 2.70 (2H, t), 2.82 (2H, t), 4.44 (2H, q), 6.42 (1H, s), 7.19-7.21 (3H, m), 7.29-7.32 (2H, m)

Reference Production Example 15

Ethyl 5-(3-phenylpropyl)isoxazole-3-carboxylate (1.15 g, 4.4 mmol) was added to ethanol (8 mL), and potassium hydroxide (0.49 g, 8.8 mmol) and water (4 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography and crystallized with t-butyl methyl ether/hexane to obtain 0.92 g of 5-(3-phenylpropyl)isoxazole-3-carboxylic acid represented by the following formula.

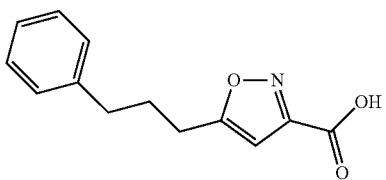 [SMILES: O=C(O)c1cc(CCCc2ccccc2)on1]

¹H-NMR (CDCl₃, TMS, δ(ppm)): 2.04-2.12 (2H, m), 2.71 (2H, t), 2.84 (2H, t), 6.47 (1H, s), 7.20-7.22 (3H, m), 7.30-7.33 (2H, m)

Reference Production Example 16

Ethyl nitroacetate (1.49 g, 12.5 mmol), phenylpropargyl ether (1.32 g, 10.0 mmol) and 1,4-diazabicyclo[2.2.2]octane (0.56 g, 5.0 mmol) were added to chloroform (amylene addition product) (3 mL), and the mixture was heated and refluxed for 24 hours. The mixture was cooled to room temperature, dilute hydrochloric acid was added thereto, and the mixture was extracted twice with ethyl acetate. The organic layer was washed with saturated saline water, dried over anhydrous sodium sulfate, and then concentrated under reduced pressure to obtain 1.13 g of ethyl 5-phenoxymethylisoxazole-3-carboxylate represented by the following formula.

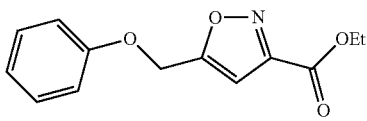 [SMILES: CCOC(=O)c1cc(COc2ccccc2)on1]

The resulting carboxylic acid was subjected to a next reaction without purification.

Reference Production Example 17

Ethyl 5-phenoxymethylisoxazole-3-carboxylate (1.13 g) obtained in Reference Production Example 16 was added to ethanol (10 mL), and potassium hydroxide (0.61 g, 11.0 mmol) and water (5 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 0.31 g of 5-phenoxymethylisoxazole-3-carboxylic acid represented by the following formula.

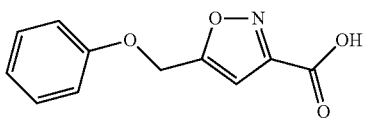 [SMILES: O=C(O)c1cc(COc2ccccc2)on1]

¹H-NMR (CDCl₃, TMS, δ(ppm)): 5.24 (2H, s), 6.82 (1H, s), 6.95-7.06 (3H, m), 7.32-7.34 (2H, m)

Reference Production Example 18

Ethyl nitroacetate (1.49 g, 40 mmol), 4-phenyl-1-butyne (1.30 g, 10.0 mmol) and 1,4-diazabicyclo[2.2.2]octane (0.56 g, 5.0 mmol) were added to chloroform (amylene addition product) (3 mL), and the mixture was heated and refluxed for 12 hours. Ethyl nitroacetate (1.49 g, 40 mmol) was added to the mixture, and the mixture was heated and refluxed for 12 hours and then cooled to room temperature. Dilute hydrochloric acid was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 1.51 g of ethyl 5-(2-phenylethyl)isoxazole-3-carboxylate represented by the following formula.

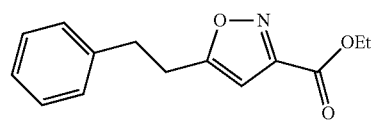 [SMILES: CCOC(=O)c1cc(CCc2ccccc2)on1]

¹H-NMR (CDCl₃, TMS, δ(ppm)): 1.41 (3H, t), 3.02-3.06 (2H, m), 3.12-3.14 (2H, m), 4.43 (2H, q), 6.36 (1H, d), 7.17-7.19 (2H, m), 7.22-7.24 (1H, m), 7.29-7.31 (2H, m)

Reference Production Example 19

Ethyl 5-(2-phenylethyl)isoxazole-3-carboxylate (1.15 g, 4.4 mmol) was added to ethanol (8 mL), and potassium hydroxide (0.49 g, 8.8 mmol) and water (4 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography and crystallized with t-butyl methyl ether/hexane to obtain 0.92 g of 5-(2-phenylethyl)isoxazole-3-carboxylic acid represented by the following formula.

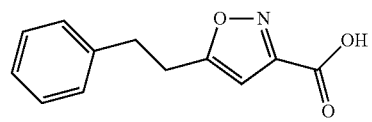 [SMILES: O=C(O)c1cc(CCc2ccccc2)on1]

¹H-NMR (CDCl₃, TMS, δ(ppm)): 3.05-3.08 (2H, m), 3.13-3.18 (2H, m), 6.41 (1H, s), 7.18-7.19 (2H, m), 7.23-7.24 (1H, m), 7.29-7.34 (2H, m)

Reference Production Example 20

Ethyl nitroacetate (1.49 g, 40 mmol), (2-phenylethyl)propargyl ether (1.60 g, 10.0 mmol) and 1,4-diazabicyclo[2.2.2]octane (0.56 g, 5.0 mmol) were added to chloroform (amylene addition product) (3 mL), and the mixture was heated and refluxed for 12 hours. Ethyl nitroacetate (1.49 g, 40 mmol) was added to the mixture, and the mixture was heated and refluxed for 12 hours and then cooled to room temperature. Dilute hydrochloric acid was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 2.62 g of ethyl 5-(2-phenylethoxymethyl)isoxazole-3-carboxylate represented by the following formula.

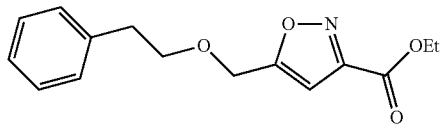 [SMILES: CCOC(=O)c1cc(COCCc2ccccc2)on1]

$^1$H-NMR (CDCl$_3$, TMS, δ(ppm)): 1.42 (3H, t), 2.92 (2H, t), 3.75 (2H, t), 4.44 (2H, q), 4.64 (2H, d), 6.57 (1H, s), 7.23-7.30 (5H, m)

Reference Production Example 21

Ethyl 5-(2-phenylethoxymethyl)isoxazole-3-carboxylate (2.62 g, 9.5 mmol) was added to ethanol (20 mL), and potassium hydroxide (0.1.08 g, 19.0 mmol) and water (10 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography and crystallized with t-butyl methyl ether/hexane to obtain 1.86 g of 5-(2-phenylethoxymethyl)isoxazole-3-carboxylic acid represented by the following formula.

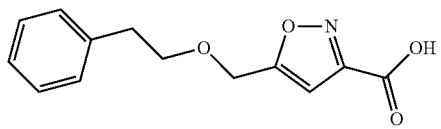 [SMILES: O=C(O)c1cc(COCCc2ccccc2)on1]

$^1$H-NMR (CDCl$_3$, TMS, δ(ppm)): 2.93 (2H, t), 3.78 (2H, t), 4.66 (2H, s), 6.62 (1H, s), 7.21-7.33 (5H, m)

Reference Production Example 22

Ethyl nitroacetate (1.49 g, 12.5 mmol), 2-phenylpropyne (1.16 g, 10 mmol) and 1,4-diazabicyclo[2.2.2]octane (0.56 g, 5.0 mmol) were added to chloroform (amylene addition product) (3 mL), and the mixture was heated and refluxed for 24 hours. Ethyl nitroacetate (1.49 g, 12.5 mmol) was added to the mixture, and the mixture was heated and refluxed for 24 hours, then cooled to room temperature, and concentrated under reduced pressure. The residue was applied to a silica gel column chromatography to obtain 5.37 g of ethyl 5-benzylisoxazole-3-carboxylate represented by the following formula.

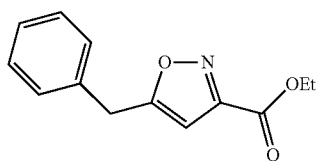 [SMILES: CCOC(=O)c1cc(Cc2ccccc2)on1]

$^1$H-NMR (CDCl$_3$, TMS, δ(ppm)): 1.38 (3H, t), 4.12 (2H, S), 4.39 (2H, q), 6.32 (1H, s), 7.23-7.35 (5H, m)

Reference Production Example 23

Ethyl 5-benzylisoxazole-3-carboxylate (563 mg, 2 mmol) was added to ethanol (8 mL), and potassium hydroxide (560 mg, 10 mmol) and water (2 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography and crystallized with t-butyl methyl ether/hexane to obtain 270 mg of 5-benzyloxymethylisoxazole-3-carboxylic acid represented by the following formula.

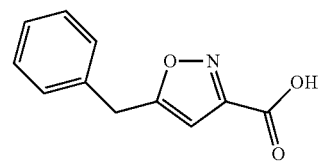 [SMILES: O=C(O)c1cc(Cc2ccccc2)on1]

$^1$H-NMR (CDCl$_3$, TMS, δ(ppm)): 4.14 (2H, S), 6.38 (1H, s), 7.29-7.36 (5H, m)

Reference Production Example 24

Ethyl nitroacetate (1.49 g, 12.5 mmol), (1-naphthylmethyl)propargyl ether (1.96 g, 10 mmol) and 1,4-diazabicyclo[2.2.2]octane (0.56 g, 5.0 mmol) were added to chloroform (amylene addition product) (3 mL). The mixture was heated and refluxed for 24 hours, then cooled to room temperature, and concentrated under reduced pressure. The residue was applied to a silica gel column chromatography to obtain 0.52 g of ethyl 5-(1-naphthylmethoxymethyl)isoxazole-3-carboxylate represented by the following formula.

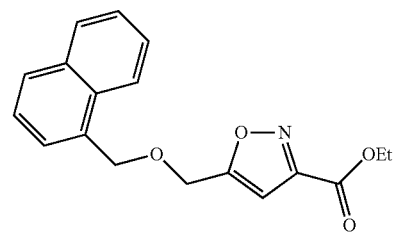 [SMILES: CCOC(=O)c1cc(COCc2cccc3ccccc23)on1]

$^1$H-NMR (CDCl$_3$, TMS, δ(ppm)): 141 (3H, t), 4.42 (2H, q), 4.68 (2H, S), 5.06 (2H, s), 6.67 (1H, s), 7.45-7.53 (4H, m), 7.83-7.86 (2H, m), 7.89 (1H, d)

Reference Production Example 25

Ethyl 5-(1-naphthylmethoxymethyl)isoxazole-3-carboxylate (520 mg, 1.7 mmol) was added to ethanol (8 mL), and potassium hydroxide (469 mg, 8.4 mmol) and water (2 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 460 mg of 5-(1-naphthyl-methoxymethyl)isoxazole-3-carboxylic acid represented by the following formula.

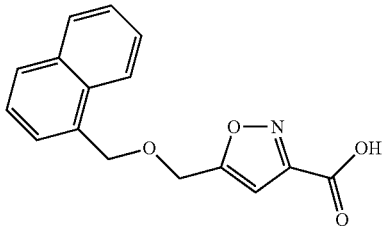 [SMILES: O=C(O)c1cc(COCc2cccc3ccccc23)on1]

The resulting carboxylic acid was used in a next step without purification.

Reference Production Example 26

Ethyl nitroacetate (3.0 g, 25.0 mmol), [1-(2-naphthyl)ethyl]propargyl ether (4.2 g, 20 mmol) and 1,4-diazabicyclo[2.2.2]octane (0.45 g, 4.0 mmol) were added to chloroform (amylene addition product) (7 mL). The mixture was heated and refluxed for 24 hours, then cooled to room temperature, and concentrated under reduced pressure. The residue was applied to a silica gel column chromatography to obtain 4.29 g of ethyl 5-[1-(2-naphthyl)ethoxymethyl]isoxazole-3-carboxylate represented by the following formula.

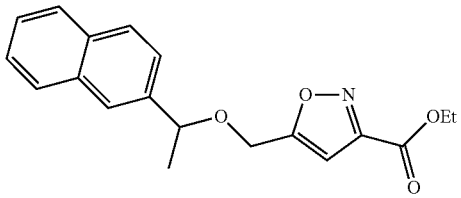 [SMILES: CCOC(=O)c1cc(COC(C)c2ccc3ccccc3c2)on1]

$^1$H-NMR (CDCl$_3$, TMS, δ(ppm)): 1.40 (3H, t), 1.56 (3H, d), 4.42-4.55 (4H, m), 4.68 (1H, q), 6.68 (1H, m), 7.47-7.51 (3H, m), 7.74 (1H, br. S), 7.82-7.88 (3H, m)

Reference Production Example 27

Ethyl 5-[1-(2-naphthyl)ethoxymethyl]isoxazole-3-carboxylate (4.29 g, 13.2 mmol) was added to ethanol (40 mL), and potassium hydroxide (2.24 g, 40.0 mmol) and water (10 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 3.31 g of 5-[1-(2-naphthyl)ethoxymethyl]isoxazole-3-carboxylic acid represented by the following formula.

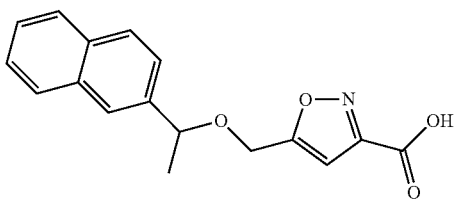 [SMILES: CC(OCc1cc(C(=O)O)no1)c1ccc2ccccc2c1]

$^1$H-NMR (CDCl$_3$, TMS, δ(ppm)): 1.59 (3H, d), 4.52 (2H, q), 4.71 (1H, q), 6.71 (1H, m), 7.50-7.52 (3H, m), 7.76 (1H, br.s), 7.84-7.90 (3H, m)

Reference Production Example 28

Phenol (0.21 g, 2.2 mmol) was dissolved in dimethylsulfoxide (2 mL), and potassium hydroxide (0.11 g, 2.1 mmol) was added thereto, and then the mixture was stirred at room temperature for 30 minutes. Ethyl 5-chloromethyl-2-thiazolecarboxylate (0.41 g, 2.0 mmol) was added thereto, and the mixture was stirred at 60° C. for 8 hours and then cooled to room temperature. Potassium hydroxide (0.59 g, 10.5 mmol) and water (10 mL) were further added thereto. The reaction mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 0.28 g of 5-phenoxymethyl-2-thiazolecarboxylic acid represented by the following formula.

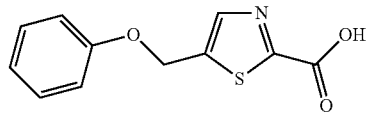 [SMILES: O=C(O)c1ncc(COc2ccccc2)s1]

$^1$H-NMR (CDCl$_3$, TMS, δ(ppm)): 5.28 (2H, s), 6.96-7.01 (3H, m), 7.27-7.33 (2H, m), 7.73 (1H, s)

Reference Production Example 29

Benzylalcohol (0.86 g, 8.0 mmol) was dissolved in dimethylsulfoxide (8 ml), and potassium hydroxide (0.45 g, 8.0 mmol) was added, and the mixture was stirred at room temperature for 30 minutes. Then, ethyl 5-chloromethyl-2-thiazolecarboxylate (0.82 g, 4.0 mmol) was added thereto, and the mixture was stirred at 60° C. for 8 hours. The mixture was cooled to room temperature, and potassium hydroxide (2.1 g, 40 mmol) and water (40 mL) were added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 0.11 g of 5-benzyloxymethyl-2-thiazolecarboxylic acid represented by the following formula.

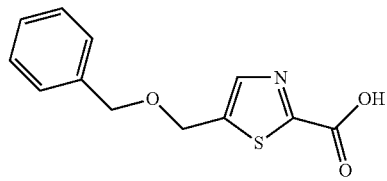 [SMILES: O=C(O)c1ncc(COCc2ccccc2)s1]

$^1$H-NMR (CDCl$_3$, TMS, δ(ppm)): 4.66 (2H, s), 4.79 (2H, d), 7.30-7.36 (5H, m), 7.65 (1H, d)

Reference Production Example 34

Ethyl 5-benzylisothiazole-3-carboxylate (0.23 g, 0.9 mmol) was added to ethanol (3.7 mL), and potassium hydroxide (0.10 g, 1.9 mmol) and water (1.9 mL) were further added thereto. The mixture was stirred at room temperature for 2 hours, then heated to 40° C. and stirred for 1 hour. 2 N Hydrochloric acid was added to the mixture, and the mixture was extracted with ethyl acetate. The organic layer was dried over anhydrous magnesium sulfate, and then concentrated under reduced pressure to obtain 0.13 g of 5-benzylisothiazole-3-carboxylic acid represented by the following formula.

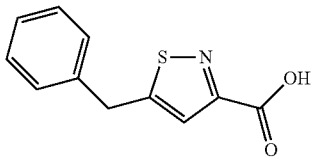 [SMILES: O=C(O)c1cc(Cc2ccccc2)sn1]

The resulting carboxylic acid was used in Production Example 56 without purification.

Reference Production Example 35

2-Oxo-1,3,4-oxathiazole-5-carboxylate (0.70 g, 4.0 mmol) and 3-phenyl-1-propyne (2.0 g, 17 mmol) were dissolved in 1,2-dichlorobenzene (11 mL). The mixture was stirred at 200° C. for 54 hours in a sealed tube, and then applied to a silica gel column chromatography to obtain 230 mg of ethyl 5-benzylisothiazole-3-carboxylate represented by the following formula.

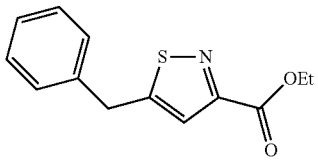

$^1$H-NMR (CDCl$_3$, TMS) δ(ppm): 7.55 (1H, t), 7.39-7.23 (5H, m), 4.42 (2H, q), 4.26-4.24 (2H, br), 1.41 (3H, t)

Reference Production Example 36

Ethyl 5-butylisothiazole-3-carboxylate (0.09 g, 0.4 mmol) was added to ethanol (1.6 mL), and potassium hydroxide (0.05 g, 0.8 mmol) and water (0.5 mL) were further added thereto. The mixture was stirred at room temperature for 2 hours, then 2 N hydrochloric acid was added, and the mixture was extracted with ethyl acetate. The organic layer was dried over anhydrous magnesium sulfate, and then concentrated under reduced pressure to obtain 0.08 g of 5-butylisothiazole-3-carboxylic acid represented by the following formula.

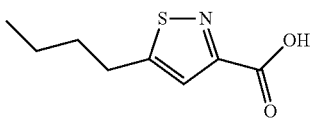

The resulting carboxylic acid was used in Production Example 57 without purification.

Reference Production Example 37

2-Oxo-1,3,4-oxathiazole-5-carboxylate (0.70 g, 4.0 mmol) and 1-hexyne (1.8 ml, 16 mmol) were dissolved in 11 ml of 1,2-dichlorobenzene. The mixture was stirred at 200° C. for 26.5 hours in a sealed tube, and then applied to a silica gel column chromatography to obtain 85 mg of ethyl 5-butylisothiazole-3-carboxylate represented by the following formula.

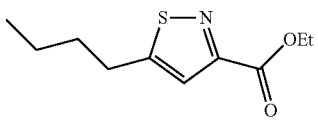

$^1$H-NMR (CDCl$_3$, TMS) δ(ppm): 7.56 (1H, t), 4.43 (2H, q), 2.94 (2H, t), 1.75-1.68 (2H, m), 1.48-1.37 (4H, m), 0.95 (3H, t)

Reference Production Example 38

Ethyl nitroacetate (2.14 g, 0 mmol), 4-trifluoromethylbenzylpropargyl ether (2.14 g, 10 mmol) and 1,4-diazabicyclo[2.2.2]octane (0.22 g, 2 mmol) were added to chloroform (amylene addition product) (3 mL). The mixture was heated and refluxed for 48 hours and cooled to room temperature, then dilute hydrochloric acid was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 2.25 g of ethyl (4-trifluoromethylbenzylorymethyl)isoxazole-3-carboxylate represented by the following formula.

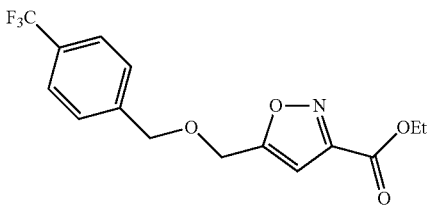 [SMILES: CCOC(=O)c1cc(COCc2ccc(C(F)(F)F)cc2)on1]

$^1$H-NMR (CDCl$_3$, TMS, δ(ppm)): 1.43 (3H, t), 4.43 (2H, q), 4.67 (2H, s), 4.71 (2H, s), 6.72 (1H, s), 7.53-7.61 (4H, m)

Reference Production Example 39

Ethyl 5-(4-trifluoromethylbenzyl)isoxazole-3-carboxylate (2.25 g, 7.5 mmol) was added to ethanol (75 mL), and potassium hydroxide (0.83 g, 14.9 mmol) and water (15 mL) were further added thereto, and then the mixture was stirred at room temperature overnight. Thereafter, the resulting mixture was concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 1.81 g of 5-(4-trifluoromethylbenzyloxymethyl)isoxazole-3-carboxylic acid represented by the following formula.

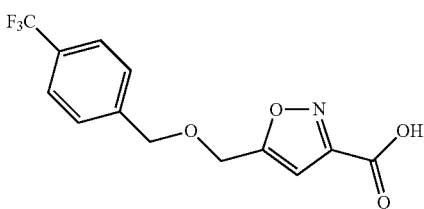 [SMILES: O=C(O)c1cc(COCc2ccc(C(F)(F)F)cc2)on1]

The resulting carboxylic acid was used in Production Example 61 without purification.

Reference Production Example 40

Ethyl nitroacetate (4.80 g, 40 mmol), 3-trifluoromethyl-propargyl ether (3.55 g, 27 mmol) and 1,4-diazabicyclo[2.2.2]octane (0.61 g, 5.4 mmol) were added to chloroform (amylene addition product) (10 mL), and the mixture was heated and refluxed for 48 hours. Thereafter, the reaction mixture was cooled to room temperature, dilute hydrochloric acid was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 5.37 g of ethyl 5-(3-trifluoromethylbenzyloxymethyl)isoxazole-3-carboxylate represented by the following formula.

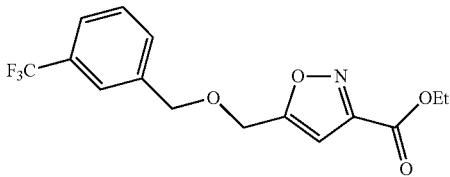 [SMILES: CCOC(=O)c1cc(COCc2cccc(C(F)(F)F)c2)on1]

$^1$H-NMR (CDCl$_3$, TMS, δ(ppm)): 1.41 (3H, t), 4.43 (2H, q), 4.65 (2H, s), 4.70 (2H, s), 6.70 (1H, s), 7.46-7.60 (4H, m)

Reference Production Example 41

Ethyl 5-(3-trifluoromethylbenzyloxymethyl)isoxazole-3-carboxylate (3.26 g, 10 mmol) was added to ethanol (60 mL), and potassium hydroxide (1.15 g, 20.5 mmol) and water (12 mL) were added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography and crystallized with t-butyl methyl ether/hexane to obtain 2.66 g of 5-(3-trifluoromethylbenzyloymethyl)isoxazole-3-carboxylic acid represented by the following formula.

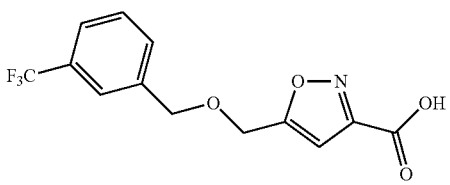 [SMILES: O=C(O)c1cc(COCc2cccc(C(F)(F)F)c2)on1]

$^1$H-NMR (CDCl$_3$, TMS, δ(ppm)): 4.68 (2H, s), 4.73 (2H, d), 6.77 (1H, s), 7.51-7.59 (4H, m)

Reference Production Example 42

Ethyl nitroacetate (198 mL, 1.78 mmol), propargyl alcohol (100 g, 1.78 mmol) and 1,4-diazabicyclo[2.2.2]octane (20.0 g, 178.3 mmol) were added to ethanol (1 L), and the mixture was heated at 80° C. for 16 hours. Thereafter, the mixture was cooled to room temperature, and the solvent was concentrated under reduced pressure. The residue was applied to a silica gel column chromatography to obtain 180 g of ethyl 5-hydroxymethylisoxazole-3-carboxylate represented by the following formula.

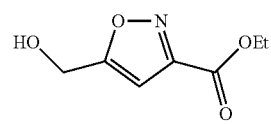

$^1$H-NMR (CDCl$_3$, TMS, δ(ppm)): 6.67 (s, 1H), 4.83 (d, 2H), 4.43 (q, 2H), 2.65 (brs, 1H), 1.41 (t, 3H)

Reference Production Example 43

60% Sodium hydride (2.45 g, 61.40 mmol) was added to dry N,N-dimethylformamide (40 ml) cooled to 0° C., under a nitrogen atmosphere, and a dry N,N-dimethylformamide (30 ml) solution of ethyl 5-hydroxymethylisoxazole-3-carboxylate (7 g, 40.89 mmol) was added dropwise thereto over 15 minutes, and then the mixture was further stirred for 30 minutes. 2-Chlorobenzyl bromide (8.4 g, 40.93 mmol) was added thereto, and the reaction mixture was heated to room temperature, and the mixture was stirred for 16 hours. The reaction mixture was poured into a saturated aqueous ammonium chloride solution, and the mixture was extracted twice with ethyl acetate. The organic layer was washed with water and saturated saline water, and then dried over anhydrous sodium sulfate. The solvent was concentrated under reduced pressure, and then the residue was applied to a silica gel column chromatography to obtain 3.9 g of ethyl 5-(2-chlorobenzyloxymethyl)isoxazole-3-carboxylate represented by the following formula.

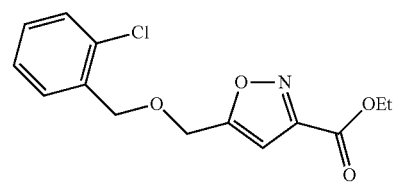 [SMILES: CCOC(=O)c1cc(COCc2ccccc2Cl)on1]

$^1$H-NMR (CDCl$_3$, TMS, δ(ppm)): 7.48 (d, 1H), 7.38 (d, 1H), 7.31-7.23 (m, 2H), 6.73 (s, 1H), 4.75 (s, 2H), 4.71 (s, 2H), 4.45 (q, 2H), 1.42 (t, 3H)

Reference Production Example 44

Ethyl 5-(2-chlorobenzyloxymethyl)isoxazole-3-carboxylate (4.0 g, 13.55 mmol) was added to ethanol (50 mL), and 2 N sodium hydroxide (30 mL) was added thereto, and then the mixture was stirred at room temperature for 16 hours. Thereafter, the resulting mixture was concentrated under reduced pressure. Dilute hydrochloric acid was added to the concentrate, the mixture was cooled to 0° C., and the precipitated solid was filtered. The solid was dried under reduced pressure to obtain 2.9 g of 5-(2-chlorophenoxymethyl)isoxazole-3-carboxylic acid represented by the following formula.

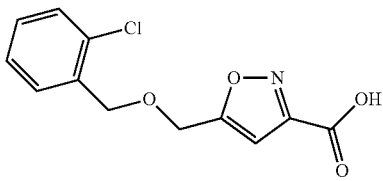 [SMILES: O=C(O)c1cc(COCc2ccccc2Cl)on1]

$^1$H-NMR (DMSO-d6, TMS, δ(ppm)): 14.1 (brs, 1H), 7.52-7.46 (m, 2H), 7.38-7.32 (m, 2H), 6.89 (s, 1H), 4.79 (s, 2H), 4.66 (s, 2H)

Reference Production Example 45

A reaction was carried out in the same manner using 3-chlorobenzyl bromide (8.4 g, 40.93 mmol), in place of 2-chlorobenzyl bromide in Reference Production Example 43 to obtain 4.4 g of ethyl 5-(3-chlorobenzyloxymethyl)isoxazole-3-carboxylate

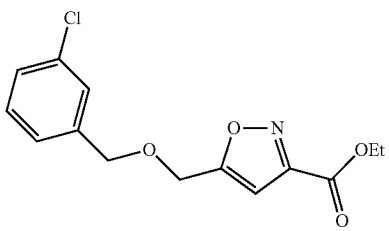

$^1$H-NMR (CDCl$_3$, TMS, δ(ppm)): 7.34-7.21 (m, 4H), 6.70 (s, 1H), 4.67 (s, 2H), 4.58 (s, 2H), 4.44 (q, 2H), 1.42 (t, 3H)

Reference Production Example 46

A reaction was carried out in the same manner using ethyl 5-(3-chlorobenzyloxymethyl)isoxazole-3-carboxylate (4.9 g, 16.61 mmol), in place of ethyl 5-(2-chlorobenzyloxymethyl)isoxazole-3-carboxylate in Reference Production Example 44 to obtain 4.4 g of 5-(3-chlorophenoxymethyl)isoxazole-3-carboxylic acid represented by the following formula.

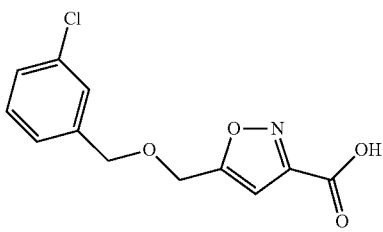

$^1$H-NMR (CDCl$_3$, TMS, δ(ppm)): 14.0 (brs, 1H), 7.42-7.36 (m, 3H), 7.31 (d, 1H), 6.81 (s, 1H), 4.75 (s, 2H), 4.59 (s, 2H)

Reference Production Example 47

A reaction was carried out in the same manner using 4-chlorobenzyl bromide (3.69 g, 17.9 mmol), in place of 2-chlorobenzyl bromide in Reference Production Example 43 to obtain 1.7 g of ethyl 5-(4-chlorobenzyloxymethyl)isoxazole-3-carboxylate represented by the following formula.

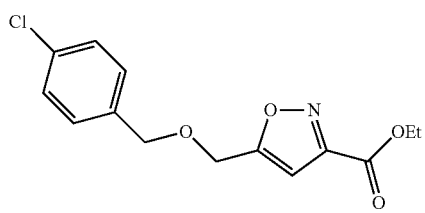 [SMILES: CCOC(=O)c1cc(COCc2ccc(Cl)cc2)on1]

$^1$H-NMR (CDCl$_3$, TMS, δ(ppm)): 7.34 (d, 2H), 7.29 (d, 2H), 6.68 (s, 1H), 4.65 (s, 2H), 4.57 (s, 2H), 4.45 (q, 2H), 1.42 (t, 3H)

Reference Production Example 48

A reaction was carried out in the same manner using ethyl 5-(4-chlorobenzyloxymethyl)isoxazole-3-carboxylate (2.3 g, 7.79 mmol), in place of ethyl 5-(2-chlorobenzyloxymethyl)isoxazole-3-carboxylate in Reference Production Example 44 to obtain 1.5 g of 5-(4-chlorophenoxymethyl)isoxazole-3-carboxylic acid represented by the following formula.

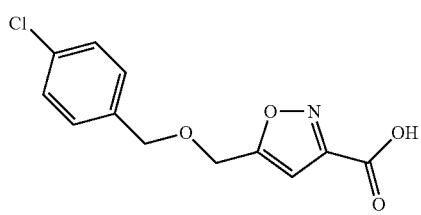 [SMILES: O=C(O)c1cc(COCc2ccc(Cl)cc2)on1]

$^1$H-NMR (CDCl$_3$, TMS, δ(ppm)): 14.0 (brs, 1H), 7.44-7.36 (m, 4H), 6.86 (s, 1H), 4.72 (s, 2H), 4.57 (s, 2H)

Reference Production Example 49

A reaction was carried out in the same manner using 3,4-dichlorobenzyl bromide (3.5 g, 14.6 mmol), in place of 2-chlorobenzyl bromide in Reference Production Example 43 to obtain 1.7 g of ethyl 5-(3,4-dichlorobenzyloxymethyl)isoxazole-3-carboxylate represented by the following formula.

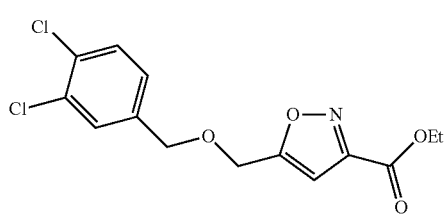 [SMILES: CCOC(=O)c1cc(COCc2ccc(Cl)c(Cl)c2)on1]

¹H-NMR (CDCl₃, TMS, δ(ppm)): 7.48 (d, 2H), 7.20 (dd, 1H), 6.7 (s, 1H), 4.7 (s, 2H), 4.6 (s, 2H), 4.45 (q, 2H), 1.42 (t, 3H)

Reference Production Example 50

A reaction was carried out in the same manner using ethyl 5-(3,4-dichlorobenzyloxymethyl)isoxazole-3-carboxylate (1.7 g, 3.34 mmol), in place of ethyl 5-(2-chlorobenzyloxymethyl)isoxazole-3-carboxylate in Reference Production Example 44 to obtain 1.7 g of 5-(3,4-dichlorobenzyloxymethyl)isoxazole-3-carboxylic acid represented by the following formula.

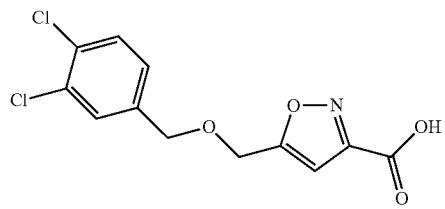 [SMILES: O=C(O)c1cc(COCc2ccc(Cl)c(Cl)c2)on1]

¹H-NMR (CDCl₃, TMS, δ(ppm)): 14.0 (brs, 1H), 7.70-7.60 (m, 2H), 7.40-7.30 (dd, 1H), 6.90 (s, 1H), 4.75 (s, 2H), 4.60 (s, 2H)

Reference Production Example 51

A reaction was carried out in the same manner using 3-fluorobenzyl bromide (3.97 g, 21.0 mmol), in place of 2-chlorobenzyl bromide in Reference Production Example 43 to obtain 1.1 g of ethyl 5-(3-fluorobenzyloxymethyl)isoxazole-3-carboxylate

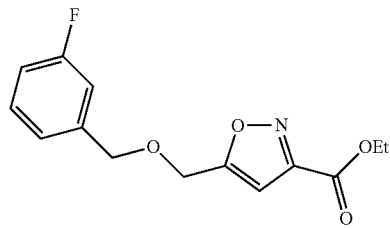

¹H-NMR (CDCl₃, TMS, δ(ppm)): 7.28-7.38 (m, 1H), 7.04-7.06 (m, 2H), 6.96-7.04 (m, 1H), 6.70 (s, 1H), 4.70 (s, 2H), 4.60 (s, 2H), 4.45 (q, 2H), 1.45 (t, 3H)

Reference Production Example 52

A reaction was carried out in the same manner using ethyl 5-(3-fluorobenzyloxymethyl)isoxazole-3-carboxylate (1.1 g, 3.34 mmol), in place of ethyl 5-(2-chlorobenzyloxymethyl)isoxazole-3-carboxylate in Reference Production Example 44 to obtain 0.9 g of 5-(3-fluorobenzyloxymethyl)isoxazole-3-carboxylic acid represented by the following formula.

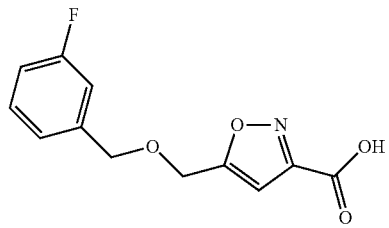 [SMILES: O=C(O)c1cc(COCc2cccc(F)c2)on1]

¹H-NMR (CDCl₃, TMS, δ(ppm)): 7.37-7.32 (m, 1H), 7.13-7.6.98 (m, 3H), 6.78 (s, 1H), 4.70 (s, 2H), 4.62 (s, 2H)

Reference Production Example 53

A reaction was carried out in the same manner using 3-bromobenzyl bromide (3.52 g, 14.1 mmol), in place of 2-chlorobenzyl bromide in Reference Production Example 43 to obtain 1.54 g of ethyl 5-(3-bromobenzyloxymethyl)isoxazole-3-carboxylate represented by the following formula.

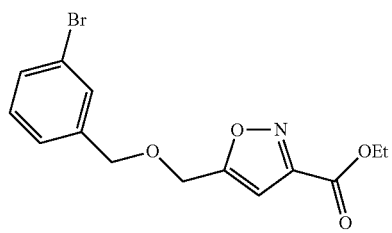 [SMILES: CCOC(=O)c1cc(COCc2cccc(Br)c2)on1]

¹H-NMR (CDCl₃, TMS, δ(ppm)): 7.50 (s, 1H), 7.44 (d, 1H), 7.25 (d, 2H), 6.70 (s, 1H), 4.67 (s, 2H), 4.57 (s, 2H), 4.45 (q, 2H), 1.43 (t, 3H)

Reference Production Example 54

A reaction was carried out in the same manner using ethyl 5-(3-bromobenzyloxymethyl)isoxazole-3-carboxylate (2.2 g, 6.47 mmol), in place of ethyl 5-(2-chlorobenzyloxymethyl)isoxazole-3-carboxylate in Reference Production Example 44 to obtain 1.4 g of 5-(3-bromorobenzylmethyl)isoxazole-3-carboxylic acid represented by the following formula.

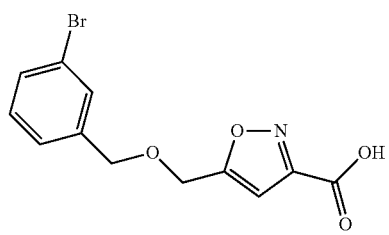 [SMILES: O=C(O)c1cc(COCc2cccc(Br)c2)on1]

¹H-NMR (DMSO-d6, TMS, δ(ppm)): 14.0 (brs, 1H), 7.52 (m, 2H), 7.33 (m, 2H), 6.88 (s, 1H), 4.70 (s, 2H), 4.60 (s, 2H)

Reference Production Example 55

A reaction was carried out in the same manner using 3-tirfluoromethoxybenzyl bromide (3.0 g, 11.68 mmol), in place of 2-chlorobenzyl bromide in Reference Production Example 43 to obtain 1.2 g of ethyl 5-(3-trifluoromethoxybenzyloxymethyl)isoxazole-3-carboxylate represented by the following formula.

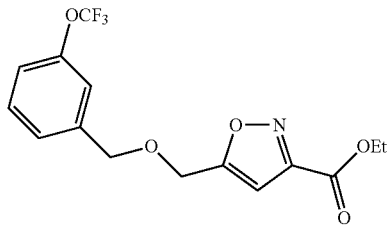 [SMILES: CCOC(=O)c1cc(COCc2cccc(OC(F)(F)F)c2)on1]

¹H-NMR (CDCl₃, TMS, δ(ppm)): 7.38 (t, 1H), 7.27 (d, 1H), 7.21 (s, 1H), 7.17 (d, 1H), 6.7 (s, 1H), 4.70 (s, 2H), 4.62 (s, 2H), 4.44 (q, 2H), 1.42 (t, 3H)

Reference Production Example 56

A reaction was carried out in the same manner using ethyl 5-(3-trifluoromethoxybenzyloxymethyl)isoxazole-3-carboxylat e (1.8 g, 5.21 mmol), in place of ethyl 5-(2-chlorobenzyloxymethyl)isoxazole-3-carboxylate in Reference Production Example 44 to obtain 1.1 g of 5-(3-trifluoromethoxybenzylmethyl)isoxazole-3-carboxylic acid represented by the following formula.

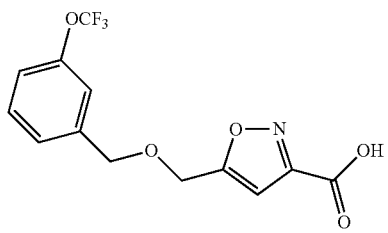 [SMILES: O=C(O)c1cc(COCc2cccc(OC(F)(F)F)c2)on1]

¹H-NMR (CDCl₃, TMS, δ(ppm)): 14.0 (brs, 1H), 7.50 (t, 1H), 7.38 (d, 1H), 7.33-7.29 (t, 2H), 6.87 (s, 1H) 4.75 (s, 2H), 4.63 (t, 2H)

Reference Production Example 57

A reaction was carried out in the same manner using 3-tirfluoromethylthiobenzyl bromide (3.5 g, 13.45 mmol), in place of 2-chlorobenzyl bromide in Reference Production Example 43 to obtain 0.2 g of ethyl 5-(3-trifluoromethylthiobenzyloxymethyl)isoxazole-3-carboxy late represented by the following formula.

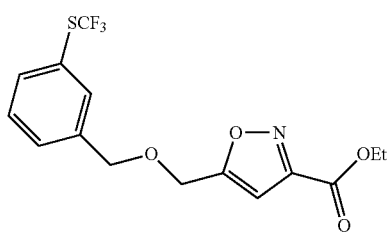

¹H-NMR (CDCl₃, TMS, δ(ppm)): 7.62 (m, 2H), 7.45 (m, 2H), 6.70 (s, 1H), 4.69 (s, 2H), 4.63 (s, 2H), 4.44 (q, 2H), 1.42 (t, 3H)

Reference Production Example 58

A reaction was carried out in the same manner using ethyl 5-(3-trifluoromethylthiobenzyloxymethyl)isoxazole-3-carboxylate (500 mg, 1.38 mmol), in place of ethyl 5-(2-chlorobenzyloxymethyl)isoxazole-3-carboxylate in Reference Production Example 44 to obtain 128 mg of 5-(3-trifluoromethylthiobenzylmethyl)isoxazole-3-carboxylic acid represented by the following formula.

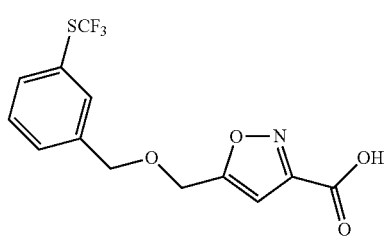

¹H-NMR (CDCl₃, TMS, δ(ppm)): 14.0 (brs, 1H), 7.67 (d, 2H), 7.56 (q, 2H), 6.87 (s, 1H), 4.76 (s, 2H), 4.65 (s, 2H)

Reference Production Example 59

A reaction was carried out in the same manner using 3-methylbenzyl bromide (2.7 g, 14.61 mmol), in place of 2-chlorobenzyl bromide in Reference Production Example 43 to obtain 1.6 g of ethyl 5-(3-methylbenzyloxymethyl)isoxazole-3-carboxylate represented by the following formula.

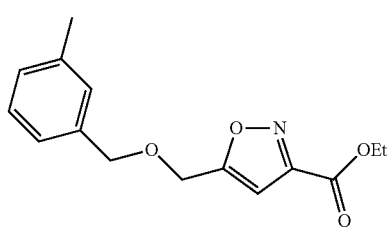 [SMILES: CCOC(=O)c1cc(COCc2cccc(C)c2)on1]

¹H-NMR (CDCl₃, TMS, δ(ppm)): 7.27-7.23 (m, 1H), 7.16-7.12 (m, 3H), 6.69 (s, 1H), 4.65 (s, 2H), 4.57 (s, 2H), 4.44 (q, 2H), 2.36 (s, 3H), 1.42 (t, 3H)

Reference Production Example 60

A reaction was carried out in the same manner using ethyl 5-(3-methylbenzyloxymethyl)isoxazole-3-carboxylate (2.2 g, 7.75 mmol), in place of ethyl 5-(2-chlorobenzyloxymethyl)isoxazole-3-carboxylate in Reference Production Example 44 to obtain 1.5 g of 5-(3-methylbenzylmethyl)isoxazole-3-carboxylic acid represented by the following formula.

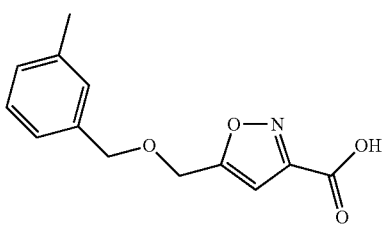 [SMILES: Cc1cccc(COCc2cc(C(=O)O)no2)c1]

¹H-NMR (DMSO-d6, TMS, δ(ppm)): 14.0 (brs, 1H), 7.24 (t, 1H), 7.15-7.13 (m, 3H), 6.85 (s, 1H), 4.69 (s, 2H), 4.53 (s, 2H), 2.30 (s, 3H)

Reference Production Example 61

A reaction was carried out in the same manner using 3-methoxybenzyl bromide (2.93 g, 14.61 mmol), in place of 2-chlorobenzyl bromide in Reference Production Example 43 to obtain 1.6 g of ethyl 5-(3-methoxybenzyloxymethyl)isoxazole-3-carboxylate represented by the following formula.

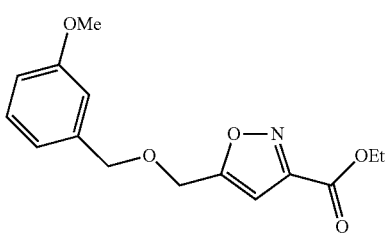 [SMILES: CCOC(=O)c1cc(COCc2cccc(OC)c2)on1]

¹H-NMR (CDCl₃, TMS, δ(ppm)): 7.30-7.28 (m, 1H), 6.93-6.85 (m, 3H), 6.69 (s, 1H), 4.65 (s, 2H), 4.59 (s, 2H), 4.44 (q, 2H), 3.82 (s, 3H), 1.42 (t, 3H)

Reference Production Example 62

A reaction was carried out in the same manner using ethyl 5-(3-methoxybenzyloxymethyl)isoxazole-3-carboxylate (2.2 g, 7.75 mmol), in place of ethyl 5-(2-chlorobenzyloxymethyl)isoxazole-3-carboxylate in Reference Production Example 44 to obtain 1.2 g of 5-(3-methoxybenzylmethyl)isoxazole-3-carboxylic acid represented by the following formula.

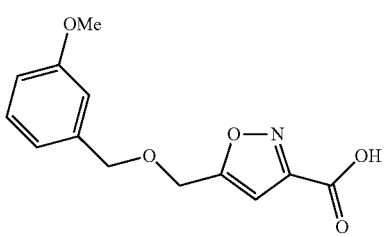 [SMILES: COc1cccc(COCc2cc(C(=O)O)no2)c1]

¹H-NMR (DMSO-d6, TMS, δ(ppm)): 14.0 (brs, 1H), 7.27 (t, 1H), 6.92-6.86 (m, 4H), 4.70 (s, 2H), 4.54 (s, 2H) 3.75 (s, 3H)

Reference Production Example 63

A reaction was carried out in the same manner using 3-cyanobenzyl bromide (1.13 g, 5.84 mmol), in place of 2-chlorobenzyl bromide in Reference Production Example 43 to obtain 0.35 g of ethyl 5-(3-cyanobenzyloxymethyl)isoxazole-3-carboxylate represented by the following formula.

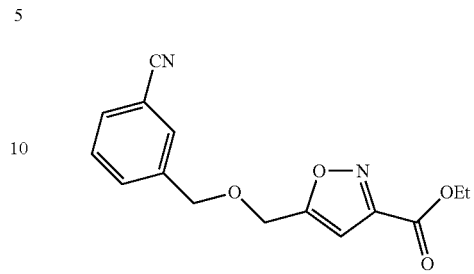

¹H-NMR (CDCl₃, TMS, δ(ppm)): 7.60 (m, 3H), 7.50 (t, 1H), 6.72 (s, 1H), 4.72 (s, 2H), 4.63 (s, 2H), 4.46 (q, 2H), 1.42 (t, 3H)

Reference Production Example 64

A reaction was carried out in the same manner using ethyl 5-(3-cyanobenzyloxymethyl)isoxazole-3-carboxylate (2.1 g, 7.34 mmol), in place of ethyl 5-(2-chlorobenzyloxymethyl)isoxazole-3-carboxylate, and lithium hydroxide (308 mg, 7.34 mmol), in place of potassium hydroxide in Reference Production Example 44 to obtain 1.5 g of 5-(3-cyanobenzylmethyl)isoxazole-3-carboxylic acid represented by the following formula.

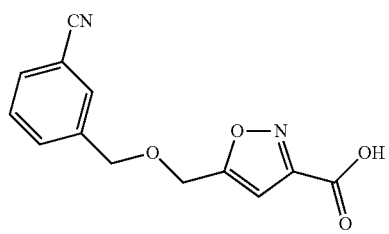 [SMILES: N#Cc1cccc(COCc2cc(C(=O)O)no2)c1]

¹H-NMR (CDCl₃, TMS, δ(ppm)): 14.0 (brs, 1H), 7.79 (m, 2H), 7.71-7.69 (d, 1H), 7.60-7.56 (d, 1H), 6.90 (s, 1H), 4.75 (s, 2H), 4.63 (s, 2H)

Reference Production Example 65

A reaction was carried out in the same manner using 3-methylthiobenzyl bromide (2.6 g, 12.28 mmol), in place of 2-chlorobenzyl bromide in Reference Production Example 43 to obtain 0.7 g of ethyl 5-(3-methylthiobenzyloxymethyl)isoxazole-3-carboxylate represented by the following formula.

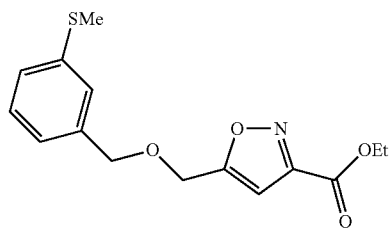 [SMILES: CCOC(=O)c1cc(COCc2cccc(SC)c2)on1]

$^1$H-NMR (CDCl$_3$, TMS, δ(ppm)): 7.37-7.31 (m, 4H), 6.69 (s, 1H) 4.67 (s, 2H), 4.60 (s, 2H), 4.48 (s, 2H), 2.50 (s, 3H) 1.42 (t, 3H)

Reference Production Example 66

A reaction was carried out in the same manner using ethyl 5-(3-methylthiobenzyloxymethyl)isoxazole-3-carboxylate (735 mg, 2.39 mmol), in place of ethyl 5-(2-chlorobenzyloxymethyl)isoxazole-3-carboxylate in Reference Production Example 44 to obtain 350 mg of 5-(3-methylthiobenzyloxymethyl)isoxazole-3-carboxylic acid represented by the following formula.

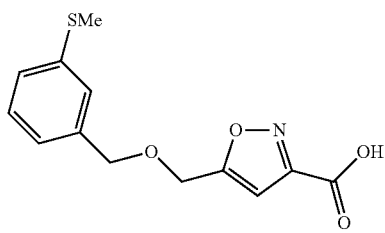 [SMILES: CSc1cccc(COCc2cc(C(=O)O)no2)c1]

$^1$H-NMR (CDCl$_3$, TMS, δ(ppm)): 14.4 (brs, 1H), 7.40-7.0 (m, 4H), 6.80 (m, 1H), 4.80-4.40 (m, 4H), 2.40 (s, 3H)

Reference Production Example 67

A reaction was carried out in the same manner using 4-fluorobenzyl bromide (3.3 g, 17.54 mmol), in place of 2-chlorobenzyl bromide in Reference Production Example 43 to obtain 1.8 g of ethyl 5-(4-fluorobenzyloxymethyl)isoxazole-3-carboxylate represented by the following formula.

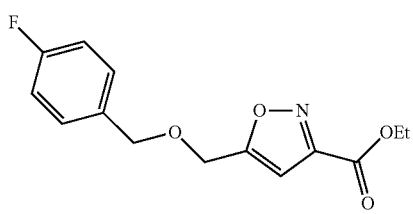 [SMILES: CCOC(=O)c1cc(COCc2ccc(F)cc2)on1]

$^1$H-NMR (CDCl$_3$, TMS, δ(ppm)): 7.34-7.29 (2H, m), 7.08-7.02 (2H, m), 6.68 (1H, s), 4.65 (2H, s), 4.57 (2H, s), 4.45 (2H, q), 1.42 (3H, t)

Reference Production Example 68

A reaction was carried out in the same manner using ethyl 5-(4-fluorobenzyloxymethyl)isoxazole-3-carboxylate (2.6 g, 6.94 mmol), in place of ethyl 5-(2-chlorobenzyloxymethyl)isoxazole-3-carboxylate in Reference Production Example 44 to obtain 1.8 g of 5-(4-fluorobenzyloxymethyl)isoxazole-3-carboxylic acid represented by the following formula.

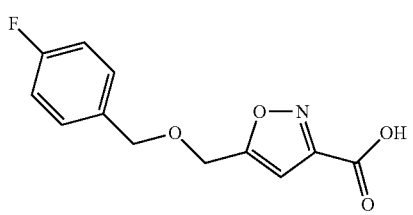 [SMILES: O=C(O)c1cc(COCc2ccc(F)cc2)on1]

$^1$H-NMR (CDCl$_3$, TMS, δ(ppm)): 14.0 (brs, 1H), 7.42-7.37 (m, 2H), 7.21-7.15 (m, 2H), 6.85 (s, 1H) 4.70 (s, 2H) 4.55 (t, 2H)

Reference Production Example 69

A reaction was carried out in the same manner using 4-bromobenzyl bromide (5.22 g, 21.03 mmol), in place of 2-chlorobenzyl bromide in Reference Production Example 43 to obtain 1.8 g of ethyl 5-(4-bromobenzyloxymethyl)isoxazole-3-carboxylate represented by the following formula.

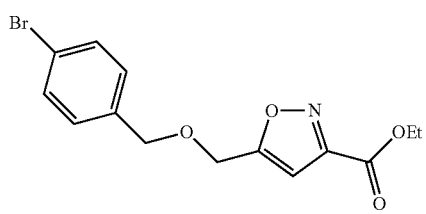 [SMILES: CCOC(=O)c1cc(COCc2ccc(Br)cc2)on1]

$^1$H-NMR (CDCl$_3$, TMS, δ(ppm)): 7.48 (d, 2H), 7.23 (t, 2H), 6.68 (s, 1H), 4.66 (s, 2H), 4.59 (s, 2H), 4.43 (q, 2H), 1.42 (t, 3H)

Reference Production Example 70

A reaction was carried out in the same manner using ethyl 5-(4-bromobenzyloxymethyl)isoxazole-3-carboxylate (2.4 g, 7.05 mmol), in place of 5-(2-chlorobenzyloxymethyl)isoxazole-3-carboxylate in Reference Production Example 44 to obtain 2.0 g of 5-(4-bromobenzyloxymethyl)isoxazole-3-carboxylic acid represented by the following formula.

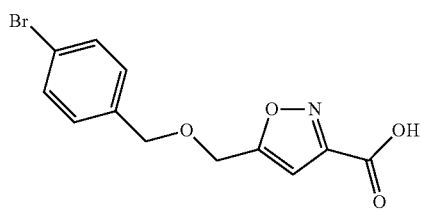

$^1$H-NMR (DMSO-d6, TMS, δ(ppm)): 14.0 (brs, 1H), 7.35 (dd, 2H), 7.31 (dd, 2H), 6.86 (s, 1H), 4.71 (s, 2H) 4.55 (s, 2H)

Reference Production Example 71

A reaction was carried out in the same manner using 4-tirfluoromethoxybenzyl bromide (4.1 g, 16.37 mmol), in place of 2-chlorobenzyl bromide in Reference Production Example 43 to obtain 2.4 g of ethyl 5-(4-trifluoromethoxybenzyloxymethyl)isoxazole-3-carboxylat e represented by the following formula.

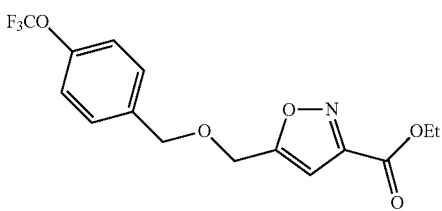

¹H-NMR (CDCl₃, TMS, δ(ppm)): 7.38 (d, 2H), 7.22 (d, 2H), 6.69 (s, 1H), 4.68 (s, 2H), 4.60 (s, 2H), 4.45 (q, 2H), 1.43 (t, 3H)

Reference Production Example 72

A reaction was carried out in the same manner using ethyl 5-(4-trifluoromethoxybenzyloxymethyl)isoxazole-3-carboxylat e (2.8 g, 8.11 mmol), in place of ethyl 5-(2-chlorobenzyloxymethyl)isoxazole-3-carboxylate in Reference Production Example 44 to obtain 2.4 g of 5-(4-trifluoromethoxybenzyloxymethyl)isoxazole-3-carboxylic acid represented by the following formula.

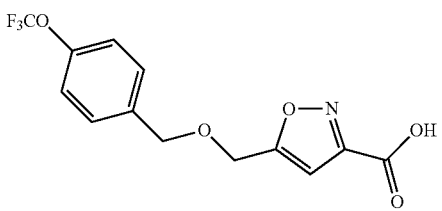

¹H-NMR (DMSO-d6, TMS, δ(ppm)): 14.0 (brs, 1H), 7.48 (d, 2H), 7.35 (d, 2H), 6.87 (s, 1H), 4.74 (s, 2H), 4.61 (s, 2H)

Reference Production Example 73

A reaction was carried out in the same manner using 4-tirfluoromethylthiobenzyl bromide (3.96 g, 14.61 mmol), in place of 2-chlorobenzyl bromide in Reference Production Example 43 to obtain 1.4 g of ethyl 5-(4-trifluoromethylthiobenzyloxymethyl)isoxazole-3-carboxy late represented by the following formula.

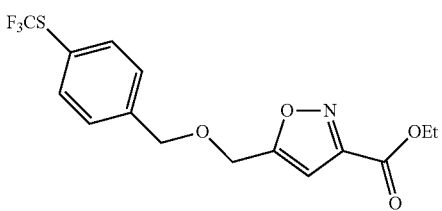 [SMILES: CCOC(=O)c1cc(COCc2ccc(OC)cc2)on1]

¹H-NMR (CDCl₃, TMS, δ(ppm)): 7.65 (d, 2H), 7.40 (d, 2H), 6.70 (s, 1H), 4.70 (s, 2H), 4.64 (s, 2H), 4.45 (q, 2H), 1.42 (t, 3H)

Reference Production Example 74

A reaction was carried out in the same manner using ethyl 5-(4-trifluoromethylthiobenzyl)oxymethylisoxazole-3-carboxy late (1.7 g, 4.70 mmol), in place of ethyl 5-(2-chlorobenzyl)oxymethylisoxazole-3-carboxylate in Reference Production Example 44 to obtain 1.2 g of 5-(4-trifluoromethylthiobenzyloxymethyl)isoxazole-3-carboxylic acid represented by the following formula.

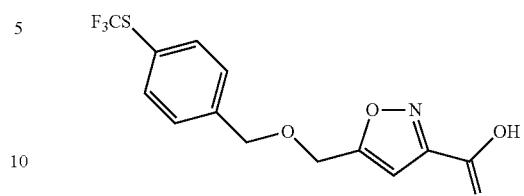

¹H-NMR (DMSO-d6, TMS, (ppm)): 14.0 (brs, 1H), 7.72 (d, 2H), 7.51 (d, 2H), 6.88 (s, 1H) 4.76 (s, 2H), 4.66 (s, 2H)

Reference Production Example 75

A reaction was carried out in the same manner using 4-methylbenzyl bromide (5.16 g, 28.04 mmol), in place of 2-chlorobenzyl bromide in Reference Production Example 43 to obtain 3.3 g of ethyl 5-(4-methylbenzyloxymethyl)isoxazole-3-carboxylate represented by the following formula.

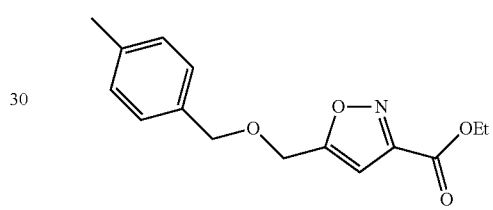

¹H-NMR (CDCl₃, TMS, δ(ppm)): 7.32 (d, 2H), 7.17 (d, 2H), 6.64 (s, 1H), 4.63 (s, 2H), 4.52 (s, 2H), 4.43 (q, 2H), 2.35 (s, 3H), 1.42 (t, 3H)

Reference Production Example 76

A reaction was carried out in the same manner using ethyl 5-(4-methylbenzyloxymethyl)isoxazole-3-carboxylate (4.0 g, 14.54 mmol), in place of ethyl 5-(2-chlorobenzyloxymethyl)isoxazole-3-carboxylate in Reference Production Example 44 to obtain 2.8 g of 5-(4-methylbenzyloxymethyl)isoxazole-3-carboxylic acid represented by the following formula.

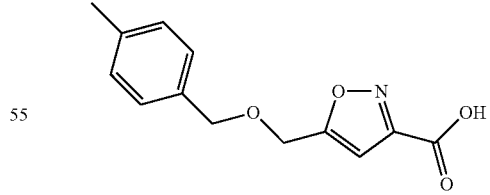

¹H-NMR (DMSO-d6, TMS, δ(ppm)): 14.0 (brs, 1H), 7.23 (d, 2H), 7.17 (d, 2H), 6.84 (s, 1H) 4.67 (s, 2H), 4.51 (s, 2H), 2.29 (s, 3H)

Reference Production Example 77

A reaction was carried out in the same manner using 4-methoxybenzyl bromide (4.1 g, 20.46 mmol), in place of 2-chlorobenzyl bromide in Reference Production Example 43 to obtain 2.5 g of ethyl 5-(4-methoxybenzyloxymethyl)isoxazole-3-carboxylate represented by the following formula.

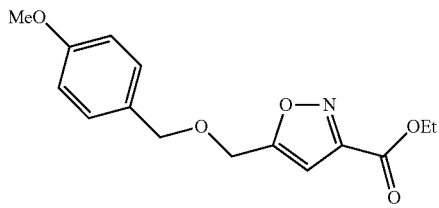

$^1$H-NMR (DMSO-d6, TMS, δ(ppm)): 7.30 (d, 2H), 6.90 (d, 2H), 6.70 (s, 1H), 4.65 (s, 2H), 4.55 (s, 2H), 4.45 (q, 2H), 3.70 (s, 3H), 1.40 (t, 3H)

Reference Production Example 78

A reaction was carried out in the same manner using ethyl 5-(4-methoxybenzyloxymethyl)isoxazole-3-carboxylate (2.5 g, 8.59 mmol), in place of ethyl 5-(2-chlorobenzyloxymethyl)isoxazole-3-carboxylate in Reference Production Example 44 to obtain 2.0 g of 5-(4-methoxybenzyloxymethyl)isoxazole-3-carboxylic acid represented by the following formula.

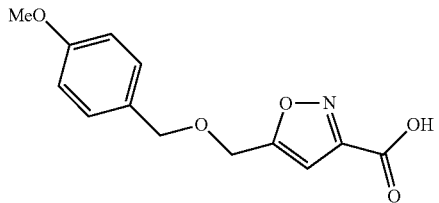

$^1$H-NMR (DMSO-d6, TMS, δ(ppm)): 14.0 (brs, 1H), 7.28 (d, 2H), 6.96-6.88 (dd, 2H), 6.84 (s, 1H), 4.68 (s, 2H), 4.50 (s, 2H), 3.76 (s, 3H)

Reference Production Example 79

A reaction was carried out in the same manner using 4-cyanobenzyl bromide (4 g, 23.40 mmol), in place of 2-chlorobenzyl bromide in Reference Production Example 43 to obtain 2.8 g of ethyl 5-(4-cyanobenzyloxymethyl)isoxazole-3-carboxylate represented by the following formula.

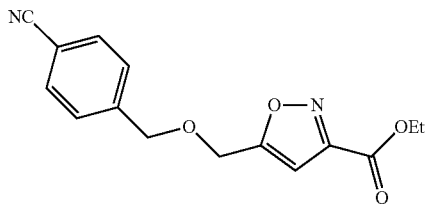 [SMILES: CCOC(=O)c1cc(COCc2ccc(C#N)cc2)on1]

$^1$H-NMR (CDCl$_3$, TMS, δ(ppm)): 7.67 (d, 2H), 7.47 (d, 2H), 6.71 (s, 1H), 4.72 (s, 2H), 4.66 (s, 2H), 4.44 (q, 2H), 1.42 (t, 3H)

Reference Production Example 80

A reaction was carried out in the same manner using ethyl 5-(4-cyanobenzyloxymethyl)isoxazole-3-carboxylate (2.8 g, 9.79 mmol), in place of ethyl 5-(2-chlorobenzyloxymethyl)isoxazole-3-carboxylate, and lithium hydroxide (411 mg, 9.79 mmol), in place of potassium hydroxide in Reference Production Example 44 to obtain 2.1 g of 5-(4-cyanobenzyloxymethyl)isoxazole-3-carboxylic acid represented by the following formula.

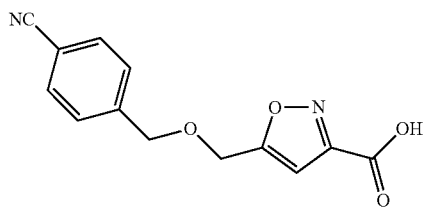 [SMILES: N#Cc1ccc(COCc2cc(C(=O)O)no2)cc1]

$^1$H-NMR (DMSO-d6, TMS, δ(ppm)): 14.0 (brs, 1H), 7.83 (d, 2H), 7.55 (d, 2H), 6.88 (s, 1H), 4.76 (s, 2H), 4.68 (s, 2H)

Reference Production Example 81

A reaction was carried out in the same manner using 4-methylthiobenzyl bromide (2.5 g, 11.69 mmol), in place of 2-chlorobenzyl bromide in Reference Production Example 43 to obtain 1.3 g of ethyl 5-(4-methylthiobenzyloxymethyl)isoxazole-3-carboxylate represented by the following formula.

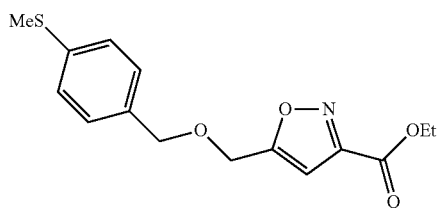 [SMILES: CCOC(=O)c1cc(COCc2ccc(SC)cc2)on1]

$^1$H-NMR(CDCl$_3$, TMS, δ(ppm)): 7.30-7.23 (m, 4H), 6.92 (s, 1H), 4.70 (s, 2H), 4.52 (s, 2H), 4.39 (q, 2H), 2.51-2.46 (m, 3H), 1.32 (t, 3H)

Reference Production Example 82

A reaction was carried out in the same manner using ethyl 5-(4-methylthiobenzyloxymethyl)isoxazole-3-carboxylate (1.5 g, 4.88 mmol), in place of ethyl 5-(2-chlorobenzyloxymethyl)isoxazole-3-carboxylate in Reference Production Example 44 to obtain 1.2 g of 5-(4-methylthiobenzyloxymethyl)isoxazole-3-carboxylic acid represented by the following formula.

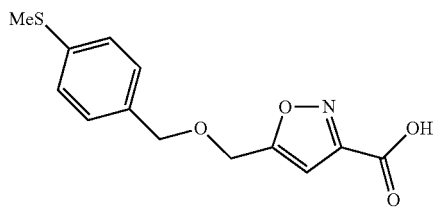 [SMILES: CSc1ccc(COCc2cc(C(=O)O)no2)cc1]

¹H-NMR (DMSO-d6, TMS, δ(ppm)): 14.0 (Brs, 1H), 7.30-7.23 (m, 4H), 6.84 (s, 1H) 4.65 (s, 2H), 4.52 (s, 2H), 2.49-2.46 (m, 3H)

Reference Production Example 83

A reaction was carried out in the same manner using 4-bromomethyl-1,3-benzodioxole (8 g, 37.2 mmol), in place of 2-chlorobenzyl bromide in Reference Production Example 43 to obtain 4.0 g of ethyl 4-[5-(1,3-benzodioxolanyl)methoxymethyl]isoxazole-3-carboxy late represented by the following formula.

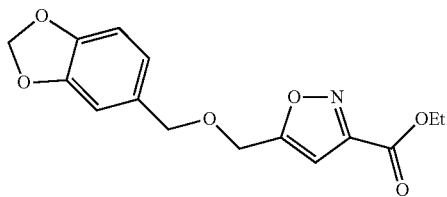 [SMILES: CCOC(=O)c1cc(COCc2ccc3c(c2)OCO3)on1]

¹H-NMR (CDCl₃, TMS, δ(ppm)): 6.84 (s, 1H), 6.79 (d, 2H), 6.67 (s, 1H), 5.99 (s, 2H), 4.62 (s, 2H), 4.60 (s, 2H), 4.48 (q, 2H), 1.42 (t, 3H).

Reference Production Example 84

A reaction was carried out in the same manner using ethyl 4-[5-(1,3-benzodioxolanyl)methoxymethyl]isoxazole-3-carboxy late (4 g, 14.4 mmol), in place of ethyl 5-(2-chlorobenzyloxymethyl)isoxazole-3-carboxylate in Reference Production Example 44 to obtain 3.0 g of 5-[5-(1,3-benzodioxolanyl)methoxymethyl]isoxazole-3-carboxylic acid represented by the following formula.

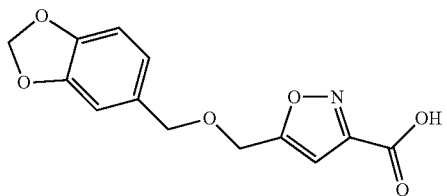 [SMILES: O=C(O)c1cc(COCc2ccc3c(c2)OCO3)on1]

¹H-NMR (DMSO-d6, TMS, δ(ppm)): 14.0 (brs, 1H), 6.81 (m, 4H), 6.08 (s, 2H) 4.66 (s, 2H) 4.46 (s, 2H)

Reference Production Example 85

60% Sodium hydride (1.05 g, 26.31 mmol) was added to dehydrated N,N-dimethylformamide (10 ml) cooled to 0° C., under a nitrogen atmosphere, and a dehydrated N,N-dimethylformamide (20 ml) solution of ethyl 5-hydroxymethylisoxazole-3-carboxylate (3.0 g, 17.54 mmol) was added dropwise thereto over 10 minutes, and then the mixture was further stirred for 30 minutes. A dry N,N-dimethylformamide (3 ml) solution of 3-(bromomethyl)thiophene (3.1 g, 17.54 mmol) was added thereto, and the reaction mixture was heated to room temperature, and stirred for 16 hours, and then added to a saturated aqueous ammonium chloride solution, and the mixture was extracted twice with ethyl acetate. The organic layer was washed with water and saturated saline water, dried over anhydrous sodium sulfate, and then concentrated under reduced pressure. The residue was applied to a silica gel column chromatography to obtain 1.65 g of ethyl 5-(thiophen-3-ylmethyl)oxymethylisoxazole-3-carboxylate represented by the following formula.

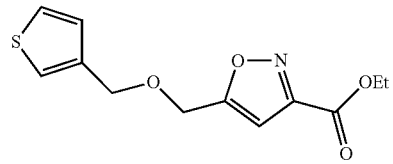 [SMILES: CCOC(=O)c1cc(COCc2ccsc2)on1]

¹H-NMR (CDCl₃, TMS, δ(ppm)): 7.34-7.32 (m, 1H), 7.26 (s, 1H), 7.08 (d, 1H), 6.67 (s, 1H), 4.64-4.62 (m, 4H), 4.44 (q, 2H), 1.42 (t, 3H)

Reference Production Example 86

Ethyl 5-(thiophen-3-ylmethyl)oxymethylisoxazole-3-carboxylate (4.0 g, 13.55 mmol) was added to ethanol (50 mL), and 2 N sodium hydroxide (30 mL) was added thereto, and then the mixture was stirred at room temperature for 16 hours. Thereafter, the resulting mixture was concentrated under reduced pressure. Dilute hydrochloric acid was added to the concentrate, the mixture was cooled to 0° C., and the precipitated solid was filtered. The solid was dried under reduced pressure to obtain 1.6 g of 5-(thiophen-3-ylmethyl)oxymethylisoxazole-3-carboxylic acid represented by the following formula.

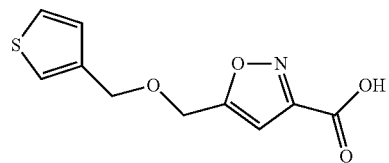 [SMILES: O=C(O)c1cc(COCc2ccsc2)on1]

¹H-NMR (DMSO-d6, TMS, δ(ppm)): 14.0 (brs, 1H), 7.54-7.52 (m, 1H), 7.48 (d, 1H), 7.10-7.08 (m, 1H), 6.84 (s, 1H), 4.68 (s, 2H), 4.56 (s, 2H)

Reference Production Example 87

60% Sodium hydride (1.40 g, 35.08 mmol) was added to dehydrated N,N-dimethylformamide (20 ml) cooled to 0° C., under a nitrogen atmosphere, and a dehydrated N,N-dimethylformamide (10 ml) solution of ethyl 5-hydroxymethylisoxazole-3-carboxylate (4.0 g, 23.39 mmol) was added dropwise thereto over 10 minutes, and then the mixture was further stirred for 30 minutes. A dehydrated N,N-dimethylformamide (10 m) solution of 2-bromomethyl-5-chlorothiophene (3.9 g, 23.39 mmol) was added thereto, and the mixture was heated to room temperature and stirred for 16 hours. The reaction mixture was added to a saturated aqueous ammonium chloride solution, and the mixture was extracted twice with ethyl acetate. The organic layer was washed with water and saturated saline water, dried over anhydrous sodium sulfate, and then concentrated under reduced pressure. The residue was applied to a silica gel column chromatography to obtain 2.6 g of ethyl5-(5-chlorothiophen-2-ylmethyl)oxymethylisoxazole-3-carboxylate represented by the following formula.

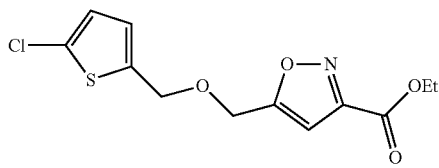 [SMILES: CCOC(=O)c1cc(COCc2ccc(Cl)s2)on1]

¹H-NMR (CDCl₃, TMS, δ(ppm)): 6.80 (m, 2H), 6.68 (s, 1H), 4.65 (s, 4H), 4.43 (q, 2H), 1.42 (t, 3H)

Reference Production Example 88

Ethyl 5-(5-chlorothiophen-2-ylmethyl)oxymethylisoxazole-3-carboxy late (3.0 g, 9.96 mmol) was added to ethanol (30 mL), and 2 N sodium hydroxide (15 mL) was further added thereto, and the mixture was stirred at room temperature for 16 hours, and then concentrated under reduced pressure. Dilute hydrochloric acid was added to the concentrate, the mixture was cooled to 0° C., and the precipitated solid was filtered. The resulting solid was dried under reduced pressure to obtain 2.5 g of 5-(5-chlorothiophen-2-ylmethyl)oxymethylisoxazole-3-carboxylic acid represented by the following formula.

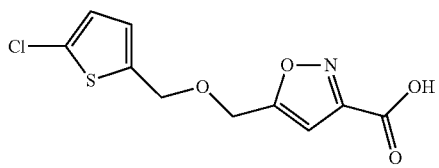 [SMILES: O=C(O)c1cc(COCc2ccc(Cl)s2)on1]

¹H-NMR (DMSO-d6, TMS, δ(ppm)): 14.0 (brs, 1H), 7.03-6.99 (m, 2H), 6.85 (s, 1H) 4.70-4.68 (m, 4H)

Reference Production Example 89

60% Sodium hydride (0.44 g, 11.4 mmol) was added to dehydrated N,N-dimethylformamide (4 ml) cooled to 0° C., under a nitrogen atmosphere, and a dehydrated N,N-dimethylformamide (5 ml) solution of ethyl 5-hydroxymethylisoxazole-3-carboxylate (1.3 g, 7.60 mmol) was added dropwise thereto, and then the mixture was further stirred for 30 minutes. A dehydrated N,N-dimethylformamide (5 ml) solution of 2-bromomethylbenzofuran (1.56 g, 7.60 mmol) was added thereto, and the mixture was heated to room temperature and stirred for 16 hours. Then, the mixture was added to a saturated aqueous ammonium chloride solution, and extracted twice with ethyl acetate. The organic layer was washed with water and saturated saline water, dried over anhydrous sodium sulfate, and then concentrated under reduced pressure. The residue was applied to a silica gel column chromatography to obtain 0.40 g of ethyl 5-(benzofuran-2-ylmethoxymethyl)isoxazole-3-carboxylate represented by the following formula.

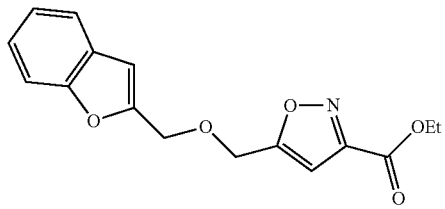 [SMILES: CCOC(=O)c1cc(COCc2cc3ccccc3o2)on1]

¹H-NMR (CDCl₃, TMS, δ(ppm)): 7.56 (d, 1H), 7.48 (d, 1H), 7.32-7.28 (m, 1H), 7.26-7.21 (m, 1H), 6.74 (s, 1H), 6.70 (s, 1H), 4.62 (s, 2H), 4.44 (s2H), 4.12 (q, 2H), 1.4 (t, 3H).

Reference Production Example 90

Ethyl 5-(benzofuran-2-ylmethoxymethyl)isoxazole-3-carboxylate (0.66 g, 1.99 mmol) was added to ethanol (6 mL), and 2 N sodium hydroxide (3 mL) was further added thereto, and the mixture was stirred at room temperature for 16 hours, and then concentrated under reduced pressure. Dilute hydrochloric acid was added to the concentrate, the mixture was cooled to 0° C., and the precipitated solid was filtered. The resulting solid was dried under reduced pressure to obtain 0.35 g of 5-(benzofuran-2-ylmethoxymethyl)isoxazole-3-carboxylic acid represented by the following formula.

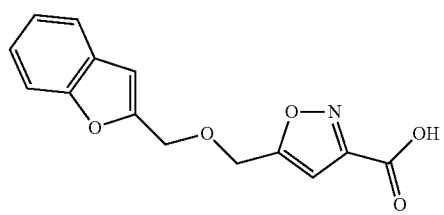 [SMILES: O=C(O)c1cc(COCc2cc3ccccc3o2)on1]

¹H-NMR (DMSO-d6, TMS, δ(ppm)): 14.0 (brs, 1H), 7.64 (d, 1H), 7.56 (d, 1H), 7.32 (t, 1H), 7.25 (t, 1H), 6.97 (s, 1H) 6.87 (s, 1H), 4.76 (s, 2H), 4.71 (s, 2H)

Reference Production Example 91

60% Sodium hydride (1.04 g, 26.3 mmol) was added to dehydrated N,N-dimethylformamide (10 ml) cooled to 00° C., under a nitrogen atmosphere, and a dehydrated N,N-dimethylformamide (10 ml) solution of ethyl 5-hydroxymethylisoxazole-3-carboxylate (3.0 g, 17.54 mmol) was added dropwise thereto, and then the mixture was further stirred for 30 minutes. A dehydrated N,N-dimethylformamide (5 ml) solution of 2-bromomethylbenzothiophene (4.0 g, 17.54 mmol) was added thereto, and the mixture was heated to room temperature and stirred for 16 hours. Then, the mixture was added to a saturated aqueous ammonium chloride solution, and extracted twice with ethyl acetate. The organic layer was washed with water and saturated saline water, dried over anhydrous sodium sulfate, and then concentrated under reduced pressure. The residue was applied to a silica gel column chromatography to obtain 1.0 g of ethyl 5-(benzothiophen-2-ylmethoxymethyl)isoxazole-3-carboxylate represented by the following formula.

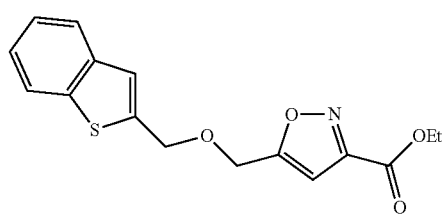 [SMILES: CCOC(=O)c1cc(COCc2cc3ccccc3s2)on1]

¹H-NMR (CDCl₃, TMS, δ(ppm)): 7.82 (d, 1H), 7.75 (d, 1H), 7.34-7.31 (m, 2H), 7.20 (m, 1H), 6.70 (s, 1H), 4.90 (s, 2H), 4.70 (s, 2H), 4.45 (q, 2H), 1.40 (s, 3H)

Reference Production Example 92

Ethyl 5-(benzothiophen-2-ylmethoxymethyl)isoxazole-3-carboxylate (1.0 g, 3.1 mmol) was added to ethanol (10 mL), and 2 N sodium hydroxide (5 mL) was further added thereto, and the mixture was stirred at room temperature for 16 hours, and then concentrated under reduced pressure. Dilute hydrochloric acid was added to the concentrate, the mixture was cooled to 0° C., and the precipitated solid was filtered. The resulting solid was dried under reduced pressure to obtain 0.35 g of 5-(benzothiophen-2-ylmethoxymethyl)isoxazole-3-carboxylic acid represented by the following formula.

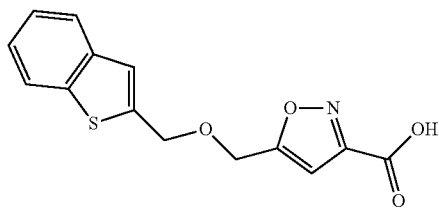 [SMILES: O=C(O)c1cc(COCc2cc3ccccc3s2)on1]

$^1$H-NMR (DMSO-d6, TMS, δ(ppm)): 14.0 (brs, 1H), 7.97-7.94 (m, 1H), 7.84-7.81 (m, 1H), 7.43 (s, 1H), 7.40-7.32 (m, 2H), 6.88 (s, 1H), 4.87 (s, 2H), 4.76 (s, 2H)

Reference Production Example 93

Ethyl nitroacetate (1.49 g, 12.5 mmol), (1-phenylethyl)propargyl ether (1.6 g, 10 mmol) and 1,4-diazabicyclo[2.2.2]octane (0.22 g, 2.0 mmol) were added to chloroform (amylene addition product) (3 mL). The mixture was heated and refluxed for 24 hours, ethyl nitroacetate (1.49 g, 12.5 mmol) was added to the mixture, and the mixture was further heated and refluxed for 4 hours, then cooled to room temperature, and concentrated under reduced pressure. The residue was applied to a silica gel column chromatography to obtain 0.86 g of ethyl 5-(1-phenylethoxymethyl)isoxazole-3-carboxylate represented by the following formula.

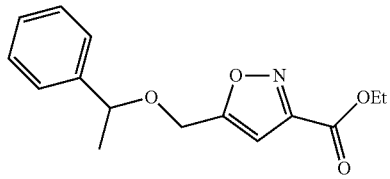 [SMILES: CCOC(=O)c1cc(COC(C)c2ccccc2)on1]

$^1$H-NMR (CDCl$_3$, TMS, δ(ppm)): 1.40 (3H, t), 1.47 (3H, d), 4.42-4.55 (4H, m), 4.52 (1H, q), 6.63 (1H, s), 7.33-7.37 (5H, m)

Reference Production Example 94

Ethyl 5-(1-phenylethoxymethyl)isoxazole-3-carboxylate (0.86 g, 3.12 mmol) was added to ethanol (10 mL), and potassium hydroxide (1.40 g, 25 mmol) and water (2 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 0.50 g of 5-(1-phenylethoxymethyl)isoxazole-3-carboxylic acid represented by the following formula.

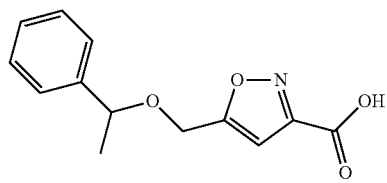 [SMILES: CC(OCc1cc(C(=O)O)no1)c1ccccc1]

The resulting carboxylic acid was used in Production Example 123 without purification.

Reference Production Example 95

Ethyl nitroacetate (1.49 g, 12.5 mmol), 1,1-diphenylmethylpropargyl ether (1.6 g, 10 mmol) and 1,4-diazabicyclo[2.2.2]octane (0.22 g, 2.0 mmol) were added to chloroform (amylene addition product) (3 mL). The mixture was heated and refluxed for 24 hours, then ethyl nitroacetate (1.49 g, 12.5 mmol) was added to the mixture, and the mixture was further heated and refluxed for 4 hours, then cooled to room temperature, and concentrated under reduced pressure. The residue was applied to a silica gel column chromatography to obtain 0.86 g of ethyl 5-(1,1-diphenylmethoxymethyl)isoxazole-3-carboxylate represented by the following formula.

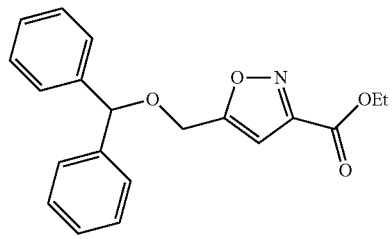 [SMILES: CCOC(=O)c1cc(COC(c2ccccc2)c2ccccc2)on1]

$^1$H-NMR (CDCl$_3$, TMS, δ(ppm)): 1.41 (3H, t), 4.41-4.55 (2H, q), 4.64 (2H, s), 5.47 (1H, s), 6.69 (1H, s), 7.25-7.34 (10H, m)

Reference Production Example 96

Ethyl 5-(1,1-diphenylmethoxymethyl)isoxazole-3-carboxylate (1.75 g, 5.2 mmol) was added to ethanol (50 mL), and potassium hydroxide (1.46 g, 26 mmol) and water (10 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 1.36 g of 5-5-(1,1-diphenylmethoxymethyl)isoxazole-3-carboxylic acid represented by the following formula.

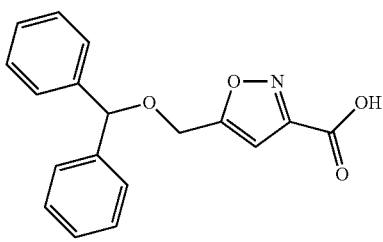 [SMILES: O=C(O)c1cc(COC(c2ccccc2)c2ccccc2)on1]

The resulting carboxylic acid was used in Production Example 124 without purification.

Reference Production Example 97

Ethyl nitroacetate (1.49 g, 12.5 mmol), (2,2,2-trifluoro-1-phenylethyl)propargyl ether (2.14 g, 10 mmol) and 1,4-diazabicyclo[2.2.2]octane (0.22 g, 2.0 mmol) were added to chloroform (amylene addition product) (3 mL). The mixture was heated and refluxed for 24 hours, ethyl nitroacetate (1.49 g, 12.5 mmol) was added to the mixture, and the mixture was further heated and refluxed for 4 hours, then cooled to room temperature, and concentrated under reduced pressure. The residue was applied to a silica gel column chromatography to obtain 1.02 g of ethyl 5-(2,2,2-trifluoro-1-phenylethoxymethyl)isoxazole-3-carboxy late represented by the following formula.

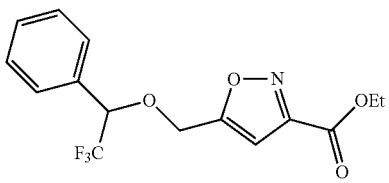 [SMILES: CCOC(=O)c1cc(COC(c2ccccc2)C(F)(F)F)on1]

$^1$H-NMR (CDCl$_3$, TMS, δ(ppm)): 1.41 (3H, t), 4.43 (2H, q), 4.65-4.76 (3H, m), 6.70 (1H, s), 7.43 (5H, m)

Reference Production Example 98

Ethyl 5-(2,2,2-trifluoro-1-phenylethoxymethyl)isoxazole-3-carboxy late (1.02 g, 3.09 mmol) was added to ethanol (15 mL), and potassium hydroxide (0.35 g, 6.2 mmol) and water (3 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 0.98 g of 5-(2,2,2-trifluoro-1-phenylethoxymethyl)isoxazole-3-carboxylic acid represented by the following formula.

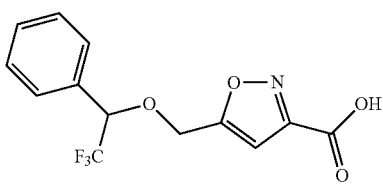 [SMILES: O=C(O)c1cc(COC(c2ccccc2)C(F)(F)F)on1]

The resulting carboxylic acid was used in Production Example 125 without purification.

Reference Production Example 99

Ethyl 5-hydroxymethylisoxazole-3-carboxylate (1.71 g, 10.0 mmol), 2,2,2-trifluoroethylmethanesulfonate (5.34 g, 30 mmol), N,N-dimethylformamide (30 ml) and 60% sodium hydride (0.48 g, 12.0 mmol) were mixed at 0° C., under a nitrogen atmosphere. The mixture was heated to room temperature and stirred for 16 hours, then added to a saturated aqueous ammonium chloride solution, and the mixture was extracted twice with ethyl acetate. The organic layer was washed with water and saturated saline water, dried over anhydrous sodium sulfate, and then concentrated under reduced pressure. The residue was applied to a silica gel column chromatography to obtain 1.02 g of ethyl 5-(2,2,2-trifluoroethoxymethyl)isoxazole-3-carboxylate represented by the following formula.

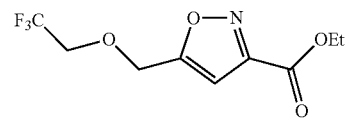 [SMILES: CCOC(=O)c1cc(COCC(F)(F)F)on1]

$^1$H-NMR (CDCl$_3$, TMS, δ(ppm)): 1.41 (3H, t), 3.91 (2H, q), 4.43 (2H, q), 4.80 (2H, s), 6.73 (1H, s)

Reference Production Example 100

Ethyl 5-(2,2,2-trifluoroethoxymethyl)isoxazole-3-carboxylate (1.02 g, 3.09 mmol) was added to ethanol (15 mL), and potassium hydroxide (0.35 g, 6.2 mmol) and water (3 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 0.98 g of 5-(2,2,2-trifluoroethoxymethyl)isoxazole-3-carboxylic acid represented by the following formula.

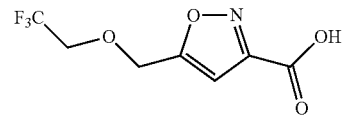 [SMILES: O=C(O)c1cc(COCC(F)(F)F)on1]

The resulting carboxylic acid was used in Production Example 126 without purification.

Reference Production Example 101

Ethyl nitroacetate (14.8 g, 125 mmol), 3-butyn-2-ol (7.0 g, 100 mmol) and 1,4-diazabicyclo[2.2.2]octane (2.24 g, 20 mmol) were added to ethanol (50 ml), and the mixture was heated at 80° C. for 48 hours, then cooled to room temperature, and concentrated under reduced pressure. The residue was applied to a silica gel column chromatography to obtain 7.25 g of ethyl 5-(1-hydroxyethyl)isoxazole-3-carboxylate represented by the following formula.

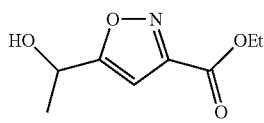

¹H-NMR (CDCl₃, TMS, δ(ppm)): 1.40 (3H, t), 1.61 (3H, d), 4.42 (2H, q), 5.05 (1H, q), 6.61 (1H, s)

Reference Production Example 102

Ethyl 5-(1-hydroxyethyl)isoxazole-3-carboxylate (1.85 g, 10.0 mmol), benzyl bromide (3.42 g, 12.0 mmol), N,N-dimethylformamide (20 ml) and 60% sodium hydride (0.49 g, 12.0 mmol) were mixed at 0° C., under a nitrogen atmosphere. The mixture was heated to room temperature and stirred for 16 hours, then added to 1 N hydrochloric acid, and the mixture was extracted twice with ethyl acetate. The organic layer was washed with water and saturated saline water, dried over anhydrous sodium sulfate, and then concentrated under reduced pressure. The residue was applied to a silica gel column chromatography to obtain 1.29 g of ethyl 5-[1-(benzyloxy)ethyl]isoxazole-3-carboxylate represented by the following formula.

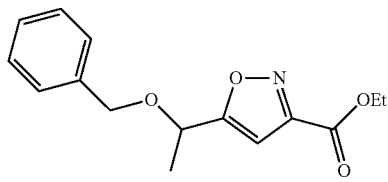 [SMILES: CCOC(=O)c1cc(C(C)OCc2ccccc2)on1]

¹H-NMR (CDCl₃, TMS, δ(ppm)): 1.55-1.61 (6H, t), 4.41-4.60 (4H, m), 4.69-4.74 (1H, m), 6.64 (1H, s), 7.32-7.38 (5H, m)

Reference Production Example 103

Ethyl 5-[1-(benzyloxy)ethyl]isoxazole-3-carboxylate (1.29 g, 4.7 mmol) was added to ethanol (20 mL), and potassium hydroxide (0.79 g, 14.1 mmol) and water (4 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 1.00 g of 5-[1-(benzyloxy)ethyl]isoxazole-3-carboxylic acid represented by the following formula.

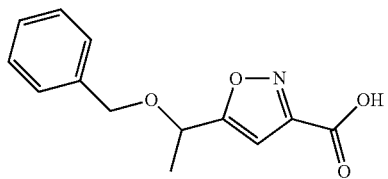 [SMILES: CC(OCc1ccccc1)c1cc(C(=O)O)no1]

¹H-NMR (CDCl₃, TMS, δ(ppm)): 1.58 (3H, d), 3.38-3.62 (2H, dd), 4.75 (1H, q), 6.68 (1H, s), 7.32-7.34 (5H, m)

Reference Production Example 104

Ethyl 5-(1-hydroxy-1-phenylmethyl)isoxazole-3-carboxylate (1.24 g, 5.0 mmol), benzyl bromide (1.03 g, 6.0 mmol), N,N-dimethylformamide (10 ml) and 60% sodium hydride (0.24 g, 6.0 mmol) were mixed at 0° C., under a nitrogen atmosphere. The mixture was heated to room temperature and stirred for 16 hours, then added to 1 N hydrochloric acid, and the mixture was extracted twice with ethyl acetate. The organic layer was washed with water and saturated saline water, dried over anhydrous sodium sulfate, and then concentrated under reduced pressure. The residue was added to ethanol (10 mL), and potassium hydroxide (0.49 g, 8.80 mmol) and water (2 mL) were added thereto, then the mixture was stirred at room temperature overnight, and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 0.44 g of 5-[1-(benzyloxy)-1-phenylmethyl]isoxazole-3-carboxylic acid represented by the following formula.

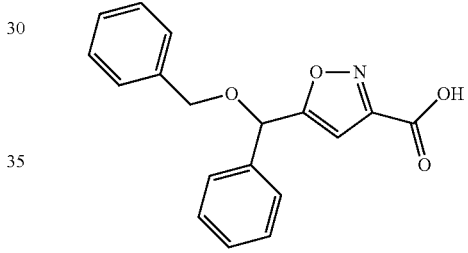

¹H-NMR (CDCl₃, TMS, δ(ppm)): 4.57 (2H, dd), 4.70 (1H, s), 6.60 (1H, s), 7.33-7.40 (5H, m)

Reference Production Example 105

60% Sodium hydride (1.04 g, 26.0 mmol) was added to dehydrated N,N-dimethylformamide (10 ml) cooled to 0° C., under a nitrogen atmosphere, and a dehydrated N,N-dimethylformamide (10 ml) solution of ethyl 5-hydroxymethylisoxazole-3-carboxylate (3.0 g, 17.54 mmol) was added dropwise thereto, and then the mixture was further stirred for 30 minutes. A dehydrated N,N-dimethylformamide (5 ml) solution of 1-bromo-3-phenylpropane (3.5 g, 17.54 mmol) was added thereto, and the mixture was heated to room temperature and stirred for 16 hours. Then, the mixture was added to a saturated aqueous ammonium chloride solution, and extracted twice with ethyl acetate. The organic layer was washed with water and saturated saline water, dried over anhydrous sodium sulfate, and then concentrated under reduced pressure. The residue was applied to a silica gel column chromatography to obtain 1.9 g of ethyl 5-(3-phenylpropoxymethyl)isoxazole-3-carboxylate represented by the following formula.

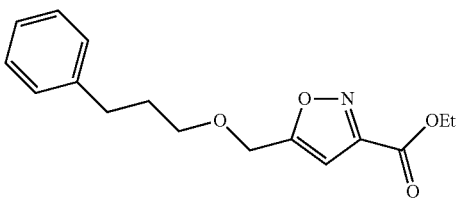 [SMILES: CCOC(=O)c1cc(COCCCc2ccccc2)on1]

¹H-NMR (CDCl₃, TMS, δ(ppm)): 7.30-7.25 (m, 2H), 7.20-7.15 (m, 3H), 6.65 (s, 1H), 4.61 (s, 2H), 4.40 (q, 2H), 3.53 (t, 2H), 2.70 (t, 2H), 1.98-1.88 (m, 2H), 1.42 (t, 3H)

Reference Production Example 106

Ethyl 5-(3-phenylpropoxymethyl)isoxazole-3-carboxylate (2.5 g, 8.7 mmol) was added to ethanol (20 mL), and 2 N sodium hydroxide (15 mL) was further added thereto. The mixture was stirred at room temperature for 16 hours, and then concentrated under reduced pressure. Dilute hydrochloric acid was added to the concentrate, the mixture was cooled to 0° C., and the precipitated solid was filtered. The resulting solid was dried under reduced pressure to obtain 1.80 g of 5-(3-phenylpropoxymethyl)isoxazole-3-carboxylic acid represented by the following formula.

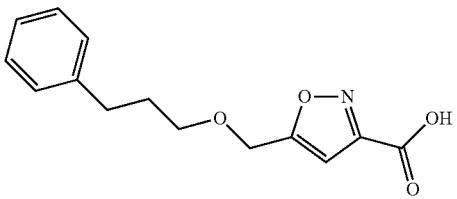 [SMILES: O=C(O)c1cc(COCCCc2ccccc2)on1]

¹H-NMR (DMSO-d6, TMS, δ(ppm)): 14.0 (brs, 1H), 7.28-7.13 (m, 5H), 6.82 (s, 1H), 4.64 (s, 2H), 3.46 (t, 2H), 2.61 (t, 2H), 1.86-1.77 (m, 2H)

Reference Production Example 107

60% Sodium hydride (1.04 g, 26.0 mmol) was added to dehydrated N,N-dimethylformamide (10 ml) cooled to 0° C., under a nitrogen atmosphere, and a dehydrated N,N-dimethylformamide (10 ml) solution of ethyl 5-hydroxymethylisoxazole-3-carboxylate (3.0 g, 17.54 mmol) was added dropwise thereto, and then the mixture was further stirred for 30 minutes. A dehydrated N,N-dimethylformamide (5 ml) solution of 1-bromo-4-phenylbutane (3.73 g, 17.54 mmol) was added thereto, and the mixture was heated to room temperature and stirred for 16 hours. Then, the mixture was added to a saturated aqueous ammonium chloride solution, and extracted twice with ethyl acetate. The organic layer was washed with water and saturated saline water, dried over anhydrous sodium sulfate, and then concentrated under reduced pressure. The residue was applied to a silica gel column chromatography to obtain 1.65 g of ethyl 5-(4-phenylbutoxymethyl)isoxazole-3-carboxylate represented by the following formula.

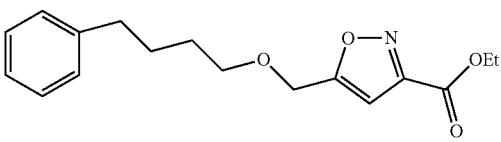 [SMILES: CCOC(=O)c1cc(COCCCCc2ccccc2)on1]

¹H-NMR (CDCl₃, TMS, δ(ppm)): 7.27 (m, 2H), 7.17 (m, 3H), 6.65 (s, 1H), 4.60 (s, 2H), 4.45 (q, 2H), 3.53 (t, 2H), 2.63 (t, 2H), 1.68 (m, 4H), 1.46 (t, 3H)

Reference Production Example 108

Ethyl 5-(4-phenylbutoxymethyl)isoxazole-3-carboxylate (2.5 g, 8.7 mmol) was added to ethanol (20 mL), and 2 N sodium hydroxide (15 mL) was further added thereto. The mixture was stirred at room temperature for 16 hours, and then concentrated under reduced pressure. Dilute hydrochloric acid was added to the concentrate, the mixture was cooled to 0° C., and the precipitated solid was filtered. The resulting solid was dried under reduced pressure to obtain 1.80 g of 5-(4-phenylbutoxymethyl)isoxazole-3-carboxylic acid represented by the following formula.

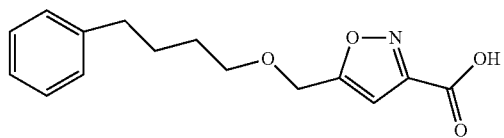 [SMILES: O=C(O)c1cc(COCCCCc2ccccc2)on1]

¹H-NMR (DMSO-d6, TMS, δ(ppm)): 7.29-7.21 (m, 5H), 6.80 (s, 1H), 4.62 (s, 2H), 3.50-3.31 (t, 2H), 2.58-2.48 (m, 3H), 1.62-1.50 (m, 4H)

Reference Production Example 109

60% Sodium hydride (1.04 g, 26.0 mmol) was added to dehydrated N,N-dimethylformamide (10 ml) cooled to 0° C., under a nitrogen atmosphere, and a dehydrated N,N-dimethylformamide (10 ml) solution of ethyl 5-hydroxymethylisoxazole-3-carboxylate (3.0 g, 17.54 mmol) was added dropwise thereto, and then the mixture was further stirred for 30 minutes. A dehydrated N,N-dimethylformamide (5 ml) solution of 1-bromo-5-phenylpentane (3.90 g, 17.54 mmol) was added thereto, and the mixture was heated to room temperature and stirred for 16 hours. Then, the mixture was added to a saturated aqueous ammonium chloride solution, and extracted twice with ethyl acetate. The organic layer was washed with water and saturated saline water, dried over anhydrous sodium sulfate, and then concentrated under reduced pressure. The residue was applied to a silica gel column chromatography to obtain 1.65 g of ethyl 5-(5-phenylpentyloxymethyl)isoxazole-3-carboxylate represented by the following formula.

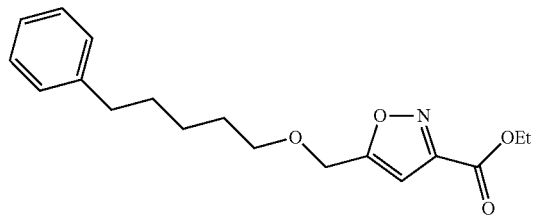 [SMILES: CCOC(=O)c1cc(COCCCCCc2ccccc2)on1]

¹H-NMR (CDCl₃, TMS, δ(ppm)): 7.29 (m, 2H), 7.17 (m, 3H), 6.65 (s, 1H), 4.61 (s, 2H), 4.44 (t, 2H), 3.51 (t, 2H), 2.61 (t, 2H), 1.62 (m, 4H), 1.42 (t, 5H)

Reference Production Example 110

Ethyl 5-(5-phenylpentyloxymethyl)isoxazole-3-carboxylate (2.2 g, 6.9 mmol) was added to a mixed solution of ethanol:water=2:1 (26 mL), and 2 N sodium hydroxide (14 mL) was further added thereto. The mixture was stirred at room temperature for 16 hours, and then concentrated under reduced pressure. Dilute hydrochloric acid was added to the concentrate, the mixture was cooled to 0° C., and the precipitated solid was filtered. The resulting solid was dried under reduced pressure to obtain 1.50 g of 5-(5-phenylpentyloxymethyl)isoxazole-3-carboxylic acid represented by the following formula.

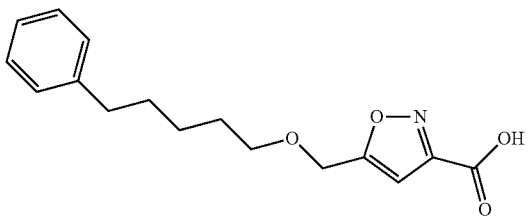 [SMILES: O=C(O)c1cc(COCCCCCc2ccccc2)on1]

$^1$H-NMR (DMSO-d6, TMS, δ(ppm)): 14.0 (s, 1H), 7.28-7.23 (m, 2H), 7.18-7.16 (m, 3H), 6.8 (s, 1H), 4.62 (s, 2H), 3.48-3.43 (t, 2H), 2.57-2.49 (m, 2H), 1.60-1.50 (m, 4H), 1.35-1.25 (m, 2H)

Reference Production Example 111

Ethyl nitroacetate (9.56 g, 80 mmol), 4-pentyn-1-ol (6.73 g, 80 mmol) and 1,4-diazabicyclo[2.2.2]octane (1.79 g, 16.0 mmol) were added to ethanol (40 ml). The mixture was heated at 80° C. for 48 hours and cooled to room temperature, and then concentrated under reduced pressure. The residue was applied to a silica gel column chromatography to obtain 8.61 g of ethyl 5-(3-hydroxypropyl)isoxazole-3-carboxylate represented by the following formula.

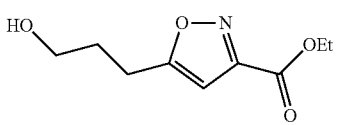 [SMILES: CCOC(=O)c1cc(CCCO)on1]

$^1$H-NMR (CDCl$_{13}$, TMS, δ(ppm)): 1.40 (3H, t), 1.97-2.03 (2H, m), 2.93 (2H, t), 3.71-3.72 (2H, m), 4.41 (2H, q), 6.43 (1H, s)

Reference Production Example 112

Ethyl 5-(3-hydroxypropyl)isoxazole-3-carboxylate (1.99 g, 10.0 mmol), benzyl bromide (1.71 g, 10.0 mmol), N,N-dimethylformamide (10 ml) and 60% sodium hydride (0.40 g, 10.0 mmol) were mixed at 0° C., under a nitrogen atmosphere. The mixture was heated to room temperature and stirred for 16 hours, then added to 1 N hydrochloric acid, and the mixture was extracted twice with ethyl acetate. The organic layer was washed with water and saturated saline water, dried over anhydrous sodium sulfate, and then concentrated under reduced pressure. The residue was applied to a silica gel column chromatography to obtain 0.91 g of ethyl 5-[3-(benzyloxy)propyl]isoxazole-3-carboxylate represented by the following formula.

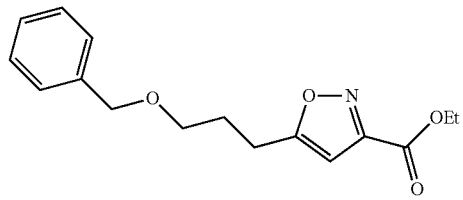 [SMILES: CCOC(=O)c1cc(CCCOCc2ccccc2)on1]

$^1$H-NMR (CDCl$_3$, TMS, δ(ppm)): 1.40 (3H, t), 1.98-2.03 (2H, m), 2.90-2.94 (2H, m), 3.49 (2H, t), 4.39 (2H, q), 4.48 (2H, s), 6.37 (1H, s), 7.27-7.36 (5H, m)

Reference Production Example 113

Ethyl 5-[3-(benzyloxy)propyl]isoxazole-3-carboxylate (0.91 g, 3.1 mmol) was added to ethanol (10 mrL), and potassium hydroxide (0.53 g, 9.5 mmol) and water (2 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 0.65 g of 5-[3-(benzyloxy)propyl]isoxazole-3-carboxylic acid represented by the following formula.

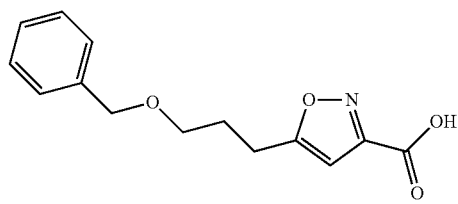 [SMILES: O=C(O)c1cc(CCCOCc2ccccc2)on1]

$^1$H-NMR (CDCl$_3$, TMS, δ(ppm)): 2.00-2.04 (2H, m), 2.95 (2H, t), 3.52 (2H, t), 4.50 (2H, s), 6.41 (1H, s), 7.27-7.36 (5H, m)

Reference Production Example 114

Ethyl nitroacetate (9.56 g, 80 mmol), 5-hexyn-1-ol (7.85 g, 80 mmol) and 1,4-diazabicyclo[2.2.2]octane (1.79 g, 16.0 mmol) were added to ethanol (40 ml). The mixture was heated at 80° C. for 48 hours and cooled to room temperature, and then concentrated under reduced pressure. The residue was applied to a silica gel column chromatography to obtain 8.61 g of ethyl 5-(4-hydroxybutyl)isoxazole-3-carboxylate represented by the following formula.

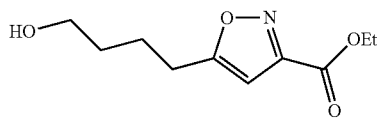 [SMILES: CCOC(=O)c1cc(CCCCO)on1]

$^1$H-NMR (CDCl$_3$, TMS, δ(ppm)): 1.42 (3H, t), 1.61-1.69 (2H, m), 1.80-1.88 (2H, m), 2.86 (2H, t), 3.70 (2H, t), 4.43 (2H, q), 6.44 (1H, s)

Reference Production Example 115

Ethyl 5-(4-hydroxybutyl)isoxazole-3-carboxylate (2.13 g, 10.0 mmol), benzyl bromide (1.71 g, 10.0 mmol), N,N- dimethylformamide (10 ml) and 60% sodium hydride (0.40 g, 10.0 mmol) were mixed at 0° C., under a nitrogen atmosphere. The mixture was heated to room temperature and stirred for 16 hours, then added to 1 N hydrochloric acid, and the mixture was extracted twice with ethyl acetate. The organic layer was washed with water and saturated saline water, dried over anhydrous sodium sulfate, and then concentrated under reduced pressure. The residue was applied to a silica gel column chromatography to obtain 0.78 g of ethyl 5-[4-(benzyloxy)butyl]isoxazole-3-carboxylate represented by the following formula.

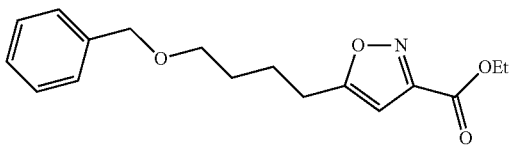 [SMILES: CCOC(=O)c1cc(CCCCOCc2ccccc2)on1]

$^1$H-NMR (CDCl$_3$, TMS, δ(ppm)): 1.40 (3H, t), 1.66-1.69 (2H, m), 1.77-1.83 (2H, m), 2.78-2.83 (2H, m), 3.47 (2H, t), 4.41 (2H, q), 4.48 (2H, s), 6.40 (1H, s), 7.26-7.37 (5H, m)

Reference Production Example 116

Ethyl 5-[4-(benzyloxy)butyl]isoxazole-3-carboxylate (0.78 g, 2.6 mmol) was added to ethanol (10 mL), and potassium hydroxide (0.58 g, 10.4 mmol) and water (2 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 0.42 g of 5-[4-(benzyloxy)butyl]isoxazole-3-carboxylic acid represented by the following formula.

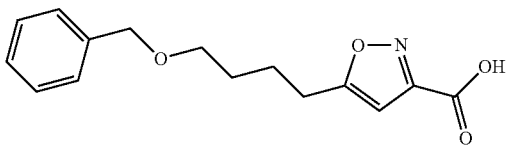 [SMILES: O=C(O)c1cc(CCCCOCc2ccccc2)on1]

$^1$H-NMR (CDCl$_3$, TMS, δ(ppm)): 1.68-1.70 (2H, m), 1.79-1.87 (2H, m), 2.83 (2H, t), 3.50 (2H, t), 4.50 (2H, s), 6.44 (1H, s), 7.26-7.37 (5H, m)

Reference Production Example 117

Ethyl nitroacetate (7.89 g, 66 mmol), 6-heptyn-1-ol (5.95 g, 53 mmol) and 1,4-diazabicyclo[2.2.2]octane (1.19 g, 10.6 mmol) were added to ethanol (40 ml). The mixture was heated at 80° C. for 24 hours and cooled to room temperature, and then concentrated under reduced pressure. The residue was applied to a silica gel column chromatography to obtain 2.59 g of ethyl 5-(5-hydroxypentyl)isoxazole-3-carboxylate represented by the following formula.

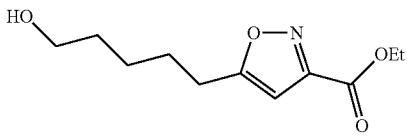 [SMILES: CCOC(=O)c1cc(CCCCCO)on1]

$^1$H-NMR (CDCl$_3$, TMS, δ(ppm)): 1.40 (3H, t), 1.42-1.47 (2H, m), 1.56-1.63 (2H, m), 1.71-1.79 (2H, m), 2.81 (2H, t), 3.62 (2H, q), 4.41 (2H, q), 6.40 (1H, s)

Reference Production Example 118

Ethyl 5-(5-hydroxypentyl)isoxazole-3-carboxylate (1.14 g, 5.0 mmol), benzyl bromide (0.86 g, 5.0 mmol), N,N-dimethylformamide (5 ml) and 60% sodium hydride (0.2 g, 5.0 mmol) were mixed at 0° C., under a nitrogen atmosphere. The mixture was heated to room temperature and stirred for 16 hours, then added to 1 N hydrochloric acid, and the mixture was extracted twice with ethyl acetate. The organic layer was washed with water and saturated saline water, dried over anhydrous sodium sulfate, and then concentrated under reduced pressure. The residue was added to ethanol (20 mL), and potassium hydroxide (1.12 g, 20 mmol) and water (4 mL) were added thereto, then the mixture was stirred at room temperature overnight, and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 1.34 g of a crude product of 5-[5-(benzyloxy)pentyl]isoxazole-3-carboxylic acid represented by the following formula.

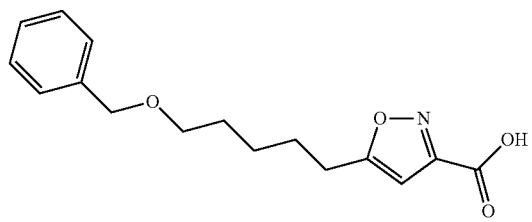 [SMILES: O=C(O)c1cc(CCCCCOCc2ccccc2)on1]

$^1$H-NMR (CDCl$_3$, TMS, δ(ppm)): 1.42-1.46 (2H, m), 1.62-1.65 (2H, m), 1.70-1.74 (2H, m), 2.76-2.81 (2H, m), 3.43-3.47 (2H, m), 4.48 (2H, s), 6.39 (1H, s), 7.31-7.37 (5H, m)

Reference Production Example 119

Ethyl nitroacetate (8.60 g, 72.3 mmol), 7-octyn-1-ol (7.63 g, 57.8 mmol) and 1,4-diazabicyclo[2.2.2]octane (1.30 g, 11.6 mmol) were added to ethanol (25 ml). The mixture was heated at 80° C. for 48 hours and cooled to room temperature, and then concentrated under reduced pressure. The residue was applied to a silica gel column chromatography to obtain 9.67 g of 5-(6-hydroxyhexyl)isoxazole-3-carboxylate represented by the following formula.

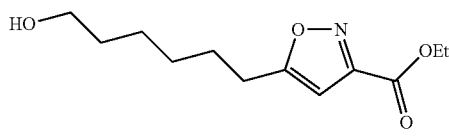 [SMILES: CCOC(=O)c1cc(CCCCCCO)on1]

$^1$H-NMR (CDCl$_3$, TMS, δ(ppm)): 1.37-1.41 (7H, t), 1.54-1.59 (2H, m), 1.70-1.76 (2H, m), 2.79 (2H, t), 3.61 (2H, t), 4.41 (2H, q), 6.39 (1H, s)

Reference Production Example 120

Ethyl 5-(6-hydroxyhexyl)isoxazole-3-carboxylate (1.14 g, 5.0 mmol), benzyl bromide (0.86 g, 5.0 mmol), N,N- dimethylformamide (5 ml) and 60% sodium hydride (0.2 g, 5.0 mmol) were mixed at 0° C., under a nitrogen atmosphere. The mixture was heated to room temperature and stirred for 16 hours, then added to 1 N hydrochloric acid, and the mixture was extracted twice with ethyl acetate. The organic layer was washed with water and saturated saline water, dried over anhydrous sodium sulfate, and then concentrated under reduced pressure. The residue was added to ethanol (20 mL), and potassium hydroxide (1.12 g, 20 mmol) and water (4 mL) were added thereto, then the mixture was stirred at room temperature overnight, and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 1.23 g of a crude product containing 5-[6-(benzyloxy)hexyl]isoxazole-3-carboxylic acid represented by the following formula.

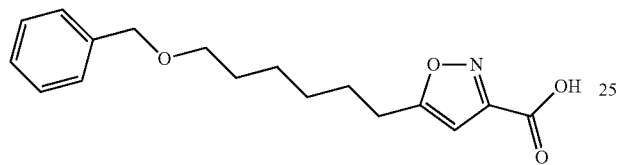

The crude product was used in Production Example 140 without purification.

Reference Production Example 121

Ethyl 5-(3-hydroxypropyl)isoxazole-3-carboxylate (1.99 g, 10.0 mmol), triphenylphosphine (5.38 g, 20.0 mmol) and phenol (1.88 g, 20.0 mmol) were added to dehydrated tetrahydrofuran (50 ml), under a nitrogen atmosphere. A tetrahydrofuran solution of diethyl azodicarboxylate (2.2 M, 10 ml, 22.0 mmol) was added dropwise thereto over 30 minutes, and the mixture was stirred at room temperature for 24 hours. Tert-butyl methyl ether was added to the reaction mixture, and the solid was filtered and removed. The filtrate was concentrated under reduced pressure, then ethanol (20 mL) was added to the residue, and potassium hydroxide (1.12 g, 20 mmol) and water (2 mL) were added thereto. The mixture was stirred at room temperature overnight, and then concentrated under reduced pressure. Water was added to the concentrate, and the mixture was washed with tert-butyl methyl ether. Then, dilute hydrochloric acid was added to the aqueous layer, and the mixture was extracted twice with ethyl acetate. The organic layer was washed with saturated saline water, dried over anhydrous sodium sulfate, and then concentrated under reduced pressure to obtain 0.49 g of 5-(3-phenoxypropyl)isoxazole-3-carboxylic acid represented by the following formula.

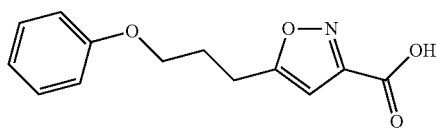 [SMILES: O=C(O)c1cc(CCCOc2ccccc2)on1]

$^1$H-NMR (CDCl$_3$, TMS, δ(ppm)): 2.18-2.25 (2H, m), 3.05 (2H, t), 4.01 (2H, t), 6.49 (1H, s), 6.81-6.97 (3H, m), 7.21-7.30 (2H, m)

Reference Production Example 122

Ethyl 5-(4-hydroxybutyl)isoxazole-3-carboxylate (1.48 g, 6.9 mmol), triphenylphosphine (3.74 g, 13.9 mmol) and phenol (1.31 g, 13.9 mmol) were added to dehydrated tetrahydrofuran (69 ml), under a nitrogen atmosphere. A tetrahydrofuran solution of diethyl azodicarboxylate (2.2 M, 6.4 ml, 13.9 mmol) was added dropwise thereto over 30 minutes, and the mixture was stirred at room temperature for 24 hours. The reaction mixture was added to dilute hydrochloric acid, and the mixture was extracted with ethyl acetate and concentrated under reduced pressure. The residue was applied to a silica gel column chromatography to obtain 1.72 g of ethyl 5-(4-phenoxybutyl)isoxazole-3-carboxylate represented by the following formula.

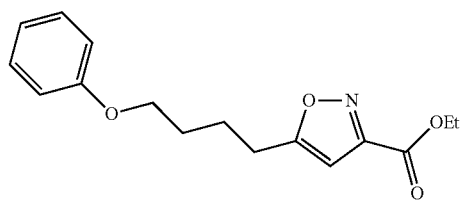 [SMILES: CCOC(=O)c1cc(CCCCOc2ccccc2)on1]

$^1$H-NMR (CDCl$_3$, TMS, δ(ppm)): 1.40 (3H, t), 1.83-1.95 (4H, m), 2.89 (2H, t), 3.98 (2H, t), 4.41 (2H, q), 6.44 (1H, s), 6.81-6.95 (3H, m), 7.21-7.29 (2H, m)

Reference Production Example 123

Ethyl 5-(4-phenoxybutyl)isoxazole-3-carboxylate (1.72 g, 5.94 mmol) was added to ethanol (10 mL), and potassium hydroxide (0.67 g, 11.9 mmol) and water (2 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain a crude product containing 3.64 g of 5-(4-phenoxybutyl)isoxazole-3-carboxylic acid represented by the following formula.

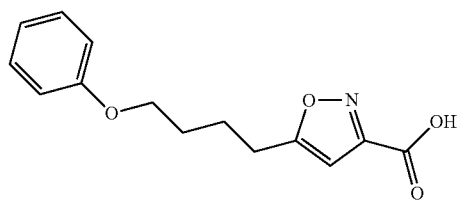 [SMILES: O=C(O)c1cc(CCCCOc2ccccc2)on1]

The crude product was used in a next step without purification.

Reference Production Example 124

Ethyl 5-(5-hydroxypentyl)isoxazole-3-carboxylate (1.14 g, 5.0 mmol), triphenylphosphine (2.69 g, 10.0 mmol) and phenol (1.31 g, 13.9 mmol) were added to dehydrated tetrahydrofuran (69 ml), under a nitrogen atmosphere. A tetrahydrofuran solution of diethyl azodicarboxylate (2.2 M, 6.4 ml, 13.9 mmol) was added dropwise thereto over 30 minutes, and the mixture was stirred at room temperature for 24 hours. The reaction mixture was added to dilute hydrochloric acid, and the mixture was extracted with ethyl acetate and concentrated under reduced pressure. The residue was applied to a silica gel column chromatography to obtain 1.19 g of ethyl 5-(5-phenoxypentyl)isoxazole-3-carboxylate represented by the following formula.

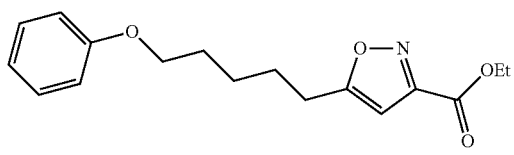 [SMILES: CCOC(=O)c1cc(CCCCCOc2ccccc2)on1]

$^1$H-NMR (CDCl$_3$, TMS, δ(ppm)): 1.40 (3H, m), 1.55-1.58 (2H, m), 1.77-1.85 (4H, m), 2.83 (2H, t), 3.93 (2H, t), 4.41 (2H, q), 6.41 (1H, s), 6.81-6.92 (3H, m), 7.21-7.29 (2H, m).

Reference Production Example 125

Ethanol (10 mL) was added to ethyl 5-(5-phenoxypentyl)isoxazole-3-carboxylate (1.19 g, 3.92 mmol), and potassium hydroxide (0.67 g, 11.9 mmol) and water (2 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 0.70 g of 5-(5-phenoxypentyl)isoxazole-3-carboxylic acid represented by the following formula.

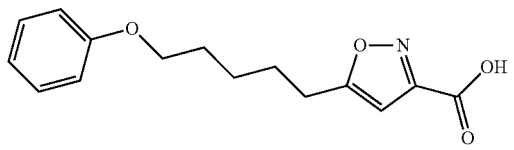 [SMILES: O=C(O)c1cc(CCCCCOc2ccccc2)on1]

$^1$H-NMR (CDCl$_3$, TMS, δ(ppm)): 1.54-1.60 (2H, m), 1.77-1.84 (4H, m), 2.86 (2H, t), 3.96 (2H, t), 6.47 (1H, s), 6.81-6.92 (3H, m), 7.21-7.29 (2H, m)

Reference Production Example 126

Ethyl 5-(6-hydroxyhexyl)isoxazole-3-carboxylate (1.21 g, 5.0 mmol), triphenylphosphine (2.69 g, 10.0 mmol) and phenol (1.31 g, 13.9 mmol) were added to dehydrated tetrahydrofuran (69 ml), under a nitrogen atmosphere. A tetrahydrofuran solution of diethyl azodicarboxylate (2.2 M, 6.4 ml, 13.9 mmol) was added dropwise thereto over 30 minutes, and the mixture was stirred at room temperature for 24 hours. The reaction mixture was added to dilute hydrochloric acid, and the mixture was extracted with ethyl acetate and concentrated under reduced pressure. The residue was applied to a silica gel column chromatography to obtain 1.41 g of ethyl 5-(6-phenoxyhexyl)isoxazole-3-carboxylate represented by the following formula.

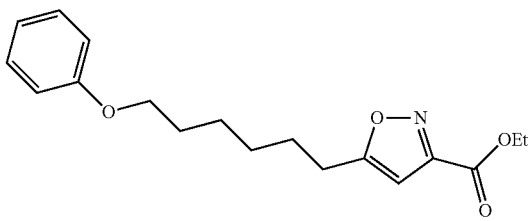 [SMILES: CCOC(=O)c1cc(CCCCCCOc2ccccc2)on1]

$^1$H-NMR (CDCl$_3$, TMS, δ(ppm)): 1.40-1.52 (7H, m), 1.71-1.79 (4H, m), 2.80 (2H, t), 3.94 (2H, t), 4.41 (2H, q), 6.40 (1H, s), 6.81-6.93 (3H, m), 7.21-7.28 (2H, m)

Reference Production Example 127

Ethanol (10 mL) was added to ethyl 5-(6-phenoxyhexyl)isoxazole-3-carboxylate (1.41 g, 4.64 mmol), and potassium hydroxide (1.29 g, 23 mmol) and water (2 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 1.32 g of 5-(6-phenoxyhexyl)isoxazole-3-carboxylic acid represented by the following formula.

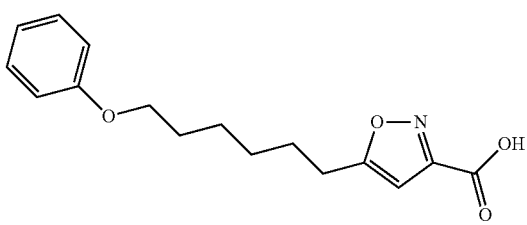 [SMILES: O=C(O)c1cc(CCCCCCOc2ccccc2)on1]

$^1$H-NMR (CDCl$_3$, TMS, δ(ppm)): 1.42-1.53 (4H, m), 1.72-1.80 (4H, m), 2.81 (2H, t), 3.94 (2H, t), 6.45 (1H, s), 6.83-6.92 (3H, m), 7.23-7.28 (2H, m)

Reference Production Example 128

Ethyl nitroacetate (2.11 g, 17.7 mmol), (2-phenoxyethyl)propargyl ether (1.96 g, 10 mmol) and 1,4-diazabicyclo[2.2.2]octane (0.56 g, 5 mmol) were added to chloroform (amylene addition product) (3 mL). The mixture was heated and refluxed for 24 hours and cooled to room temperature, then dilute hydrochloric acid was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 1.56 g of ethyl 5-(2-phenoxyethoxymethyl)isoxazole-3-carboxylate represented by the following formula.

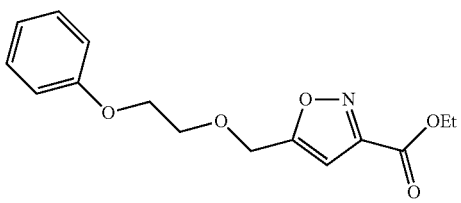 [SMILES: CCOC(=O)c1cc(COCCOc2ccccc2)on1]

¹H-NMR (CDCl₃, TMS, δ(ppm)): 1.40 (3H, t), 3.91 (2H, t), 4.15 (2H, t), 4.42 (2H, q), 4.77 (2H, s), 6.71 (1H, s), 6.89 (2H, d), 6.95 (1H, t), 7.24-7.29 (2H, m)

Reference Production Example 129

Ethyl 5-(2-phenoxyethoxymethyl)isoxazole-3-carboxylate (1.56 g, 2.6 mmol) was added to ethanol (10 mL), and potassium hydroxide (0.58 g, 10.4 mmol) and water (2 mL) were further added thereto. The mixture was stirred at room temperature overnight and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 1.40 g of 5-(2-phenylethoxymethyl)isoxazole-3-carboxylic acid represented by the following formula.

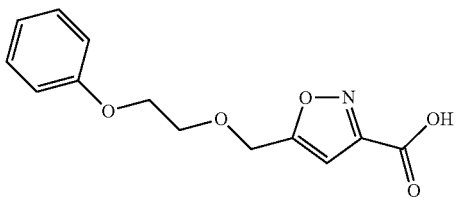 [SMILES: O=C(O)c1cc(COCCOc2ccccc2)on1]

¹H-NMR (CDCl₃, TMS, δ(ppm)): 3.91 (2H, t), 4.16 (2H, t), 4.79 (2H, s), 6.76 (1H, s), 6.89 (2H, d), 6.95 (1H, t), 7.24-7.30 (2H, m)

Reference Production Example 130

A solution obtained by adding ethyl 5-hydroxymethyl-isoxazole-3-carboxylate (7 g, 40.89 mmol) and 2-chlorophenol (4.59 mL, 44.98 mmol) to dehydrated tetrahydrofuran (70 ml) was cooled to 0° C. Triphenylphosphine (11.47 mL, 81.78 mmol), triethylamine (11.47 mL, 81.78 mmol) and diisopropyl azodicarboxylate (12.33 g, 61.33 mmol) were added thereto, under a nitrogen atmosphere. The reaction mixture was heated to room temperature and stirred for 2 hours, then poured into water, and the mixture was extracted twice with ethyl acetate. The organic layer was washed with water and saturated saline water, dried over anhydrous sodium sulfate, and then concentrated under reduced pressure. The residue was applied to a silica gel column chromatography to obtain 5.5 g of ethyl 5-(2-chlorophenoxymethyl)isoxazole-3-carboxylate represented by the following formula.

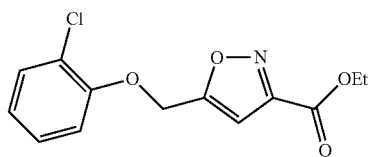 [SMILES: CCOC(=O)c1cc(COc2ccccc2Cl)on1]

¹H-NMR (CDCl₃, TMS, δ(ppm)): 7.40 (d, 1H), 7.22 (t, 1H), 6.97 (m, 2H), 6.81 (s, 1H), 5.27 (s, 2H), 4.50 (q, 2H), 1.42 (t, 3H)

Reference Production Example 131

Ethyl 5-(2-chlorophenoxymethyl)isoxazole-3-carboxylate (5.5 g, 19.57 mmol) was added to ethanol (55 mL), and lithium hydroxide (2.46 g, 58.7 mmol) and water (27.5 mL) were further added thereto. The mixture was stirred at room temperature for 16 hours and then concentrated under reduced pressure. Dilute hydrochloric acid was added to the concentrate, the mixture was cooled to 0° C., and the precipitated solid was filtered. The resulting solid was dried under reduced pressure to obtain 3.8 g of 5-(2-chlorophenoxymethyl)isoxazole-3-carboxylic acid represented by the following formula.

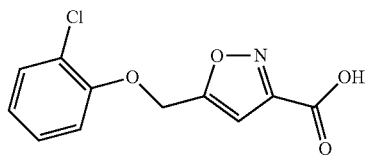 [SMILES: O=C(O)c1cc(COc2ccccc2Cl)on1]

¹H-NMR (DMSO-d6, TMS, δ(ppm)): 14.1 (brs, 1H), 7.46 (d, 1H), 7.36-7.30 (m, 2H), 7.02 (t, 1H), 6.95 (s, 1H), 5.45 (s, 2H)

Reference Production Example 132

A reaction was carried out in the same manner using 3-chlorophenol (4.59 mL, 44.98 mmol), in place of 2-chlorophenol in Reference Production Example 130 to obtain 5.5 g of ethyl 5-(3-chlorophenoxymethyl)isoxazole-3-carboxylate represented by the following formula.

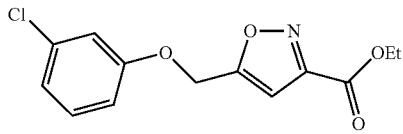 [SMILES: CCOC(=O)c1cc(COc2cccc(Cl)c2)on1]

¹H-NMR (CDCl₃, TMS, δ(ppm)): 7.23 (t, 1H), 7.01 (d, 1H), 6.96 (s, 1H), 6.84 (d, 1H), 6.76 (s, 1H), 5.19 (s, 2H), 4.45 (q, 2H), 1.42 (t, 3H)

Reference Production Example 133

A reaction was carried out in the same manner using ethyl 5-(3-chlorophenoxymethyl)isoxazole-3-carboxylate (5.5 g, 19.57 mmol), in place of ethyl 5-(2-chlorophenoxymethyl) isoxazole-3-carboxylate in Reference Production Example 131 to obtain 4.3 g of 5-(3-chlorophenoxymethyl)isoxazole-3-carboxylic acid represented by the following formula.

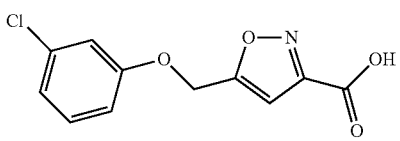 [SMILES: O=C(O)c1cc(COc2cccc(Cl)c2)on1]

$^1$H-NMR (DMSO-d6, TMS, δ(ppm)): 14.2 (brs, 1H), 7.32 (t, 1H), 7.16 (s, 1H), 7.04 (m, 3H), 5.36 (s, 2H)

Reference Production Example 134

A reaction was carried out in the same manner using 4-chlorophenol (4.59 mL, 44.98 mmol), in place of 2-chlorophenol in Reference Production Example 130 to obtain 2 g of ethyl 5-(4-chlorophenoxymethyl)isoxazole-3-carboxylate represented by the following formula.

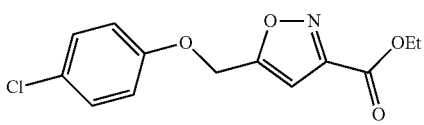 [SMILES: CCOC(=O)c1cc(COc2ccc(Cl)cc2)on1]

$^1$H-NMR (CDCl$_3$, TMS, δ(ppm)): 7.27 (d, 2H), 6.89 (d, 2H), 6.74 (s, 1H), 5.18 (s, 2H), 4.45 (q, 2H), 1.42 (t, 3H)

Reference Production Example 135

A reaction was carried out in the same manner using ethyl 5-(4-chlorophenoxymethyl)isoxazole-3-carboxylate (2 g, 7.11 mmol), in place of ethyl 5-(2-chlorophenoxymethyl)isoxazole-3-carboxylate in Reference Production Example 131 to obtain 1.6 g of 5-(4-chlorophenoxymethyl)isoxazole-3-carboxylic acid represented by the following formula.

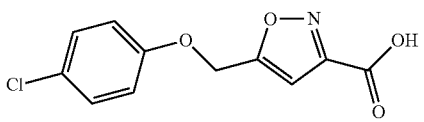 [SMILES: O=C(O)c1cc(COc2ccc(Cl)cc2)on1]

$^1$H-NMR (DMSO-d6, TMS, δ(ppm)): 14.2 (brs, 1H), 7.36 (d, 2H), 7.09 (d, 2H), 6.95 (s, 1H), 5.35 (s, 2H)

Reference Production Example 136

A reaction was carried out in the same manner using 3,4-dichlorophenol (7.3 g, 44.98 mmol), in place of 2-chlorophenol in Reference Production Example 130 to obtain 5.0 g of ethyl 5-(3,4-dichlorophenoxymethyl)isoxazole-3-carboxylate represented by the following formula.

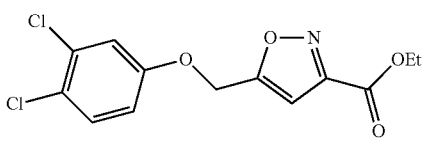 [SMILES: CCOC(=O)c1cc(COc2ccc(Cl)c(Cl)c2)on1]

$^1$H-NMR (CDCl$_3$, TMS, δ(ppm)): 7.37 (d, 1H), 7.07 (d, 1H), 6.82 (dd, 1H), 6.75 (s, 1H), 5.18 (s, 2H), 4.50 (q, 2H), 1.42 (t, 3H)

Reference Production Example 137

A reaction was carried out in the same manner using ethyl 5-(3,4-dichlorophenoxymethyl)isoxazole-3-carboxylate (5.0 g, 15.8 mmol), in place of ethyl 5-(2-chlorophenoxymethyl)isoxazole-3-carboxylate in Reference Production Example 131 to obtain 3.5 g of 5-(3,4-dichlorophenoxymethyl)isoxazole-3-carboxylic acid represented by the following formula.

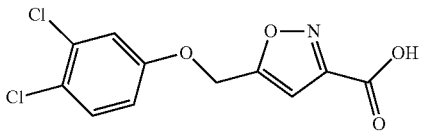 [SMILES: O=C(O)c1cc(COc2ccc(Cl)c(Cl)c2)on1]

$^1$H-NMR (DMSO-d6, TMS, δ(ppm)): 14.2 (brs, 1H), 7.57 (d, 1H), 7.42 (d, 1H), 7.1 (dd, 1H), 6.97 (s, 1H), 5.40 (s, 2H)

Reference Production Example 138

A reaction was carried out in the same manner using 4-fluorophenol (5.0 g, 44.98 mmol), in place of 2-chlorophenol in Reference Production Example 130 to obtain 2.7 g of ethyl 5-(4-fluorophenoxymethyl)isoxazole-3-carboxylate represented by the following formula.

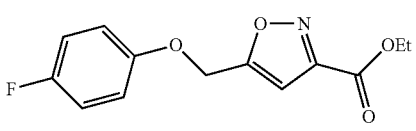 [SMILES: CCOC(=O)c1cc(COc2ccc(F)cc2)on1]

$^1$H-NMR (CDCl$_3$, TMS, δ(ppm)): 6.98 (d, 2H), 6.92 (d, 2H), 6.74 (s, 1H), 5.17 (s, 2H), 4.45 (q, 2H), 1.42 (t, 3H)

Reference Production Example 139

A reaction was carried out in the same manner using ethyl 5-(4-fluorophenoxymethyl)isoxazole-3-carboxylate (5.3 g, 20 mmol), in place of ethyl 5-(2-chlorophenoxymethyl)isoxazole-3-carboxylate in Reference Production Example 131 to obtain 1.7 g of 5-(4-fluorophenoxy)methylisoxazole-3-carboxylic acid represented by the following formula.

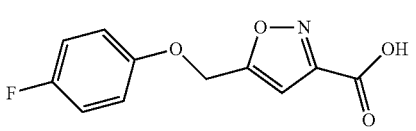

$^1$H-NMR (DMSO-d6, TMS, δ(ppm)): 14.2 (brs, 1H), 7.15 (m, 2H), 7.07 (m, 2H), 6.94 (s, 1H), 5.32 (s, 2H)

Reference Production Example 140

A reaction was carried out in the same manner using 4-bromophenol (7 g, 40.89 mmol), in place of 2-chlorophenol in Reference Production Example 130 to obtain 7.0 g of ethyl 5-(4-bromophenoxymethyl)isoxazole-3-carboxylate represented by the following formula.

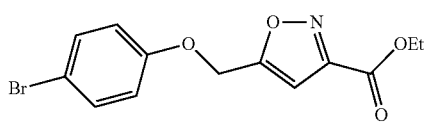

Ethyl 5-(4-bromophenoxymethyl)isoxazole-3-carboxylate was used in the production of 5-(4-bromophenoxymethyl)isoxazole-3-carboxylic acid without purification.

Reference Production Example 141

A reaction was carried out in the same manner using ethyl 5-(4-bromophenoxymethyl)isoxazole-3-carboxylate (7 g, 21.47 mmol), in place of ethyl 5-(2-chlorophenoxymethyl)isoxazole-3-carboxylate in Reference Production Example 131 to obtain 3.0 g of 5-(4-bromophenoxymethyl)isoxazole-3-carboxylic acid represented by the following formula.

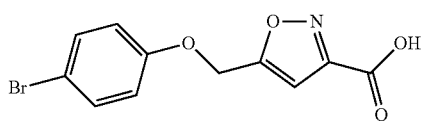

$^1$H-NMR (DMSO-d6, TMS, δ(ppm)): 14.1 (brs, 1H), 7.48 (d, 2H), 7.05 (d, 2H), 6.96 (s, 1H), 5.50 (s, 2H)

Reference Production Example 142

A reaction was carried out in the same manner using 4-trifluoromethylphenol (3.12 g, 19.29 mmol), in place of 2-chlorophenol in Reference Production Example 130 to obtain 2.4 of ethyl 5-(4-trifluoromethylphenoxymethyl)isoxazole-3-carboxylate represented by the following formula.

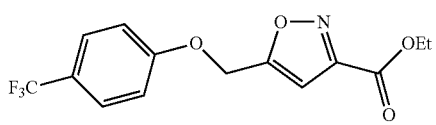 [SMILES: CCOC(=O)c1cc(COc2ccc(C(F)(F)F)cc2)on1]

$^1$H-NMR (CDCl$_3$, TMS, δ(ppm)): 7.58 (d, 2H), 7.02 (d, 2H), 6.77 (s, 1H), 5.45 (s, 2H), 4.44 (q, 2H), 1.42 (t, 3H)

Reference Production Example 143

A reaction was carried out in the same manner using ethyl 5-(4-trifluoromethylphenoxymethyl)isoxazole-3-carboxylate (3.2 g, 10.15 mmol), in place of ethyl 5-(2-chlorophenoxymethyl)isoxazole-3-carboxylate in Reference Production Example 131 to obtain 2.6 g of 5-(4-trifluoromethylphenoxymethyl)isoxazole-3-carboxylic acid represented by the following formula.

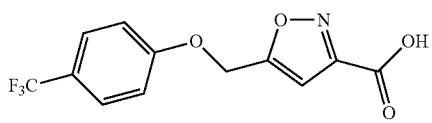 [SMILES: O=C(O)c1cc(COc2ccc(C(F)(F)F)cc2)on1]

$^1$H-NMR (DMSO-d6, TMS, δ(ppm)): 14.0 (brs, 1H), 7.70 (d, 2H), 7.25 (d, 2H), 6.99 (s, 1H), 5.46 (s, 2H)

Reference Production Example 144

A reaction was carried out in the same manner using 4-trifluoromethoxyphenol (0.837 mL, 6.43 mmol), in place of 2-chlorophenol in Reference Production Example 130 to obtain 600 mg of ethyl 5-(4-trifluoromethoxyphenoxymethyl)isoxazole-3-carboxylate represented by the following formula.

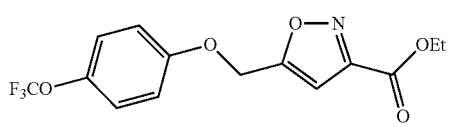 [SMILES: CCOC(=O)c1cc(COc2ccc(OC(F)(F)F)cc2)on1]

$^1$H-NMR (CDCl$_3$, TMS, δ(ppm)): 7.16 (d, 2H), 6.95 (d, 2H), 6.76 (s, 1H), 5.20 (s, 2H), 4.45 (q, 2H), 1.42 (t, 3H)

Reference Production Example 145

A reaction was carried out in the same manner using ethyl 5-(4-trifluoromethoxyphenoxymethyl)isoxazole-3-carboxylate (600 mg, 1.812 mmol), in place of ethyl 5-(2-chlorophenoxymethyl)isoxazole-3-carboxylate in Reference Production Example 131 to obtain 500 mg of 5-(4-trifluoromethoxyphenoxymethyl)isoxazole-3-carboxylic acid represented by the following formula.

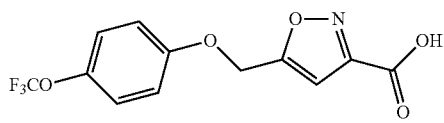

$^1$H-NMR (CDCl$_3$, TMS, δ(ppm)): 14.1 (brs, 1H), 7.32 (d, 2H), 7.16 (d, 2H), 6.97 (s, 1H), 5.38 (s, 2H)

Reference Production Example 146

A reaction was carried out in the same manner using 4-(trifluoromrnethylthio)phenol (1.24 g, 6.427 mmol), in place of 2-chlorophenol in Reference Production Example 130 to obtain 1.0 g of ethyl 5-(4-trifluoromethylthiophenoxymethyl)isoxazole-3-carboxylate represented by the following formula.

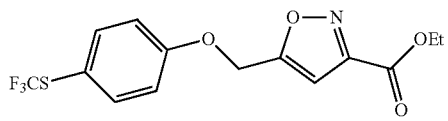

$^1$H-NMR (CDCl$_3$, TMS, δ(ppm)): 7.16 (d, 2H), 6.95 (d, 2H), 6.76 (s, 1H), 5.20 (s, 2H), 4.45 (q, 2H), 1.42 (t, 3H)

Reference Production Example 147

A reaction was carried out in the same manner using ethyl 5-(4-trifluoromethylthiophenoxymethyl)isoxazole-3-carboxylate (4.5 g, 12.9 mmol), in place of ethyl 5-(2-chlorophenoxymethyl)isoxazole-3-carboxylate in Reference Production Example 131 to obtain 3.0 g of 5-(4-trifluoromethylthiophenoxymethyl)isoxazole-3-carboxylic acid represented by the following formula.

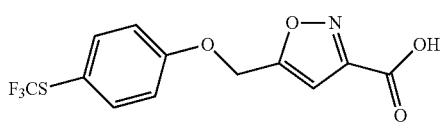

¹H-NMR (CDCl₃, TMS, δ(ppm)): 14.10 (brs, 1H), 7.68 (d, 2H), 7.21 (d, 2H), 6.98 (s, 1H), 5.43 (s, 2H)

Reference Production Example 148

A reaction was carried out in the same manner using 3-fluorophenol (4.32 g, 38.5 mmol), in place of 2-chlorophenol in Reference Production Example 130 to obtain 4.1 g of ethyl 5-(3-fluorophenoxymethyl)isoxazole-3-carboxylate represented by the following formula.

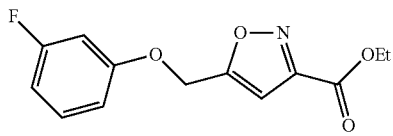 [SMILES: CCOC(=O)c1cc(COc2cccc(F)c2)on1]

¹H-NMR (CDCl₃, TMS, δ(ppm)): 6.76 (m, 5H), 5.20 (s, 2H), 4.45 (q, 2H), 1.41 (t, 3H).

Reference Production Example 149

A reaction was carried out in the same manner using ethyl 5-(3-fluorophenoxymethyl)isoxazole-3-carboxylate (4.5 g, 17.30 mmol), in place of ethyl 5-(2-chlorophenoxymethyl)isoxazole-3-carboxylate in Reference Production Example 131 to obtain 3.2 g of 5-(3-fluorophenoxymethyl)isoxazole-3-carboxylic acid represented by the following formula.

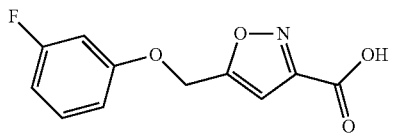

¹H-NMR (CDCl₃, TMS, δ(ppm)): 14.0 (brs, 1H), 7.34 (q, 1H), 6.93 (m, 4H) 5.37 (s, 2H)

Reference Production Example 150

A reaction was carried out in the same manner using 3-bromophenol (6.6 g, 38.58 mmol), in place of 2-chlorophenol in Reference Production Example 130 to obtain 3.6 g of ethyl 5-(3-bromophenoxymethyl)isoxazole-3-carboxylate represented by the following formula.

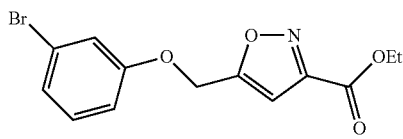

¹H-NMR (CDCl₃, TMS, δ(ppm)): 7.16 (m, 2H), 7.12 (s, 1H), 6.90-6.87 (m, 1H), 6.76 (s, 1H), 5.40 (s, 2H), 4.48-4.42 (q, 2H), 1.44-1.40 (t, 3H)

Reference Production Example 151

A reaction was carried out in the same manner using ethyl 5-(3-bromophenoxymethyl)isoxazole-3-carboxylate (4.2 g, 12.88 mmol), in place of ethyl 5-(2-chlorophenoxymethyl) isoxazole-3-carboxylate in Reference Production Example 131 to obtain 3.4 g of 5-(3-bromophenoxymethyl)isoxazole-3-carboxylic acid represented by the following formula.

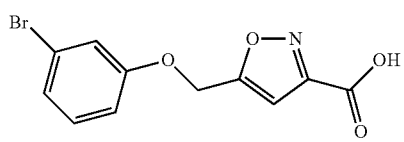

¹H-NMR (CDCl₃, TMS, δ(ppm)): 14.0 (s, 1H), 7.31 (s, 1H), 7.26 (d, 1H), 7.19 (d, 1H), 7.08 (d, 1H), 6.96 (s, 1H), 5.38 (s, 2H)

Reference Production Example 152

A reaction was carried out in the same manner using 3-trifluoromethylphenol (2.65 g, 16.3 mmol), in place of 2-chlorophenol in Reference Production Example 130 to obtain 2.2 g of ethyl 5-(3-trifluoromethylphenoxymethyl) isoxazole-3-carboxylate represented by the following formula.

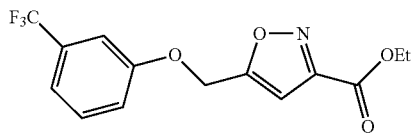 [SMILES: CCOC(=O)c1cc(COc2cccc(C(F)(F)F)c2)on1]

¹H-NMR (CDCl₃, TMS, δ(ppm)): 7.50-7.40 (m, 1H), 7.36-7.26 (m, 1H), 7.20 (s, 1H), 7.26-7.1 (dd, 1H), 6.80 (s, 1H), 5.25 (s, 2H), 4.45 (q, 2H), 1.40 (t, 3H)

Reference Production Example 153

A reaction was carried out in the same manner using ethyl 5-(3-trifluoromethylphenoxymethyl)isoxazole-3-carboxylate (2.7 g, 8.57 mmol), in place of ethyl 5-(2-chlorophenoxymethyl)isoxazole-3-carboxylate in Reference Production Example 131 to obtain 1.9 g of 5-(3-trifluoromethylphenoxymethyl)isoxazole-3-carboxylic acid represented by the following formula.

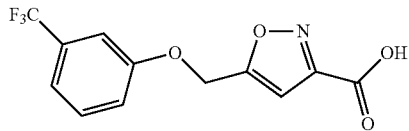 [SMILES: O=C(O)c1cc(COc2cccc(C(F)(F)F)c2)on1]

¹H-NMR (CDCl₃, TMS, δ(ppm)): 14.0 (brs, 1H), 7.58 (t, 1H), 7.46-7.28 (m, 3H), 7.0 (s, 1H), 5.50 (s, 2H)

Reference Production Example 154

A reaction was carried out in the same manner using 3-trifluoromethoxyphenol (3.42 g, 19.29 mmol), in place of 2-chlorophenol in Reference Production Example 130 to obtain 3.0 g of ethyl 5-(3-trifluoromethoxyphenoxymethyl)isoxazole-3-carboxylate represented by the following formula.

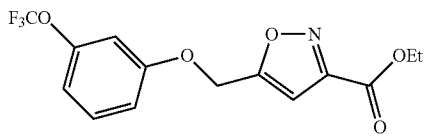

$^1$H-NMR (CDCl$_3$, TMS, δ(ppm)): 7.32 (t, 1H), 6.89 (t, 2H), 6.81 (m, 2H), 5.2 (s, 2H), 4.45 (q, 2H), 1.42 (t, 3H)

Reference Production Example 155

A reaction was carried out in the same manner using ethyl 5-(3-trifluoromethoxyphenoxymethyl)isoxazole-3-carboxylate (4.0 g, 12.08 mmol), in place of ethyl 5-(2-chlorophenoxymethyl)isoxazole-3-carboxylate in Reference Production Example 131 to obtain 3.2 g of 5-(3-trifluoromethoxyphenoxymethyl)isoxazole-3-carboxylic acid represented by the following formula.

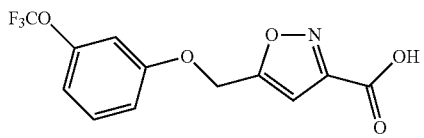

$^1$H-NMR (CDCl$_3$, TMS, δ(ppm)): 14.0 (brs, 1H), 7.45 (t, 1H), 7.12 (d, 2H), 7.01 (d, 2H) 5.41 (s, 2H)

Reference Production Example 156

A reaction was carried out in the same manner using 3-(trifluoromethylthio)phenol (1.49 g, 7.68 mmol), in place of 2-chlorophenol in Reference Production Example 130 to obtain 1.8 g of ethyl 5-(3-trifluoromethylthiophenoxymethyl)isoxazole-3-carboxylate represented by the following formula.

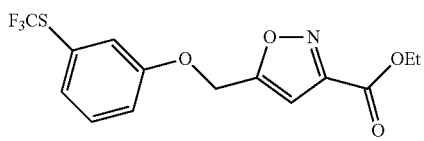

$^1$H-NMR (CDCl$_3$, TMS, δ(ppm)): 7.38 (s, 1H), 7.36 (s, 1H), 7.26 (s, 1H), 7.10 (d, 1H), 6.78 (s, 1H), 5.23 (s, 2H), 4.45 (q, 2H), 1.42 (t, 3H)

Reference Production Example 157

A reaction was carried out in the same manner using ethyl 5-(3-trifluoromethylthiophenoxymethyl)isoxazole-3-carboxylate (1.7 g, 4.91 mmol), in place of ethyl 5-(2-chlorophenoxymethyl)isoxazole-3-carboxylate in Reference Production Example 131 to obtain 1.2 g of 5-(3-trifluoromethylthiophenoxymethyl)isoxazole-3-carboxylic acid represented by the following formula.

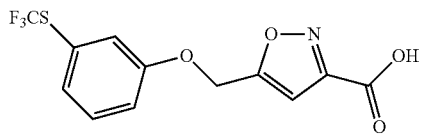

$^1$H-NMR (CDCl$_3$, TMS, δ(ppm)): 14.2 (brs, 1H), 7.5 (t, 1H), 7.40 (s, 1H), 7.36-7.31 (m, 2H), 6.98 (s, 1H), 5.43 (s, 2H)

Reference Production Example 158

A reaction was carried out in the same manner using sesamol (6.21 g, 45.02 mmol), in place of 2-chlorophenol in Reference Production Example 130 to obtain 4.3 g of ethyl 5-[5-(1,3-benzodioxolanyl)oxymethyl]isoxazole-3-carboxylate represented by the following formula.

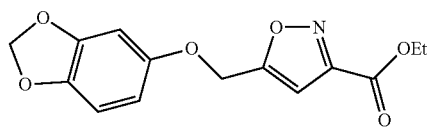 [SMILES: CCOC(=O)c1cc(COc2ccc3c(c2)OCO3)on1]

$^1$H-NMR (CDCl$_3$, TMS, δ(ppm)): 6.73-6.69 (m, 2H), 6.53-6.52 (d, 1H), 6.37-6.35 (m, 1H), 5.90 (s, 2H), 5.12 (s, 2H), 4.47-4.41 (q, 2H), 1.43-1.39 (q, 3H)

Reference Production Example 159

A reaction was carried out in the same manner using ethyl 5-[(5-(1,3-benzodioxolanyl)oxymethyl]isoxazole-3-carboxylat e (5 g, 17.18 mmol), in place of ethyl 5-(2-chlorophenoxymethyl)isoxazole-3-carboxylate in Reference Production Example 131 to obtain 2.2 g of 5-[5-(1,3-benzodioxolanyl)oxymethyl]isoxazole-3-carboxylic acid represented by the following formula.

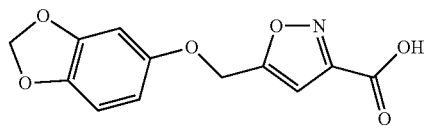 [SMILES: O=C(O)c1cc(COc2ccc3c(c2)OCO3)on1]

$^1$H-NMR (DMSO-d6, TMS, δ(ppm)): 14.0 (brs, 1H), 6.92 (s, 1H), 6.84-6.81 (d, 1H), 6.76 (d, 1H), 6.50-6.47 (m, 1H), 5.97 (s, 2H), 5.28 (s, 2H)

Reference Production Example 160

A reaction was carried out in the same manner using 3,4-dimethoxyphenol (1.3 g, 8.54 mmol), in place of 2-chlorophenol in Reference Production Example 130 to obtain 1.9 g of ethyl 5-(3,4-dimethoxyphenoxymethyl)isoxazole-3-carboxylate represented by the following formula.

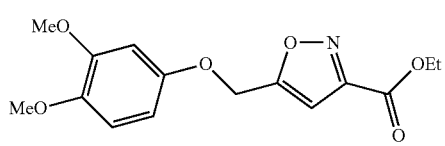 [SMILES: CCOC(=O)c1cc(COc2ccc(OC)c(OC)c2)on1]

¹H-NMR (CDCl₃, TMS, δ(ppm)): 6.85-6.70 (m, 2H), 6.60 (d, 1H), 6.45 (dd, 1H), 5.15 (s, 2H), 4.45 (q, 2H), 3.86 (s, 3H), 3.84 (s, 3H), 1.42 (t, 3H)

Reference Production Example 161

A reaction was carried out in the same manner using ethyl 5-(3,4-dimethoxyphenoxy)methylisoxazole-3-carboxylate (1.9 g, 6.18 mmol), in place of ethyl 5-(2-chlorophenoxymethyl)isoxazole-3-carboxylate in Reference Production Example 131 to obtain 1.6 g of 5-(3,4-dimethoxyphenoxy)methylisoxazole-3-carboxylic acid represented by the following formula.

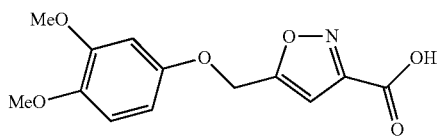 [SMILES: COc1ccc(OCc2cc(C(=O)O)no2)cc1OC]

¹H-NMR (DMSO-d6, TMS, δ(ppm)): 14.1 (brs, 1H), 6.92 (s, 1H), 6.86 (d, 2H), 6.70 (d, 1H), 6.58 (dd, 1H), 5.30 (s, 1H), 3.56 (s, 3H), 3.40 (s, 3H)

Reference Production Example 162

2-Bromonaphthalene (4.14 g, 20.0 mmol), 4-penten-2-ol (2.60 g, 30.0 mmol), palladium acetate (2.00 g, 9.0 mmol), tetrabutylammonium chloride (11.1 g, 40.0 mmol), lithium chloride (0.85 g, 20.0 mmol) and lithium acetate dihydrate (5.20 g, 50.0 mmol) were added to N,N-dimethylformamide (40 ml), and the mixture was stirred at 100° C. for 72 hours, under a nitrogen atmosphere. The reaction mixture was cooled to room temperature and added to 1 N hydrochloric acid, then the solid was filtered with celite and removed, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 3.47 g of 5-(2-naphthyl)pentan-2-one represented by the following formula.

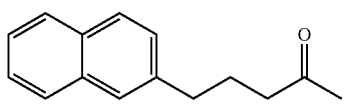 [SMILES: CC(=O)CCCc1ccc2ccccc2c1]

¹H-NMR (CDCl₃, TMS, δ(ppm)): 1.98 (2H, dt), 2.06 (3H, s), 2.44 (2H, t), 2.76 (2H, t), 7.29 (1H, dd), 7.40-7.44 (3H, m), 7.58 (1H, s), 7.74-7.79 (3H, m)

Reference Production Example 163

5-(2-Naphthyl)pentan-2-one (3.47 g, 16.3 mmol) and diethyl oxalate (2.40 g, 16.3 mmol) were dissolved in ethanol (33 ml), and the mixture was cooled to 0° C. under a nitrogen atmosphere. Sodium ethoxide (20% ethanol solution, 5.58 g, 16.3 mmol) was added dropwise to the cooled solution over 30 minutes, and the mixture was stirred at room temperature overnight and then concentrated under reduced pressure. 1 N Hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 4.48 g of ethyl 7-(2-naphthyl)-2,4-dioxoheptanoate represented by the following formula.

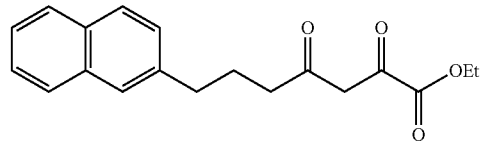 [SMILES: CCOC(=O)C(=O)CC(=O)CCCc1ccc2ccccc2c1]

¹H-NMR (CDCl₃, TMS, δ(ppm)): 1.35 (3H, t), 2.08 (2H, t), 2.53 (2H, t), 2.83 (2H, t), 4.37 (2H, q), 6.32 (1H, s), 7.30 (1H, dd), 7.40-7.47 (3H, m), 7.60 (1H, s), 7.75-7.781 (3H, m)

Reference Production Example 164

Ethyl 7-(2-naphthyl)-2,4-dioxoheptanoate (4.48 g, 15.0 mmol) was dissolved in ethanol (30 ml), and hydroxylamine hydrochloride (1.15 g, 16.5 mmol) was added thereto, and the mixture was heated and refluxed for 6 hours, under a nitrogen atmosphere. The reaction mixture was cooled to room temperature, and concentrated under reduced pressure. 1 N Hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 3.14 g of ethyl 5-[3-(2-naphthyl)propyl]isoxazole-3-carboxylate represented by the following formula.

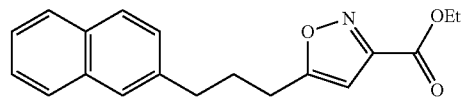 [SMILES: CCOC(=O)c1cc(CCCc2ccc3ccccc3c2)on1]

¹H-NMR (CDCl₃, TMS, δ(ppm)): 1.42 (3H, t), 2.15 (2H, dt), 2.83-2.88 (4H, m), 4.43 (2H, q), 6.43 (1H, s), 7.33 (1H, dd), 7.42-7.49 (3H, m), 7.62 (1H, s), 7.78-7.83 (3H, m)

Reference Production Example 165

Ethyl 5-[3-(2-naphthyl)propyl]isoxazole-3-carboxylate (3.14 g, 10.1 mmol) was dissolved in ethanol (50 ml), and water (10 ml) and potassium hydroxide (2.85 g, 50.7 mmol) were added thereto. The mixture was stirred at room temperature for 1 hour and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 2.19 g of 5-[3-(2-naphthyl)propyl]isoxazole-3-carboxylic acid represented by the following formula.

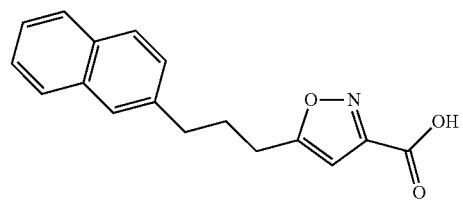 [SMILES: O=C(O)c1cc(CCCc2ccc3ccccc3c2)on1]

$^1$H-NMR (CDCl$_3$, TMS, δ(ppm)): 2.15-2.19 (2H, m), 2.84-2.87 (4H, m), 6.45 (1H, s), 7.30 (1H, dd), 7.40-7.48 (3H, m), 7.61 (1H, s), 7.76-7.81 (3H, m)

Reference Production Example 166

5-Bromo-2,2-difluoro-1,3-benzodioxole (4.74 g, 20.0 mmol), 4-penten-2-ol (2.60 g, 30.0 mmol), palladium acetate (2.00 g, 9.0 mmol), tetrabutylammonium chloride (11.1 g, 40.0 mmol), lithium chloride (0.85 g, 20.0 mmol) and lithium acetate dihydrate (5.20 g, 50.0 mmol) were added to N,N-dimethylformamide (40 ml), and the mixture was stirred at 100° C. for 72 hours, under a nitrogen atmosphere. The mixture was cooled to room temperature and added to 1 N hydrochloric acid, then the solid was filtered with celite and removed, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 2.95 g of 5-[5-(2,2-difluoro-1,3-benzodioxolanyl)]pentan-2-on represented by the following formula.

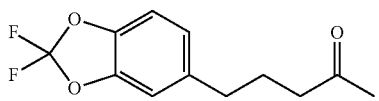 [SMILES: CC(=O)CCCc1ccc2c(c1)OC(F)(F)O2]

$^1$H-NMR (CDCl$_3$, TMS, δ(ppm)): 1.86 (2H, dt), 2.12 (3H, s), 2.42 (2H, t), 2.59 (2H, t), 6.83-6.95 (3H, m)

Reference Production Example 167

5-[5-(2,2-Difluoro-1,3-benzodioxolanyl)]pentan-2-on (2.84 g, 11.7 mmol) and diethyl oxalate (1.88 g, 12.9 mmol) were dissolved in ethanol (26 ml), and the mixture was cooled to 0° C. under a nitrogen atmosphere. Sodium ethoxide (20% ethanol solution, 4.39 g, 12.9 mmol) was added dropwise to the cooled solution over 30 minutes, and the mixture was stirred at room temperature overnight and then concentrated under reduced pressure. 1 N Hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 2.84 g of ethyl 7-[5-(2,2-difluoro-1,3-benzodioxolanyl)]-2,4-dioxoheptanoate represented by the following formula.

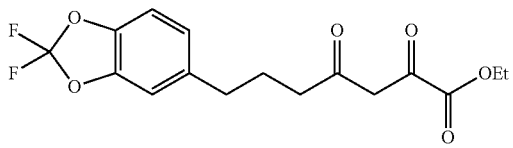 [SMILES: CCOC(=O)C(=O)CC(=O)CCCc1ccc2c(c1)OC(F)(F)O2]

$^1$H-NMR (CDCl$_3$, TMS, δ(ppm)): 1.36 (3H, t), 1.95 (2H, dt), 2.49 (2H, t), 2.64 (2H, t), 4.33 (2H, q), 6.33 (1H, s), 6.84-6.95 (3H, m)

Reference Production Example 168

Ethyl 7-[5-(2,2-difluoro-1,3-benzodioxolanyl)]-2,4-dioxoheptanoate (2.84 g, 8.3 mmol) was dissolved in ethanol (20 ml), and hydroxylamine hydrochloride (0.68 g, 9.3 mmol) was added thereto, and the mixture was heated and refluxed for 6 hours, under a nitrogen atmosphere. The reaction mixture was cooled to room temperature, and then concentrated under reduced pressure. 1 N Hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 2.67 g of ethyl 5-[3-(2,2-difluoro-1,3-benzodioxolan-5-yl)propyl]isoxazole-3-carboxylate represented by the following formula.

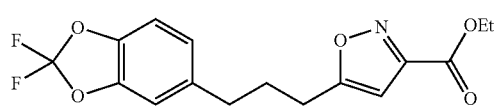 [SMILES: CCOC(=O)c1cc(CCCc2ccc3c(c2)OC(F)(F)O3)on1]

$^1$H-NMR (CDCl$_3$, TMS, δ(ppm)): 1.40 (3H, t), 2.02 (2H, dt), 2.67 (2H, t), 2.80 (2H, t), 4.41 (2H, q), 6.41 (1H, s), 6.84-6.97 (3H, m)

Reference Production Example 169

Ethyl 5-[3-(2,2-difluoro-1,3-benzodioxolan-5-yl) propyl]isoxazole-3-carboxylate (2.67 g, 7.8 mmol) was added to ethanol (20 ml), and water (10 ml) and potassium hydroxide (1.32 g, 23.6 mmol) were added thereto. The mixture was stirred at room temperature for 1 hour and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 1.10 g of 5-[3-(2,2-difluoro-1,3-benzodioxolan-5-yl)propyl]isoxazole-3-carboxylic acid represented by the following formula.

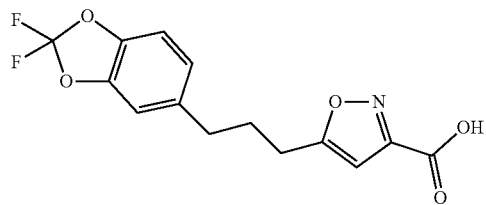 [SMILES: O=C(O)c1cc(CCCc2ccc3c(c2)OC(F)(F)O3)on1]

$^1$H-NMR (CDCl$_3$, TMS, δ(ppm)): 2.04 (2H, dt), 2.68 (2H, t), 2.83 (2H, t), 6.47 (1H, s), 6.85-6.98 (3H, m)

Reference Production Example 170

5-Bromo-1,3-benzodioxole (4.02 g, 20.0 mmol), 4-penten-2-ol (2.60 g, 30.0 mmol), palladium acetate (2.00 g, 9.0 mmol), tetrabutylammonium chloride (11.1 g, 40.0 mmol), lithium chloride (0.85 g, 20.0 mmol) and lithium acetate dihydrate (5.20 g, 50.0 mmol) were added to N,N-dimethylformamide (40 ml), and the mixture was stirred at 100° C. for 72 hours, under a nitrogen atmosphere. The mixture was cooled to room temperature and added to 1 N hydrochloric acid, then the solid was filtered with celite and removed, and the mixture was extracted twice with ethyl acetate. The organic layer was washed with saturated saline water, dried over anhydrous magnesium sulfate, and then concentrated under reduced pressure. The residue was applied to a silica gel column chromatography to obtain 1.82 g of 5-(1,3-benzodioxolan-5-yl)pentan-2-on represented by the following formula.

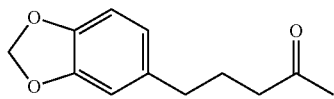

$^1$H-NMR (CDCl$_3$, TMS, δ(ppm)): 1.84 (2H, dt), 2.11 (3H, s), 2.41 (2H, t), 2.52 (2H, t), 5.91 (2H, s), 6.58-6.72 (3H, m)

Reference Production Example 171

5-(1,3-Benzodioxolan-5-yl)pentan-2-on (2.84 g, 11.7 mmol) and diethyl oxalate (1.88 g, 12.9 mmol) were dissolved in ethanol (26 ml), and the mixture was cooled to 0° C. under a nitrogen atmosphere. Sodium ethoxide (20% ethanol solution, 4.39 g, 12.9 mmol) was added dropwise thereto over 30 minutes, and the mixture was stirred at room temperature overnight. 1 N Hydrochloric acid was added to the concentrate obtained by concentrating the mixture under reduced pressure, and the mixture was extracted twice with ethyl acetate. The organic layer was washed with saturated saline water, dried over anhydrous sodium sulfate, and then concentrated under reduced pressure. The residue was applied to a silica gel column chromatography to obtain 2.84 g of ethyl 7-(1,3-benzodioxolan-5-yl)-2,4-dioxoheptanoate represented by the following formula.

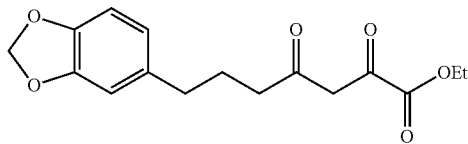 [SMILES: CCOC(=O)C(=O)CC(=O)CCCc1ccc2c(c1)OCO2]

$^1$H-NMR (CDCl$_3$, TMS, δ(ppm)): 1.36 (3H, t), 1.93 (2H, dt), 2.47 (2H, t), 2.57 (2H, t), 4.33 (2H, q), 5.91 (2H, s), 6.32 (1H, s), 6.60-6.72 (3H, m)

Reference Production Example 172

Ethyl 7-(1,3-benzodioxolan-5-yl)-2,4-dioxoheptanoate (2.84 g, 8.3 mmol) was dissolved in ethanol (20 ml), and hydroxylamine hydrochloride (0.68 g, 9.3 mmol) was added thereto, and the mixture was heated and refluxed for 6 hours, under a nitrogen atmosphere. The reaction mixture was cooled to room temperature, and then concentrated under reduced pressure. 1 N Hydrochloric acid was added to the concentrate, and the mixture was extracted twice with ethyl acetate. The organic layer was washed with saturated saline water, dried over anhydrous sodium sulfate, and then concentrated under reduced pressure. The residue was dissolved in ethanol (20 ml), and water (10 ml) and potassium hydroxide (1.32 g, 23.6 mmol) were added thereto, and the mixture was stirred at room temperature for 1 hour, and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure. The residue was applied to a silica gel column chromatography to obtain 1.10 g of 5-[3-(1,3-benzodioxolan-5-yl)propyl]isoxazole-3-carboxylic acid represented by the following formula.

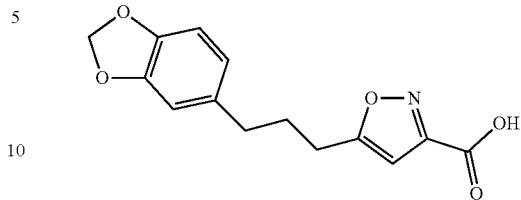

$^1$H-NMR (CDCl$_3$, TMS, δ(ppm)): 2.01 (2H, dt), 2.61 (2H, t), 2.81 (2H, t), 5.92 (2H, s), 6.45 (1H, s), 6.62-6.74 (3H, m)

Reference Production Example 173

Ethyl 5-hydroxymethylisoxazole-3-carboxylate (1.85 g, 10.0 mmol) and 5-bromomethyl-2,2-difluro-1,3-benzodioxolane (3.21 g, 12.0 mmol) were dissolved in N,N-dimethylformamide (20 ml), under a nitrogen atmosphere. 60% Sodium hydride (0.49 g, 12.3 mmol) was added at 0° C., and the mixture was heated to room temperature and stirred for 16 hours. The reaction mixture was poured into 1 N hydrochloric acid, and the mixture was extracted twice with ethyl acetate. The organic layer was washed with water and saturated saline water, dried over anhydrous sodium sulfate, and then concentrated under reduced pressure. The residue was added to ethanol (40 mL), and potassium hydroxide (2.24 g, 40.0 mmol) and water (10 mL) were further added thereto. The mixture was stirred at room temperature overnight, and then concentrated under reduced pressure. Dilute hydrochloric acid was added to the concentrate, and the mixture was extracted twice with ethyl acetate. The organic layer was washed with saturated saline water, dried over anhydrous sodium sulfate, and then concentrated under reduced pressure to obtain 2.07 g of 5-[(2,2-difluoro-1,3-benzodioxolan-5-yl)methoxymethyl)isoxazole-3-carboxylic acid represented by the following formula.

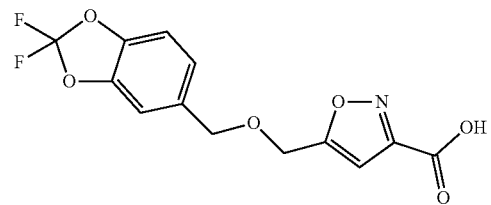 [SMILES: O=C(O)c1cc(COCc2ccc3c(c2)OC(F)(F)O3)on1]

$^1$H-NMR (CDCl$_3$, TMS, δ(ppm)): 4.57 (2H, s), 4.66 (2H, s), 6.71 (1H, s), 7.03 (2H, s), 7.09 (1H, s)

Reference Production Example 174

2-Fluoro-1-bromobenzene (14.02 g, 80.1 mmol), 4-penten-2-ol (10.35 g, 120.1 mmol), palladium acetate (8.09 g, 36.05 mmol), tetrabutylammonium chloride (44.53 g, 160.2 mmol), lithium chloride (3.40 g, 80.1 mmol) and lithium acetate dihydrate (20.43 g, 200.2 mmol) were added to N,N-dimethylformamide (160 ml), and the mixture was stirred at 100° C. for 30 hours, under a nitrogen atmosphere. The mixture was cooled to room temperature and added to 1 N hydrochloric acid, then the solid was filtered with celite and removed, and the mixture was extracted three times with ethyl acetate. The organic layer was washed with saturated saline water, dried over anhydrous magnesium sulfate, and then concentrated under reduced pressure. The residue was applied to a silica gel column chromatography to obtain 9.10 g of 5-(2-fluorophenyl)pentan-2-one represented by the following formula.

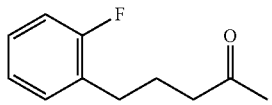

¹H-NMR (CDCl₃, TMS, δ(ppm)): 1.86-1.94 (2H, m), 2.13 (3H, s), 2.46 (2H, t), 2.66 (2H, t), 6.98-7.08 (2H, m), 7.15-7.21 (2H, m)

Reference Production Example 175

5-(2-Fluorophenyl)pentan-2-one (9.08 g, 50.3 mmol) and diethyl oxalate (8.2 mL, 60.4 mmol) were dissolved in ethanol (84 ml), and the mixture was cooled to −10° C. under a nitrogen atmosphere. Sodium ethoxide (20% ethanol solution, 17.1 g, 50.3 mmol) was added dropwise thereto over 30 minutes, and the mixture was stirred at room temperature overnight and then concentrated under reduced pressure. 1 N Hydrochloric acid was added to the reaction mixture, and the mixture was extracted three times with ethyl acetate. The organic layer was washed with saturated saline water, dried over anhydrous magnesium sulfate, and then concentrated under reduced pressure. The residue was applied to a silica gel column chromatography to obtain 10.49 g of ethyl 7-(2-fluorophenyl)-2,4-dioxoheptanoate represented by the following formula.

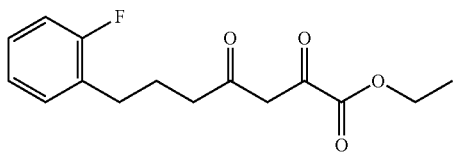 [SMILES: CCOC(=O)C(=O)CC(=O)CCCc1ccccc1F]

¹H-NMR (CDCl₃, TMS, δ(ppm)): 1.36-1.40 (3H, m), 1.95-2.03 (2H, m), 2.53 (2H, t), 2.71 (2H, t), 4.31-4.39 (2H, m), 6.36 (1H, s), 6.98-7.09 (2H, m), 7.15-7.22 (2H, m)

Reference Production Example 176

Ethyl 7-(2-fluorophenyl)-2,4-dioxoheptanoate (10.48 g, 37.3 mmol) was dissolved in ethanol (124 ml), and hydroxylamine hydrochloride (5.2 g, 74.7 mmol) was added thereto, and the mixture was heated and refluxed for 12 hours, under a nitrogen atmosphere. The reaction mixture was cooled to room temperature, and then concentrated under reduced pressure. 1 N Hydrochloric acid was added to the concentrate, and the mixture was extracted three times with ethyl acetate. The organic layer was washed with saturated saline water, dried over anhydrous magnesium sulfate, and then concentrated under reduced pressure. The residue was applied to a silica gel column chromatography to obtain 4.40 g of ethyl 5-[3-(2-fluorophenyl)propyl]isoxazole-3-carboxylate represented by the following formula.

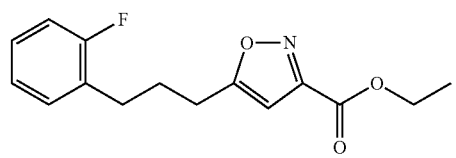 [SMILES: CCOC(=O)c1cc(CCCc2ccccc2F)on1]

¹H-NMR (CDCl₃, TMS, δ(ppm)): 1.41 (3H, t), 2.02-2.09 (2H, m), 2.73 (2H, t), 2.84 (2H, t), 4.44 (2H, q), 6.44 (1H, s), 7.00-7.09 (2H, m), 7.15-7.23 (2H, m)

Reference Production Example 177

Ethyl 5-[3-(2-fluorophenyl)propyl]isoxazole-3-carboxylate (3.0 g, 10.8 mmol) was dissolved in ethanol (40 mL), and an aqueous solution obtained by dissolving potassium hydroxide (1.21 g, 21.6 mmol) to water (20 mL) was added thereto at room temperature. The mixture was stirred for 2 hours and then concentrated under reduced pressure. Dilute hydrochloric acid was added to the residue to have a pH of 2, and the mixture was extracted three times with ethyl acetate. The organic layer was washed with saturated saline water, dried over anhydrous magnesium sulfate, and then concentrated under reduced pressure to obtain 2.42 g of 5-[3-(2-fluorophenyl)propyl]isoxazole-3-carboxylic acid represented by the following formula.

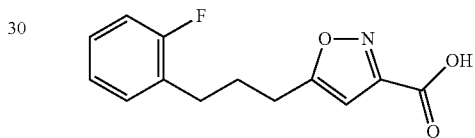

The product was subjected to a next reaction without purification.

¹H-NMR (CDCl₃, TMS, δ(ppm)): 2.03-2.11 (2H, m), 2.75 (2H, t), 2.86 (2H, t), 5.64 (1H, br), 6.49 (1H, s), 7.01-7.10 (2H, m), 7.16-7.23 (2H, m)

Reference Production Example 178

3,4-Dichlorobromobenzene (4.52 g, 20.0 mmol), 4-penten-2-ol (2.58 g, 30.0 mmol), palladium acetate (2.02 g, 9.0 mmol), tetrabutylammonium chloride (11.12 g, 40.0 mmol), lithium chloride (0.85 g, 20.0 mmol) and lithium acetate dihydrate (5.10 g, 50.0 mmol) were added to N,N-dimethylformamide (40 ml), and the mixture was stirred at 100° C. for 30 hours, under a nitrogen atmosphere. The mixture was cooled to room temperature and added to 1 N hydrochloric acid, then the solid was filtered with celite and removed, and the mixture was extracted three times with ethyl acetate. The organic layer was washed with saturated saline water, dried over anhydrous sodium sulfate, and then concentrated under reduced pressure. The residue was applied to a silica gel column chromatography to obtain 3.35 g of 5-(3,4-dichlorophenyl)pentan-2-one represented by the following formula.

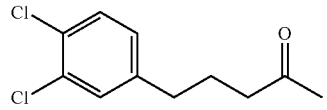

¹H-NMR (CDCl₃, TMS, δ(ppm)): 1.83-1.94 (2H, m), 2.13 (3H, s), 2.44 (2H, t), 2.58 (2H, t), 7.01 (1H, dd), 7.26 (1H, d), 7.34 (1H, d)

Reference Production Example 179

5-(3,4-Dichlorophenyl)pentan-2-one (2.31 g, 10.0 mmol) and diethyl oxalate (1.75 g, 12.0 mmol) were dissolved in ethanol (20 ml), and the mixture was cooled to 0° C. under a nitrogen atmosphere. Sodium ethoxide (20% ethanol solution, 3.40 g, 10.0 mmol) was added dropwise thereto over 30 minutes, and the mixture was stirred at room temperature overnight and then concentrated under reduced pressure. 1 N Hydrochloric acid was added to the concentrate, and the mixture was extracted three times with ethyl acetate. The organic layer was washed with saturated saline water, dried over anhydrous sodium sulfate, and then concentrated under reduced pressure. The residue was applied to a silica gel column chromatography to obtain 1.58 g of ethyl 7-(3,4-dichlorophenyl)-2,4-dioxoheptanoate represented by the following formula.

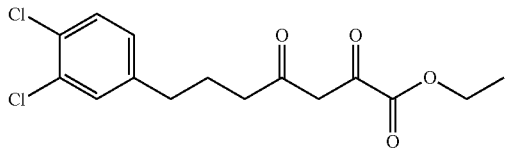 [SMILES: CCOC(=O)C(=O)CC(=O)CCCc1ccc(Cl)c(Cl)c1]

¹H-NMR (CDCl₃, TMS, δ(ppm)): 1.38 (3H, t), 1.92-2.02 (2H, m), 2.51 (2H, t), 2.63 (2H, t), 4.37 (2H, q), 6.34 (1H, s), 7.02 (1H, dd), 7.27 (1H, d), 7.36 (1H, d)

Reference Production Example 180

Ethyl 7-(3,4-dichlorophenyl)-2,4-dioxoheptanoate (1.58 g, 2.8 mmol) was dissolved in ethanol (15 ml), and hydroxylamine hydrochloride (0.72 g, 10.4 mmol) was added thereto, and the mixture was heated and refluxed for 12 hours, under a nitrogen atmosphere. The reaction mixture was cooled to room temperature, and then concentrated under reduced pressure. 1 N Hydrochloric acid was added to the concentrate, and the mixture was extracted three times with ethyl acetate. The organic layer was washed with saturated saline water, dried over anhydrous sodium sulfate, and then concentrated under reduced pressure. The residue was applied to a silica gel column chromatography to obtain 1.24 g of ethyl 5-[3-(3,4-dichlorophenyl)propyl]isoxazole-3-carboxylate represented by the following formula.

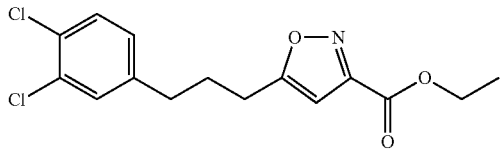 [SMILES: CCOC(=O)c1cc(CCCc2ccc(Cl)c(Cl)c2)on1]

¹H-NMR (CDCl₃, TMS, δ(ppm)): 1.42 (3H, t), 1.99-2.08 (2H, m), 2.65 (2H, t), 2.82 (2H, t), 4.44 (2H, q), 6.43 (1H, s), 7.01 (1H, dd), 7.27 (1H, d), 7.36 (1H, d)

Reference Production Example 181

Ethyl 5-[3-(3,4-dichlorophenyl)propyl]isoxazole-3-carboxylate (0.99 g, 3.0 mmol) was dissolved in ethanol (6 ml), and an aqueous solution obtained by dissolving potassium hydroxide (0.84 g, 15.0 mmol) to water (3 mL) was added thereto at room temperature. The mixture was stirred at 80° C. for 4 hours. Water was added to the reaction mixture, and the mixture was concentrated under reduced pressure. Tert-butyl methyl ether was added to the concentrate, and the aqueous layer was fractionated. Dilute hydrochloric acid was added to the resulting aqueous layer, and the mixture was extracted three times with ethyl acetate. The organic layer was washed with saturated saline water, dried over anhydrous sodium sulfate, and then concentrated under reduced pressure to obtain 0.98 g of 5-[3-(3,4-dichlorophenyl)propyl]isoxazole-3-carboxylic acid represented by the following formula.

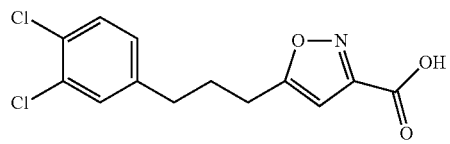

The product was subjected to a next reaction without purification.

Reference Production Example 182

5-(6-Methoxy-2-naphthyl)pentan-2-one (1.78 g, 7.3 mmol) and diethyl oxalate (1.29 g, 8.8 mmol) were dissolved in ethanol (15 ml), and the mixture was cooled to 0° C. under a nitrogen atmosphere. Sodium ethoxide (20% ethanol solution, 2.48 g, 7.3 mmol) was added dropwise thereto over 20 minutes, and the mixture was stirred at room temperature overnight and then concentrated under reduced pressure. 1 N Hydrochloric acid was added to the concentrate, and the mixture was extracted three times with ethyl acetate. The organic layer was washed with saturated saline water, dried over anhydrous sodium sulfate, and then concentrated under reduced pressure. The residue was applied to a silica gel column chromatography to obtain 1.33 g of ethyl 7-(6-methoxy-2-naphthyl)-2,4-dioxoheptanoate represented by the following formula.

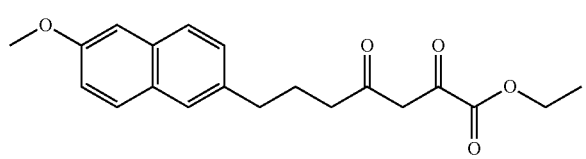 [SMILES: CCOC(=O)C(=O)CC(=O)CCCc1ccc2cc(OC)ccc2c1]

¹H-NMR (CDCl₃, TMS, δ(ppm)): 1.37 (3H, t), 2.02-2.12 (2H, m), 2.53 (2H, t), 2.80 (2H, t), 3.92 (3H, s), 4.34 (2H, q), 6.33 (1H, s), 7.10-7.15 (2H, m), 7.26-7.30 (1H, m), 7.54 (1H, s), 7.65-7.71 (2H, m)

Reference Production Example 183

Ethyl 7-(6-methoxy-2-naphthyl)-2,4-dioxoheptanoate (1.33 g, 3.9 mmol) was dissolved in ethanol (12 ml), and hydroxylamine hydrochloride (0.59 g, 8.5 mmol) was added thereto, and the mixture was heated and refluxed for 8 hours, under a nitrogen atmosphere. The reaction mixture was cooled to room temperature, and then concentrated under reduced pressure. 1 N Hydrochloric acid was added to the concentrate, and the mixture was extracted three times with ethyl acetate. The organic layer was washed with saturated saline water, dried over anhydrous sodium sulfate, and then concentrated under reduced pressure. The residue was applied to a silica gel column chromatography to obtain 0.98 g of ethyl 5-[3-(6-methoxy-2-naphthyl)propyl)propyl]isoxazole-3-carboxylate represented by the following formula.

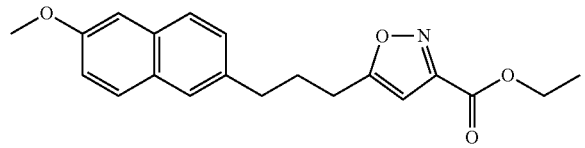 [SMILES: CCOC(=O)c1cc(CCCc2ccc3cc(OC)ccc3c2)on1]

¹H-NMR (CDCl₃, TMS, δ(ppm)): 1.42 (3H, t), 2.08-2.18 (2H, m), 2.62 (2H, t), 2.84 (2H, t), 3.92 (3H, s), 4.43 (2H, q), 6.43 (1H, s), 7.10-7.16 (2H, m), 7.26-7.30 (1H, m), 7.54 (1H, s), 7.66-7.71 (2H, m)

Reference Production Example 184

Ethyl 5-[3-(6-methoxy-2-naphthyl)propyl]isoxazole-3-carboxylate (0.98 g, 2.9 mmol) was dissolved in ethanol (6 ml), and an aqueous solution obtained by dissolving potassium hydroxide (0.81 g, 14.4 mmol) to water (3 mL) was added thereto at room temperature. The mixture was stirred at 80° C. for 3 hours. Water was added to the reaction mixture, and the mixture was concentrated under reduced pressure. Tert-butyl methyl ether was added to the concentrate, and the aqueous layer was fractionated. Dilute hydrochloric acid was added to the resulting aqueous layer, and the mixture was extracted three times with ethyl acetate. The organic layer was washed with saturated saline water, dried over anhydrous sodium sulfate, and then concentrated under reduced pressure to obtain 0.73 g of 5-[3-(6-methoxy-2-naphthyl)propyl]isoxazole-3-carboxylic acid represented by the following formula.

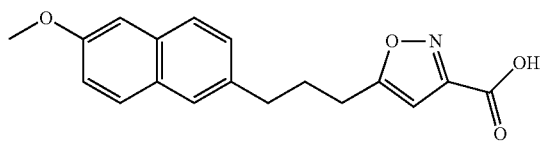 [SMILES: COc1ccc2cc(CCCc3cc(C(=O)O)no3)ccc2c1]

The product was subjected to a next reaction without purification.

Reference Production Example 185

Triethylamine (1.4 mL), bis(triphenylphosphine)palladium(II) dichloride (0.05 g, 0.07 mmol) and copper iodide (0.03 g, 0.14 mmol) were added to an N,N-dimethylformamide (3 mL) solution of N-(tetrahydrofuran-3-ylmethyl)-5-(2-fluorobenzyloxymethyl)-4-iodoisoxazole-3-carboxamide (0.64 g, 1.40 mmol), and the mixture was ice-cooled and put under a nitrogen atmosphere. Subsequently, trimethylsilylacetylene (0.21 mL, 1.55 mmol) was added dropwise thereto, and the mixture was stirred for 1 hour while slowly returning to room temperature. The mixture was filtered with celite, and the filtrate was concentrated under reduced pressure. The residue was applied to a silica gel column chromatography to obtain 0.40 g of N-(tetrahydrofuran-3-ylmethyl)-5-(2-fluorobenzyloxymethyl)-4-trimethylsilanylethynylisoxazole-3-carboxamide represented by the following formula.

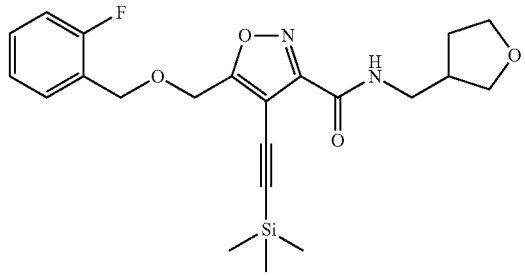 [SMILES: C[Si](C)(C)C#Cc1c(C(=O)NCC2CCOC2)noc1COCc1ccccc1F]

¹H-NMR (CDCl₃, TMS, δ(ppm)): 0.25 (s, 9H), 1.63-1.71 (m, 1H), 2.06-2.13 (m, 1H), 2.56-2.62 (m, 1H), 3.46-3.50 (m, 2H), 3.57-3.60 (m, 1H), 3.73-3.79 (m, 1H), 3.84-3.94 (m, 2H), 4.69 (s, 2H), 4.74 (s, 2H), 6.96 (brs, 1H), 7.04-7.08 (m, 1H), 7.13-7.17 (m, 1H), 7.28-7.33 (m, 1H), 7.41-7.45 (m, 1H)

Reference Production Example 186

Triethylamine (1.26 mL), bis(triphenylphosphine)palladium(II) dichloride (0.04 g, 0.06 mmol) and copper iodide (0.02 g, 0.12 mmol) were added to an N,N-dimethylformamide (2.5 mL) solution of N-(tetrahydrofuran-3-ylmethyl)-5-(2-naphthylmethoxymethyl)-4-iodoisoxazole-3-carboxamide (0.62 g, 1.26 mmol), and the mixture was ice-cooled and put under a nitrogen atmosphere. Subsequently, trimethylsilylacetylene (0.19 mL, 1.38 mmol) was added dropwise thereto, and the mixture was stirred for 7 hours while slowly returning to room temperature. The reaction mixture was filtered with celite, and the filtrate was concentrated under reduced pressure. The residue was applied to a silica gel column chromatography to obtain 0.36 g of N-(tetrahydrofuran-3-ylmethyl)-5-(2-naphthylmethoxymethyl)-4-trimethylsilanylethynylisoxazole-3-carboxamide represented by the following formula.

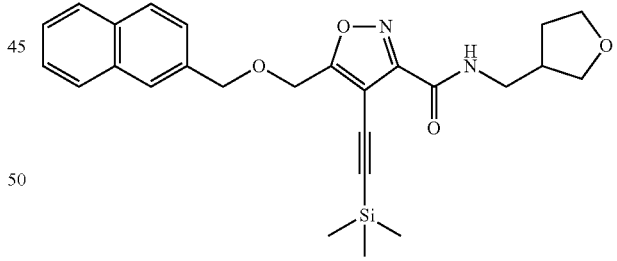

¹H-NMR (CDCl₃, TMS, δ(ppm)): 0.22 (s, 9H), 1.62-1.71 (m, 1H), 2.04-2.15 (m, 1H), 2.57-2.61 (m, 1H), 3.45-3.49 (m, 2H), 3.56-3.60 (m, 1H), 3.73-3.79 (m, 1H), 3.83-3.94 (m, 2H), 4.74 (s, 2H), 4.78 (s, 2H), 6.91 (brs, 1H), 7.47-7.50 (m, 3H), 7.81-7.86 (m, 4H)

Reference Production Example 187

3-Fluorobromobenzene (3.50 g, 20.0 mmol), 4-penten-2-ol (2.58 g, 30.0 mmol), palladium acetate (2.02 g, 9.0 mmol), tetrabutylammonium chloride (11.12 g, 40.0 mmol), lithium chloride (0.85 g, 20.0 mmol) and lithium acetate dihydrate (5.10 g, 50.0 mmol) were added to N,N-dimethylformamide (40 ml), and the mixture was stirred at 100° C. for 30 hours, under a nitrogen atmosphere. The mixture was cooled to room temperature and added to 1 N hydrochloric acid, then the solid was filtered with celite and removed, and the mixture was extracted three times with ethyl acetate. The organic layer was washed with saturated saline water, dried over anhydrous sodium sulfate, and then concentrated under reduced pressure. The residue was applied to a silica gel column chromatography to obtain 2.13 g of 5-(3-fluorophenyl)pentan-2-one represented by the following formula.

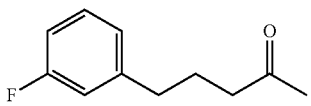

$^1$H-NMR (CDCl$_3$, TMS, δ(ppm)): 1.85-1.94 (2H, m), 2.13 (3H, s), 2.44 (2H, t), 2.62 (2H, t), 6.85-6.96 (3H, m), 7.20-7.26 (1H, m)

Reference Production Example 188

5-(3-Fluorophenyl)pentan-2-one (2.13 g, 11.8 mmol) and diethyl oxalate (2.08 g, 14.2 mmol) were dissolved in ethanol (20 ml), and the mixture was cooled to −10° C. under a nitrogen atmosphere. Sodium ethoxide (20% ethanol solution, 4.01 g, 11.8 mmol) was added dropwise thereto over 30 minutes, and the mixture was stirred at room temperature overnight and then concentrated under reduced pressure. 1 N Hydrochloric acid was added to the concentrate, and the mixture was extracted three times with ethyl acetate. The organic layer was washed with saturated saline water, dried over anhydrous sodium sulfate, and then concentrated under reduced pressure. The residue was applied to a silica gel column chromatography to obtain 2.02 g of ethyl 7-(3-fluorophenyl)-2,4-dioxoheptanoate represented by the following formula.

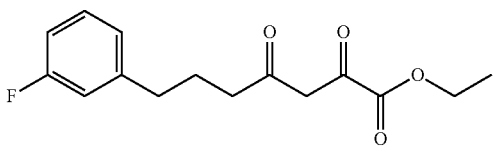 [SMILES: CCOC(=O)C(=O)CC(=O)CCCc1cccc(F)c1]

$^1$H-NMR (CDCl$_3$, TMS, δ(ppm)): 1.38 (3H, t), 1.93-2.03 (2H, m), 2.61 (2H, t), 2.67 (2H, t), 4.36 (2H, q), 6.34 (1H, s), 6.86-6.97 (3H, m), 7.20-7.26 (1H, m)

Reference Production Example 189

Ethyl 7-(3-fluorophenyl)-2,4-dioxoheptanoate (2.02 g, 7.2 mmol) was dissolved in ethanol (24 ml), and hydroxylamine hydrochloride (1.11 g, 16.0 mmol) was added thereto, and the mixture was heated and refluxed for 12 hours, under a nitrogen atmosphere. The reaction mixture was cooled to room temperature, and then concentrated under reduced pressure. 1 N Hydrochloric acid was added to the concentrate, and the mixture was extracted three times with ethyl acetate. The organic layer was washed with saturated saline water, dried over anhydrous sodium sulfate, and then concentrated under reduced pressure. The residue was applied to a silica gel column chromatography to obtain 0.49 g of ethyl 5-[3-(3-fluorophenyl)propyl]isoxazole-3-carboxylate represented by the following formula.

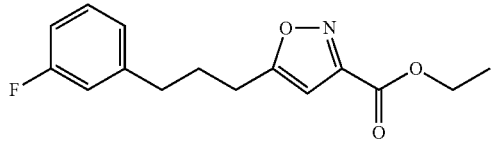 [SMILES: CCOC(=O)c1cc(CCCc2cccc(F)c2)on1]

$^1$H-NMR (CDCl$_3$, TMS, δ(ppm)): 1.42 (3H, t), 2.01-2.10 (2H, m), 2.69 (2H, t), 2.82 (2H, t), 4.44 (2H, q), 6.42 (1H, s), 6.86-6.97 (3H, m), 7.23-7.30 (1H, m)

Reference Production Example 190

Ethyl 5-[3-(3-fluorophenyl)propyl]isoxazole-3-carboxylate (0.49 g, 1.8 mmol) was dissolved in ethanol (3.6 ml), and an aqueous solution obtained by dissolving potassium hydroxide (0.49 g, 8.8 mmol) to water (1.8 mL) was added thereto at room temperature. The mixture was stirred at 80° C. for 3 hours. Water was added to the reaction mixture, and the mixture was concentrated under reduced pressure. Tert-butyl methyl ether was added to the concentrate, and the aqueous layer was fractionated. Dilute hydrochloric acid was added to the resulting aqueous layer, and the mixture was extracted three times with ethyl acetate. The organic layer was washed with saturated saline water, dried over anhydrous sodium sulfate, and then concentrated under reduced pressure to obtain 0.43 g of 5-[3-(3-fluorophenyl)propyl]isoxazole-3-carboxylic acid represented by the following formula.

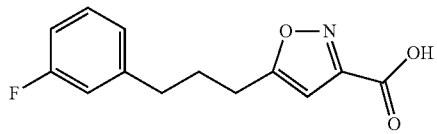 [SMILES: O=C(O)c1cc(CCCc2cccc(F)c2)on1]

The product was subjected to a next reaction without purification.

Reference Production Example 191

4-Chloro-1-bromobenzene (3.83 g, 20.0 mmol), 4-penten-2-ol (2.07 g, 24.0 mmol), palladium acetate (2.02 g, 9.0 mmol), tetrabutylammonium chloride (11.12 g, 40.0 mmol), lithium chloride (0.85 g, 20.0 mmol) and lithium acetate dihydrate (5.10 g, 50.0 mmol) were added to N,N-dimethylformamide (40 ml), and the mixture was stirred at 100° C. for 30 hours, under a nitrogen atmosphere. The mixture was cooled to room temperature and added to 1 N hydrochloric acid, then the solid was filtered with celite and removed, and the mixture was extracted three times with ethyl acetate. The organic layer was washed with saturated saline water, dried over anhydrous sodium sulfate, and then concentrated under reduced pressure. The residue was applied to a silica gel column chromatography to obtain 2.49 g of 5-(4-chlorophenyl)pentan-2-one represented by the following formula.

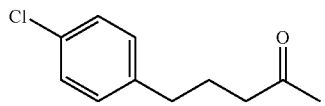

¹H-NMR (CDCl₃, TMS, δ(ppm)): 1.83-1.92 (2H, m), 2.12 (3H, s), 2.43 (2H, t), 2.59 (2H, t), 7.10 (2H, dt), 7.25 (2H, dt).

Reference Production Example 192

5-(4-Chlorophenyl)pentan-2-one (1.97 g, 10.0 mmol) and diethyl oxalate (1.75 g, 12.0 mmol) were dissolved in ethanol (20 ml), and the mixture was cooled to 0° C. under a nitrogen atmosphere. Sodium ethoxide (20% ethanol solution, 3.40 g, 10.0 mmol) was added dropwise thereto over 30 minutes, and the mixture was stirred at room temperature overnight and then concentrated under reduced pressure. 1 N Hydrochloric acid was added to the concentrate, and the mixture was extracted three times with ethyl acetate. The organic layer was washed with saturated saline water, dried over anhydrous sodium sulfate, and then concentrated under reduced pressure. The residue was applied to a silica gel column chromatography to obtain 1.70 g of ethyl 7-(4-chlorophenyl)-2,4-dioxoheptanoate represented by the following formula.

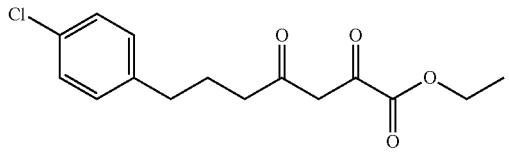 [SMILES: CCOC(=O)C(=O)CC(=O)CCCc1ccc(Cl)cc1]

¹H-NMR (CDCl₃, TMS, δ(ppm)): 1.38 (3H, t), 1.92-2.02 (2H, m), 2.50 (2H, t), 2.64 (2H, t), 4.35 (2H, q), 6.34 (1H, s), 7.11 (2H, dt), 7.26 (2H, dt).

Reference Production Example 193

Ethyl 7-(4-chlorophenyl)-2,4-dioxoheptanoate (1.57 g, 5.3 mmol) was dissolved in ethanol (15 ml), and hydroxylamine hydrochloride (0.74 g, 10.6 mmol) was added thereto, and the mixture was heated and refluxed for 8 hours, under a nitrogen atmosphere. The reaction mixture was cooled to room temperature, and then concentrated under reduced pressure. 1 N Hydrochloric acid was added to the concentrate, and the mixture was extracted three times with ethyl acetate. The organic layer was washed with saturated saline water, dried over anhydrous sodium sulfate, and then concentrated under reduced pressure. The residue was applied to a silica gel column chromatography to obtain 0.96 g of ethyl 5-[3-(4-chlorophenyl)propyl]isoxazole-3-carboxylate represented by the following formula.

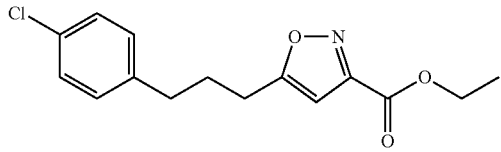 [SMILES: CCOC(=O)c1cc(CCCc2ccc(Cl)cc2)on1]

¹H-NMR (CDCl₃, TMS, δ(ppm)): 1.42 (3H, t), 1.99-2.08 (2H, m), 2.64 (2H, t), 2.81 (2H, t), 4.44 (2H, q), 6.41 (1H, s), 7.10 (2H, dt), 7.27 (2H, dt).

Reference Production Example 194

Ethyl 5-[3-(4-chlorophenyl)propyl]isoxazole-3-carboxylate (0.96 g, 3.3 mmol) was dissolved in ethanol (8 ml), and an aqueous solution obtained by dissolving potassium hydroxide (0.92 g, 16.4 mmol) to water (4 mL) was added thereto at room temperature. The mixture was stirred at 80° C. for 3 hours. Water was added to the reaction mixture, and the mixture was concentrated under reduced pressure. Tert-butyl methyl ether was added to the concentrate, and the aqueous layer was fractionated. Dilute hydrochloric acid was added to the resulting aqueous layer, and the mixture was extracted three times with ethyl acetate. The organic layer was washed with saturated saline water, dried over anhydrous sodium sulfate, and then concentrated under reduced pressure to obtain 0.86 g of 5-[3-(4-chlorophenyl)propyl]isoxazole-3-carboxylic acid represented by the following formula.

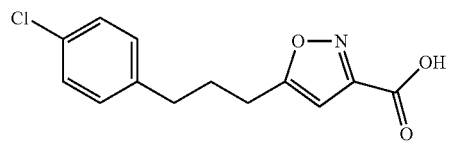 [SMILES: O=C(O)c1cc(CCCc2ccc(Cl)cc2)on1]

The product was subjected to a next reaction without purification.

Reference Production Example 195

Methanesulfonyl chloride (5.42 mL, 38.90 mmol) was added to a chloroform solution (amylene addition product, 100 mL) of ethyl 5-hydroxymethylisoxazole-3-carboxylate (5.12 g, 29.92 mmol) and triethylamine (2.66 mL, 34.40 mmol) under ice-water cooling, and the mixture was stirred at room temperature or lower for 2 hours. Then, the mixture was poured into ice water, and extracted twice with chloroform. The organic layer was washed with saturated saline water, dried over magnesium sulfate and then concentrated under reduced pressure, and the residue was applied to a silica gel column chromatography to obtain 6.02 g of ethyl 5-methanesulfonyloxymethylisoxazole-3-carboxylate represented by the following formula.

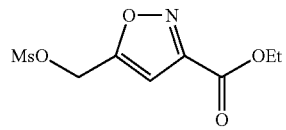 [SMILES: CCOC(=O)c1cc(COS(C)(=O)=O)on1]

¹H-NMR (CDCl₃, TMS, δ(ppm)): 1.43 (3H, t) 3.09 (3H, s), 4.46 (2H, q), 5.36 (2H, s), 6.87 (1H, s).

Reference Production Example 196

Potassium carbonate (0.79 g, 5.71 mmol) and 2-naphthylmethanethiol (1.00 g, 5.71 mmol) were added to a tetrahydrofuran (5 mL) and acetonitrile (5 mL) solution of ethyl 5-methanesulfonyloxymethylisoxazole-3-carboxylate (1.43 g, 5.71 mmol). The mixture was stirred at room temperature for 2 hours and concentrated under reduced pressure, and then ethyl acetate and water were added to the resulting residue. The organic layer was washed with saturated saline water, and dried over magnesium sulfate, and then concentrated under reduced pressure. The residue was applied to a silica gel column chromatography to obtain 1.20 g of ethyl 5-(2-naphthylmethylthiomethyl)isoxazole-3-carboxylate represented by the following formula.

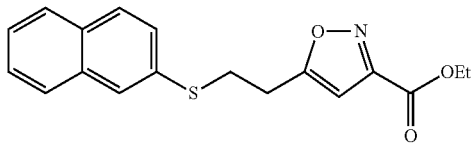 [SMILES: CCOC(=O)c1cc(CCSc2ccc3ccccc3c2)on1]

$^1$H-NMR (CDCl$_3$, TMS, δ(ppm)): 1.42 (t, J=7.2 Hz, 3H), 3.65 (s, 2H), 3.91 (s, 2H), 4.44 (q, J=7.2 Hz, 2H), 6.53 (s, 1H), 7.53-7.45 (m, 3H), 7.70 (s, 1H), 7.79-7.85 (m, 3H).

Reference Production Example 197

Ethyl 5-(2-naphthylmethylthiomethyl)isoxazole-3-carboxylate (1.20 g, 3.67 mmol) was added to a mixture of tetrahydrofuran (20 mL) and a 1 mol/L aqueous sodium hydroxide solution (20 mL), and the mixture was stirred at room temperature for 30 minutes, then made acidic by adding concentrated hydrochloric acid, and extracted twice with ethyl acetate. The organic layer was washed with saturated saline water, and dried over magnesium sulfate, and then concentrated under reduced pressure. The resulting solid was dissolved in ethyl acetate (35 mL), and N,N-dimethylformamide (about 0.1 mL) and oxalyl chloride (about 0.5 mL) were added thereto. The mixture was stirred at room temperature for 20 minutes and concentrated under reduced pressure, and then the residue was diluted with ethyl acetate (30 mL) to obtain an ethyl acetate solution of 5-(2-naphthylmethylthiomethyl)isoxazole-3-carboxylic acid chloride (<3.67 mmol) represented by the following formula.

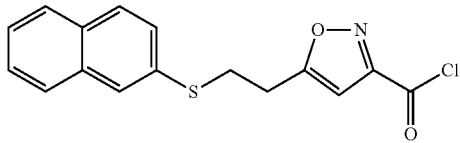 [SMILES: O=C(Cl)c1cc(CCSc2ccc3ccccc3c2)on1]

Reference Production Example 198

Potassium carbonate (416 mg, 3.01 mmol) and benzyl mercaptan (374 mg, 3.01 mmol) were added to an N,N-dimethylformamide solution (2.4 mL) of ethyl 5-methanesulfonyloxymethylisoxazole-3-carboxylate (600 mg, 2.41 mmol), and the mixture was stirred at room temperature for 2 hours, and then diluted with ethyl acetate. The reaction mixture was washed with water and saturated saline water, dried over magnesium sulfate and then concentrated under reduced pressure, and the residue was applied to a silica gel column chromatography to obtain 620 mg of ethyl 5-benzylthiomethylisoxazole-3-carboxylate. Tetrahydrofuran (15 mL) and a 1 mol/L aqueous sodium hydroxide solution (15 mL) were added thereto, and the mixture was stirred at room temperature for 30 minutes, then made acidic by adding concentrated hydrochloric acid to the aqueous layer obtained by adding tert-butyl methyl ether and water, and extracted twice with ethyl acetate. The organic layer was washed with saturated saline water, dried over anhydrous magnesium sulfate, and then concentrated under reduced pressure. The residue was suspended in tert-butyl methyl ether, and the suspension was filtered to obtain 515 mg of 5-benzylthiomethylisoxazole-3-carboxylic acid represented by the following formula.

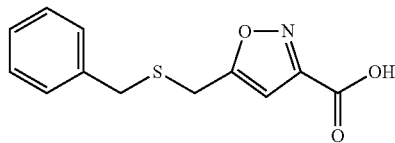 [SMILES: O=C(O)c1cc(CSCc2ccccc2)on1]

$^1$H-NMR (DMSO-d$_6$, TMS, δ(ppm)): 3.80 (s, 2H), 3.89 (s, 2H), 6.66 (s, 1H), 7.22-7.36 (m, 5H).

Reference Production Example 199

Ethyl 5-hydroxymethylisoxazole-3-carboxylate (0.29 g, 1.7 mmol) was dissolved in tetrahydrofuran (10 mL), and 3-fluoro-2-naphthylmethyl bromide (0.48 g, 2.0 mmol) and 18-crown-6 (0.05 g, 0.2 mmol) were added thereto. Sodium hydride (60% oil-based) (0.14 g, 3.4 mmol) was slowly added thereto at room temperature, and the mixture was stirred at room temperature overnight. Then, dilute hydrochloric acid was added thereto, and the mixture was extracted three times with ethyl acetate. The organic layer was washed with saturated saline water, dried over anhydrous sodium sulfate, and then concentrated under reduced pressure. The residue was dissolved in ethanol (4 mL), and an aqueous solution obtained by dissolving potassium hydroxide (0.56 g, 10 mmol) in water (2 mL) was added thereto at room temperature, and then the mixture was stirred at 80° C. for 3 hours. Water was added to the reaction mixture, and the mixture was concentrated under reduced pressure. Tert-butyl methyl ether was added to the concentrate, and the aqueous layer was fractionated. Dilute hydrochloric acid was added to the resulting aqueous layer, and the mixture was extracted three times with ethyl acetate. The organic layer was washed with saturated saline water, dried over anhydrous sodium sulfate, and then concentrated under reduced pressure to obtain 0.48 g of 5-(3-fluoro-2-naphthylmethoxymethyl)isoxazole-3-carboxylic acid represented by the following formula.

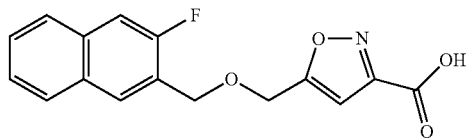 [SMILES: O=C(O)c1cc(COCc2cc3ccccc3cc2F)on1]

The product was subjected to a next reaction without purification.

Reference Production Example 200

Ethyl 5-hydroxymethylisoxazole-3-carboxylate (0.72 g, 4.2 mmol) was dissolved in tetrahydrofuran (25 mL), and 1-fluoro-2-naphthylmethyl bromide (1.20 g, 5.0 mmol) and 18-crown-6 (0.11 g, 0.4 mmol) were added thereto. Sodium hydride (60% oil-based) (0.34 g, 8.4 mmol) was slowly added thereto at room temperature, and the mixture was stirred at room temperature overnight. Then, dilute hydrochloric acid was added thereto, and the mixture was extracted three times with ethyl acetate. The organic layer was washed with saturated saline water, dried over anhydrous sodium sulfate, and then concentrated under reduced pressure. The residue was dissolved in ethanol (10 mL), and an aqueous solution obtained by dissolving potassium hydroxide (1.40 g, 25 mmol) in water (5 mL) was added thereto at room temperature, and then the mixture was stirred at 80° C. for 3 hours. Water was added to the reaction mixture, and the mixture was concentrated under reduced pressure. Tert-butyl methyl ether was added to the concentrate, and the aqueous layer was fractionated. Dilute hydrochloric acid was added to the resulting aqueous layer, and the mixture was extracted three times with ethyl acetate. The organic layer was washed with saturated saline water, dried over anhydrous sodium sulfate, and then concentrated under reduced pressure to obtain 0.59 g of 5-(1-fluoro-2-naphthylmethoxymethyl)isoxazole-3-carboxylic acid represented by the following formula.

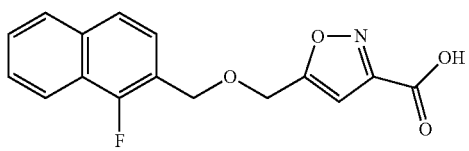 [SMILES: O=C(O)c1cc(COCc2ccc3ccccc3c2F)on1]

The product was subjected to a next reaction without purification.

Reference Production Example 201

Ethyl 5-hydroxymethylisoxazole-3-carboxylate (0.86 g, 5.0 mmol) was dissolved in tetrahydrofuran (25 mL), and 2,5-difluorobenzyl bromide (1.24 g, 6.0 mmol) and 18-crown-6 (0.13 g, 0.5 mmol) were added thereto. Sodium hydride (60% oil-based) (0.40 g, 10.0 mmol) was slowly added thereto at room temperature, and the mixture was stirred at room temperature overnight. Then, dilute hydrochloric acid was added thereto, and the mixture was extracted three times with ethyl acetate. The organic layer was washed with saturated saline water, dried over anhydrous sodium sulfate, and then concentrated under reduced pressure. The residue was dissolved in ethanol (10 mL), and an aqueous solution obtained by dissolving potassium hydroxide (1.40 g, 25 mmol) in water (5 mL) was added thereto at room temperature, and then the mixture was stirred at 80° C. for 3 hours. Water was added to the reaction mixture, and the mixture was concentrated under reduced pressure. Tert-butyl methyl ether was added to the concentrate, and the aqueous layer was fractionated. Dilute hydrochloric acid was added to the resulting aqueous layer, and the mixture was extracted three times with ethyl acetate. The organic layer was washed with saturated saline water, dried over anhydrous sodium sulfate, and then concentrated under reduced pressure to obtain 1.08 g of 5-(2,5-difluorobenzylymethyloxymethyl)isoxazole-3-carboxylic acid represented by the following formula.

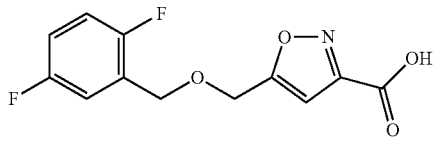 [SMILES: O=C(O)c1cc(COCc2cc(F)ccc2F)on1]

The product was subjected to a next reaction without purification.

Reference Production Example 202

Ethyl 5-hydroxymethylisoxazole-3-carboxylate (1.71 g, 10 mmol) was dissolved in tetrahydrofuran (35 mL), and 4-chloro-2-fluorobenzyl bromide (2.68 g, 12 mmol) and 18-crown-6 (0.26 g, 1 mmol) were added thereto. Sodium hydride (60% oil-based) (0.80 g, 20 mmol) was slowly added thereto at room temperature, and the mixture was stirred at room temperature overnight. Then, dilute hydrochloric acid was added thereto, and the mixture was extracted three times with ethyl acetate. The organic layer was washed with saturated saline water, dried over anhydrous sodium sulfate, and then concentrated under reduced pressure. The residue was dissolved in ethanol (20 mL), and an aqueous solution obtained by dissolving potassium hydroxide (2.81 g, 50 mmol) in water (10 mL) was added thereto at room temperature, and then the mixture was stirred at 80° C. for 3 hours. Water was added to the reaction mixture, and the mixture was concentrated under reduced pressure. Tert-butyl methyl ether was added to the concentrate, and the aqueous layer was fractionated. Dilute hydrochloric acid was added to the resulting aqueous layer, and the mixture was extracted three times with ethyl acetate. The organic layer was washed with saturated saline water, dried over anhydrous sodium sulfate, and then concentrated under reduced pressure to obtain 2.29 g of 5-(4-chloro-2-fluorobenzyloxymethyl)isoxazole-3-carboxylic acid represented by the following formula.

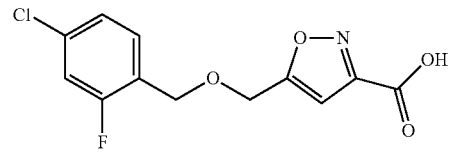 [SMILES: O=C(O)c1cc(COCc2ccc(Cl)cc2F)on1]

The product was subjected to a next reaction without purification.

Reference Production Example 203

A reaction was carried out in the same manner using 3-chloro-4-fluorobenzyl bromide (2.68 g, 12 mmol), in place of 4-chloro-2-fluorobenzyl bromide in Reference Production Example 202 to obtain 2.55 g of 5-(3-chloro-4-fluorobenzyloxymethyl)isoxazole-3-carboxylic acid represented by the following formula.

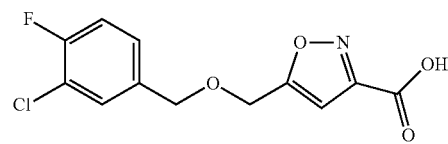

The product was subjected to a next reaction without purification.

Reference Production Example 204

A reaction was carried out in the same manner using 3,5-dibromobenzyl bromide (3.95 g, 12 mmol), in place of 4-chloro-2-fluorobenzyl bromide in Reference Production Example 202 to obtain 3.25 g of 5-(3,5-dibromobenzyloxymethyl)isoxazole-3-carboxylic acid represented by the following formula.

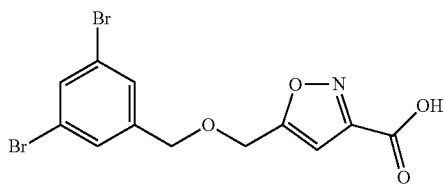

The product was subjected to a next reaction without purification.

Reference Production Example 205

A reaction was carried out in the same manner using 3,4-difluorobenzyl bromide (1.24 g, 6.0 mmol), in place of 2,5-difluorobenzyl bromide in Reference Production Example 201 to obtain 1.06 g of 5-(3,4-difluorobenzyloxymethyl)isoxazole-3-carboxylic acid represented by the following formula.

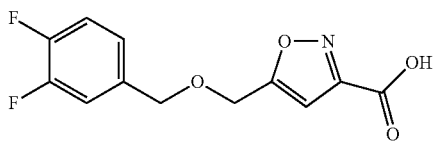 [SMILES: O=C(O)c1cc(COCc2ccc(F)c(F)c2)on1]

The product was subjected to a next reaction without purification.

Reference Production Example 206

A reaction was carried out in the same manner using 2-fluorobenzyl bromide (1.13 g, 6.0 mmol), in place of 2,5-difluorobenzyl bromide in Reference Production Example 201 to obtain 1.98 g of 5-(2-fluorobenzyloxymethyl)isoxazole-3-carboxylic acid represented by the following formula.

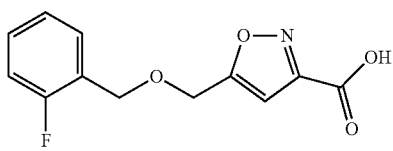 [SMILES: O=C(O)c1cc(COCc2ccccc2F)on1]

The product was subjected to a next reaction without purification.

Reference Production Example 207

A reaction was carried out in the same manner using 2-bromobenzyl bromide (1.50 g, 6.0 mmol), in place of 2,5-difluorobenzyl bromide in Reference Production Example 201 to obtain 1.21 g of 5-(2-bromobenzyloxymethyl)isoxazole-3-carboxylic acid represented by the following formula.

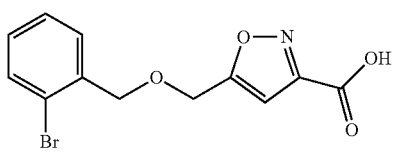 [SMILES: O=C(O)c1cc(COCc2ccccc2Br)on1]

The product was subjected to a next reaction without purification.

Reference Production Example 208

Ethyl 5-hydroxymethylisoxazole-3-carboxylate (1.71 g, 10.0 mmol) was dissolved in tetrahydrofuran (50 mL), and 3,5-difluorobenzyl bromide (2.48 g, 12.0 mmol) and 18-crown-6 (0.26 g, 1.0 mmol) were added thereto. Sodium hydride (60% oil-based) (0.80 g, 20.0 mmol) was slowly added thereto at room temperature, and the mixture was stirred at room temperature overnight. Then, dilute hydrochloric acid was added thereto, and the mixture was extracted three times with ethyl acetate. The organic layer was washed with saturated saline water, dried over anhydrous sodium sulfate, and then concentrated under reduced pressure. The residue was dissolved in ethanol (20 mL), and an aqueous solution obtained by dissolving potassium hydroxide (2.81 g, 50 mmol) in water (10 mL) was added thereto at room temperature, and then the mixture was stirred at 80° C. for 3 hours. Water was added to the reaction mixture, and the mixture was concentrated under reduced pressure. Tert-butyl methyl ether was added to the concentrate, and the aqueous layer was fractionated. Dilute hydrochloric acid was added to the resulting aqueous layer, and the mixture was extracted three times with ethyl acetate. The organic layer was washed with saturated saline water, dried over anhydrous sodium sulfate, and then concentrated under reduced pressure to obtain 1.38 g of 5-(3,5-difluorobenzyloxymethyl)isoxazole-3-carboxylic acid represented by the following formula.

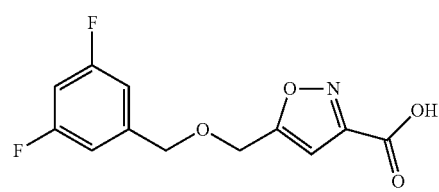 [SMILES: O=C(O)c1cc(COCc2cc(F)cc(F)c2)on1]

The product was subjected to a next reaction without purification.

Reference Production Example 209

A reaction was carried out in the same manner using 3,4,5-trifluorobenzyl bromide (2.70 g, 12.0 mmol), in place of 3,5-difluorobenzyl bromide in Reference Production Example 208 to obtain 2.21 g of 5-(3,4,5-trifluorobenzyloxymethyl)isoxazole-3-carboxylic acid represented by the following formula.

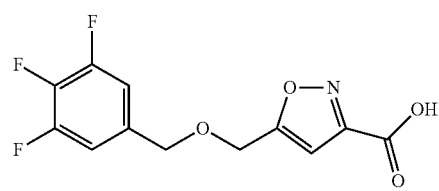 [SMILES: O=C(O)c1cc(COCc2cc(F)c(F)c(F)c2)on1]

The product was subjected to a next reaction without purification.

Reference Production Example 210

A reaction was carried out in the same manner using 3-chloro-5-fluorobenzyl bromide (2.68 g, 12 mmol), in place of 4-chloro-2-fluorobenzyl bromide in Reference Production Example 202 to obtain 2.03 g of 5-(3-chloro-5-fluorobenzyloxymethyl)isoxazole-3-carboxylic acid represented by the following formula.

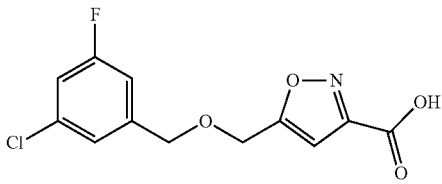 [SMILES: O=C(O)c1cc(COCc2cc(F)cc(Cl)c2)on1]

The product was subjected to a next reaction without purification.

Reference Production Example 211

A reaction was carried out in the same manner using 2,3,5,6-tetrafluorobenzyl bromide (2.92 g, 12.0 mmol), in place of 3,5-difluorobenzyl bromide in Reference Production Example 208 to obtain 0.19 g of 5-(2,3,5,6-tetrafluorobenzyloxymethyl)isoxazole-3-carboxyli c acid represented by the following formula.

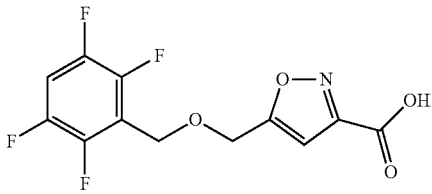 [SMILES: O=C(O)c1cc(COCc2c(F)c(F)cc(F)c2F)on1]

The product was subjected to a next reaction without purification.

Reference Production Example 212

A reaction was carried out in the same manner using 2,3,4-trifluorobenzyl bromide (1.35 g, 6.0 mmol), in place of 2,5-difluorobenzyl bromide in Reference Production Example 201 to obtain 1.21 g of 5-(2,3,4-trifluorobenzyloxymethyl)isoxazole-3-carboxylic acid represented by the following formula.

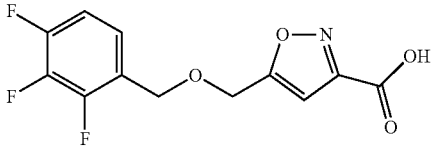 [SMILES: O=C(O)c1cc(COCc2ccc(F)c(F)c2F)on1]

The product was subjected to a next reaction without purification.

Reference Production Example 213

A reaction was carried out in the same manner using 3,5-dimethylbenzyl bromide (2.39 g, 12 mmol), in place of 4-chloro-2-fluorobenzyl bromide in Reference Production Example 202 to obtain 1.93 g of 5-(3,5-dimethylbenzyloxymethyl)isoxazole-3-carboxylic acid represented by the following formula.

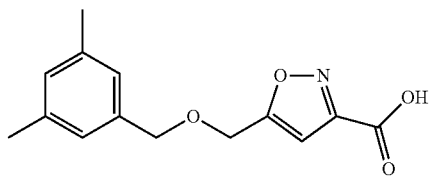 [SMILES: Cc1cc(C)cc(COCc2cc(C(=O)O)no2)c1]

The product was subjected to a next reaction without purification.

Reference Production Example 214

A reaction was carried out in the same manner using 4-bromo-3-fluorobenzyl bromide (3.22 g, 12 mmol), in place of 4-chloro-2-fluorobenzyl bromide in Reference Production Example 202 to obtain 2.41 g of 5-(4-bromo-3-fluorobenzyloxymethyl)isoxazole-3-carboxylic acid represented by the following formula.

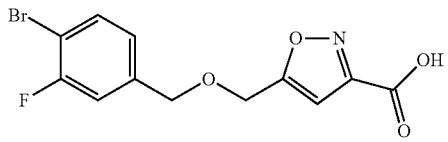

The product was subjected to a next reaction without purification.

Reference Production Example 215

A reaction was carried out in the same manner using 4-methyl-2,3,5,6-tetrafluorobenzyl bromide (3.08 g, 12.0 mmol), in place of 3,5-difluorobenzyl bromide in Reference Production Example 208 to obtain 0.29 g of 5-(4-methyl-2,3,5,6-tetrafluorobenzyloxymethyl)isoxazole-3-carboxylic acid represented by the following formula.

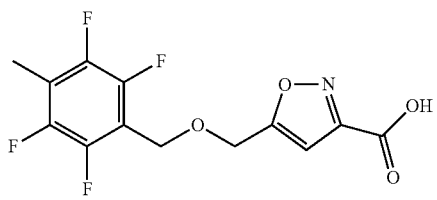 [SMILES: Cc1c(F)c(F)c(COCc2cc(C(=O)O)no2)c(F)c1F]

The product was subjected to a next reaction without purification.

Reference Production Example 216

A reaction was carried out in the same manner using 2,3-difluorobenzyl bromide (1.24 g, 6.0 mmol), in place of 2,5-difluorobenzyl bromide in Reference Production Example 201 to obtain 1.05 g of 5-(2,3-difluorobenzyloxymethyl)isoxazole-3-carboxylic acid represented by the following formula.

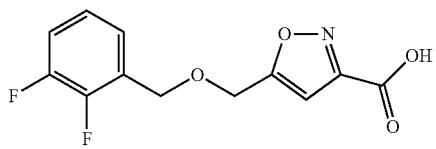 [SMILES: O=C(O)c1cc(COCc2cccc(F)c2F)on1]

The product was subjected to a next reaction without purification.

Reference Production Example 217

A reaction was carried out in the same manner using 2,6-difluorobenzyl bromide (1.24 g, 6.0 mmol), in place of 2,5-difluorobenzyl bromide in Reference Production Example 201 to obtain 1.02 g of 5-(2,6-difluorobenzyloxymethyl)isoxazole-3-carboxylic acid represented by the following formula.

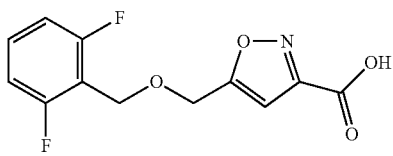 [SMILES: O=C(O)c1cc(COCc2c(F)cccc2F)on1]

The product was subjected to a next reaction without purification.

Reference Production Example 218

Ethyl 5-hydroxymethylisoxazole-3-carboxylate (1.71 g, 10.0 mmol) was dissolved in N,N-dimethylformamide (50 mL), and 4-chloro-3-fluorobenzyl bromide (2.79 g, 12.5 mmol) was added to the resulting solution. Sodium hydride (60% oil-based) (0.40 g, 10.0 mmol) was slowly added thereto under cooling with ice water bath, and the mixture was stirred at room temperature for 1 hour. Then, dilute hydrochloric acid was added thereto, and the mixture was extracted three times with ethyl acetate. The organic layer was washed with saturated saline water, dried over anhydrous sodium sulfate, and then concentrated under reduced pressure. The residue was dissolved in ethanol (20 mL), and an aqueous solution obtained by dissolving potassium hydroxide (2.81 g, 50 mmol) in water (10 mL) was added thereto at room temperature, and then the mixture was stirred at 80° C. for 3 hours. Water was added to the reaction mixture, and the mixture was concentrated under reduced pressure. Tert-butyl methyl ether was added to the concentrate, and the aqueous layer was fractionated. Dilute hydrochloric acid was added to the resulting aqueous layer, and the mixture was extracted three times with ethyl acetate. The organic layer was washed with saturated saline water, dried over anhydrous sodium sulfate, and then concentrated under reduced pressure to obtain 1.06 g of 5-(4-chloro-3-fluorobenzyloxymethyl)isoxazole-3-carboxylic acid represented by the following formula.

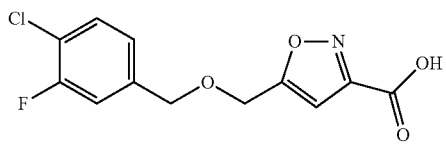

The product was subjected to a next reaction without purification.

Reference Production Example 219

A reaction was carried out in the same manner using 3-fluoro-4-methoxybenzyl bromide (3.22 g, 12 mmol), in place of 4-chloro-2-fluorobenzyl bromide in Reference Production Example 202 to obtain 1.98 g of 5-(3-fluoro-4-methoxybenzyloxymethyl)isoxazole-3-carboxylic acid represented by the following formula.

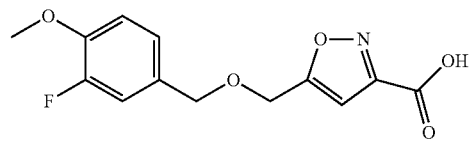 [SMILES: COc1ccc(COCc2cc(C(=O)O)no2)cc1F]

The product was subjected to a next reaction without purification.

Reference Production Example 220

A reaction was carried out in the same manner using 2,4-difluorobenzyl bromide (2.48 g, 12 mmol), in place of 4 chloro-2-fluorobenzyl bromide in Reference Production Example 202 to obtain 2.03 g of 5-(2,4-difluorobenzyloxymethyl)isoxazole-3-carboxylic acid represented by the following formula.

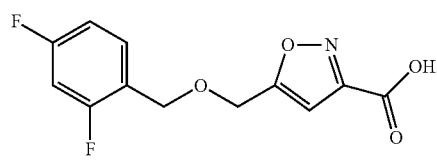 [SMILES: O=C(O)c1cc(COCc2ccc(F)cc2F)on1]

The product was subjected to a next reaction without purification.

Reference Production Example 221

A reaction was carried out in the same manner using 5-bromomethylbenzothiophene (500 mg, 2.20 mmol), in place of 2-chlorobenzyl bromide in Reference Production Example 43 to obtain 300 rag of ethyl 5-(5-benzothiophenylmethoxymethyl)isoxazole-3-carboxylate represented by the following formula.

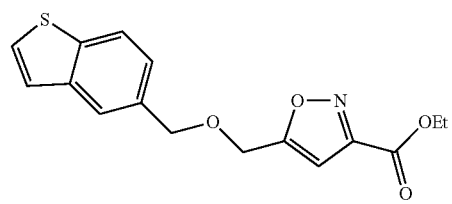 [SMILES: CCOC(=O)c1cc(COCc2ccc3sccc3c2)on1]

$^1$H-NMR (CDCl$_3$, TMS, δ(ppm)): 7.89 (1H, d), 7.80 (1H, s), 7.48 (1H, d), 7.34 (2H, dd), 6.71 (1H, s), 4.73 (2H, s), 4.68 (2H, d), 4.45 (2H, q), 1.42 (3H, t)

Reference Production Example 222

A reaction was carried out in the same manner using ethyl 5-(5-benzothiophenylmethoxymethyl)isoxazole-3-carboxylate (300 mg, 0.945 mmol), in place of ethyl 5-(2-chlorobenzyloxymethyl)isoxazole-3-carboxylate in Reference Production Example 44 to obtain 240 mg of 5-(5-benzothiophenylmethoxymethyl)isoxazole-3-carboxylic acid represented by the following formula.

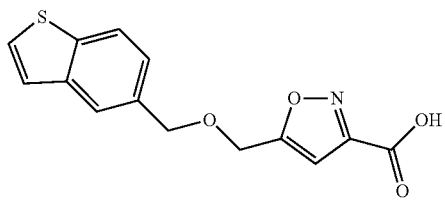 [SMILES: O=C(O)c1cc(COCc2ccc3sccc3c2)on1]

$^1$H-NMR (DMSO-d$_6$, TMS, δ(ppm)): 7.89 (1H, d), 7.81 (1H, s), 7.49 (1H, d), 7.35 (2H, d), 6.76 (1H, s), 4.75 (2H, s), 4.70 (2H, s)

Reference Production Example 223

Ethyl 5-(diethoxyphosphoryloxymethyl)isoxazole-3-carboxylate (300 mg, 0.98 mmol), 1,3-benzodioxole-5-boronic acid (281 mg, 1.27 mmol) and potassium carbonate (270 mg, 1.95 mmol) were added to a mixture of toluene (5 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours, and cooled. Then, water was poured thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 180 mg of ethyl 5-(1,3-benzodioxol-5-ylmethyl)isoxazole-3-carboxylate represented by the following formula.

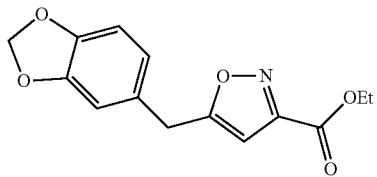 [SMILES: CCOC(=O)c1cc(Cc2ccc3c(c2)OCO3)on1]

$^1$H-NMR (CDCl$_3$, TMS, δ(ppm)): 1.40 (3H, s), 4.04 (2H, s), 4.42 (2H, q), 5.96 (2H, 8), 6.33 (1H, s), 6.71 (1H, d), 6.72 (1H, s), 6.77 (1H, d)

Reference Production Example 224

Ethyl 5-(1,3-benzodioxol-5-ylmethyl)isoxazole-3-carboxylate (2.60 g, 9.45 mmol) was added to a mixture of ethanol (25 mL) and a 2 mol/L aqueous sodium hydroxide solution (12 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of diethyl ether and petroleum ether to obtain 2.00 g of 5-(1,3-benzodioxolan-5-ylmethyl)isoxazole-3-carboxylic acid represented by the following formula.

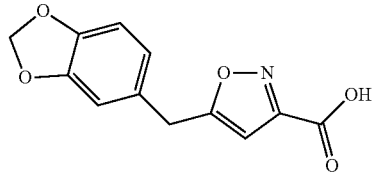 [SMILES: O=C(O)c1cc(Cc2ccc3c(c2)OCO3)on1]

$^1$H-NMR (DMSO-d$_6$, TMS) δ(ppm): 4.11 (2H, s), 6.00 (2H, s), 6.54 (1H, s), 6.74-6.80 (1H, m), 6.84-6.92 (2H, m), 13.90 (1H, br s)

Reference Production Example 225

Ethyl 5-(diethoxyphosphoryloxymetyl)isoxazole-3-carboxylate (300 mg, 0.98 mmol), 3,5-difluorophenylboronic acid (200 mg, 1.27 mmol) and potassium carbonate (269 mg, 1.95 mmol) were added to a mixture of toluene (5 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours and then cooled. Water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 162 mg of ethyl 5-(3,5-difluorobenzyl)isoxazole-3-carboxylate represented by the following formula.

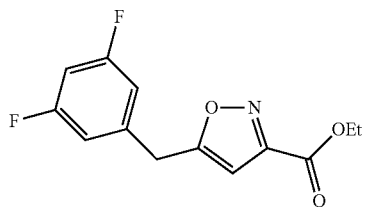 [SMILES: CCOC(=O)c1cc(Cc2cc(F)cc(F)c2)on1]

$^1$H-NMR (CDCl$_3$, TMS) δ(ppm): 1.41 (3H, t), 4.12 (2H, s), 4.43 (2H, q), 6.42 (1H, s), 6.72-6.82 (3H, m)

Reference Production Example 226

Ethyl 5-(3,5-difluorobenzyl)isoxazole-3-carboxylate (2.30 g, 8.61 mmol) was added to a mixture of ethanol (25 mL) and a 2 mol/L aqueous sodium hydroxide solution (12 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of diethyl ether and petroleum ether to obtain 1.50 g of 5-(3,5-difluorobenzyl)isoxazole-3-carboxylic acid represented by the following formula.

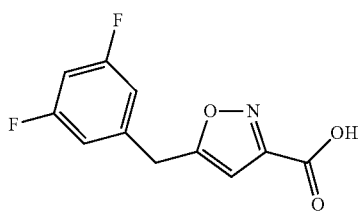

¹H-NMR (DMSO-d₆, TMS) δ(ppm): 4.28 (2H, s), 6.64 (1H, s), 7.05-7.20 (3H, m), 13.95 (1H, br s)

Reference Production Example 227

Ethyl 5-(diethoxyphosphoryloxymethyl)isoxazole-3-carboxylate (300 mg, 0.98 mmol), 3,4-difluorophenylboronic acid (200 mg, 1.27 mmol) and potassium carbonate (269 mg, 1.95 mmol) were added to a mixture of toluene (5 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours and then cooled. Water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 154 mg of ethyl 5-(3,4-difluorobenzyl)isoxazole-3-carboxylate represented by the following formula.

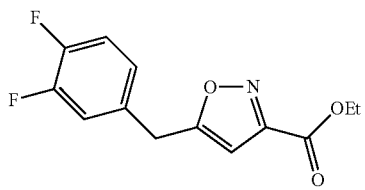 [SMILES: CCOC(=O)c1cc(Cc2ccc(F)c(F)c2)on1]

¹H-NMR (CDCl₃, TMS) δ(ppm): 1.40 (3H, t), 4.10 (2H, s), 4.43 (2H, q), 6.37 (1H, s), 6.94-7.18 (3H, m)

Reference Production Example 228

Ethyl 5-(3,4-difluorobenzyl)isoxazole-3-carboxylate (2.20 g, 8.23 mmol) was added to a mixture of ethanol (25 mL) and a 2 mol/L aqueous sodium hydroxide solution (12 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of diethyl ether and petroleum ether to obtain 1.56 g of 5-(3,4-difluorobenzyl)isoxazole-3-carboxylic acid represented by the following formula.

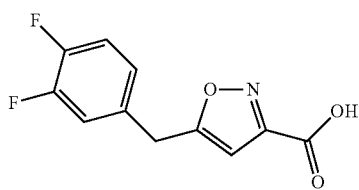

¹H-NMR (DMSO-d₆, TMS) δ(ppm): 4.23 (2H, s), 6.60 (1H, s), 7.12-7.21 (1H, m), 7.35-7.45 (2H, m), 13.95 (1H, br s)

Reference Production Example 229

Ethyl 5-(diethoxyphosphoryloxymethyl)isoxazole-3-carboxylate (300 mg, 0.98 mmol), 3,5-dichlorophenylboronic acid (242 mg, 1.27 mmol) and potassium carbonate (269 mg, 1.95 mmol) were added to a mixture of toluene (5 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours and then cooled. Water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 170 mg of ethyl 5-(3,5-dichlorobenzyl)isoxazole-3-carboxylate represented by the following formula.

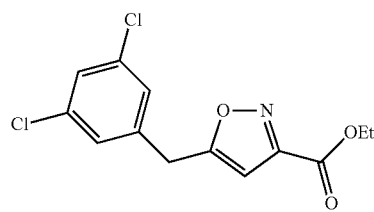 [SMILES: CCOC(=O)c1cc(Cc2cc(Cl)cc(Cl)c2)on1]

¹H-NMR (CDCl₃, TMS) δ(ppm): 1.41 (3H, t), 4.10 (2H, s), 4.43 (2H, q), 6.42 (1H, s), 7.12-7.16 (2H, m), 7.29-7.32 (1H, m)

Reference Production Example 230

Ethyl 5-(3,5-dichlorobenzyl)isoxazole-3-carboxylate (2.45 g, 8.20 mmol) was added to a mixture of ethanol (25 mL) and a 2 mol/L aqueous sodium hydroxide solution (12 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of diethyl ether and petroleum ether to obtain 1.70 g of 5-(3,5-dichlorobenzyl)isoxazole-3-carboxylic acid represented by the following formula.

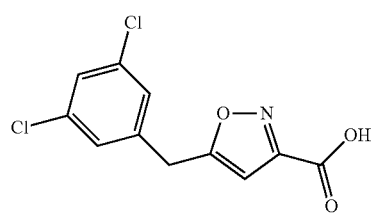 [SMILES: O=C(O)c1cc(Cc2cc(Cl)cc(Cl)c2)on1]

¹H-NMR (DMSO-d₆, TMS) δ(ppm): 4.27 (2H, s), 6.65 (1H, s), 7.40-7.44 (2H, m), 7.53-7.56 (1H, m), 13.96 (1H, br s)

Reference Production Example 231

An aqueous saturated sodium carbonate solution (1 mL) was added to a toluene solution (4 mL) of ethyl 5-(diethoxyphosphoryloxymethyl)isoxazole-3-carboxylate (100 mg, 0.33 mmol) and 2-thienylboronic acid (54 mg, 0.42 mmol). 1,1'-Bis(diphenylphosphino)ferrocene-palladium(II) dichloride (24 mg, 0.03 mmol) was added thereto, under an argon atmosphere, and the mixture was stirred at 75 to 80° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 32 mg of ethyl 5-(2-thienylmethyl)isoxazole-3-carboxylate represented by the following formula.

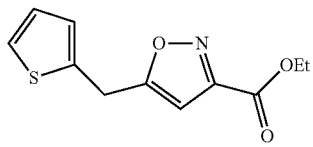

$^1$H-NMR (CDCl$_3$, TMS) δ(ppm): 1.40 (3H, t), 4.16 (2H, s), 4.43 (2H, q), 6.38 (1H, s), 6.75-7.01 (1H, m), 7.10-7.14 (1H, m), 7.32 (1H, dd)

Reference Production Example 232

Ethyl 5-(2-thienylmethyl)isoxazole-3-carboxylate (750 mg, 3.16 mmol) was added to a mixture of ethanol (8 mL) and a 2 mol/L aqueous sodium hydroxide solution (4 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed twice with a mixture of diethyl ether and petroleum ether to obtain 200 mg of 5-(2-thienylmethyl)isoxazole-3-carboxylic acid represented by the following formula.

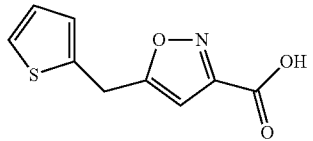 [SMILES: O=C(O)c1cc(Cc2cccs2)on1]

$^1$H-NMR (DMSO-d$_6$, TMS) δ(ppm): 4.47 (2H, s), 6.61 (1H, s), 6.96-7.04 (2H, m), 7.41-7.46 (1H, m), 13.95 (1H, br s)

Reference Production Example 233

An aqueous saturated sodium carbonate solution (1 mL) was added to a toluene solution (4 mL) of ethyl 5-(diethoxyphosphoryloxymetyl)isoxazole-3-carboxylate (100 mg, 0.33 mmol) and 3-thienylboronic acid (54 mg, 0.42 mmol). 1,1'-Bis(diphenylphosphino)ferrocene-palladium(II) dichloride (24 mg, 0.03 mmol) was added thereto, under an argon atmosphere, and the mixture was stirred at 75 to 80° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 56 mg of ethyl 5-(3-thienylmethyl)isoxazole-3-carboxylate represented by the following formula.

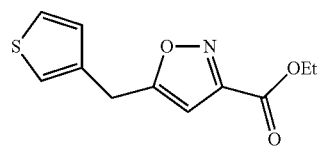 [SMILES: CCOC(=O)c1cc(Cc2ccsc2)on1]

$^1$H-NMR (CDCl$_3$, TMS) δ(ppm): 1.40 (3H, t), 4.16 (2H, s), 4.43 (2H, q), 6.34 (1H, s), 6.99 (1H, d), 7.10-7.13 (1H, m), 7.30-7.34 (1H, m)

Reference Production Example 234

Ethyl 5-(3-thienylmethyl)isoxazole-3-carboxylate (900 mg, 3.79 mmol) was added to a mixture of ethanol (9 mL) and a 2 mol/L aqueous sodium hydroxide solution (4 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed twice with a mixture of diethyl ether and petroleum ether to obtain 300 mg of 5-(3-thienylmethyl)isoxazole-3-carboxylic acid represented by the following formula.

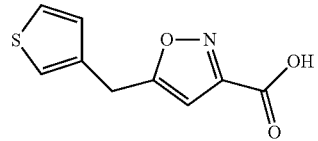 [SMILES: O=C(O)c1cc(Cc2ccsc2)on1]

$^1$H-NMR (DMSO-d$_6$, TMS) δ(ppm): 4.22 (2H, s), 6.56 (1H, s), 7.04-7.08 (1H, m), 7.34-7.38 (1H, m), 7.50-7.56 (1H, m), 13.90 (1H, br s)

Reference Production Example 235

An aqueous saturated sodium carbonate solution (1 mL) was added to a toluene solution (4 mL) of ethyl 5-(diethoxyphosphoryloxymethyl)isoxazole-3-carboxylate (100 mg, 0.33 mmol) and 2-furanylboronic acid (48 mg, 0.42 mmol). 1,1'-Bis(diphenylphosphino)ferrocene-palladium(II) dichloride (24 mg, 0.03 mmol) was added thereto, under an argon atmosphere, and the mixture was stirred at 75 to 80° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 21 mg of ethyl 5-(2-furanylmethyl)isoxazole-3-carboxylate represented by the following formula.

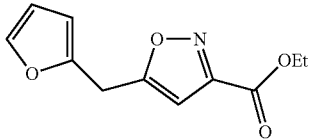 [SMILES: CCOC(=O)c1cc(Cc2ccco2)on1]

$^1$H-NMR (CDCl$_3$, TMS) δ(ppm): 1.40 (3H, t), 4.19 (2H, s), 4.43 (2H, q), 6.21 (1H, d), 6.35 (1H, dd), 6.46 (1H, s), 7.38 (1H, d)

Reference Production Example 236

Ethyl 5-(2-furanylmethyl)isoxazole-3-carboxylate (1.00 g, 4.52 mmol) was added to a mixture of ethanol (10 mL) and a 2 mol/L aqueous sodium hydroxide solution (5 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of ethyl acetate and petroleum ether to obtain 150 mg of 5-(2-furanylmethyl)isoxazole-3-carboxylic acid represented by the following formula.

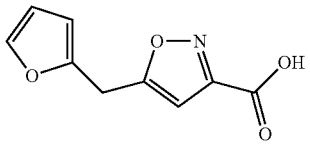

$^1$H-NMR (DMSO-d$_6$, TMS) δ(ppm): 4.32 (2H, s), 6.28-6.32 (1H, m), 6.41-6.45 (1H, m), 6.60 (1H, s), 7.58-7.63 (1H, m), 13.94 (1H, br s)

Reference Production Example 237

An aqueous saturated sodium carbonate solution (1 mL) was added to a toluene solution (4 mL) of ethyl 5-(diethoxyphosphoryloxymethyl)isoxazole-3-carboxylate (100 mg, 0.33 mmol) and 3-furanylboronic acid (48 mg, 0.42 mmol). 1,1′-Bis(diphenylphosphino)ferrocene-palladium(II) dichloride (24 mg, 0.03 mmol) was added thereto, under an argon atmosphere, and the mixture was stirred at 75 to 80° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 22 mg of ethyl 5-(3-furanylmethyl)isoxazole-3-carboxylate represented by the following formula.

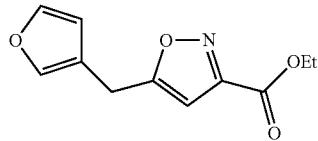 [SMILES: CCOC(=O)c1cc(Cc2ccoc2)on1]

$^1$H-NMR (CDCl$_3$, TMS) δ(ppm): 1.40 (3H, t), 3.97 (2H, s), 4.43 (2H, q), 6.34 (1H, s), 6.40 (1H, s), 7.38 (1H, s), 7.41-7.42 (1H, m)

Reference Production Example 238

Ethyl 5-(3-furanylmethyl)isoxazole-3-carboxylate (800 mg, 3.62 mmol) was added to a mixture of ethanol (8 mL) and a 2 mol/L aqueous sodium hydroxide solution (4 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of ethyl acetate and petroleum ether to obtain 531 mg of 5-(3-furanylmethyl)isoxazole-3-carboxylic acid represented by the following formula.

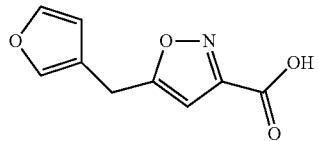 [SMILES: O=C(O)c1cc(Cc2ccoc2)on1]

$^1$H-NMR (DMSO-d$_6$, TMS) δ(ppm): 4.03 (1H, s), 6.45-6.48 (1H, m), 6.56 (1H, s), 7.58-7.66 (2H, m), 13.92 (1H, br s)

Reference Production Example 239

Ethyl 5-(diethoxyphosphoryloxymetyl)isoxazole-3-carboxylate (300 mg, 0.98 mmol), 3-methoxyphenylboronic acid (193 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 213 mg of ethyl 5-(3-methoxybenzyl)isoxazole-3-carboxylate represented by the following formula.

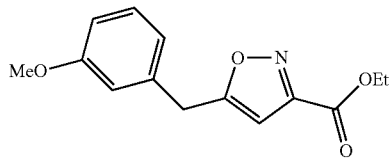 [SMILES: CCOC(=O)c1cc(Cc2cccc(OC)c2)on1]

$^1$H-NMR (CDCl$_3$, TMS) δ(ppm): 1.39 (3H, t), 3.80 (3H, s), 4.10 (2H, s), 4.41 (2H, q), 6.35 (1H, s), 6.76-6.86 (3H, m), 7.23-7.29 (1H, m)

Reference Production Example 240

Ethyl 5-(3-methoxybenzyl)isoxazole-3-carboxylate (200 mg, 0.77 mmol) was added to a mixture of ethanol (2 mL) and a 2 mol/L aqueous sodium hydroxide solution (1 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with petroleum ether to obtain 130 mg of 5-(3-methoxybenzyl)isoxazole-3-carboxylic acid represented by the following formula.

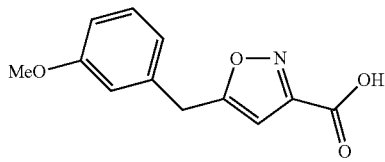 [SMILES: COc1cccc(Cc2cc(C(=O)O)no2)c1]

$^1$H-NMR (DMSO-d$_6$, TMS) δ(ppm): 3.74 (3H, s), 4.18 (2H, s), 6.57 (1H, s), 6.82-6.90 (3H, m), 7.26 (1H, dd), 13.91 (1H, br s)

Reference Production Example 241

Ethyl 5-(diethoxyphosphoryloxymethyl)isoxazole-3-carboxylate (300 mg, 0.98 mmol), 3-trifluoromethoxyphenylboronic acid (262 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 200 mg of ethyl 5-(3-trifluoromethoxybenzyl)isoxazole-3-carboxylate represented by the following formula.

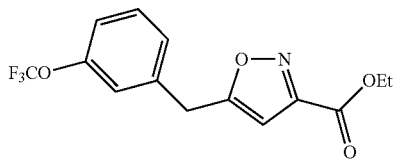 [SMILES: CCOC(=O)c1cc(Cc2cccc(OC(F)(F)F)c2)on1]

$^1$H-NMR (CDCl$_3$, TMS) δ(ppm): 1.40 (3H, t), 4.16 (2H, s), 4.43 (2H, q), 6.38 (1H, s), 7.08-7.22 (3H, m), 7.34-7.42 (1H, m)

Reference Production Example 242

Ethyl 5-(3-trifluoromethoxybenzyl)isoxazole-3-carboxylate (2.60 g, 8.44 mmol) was added to a mixture of ethanol (25 mL) and a 2 mol/L aqueous sodium hydroxide solution (12 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of diethyl ether and petroleum ether to obtain 1.80 g of 5-(3-trifluoromethoxybenzyl)isoxazole-3-carboxylic acid represented by the following formula.

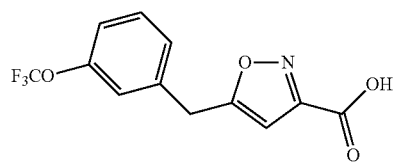 [SMILES: O=C(O)c1cc(Cc2cccc(OC(F)(F)F)c2)on1]

$^1$H-NMR (DMSO-d$_6$, TMS) δ(ppm): 4.31 (2H, s), 6.61 (1H, s), 7.24-7.38 (3H, m), 7.45-7.54 (1H, m), 13.92 (1H, br s)

Reference Production Example 243

Ethyl 5-(diethoxyphosphoryloxymethyl)isoxazole-3-carboxylate (300 mg, 0.98 mmol), 4-methoxyphenylboronic acid (193 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 150 mg of ethyl 5-(4-methoxybenzyl)isoxazole-3-carboxylate represented by the following formula.

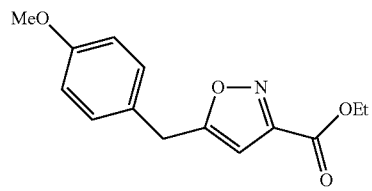 [SMILES: CCOC(=O)c1cc(Cc2ccc(OC)cc2)on1]

$^1$H-NMR (CDCl$_3$, TMS) δ(ppm): 1.39 (3H, t), 3.80 (3H, s), 4.07 (2H, s), 4.21 (2H, q), 6.30 (1H, s), 6.88 (sH, d), 7.17 (2H, d)

Reference Production Example 244

Ethyl 5-(4-methoxybenzyl)isoxazole-3-carboxylate (2.40 g, 9.20 mmol) was added to a mixture of ethanol (25 mL) and a 2 mol/L aqueous sodium hydroxide solution (12 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of diethyl ether and petroleum ether to obtain 1.50 g of 5-(4-methoxybenzyl)isoxazole-3-carboxylic acid represented by the following formula.

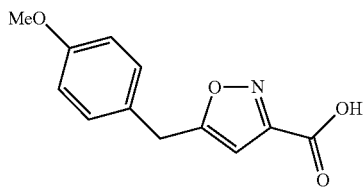 [SMILES: COc1ccc(Cc2cc(C(=O)O)no2)cc1]

$^1$H-NMR (DMSO-d$_6$, TMS) δ(ppm): 3.73 (3H, s), 4.13 (2H, s), 6.51 (1H, s), 6.87-6.93 (2H, m), 7.19-7.26 (2H, m), 13.90 (1H, br s)

Reference Production Example 245

Ethyl 5-(diethoxyphosphoryloxymethyl)isoxazole-3-carboxylate (300 mg, 0.98 mmol), 4-trifluoromethoxyphenylboronic acid (262 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 182 mg of ethyl 5-(4-trifluoromethoxybenzyl)isoxazole-3-carboxylate represented by the following formula.

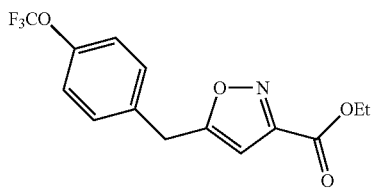 [SMILES: CCOC(=O)c1cc(Cc2ccc(OC(F)(F)F)cc2)on1]

$^1$H-NMR (CDCl$_3$, TMS) δ(ppm): 1.40 (3H, t), 4.15 (2H, s), 4.42 (2H, q), 6.37 (1H, s), 7.17-7.21 (2H, m), 7.24-7.32 (2H, m)

Reference Production Example 246

Ethyl 5-(4-trifluoromethoxybenzyl)isoxazole-3-carboxylate (2.60 g, 8.25 mmol) was added to a mixture of ethanol (25 mL) and a 2 mol/L aqueous sodium hydroxide solution (12 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of diethyl ether and petroleum ether to obtain 1.70 g of 5-(4-trifluoromethoxybenzyl)isoxazole-3-carboxylic acid represented by the following formula.

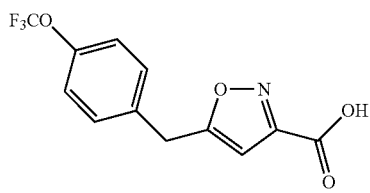 [SMILES: O=C(O)c1cc(Cc2ccc(OC(F)(F)F)cc2)on1]

$^1$H-NMR (DMSO-d$_6$, TMS) δ(ppm): 4.28 (2H, s), 6.61 (1H, s), 7.31-7.38 (2H, m), 7.40-7.48 (2H, m), 13.92 (1H, br s)

Reference Production Example 247

Ethyl 5-(diethoxyphosphoryloxymethyl)isoxazole-3-carboxylate (300 mg, 0.98 mmol), 4-trifluoromethylphenylboronic acid (241 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 166 mg of ethyl 5-(4-trifluoromethylbenzyl)isoxazole-3-carboxylate represented by the following formula.

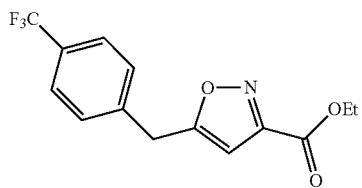 [SMILES: CCOC(=O)c1cc(Cc2ccc(C(F)(F)F)cc2)on1]

$^1$H-NMR (CDCl$_3$, TMS) δ(ppm): 1.40 (3H, t), 4.20 (2H, s), 4.43 (2H, q), 6.38 (1H, s), 7.42-7.60 (4H, m)

Reference Production Example 248

Ethyl 5-(4-trifluoromethoxybenzyl)isoxazole-3-carboxylate (2.40 g, 8.02 mmol) was added to a mixture of ethanol (25 mL) and a 2 mol/L aqueous sodium hydroxide solution (12 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of diethyl ether and petroleum ether to obtain 1.70 g of 5-(4-trifluoromethylbenzyl)isoxazole-3-carboxylic acid represented by the following formula.

401

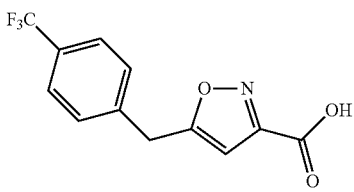

¹H-NMR (DMSO-d₆, TMS) δ(ppm): 4.36 (2H, s), 6.64 (1H, s), 7.52-7.58 (2H, m), 7.69-7.76 (2H, m), 13.92 (1H, br s)

Reference Production Example 249

Ethyl 5-(diethoxyphosphoryloxymethyl)isoxazole-3-carboxylate (300 mg, 0.98 mmol), 2-methoxyphenylboronic acid (193 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 140 mg of ethyl 5-(2-methoxybenzyl)isoxazole-3-carboxylate represented by the following formula.

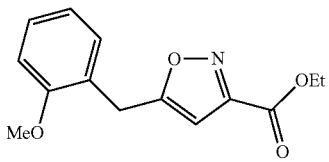 [SMILES: CCOC(=O)c1cc(Cc2ccccc2OC)on1]

¹H-NMR (CDCl₃, TMS) δ(ppm): 1.39 (3H, t), 3.82 (3H, s), 4.12 (2H, s), 4.41 (2H, q), 6.28 (1H, s), 6.86-6.96 (2H, m), 7.16-7.20 (1H, m)

Reference Production Example 250

Ethyl 5-(2-methoxybenzyl)isoxazole-3-carboxylate (2.00 g, 7.66 mmol) was added to a mixture of ethanol (20 mL) and a 2 mol/L aqueous sodium hydroxide solution (10 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of diethyl ether and petroleum ether to obtain 1.40 g of 5-(2-methoxybenzyl)isoxazole-3-carboxylic acid represented by the following formula.

402

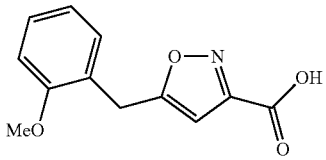 [SMILES: COc1ccccc1Cc1cc(C(=O)O)no1]

¹H-NMR (DMSO-d₆, TMS) δ(ppm): 3.79 (3H, s), 4.13 (2H, s), 6.41 (1H, s), 6.90-6.96 (1H, m), 7.01-7.05 (1H, m), 7.18-7.24 (1H, m), 7.26-7.33 (1H, m), 13.90 (1H, br s)

Reference Production Example 251

Ethyl 5-(diethoxyphosphoryloxymethyl)isoxazole-3-carboxylate (300 mg, 0.98 mmol), 3-fluorophenylboronic acid (175 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95@C for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 157 mg of ethyl 5-(3-fluorobenzyl)isoxazole-3-carboxylate represented by the following formula.

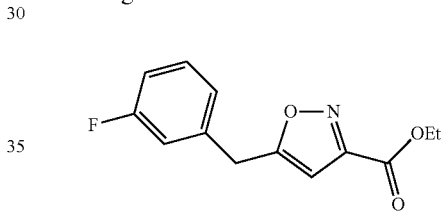

¹H-NMR (CDCl₃, TMS) δ(ppm): 1.39 (3H, t), 4.17 (2H, s), 4.41 (2H, q), 6.37 (1H, s), 7.06-7.16 (2H, m), 7.22-7.33 (2H, m)

Reference Production Example 252

Ethyl 5-(3-fluorobenzyl)isoxazole-3-carboxylate (150 mg, 0.60 mmol) was added to a mixture of ethanol (2 mL) and a 2 mol/L aqueous sodium hydroxide solution (1 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with petroleum ether to obtain 100 mg of 5-(3-fluorobenzyl)isoxazole-3-carboxylic acid represented by the following formula.

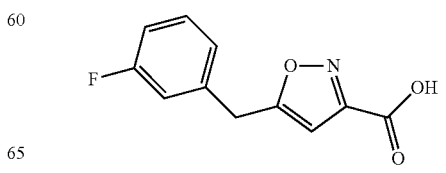

$^1$H-NMR (DMSO-d$_6$, TMS) δ(ppm): 4.25 (2H, s), 6.60 (1H, s), 7.08-7.22 (3H, m), 7.36-7.44 (1H, m), 13.92 (1H, br s)

Reference Production Example 253

Ethyl 5-(diethoxyphosphoryloxymethyl)isoxazole-3-carboxylate (300 mg, 0.98 mmol), 4-fluorophenylboronic acid (175 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 150 mg of ethyl 5-(4-fluorobenzyl)isoxazole-3-carboxylate represented by the following formula.

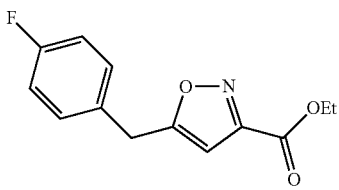 [SMILES: CCOC(=O)c1cc(Cc2ccc(F)cc2)on1]

$^1$H-NMR (CDCl$_3$, TMS) δ(ppm): 1.39 (3H, t), 4.11 (2H, s), 4.42 (2H, q), 6.33 (1H, s), 7.00-7.07 (2H, m), 7.19-7.25 (2H, m)

Reference Production Example 254

Ethyl 5-(4-fluorobenzyl)isoxazole-3-carboxylate (150 mg, 0.60 mmol) was added to a mixture of ethanol (2 mL) and a 2 mol/L aqueous sodium hydroxide solution (1 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with petroleum ether to obtain 100 mg of 5-(4-fluorobenzyl)isoxazole-3-carboxylic acid represented by the following formula.

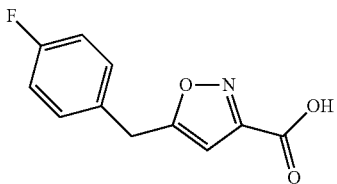 [SMILES: O=C(O)c1cc(Cc2ccc(F)cc2)on1]

$^1$H-NMR (DMSO-d$_6$, TMS) δ(ppm): 4.22 (2H, s), 6.56 (1H, s), 7.14-7.22 (2H, m), 7.32-7.39 (2H, m), 13.92 (1H, br s)

Reference Production Example 255

Ethyl 5-(diethoxyphosphoryloxymetyl)isoxazole-3-carboxylate (300 mg, 0.98 mmol), 2-fluorophenylboronic acid (175 mg, 1.27 mmol) and potassium carbonate (269 mg, 1.95 mmol) were added to mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 146 mg of ethyl 5-(2-fluorobenzyl)isoxazole-3-carboxylate represented by the following formula.

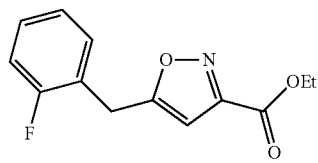 [SMILES: CCOC(=O)c1cc(Cc2ccccc2F)on1]

$^1$H-NMR (CDCl$_3$, TMS) δ(ppm): 1.40 (3H, t), 4.13 (2H, s), 4.42 (2H, q), 6.37 (1H, s), 6.94-7.06 (3H, m), 7.27-7.36 (1H, m)

Reference Production Example 256

Ethyl 5-(2-fluorobenzyl)isoxazole-3-carboxylate (140 mg, 0.56 mmol) was added to a mixture of ethanol (2 mL) and a 2 mol/L aqueous sodium hydroxide solution (1 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with petroleum ether to obtain 90 mg of 5-(2-fluorobenzyl)isoxazole-3-carboxylic acid represented by the following formula.

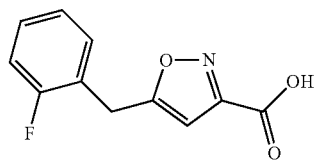

$^1$H-NMR (DMSO-d$_6$, TMS) δ(ppm): 4.26 (2H, s), 6.55 (1H, s), 7.17-7.27 (2H, m), 7.33-7.43 (2H, m), 13.92 (1H, br s)

Reference Production Example 257

Ethyl 5-(diethoxyphosphoryloxymethyl)isoxazole-3-carboxylate (200 mg, 0.65 mmol), 3-chlorophenylboronic acid (132 mg, 0.84 mmol) and potassium carbonate (179 mg, 1.30 mmol) were added to a mixture of toluene (4 mL) and water (1 mL). Palladium acetate (7 mg, 0.03 mmol) and triphenylphosphine (34 mg, 0.13 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 110 mg of ethyl 5-(3-chlorobenzyl)isoxazole-3-carboxylate represented by the following formula.

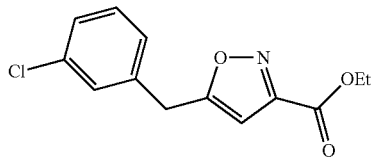 [SMILES: CCOC(=O)c1cc(Cc2cccc(Cl)c2)on1]

$^1$H-NMR (CDCl$_3$, TMS) δ(ppm): 1.40 (3H, t), 4.12 (2H, s), 4.42 (2H, q), 6.37 (1H, s), 7.12-7.16 (1H, m), 7.23-7.30 (3H, m)

Reference Production Example 258

Ethyl 5-(3-chlorobenzyl)isoxazole-3-carboxylate (110 mg, 0.41 mmol) was added to a mixture of ethanol (2 mL) and a 2 mol/L aqueous sodium hydroxide solution (1 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with petroleum ether to obtain 70 mg of 5-(3-chlorobenzyl)isoxazole-3-carboxylic acid represented by the following formula.

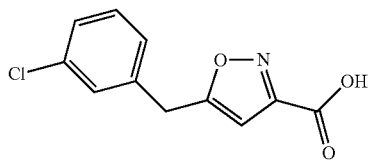 [SMILES: O=C(O)c1cc(Cc2cccc(Cl)c2)on1]

$^1$H-NMR (DMSO-d$_6$, TMS) δ(ppm): 4.25 (2H, s), 6.61 (1H, s), 7.26-7.30 (1H, m), 7.33-7.42 (3H, m), 13.92 (1H, br s)

Reference Production Example 259

Ethyl 5-(diethoxyphosphoryloxymethyl)isoxazole-3-carboxylate (300 mg, 0.98 mmol), 4-chlorophenylboronic acid (199 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 132 mg of ethyl 5-(4-chlorobenzyl)isoxazole-3-carboxylate represented by the following formula.

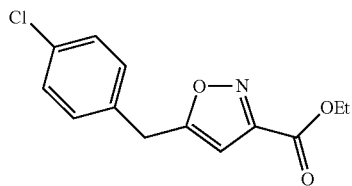 [SMILES: CCOC(=O)c1cc(Cc2ccc(Cl)cc2)on1]

$^1$H-NMR (CDCl$_3$, TMS) δ(ppm): 1.40 (3H, t), 4.11 (2H, s), 4.42 (2H, q), 6.34 (1H, s), 7.19 (2H, d), 7.32 (2H, d)

Reference Production Example 260

Ethyl 5-(4-chlorobenzyl)isoxazole-3-carboxylate (2.60 g, 9.81 mmol) was added to a mixture of ethanol (25 mL) and a 2 mol/L aqueous sodium hydroxide solution (12 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with petroleum ether to obtain 1.70 g of 5-(4-chlorobenzyl)isoxazole-3-carboxylic acid represented by the following formula.

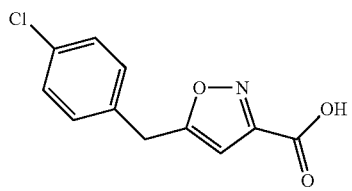 [SMILES: O=C(O)c1cc(Cc2ccc(Cl)cc2)on1]

$^1$H-NMR (DMSO-d$_6$, TMS) δ(ppm): 4.23 (2H, s), 6.58 (1H, s), 7.30-7.36 (2H, m), 7.36-7.44 (2H, m), 13.90 (1H, br s)

Reference Production Example 261

Ethyl 5-(diethoxyphosphoryloxymethyl)isoxazole-3-carboxylate (300 mg, 0.98 mmol), 2-chlorophenylboronic acid (199 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 140 mg of ethyl 5-(2-chlorobenzyl)isoxazole-3-carboxylate represented by the following formula.

$^1$H-NMR (CDCl$_3$, TMS) δ(ppm): 1.39 (3H, t), 4.23 (2H, s), 4.41 (2H, q), 6.34 (1H, s), 7.22-7.30 (3H, m), 7.38-7.45 (1H, m)

Reference Production Example 262

Ethyl 5-(2-chlorobenzyl)isoxazole-3-carboxylate (2.70 g, 10.18 mmol) was added to a mixture of ethanol (25 mL) and a 2 mol/L aqueous sodium hydroxide solution (12 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of diethyl ether and petroleum ether to obtain 1.90 g of 5-(2-chlorobenzyl)isoxazole-3-carboxylic acid represented by the following formula.

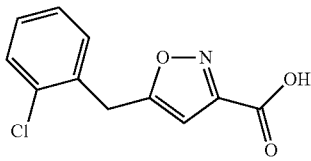 [SMILES: O=C(O)c1cc(Cc2ccccc2Cl)on1]

$^1$H-NMR (DMSO-d$_6$, TMS) δ(ppm): 4.32 (2H, s), 6.51 (1H, s), 7.30-7.52 (4H, m), 13.96 (1H, br s)

Reference Production Example 263

Ethyl 5-(diethoxyphosphoryloxymethyl)isoxazole-3-carboxylate (100 mg, 0.33 mmol), 2,3,4-trifluorophenylboronic acid (75 mg, 0.42 mmol) and potassium carbonate (133 mg, 0.65 mmol) were added to a mixture of toluene (4 mL) and water (1 mL). Palladium acetate (4 mg, 0.02 mmol) and triphenylphosphine (17 mg, 0.07 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 40 mg of ethyl 5-(2,3,4-trifluorobenzyl)isoxazole-3-carboxylate represented by the following formula.

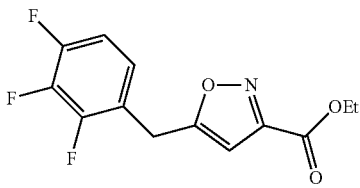 [SMILES: CCOC(=O)c1cc(Cc2ccc(F)c(F)c2F)on1]

$^1$H-NMR (CDCl$_3$, TMS) δ(ppm): 1.40 (3H, t), 4.16 (2H, s), 4.43 (2H, q), 6.41 (1H, s), 6.94-7.20 (2H, m)

Reference Production Example 264

Ethyl 5-(2,3,4-trifluorobenzyl)isoxazole-3-carboxylate (1.50 g, 5.26 mmol) was added to a mixture of ethanol (15 mL) and a 2 mol/L aqueous sodium hydroxide solution (7.5 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of diethyl ether and petroleum ether to obtain 1.10 g of 5-(2,3,4-trifluorobenzyl)isoxazole-3-carboxylic acid represented by the following formula.

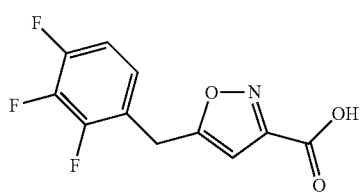 [SMILES: O=C(O)c1cc(Cc2ccc(F)c(F)c2F)on1]

$^1$H-NMR (DMSO-d$_6$, TMS) δ(ppm): 4.31 (2H, s), 6.62 (1H, s), 7.23-7.40 (2H, m), 13.98 (1H, br s)

Reference Production Example 265

Ethyl 5-(diethoxyphosposphoryloxymethyl)isoxazole-3-carboxylate (300 mg, 0.98 mmol), 3,4-dichlorophenylboronic acid (199 mg, 1.27 mmol) and potassium carbonate (269 mg, 1.95 mmol) were added to a mixture of toluene (5 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 181 mg of ethyl 5-(3,4-dichlorobenzyl)isoxazole-3-carboxylate represented by the following formula.

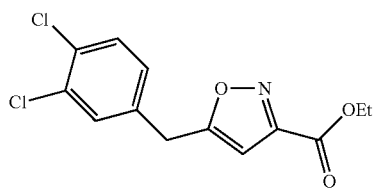 [SMILES: CCOC(=O)c1cc(Cc2ccc(Cl)c(Cl)c2)on1]

$^1$H-NMR (CDCl$_3$, TMS) δ(ppm): 1.40 (3H, t), 4.10 (2H, s), 4.43 (2H, q), 6.39 (1H, s), 7.10 (1H, dd), 7.35 (1H, d), 7.42 (1H, d)

Reference Production Example 266

Ethyl 5-(3,4-dichlorobenzyl)isoxazole-3-carboxylate (2.60 g, 8.66 mmol) was added to a mixture of ethanol (25 mL) and a 2 mol/L aqueous sodium hydroxide solution (12 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with a mixture of diethyl ether and petroleum ether to obtain 1.86 g of 5-(3,4-dichlorobenzyl)isoxazole-3-carboxylic acid represented by the following formula.

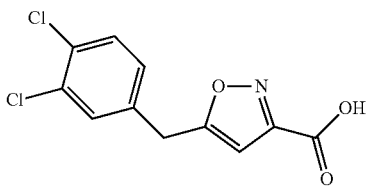 [SMILES: O=C(O)c1cc(Cc2ccc(Cl)c(Cl)c2)on1]

$^1$H-NMR (DMSO-d$_6$, TMS) δ(ppm): 4.26 (2H, s), 6.62 (1H, s), 7.30-7.34 (1H, m), 7.60-7.66 (2H, m), 13.95 (1H, br s)

Reference Production Example 267

Ethyl 5-(diethoxyphosphoryloxymethyl)isoxazole-3-carboxylate (100 mg, 0.33 mmol), 2-biphenylboronic acid (77 mg, 0.39 mmol) and potassium carbonate (87 mg, 0.65 mmol) were added to a mixture of toluene (4 mL) and water (1 mL). Palladium acetate (4 mg, 0.02 mmol) and triphenylphosphine (17 mg, 0.07 mmol) were added thereto, under an argon atmosphere, and the mixture was stirred at 90 to 95° C. for 1 hour, under microwave irradiation, then diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 40 mg of ethyl 5-(2-biphenylmethyl)isoxazole-3-carboxylate represented by the following formula.

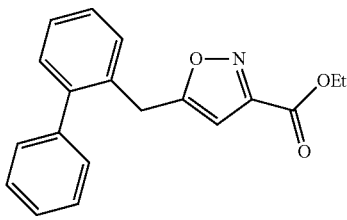 [SMILES: CCOC(=O)c1cc(Cc2ccccc2-c2ccccc2)on1]

$^1$H-NMR (CDCl$_3$, TMS) δ(ppm): 1.39 (3H, t), 4.08 (2H, s), 4.41 (2H, q), 6.16 (1H, s), 7.21-7.42 (9H, m)

Reference Production Example 268

Ethyl 5-(2-biphenylmethyl)isoxazole-3-carboxylate (1.80 g, 5.86 mmol) was added to a mixture of ethanol (20 mL) and a 2 mol/L aqueous sodium hydroxide solution (10 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with petroleum ether to obtain 1.32 g of 5-(2-biphenylmethyl)isoxazole-3-carboxylic acid represented by the following formula.

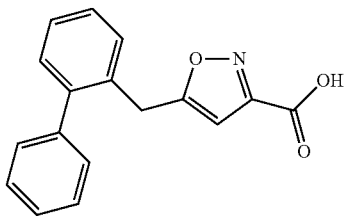 [SMILES: O=C(O)c1cc(Cc2ccccc2-c2ccccc2)on1]

$^1$H-NMR (DMSO-d$_6$, TMS) δ(ppm): 4.15 (2H, s), 6.24 (1H, s), 7.22-7.32 (3H, m), 7.35-7.48 (6H, m), 13.90 (1H, br s)

Reference Production Example 269

Ethyl 5-(diethoxyphosphohoryloxymethyl)isoxazole-3-carboxylate (100 mg, 0.33 mmol), 3-biphenylboronic acid (77 mg, 0.39 mmol) and potassium carbonate (87 mg, 0.65 mmol) were added to a mixture of toluene (4 mL) and water (1 mL). Palladium acetate (4 mg, 0.02 mmol) and triphenylphosphine (17 mg, 0.07 mmol) were added thereto, under an argon atmosphere, and the mixture was stirred at 90 to 95° C. for 1 hour, under microwave irradiation. The reactant was diluted with ethyl acetate, and filtered using celite. The filtrate was added to water, and the mixture was extracted twice with ethyl acetate. The organic layer was washed with saturated saline water, dried over anhydrous sodium sulfate, and then concentrated under reduced pressure. The residue was applied to a silica gel column chromatography to obtain 30 rag of ethyl 5-(3-biphenylmethyl)isoxazole-3-carboxylate represented by the following formula.

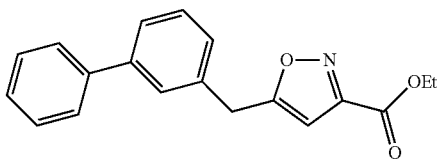 [SMILES: CCOC(=O)c1cc(Cc2cccc(-c3ccccc3)c2)on1]

$^1$H-NMR (CDCl$_3$, TMS) δ(ppm): 1.39 (3H, t), 4.20 (2H, s), 4.41 (2H, q), 6.38 (1H, s), 7.21-7.26 (1H, m), 7.32-7.60 (8H, m)

Reference Production Example 270

Ethyl 5-(3-biphenylmethyl)isoxazole-3-carboxylate (1.50 g, 4.88 mmol) was added to a mixture of ethanol (15 mL) and a 2 mol/L aqueous sodium hydroxide solution (7 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline sulfate, dried over anhydrous sodium sulfate, and then concentrated under reduced pressure. The residue was washed with petroleum ether to obtain 1.10 g of 5-(3-biphenylmethyl)isoxazole-3-carboxylic acid represented by the following formula.

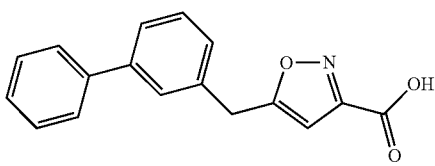 [SMILES: O=C(O)c1cc(Cc2cccc(-c3ccccc3)c2)on1]

¹H-NMR (DMSO-d₆, TMS) δ(ppm): 4.30 (2H, s), 6.62 (1H, s), 7.28-7.50 (5H, m), 7.56-7.68 (4H, m), 13.92 (1H, br s)

Reference Production Example 271

Ethyl 5-(diethoxyphosphoryloxymethyl)isoxazole-3-carboxylate (300 mg, 0.98 mmol), 3-methylphenylboronic acid (173 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours and then cooled. Water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 124 mg of ethyl 5-(3-methylbenzyl)isoxazole-3-carboxylate represented by the following formula.

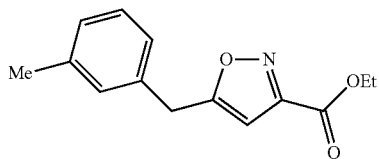 [SMILES: CCOC(=O)c1cc(Cc2cccc(C)c2)on1]

¹H-NMR (CDCl₃, TMS) δ(ppm): 1.39 (3H, t), 2.34 (3H, s), 4.08 (2H, s), 4.41 (2H, q), 6.31 (1H, s), 7.04-7.22 (4H, m)

Reference Production Example 272

Ethyl 5-(3-methylbenzyl)isoxazole-3-carboxylate (2.20 g, 8.98 mmol) was added to a mixture of ethanol (22 mL) and a 2 mol/L aqueous sodium hydroxide solution (11 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with petroleum ether to obtain 1.66 g of 5-(3-methylbenzyl)isoxazole-3-carboxylic acid represented by the following formula.

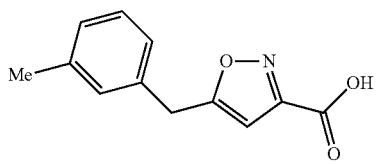 [SMILES: Cc1cccc(Cc2cc(C(=O)O)no2)c1]

¹H-NMR (DMSO-d₆, TMS) δ(ppm): 2.29 (3H, s), 4.16 (2H, s), 6.57 (1H, s), 7.04-7.14 (3H, m), 7.19-7.28 (1H, m), 13.92 (1H, br s)

Reference Production Example 273

Ethyl 5-(diethoxyphosphoryloxymethyl)isoxazole-3-carboxylate (300 mg, 0.98 mmol), 4-methylphenylboronic acid (173 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours and then cooled. Water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 130 mg of ethyl 5-(4-methylbenzyl)isoxazole-3-carboxylate represented by the following formula.

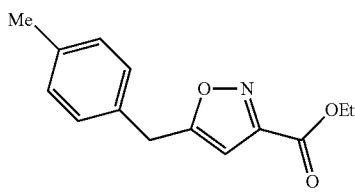 [SMILES: CCOC(=O)c1cc(Cc2ccc(C)cc2)on1]

¹H-NMR (CDCl₃, TMS) δ(ppm): 1.39 (3H, t), 2.34 (3H, s), 4.08 (2H, s), 4.41 (2H, q), 6.30 (1H, s), 7.05-7.20 (4H, m)

Reference Production Example 274

Ethyl 5-(4-methylbenzyl)isoxazole-3-carboxylate (2.10 g, 8.57 mmol) was added to a mixture of ethanol (20 mL) and a 2 mol/L aqueous sodium hydroxide solution (10 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with petroleum ether to obtain 1.58 g of 5-(4-methylbenzyl)isoxazole-3-carboxylic acid represented by the following formula.

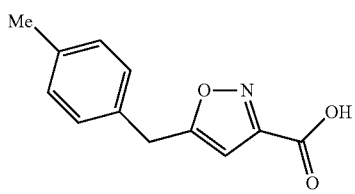

¹H-NMR (DMSO-d₆, TMS) δ(ppm): 2.28 (3H, s), 4.16 (2H, s), 6.54 (1H, s), 7.12-7.22 (4H, m), 13.91 (1H, br s)

Reference Production Example 275

Ethyl 5-(diethoxyphosphoryloxymetyl)isoxazole-3-carboxylate (300 mg, 0.98 mmol), 2-methylphenylboronic acid (173 mg, 1.27 mmol) and potassium carbonate (269 mg, 1.95 mmol) were added to a mixture of toluene (4 mL) and water (1 mL). Palladium acetate (11 mg, 0.05 mmol) and triphenylphosphine (51 mg, 0.19 mmol) were added thereto, under an argon atmosphere, and the mixture was stirred at 90 to 95° C. for 4 hours and then cooled. Water was added thereto, and the mixture was extracted twice with ethyl acetate. The organic layer was washed with saturated saline water, dried over anhydrous sodium sulfate, and then concentrated under reduced pressure. The residue was applied to a silica gel column chromatography to obtain 120 mg of ethyl 5-(2-methylbenzyl)isoxazole-3-carboxylate represented by the following formula.

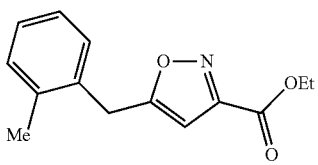

$^1$H-NMR (CDCl$_3$, TMS) δ(ppm): 1.39 (3H, t), 2.29 (3H, s), 4.11 (2H, s), 4.40 (2H, q), 6.21 (1H, s), 7.08-7.24 (4H, m)

Reference Production Example 276

Ethyl 5-(2-methylbenzyl)isoxazole-3-carboxylate (2.00 g, 8.16 mmol) was added to a mixture of ethanol (20 mL) and a 2 mol/L aqueous sodium hydroxide solution (10 mL) at 0° C., and the mixture was stirred at room temperature for 16 hours, then diluted with water, and concentrated under reduced pressure. The concentrate was made acidic by adding 1 mol/L hydrochloric acid at 0° C., and the mixture was extracted twice with ethyl acetate. The organic layer was washed with saturated saline water, dried over anhydrous sodium sulfate, and then concentrated under reduced pressure. The residue was washed with petroleum ether to obtain 1.46 g of 5-(2-methylbenzyl)isoxazole-3-carboxylic acid represented by the following formula.

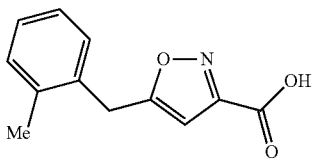 [SMILES: Cc1ccccc1Cc1cc(C(=O)O)no1]

$^1$H-NMR (DMSO-d$_6$, TMS) δ(ppm): 2.27 (3H, s), 4.20 (2H, s), 6.48 (1H, s), 7.14-7.24 (4H, m), 13.91 (1H, br s)

Reference Production Example 277

60% sodium hydride (0.29 g, 7.14 mmol) was added to N,N-dimethylformamide, and the mixture was stirred at 50° C. A N,N-dimethylformamide (3 mL) solution of ethyl 1,2,3-triazole-4-carboxylate (1.00 g, 7.14 mmol) was slowly added to the mixture, and the mixture was stirred at 50° C. for 1 hour. Then, 1-bromobutane (1.08 g, 7.85 mmol) was added dropwise thereto, and the mixture was heated to 60° C. and stirred for 3 hours. The reaction mixture was cooled to room temperature, water was added thereto, and the mixture was extracted three times with ethyl acetate. The organic layer was washed with saturated saline water, and then concentrated under reduced pressure. The residue was applied to a silica gel column chromatography to obtain 0.65 g of ethyl 1-butyl-1H-1,2,3-triazole-4-carboxylate represented by the following formula:

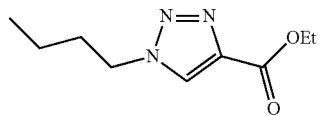

and 0.24 g of ethyl 2-butyl-2H-1,2,3-triazole-4-carboxylate represented by the following formula.

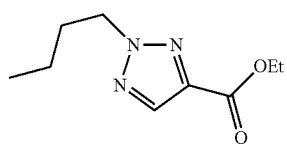

Ethyl 1-butyl-1H-1,2,3-triazole-4-carboxylate $^1$H-NMR (CDCl$_3$, TMS, δ(ppm)): 0.95 (t, 3H), 1.34 (tq, 2H), 1.41 (t, 3H), 1.98 (tt, 2H), 4.43 (q, 2H), 4.50 (t, 2H), 8.04 (s, 1H)

Ethyl 2-butyl-2H-1,2,3-triazole-4-carboxylate $^1$H-NMR (CDCl$_3$, TMS, δ(ppm)): 0.97 (t, 3H), 1.32-1.44 (m, 5H), 1.92 (tt, 2H), 4.40-4.46 (m, 4H), 8.07 (s, 1H)

Reference Production Example 278

Ethyl 1-butyl-1H-1,2,3-triazole-4-carboxylate (0.65 g, 3.30 mmol) was added to ethanol (1 mL), and potassium hydroxide (0.23 g, 4.05 mmol) and water (7 mL) were further added thereto. The mixture was stirred at room temperature overnight and then concentrated under reduced pressure. Dilute hydrochloric acid was added to the concentrate, and the mixture was extracted twice with chloroform. The organic layer was washed with saturated saline water, and dried over anhydrous sodium sulfate, then concentrated under reduced pressure to obtain 0.56 g of 1-butyl-1H-1,2,3-triazole-4-carboxylic acid represented by the following formula.

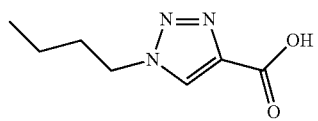

$^1$H-NMR (CDCl$_3$, TMS, δ(ppm)): 0.94 (t, 3H), 1.33 (tq, 2H), 1.98 (tt, 2H), 4.50 (t, 2H), 8.07 (s, 1H)

Reference Production Example 279

Ethyl 2-butyl-2H-1,2,3-triazole-4-carboxylate (0.24 g, 1.22 mmol) was added to ethanol (0.5 mL), and potassium hydroxide (0.08 g, 1.46 mmol) and water (3 mL) were further added thereto. The mixture was stirred at room temperature for 4 hours and then concentrated under reduced pressure. Dilute hydrochloric acid was added to the concentrate, and the mixture was extracted twice with chloroform.

The organic layer was washed with saturated saline water, and dried over anhydrous sodium sulfate, then concentrated under reduced pressure to obtain 0.17 g of 2-butyl-2H-1,2,3-triazole-4-carboxylic acid represented by the following formula.

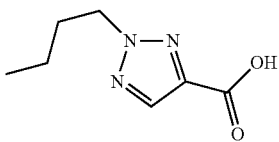

¹H-NMR (CDCl₃, TMS, δ(ppm)): 0.98 (t, 3H), 1.38 (tq, 2H), 1.95 (tt, 2H), 4.45 (t, 2H), 8.15 (s, 1H)

Reference Production Example 280

1-(2-Phenylmethoxy)-2-butanone (1.55 g, 8.70 mmol) and diethyl oxalate (1.53 g, 10.44 mmol) were dissolved in ethanol (17.4 ml), and the mixture was cooled to −10° C. or less under a nitrogen atmosphere. Sodium ethoxide (20% ethanol solution, about 3 g, about 8.70 mmol) was added dropwise to the mixture over 15 minutes, and the mixture was stirred for 1 hour and 45 minutes while slowly heating to room temperature, then neutralized with 1 mol/L hydrochloric acid under ice-water cooling, and extracted with methyl-tert-butyl ether. The organic layer was washed with saturated saline water, dried over anhydrous sodium sulfate, and then concentrated under reduced pressure. The residue was applied to a silica gel column chromatography to obtain 0.60 g of ethyl 2,4-dioxo-3-methyl-5-(phenylmethoxy)-2-pentanoate represented by the following formula.

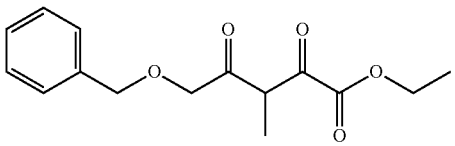 [SMILES: CCOC(=O)C(=O)C(C)C(=O)COCc1ccccc1]

¹H-NMR (CDCl₃, TMS, δ(ppm)): 1.23-1.35 (6H, m), 4.09-4.39 (5H, m), 4.54 (2H, s), 7.28-7.43 (5H, m)

Reference Production Example 281

Ethyl 2,4-dioxo-3-methyl-5-(phenylmethoxy)-2-pentanoate (800 mg, 2.88 mmol) was dissolved in ethanol (3 ml), and hydroxylamine hydrochloride (400 mg, 5.76 mmol) was added thereto, and the mixture was heated and refluxed for 5 hours, under a nitrogen atmosphere. The reaction mixture was cooled to room temperature, and concentrated under reduced pressure, then diluted with ethyl acetate, and sequentially washed with water and saturated saline water. The organic layer was dried over anhydrous sodium sulfate and concentrated under reduced pressure. The residue was applied to a silica gel column chromatography to obtain 300 mg of ethyl 5-benzyloxymethyl-4-methylisoxazole-3-carboxylate represented by the following formula.

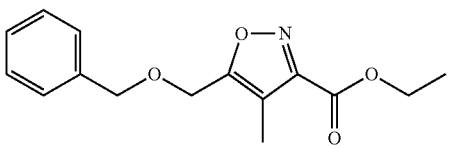 [SMILES: CCOC(=O)c1noc(COCc2ccccc2)c1C]

¹H-NMR (CDCl₃, TMS, δ(ppm)): 1.43 (3H, t), 2.21 (3H, s), 4.45 (2H, q), 4.56 (2H, s), 4.62 (2H, s), 7.29-7.41 (5H, m)

Reference Production Example 282

Ethyl nitroacetate (0.56 g, 4.20 mmol), (5-phenyl-2-thienylmethyl)propargyl ether (0.48 g, 2.10 mmol) and 1,4-diazabicyclo[2.2.2]octane (0.05 g, 0.42 mmol) were added to chloroform (amylene addition product) (1 mL). The mixed liquid was heated and refluxed for 14 hours. Thereafter, the reaction mixture was cooled to room temperature, dilute hydrochloric acid was added thereto, and the mixture was extracted twice with ethyl acetate. The organic layer was washed once with a saturated aqueous sodium bicarbonate solution, and then washed with saturated saline water. The organic layer was dried over anhydrous sodium sulfate, then filtered, and the filtrate was concentrated under reduced pressure. The residue was applied to a silica gel column chromatography to obtain 0.52 g of ethyl 5-(5-phenyl-2-thienylmethoxymethyl)isoxazole-3-carboxylate represented by the following formula.

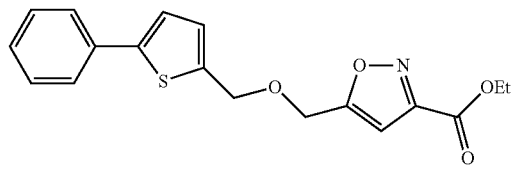 [SMILES: CCOC(=O)c1cc(COCc2ccc(-c3ccccc3)s2)on1]

¹H-NMR (CDCl₃, TMS, δ(ppm)): 1.42 (t, 3H), 4.45 (q, 2H), 4.70 (s, 2H), 4.77 (s, 2H), 6.71 (br s, 1H), 7.01 (d, 1H), 7.19 (d, 1H), 7.28-7.32 (1H, m), 7.37-7.41 (2H, m), 7.58-7.60 (2H, m)

Reference Production Example 283

Ethyl 5-(5-phenyl-2-thienylmethoxymethyl)isoxazole-3-carboxylate (0.82 g, 2.51 mmol) was added to ethanol (4 mL), and potassium hydroxide (0.17 g, 3.01 mmol) and water (6.5 mL) were added thereto. Then, the mixture was stirred at room temperature overnight. Thereafter, the resulting mixture was concentrated under reduced pressure. Dilute hydrochloric acid was added to the reaction mixture, and the mixture was extracted twice with chloroform. The organic layer was washed with saturated saline water, dried over anhydrous sodium sulfate and then filtered, and the filtrate was concentrated under reduced pressure to obtain 0.68 g of 5-(5-phenyl-2-thienylmethoxymethyl)isoxazole-3-carboxylic acid represented by the following formula.

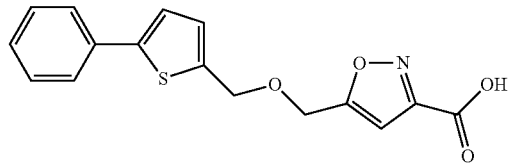 [SMILES: O=C(O)c1cc(COCc2ccc(-c3ccccc3)s2)on1]

¹H-NMR (CDCl₃, TMS, δ(ppm)): 4.71 (s, 2H), 4.78 (s, 2H), 6.77 (s, 1H), 7.02 (d, 1H), 7.20 (d, 1H), 7.28-7.32 (1H, m), 7.37-7.41 (2H, m), 7.58-7.60 (2H, m)

Reference Production Example 284

Ethyl 5-hydroxymethylisoxazole-3-carboxylate (1.73 g, 10.1 mmol), triphenylphosphine (2.65 g, 10.1 mmol) and 5,6,7,8-tetrahydro-2-naphthol (1.50 g, 10.1 mmol) were added to dry tetrahydrofuran (30 ml), under a nitrogen atmosphere. A toluene solution of diisopropyl azodicarboxylate (40%, 5.63 g, 11.1 mmol) was added dropwise thereto, and the mixture was stirred at room temperature overnight. The reaction mixture was added to dilute hydrochloric acid, and the mixture was extracted with ethyl acetate. The solvent was concentrated under reduced pressure, and then the residue was applied to a silica gel column chromatography to obtain 0.69 g of ethyl 5-(5,6,7,8-tetrahydronaphthalen-2-yloxymethyl)isoxazole-3-carboxylate represented by the following formula.

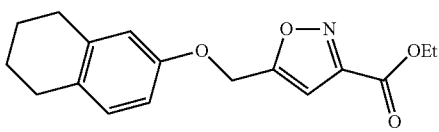 [SMILES: CCOC(=O)c1cc(COc2ccc3c(c2)CCCC3)on1]

$^1$H-NMR (CDCl$_3$, TMS, δ(ppm)): 1.42 (3H, t), 1.76-1.79 (4H, m), 2.72 (4H, br), 4.44 (2H, q), 5.17 (2H, s), 6.65 (1H, d), 6.69-6.71 (1H, m), 6.74 (1H, br s), 6.99 (1H, d)

Reference Production Example 285

Ethyl 5-(5,6,7,8-tetrahydronaphthalen-2-yloxymethyl)isoxazole-3-carboxylate (0.69 g, 2.29 mmol) was added to ethanol (3.5 mL), and potassium hydroxide (0.15 g, 2.75 mmol) and water (5.5 mL) were added thereto. Then, the mixture was stirred at room temperature for 8 hours. Thereafter, the resulting mixture was concentrated under reduced pressure. Dilute hydrochloric acid was added to the reaction mixture, and the mixture was extracted twice with chloroform. The organic layer was washed with saturated saline water, dried over anhydrous sodium sulfate and then filtered, and the filtrate was concentrated under reduced pressure to obtain 0.59 g of 5-(5,6,7,8-tetrahydronaphthalen-2-yloxymethyl)isoxazole-3-carboxylic acid represented by the following formula.

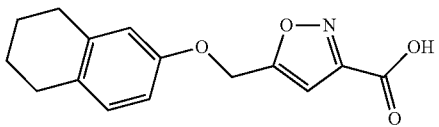 [SMILES: O=C(O)c1cc(COc2ccc3c(c2)CCCC3)on1]

$^1$H-NMR (CDCl$_3$, TMS, δ(ppm)): 1.76-1.79 (4H, m), 2.72 (4H, br), 5.19 (2H, s), 6.66 (1H, d), 6.69-6.72 (1H, m), 6.79 (1H, br s), 6.99 (1H, d)

Reference Production Example 286

Ethyl 5-(3-hydroxypropyl)isoxazole-3-carboxylate (6.37 g, 32 mmol) and carbon tetrabromide (15.90 g, 48 mmol) were added to tetrahydrofuran (200 ml). Triphenylphosphine (8.39 g, 48 mmol) was added to the mixed liquid over 30 minutes, and the mixture was stirred at room temperature for 18 hours. The solvent was concentrated under reduced pressure, and the residue was applied to a silica gel column chromatography to obtain 2.13 g of ethyl 5-(3-bromopropyl)isoxazole-3-carboxylate represented by the following formula.

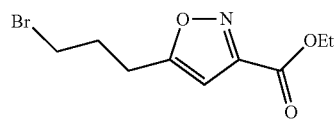 [SMILES: CCOC(=O)c1cc(CCCBr)on1]

$^1$H-NMR (CDCl$_3$, TMS, δ(ppm)): 1.40 (3H, t), 1.82-1.85 (2H, m), 3.01 (2H, t), 3.41-3.44 (2H, m), 4.41 (2H, q), 6.47 (1H, s)

Reference Production Example 287

Benzyloxynitroethane (1.81 g, 10 mmol), ethyl propiolate (0.98 g, 10 mmol) and 4-(dimethylamino)pyridine (0.30 g, 2.5 mmol) were added to dry tetrahydrofuran (26 mL). Di-tert-butyl carbonate (3.82 g, 17.5 mmol) was added to the mixed liquid, and the mixture was stirred at room temperature for 24 hours, and then heated at 50° C. for 5 hours. Thereafter, the reaction mixture was cooled to room temperature, water was added thereto, and the mixture was extracted twice with ethyl acetate. The organic layer was washed with saturated saline water, dried over anhydrous sodium sulfate and then filtered, and the filtrate was concentrated under reduced pressure. The residue was applied to a silica gel column chromatography to obtain 1.21 g of ethyl 3-benzyloxymethylisoxazole-5-carboxylate represented by the following formula.

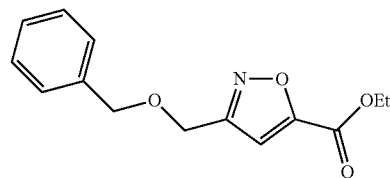 [SMILES: CCOC(=O)c1cc(COCc2ccccc2)no1]

$^1$H-NMR (CDCl$_3$, TMS, δ(ppm)): 1.40 (3H, t), 4.43 (2H, q), 4.56 (2H, s), 4.65 (2H, s), 7.00 (1H, s), 7.25-7.38 (5H, m)

Reference Production Example 288

Ethyl 3-benzyloxymethylisoxazole-5-carboxylate (1.21 g, 4.6 mmol) was added to ethanol (30 mL), and potassium hydroxide (0.78 g, 13.9 mmol) and water (10 mL) were further added thereto, and then the mixture was stirred at room temperature overnight. Thereafter, the resulting mixture was concentrated under reduced pressure. Dilute hydrochloric acid was added to the reaction mixture, and the mixture was extracted twice with ethyl acetate. The organic layer was washed with saturated saline water, dried over anhydrous sodium sulfate and then filtered, and the filtrate was concentrated under reduced pressure. The residue was applied to a silica gel column chromatography and crystallized with t-butyl methyl ether/hexane to obtain 0.49 g of 5-benzyloxymethylisoxazole-3-carboxylic acid represented by the following formula.

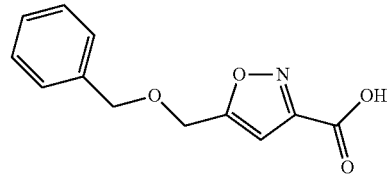 [SMILES: O=C(O)c1cc(COCc2ccccc2)on1]

¹H-NMR (CDCl₃, TMS, δ(ppm)): 7.25-7.38 (5H, m), 7.12 (1H, d), 4.68 (2H, s), 4.58 (2H, s)

Reference Production Example 289

2-Benzyloxyacetone (5.15 g, 32.0 mmol) and diethyl oxalate (4.64 g, 32.0 mmol) were dissolved in ethanol (32 ml), and the mixture was cooled to 0° C. under a nitrogen atmosphere. Sodium ethoxide (20% ethanol solution, 10.89 g, 32.0 mmol) was added dropwise to the solution over 30 minutes, and the mixture was stirred at room temperature overnight. Thereafter, the resulting mixture was concentrated under reduced pressure. 1 N Hydrochloric acid was added to the reaction mixture, and the mixture was extracted twice with ethyl acetate. The organic layer was washed with saturated saline water, dried over anhydrous sodium sulfate and then filtered, and the filtrate was concentrated under reduced pressure. The residue was applied to a silica gel column chromatography to obtain 6.31 g of ethyl 5-benzyloxy-2,4-dioxopentanoate represented by the following formula.

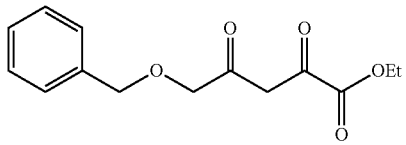 [SMILES: CCOC(=O)C(=O)CC(=O)COCc1ccccc1]

¹H-NMR (CDCl₃, TMS, δ(ppm)): 1.37 (3H, t), 4.34 (2H, q), 4.62 (2H, s), 6.67 (1H, s), 7.37-7.39 (5H, m)

Reference Production Example 290

Ethyl 5-benzyloxy-2,4-dioxopentanoate (2.64 g, 10.0 mmol) was dissolved in ethanol (20 ml), and hydrazine monohydrate (0.50 g, 10.0 mmol) was added thereto, and the mixture was heated and refluxed for 6 hours, under a nitrogen atmosphere. The reaction mixture was cooled to room temperature, and then concentrated under reduced pressure. 1 N Hydrochloric acid was added to the reaction mixture, and the mixture was extracted twice with ethyl acetate. The organic layer was washed with saturated saline water, dried over anhydrous sodium sulfate and then filtered, and the filtrate was concentrated under reduced pressure. The residue was applied to a silica gel column chromatography to obtain 1.65 g of ethyl 3-benzyloxymethylpyrazole-5-carboxylate represented by the following formula.

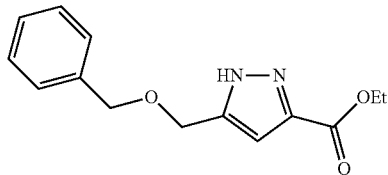 [SMILES: CCOC(=O)c1cc(COCc2ccccc2)[nH]n1]

¹H-NMR (CDCl₃, TMS, δ(ppm)): 1.38 (3H, t), 4.38 (2H, q), 4.56 (2H, s), 4.60 (2H, s), 6.81 (1H, s), 7.25-7.37 (5H, m)

Reference Production Example 291

Ethyl 3-benzyloxymethylpyrazole-5-carboxylate (0.58 g, 2.5 mmol) was added to ethanol (10 mL), and potassium hydroxide (0.56 g, 10.0 mmol) and water (2.5 mL) were further added thereto, and then the mixture was stirred at room temperature overnight. Thereafter, the resulting mixture was concentrated under reduced pressure. Dilute hydrochloric acid was added to the reaction mixture, and the mixture was extracted twice with ethyl acetate. The organic layer was washed with saturated saline water, dried over anhydrous sodium sulfate and then filtered, and the filtrate was concentrated under reduced pressure. The residue was applied to a silica gel column chromatography and crystallized with t-butyl methyl ether/hexane to obtain 0.48 g of 5-benzyloxymethylpyrazole-3-carboxylic acid represented by the following formula.

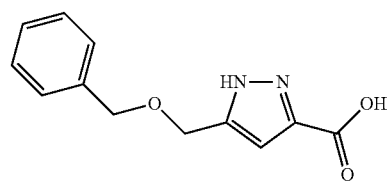 [SMILES: O=C(O)c1cc(COCc2ccccc2)[nH]n1]

¹H-NMR (CDCl₃, TMS, δ(ppm)): 7.25-7.37 (5H, m), 6.83 (1H, d), 4.63 (2H, s), 4.59 (2H, s)

Reference Production Example 292

Ethyl 3-benzyloxymethylpyrazole-5-carboxylate (1.26 g, 5.4 mmol) was added to dry N, N-dimethylformamide (15 ml), under a nitrogen atmosphere. Potassium carbonate (0.75 g, 5.4 mmol) and iodomethane (1.53 g, 10.8 mmol) were added thereto, and the mixture was stirred at 60° C. for 12 hours. The reaction mixture was cooled to room temperature and poured into 1 N hydrochloric acid, and the mixture was extracted twice with ethyl acetate. The organic layer was washed with water and saturated saline water, and then dried over sodium sulfate. The solvent was concentrated under reduced pressure, then ethanol (25 mL) was added to the residue, and potassium hydroxide (1.51 g, 27.0 mmol) and water (7 ml) were added thereto, and then the mixture was stirred at room temperature for 18 hours. Thereafter, the resulting mixture was concentrated under reduced pressure. Dilute hydrochloric acid was added to the reaction mixture, the mixture was cooled to 0° C., and the precipitated solid was filtered. The solid was dried under reduced pressure to obtain 1.47 g of a 56:44 mixture of 3-benzyloxymethyl-1-methyl-1H-pyrazole-5-carboxylic acid represented by the following formula:

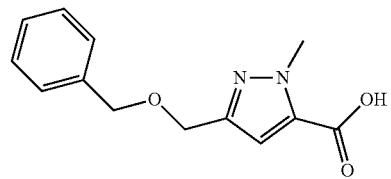 [SMILES: Cn1nc(COCc2ccccc2)cc1C(=O)O]

and 5-benzyloxymethyl-1-methyl-1H-pyrazole-3-carboxylic acid represented by the following formula.

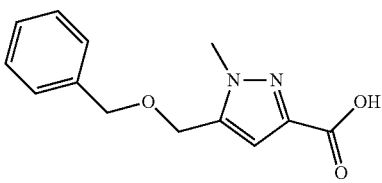 [SMILES: Cn1nc(C(=O)O)cc1COCc1ccccc1]

The resulting mixture was subjected to a next reaction as it was.

3-benzyloxymethyl-1-methyl-1H-pyrazole-5-carboxylic acid $^1$H-NMR (CDCl$_3$, TMS, δ(ppm)): 4.16 (3H, s), 4.54 (2H, s), 4.57 (2H, s), 6.97 (1H, s), 7.33-7.36 (5H, m)

5-benzyloxymethyl-1-methyl-1H-pyrazole-3-carboxylic acid $^1$H-NMR (CDCl$_3$, TMS, δ(ppm)): 3.95 (3H, s), 4.51 (2H, s), 4.53 (2H, s), 6.81 (1H, s), 7.33-7.36 (5H, m)

Reference Production Example 293

Ethyl 5-hydroxymethylisoxazole-3-carboxylate (0.86 g, 5.0 mmol) was added to dry tetrahydrofuran (25 ml), under a nitrogen atmosphere, and the mixture was cooled to 0° C. 60% sodium hydride (0.40 g, 10.0 mmol) was added thereto, and the mixture was further stirred for 30 minutes. 2-Methoxybenzyl chloride (0.94 g, 6.0 mmol) was added thereto, and the reaction solution was heated to room temperature, and then the mixture was stirred for 16 hours. The reaction mixture was poured into a saturated aqueous ammonium chloride solution, and the mixture was extracted twice with ethyl acetate. The organic layer was washed with water and saturated saline water, and then dried over sodium sulfate. The solvent was concentrated under reduced pressure, then the residue was added to ethanol (25 mL), and 2 N sodium hydroxide (15 mL) was added thereto, and then the mixture was stirred at room temperature for 16 hours. Thereafter, the resulting mixture was concentrated under reduced pressure. Dilute hydrochloric acid was added to the reaction mixture, the mixture was cooled to 0° C., and the precipitated solid was filtered. The solid was dried under reduced pressure to obtain 1.15 g of 5-(2-methoxybenzyloxymethyl)isoxazole-3-carboxylic acid represented by the following formula.

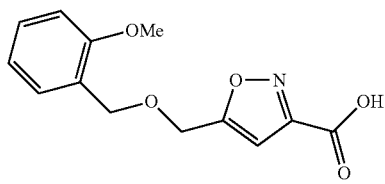 [SMILES: COc1ccccc1COCc1cc(C(=O)O)no1]

$^1$H-NMR (CDCl$_3$, TMS, δ(ppm)): 7.28-7.35 (m, 2H), 6.87-6.97 (m, 2H), 6.74 (s, 1H), 4.71 (s, 2H), 4.65 (s, 2H). 3.83 (s, 3H)

Reference Production Example 294

Ethyl 5-hydroxymethylisoxazole-3-carboxylate (0.86 g, 5.0 mmol) was added to dry tetrahydrofuran (25 ml), under a nitrogen atmosphere, and the mixture was cooled to 0° C. 60% sodium hydride (0.40 g, 10.0 mmol) was added thereto, and the mixture was further stirred for 30 minutes. 2-Methylbenzyl bromide (1.1 g, 6.0 mmol) was added thereto, and the reaction solution was heated to room temperature, and then the mixture was stirred for 16 hours. The reaction mixture was poured into a saturated aqueous ammonium chloride solution, and the mixture was extracted twice with ethyl acetate. The organic layer was washed with water and saturated saline water, and then dried over sodium sulfate. The solvent was concentrated under reduced pressure, then the residue was added to ethanol (25 mL), and 2 N sodium hydroxide (15 mL) was added thereto, and then the mixture was stirred at room temperature for 16 hours. Thereafter, the resulting mixture was concentrated under reduced pressure. Dilute hydrochloric acid was added to the reaction mixture, the mixture was cooled to 0° C., and the precipitated solid was filtered. The solid was dried under reduced pressure to obtain 1.15 g of 5-(2-methylbenzyloxymethyl)isoxazole-3-carboxylic acid represented by the following formula.

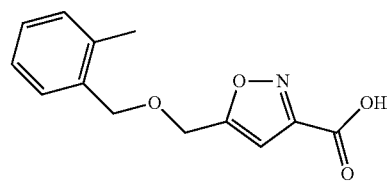 [SMILES: Cc1ccccc1COCc1cc(C(=O)O)no1]

$^1$H-NMR (CDCl$_3$, TMS, δ(ppm)): 7.17-7.30 (m, 4H), 6.71 (s, 1H), 4.67 (s, 2H), 4.62 (s, 2H). 2.31 (s, 3H)

Reference Production Example 295

Ethyl 5-hydroxymethylisoxazole-3-carboxylate (5.14 g, 30.0 mmol) was added to dry N,N-dimethylformamide (60 ml), under a nitrogen atmosphere, and the mixture was cooled to 0° C. 60% sodium hydride (1.32 g, 33.0 mmol) was added thereto, and the mixture was further stirred for 30 minutes. Propargyl bromide (3.92 g, 33.0 mmol) was added thereto, and the reaction solution was heated to room temperature, and then the mixture was stirred for 16 hours. The reaction mixture was poured into a saturated aqueous ammonium chloride solution, and the mixture was extracted twice with ethyl acetate. The organic layer was sequentially washed with water and saturated saline water, dried over anhydrous sodium sulfate and then filtered, and the filtrate was concentrated under reduced pressure. The residue was applied to a silica gel column chromatography to obtain 3.33 g of ethyl 5-propargyloxymethylisoxazole-3-carboxylate represented by the following formula.

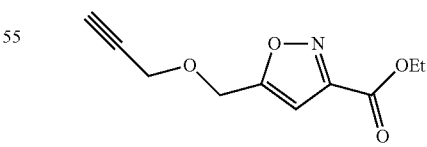

$^1$H-NMR (CDCl$_3$, TMS, δ(ppm)): 6.71 (s, 1H), 4.74 (s, 2H), 4.43 (2H, q), 4.24 (d, 2H). 2.52 (t, 1H), 4.14 (t, 3H)

Reference Production Example 296

Ethyl 5-propargyloxymethylisoxazole-3-carboxylate (3.33 g, 15.9 mmol) was added to ethanol (30 mL), and lithium hydroxide (0.77 g, 31.8 mmol) and water (30 mL) were further added thereto, and then the mixture was stirred at room temperature overnight. Thereafter, the resulting mixture was concentrated under reduced pressure. Dilute hydrochloric acid was added to the reaction mixture, and the mixture was extracted twice with ethyl acetate. The organic layer was washed with saturated saline water, dried over anhydrous sodium sulfate and then filtered, and the filtrate was concentrated under reduced pressure to obtain 2.88 g of 5-propargyloxymethylisoxazole-3-carboxylic acid represented by the following formula.

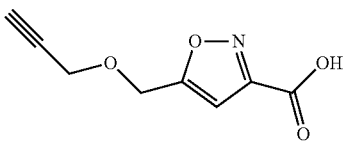

The product was subjected to a next reaction without purification.

Reference Production Example 297

Ethyl 1H-tetrazole-5-carboxylate sodium salt (1.00 g, 6.09 mmol) was added to dimethylformamide (10 mL), and the mixture was stirred at 50° C. 1-Bromobutane (0.92 g, 6.70 mmol) was added dropwise to the mixed liquid, then the mixture was heated to 60° C., and the mixture was stirred for 4 hours. The reaction mixture was cooled to room temperature, then tap water was added thereto, and the mixture was extracted twice with ethyl acetate. The organic layer was washed with saturated saline water, and then concentrated under reduced pressure. The residue was applied to a silica gel column chromatography to obtain 0.59 g of ethyl 2-butyl-2H-tetrazole-5-carboxylate represented by the following formula.

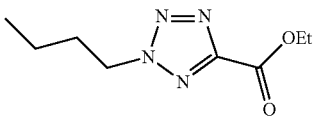

$^1$H-NMR (CDCl$_3$, TMS, δ(ppm)): 0.98 (t, 3H), 1.38 (tq, 2H), 1.49 (t, 3H), 1.93 (tt, 2H), 4.54 (q, 2H), 4.75 (t, 2H)

Reference Production Example 298

Ethyl 2-butyl-2H-tetrazole-5-carboxylate (0.59 g, 2.98 mmol) was added to ethanol (1 mL), and potassium hydroxide (0.20 g, 3.58 mmol) and water (7 mL) were added thereto, and then the mixture was stirred at room temperature for 2 hours. Thereafter, the resulting mixture was concentrated under reduced pressure. Dilute hydrochloric acid was added to the reaction mixture, and the mixture was extracted twice with chloroform. The organic layer was washed with saturated saline water, dried over anhydrous sodium sulfate and then filtered, and the filtrate was concentrated under reduced pressure to obtain 0.39 g of 2-butyl-2H-tetrazole-5-carboxylic acid represented by the following formula.

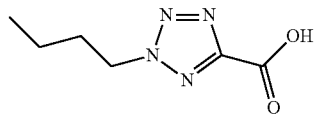

$^1$H-NMR (CDCl$_3$, TMS, δ(ppm)): 0.99 (t, 3H), 1.39 (tq, 2H), 2.08 (tt, 2H), 4.75 (t, 2H)

Reference Production Example 299

Ethyl 2-amino-2-(hydroxyimino) acetate (4.62 g, 35 mmol) and diisopropylethylamine (7.24 g, 56 mmol) were added to chloroform (amylene addition product) (100 mL). Valeryl chloride (4.22 g, 35 mmol) was added to the mixed liquid at −30 to −20° C., and then the mixture was stirred at room temperature for 24 hours. Thereafter, ice water was added to the reaction mixture, and the mixture was extracted three times with chloroform. The organic layer was washed with saturated saline water, dried over anhydrous sodium sulfate and then filtered, and the filtrate was concentrated under reduced pressure. The residue was dissolved in pyridine (120 mL), and the mixture was stirred under heat-reflux for 20 hours. The reaction mixture was concentrated under reduced pressure, then the residue was dissolved in ethyl acetate, and the organic layer was washed three times with water. The organic layer was washed with saturated saline water, dried over anhydrous sodium sulfate and then filtered, and the filtrate was concentrated under reduced pressure. The residue was applied to a silica gel column chromatography to obtain 3.69 g of ethyl 5-butyl-1,2,4-oxadiazole-3-carboxylate represented by the following formula.

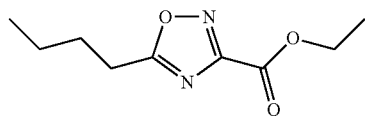

$^1$H-NMR (CDCl$_3$, TMS, δ(ppm)): 0.96 (3H, t), 1.40-1.50 (5H, m), 1.81-1.89 (2H, m), 2.98 (2H, t), 4.51 (2H, q)

Reference Production Example 300

Potassium hydroxide (1.12 g, 20 mmol) and water (3 mL) were added to ethanol (27 mL), and the mixture was stirred at room temperature for 10 minutes. Ethyl 5-butyl-1,2,4-oxadiazole-3-carboxylate (1.98 g, 10 mmol) was added to the mixed liquid at room temperature, and then the mixture was stirred at room temperature overnight. The reaction mixture was concentrated under reduced pressure, and the residue was dissolved in water, and then the aqueous layer was washed with tert-butyl methyl ether. Dilute hydrochloric acid was added to the aqueous layer, and the mixture was extracted three times with ethyl acetate. The organic layer was washed with saturated saline water, dried over anhydrous sodium sulfate and then filtered, and the filtrate was concentrated under reduced pressure to obtain 1.81 g of 5-butyl-1,2,4-oxadiazole-3-carboxylic acid represented by the following formula.

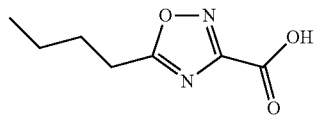

The product was subjected to a next reaction without purification.

Reference Production Example 301

N-Hydroxy pentanamidine (6.39 g, 55 mmol) and pyridine (13.05 g, 165 mmol) were added to chloroform (amylene addition product) (55 mL), and then ethyl chloroglyoxylate (11.26 g, 83 mmol) was added to the mixed liquid at 0° C. The mixture was stirred at 0° C. for 30 minutes, and then stirred at room temperature all night. Thereafter, water was added to the reaction mixture, and the mixture was extracted with chloroform, and then the organic layer was washed with water. The organic layer was washed with saturated saline water, dried over anhydrous sodium sulfate and then filtered, and the filtrate was concentrated under reduced pressure. The residue was applied to a silica gel column chromatography to obtain 7.84 g of ethyl 3-butyl-1,2,4-oxadiazole-5-carboxylate represented by the following formula.

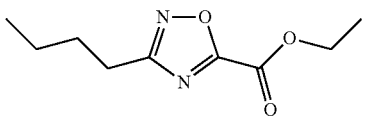

$^1$H-NMR (CDCl$_3$, TMS, δ(ppm)): 0.95 (3H, t), 1.35-1.43 (2H, m), 1.47 (3H, t), 1.73-1.82 (2H, m), 2.84 (2H, t), 4.53 (2H, q)

Reference Production Example 302

Palladium acetate (28 mg, 0.13 mmol), (2-biphenyl)dicyclohexylphosphine (88 mg, 0.25 mmol) and cesium carbonate (1.63 g, 5.0 mmol) were added to tetrahydrofuran (7 mL). Ethyl oxazole-4-carboxylate (0.35 g, 2.5 mmol) and 1-bromobutane (0.69 g, 5.0 mmol) were added to the mixed liquid at room temperature. The air in the reaction vessel was replaced with nitrogen, and then the mixture was stirred at 110° C. for 18 hours. Water was added to the reaction mixture, and the mixture was extracted three times with ethyl acetate. The organic layer was washed with saturated saline water, dried over anhydrous sodium sulfate and then filtered, and the filtrate was concentrated under reduced pressure. The residue was applied to a silica gel column chromatography to obtain 0.19 g of ethyl 2-butyl-oxazole-4-carboxylate represented by the following formula.

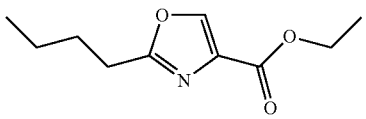

$^1$H-NMR (CDCl$_3$, TMS, δ(ppm)): 0.93 (3H, t), 1.33-1.43 (5H, m), 1.72-1.81 (2H, m), 2.82 (2H, t), 4.39 (2H, q), 8.14 (1H, s)

Reference Production Example 303

Ethyl 2-butyl-oxadiazole-4-carboxylate (0.19 g, 1.0 mmol) was added to ethanol (2.7 mL). Potassium hydroxide (0.11 g, 1.9 mmol) and water (0.3 mL) were added to the mixed liquid at room temperature, and then the mixture was stirred at room temperature overnight. The reaction mixture was concentrated under reduced pressure, and the residue was dissolved in water, and then the aqueous layer was washed with tert-butyl methyl ether. Dilute hydrochloric acid was added to the aqueous layer, and the mixture was extracted three times with ethyl acetate. The organic layer was washed with saturated saline water, dried over anhydrous sodium sulfate and then filtered, and the filtrate was concentrated under reduced pressure to obtain 0.10 g of 2-butyl-oxazole-4-carboxylic acid represented by the following formula.

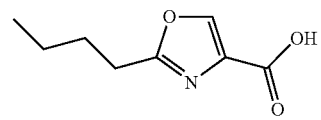

The product was subjected to a next reaction without purification.

Reference Production Example 304

1-Amino-2-hexanone hydrochloride (1.66 g, 11 mmol) was added to chloroform (amylene addition product) (22 mL), and then ethyl chloroglyoxylate (1.50 g, 11 mmol) and diisopropylethylamine (3.62 g, 28 mmol) were added to the mixed liquid at 0° C. The mixture was stirred at 0° C. for 30 minutes, and then stirred at room temperature all night. Water was added to the reaction mixture, and the mixture was extracted three times with chloroform. The organic layer was washed with saturated saline water, dried over anhydrous magnesium sulfate and then filtered, and the filtrate was concentrated under reduced pressure. The residue was dissolved in toluene (24 mL), phosphoryl chloride (5.52 g, 36 mmol) was added thereto, and the mixture was stirred under heat-reflux for 15 hours. A saturated aqueous sodium bicarbonate solution was slowly added to the reaction mixture, and then the organic layer was washed twice with a saturated aqueous sodium bicarbonate solution. The organic layer was dried over anhydrous sodium sulfate, then filtered, and the filtrate was concentrated under reduced pressure. The residue was applied to a silica gel column chromatography to obtain 1.90 g of ethyl 5-butyl-oxazole-2-carboxylate represented by the following formula.

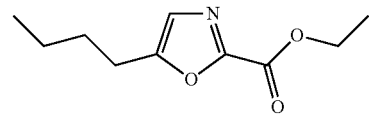

$^1$H-NMR (CDCl$_3$, TMS, δ(ppm)): 0.94 (3H, t), 1.34-1.46 (5H, m), 1.64-1.73 (2H, m), 2.74 (2H, t), 4.46 (2H, q), 6.96 (1H, s)

Reference Production Example 305

Ethyl 5-(3-bromopropyl)-isoxazole-3-carboxylate (2.10 g, 7.99 mmol) was added to ethanol (6 mL), and potassium hydroxide (0.54 g, 9.60 mmol) and water (10 mL) were added thereto, and then the mixture was stirred at room temperature overnight. Thereafter, the resulting mixture was concentrated under reduced pressure. Dilute hydrochloric acid was added to the reaction mixture, and the mixture was extracted twice with chloroform. The organic layer was washed with saturated saline water, dried over anhydrous sodium sulfate and then filtered, and the filtrate was concentrated under reduced pressure to obtain 1.70 g of 5-(3-bromopropyl)-isoxazole-3-carboxylic acid represented by the following formula.

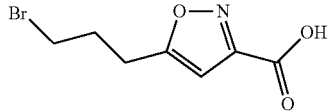 [SMILES: O=C(O)c1cc(CCCBr)on1]

¹H-NMR (CDCl₃, TMS, δ(ppm)): 2.29 (tt, 2H), 3.05 (t, 2H), 3.46 (t, 2H), 6.54 (s, 1H)

Reference Production Example 306

2-Naphthalenemethanol (2.62 g, 10.0 mmol) was added to dry tetrahydrofuran (25 m), under a nitrogen atmosphere, and the mixture was cooled to 0° C. Sodium hydride (0.80 g, 20.0 mmol) was added thereto, and the mixture was further stirred for 30 minutes. Ethyl 4-chloro-5-chloromethyl-1-methyl-1H-pyrazole-3-carboxylate (2.57 g, 10.9 mmol) was added thereto, and the reaction solution was heated to room temperature, and then the mixture was stirred for 48 hours. The reaction mixture was poured into dilute hydrochloric acid, and the mixture was extracted twice with ethyl acetate. The organic layer was washed with water and saturated saline water, and then dried over sodium sulfate. The solvent was concentrated under reduced pressure, then ethanol (50 mL) and water (10 m) were added to the residue, and potassium hydroxide (3.06 g, 54.5 mmol) was added thereto. Then, the mixture was stirred at room temperature for 12 hours. Thereafter, the resulting mixture was concentrated under reduced pressure. Dilute hydrochloric acid was added to the reaction mixture, the mixture was cooled to 0° C., and the precipitated solid was filtered. The solid was dried under reduced pressure to obtain 0.72 g of 4-chloro-5-(2-naphthylmethyloxymethyl)-1-methyl-1H-pyrazole-3-carboxylic acid represented by the following formula.

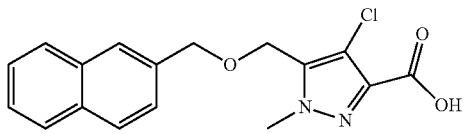 [SMILES: Cn1nc(C(=O)O)c(Cl)c1COCc1ccc2ccccc2c1]

¹H-NMR (CDCl3, TMS, δ(ppm)): 7.77-7.85 (m, 4H), 7.46-7.51 (m, 3H), 4.67 (s, 2H), 4.61 (s, 2H). 3.97 (s, 3H)

Next, specific examples of the compound of the present invention are shown below.

An amide compound represented by formula (Y-1),

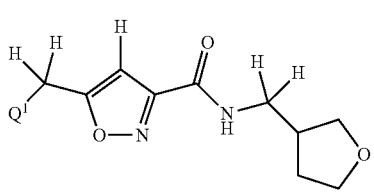

(Y-1)

wherein $Q^1$ represents any group selected from the following group (Q-1);

An amide compound represented by formula (Y-2),

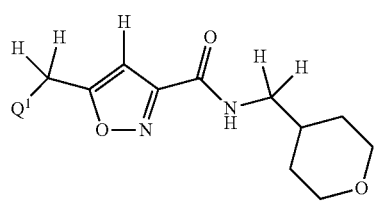

(Y-2)

wherein $Q^1$ represents any group selected from the following group (Q-1);

(Group Q-1)

an ethyl group, a propyl group, a butyl group, a pentyl group, a 2,2,2-trifluoroethyl group, a 3,3,3-trifluoropropyl group, a 4,4,4-trifluorobutyl group, a 5,5,5-trifluoropentyl group, a phenyl group, a benzyl group, a 2-phenylethyl group, a 3-phenylpropyl group, a 4-phenylbutyl group, a 2-fluorophenyl group, a 2-fluorobenzyl group, a 2-(2-fluorophenyl)ethyl group, a 3-(2-fluorophenyl)propyl group, a 4-(2-fluorophenyl)butyl group, a 3-fluorophenyl group, a 3-fluorobenzyl group, a 2-(3-fluorophenyl)ethyl group, a 3-(3-fluorophenyl)propyl group, a 4-(3-fluorophenyl)butyl group, a 4-fluorophenyl group, a 4-fluorobenzyl group, a 2-(4-fluorophenyl)ethyl group, a 3-(4-fluorophenyl)propyl group, a 4-(4-fluorophenyl)butyl group, a 2-chlorophenyl group, a 2-chlorobenzyl group, a 2-(2-chlorophenyl)ethyl group, a 3-(2-chlorophenyl)propyl group, a 4-(2-chlorophenyl)butyl group, a 3-chlorophenyl group, a 3-chlorobenzyl group, a 2-(3-chlorophenyl)ethyl group, a 3-(3-chlorophenyl)propyl group, a 4-(3-chlorophenyl)butyl group, a 4-chlorophenyl group, a 4-chlorobenzyl group, a 2-(4-chlorophenyl)ethyl group, a 3-(4-chlorophenyl)propyl group, a 4-(4-chlorophenyl)butyl group, a 2-bromophenyl group, a 2-bromobenzyl group, a 2-(2-bromophenyl)ethyl group, a 3-(2-bromophenyl)propyl group, a 4-(2-bromophenyl)butyl group, a 3-bromophenyl group, a 3-bromobenzyl group, a 2-(3-bromophenyl)ethyl group, a 3-(3-bromophenyl)propyl group, a 4-(3-bromophenyl)butyl group, a 4-bromophenyl group, a 4-bromobenzyl group, a 2-(4-bromophenyl)ethyl group, a 3-(4-bromophenyl)propyl group, a 4-(4-bromophenyl)butyl group, a 3-bromo-5-fluorophenyl group, a 3-bromo-5-fluorobenzyl group, a 2-(3-bromo-5-fluorophenyl)ethyl group, a 3-(3-bromo-5-fluorophenyl)propyl group, a 4-(3-bromo-5-fluorophenyl)butyl group, a 2-trifluoromethylphenyl group, a 2-trifluoromethylbenzyl group, a 2-(2-trifluoromethylphenyl)ethyl group, a 3-(2-trifluoromethylphenyl)propyl group, a 4-(2-trifluoromethylphenyl)butyl group, a 3-trifluoromethylphenyl group, a 3-trifluoromethylbenzyl group, a 2-(3-trifluoromethylphenyl)ethyl group, a 3-(3-trifluoromethylphenyl)propyl group, a 4-(3-trifluoromethylphenyl)butyl group, a 4-trifluoromethylphenyl group, a 4-trifluoromethylbenzyl group, a 2-(4-trifluoromethylphenyl)ethyl group, a 3-(4-trifluoromethylphenyl)propyl group, a 4-(4-trifluoromethylphenyl)butyl group, a 2-trifluoromethoxyphenyl group, a 2-trifluoromethoxybenzyl group, a 2-(2-trifluoromethoxyphenyl)ethyl group, a 3-(2-trifluoromethoxyphenyl)propyl group, a 4-(2-trifluoromethoxyphenyl)butyl group, a 3-trifluoromethoxyphenyl group, a 3-trifluoromethoxybenzyl group, a 2-(3-trifluoromethoxyphenyl)ethyl group, a 3-(3-trifluoromethoxyphenyl)propyl group, a 4-(3-trifluoromethoxyphenyl)butyl group, a 4-trifluoromethoxyphenyl group, a 4-trifluoromethoxybenzyl group, a 2-(4- trifluoromethoxyphenyl)ethyl group, a 3-(4-trifluoromethoxyphenyl)propyl group, a 4-(4-trifluoromethoxyphenyl)butyl group, a 2-trifluoromethylsulfanylphenyl group, a 2-trifluoromethylsulfanylbenzyl group, a 2-(2-trifluoromethylsulfanylphenyl)ethyl group, a 3-(2-trifluoromethylsulfanylphenyl)propyl group, a 4-(2-trifluoromethylsulfanylphenyl)butyl group, a 3-trifluoromethylsulfanylphenyl group, a 3-trifluoromethylsulfanylbenzyl group, a 2-(3-trifluoromethylsulfanylphenyl)ethyl group, a 3-(3-trifluoromethylsulfanylphenyl)propyl group, a 4-(3-trifluoromethyl-sulfanylphenyl)butyl group, a 4-trifluoromethylsulfanylphenyl group, a 4-trifluoromethylsulfanylbenzyl group, a 2-(4-trifluoromethylsulfanylphenyl)ethyl group, a 3-(4-trifluoromethylsulfanylphenyl)propyl group, a 4-(4-trifluoromethylsulfanylphenyl)butyl group, a 1-naphthyl group, a 1-naphthylmethyl group, a 2-(1-naphthyl)ethyl group, a 3-(1-naphthyl)propyl group, a 4-(1-naphthyl)butyl group, a 2-naphthyl group, a 2-naphthylmethyl group, a 2-(2-naphthyl)ethyl group, a 3-(2-naphthyl)propyl group, a 8-fluoro-2-naphthyl group, a (8-fluoro-2-naphthyl)methyl group, a 2-(8-fluoro-2-naphthyl)ethyl group, a 3-(8-fluoro-2-naphthyl)propyl group, a 8-chloro-2-naphthyl group, a (8-chloro-2-naphthyl)methyl group, a 2-(8-chloro-2-naphthyl)ethyl group, a 3-(8-chloro-2-naphthyl)propyl group, a 8-bromo-2-naphthyl group, a (8-bromo-2-naphthyl)methyl group, a 2-(8-bromo-2-naphthyl)ethyl group, and a 3-(8-bromo-2-naphthyl)propyl group.

An amide compound represented by formula (Y-3),

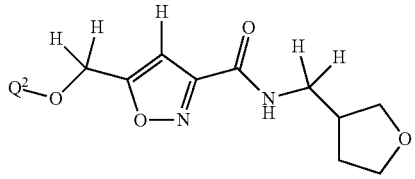

(Y-3)

wherein $Q^2$ represents any group selected from the following group (Q-2);

An amide compound represented by formula (Y-4),

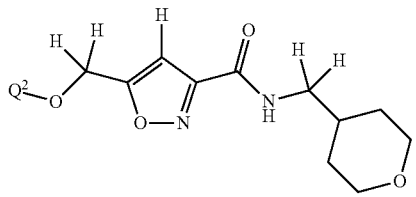

(Y-4)

wherein $Q^2$ represents any group selected from the following group (Q-2);

(Group Q-2)

an ethyl group, a propyl group, a butyl group, a 2,2,2-trifluoroethyl group, a 3,3,3-trifluoropropyl group, a 4,4,4-trifluorobutyl group, a phenyl group, a benzyl group, a 2-phenylethyl group, a 3-phenylpropyl group, a 2-fluorophenyl group, a 2-fluorobenzyl group, a 2-(2-fluorophenyl)ethyl group, a 3-(2-fluorophenyl)propyl group, a 3-fluorophenyl group, a 3-fluorobenzyl group, a 2-(3-fluorophenyl)ethyl group, a 3-(3-fluorophenyl)propyl group, a 4-fluorophenyl group, a 4-fluorobenzyl group, a 2-(4-fluorophenyl)ethyl group, a 3-(4-fluorophenyl)propyl group, a 2-chlorophenyl group, a 2-chlorobenzyl group, a 2-(2-chlorophenyl)ethyl group, a 3-(2-chlorophenyl)propyl group, a 3-chlorophenyl group, a 3-chlorobenzyl group, a 2-(3-chlorophenyl)ethyl group, a 3-(3-chlorophenyl)propyl group, a 4-chlorophenyl group, a 4-chlorobenzyl group, a 2-(4-chlorophenyl)ethyl group, a 3-(4-chlorophenyl)propyl group, a 2-bromophenyl group, a 2-bromobenzyl group, a 2-(2-bromphenyl)ethyl group, a 3-(2-bromophenyl)propyl group, a 3-bromophenyl group, a 3-bromobenzyl group, a 2-(3-bromophenyl)ethyl group, a 3-(3-bromophenyl)propyl group, a 4-bromophenyl group, a 4-bromobenzyl group, a 2-(4-bromophenyl)ethyl group, a 3-(4-bromophenyl) propyl group, a 3-bromo-5-fluorophenyl group, a 3-bromo-5-fluorobenzyl group, a 2-(3-bromo-5-fluorophenyl)ethyl group, a 3-(3-bromo-5-fluorophenyl)propyl group, a 2-trifluoromethylphenyl group, a 2-trifluoromethylbenzyl group, a 2-(2-trifluoromethylphenyl)ethyl group, a 3-(2-trifluoromethylphenyl)propyl group, a 3-trifluoromethylphenyl group, a 3-trifluoromethylbenzyl group, a 2-(3-trifluoromethylphenyl)ethyl group, a 3-(3-trifluoromethylphenyl) propyl group, a 4-trifluoromethylphenyl group, a 4-trifluoromethylbenzyl group, a 2-(4-trifluoromethylphenyl)ethyl group, a 3-(4-trifluoromethylphenyl)propyl group, a 2-trifluoromethoxyphenyl group, a 2-trifluoromethoxybenzyl group, a 2-(2-trifluoromethoxyphenyl)ethyl group, a 3-(2-trifluoromethoxyphenyl)propyl group, a 3-trifluoromethoxyphenyl group, a 3-trifluoromethoxybenzyl group, a 2-(3-trifluoromethoxyphenyl)ethyl group, a 3-(3-trifluoromethoxyphenyl)propyl group, a 4-trifluoromethoxyphenyl group, a 4-trifluoromethoxybenzyl group, a 2-(4-trifluoromethoxyphenyl)ethyl group, a 3-(4-trifluoromethoxyphenyl)propyl group, a 2-trifluoromethylsulfanylphenyl group, a 2-trifluoromethylsulfanylbenzyl group, a 2-(2-trifluoromethylsulfanylphenyl)ethyl group, a 3-(2-trifluoromethylsulfanylphenyl)propyl group, a 3-trifluoromethylsulfanylphenyl group, a 3-trifluoromethylsulfanylbenzyl group, a 2-(3-trifluoromethylsulfanylphenyl)ethyl group, a 3-(3-trifluoromethyl-sulfanylphenyl)propyl group, a 4-trifluoromethylsulfanylphenyl group, a 4-trifluoromethylsulfanylbenzyl group, a 2-(4-trifluoromethylsulfanylphenyl)ethyl group, a 3-(4-trifluoromethylsulfanylphenyl)propyl group, a 1-naphthyl group, a 1-naphthylmethyl group, a 2-(1-naphthyl)ethyl group, a 3-(1-naphthyl)propyl group, a 2-naphthyl group, a 2-naphthylmethyl group, a 2-(2-naphthyl)ethyl group, a 3-(2-naphthyl)propyl group, a 8-fluoro-2-naphthyl group, a (8-fluoro-2-naphthyl)methyl group, a 2-(8-fluoro-2-naphthyl)ethyl group, a 3-(8-fluoro-2-naphthyl)propyl group, a 8-chloro-2-naphthyl group, a (8-chloro-2-naphthyl)methyl group, a 2-(8-chloro-2-naphthyl)ethyl group, a 3-(8-chloro-2-naphthyl)propyl group, a 8-bromo-2-naphthyl group, a (8-bromo-2-naphthyl)methyl group, a 2-(8-bromo-2-naphthyl)ethyl group, and a 3-(8-bromo-2-naphthyl)propyl group.

Next, formulation examples are shown. Here, the part means part by weight.

Formulation Example 1

20 parts of any one of Compounds of Present Invention described in Formulation Examples 1 to 325 is dissolved in 65 parts of xylene, and 15 parts of Sorpol 3005X (a registered trademark of TOHO Chemical Industry Co., Ltd.)

is added, and then the mixture is well mixed with stirring to obtain an emulsifiable concentrate.

Formulation Example 2

5 parts of Sorpol 3005X is added to 40 parts of any one of Compounds of Present Invention described in Formulation Examples 1 to 325, and the mixture is well mixed. 32 parts of Carplex #80 (synthetic hydrated silicon oxide, a registered trademark of Shionogi & Co., Ltd.) and 23 parts of 300-mesh diatomaceous earth are added thereto, and the mixture is mixed with stirring with a juice blender to obtain wettable powder.

Formulation Example 3

1.5 parts of any one of Compounds of Present Invention described in Formulation Examples 1 to 325 and 1 part of Tokuseal GUN (synthetic hydrous silicon oxide, manufactured by Tokuyama Corporation), 2 parts of Reax 85A (sodium lignin sulfonate, manufactured by West Vaco Chemicals), 30 parts of Bentonite Fuji (bentonite, manufactured by HOJUN., Co. Ltd.) and 65.5 parts of Shokozan A clay (kaolin clay, manufactured by SHOKOZAN MINING Co., Ltd.) are well pulverized and mixed, and water is added thereto. The mixture is well kneaded, then granulated by an extrusion granulator, and dried to obtain 1.5% granules.

Formulation Example 4

10 parts of any one of Compounds of Present Invention described in Formulation Examples 1 to 325, 10 parts of phenylxylylethane and 0.5 parts of SUMIDUR L-75 (tolylene diisocyanate, manufactured by Sumitomo Bayer Urethane Co., Ltd.) are mixed, then added to 20 parts of a 10% aqueous solution of gum arabic, and the mixture is stirred with a homomixer to obtain an emulsion with an average particle size of 20 µm. 2 parts of ethylene glycol is added thereto, and the mixture is further stirred in a warm bath at a temperature of 60° C. for 24 hours to obtain microcapsule slurry.

On the other hand, 0.2 parts of xanthan gum and 1.0 parts of VEEGUM R (aluminum magnesium silicate, manufactured by Sanyo Chemical Industries, Ltd.) are dispersed in 56.3 parts of ion-exchanged water to obtain a thickener solution. Then, 42.5 parts of the microcapsule slurry and 57.5 parts of the thickener solution are mixed to obtain a microcapsule formulation.

Formulation Example 5

10 parts of any one of Compounds of Present Invention described in Formulation Examples 1 to 325 and 10 parts of phenylxylylethane are mixed and then added to 20 parts of a 10% aqueous solution of polyethylene glycol, and the mixture is stirred with a homomixer to obtain an emulsion with an average particle size of 3 µm. On the other hand, 0.2 parts of xanthan gum and 1.0 parts of VEEGUM R (aluminum magnesium silicate, manufactured by Sanyo Chemical Industries, Ltd.) are dispersed in 58.8 parts of ion-exchanged water to obtain a thickener solution. Then, 40 parts of the emulsion solution and 60 parts of the thickener solution are mixed to obtain flowable.

Formulation Example 6

3 parts of Carplex #80 (synthetic hydrated silicon oxide, a registered trademark of Shionogi & Co., Ltd.), 0.3 parts of PAP (a mixture of monoisopropyl phosphate and diisopropyl phosphate) and 91.7 parts of talc (300 mesh) are added to 5 parts of any one of Compounds of Present Invention described in Formulation Examples 1 to 325, and the mixture is mixed with stirring with a juice blender to obtain a dust formulation.

Formulation Example 7

0.1 parts of any one of Compounds of Present Invention described in Formulation Examples 1 to 325 is dissolved in 10 parts of isopropyl alcohol, and the solution is mixed with 89.9 parts of deodorized kerosene to obtain an oil formulation.

Formulation Example 8

1 part of any one of Compounds of Present Invention described in Formulation Examples 1 to 325, 5 parts of dichloromethane and 34 parts of deodorized kerosene are mixed and dissolved, and filled into an aerosol container, and a valve portion is installed. Then, 60 parts of power propellant (liquefied petroleum gas) is filled therein under pressure through the valve portion to obtain an oil-based aerosol.

Formulation Example 9

A mixed solution of 0.6 parts of any one of Compounds of Present Invention described in Formulation Examples 1 to 325, 5 parts of xylene, 3.4 parts of deodorized kerosene and 1 part of ATMOS 300 (emulsifier, a registered trademark of Atlas Chemical, Inc.) and 50 parts of water are filled into an aerosol container, and 40 parts of power propellant (liquefied petroleum gas) is filled therein under pressure through the valve portion to obtain an aqueous aerosol.

Formulation Example 10

0.3 g of any one of Compounds of Present Invention described in Formulation Examples 1 to 325 is dissolved in 20 ml of acetone, and the solution is uniformly mixed with stirring with 99.7 g of a base material for incense (obtained by mixing Tabu powder, Pyrethrum marc and wooden powder at a ratio of 4:3:3). Then, 100 ml of water is added thereto, and the mixture is thoroughly kneaded, molded and dried to obtain insecticidal incense.

Formulation Example 11

0.8 g of any one of Compounds of Present Invention described in Formulation Examples 1 to 325 and 0.4 g of piperonyl butoxide are dissolved by adding acetone, and the total volume is adjusted to 10 ml with acetone. Then, 0.5 ml of this solution is uniformly impregnated into a base material for an insecticidal mat for electric heating (a plate obtained by hardening fibrils of a mixture of cotton linters and pulp) with a size of 2.5 cm×1.5 cm and a thickness of 0.3 cm to obtain an insecticidal mat for electric heating.

Formulation Example 12

3 parts of any one of Compounds of Present Invention described in Formulation Examples 1 to 325 is dissolved in 97 parts of deodorized kerosene to obtain a liquid formulation, and this is poured into a vessel made of vinyl chloride. A liquid absorptive core whose upper part can be heated by a heater (an inorganic powder is hardened with a binder and sintered) is inserted thereinto to obtain a part to be used for a liquid absorptive core type thermal transpiration apparatus.

Formulation Example 13

100 rag of any one of Compounds of Present Invention described in Formulation Examples 1 to 325 is dissolved in an appropriate amount of acetone, and the solution is impregnated in a porous ceramic plate with a size of 4.0 cm×4.0 cm and 1.2 cm in thickness to obtain a heating type smoking agent.

Formulation Example 14

100 μg of any one of Compounds of Present Invention described in Formulation Examples 1 to 325 is dissolved in an appropriate amount of acetone, and the solution is uniformly applied to a filter paper with a size of 2 cm×2 cm and a thickness of 0.3 mm and then air-dried to remove acetone to obtain a volatile agent for use at room temperature.

Formulation Example 15

10 parts of any one of Compounds of Present Invention described in Formulation Examples 1 to 325, 35 parts of white carbon containing 50 parts of polyoxyethylene alkyl ether sulfate ammonium salt and 55 parts of water are mixed and finely pulverized by a wet pulverization method to obtain a formulation.

Next, the arthropod pest control effect of the compound of the present invention is shown as test examples.

Test Example 1

The formulations of Compounds of Present Invention (10), (11), (12), (13), (14), (15), (19), (20), (21), (22), (23), (25), (26), (27), (28), (29), (30), (31), (32), (33), (34), (36), (37), (38), (43), (63), (64), (65), (113), (114), (118), (119), (131), (139), (140), (141), (143), (146), (149), (158), (240), (290), (332), (334) and (337) obtained in Formulation Example 7 were diluted with a mixed liquid of isopropyl alcohol/deodorized kerosene=1/9, so as to have a concentration of the active ingredient of 2.0% w/v, to prepare a test drug solution.

Ten *Blattella germanica* (5 males and 5 females) were released in a test container (8.75 cm in diameter, 7.5 cm in height, and the bottom made of 16 mesh metallic wire) with the inner wall on which butter was applied, and the container was placed on the bottom of a test chamber (bottom: 46 cm×46 cm, height: 70 cm). From a height of 60 cm above the upper surface of the container, 1.5 ml of the test drug solution was sprayed using a spray gun (a spraying pressure of 0.42 kg/cm$^2$). Thirty seconds after spraying, the container was taken out from the test chamber, and after 2 minutes, 5 minutes and 15 minutes, the number of knocked-down insects was counted to obtain a knockdown rate. The knockdown rate was calculated by the following equation.

Knockdown Rate (%)=(Number of Knocked-down Insects/Number of Tested Insects)×100

As a result, in the treatment with Compounds of Present Invention (10), (11), (12), (13), (14), (15), (19), (20), (21), (22), (23), (25), (26), (27), (28), (29), (30), (31), (32), (33), (34), (36), (37), (38), (43), (63), (64), (65), (113), (114), (118), (119), (131), (139), (140), (141), (143), (146), (149), (158), (240), (290), (332), (334) and (337), the knockdown rate of the test insects within 15 minutes was 80% or more.

Test Example 2

The formulations of Compounds of Present Invention (66), (67), (68), (69), (70), (72), (73), (74), (75), (76), (77), (78), (79), (80), (82), (83), (84), (85), (88), (89), (90), (91), (92), (93), (94), (97), (98), (99), (100), (103), (104), (105), (106), (109), (110), (111), (112), (120), (121), (122), (124), (132), (133), (134), (149), (165), (169), (170), (172), (174), (175), (176), (177), (178), (180), (184), (186), (190), (194), (195), (196), (198), (200), (204), (210), (211), (213), (217), (221), (226), (228), (230), (234), (235), (239), (240), (246), (252), (253), (255), (257), (258), (260), (261), (263), (264), (265), (266), (267), (268), (270), (274), (276), (277), (278), (282), (286), (290), (294), (298), (305), (306), (309), (312), (313), (314), (317), (318), (319), (321), (322), (324), (325), (327), (328), (329), (332), (334), (336) and (338) obtained in Formulation Example 7 were diluted with a mixed liquid of isopropyl alcohol/deodorized kerosene=1/9, so as to have a concentration of the active ingredient of 0.1% w/v, to prepare a test drug solution.

Ten *Blattella germanica* (5 males and 5 females) were released in a test container (8.75 cm in diameter, 7.5 cm in height, and the bottom made of 16 mesh metallic wire) with the inner wall on which butter was applied, and the container was placed on the bottom of a test chamber (bottom: 46 cm×46 cm, height: 70 cm). From a height of 60 cm above the upper surface of the container, 1.5 ml of the test drug solution was sprayed using a spray gun (a spraying pressure of 0.42 kg/cm$^2$). Thirty seconds after spraying, the container was taken out from the test chamber, and after 2 minutes, 5 minutes and 15 minutes, the number of knocked-down insects was counted to obtain a knockdown rate. The knockdown rate was calculated by the following equation.

Knockdown Rate (%)=(Number of Knocked-down Insects/Number of Tested Insects)×100

As a result, in the treatment with Compounds of Present Invention (66), (67), (68), (69), (70), (72), (73), (74), (75), (76), (77), (78), (79), (80), (82), (83), (84), (85), (88), (89), (90), (91), (92), (93), (94), (97), (98), (99), (100), (103), (104), (105), (106), (109), (110), (111), (112), (120), (121), (122), (124), (132), (133), (134), (149), (165), (169), (170), (172), (174), (175), (176), (177), (178), (180), (184), (186), (190), (194), (195), (196), (198), (200), (204), (210), (211), (213), (217), (221), (226), (228), (230), (234), (235), (239), (240), (246), (252), (253), (255), (257), (258), (260), (261), (263), (264), (265), (266), (267), (268), (270), (274), (276), (277), (278), (282), (286), (290), (294), (298), (305), (306), (309), (312), (313), (314), (317), (318), (319), (321), (322), (324), (325), (327), (328), (329), (332), (334), (336) and (338) obtained in Formulation Example 7, the knockdown rate of the test insects within 15 minutes was 80% or more.

Test Example 3

The formulations of Compounds of Present Invention (11), (13), (14), (15), (20), (21), (22), (26), (27), (30), (33), (34), (36), (63), (64), (65), (113), (118), (119), (120), (131), (132), (139), (140), (141), (143), (146), (150), (158), (159), (160), (169), (176), (213), (235), (240), (242), (264), (290), (332) and (334) obtained in Formulation Example 7 were diluted with a mixed liquid of isopropyl alcohol/deodorized kerosene=1/9, so as to have a concentration of the active ingredient of 2.0% w/v, to prepare a test drug solution.

Ten adult *Musca domestica* (five males and five females) were released in a polyethylene cup (bottom diameter: 10.6 cm), and the cup was covered with a 16-mesh nylon gauze.

The polyethylene cup was placed on the bottom of a test chamber (bottom: 46 cm×46 cm, height: 70 cm). From a height of 30 cm above the upper surface of the polyethylene cup, 0.5 ml of the test drug solution was sprayed using a spray gun (a spraying pressure of 0.9 kg/cm$^2$). Immediately after spraying, the cup was taken out from the test chamber, and after 2 minutes, 5 minutes and 15 minutes, the number of knocked-down insects was counted to obtain a knockdown rate. The knockdown rate was calculated by the following equation.

Knockdown Rate (%)=(Number of Knocked-down Insects/Number of Tested Insects)×100

As a result, in the treatment with Compounds of Present Invention (11), (13), (14), (15), (20), (21), (22), (26), (27), (30), (33), (34), (36), (63), (64), (65), (113), (118), (119), (120), (131), (132), (139), (140), (141), (143), (146), (150), (158), (159), (160), (169), (176), (213), (235), (240), (242), (264), (290), (332) and (334), the knockdown rate of the test insects within 15 minutes was 80% or more.

Test Example 4

The formulations of Compounds of Present Invention (11), (12), (13), (14), (15), (18), (20), (21), (22), (23), (25), (26), (27), (28), (29), (30), (31), (32), (33), (34), (35), (36), (37), (38), (40), (43), (47), (48), (63), (64), (65), (66), (67), (68), (69), (70), (71), (72), (73), (74), (75), (76), (77), (78), (79), (80), (81), (82), (83), (84), (85), (88), (89), (90), (91), (92), (93), (94), (95), (96), (97), (98), (99), (100), (103), (104), (105), (106), (107), (108), (109), (110), (111), (112), (113), (114), (117), (118), (119), (120), (121), (122), (123), (124), (125), (131), (132), (133), (134), (135), (136), (137), (138), (139), (140), (141), (143), (145), (146), (147), (148), (149), (150), (158), (159), (160), (161), (162), (163), (169), (171), (170), (172), (174), (175), (176), (177), (178), (179), (180), (181), (182), (183), (184), (185), (186), (187), (188), (189), (190), (191), (192), (193), (194), (195), (196), (197), (198), (199), (200), (201), (202), (203), (204), (209), (210), (211), (213), (217), (221), (226), (227), (228), (229), (230), (231), (232), (233), (234), (235), (236), (237), (238), (239), (240), (240), (241), (242), (244), (245), (246), (247), (248), (249), (250), (251), (252), (253), (254), (255), (256), (257), (258), (259), (260), (261), (262), (263), (264), (265), (266), (267), (268), (269), (270), (271), (272), (273), (274), (275), (276), (277), (278), (282), (286), (290), (294), (295), (296), (297), (298), (299), (300), (305), (306), (307), (308), (309), (312), (313), (314), (315), (316), (317), (318), (319), (320), (321), (322), (323), (324), (325), (327), (328), (329), (332), (333), (334), (335), (336), (337) and (338) obtained in Formulation Example 7 were diluted with a mixed liquid of isopropyl alcohol/deodorized kerosene=1/9, so as to have a concentration of the active ingredient of 0.1% w/v, to prepare a test drug solution.

Ten adult *Culex pipiens pallens* were released in a polyethylene cup (bottom diameter: 10.6 cm), and the cup was covered with a 16-mesh nylon gauze. The polyethylene cup was placed on the bottom of a test chamber (bottom: 46 cm×46 cm, height: 70 cm). From a height of 30 cm above the upper surface of the polyethylene cup, 0.5 ml of the test drug solution was sprayed using a spray gun (a spraying pressure of 0.4 kg/cm$^2$). Immediately after spraying, the cup was taken out from the test chamber, and after 2 minutes, 5 minutes and 15 minutes, the number of knocked-down insects was counted to obtain a knockdown rate. The knockdown rate was calculated by the following equation.

Knockdown Rate (%)=(Number of Knocked-down Insects/Number of Tested Insects)×100

As a result, in the treatment with Compounds of Present Invention (11), (12), (13), (14), (15), (18), (20), (21), (22), (23), (25), (26), (27), (28), (29), (30), (31), (32), (33), (34), (35), (36), (37), (38), (40), (43), (47), (48), (63), (64), (65), (66), (67), (68), (69), (70), (71), (72), (73), (74), (75), (76), (77), (78), (79), (80), (81), (82), (83), (84), (85), (88), (89), (90), (91), (92), (93), (94), (95), (96), (97), (98), (99), (100), (103), (104), (105), (106), (107), (108), (109), (110), (111), (112), (113), (114), (117), (118), (119), (120), (121), (122), (123), (124), (125), (131), (132), (133), (134), (135), (136), (137), (138), (139), (140), (141), (143), (145), (146), (147), (148), (149), (150), (158), (159), (160), (161), (162), (163), (169), (171), (170), (172), (174), (175), (176), (177), (178), (179), (180), (181), (182), (183), (184), (185), (186), (187), (188), (189), (190), (191), (192), (193), (194), (195), (196), (197), (198), (199), (200), (201), (202), (203), (204), (209), (210), (211), (213), (217), (221), (226), (227), (228), (229), (230), (231), (232), (233), (234), (235), (236), (237), (238), (239), (240), (240), (241), (242), (244), (245), (246), (247), (248), (249), (250), (251), (252), (253), (254), (255), (256), (257), (258), (259), (260), (261), (262), (263), (264), (265), (266), (267), (268), (269), (270), (271), (272), (273), (274), (275), (276), (277), (278), (282), (286), (290), (294), (295), (296), (297), (298), (299), (300), (305), (306), (307), (308), (309), (312), (313), (314), (315), (316), (317), (318), (319), (320), (321), (322), (323), (324), (325), (327), (328), (329), (332), (333), (334), (335), (336), (337) and (338), the knockdown rate of the test insects within 15 minutes was 80% or more.

Test Example 5

Each of the formulations of Compounds of Present Invention (9), (22), (26), (34), (54), (66), (67), (68), (69), (72), (76), (79), (82), (84), (90), (100), (105), (121), (132), (150), (176), (195), (200), (234), (246), (252), (260), (264), (266), (267), (268), (270), (271), (274), (275), (278), (282), (286), (290), (294), (299), (305), (306), (308), (309), (313), (314), (315), (319), (321), (322), (324), (325), (333) and (335) obtained in Formulation Example 15 was diluted with water, so as to have a concentration of the active ingredient of 500 ppm, to prepare a test drug solution.

A filter paper having a diameter of 5.5 cm was spread on the bottom of a polyethylene cup having the same diameter and 0.7 ml of the test drug solution was added dropwise onto the filter paper, and 30 mg of sucrose was uniformly placed as bait.

Into the polyethylene cup, 10 female imagoes of *Musca domestica* were released, and the cup was sealed with a lid. After 24 hours, the life and death of *Musca domestica* was examined, and the death rate was calculated. The death rate was calculated by the following equation.

Death rate (%)=(Number of dead insects/Number of tested insects)×100

As a result, in the treatment with Compounds of Present Invention (9), (22), (26), (34), (54), (66), (67), (68), (69), (72), (76), (79), (82), (84), (90), (100), (105), (121), (132), (150), (176), (195), (200), (234), (246), (252), (260), (264), (266), (267), (268), (270), (271), (274), (275), (278), (282), (286), (290), (294), (299), (305), (306), (308), (309), (313), (314), (315), (319), (321), (322), (324), (325), (333) and (335), the death rate was 90% or more.

Test Example 6

Each of the formulations of Compounds of Present Invention (39), (63), (71), (72), (92), (93), (95), (106), (150), (171), (170), (181), (182), (183), (187), (188), (189), (190), (191), (192), (200), (201), (201), (234), (246), (290) and (299) obtained in Formulation Example 15 was diluted with water, so as to have a concentration of the active ingredient of 500 ppm, to prepare a test drug solution.

20 last-instar larvae of Culex pipiens pallens were released into a liquid to which 0.7 ml of the above test drug solution was added to 100 ml of ion-exchanged water (a concentration of the active ingredient of 3.5 ppm). One day later, the life and death of the Culex pipiens pallens was examined, and the death rate was calculated. The death rate was calculated by the following equation.

Death rate (%)=(Number of dead insects/Number of tested insects)×100

As a result, in the treatment with Compounds of Present Invention (39), (63), (71), (72), (92), (93), (95), (106), (150), (171), (170), (181), (182), (183), (187), (188), (189), (190), (191), (192), (200), (201), (234), (246), (290) and (299), the death rate was 90% or more.

Test Example 7

Each of the formulations of Compounds of Present Invention (20), (21), (39), (63), (70), (73), (76), (77), (78), (91), (92), (93), (95), (96), (105), (106), (119), (146), (150), (167), (171), (170), (181), (182), (183), (187), (188), (189), (190), (191), (192), (198), (199), (200), (201), (252), (258), (260), (282), (315) and (332) obtained in Formulation Example 15 was diluted with water, so as to have a concentration of the active ingredient of 500 ppm, to prepare a test drug solution.

20 last-instar larvae of Culex pipiens pallens were released into a liquid to which 0.7 ml of the above test drug solution was added to 100 ml of ion-exchanged water (a concentration of the active ingredient of 3.5 ppm). Eight days later, the life and death of the Culex pipiens pallens was examined, and the death rate was calculated. The death rate was calculated by the following equation.

Death rate (%)=(Number of dead insects/Number of tested insects)×100

As a result, in the treatment with Compounds of Present Invention (20), (21), (39), (63), (70), (73), (76), (77), (78), (91), (92), (93), (95), (96), (105), (106), (119), (146), (150), (167), (171), (170), (181), (182), (183), (187), (188), (189), (190), (191), (192), (198), (199), (200), (201), (252), (258), (260), (282), (315) and (332), the death rate was 90% or more.

Test Example 8

Each of the formulations of Compounds of Present Invention (65), (73), (81), (94), (119), (129), (131), (144), (153) and (154) obtained in Formulation Example 15 was diluted with water, so as to have a concentration of the active ingredient of 500 ppm, to prepare a test spray solution.

On the other hand, cucumber was planted in a polyethylene cup and grown until the first true leaf was spread, and about 20 Aphis gossypii were allowed to parasitize the cucumber. One day after, the test spray solution was sprayed to the cucumber at a ratio of 20 ml/cup. Sir days after spraying, the number of Aphis gossypii was investigated, and the controlling value was calculated according to the following equation.

Controlling value (%)={1−(Cb×Tai)/(Cai×Tb)}×100

In the equation, the symbols represent as follows.
Cb: the number of insects in a non-treated section before treatment
Cai: the number of insects in a non-treated section on observation
Tb: the number of insects in a treated section before treatment
Tai: the number of insects in a treated section on observation As a result, in the treatment with Compounds of Present Invention (65), (73), (81), (94), (119), (129), (131), (144), (153) and (154), the control value was 90% or more.

Test Example 9

The formulations of Compounds of Present Invention (3), (9), (18), (30), (31), (33), (34), (36), (43), (51), (52), (54), (57), (58), (90), (105), (106), (129), (142), (154), (194) and (204) obtained in Formulation Example 15 were diluted with water, so as to have a concentration of the active ingredient of 500 ppm, to prepare a test treatment solution.

On the other hand, cucumber was planted in a polyethylene cup with a plurality of small holes on the bottom and grown until the first true leaf was spread. A cup in which cucumber was planted was put in a plastic cup with 5 ml of the test treatment solution, so that the soil in the cup was in contact with the treatment liquid. After five days, about 20 Aphis gossypii were allowed to parasitize the cucumber, and seven days after putting insects, the number of Aphis gossypii was investigated, and the controlling value was calculated according to the following equation.

Controlling value (%)={1−(Cb×Tai)/(Cai×Tb)}×100

In the equation, the symbols represent as follows.
Cb: the number of insects in a non-treated section before treatment
Cai: the number of insects in a non-treated section on observation
Tb: the number of insects in a treated section before treatment
Tai: the number of insects in a treated section on observation As a result, in the section treated with a test treatment solution of Compounds of Present Invention (3), (9), (18), (30), (31), (33), (34), (36), (43), (51), (52), (54), (57), (58), (90), (105), (106), (129), (142), (154), (194) and (204), the controlling value was 90% or more.

Test Example 10

The formulations of Compounds of Present Invention (13), (15), (23), (39), (65), (69), (70), (71), (72), (73), (76), (79), (81), (83), (91), (92), (93), (94), (97), (98), (100), (103), (104), (105), (106), (118), (119), (150), (171), (170), (188), (190), (191), (201), (234), (246), (258), (272), (290), (294), (306), (313) and (318) obtained in Formulation Example 15 were diluted with water, so as to have a concentration of the active ingredient of 500 ppm, to prepare a test spray solution.

On the other hand, cabbage was planted in a polyethylene cup, and grown until the third-fourth true leaf was spread. The test spray solution was sprayed to the cabbage at a ratio of 20 ml/cup. After the drug solution sprayed on the cabbage was dried, 10 third instar larvae of Plutella xylostella were allowed to parasitize the cabbage. After five days, the number of Plutella xylostella was investigated, and the controlling value was calculated according to the following standard.

Controlling value (%)={1−(Cb×Tai)/(Cai×Tb)}×100

In the equation, the symbols represent as follows.
Cb: the number of insects in a non-treated section before treatment
Cai: the number of insects in a non-treated section on observation
Tb: the number of insects in a treated section before treatment
Tai: the number of insects in a treated section on observation As a result, in the section treated with a test treatment solution of Compounds of Present Invention (13), (15), (23), (39), (65), (69), (70), (71), (72), (73), (76), (79), (81), (83), (91), (92), (93), (94), (97), (98), (100), (103), (104), (105), (106), (118), (119), (150), (171), (170), (188), (190), (191), (201), (234), (246), (258), (272), (290), (294), (306), (313) and (318), the controlling value was 90% or more.

Test Example 11

The formulations of Compounds of Present Invention (20), (65), (69), (72), (73), (76), (77), (79), (81), (105), (106), (112), (171), (183), (190), (191), (196), (197), (198), (200), (201), (234), (246), (258), (260), (272), (290), (306), (315), (318), (321) and (325) obtained in Formulation Example 15 were diluted with water, so as to have a concentration of the active ingredient of 500 ppm, to prepare a test spray solution.

On the other hand, cabbage was planted in a polyethylene cup, and grown until the third-fourth true leaf was spread. The test spray solution was sprayed to the cabbage at a ratio of 20 ml/cup. After the drug solution sprayed orn the cabbage was dried, 10 fourth instar larvae of *Spodoptera litura* were allowed to parasitize the cabbage. After 4 days, the number of surviving *Spodoptera litura* on the cabbage leaves was examined, and the controlling value was calculated according to the following equation.

Controlling value (%)={1−(Cb×Tai)/(Cai/Tb)}×100

In the equation, the symbols represent as follows.
Cb: the number of insects in a non-treated section before treatment
Cai: the number of insects in a non-treated section on observation
Tb: the number of insects in a treated section before treatment
Tai: the number of insects in a treated section on observation As a result, in the section treated with Compounds of Present Invention (20), (65), (69), (72), (73), (76), (77), (79), (81), (105), (106), (112), (171), (183), (190), (191), (196), (197), (198), (200), (201), (234), (246), (258), (260), (272), (290), (306), (315), (318), (321) and (325), the controlling value was 80% or more.

Test Example 12

The formulations of Compounds of Present Invention (39), (65), (73), (122), (150), (171), (170), (183) and (234) obtained in Formulation Example 15 were diluted with water, so as to have a concentration of the active ingredient of 500 ppm, to prepare a test spray solution.

On the other hand, 20 ml of the test spray solution was each sprayed on an apple seedling (28 days after sowing, a tree height of about 15 cm) planted in a plastic cup. After the drug solution sprayed on the apple was air-dried, about 30 first-instar larvae of *Adoxophyes orana fasciata* were released.

Seven days after spraying, the number of surviving *Adoxophyes orana fasciata* on the apple seedling was investigated, and the controlling value was calculated according to the following equation.

Controlling value (%)={1−(Cb×Tai)/(Cai×Tb)}×100

In the equation, the symbols represent as follows.
Cb: the number of insects in a non-treated section before treatment
Cai: the number of insects in a non-treated section on observation
Tb: the number of insects in a treated section before treatment
Tai: the number of insects in a treated section on observation As a result, in the section treated with Compounds of Present Invention (39), (65), (73), (122), (150), (171), (170), (183) and (234), the control value was 100%.

INDUSTRIAL APPLICABILITY

The compound of the present invention has a controlling effect on arthropod pests and is useful as an active ingredient of an arthropod pest control agent.

The invention claimed is:
1. An amide compound represented by formula (I-s):

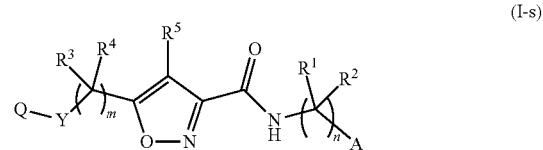

wherein A represents a 3 to 7-membered saturated heterocyclic ring which contains, as ring-forming component(s), one or more atoms or groups selected from the group consisting of an oxygen atom and —S(O)$_t$—, and the saturated heterocyclic ring may have one to three atoms or groups selected from group D,
t represents 0, 1 or 2,
$R^1$ and $R^2$ are the same or different and represent a C1 to C4 alkyl group optionally having one or more halogen atoms or a hydrogen atom,
n represents 0, 1 or 2,
$R^5$ is a halogen atom, a cyano group, a formyl group, a carboxyl group, a C1 to C4 alkoxycarbonyl group optionally having one or more halogen atoms, a carbamoyl group, a C1 to C3 hydrocarbon group optionally having one or more atoms or groups selected from the group consisting of —OR$^7$ and halogen atoms, or a hydrogen atom,
$R^7$ represents —C(=S)SR$^8$ or a hydrogen atom,
$R^8$ represents a C1 to C3 hydrocarbon group optionally having one or more halogen atoms,
$R^3$ and $R^4$ are the same or different and represent a C1 to C4 alkyl group optionally having one or more halogen atoms, a halogen atom, a phenyl group optionally having one or more atoms or groups selected from group B, or a hydrogen atom,
Y represents a single bond, an oxygen atom or —S(O)$_u$—,when Y is a single bond, m represents 0, when Y is an oxygen atom or —S(O)$_u$—, m represents 0, 1, 2, 3, 4, 5, 6 or 7,
when Y is a single bond, Q represents a C1 to C8 chain hydrocarbon group having one or more atoms or groups selected from group F, when Y is an oxygen atom, and m is 0, 2, 3, 4, 5, 6 or 7, or when Y is —S(O)$_u$—, Q represents a C1 to C8 chain hydrocarbon group optionally having one or more atoms or groups selected from group G, or a group selected from group A, and when Y is an oxygen atom, and m is 1, Q represents a C1 to C8 chain hydrocarbon group optionally having one or more atoms or groups selected from group G, or a group selected from group H, u represents 0, 1 or 2, Group A: A group consisting of C3 to C8 cycloalkyl-groups optionally having one or more atoms or groups selected from group B, indanyl groups optionally having one or more atoms or groups selected from group B, 1,2,3,4-tetrahydronaphthyl groups optionally having one or more atoms or groups selected from group B, phenyl groups optionally having one or more atoms or groups selected from group B, naphthyl groups optionally having one or more atoms or groups selected from group B, Group B: A group consisting of C1 to C4 alkyl groups optionally having one or more halogen atoms, C1 to C4 alkyl groups optionally having one or more benzyloxy groups, C1 to C4 alkoxy groups optionally having one or more halogen atoms, C1 to C4 alkylthio groups optionally having one or more halogen atoms, C1 to C4 alkylsulfinyl groups optionally having one or more halogen atoms, C1 to C4 alkylsulfonyl groups optionally having one or more halogen atoms, C1 to C4 alkoxycarbonyl groups optionally having one or more halogen atoms, vinyl groups optionally having one or more atoms or groups selected from group E, ethynyl groups optionally having an atom or group selected from group E, a phenyl group, a phenoxy group, a cyano group, a nitro group, a carboxyl group, a hydroxyl group, —CONR$^{12}$R$^{13}$ group, a methoxymethyl group, and halogen atoms, R$^{12}$ and R$^{13}$ are the same or different and represent a C1 to C4 alkyl group optionally having one or more halogen atoms or a hydrogen atom, Group D: A group consisting of C1 to C4 alkyl groups optionally having one or more halogen atoms, C1 to C4 alkoxy groups optionally having one or more halogen atoms, and halogen atoms, Group E: A group consisting of C1 to C4 alkyl groups optionally having one or more halogen atoms and halogen atoms, Group F: A group consisting of C3 to C8 cycloalkyl groups optionally having one or more atoms or groups selected from group B, indanyl groups optionally having one or more atoms or groups selected from group B, 1,2,3,4-tetrahydronaphthyl groups optionally having one or more atoms or groups selected from group B, phenyl groups optionally having one or more atoms or groups selected from group B, naphthyl groups optionally having one or more atoms or groups selected from group B, halogen atoms, C1 to C4 alkoxycarbonyl group optionally having one or more halogen atoms, a cyano group, a nitro group, a carboxyl group, a hydroxyl group, and —CONR$^{12}$R$^{13}$ group, Group G: A group consisting of C3 to C8 cycloalkyl groups optionally having one or more atoms or groups selected from group B, indanyl groups optionally having one or more atoms or groups selected from group B, 1,2,3,4-tetrahydronaphthyl groups optionally having one or more atoms or groups selected from group B, phenyl groups optionally having one or more atoms or groups selected from group B, phenoxy groups optionally having one or more atoms or groups selected from group B, naphthyl groups optionally having one or more atoms or groups selected from group B, halogen atoms, C1 to C4 alkoxycarbonyl group optionally having one or more halogen atoms, a cyano group, a nitro group, a carboxyl group, a hydroxyl group, and —CONR$^{12}$R$^{13}$ group, Group H: A group consisting of C3 to C8 cycloalkyl groups optionally having one or more atoms or groups selected from group B, indanyl groups optionally having one or more atoms or groups selected from group B.

2. The amide compound according to claim 1, wherein

R$^5$ is a halogen atom, a cyano group, a methyl group or a hydrogen atom,

R$^3$ and R$^4$ are the same or different, and are a C1 to C4 alkyl group optionally having one or more halogen atoms, a halogen atom or a hydrogen atom, when Y is an oxygen atom, or —S(O)$_u$—, m is 0, 1, 2, 3, or 4, Q is a C1 to C8 chain hydrocarbon group optionally having one or more atoms or groups selected from group F, and group B is a group consisting of C1 to C4 alkyl groups optionally having one or more halogen atoms, C1 to C4 alkoxy groups optionally having one or more halogen atoms, C1 to C4 alkylthio groups optionally having one or more halogen atoms, C1 to C4 alkylsulfinyl groups optionally having one or more halogen atoms, C1 to C4 alkylsulfonyl groups optionally having one or more halogen atoms, C1 to C4 alkoxycarbonyl groups optionally having one or more halogen atoms, vinyl groups optionally having one or more atoms or groups selected from group E, ethynyl groups optionally having an atom or group selected from group E, a cyano group, a nitro group, a carboxyl group, a hydroxyl group, —CONR$^{12}$R$^{13}$ group, a methoxymethyl group, and halogen atoms.

3. The amide compound according to claim 1, wherein A is a group represented by the following formula (III-a) or (III-b):

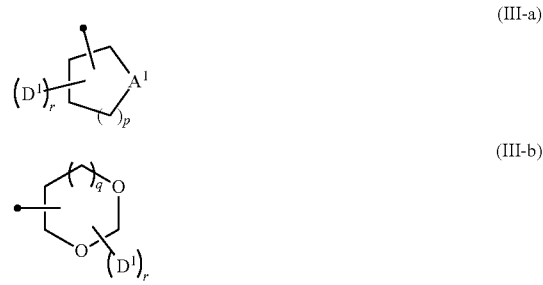

wherein A$^1$ represents an oxygen atom or a sulfur atom, D$^1$ represents an atom or group selected from group D, r represents 0 or 1, p represents 0, 1 or 2, and q represents 0 or 1.

4. The amide compound according to claim 1, wherein A is a group represented by the following formula (III-c):
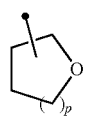
wherein p represents 0, 1 or 2.
5. The amide compound according to claim 1, wherein n is 1.
6. The amide compound according to claim 1, wherein m is 1.
7. The amide compound according to claim 1, wherein Y is an oxygen atom.
8. The amide compound according to claim 1, wherein Y is a single bond.
* * * * *